(12) United States Patent
Blatt et al.

(10) Patent No.: US 7,491,794 B2
(45) Date of Patent: Feb. 17, 2009

(54) MACROCYCLIC COMPOUNDS AS INHIBITORS OF VIRAL REPLICATION

(75) Inventors: Lawrence M. Blatt, San Francisco, CA (US); Steven W. Andrews, Longmont, CO (US); Kevin R. Condroski, Broomfield, CO (US); Yutong Jiang, Longmont, CO (US); April L. Kennedy, Denver, CO (US); Peter J. Stengel, Longmont, CO (US); Steven M. Wenglowsky, Boulder, CO (US)

(73) Assignee: Intermune, Inc., Brisbane, CA (US)

( * ) Notice: Subject to any disclaimer, the term of this patent is extended or adjusted under 35 U.S.C. 154(b) by 399 days.

(21) Appl. No.: 11/093,884

(22) Filed: Mar. 29, 2005

(65) Prior Publication Data

US 2005/0267018 A1    Dec. 1, 2005

Related U.S. Application Data

(63) Continuation-in-part of application No. 11/064,445, filed on Feb. 23, 2005, now abandoned, which is a continuation of application No. PCT/US2004/033970, filed on Oct. 13, 2004.

(60) Provisional application No. 60/511,541, filed on Oct. 14, 2003, provisional application No. 60/612,460, filed on Sep. 22, 2004, provisional application No. 60/612,381, filed on Sep. 22, 2004, provisional application No. 60/562,418, filed on Apr. 14, 2004, provisional application No. 60/558,161, filed on Mar. 30, 2004.

(51) Int. Cl.
*A61K 38/12* (2006.01)
(52) U.S. Cl. .................................. 530/317
(58) Field of Classification Search ........................ None
See application file for complete search history.

(56) References Cited

U.S. PATENT DOCUMENTS

| | | | |
|---|---|---|---|
| 5,624,949 A | 4/1997 | Heath et al. |
| 5,656,627 A | 8/1997 | Bemis et al. |
| 5,756,466 A | 5/1998 | Bemis et al. |
| 5,847,135 A | 12/1998 | Bemis et al. |
| 6,858,600 B2 | 2/2000 | Hamilton et al. |
| 6,268,207 B1 | 7/2001 | Bailey |
| 6,323,180 B1 | 11/2001 | Llinas-Brunet et al. |
| 6,410,531 B1 | 6/2002 | Llinas-Brunet et al. |
| 6,420,380 B2 | 7/2002 | Llinas-Brunet et al. |
| 6,534,523 B1 | 3/2003 | Llinas-Brunet et al. |
| 6,608,027 B1 | 8/2003 | Tsantrizo et al. |
| 6,642,204 B2 | 11/2003 | Llinas-Brunet et al. |
| 6,693,072 B2 | 2/2004 | Gallion et al. |
| 6,767,991 B1 | 7/2004 | Llinas-Brunet et al. |
| 6,828,301 B2 | 12/2004 | Chen et al. |
| 6,846,802 B2 | 1/2005 | Chen et al. |
| 6,867,185 B2 | 3/2005 | Campbell et al. |
| 6,867,303 B2 | 3/2005 | Grela |
| 6,869,964 B2 | 3/2005 | Campbell et al. |
| 6,872,805 B2 | 3/2005 | Campbell et al. |
| 6,878,722 B2 | 4/2005 | Campbell et al. |
| 6,909,000 B2 | 6/2005 | Farmer et al. |
| 6,914,122 B2 | 7/2005 | Venkatraman et al. |
| 6,919,423 B2 | 7/2005 | Llinas-Brunet |
| 6,995,174 B2 | 2/2006 | Wang et al. |
| 7,012,066 B2 | 3/2006 | Saksena et al. |
| 7,041,698 B2 | 5/2006 | Ripka et al. |
| 7,091,184 B2 | 8/2006 | Llinas-Brunet et al. |
| 7,119,072 B2 | 10/2006 | Llinas-Brunet et al. |
| 7,125,845 B2 | 10/2006 | Wu et al. |
| 7,132,504 B2 | 11/2006 | Scola et al. |
| 7,135,462 B2 | 11/2006 | Scola et al. |
| 7,148,347 B2 | 12/2006 | Brandenburg et al. |
| 7,157,424 B2 | 1/2007 | Chen et al. |
| 7,173,004 B2 | 2/2007 | McPhee et al. |
| 7,173,057 B2 | 2/2007 | Chen et al. |
| 7,176,208 B2 | 2/2007 | Nakajima et al. |
| 7,183,374 B2 | 2/2007 | Brenner et al. |
| 7,186,747 B2 | 3/2007 | Arasappan et al. |
| 7,189,844 B2 | 3/2007 | Gallou et al. |
| 7,208,600 B2 | 4/2007 | Cottrell et al. |

(Continued)

FOREIGN PATENT DOCUMENTS

CA    2370400    8/2003

(Continued)

OTHER PUBLICATIONS

A. Marchetti et al., "Synthesis of Two Novel Cyclic Biphenyl Ether Analogs of an Inhibitor of HCV NS3 Protease", *Synlett.* 1999, S1, 1000-1002.

(Continued)

*Primary Examiner*—Cecilia Tsang
*Assistant Examiner*—Thomas S Heard
(74) *Attorney, Agent, or Firm*—Knobbe Martens Olson & Bear LLP; John Bendrick

(57) ABSTRACT

The embodiments provide compounds of the general formulas I-XIX, as well as compositions, including pharmaceutical compositions, comprising a subject compound. The embodiments further provide treatment methods, including methods of treating flaviviral infection, including hepatitis C virus infection and methods of treating liver fibrosis, the methods generally involving administering to an individual in need thereof an effective amount of a subject compound or composition.

1 Claim, No Drawings

U.S. PATENT DOCUMENTS

| | | | |
|---|---|---|---|
| 7,273,851 | B2 | 9/2007 | Miao et al. |
| 7,273,885 | B2 | 9/2007 | Pitlik et al. |
| 7,309,708 | B2 | 12/2007 | Tu et al. |
| 2002/0016294 | A1 | 2/2002 | Venkatraman et al. |
| 2002/0016442 | A1 | 2/2002 | Llinas-Brunet et al. |
| 2002/0037998 | A1 | 3/2002 | Llinas-Brunet et al. |
| 2002/0107181 | A1 | 8/2002 | Chen et al. |
| 2002/0111313 | A1 | 8/2002 | Campbell et al. |
| 2003/0181363 | A1 | 9/2003 | Llinas-Brunet et al. |
| 2003/0186895 | A1 | 10/2003 | Llinas-Brunet et al. |
| 2003/0191067 | A1 | 10/2003 | Llinas-Brunet et al. |
| 2003/0195228 | A1 | 10/2003 | Chen et al. |
| 2003/0224977 | A1 | 12/2003 | Llinas-Brunet et al. |
| 2004/0002448 | A1 | 1/2004 | Tsantrizos et al. |
| 2004/0033959 | A1 | 2/2004 | Chen et al. |
| 2004/0038872 | A1 | 2/2004 | Campbell et al. |
| 2004/0048802 | A1 | 3/2004 | Ripka et al. |
| 2004/0072761 | A1 | 4/2004 | Campbell et al. |
| 2004/0077551 | A1 | 4/2004 | Campbell et al. |
| 2004/0106559 | A1 | 6/2004 | Wang et al. |
| 2004/0138109 | A1 | 7/2004 | Chen et al. |
| 2004/0180815 | A1 | 9/2004 | Nakaima et al. |
| 2004/0229776 | A1 | 11/2004 | Chen et al. |
| 2004/0229777 | A1 | 11/2004 | Cerreta et al. |
| 2004/0248779 | A1 | 12/2004 | Dersch et al. |
| 2004/0266668 | A1 | 12/2004 | Nakajima et al. |
| 2005/0049187 | A1 | 3/2005 | Brandenburg et al. |
| 2005/0065073 | A1 | 3/2005 | Wu et al. |
| 2005/0075279 | A1 | 4/2005 | Llinas-Brunet et al. |
| 2005/0080005 | A1 | 4/2005 | Llinas-Brunet et al. |
| 2005/0090432 | A1 | 4/2005 | McPhee et al. |
| 2005/0119189 | A1 | 6/2005 | Cottrell et al. |
| 2005/0119453 | A1 | 6/2005 | Brenner et al. |
| 2005/0136400 | A1 | 6/2005 | Lin et al. |
| 2005/0143316 | A1 | 6/2005 | Tu et al. |
| 2005/0153877 | A1 | 7/2005 | Miao et al. |
| 2005/0153900 | A1 | 7/2005 | Velazquez et al. |
| 2005/0197301 | A1 | 9/2005 | Njoroge et al. |
| 2005/0209135 | A1 | 9/2005 | Busacca et al. |
| 2005/0215486 | A1 | 9/2005 | Cottrell et al. |
| 2005/0222047 | A1 | 10/2005 | Chen et al. |
| 2005/0245458 | A1 | 11/2005 | Arasappan et al. |
| 2005/0261200 | A1 | 11/2005 | Miao et al. |
| 2005/0267040 | A1 | 12/2005 | Scola et al. |
| 2005/0267043 | A1 | 12/2005 | Bogen et al. |
| 2005/0272663 | A1 | 12/2005 | Arasappan et al. |
| 2006/0046956 | A1 | 3/2006 | Sannigrahi et al. |
| 2006/0122123 | A1 | 6/2006 | Chaudhary et al. |
| 2006/0183694 | A1 | 8/2006 | Sin et al. |
| 2006/0210969 | A1 | 9/2006 | Rice et al. |
| 2007/0054842 | A1 | 3/2007 | Blatt et al. |
| 2007/0093414 | A1 | 4/2007 | Carini et al. |
| 2007/0161574 | A1 | 7/2007 | Rosenquist et al. |

FOREIGN PATENT DOCUMENTS

| | | |
|---|---|---|
| CL | 01958-1996 | 7/1997 |
| CL | REG. 39715 | 6/1998 |
| CL | 01184-1998 | 3/1999 |
| WO | WO 97/18207 | 5/1997 |
| WO | WO 98/51665 | 11/1998 |
| WO | WO 00/09543 A | 2/2000 |
| WO | WO 00/09558 | 2/2000 |
| WO | WO 00/59929 A | 10/2000 |
| WO | WO 01/74768 | 10/2001 |
| WO | WO 01/81325 | 11/2001 |
| WO | WO 02/18369 | 3/2002 |
| WO | WO 02/060926 | 8/2002 |
| WO | WO 03/062265 | 7/2003 |
| WO | WO 03/064416 | 8/2003 |
| WO | WO 03/064455 A | 8/2003 |
| WO | WO 03/064456 A | 8/2003 |
| WO | WO 03/099274 | 12/2003 |
| WO | WO 2004/026896 | 4/2004 |
| WO | WO 2004/039833 | 5/2004 |
| WO | WO 2004/096286 | 11/2004 |
| WO | WO 2004/113365 | 12/2004 |
| WO | WO 2005/010029 | 2/2005 |
| WO | WO 2005/046712 | 5/2005 |
| WO | WO 2005/051410 | 6/2005 |
| WO | WO 2005/073195 A2 | 8/2005 |
| WO | WO 2005/073216 A2 | 8/2005 |
| WO | WO 2005/107745 | 11/2005 |
| WO | WO 2005/113581 | 12/2005 |
| WO | WO 2006/020276 | 2/2006 |
| WO | WO 2006/043145 | 4/2006 |
| WO | WO 2006/086381 | 8/2006 |
| WO | WO 2007/015824 | 2/2007 |
| WO | WO 2007/044893 | 4/2007 |
| WO | WO 2007/044933 | 4/2007 |

OTHER PUBLICATIONS

A. Faucher et al., "Synthesis of BILN 2061, an HCV NS3 Protease Inhibitor with Proven Antiviral Effect in Humans," Organic Letters (2004), 6(17), 2901-2904.

S. LaPlante et al., "Dynamics and structure-based design of drugs targeting the critical serine protease of the hepatitis C virus from a peptidic substrate to BILN 2061", Current Medicinal Chemistry: Anti-Infective Agents (2005), 4(2), 111-132 (Abstract Only).

D. Thibeault et al., "Sensitivity of NS3 serine proteases from hepatitis C virus genotypes 2 and 3 to the inhibitor BILN 2061", Journal of Virology (2004), 78(14), 7352-7359.

N. Goudreau et al., "Potent Inhibitors of the Hepatitis C Virus NS3 Protease: Design and Synthesis of Macrocyclic Substrate-Based β-Strand Mimics," Journal of Organic Chemistry (2004), 69(19), 6185-6201.

L. Lu et al., "Mutations conferring resistance to a potent hepatitis C virus serine protease inhibitor in vitro," Antimicrobial Agents and Chemotherapy (2004), 48(6), 2260-2266.

H. Hinrichsen et al., "Short-term antiviral efficacy of BILN 2061, a hepatitis C virus serine protease inhibitor, in hepatitis C genotype 1 patients," astroenterology (2004), 127(5), 1347-1355.

Ni, Zhi-Jie; Wagman, Allan S., "Progress and development of small molecule HCV antivirals," Current Opinion in Drug Discovery & Development (2004), 7(4), 446-459. (Abstract only).

Tsantrizos, Youla S., "The design of a potent inhibitor of the hepatitis C virus NS3 protease: BILN 2061—From the NMR tube to the clinic," Biopolymers (2004), 76(4), 309-323. (Abstract Only).

LaPlante, Steven R.; Llinas-Brunet, Montse, "Dynamics and structure-based design of drugs targeting the critical serine protease of the hepatitis C virus—from a peptidic substrate to BILN 2061," Current Medicinal Chemistry: Anti-Infective Agents (2005), 4(2), 111-132. (Abstract Only).

Llinas-Brunet et al., "Structure-Activity Study on a Novel Series of Macrocyclic Inhibitors fo the Hepatitis C Virus NS3 Protease Leading to the Discovery of BILN 2061," J. Med. Chem. 2004, 47, 1605-1608.

Graham R. Foster, FRCP, Ph.D., "Past, Present, and Future Hepatitis C," Seminars in Liver Disease/vol. 24, 97-104, Supplement 2, 2004.

Vittorio Farina, "Efficient Synthesis of BILN 2061, a Potent HCV Protease inhibitor, by a Convergent Approach Based on Ring-Closing Metathesis," ACS ProSpectives Conference Series, Process Chemistry in the Pharmaceutical Industry, Feb. 6-9, 2005.

Nathalie Goudreau & Montse Llinas-Brunet, "The therapeutic potential of NS3 protease inhibitors in HCV infection", Expert Opinion, 2005, pp. 1129-1144, Ashley Publications Ltd.

International Search Report for PCT/US/2005/010494.

International Search Report for PCT/US04/33970.

Notification Concerning Transmittal of Copy of International Preliminary Report on Patentability (Chapter 1 of the Patent Cooperation Treaty) for PCT/US2004/033970 (filed on Oct. 13, 2004), mailed on Apr. 27, 2006.

Thorstensson et al., "Synthesis of Novel Potent Hepatitis C Virus NS3 Protease Inhibitors. Discovery of 4-Hydroxy-cyclopent-2ene-1,2-dicarboxylic Acid as a *N*-Acyl-L-Hydroxy-proline Bioisostere" Bioorganic & Medical Chemistry (2006), doi: 10.1016/j.bmc.2006.10.044.

U.S. Appl. No. 11/773,912, filed Jul. 5, 2007, Scott et al.

Beaulieu et al., "Synthesis of (1*R*,2*S*)-1-Amino-2-vinylcyclopropanecarboxylic Acid Vinyl-ACCA) Derivatives: Key Intermediates for the Preparation of Inhibitors of the Hepatitis C Virus NS3 Protease," *J. Org. Chem.* (2005) 70(15): 5869-5879.

Belokon et al., "A General Method for the Asymmetric Synthesis of *anti*-Diastereoisomers of β-Substituted L-2-Aminobutanoic Acids via Chiral Nickel Schiff's Base Complexes of Dehydroaminobutanoic Acid. X-Ray Crystal and Molecular Structure of the Nickel Complex of the Schiff's Base from [(Benzylprolyl)amino]benzophenone and Dehydroaminobutanoic Acid", *J. Chem. Soc. Perkin Trans. 1*, (1990) 8: 2301-2310.

Franciscus, "¿Qué Hemos Aprendido sobre la Hepatitis C en la Conferencia AASLD de 2002?" *HCV Advocate* at http://www.hcvadvocate.org/pdf/AASLD_2002_sp-3.pdf, 8 pages.

Galgoci et al., "A convenient synthesis of methyl (Z)-1-carbamoyl-2-ethenylcyclopropanecarboxylate and (Z)-1-carbamoyl-2-ethenylcyclopropanecarboxylic acid," *Synth. Commun.*, (1994) 24(17):2477-2483.

Gonzalez et al., "Synthetic studies on *L*-Proline and (4*R*)-hydroxy-*L*-proline derivatives" *Synthesis* (2004) 8:1171-1182.

Goudreau et al, "The Therapeutic Potential of NS3 Protease Inhibitors in HCV Infection," *Expert Opin. Investig. Drugs* (2005) 1129-1144.

Lin et al., "Combination of a hepatitis C virus NS3-NS4A protease inhibitor and alpha interferon synergistically inhibits viral RNA replication and facilitates viral RNA clearance in replicon cells" *Antimicrobal Agents & Chemo.* (2004) 48(12): 4784-4792.

Perni et al, "Inhibitors of Hepatitis C Virus NS3-4A protease 1. Non-Charged Tetrapeptide Variants" *Bioorg. Med. Chem. Lett.* (2003) 13(22):4059-4063.

Perni et al, "Inhibitors of hepatitis C virus NS3-4A protease 2. Warhead SAR and optimization" *Bioorg. Med. Chem. Lett.* (2004) 14(6):1441-1446.

Perni et al, "Inhibitors of hepatitus C virus NS3-4A protease. Part 3. P2 proline variants" *Bioorg. Med. Chem. Lett.* (2004) 14(8):1939-1942.

Sun et al, "P4 cap modified tetrapeptidyl α-ketoamides as potent HCV NS3 protease inhibitors" *Bioorg. Med. Chem. Lett.* (2004) 14(16):4333-4338.

Sulkowski, "Orally available Hepatitis C Virus (HCV) protease inhibitor (BILN 2061) demonstrates potent anti-viral activity in persons infected with HCV genotype 1" AASLD Conference Report (2002) 1 page, Link: www.natap.org/2002/AASLD/day14.htm.

Tsantrizos et al., "Macrocyclic Inhibitors of the NS3 Protease as Potential Therapeutic Agents of Hepatitis C Virus Infection," *Angew. Chem. Int. Ed.*, (2003), 42(12):1356-1360.

International Search Report dated Aug. 29, 2005 for PCT/US04/033970 filed Oct. 13, 2004, 2 pages.

International Search Report and Written Opinion mailed May 31, 2007 for PCT/US2006/027738 filed Jul. 17, 2006, 22 pages.

International Preliminary Report on Patentability mailed Nov. 23, 2007 for PCT/US2006/027738 filed Jul. 17, 2006, 9 pages.

Office Action dated Mar. 21, 2007 for Chilean Application No. 2637-2004 filed Oct. 14, 2004, 8 pages.

Examination Report of IP Australia mailed Oct. 11, 2006 for Singapore Application No. 200602149-7 filed Oct. 13, 2004, 4 pages.

Search Report dated Nov. 21, 2007 and Documentary Conclusion dated Dec. 13, 2007 in Georgia Application No. 2005 009383 filed Oct. 13, 2004, 8 pages.

Search Report dated Sep. 19, 2007 and Documentary Conclusions dated Nov. 22, 2007 in Georgia Application No. 2005 009674 filed Mar. 29, 2005, 8 pages.

Examination Report of IP Australia mailed Oct. 26, 2007 for Singapore Application No. 200606085-9 filed Mar. 29, 2005, 10 pages.

Opposition Brief by ALAFAR filed Apr. 20, 2007 in Ecuador Patent Application No. SP-06-6959 filed Mar. 29, 2005, 14 pages.

www.medknowledge.de/neu/2002/IV-2002-32-biln-2061-pipeline.htm.

Goodman & Gilman Pharmacological Basis of Therapeutics, 9th Edition, vol. I, *McGraw-Hill*, Interamericana, Mexico (1996) p. 47, with partial translation, 2 pages.

MACROCYCLIC COMPOUNDS AS INHIBITORS OF VIRAL REPLICATION

CROSS-REFERENCE TO RELATED APPLICATIONS

This application is a continuation-in-part of U.S. patent application Ser. No. 11/064,445, filed Feb. 23, 2005, now abandoned which is a continuation of PCT/US04/33970, filed Oct. 13, 2004, which claims priority under 35 U.S.C. § 119(e) to U.S. Provisional Application No. 60/511,541, filed Oct. 14, 2003 and U.S. Provisional Application No. 60/612,460, filed Sep. 22, 2004; this application also claims priority to U.S. Provisional Application No. 60/612,381, filed Sep. 22, 2004; U.S. Provisional Application No. 60/562,418, filed Apr. 14, 2004; and U.S. Provisional Application No. 60/558,161, filed Mar. 30, 2004; all of which are incorporated herein by reference in their entireties.

BACKGROUND OF THE INVENTION

1. Field of the Invention

The present invention relates to compounds, processes for their syntheses, pharmaceutical compositions, and methods for the treatment of flaviviral infections, such as hepatitis C virus (HCV) infection. In particular, the present invention provides novel peptide analogs, pharmaceutical compositions containing such analogs and methods for using these analogs in the treatment of flaviviral infection.

2. Description of the Related Art

Hepatitis C virus (HCV) infection is the most common chronic blood borne infection in the United States. Although the numbers of new infections have declined, the burden of chronic infection is substantial, with Centers for Disease Control estimates of 3.9 million (1.8%) infected persons in the United States. Chronic liver disease is the tenth leading cause of death among adults in the United States, and accounts for approximately 25,000 deaths annually, or approximately 1% of all deaths. Studies indicate that 40% of chronic liver disease is HCV-related, resulting in an estimated 8,000-10,000 deaths each year. HCV-associated end-stage liver disease is the most frequent indication for liver transplantation among adults.

Antiviral therapy of chronic hepatitis C has evolved rapidly over the last decade, with significant improvements seen in the efficacy of treatment. Nevertheless, even with combination therapy using pegylated IFN-α plus ribavirin, 40% to 50% of patients fail therapies, i.e., are nonresponders or relapsers. These patients currently have no effective therapeutic alternative. In particular, patients who have advanced fibrosis or cirrhosis on liver biopsy are at significant risk of developing complications of advanced liver disease, including ascites, jaundice, variceal bleeding, encephalopathy, and progressive liver failure, as well as a markedly increased risk of hepatocellular carcinoma.

The high prevalence of chronic HCV infection has important public health implications for the future burden of chronic liver disease in the United States. Data derived from the National Health and Nutrition Examination Survey (NHANES III) indicate that a large increase in the rate of new HCV infections occurred from the late 1960s to the early 1980s, particularly among persons between 20 to 40 years of age. It is estimated that the number of persons with long-standing HCV infection of 20 years or longer could more than quadruple from 1990 to 2015, from 750,000 to over 3 million. The proportional increase in persons infected for 30 or 40 years would be even greater. Since the risk of HCV-related chronic liver disease is related to the duration of infection, with the risk of cirrhosis progressively increasing for persons infected for longer than 20 years, this increase in the number of persons with long-standing HCV infection could result in a substantial increase in cirrhosis-related morbidity and mortality among patients infected between the years of 1965-1985.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins of the virus. In the case of HCV, the generation of mature non-structural proteins (NS2, NS3, NS4, NS4A, NS4B, NS5A, and NS5B) is effected by two viral proteases. The first viral protease cleaves at the NS2-NS3 junction of the polyprotein. The second viral protease is serine protease contained within the N-terminal region of NS3 (herein referred to as "NS3 protease"). NS3 protease mediates all of the subsequent cleavage events at sites downstream relative to the position of NS3 in the polyprotein (i.e., sites located between the C-terminus of NS3 and the C-terminus of the polyprotein). NS3 protease exhibits activity both in cis, at the NS3-NS4 cleavage site, and in trans, for the remaining NS4A-NS4B, NS4B-NS5A, and NS5A-NS5B sites. The NS4A protein is believed to serve multiple functions, acting as a cofactor for the NS3 protease and possibly assisting in the membrane localization of NS3 and other viral replicase components. Apparently, the formation of the complex between NS3 and NS4A is necessary for NS3-mediated processing events and enhances proteolytic efficiency at all sites recognized by NS3. The NS3 protease also exhibits nucleoside triphosphatase and RNA helicase activities. NS5B is an RNA-dependent RNA polymerase involved in the replication of HCV RNA.

Literature

METAVIR (1994) *Hepatology* 20:15-20; Brunt (2000) *Hepatol.* 31:241-246; Alpini (1997) *J. Hepatol.* 27:371-380; Baroni et al. (1996) *Hepatol.* 23:1189-1199; Czaja et al. (1989) *Hepatol.* 10:795-800; Grossman et al. (1998) *J. Gastroenterol. Hepatol.* 13:1058-1060; Rockey and Chung (1994) *J. Invest. Med.* 42:660-670; Sakaida et al. (1998) *J. Hepatol.* 28:471-479; Shi et al. (1997) *Proc. Natl. Acad. Sci. USA* 94:10663-10668; Baroni et al. (1999) *Liver* 19:212-219; Lortat-Jacob et al. (1997) *J. Hepatol.* 26:894-903; Llorent et al. (1996) *J. Hepatol.* 24:555-563; U.S. Pat. No. 5,082,659; European Patent Application EP 294,160; U.S. Pat. No. 4,806,347; Balish et al. (1992) *J. Infect. Diseases* 166:1401-1403; Katayama et al. (2001) *J. Viral Hepatitis* 8:180-185; U.S. Pat. No. 5,082,659; U.S. Pat. No. 5,190,751; U.S. Pat. No. 4,806,347; Wandl et al. (1992) *Br. J. Haematol.* 81:516-519; European Patent Application No. 294,160; Canadian Patent No. 1,321,348; European Patent Application No. 276, 120; Wandl et al. (1992) *Sem. Oncol.* 19:88-94; Balish et al. (1992) *J. Infectious Diseases* 166:1401-1403; Van Dijk et al. (1994) *Int. J. Cancer* 56:262-268; Sundmacher et al. (1987) *Current Eye Res.* 6:273-276; U.S. Pat. Nos. 6,172,046; 6,245, 740; 5,824,784; 5,372,808; 5,980,884; published international patent applications WO 96/21468; WO 96/11953; WO 00/59929; WO 00/66623; WO2003/064416; WO2003/ 064455; WO2003/064456; WO 97/06804; WO 98/17679; WO 98/22496; WO 97/43310; WO 98/46597; WO 98/46630; WO 99/07733; WO 99/07734, WO 00/09543; WO 00/09558; WO 99/38888; WO 99/64442; WO 99/50230; WO 95/33764; Torre et al. (2001) *J. Med. Virol.* 64:455-459; Bekkering et al.

(2001) *J. Hepatol.* 34:435-440; Zeuzem et al. (2001) *Gastroenterol.* 120:1438-1447; Zeuzem (1999) *J. Hepatol.* 31:61-64; Keeffe and Hollinger (1997) *Hepatol.* 26:11 S-107S; Wills (1990) *Clin. Pharmacokinet.* 19:390-399; Heathcote et al. (2000) *New Engl. J. Med.* 343:1673-1680; Husa and Husova (2001) *Bratisl. Lek. Listy* 102:248-252; Glue et al. (2000) *Clin. Pharmacol.* 68:556-567; Bailon et al. (2001) *Bioconj. Chem.* 12:195-202; and Neumann et al. (2001) *Science* 282:103; Zalipsky (1995) *Adv. Drug Delivery Reviews* S. 16, 157-182; Mann et al. (2001) *Lancet* 358:958-965; Zeuzem et al. (2000) *New Engl. J. Med.* 343:1666-1672; U.S. Pat. Nos. 5,633,388; 5,866,684; 6,018,020; 5,869,253; 6,608,027; 5,985,265; 5,908,121; 6,177,074; 5,985,263; 5,711,944; 5,382,657; and 5,908,121; Osborn et al. (2002) *J. Pharmacol. Exp. Therap.* 303:540-548; Sheppard et al. (2003) *Nat. Immunol.* 4:63-68; Chang et al. (1999) *Nat. Biotechnol.* 17:793-797; Adolf (1995) *Multiple Sclerosis* 1 Suppl. 1:S44-S47; Chu et al., *Tet. Lett.* (1996), 7229-7232; Ninth Conference on Antiviral Research, Urabandai, Fukyshima, Japan (1996) (*Antiviral Research*, (1996), 30:1, A23 (abstract 19)); Steinkuhler et al., *Biochem.*, 37: 8899-8905; Ingallinella et al., *Biochem.*, 37: 8906-8914.

SUMMARY OF THE INVENTION

The embodiments provide a compound having the Formula I:

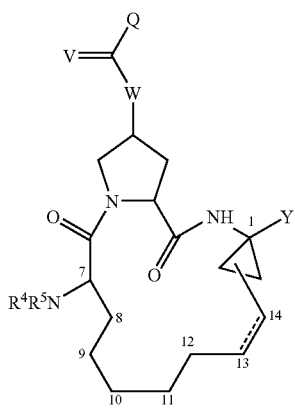

wherein:
Q is a core ring selected from:

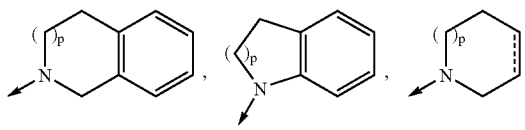

wherein the core ring can be unsubstituted or substituted with H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl, substituted $C_{1-6}$ alkyl, $C_{1-6}$ alkoxy, substituted $C_{1-6}$ alkoxy, $C_{6\ OR\ 10}$ aryl, pyridyl, pyrimidyl, thienyl, furanyl, thiazolyl, oxazolyl, phenoxy, thiophenoxy, sulphonamido, urea, thiourea, amido, keto, carboxyl, carbamyl, sulphide, sulphoxide, sulphone, amino, alkoxyamino, alkyoxyheterocyclyl, alkylamino, alkylcarboxy, carbonyl, spirocyclic cyclopropyl, spirocyclic cyclobutyl, spirocyclic cyclopentyl, or spirocyclic cyclohexyl, or Q is $R^1$-$R^2$, wherein $R^1$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; and $R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is a sulfonimide of the formula $—C(O)NHS(O)_2R^9$, where $R^9$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl, or $R^9$ is $NR^{1a}R^{1b}$ or $R^9$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^9$ is a $C_{1-6}$ alkyl optionally substituted with up to 5 fluoro groups, $NR^6R^7$, $NR^{1a}R^{1b}$, or $(CO)OH$, or $R^9$ is a heteroaromatic ring optionally substituted up to two times with halo, cyano, nitro, hydroxyl, or $C_{1-6}$ alkoxy; or Y is a carboxylic acid or pharmaceutically acceptable salt, solvate, or prodrug thereof;

wherein $R^{1a}$ and $R^{1b}$ are each independently H, $C_{1-6}$ alkyl, $C_{3-7}$ cycloalkyl, or $C_{4-10}$ alkylcycloalkyl, which are all optionally substituted from one to three times with halo, cyano, nitro, $C_{1-6}$ alkoxy, amido, or phenyl, or $R^{1a}$ and $R^{1b}$ are each independently H and $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro, or $R^{1a}$ and $R^{1b}$ are each independently H, heterocycle, which is a five-, six-, or seven-membered, saturated or unsaturated heterocyclic molecule, containing from one to four heteroatoms selected from the group consisting of nitrogen, oxygen, and sulfur, or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl, or $NR^{1a}R^{1b}$ is a heteroaryl selected from the group consisting of:

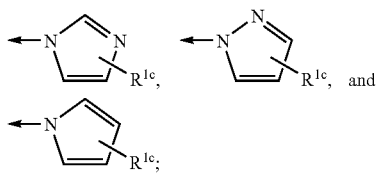

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl, or $R^{1c}$ is $NH(CO)OR^{1e}$, wherein $R^{1e}$ is $C_{1-6}$ alkyl or $C_{3-6}$ cycloalkyl;

p=0 or 1;

V is selected from O, S, or NH;

when V is O or S, W is selected from O, $NR^{15}$, or $CR^{15}$;
when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

the dashed lines represent an optional double bond;

$R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

The embodiments provide a compound having the Formula II, III, or IV:

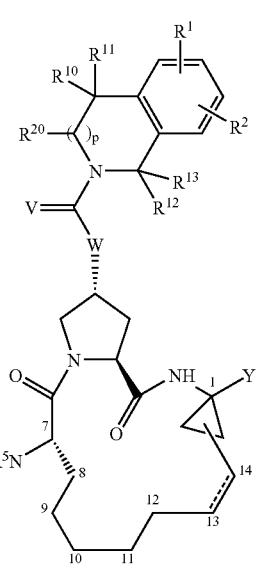

II

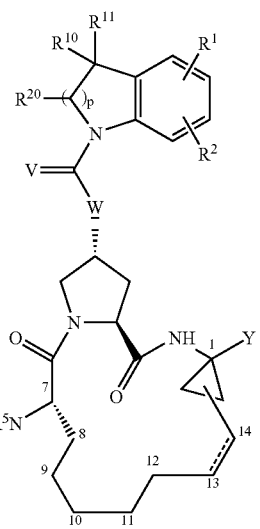

III

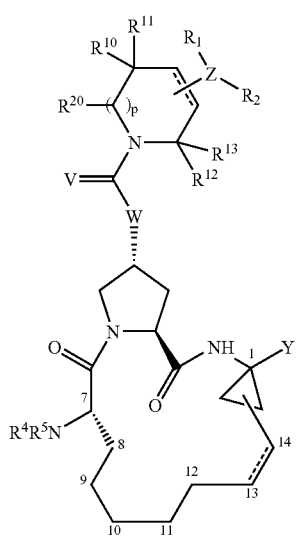

IV wherein:

a) $R^1$ and $R^2$ are each independently H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro, $C_{6\ OR\ 10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$, $NHS(O)_2R^8$, $(CH_2)_nNR^6R^7$, $O(CH_2)_nNR^6R^7$, or $O(CH_2)_nR^9$ where $R^9$ is imidazolyl or pyrazolyl; said thienyl, pyrimidyl, furanyl, thiazolyl and oxazolyl in the definition of $R^1$ and $R^2$ are optionally substituted by up to two halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, pyridyl, phenoxy and thiophenoxy in the definition of $R^1$ and $R^2$ are optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

b) m=0, 1, or 2;

c) $R^4$ is H, $C_{1-6}$ alkyl, $C_{3-7}$ cycloalkyl, $C_{4-10}$ alkylcycloalkyl phenyl or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

d) $R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

e) $R^6$ and $R^7$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

f) $R^8$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

g) Y is a sulfonimide of the formula —$C(O)NHS(O)_2R^9$, where $R^9$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl, or $R^9$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^9$ is a $C_{1-6}$ alkyl optionally substituted with up to 5 fluoro groups, $NR^6R^7$, or $(CO)OH$, or $R^9$ is a heteroaromatic ring optionally substituted up to two times with halo, cyano, nitro, hydroxyl, or $C_{1-6}$ alkoxy; or Y is a carboxylic acid or pharmaceutically acceptable salt, solvate, or prodrug thereof;

h) $R^{10}$ and $R^{11}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{10}$ and $R^{11}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{10}$ and $R^{11}$ are taken together with the carbon to which they are attached to form cyclopropyl, cyclobutyl, cyclopentyl, or cyclohexyl; or $R^{10}$ and $R^{11}$ are combined as O;

i) p=0 or 1;

j) $R^{12}$ and $R^{13}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl; or $R^{12}$ and $R^{13}$ are each independently $C_{1-6}$ alkyl optionally substituted with $(CH_2)_nOR^8$;

k) $R^{20}$ is H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, or $(CH_2)_nNR^6R^7$ $(CH_2)_nC(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro;

l) n=1-4;

m) V is selected from O, S, or NH;

n) when V is O or S, W is selected from O, $NR^{15}$, or $CR^{15}$; when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

o) the dashed line represents an optional double bond;

p) $R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6 \text{ OR } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and q) $R^{22}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

The embodiments provide a compound having the Formula XI:

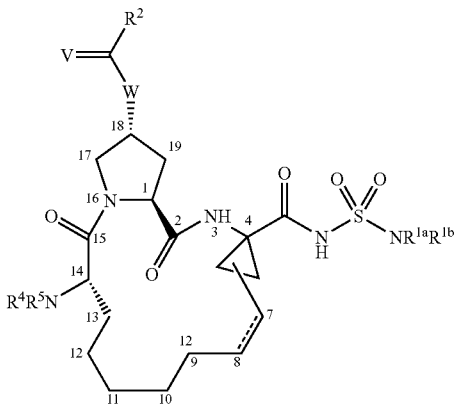

wherein:

a) $R^{1a}$ and $R^{1b}$ are each independently H, $C_{1-6}$ alkyl, $C_{3-7}$ cycloalkyl, or $C_{4-10}$ alkylcycloalkyl, which are all optionally substituted from one to three times with halo, cyano, nitro, $C_{1-6}$ alkoxy, amido, or phenyl;

or $R^{1a}$ and $R^{1b}$ are each independently H and $C_{6 \text{ OR } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

or $R^{1a}$ and $R^{1b}$ are each independently H or heterocycle, which is a five-, six-, or seven-membered, saturated or unsaturated heterocyclic molecule, containing from one to four heteroatoms selected from the group consisting of nitrogen, oxygen and sulfur;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

or $NR^{1a}R^{1b}$ is a heteroaryl selected from the group consisting of:

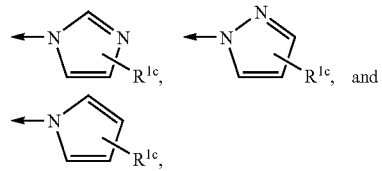

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $R^{1c}$ is $NH(CO)OR^{1e}$ wherein $R^{1e}$ is $C_{1-6}$ alkyl, or $C_{3-6}$ cycloalkyl;

b) W is O or NH;

c) V is selected from O, S, or NH;

d) when V is O or S, W is selected from O, $NR^{15}$, or $CR^{15}$; when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

e) $R^2$ is a bicyclic secondary amine with the structure of:

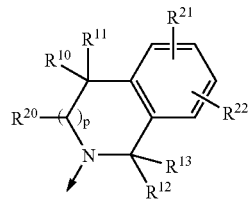

wherein $R^{21}$ and $R^{22}$ are each independently H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro, $C_{6 \text{ OR } 10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$ (m=0, 1 or 2), or $NHS(O)_2R^8$; said thienyl, pyrimidyl, furanyl, thiazolyl and oxazolyl in the definition of $R^{21}$ and $R^{22}$ are optionally substituted by up to two halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6 \text{ OR } 10}$ aryl, pyridyl, phenoxy and thiophenoxy in the definition of $R^{21}$ and $R^{22}$ are optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein $R^{10}$ and $R^{11}$ are each independently H, $C_{1-6}$ alkyl, $C_{3-7}$ cycloalkyl, $C_{4-10}$ alkylcycloalkyl, $C_{6 \text{ OR } 10}$ aryl, hydroxy-$C_{1-6}$ alkyl, $C_{1-6}$ alkyl optionally substituted with up to 5 fluoro, $(CH_2)_nNR^6R^7$, or $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6 \text{ OR } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{10}$ and $R^{11}$ are taken together with the carbon to which they are attached to form cyclopropyl, cyclobutyl, cyclopentyl, or cyclohexyl; or $R^{10}$ and $R^{11}$ are combined as O;

wherein p=0 or 1;

wherein $R^{12}$ and $R^{13}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl;

wherein $R^{20}$ is H, $C_{1-6}$ alkyl, $C_{3-7}$ cycloalkyl, $C_{4-10}$ alkylcycloalkyl, $C_6$ or 10 aryl, hydroxy-$C_{1-6}$ alkyl, $C_{1-6}$ alkyl optionally substituted with up to 5 fluoro, $(CH_2)_nNR^6R^7$ or $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein n=0-4;

wherein $R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

or $R^2$ is $R^{2a}$-$R^{2b}$ when W=NH and V=O, wherein $R^{2a}$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^{2b}$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

said $R^{2c}$ and $R^{2d}$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{2c}$ and $R^{2d}$ are taken together with the nitrogen to which they are attached to form indolinyl, pyrrolidinyl, piperidinyl, piperazinyl, or morpholinyl;

f) $R^4$ is H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

g) $R^5$ is H, $C_{1-6}$ alkyl, $C(O)NR^6R^7$, $C(S)NR^6R^7$, $C(O)R^8$, $C(O)OR^8$, or $S(O)_2R^8$;

h) $R^8$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; and i) the dashed line represents an optional double bond.

The embodiments provide a compound having the Formula XVIII:

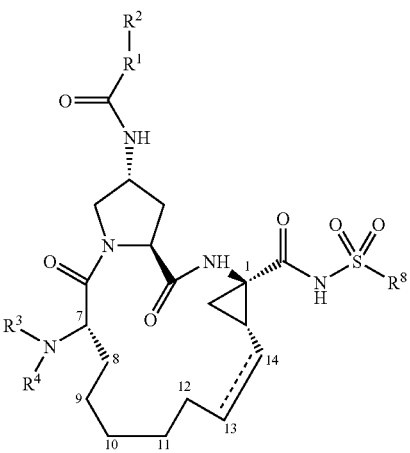

XVIII wherein a) $R^1$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^5R^6$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

b) $R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^5R^6$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

c) $R^3$ is H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

d) $R^4$ is $C_{1-6}$ alkyl, $C(O)NR^5R^6$, $C(S)NR^5R^6$, $C(O)R^7$, $C(O)OR^7$, or $S(O)_2R^7$;

e) $R^5$ and $R^6$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^5$ and $R^6$ are taken together with the nitrogen to which they are attached to form indolinyl, pyrrolidinyl, piperidinyl, piperazinyl, or morpholinyl;

f) $R^7$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^7$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

g) $R^8$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy; and h) the dashed line represents an optional double bond; or a pharmaceutically acceptable salt thereof.

The embodiments provide a compound of the formula:

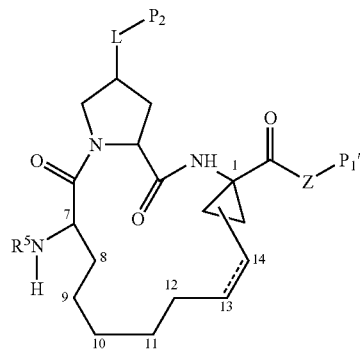

wherein:

a) Z is a group configured to hydrogen bond to an NS3 protease His57 imidazole moiety and to hydrogen bond to a NS3 protease Gly137 nitrogen atom;

b) $P_1'$ is a group configured to form a non-polar interaction with at least one NS3 protease S1' pocket moiety selected from the group consisting of Lys136, Gly137, Ser139, His57, Gly58, Gln41, Ser42, and Phe43;

c) L is a linker group consisting of from 1 to 5 atoms selected from the group consisting of carbon, oxygen, nitrogen, hydrogen, and sulfur;

d) P2 is selected from the group consisting of unsubstituted aryl, substituted aryl, unsubstituted heteroaryl, substituted heteroaryl, unsubstituted heterocyclic and substituted heterocyclic; P2 being positioned by L to form a non-polar interaction with at least one NS3 protease S2 pocket moiety selected from the group consisting of His57, Arg155, Val78, Asp79, Gln80 and Asp81;

e) the dashed line represents an optional double bond;

f) $R^5$ is selected from the group consisting of H, $C(O)NR^6R^7$ and $C(O)OR^8$;

g) $R^6$ and $R^7$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl; and h) $R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring.

The embodiments provide a compound having the formula:

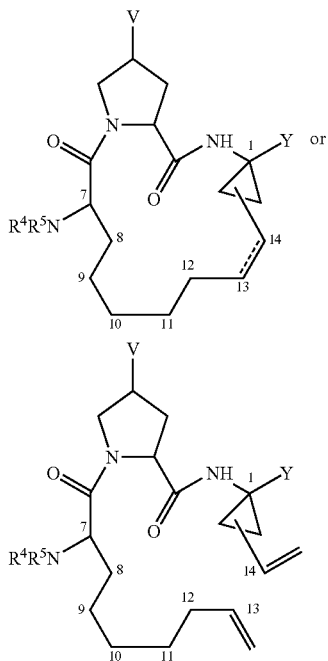

wherein:

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is a sulfonimide of the formula —$C(O)NHS(O)_2R^9$, where $R^9$ is $C_{1-3}$ alkyl, $C_{3-7}$ cycloalkyl, or phenyl which is optionally substituted by up to two halo, cyano, nitro, hydroxy, $C_{1-3}$ alkyl, $C_{3-7}$ cycloalkyl, or $C_{1-3}$ alkoxy, or Y is a carboxylic acid V is selected from OH, SH, or $NH_2$;

the dashed line represents an optional double bond;

$R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

The embodiments provide a compound having the formula:

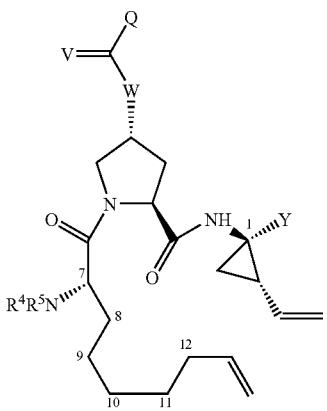

wherein:

Q is a core ring selected from:

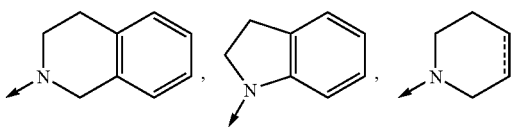

wherein the core ring can be unsubstituted or substituted H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl, substituted $C_{1-6}$ alkyl, $C_{1-6}$ alkoxy, substituted $C_{1-6}$ alkoxy, $C_{6\ or\ 10}$ aryl, pyridyl, pyrimidyl, thienyl, furanyl, thiazolyl, oxazolyl, phenoxy, thiophenoxy, sulphonamido, urea, thiourea, amido, keto, carboxyl, carbamyl, sulphide, sulphoxide, sulphone, amino, alkoxyamino, alkyoxyheterocyclyl, alkylamino, alkylcarboxy, carbonyl, spirocyclic cyclopropyl, spirocyclic cyclobutyl, spirocyclic cyclopentyl, or spirocyclic cyclohexyl, or Q is $R^1$-$R^2$, wherein $R^1$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; and $R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6 \ OR \ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is $COOR^9$, wherein $R^9$ is $C_{1-6}$ alkyl; or Y is a sulfonimide of the formula —$C(O)NHS(O)_2R^9$, where $R^9$ is $C_{1-3}$ alkyl, $C_{3-7}$ cycloalkyl, or phenyl which is optionally substituted by up to two halo, cyano, nitro, hydroxy, $C_{1-3}$ alkyl, $C_{3-7}$ cycloalkyl, or $C_{1-3}$ alkoxy, or Y is a carboxylic acid V and W are each individually selected from O, S, or NH; the dashed line represents an optional double bond;

$R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6 \ OR \ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

The embodiments provide pharmaceutical compositions comprising preferred compounds and pharmaceutically acceptable carriers.

The embodiments provide a method of treating a hepatitis C virus infection in an individual, the method comprising administering to the individual an effective amount of the preferred compounds.

The embodiments provide a method of treating liver fibrosis in an individual, the method comprising administering to the individual an effective amount of the preferred compounds.

The embodiments provide a method of increasing liver function in an individual having a hepatitis C virus infection, the method comprising administering to the individual an effective amount of the preferred compounds.

The chemical formulas representing the compounds described herein also represent pharmaceutically acceptable salts, solvates, esters, and prodrug derivatives thereof.

DETAILED DESCRIPTION OF THE PREFERRED EMBODIMENT

Definitions

As used herein, the term "hepatic fibrosis," used interchangeably herein with "liver fibrosis," refers to the growth of scar tissue in the liver that may occur in the context of a chronic hepatitis infection.

The terms "individual," "host," "subject," and "patient" are used interchangeably herein, and refer to a mammal, including, but not limited to, primates, including simians and humans.

As used herein, the term "liver function" refers to a normal function of the liver, including, but not limited to, a synthetic function, including, but not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

As used herein, the terms "HCV NS3 protease inhibitor" and "NS3 protease inhibitor" refer to any agent that inhibits the protease activity of HCV NS3/NS4A complex. Unless specifically stated otherwise, the term "NS3 inhibitor" is used interchangeably with the terms "HCV NS3 protease inhibitor" and "NS3 protease inhibitor."

As used herein, the term "polyol" or "poly-ol" denotes a hydrocarbon including at least two hydroxyls bonded to carbon atoms, and includes sugars (reducing and nonreducing sugars), sugar alcohols and sugar acids. Polyols may include other functional groups. Examples of polyols include sugar alcohols such as mannitol and trehalose, and polyethers. A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols.

As to sugar acids, these include L-gluconate and metallic salts thereof.

The term "polyether" as used herein denotes a hydrocarbon containing at least three ether bonds. Polyethers may include other functional groups. Polyethers include polyethylene glycol (PEG).

The term "sustained viral response" (SVR; also referred to as a "sustained response" or a "durable response"), as used herein, refers to the response of an individual to a treatment regimen for HCV infection, in terms of serum HCV titer. Generally, a "sustained viral response" refers to no detectable HCV RNA (e.g., less than about 500, less than about 200, or less than about 100 genome copies per milliliter serum) found in the patient's serum for a period of at least about one month, at least about two months, at least about three months, at least about four months, at least about five months, or at least about six months following cessation of treatment.

"Treatment failure patients" as used herein generally refers to HCV-infected patients who failed to respond to previous therapy for HCV (referred to as "non—responders") or who initially responded to previous therapy, but in whom the therapeutic response was not maintained (referred to as "relapsers"). The previous therapy generally may include treatment with IFN-α monotherapy or IFN-α combination therapy, where the combination therapy may include administration of IFN-α and an antiviral agent such as ribavirin.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, murines, simians, humans, mammalian farm animals, mammalian sport animals, and mammalian pets.

As used herein, the term "pirfenidone" refers to 5-methyl-1-phenyl-2-(1H)-pyridone. As used herein, the term "pirfenidone analog" refers to any compound of Formula I, IIA or IIB in the section entitled "Pirfenidone and Analogs Thereof" below. A "specific pirfenidone analog," and all grammatical variants thereof, refers to, and is limited to, each and every pirfenidone analog shown in Table 1 in the section entitled "Pirfenidone and Analogs Thereof" below.

As used herein, the term "a Type I interferon receptor agonist" refers to any naturally occurring or non-naturally occurring ligand of human Type I interferon receptor, which binds to and causes signal transduction via the receptor. Type I interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

As used herein, the term "Type II interferon receptor agonist" refers to any naturally occurring or non-naturally occurring ligand of human Type II interferon receptor that binds to and causes signal transduction via the receptor. Type II interferon receptor agonists include native human interferon-γ, recombinant IFN-γ species, glycosylated IFN-γ species, pegylated IFN-γ species, modified or variant IFN-γ species, IFN-γ fusion proteins, antibody agonists specific for the receptor, non-peptide agonists, and the like.

As used herein, the term "a Type III interferon receptor agonist" refers to any naturally occurring or non-naturally occurring ligand of humanIL-28 receptor α ("IL-28R"), the amino acid sequence of which is described by Sheppard, et al., infra., that binds to and causes signal transduction via the receptor.

As used herein, the term "interferon receptor agonist" refers to any Type I interferon receptor agonist, Type II interferon receptor agonist, or Type III interferon receptor agonist.

The term "dosing event" as used herein refers to administration of an antiviral agent to a patient in need thereof, which event may encompass one or more releases of an antiviral agent from a drug dispensing device. Thus, the term "dosing event," as used herein, includes, but is not limited to, installation of a continuous delivery device (e.g., a pump or other controlled release injectable system); and a single subcutaneous injection followed by installation of a continuous delivery system.

"Continuous delivery" as used herein (e.g., in the context of "continuous delivery of a substance to a tissue") is meant to refer to movement of drug to a delivery site, e.g., into a tissue in a fashion that provides for delivery of a desired amount of substance into the tissue over a selected period of time, where about the same quantity of drug is received by the patient each minute during the selected period of time.

"Controlled release" as used herein (e.g., in the context of "controlled drug release") is meant to encompass release of substance (e.g., a Type I or Type III interferon receptor agonist, e.g., IFN-α) at a selected or otherwise controllable rate, interval, and/or amount, which is not substantially influenced by the environment of use. "Controlled release" thus encompasses, but is not necessarily limited to, substantially continuous delivery, and patterned delivery (e.g., intermittent delivery over a period of time that is interrupted by regular or irregular time intervals).

"Patterned" or "temporal" as used in the context of drug delivery is meant to encompass delivery of drug in a pattern, generally a substantially regular pattern, over a pre-selected period of time (e.g., other than a period associated with, for example a bolus injection). "Patterned" or "temporal" drug delivery is meant to encompass delivery of drug at an increasing, decreasing, substantially constant, or pulsatile, rate or range of rates (e.g., amount of drug per unit time, or volume of drug formulation for a unit time), and further encompasses delivery that is continuous or substantially continuous, or chronic.

The term "controlled drug delivery device" is meant to encompass any device wherein the release (e.g., rate, timing of release) of a drug or other desired substance contained therein is controlled by or determined by the device itself and not substantially influenced by the environment of use, or releasing at a rate that is reproducible within the environment of use.

By "substantially continuous" as used in, for example, the context of "substantially continuous infusion" or "substantially continuous delivery" is meant to refer to delivery of drug in a manner that is substantially uninterrupted for a pre-selected period of drug delivery, where the quantity of drug received by the patient during any 8 hour interval in the pre-selected period never falls to zero. Furthermore, "substantially continuous" drug delivery may also encompass delivery of drug at a substantially constant, pre-selected rate or range of rates (e.g., amount of drug per unit time, or volume of drug formulation for a unit time) that is substantially uninterrupted for a pre-selected period of drug delivery.

By "substantially steady state" as used in the context of a biological parameter that may vary as a function of time, it is meant that the biological parameter exhibits a substantially constant value over a time course, such that the area under the curve defined by the value of the biological parameter as a function of time for any 8 hour period during the time course (AUC8 hr) is no more than about 20% above or about 20% below, and preferably no more than about 15% above or about 15% below, and more preferably no more than about 10% above or about 10% below, the average area under the curve of the biological parameter over an 8 hour period during the time course (AUC8 hr average). The AUC8 hr average is defined as the quotient (q) of the area under the curve of the biological parameter over the entirety of the time course (AUCtotal) divided by the number of 8 hour intervals in the time course (total/3 days), i.e., q=(AUCtotal)/(total/3 days). For example, in the context of a serum concentration of a drug, the serum concentration of the drug is maintained at a substantially steady state during a time course when the area under the curve of serum concentration of the drug over time for any 8 hour period during the time course (AUC8 hr) is no more than about 20% above or about 20% below the average area under the curve of serum concentration of the drug over an 8 hour period in the time course (AUC8 hr average), i.e., the AUC8 hr is no more than 20% above or 20% below the AUC8 hr average for the serum concentration of the drug over the time course.

As used herein, "hydrogen bond" refers to an attractive force between an electronegative atom (such as oxygen, nitrogen, sulfur or halogen) and a hydrogen atom which is linked covalently to another electronegative atom (such as oxygen, nitrogen, sulfur or halogen). See, e.g., Stryer et. al. "Biochemistry", Fifth Edition 2002, Freeman & Co. N.Y. Typically, the hydrogen bond is between a hydrogen atom and two unshared electrons of another atom. A hydrogen bond between hydrogen and an electronegative atom not covalently bound to the hydrogen may be present when the hydrogen atom is at a distance of about 2.5 angstroms to about 3.8 angstroms from the not-covalently bound electronegative atom, and the angle formed by the three atoms (electronegative atom covalently bound to hydrogen, hydrogen, and electronegative atom not-covalently bound electronegative atom) deviates from 180 degrees by about 45 degrees or less. The distance between the hydrogen atom and the not-covalently bound electronegative atom may be referred to herein as the "hydrogen bond length," and the angle formed by the three atoms (electronegative atom covalently bound to hydrogen, hydrogen, and electronegative atom not-covalently bound electronegative atom) may be referred to herein as the "hydrogen bond angle." In some instances, stronger hydrogen bonds are formed when the hydrogen bond length is shorter; thus, in some instances, hydrogen bond lengths may range from about 2.7 angstroms to about 3.6 angstroms, or about 2.9 angstroms to about 3.4 angstroms. In some instances, stronger hydrogen bonds are formed when the hydrogen bond angle is closer to being linear; thus, in some instances, hydrogen bond angles may deviate from 180 degrees by about 25 degrees or less, or by about 10 degrees or less.

As used herein, "non-polar interaction" refers to proximity of non-polar molecules or moieties, or proximity of molecules or moieties with low polarity, sufficient for van der Waals interaction between the moieties and/or sufficient to exclude polar solvent molecules such as water molecules. See, e.g., Stryer et. al. "Biochemistry", Fifth Edition 2002, Freeman & Co. N.Y. Typically, the distance between atoms (excluding hydrogen atoms) of non-polar interacting moieties may range from about 2.9 angstroms to about 6 angstroms. In some instances, the space separating non-polar interacting moieties is less than the space that would accommodate a water molecule. As used herein a non-polar moiety or moiety with low polarity refers to moieties with low dipolar moments (typically dipolar moments less than the dipolar moment of O—H bonds of $H_2O$ and N—H bonds of $NH_3$) and/or moieties that are not typically present in hydrogen bonding or electrostatic interactions. Exemplary moieties with low polarity are alkyl, alkenyl, and unsubstituted aryl moieties.

As used herein, an NS3 protease S1'pocket moiety refers to a moiety of the NS3 protease that interacts with the amino acid positioned one residue C-terminal to the cleavage site of the substrate polypeptide cleaved by NS3 protease (e.g., the NS3 protease moieties that interact with amino acid S in the polypeptide substrate DLEVVT-STWVLV). Exemplary moieties include, but are not limited to, atoms of the peptide backbone or side chains of amino acids Lys136, Gly137, Ser139, His57, Gly58, Gln41, Ser42, and Phe43, see Yao. et. al., Structure 1999, 7, 1353.

As used herein, an NS3 protease S2 pocket moiety refers to a moiety of the NS3 protease that interacts with the amino acid positioned two residues N-terminal to the cleavage site of the substrate polypeptide cleaved by NS3 protease (e.g., the NS3 protease moieties that interact with amino acid V in the polypeptide substrate DLEVVT-STWVLV). Exemplary moieties include, but are not limited to, atoms of the peptide backbone or side chains of amino acids His57, Arg155, Val78, Asp79, Gln80 and Asp81, see Yao. et. al., Structure 1999, 7, 1353.

As used herein, a first moiety "positioned by" a second moiety refers to the spatial orientation of a first moiety as determined by the properties of a second moiety to which the first atom or moiety is covalently bound. For example, a phenyl carbon may position an oxygen atom bonded to the phenyl carbon in a spatial position such that the oxygen atom hydrogen bonds with a hydroxyl moiety in an NS3 active site.

Before the embodiments are further described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The embodiments provide compounds of Formulas I-XIX, as well as pharmaceutical compositions and formulations comprising any compound of Formulas I-XIX. A subject compound is useful for treating flaviviral infection, such as HCV infection and other disorders, as discussed below.

Compositions

Various embodiments of compositions are described below. For ease of discussion, the description of these embodiments is divided into Sections A, B, C, D and E. Various terms that may be defined within a particular Section are understood to apply within that Section, and also to apply elsewhere herein when reference to that particular Section is made. Likewise, any references within a Section to a particular number or label should be understood in the context of the corresponding numbering or labeling scheme used within that Section, rather than in the context of a possibly similar or identical numbering or labeling scheme used in an unrelated section, unless otherwise indicated.

Section A

Section A embodiments provide compounds having the general Formula I:

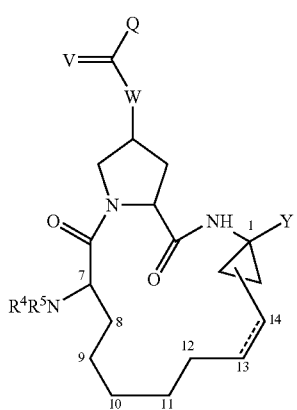

I wherein:
Q is a core ring selected from:

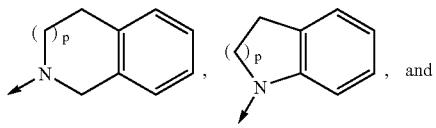

-continued

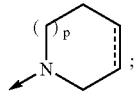

wherein the core ring can be unsubstituted or substituted with H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl, substituted $C_{1-6}$ alkyl, $C_{1-6}$ alkoxy, substituted $C_{1-6}$ alkoxy, $C_{6\,OR\,10}$ aryl, pyridyl, pyrimidyl, thienyl, furanyl, thiazolyl, oxazolyl, phenoxy, thiophenoxy, sulphonamido, urea, thiourea, amido, keto, carboxyl, carbamyl, sulphide, sulphoxide, sulphone, amino, alkoxyamino, alkyoxyheterocyclyl, alkylamino, alkylcarboxy, carbonyl, spirocyclic cyclopropyl, spirocyclic cyclobutyl, spirocyclic cyclopentyl, or spirocyclic cyclohexyl, or Q is $R^1$-$R^2$, wherein $R^1$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, or $C_{1-6}$ alkoxy optionally substituted with up to 5 fluoro; and $R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6\,OR\,10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is a sulfonimide of the formula —C(O)NHS(O)$_2R^9$, where $R^9$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl, or $R^9$ is $NR^{1a}R^{1b}$ or $R^9$ is $C_{6 \text{ OR } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^9$ is a $C_{1-6}$ alkyl optionally substituted with up to 5 fluoro groups, $NR^6R^7$, $NR^{1a}R^{1b}$, or (CO)OH, or $R^9$ is a heteroaromatic ring optionally substituted up to two times with halo, cyano, nitro, hydroxyl, or $C_{1-6}$ alkoxy; or Y is a carboxylic acid or pharmaceutically acceptable salt, solvate, or prodrug thereof;

wherein $R^{1a}$ and $R^{1b}$ are each independently H, $C_{1-6}$ alkyl, $C_{3-7}$ cycloalkyl, or $C_{4-10}$ alkylcycloalkyl, which are all optionally substituted from one to three times with halo, cyano, nitro, $C_{1-6}$ alkoxy, amido, or phenyl, or $R^{1a}$ and $R^{1b}$ are each independently H and $C_{6 \text{ OR } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro, or $R^{1a}$ and $R^{1b}$ are each independently H, heterocycle, which is a five-, six-, or seven-membered, saturated or unsaturated heterocyclic molecule, containing from one to four heteroatoms selected from the group consisting of nitrogen, oxygen, and sulfur, or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl, or $NR^{1a}R^{1b}$ is a heteroaryl selected from the group consisting of:

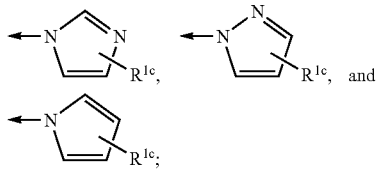

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl, or $R^{1c}$ is $NH(CO)OR^{1e}$, wherein $R^{1e}$ is $C_{1-6}$ alkyl or $C_{3-6}$ cycloalkyl;

p=0 or 1;

V is selected from O, S, or NH;

when V is O or S, W is selected from O, $NR^{15}$, or $CR^{15}$;

when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

the dashed lines represent an optional double bond;

$R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6 \text{ OR } 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

In preferred embodiments, Section A embodiments provide compounds having the general Formula I, in which the core ring is

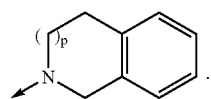

In preferred embodiments, Section A embodiments provide compounds having the general Formula I, in which the core ring is

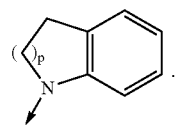

In preferred embodiments, Section A embodiments provide compounds having the general Formula I, in which the core ring is

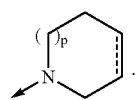

In preferred embodiments, Section A embodiments provide compounds having the general Formula Ia:

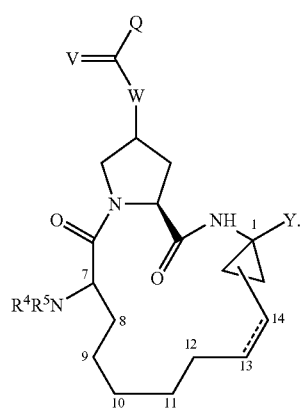

Ia

In preferred embodiments, Section A embodiments provide compounds having the general Formula Ib:

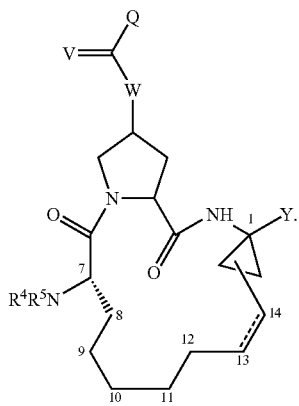

Ib

In preferred embodiments, Section A embodiments provide compounds having the general Formula Ic:

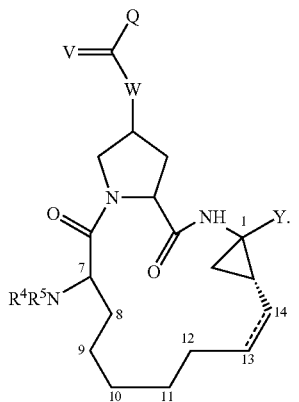

Ic

In preferred embodiments, Section A embodiments provide compounds having the general Formula Id:

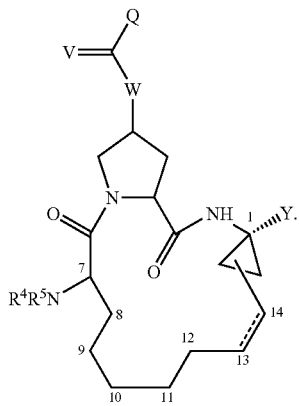

Id

In preferred embodiments, Section A embodiments provide compounds having the general Formula Ie:

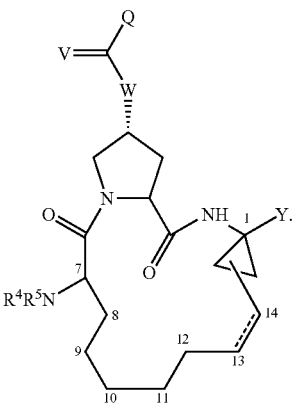

Ie

In preferred embodiments, Section A embodiments provide compounds having the general Formula If:

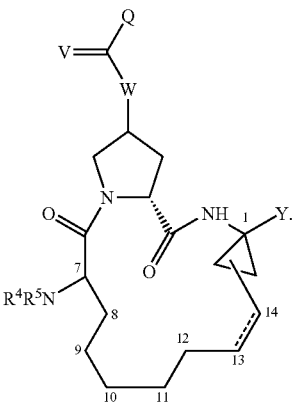

If

In preferred embodiments, Section A embodiments provide compounds having the general Formula Ig:

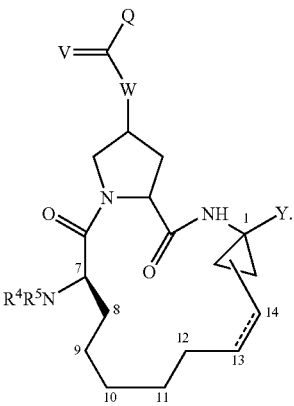

Ig

In preferred embodiments, Section A embodiments provide compounds having the general Formula Ih:

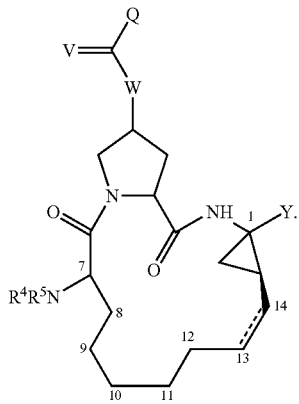

Ih

In preferred embodiments, Section A embodiments provide compounds having the general Formula II:

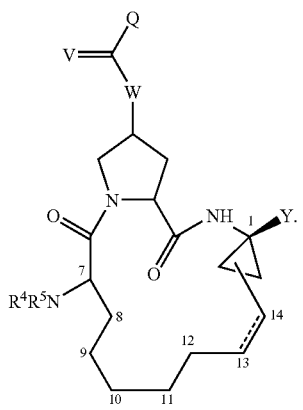

Ii

In preferred embodiments, Section A embodiments provide compounds having the general Formula Ij:

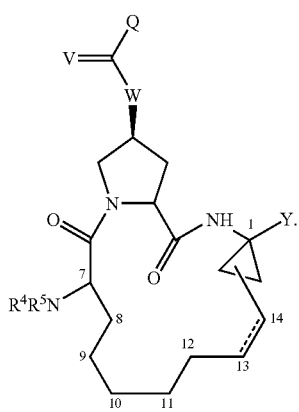

Ij

In preferred embodiments, Section A embodiments provide compounds having the general Formula Iz:

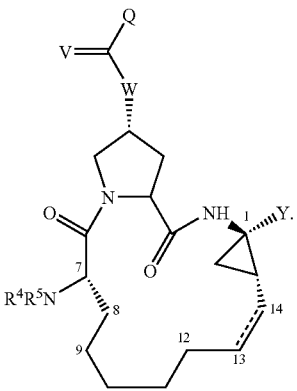

Iz

In preferred embodiments, Section A embodiments provide compounds having the general Formula I, in which Y is sulfonimide of the formula —C(O)NHS(O)$_2$R$^9$, where R$^9$ is selected from the group consisting of C$_{1-6}$ alkyl, C$_{3-7}$ cycloalkyl, C$_{4-10}$ alkylcycloalkyl, and NR$^{1a}$R$^{1b}$, wherein R$^{1a}$ and R$^{1b}$ are each independently H, C$_{1-6}$ alkyl, or C$_{3-7}$ cycloalkyl.

In preferred embodiments, Section A embodiments provide compounds having the general Formula I, in which the C13-C14 double bond is cis.

In preferred embodiments, Section A embodiments provide compounds having the general Formula I, in which the C13-C14 double bond is trans.

In certain embodiments, the compounds of general Formula I do not include the compounds disclosed in PCT/US04/33970. For example, in certain embodiments, the compounds of general Formula I do not include the compounds of Formulas II, III, and IV in Section B below.

Section B

Section B embodiments provide compounds having the general Formulas II, III, and IV:

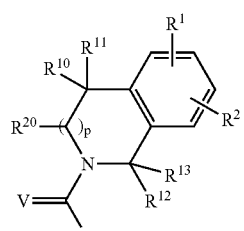

II

-continued

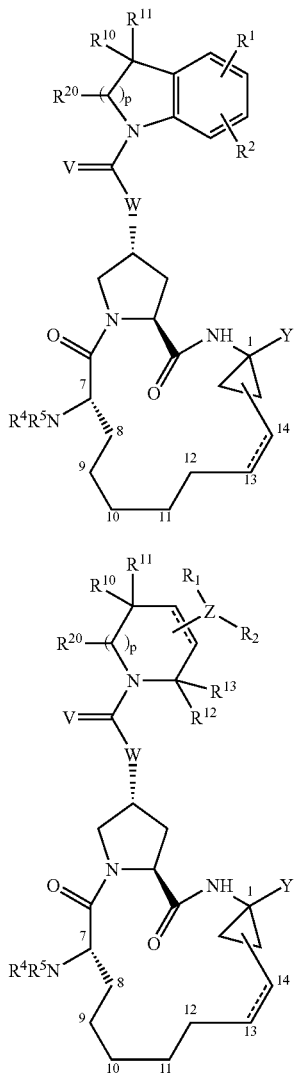

wherein:

R¹ and R² are each independently H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro, $C_{6\ OR\ 10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$, $NHS(O)_2R^8$, $(CH_2)_nNR^6R^7$, $O(CH_2)_nNR^6R^7$, or $O(CH_2)_nR^9$ where $R^9$ is imidazolyl or pyrazolyl; said thienyl, pyrimidyl, furanyl, thiazolyl and oxazolyl in the definition of R¹ and R² are optionally substituted by up to two halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, pyridyl, phenoxy and thiophenoxy in the definition of R¹ and R² are optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

m=0, 1, or 2;

R⁴ is H, $C_{1-6}$ alkyl, $C_{3-7}$ cycloalkyl, $C_{4-10}$ alkylcycloalkyl phenyl or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

R⁵ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

R⁶ and R⁷ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, or $C_{1-6}$ alkyl optionally substituted with up to 5 fluoro, $C_{1-6}$ alkoxy optionally substituted with up to 5 fluoro; or R⁶ and R⁷ are taken together with the nitrogen to which they are attached to form indolinyl, pyrrolidinyl, piperidinyl, piperazinyl, or morpholinyl;

R⁸ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or R⁸ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or R⁸ is $C_{1-6}$ alkyl optionally substituted with up to 5 fluoro groups; or R⁸ is a tetrahydrofuran ring linked through the $C_3$ or $C_4$ position of the tetrahydrofuran ring; or R⁸ is a tetrahydropyranyl ring linked through the $C_4$ position of the tetrahydropyranyl ring;

Y is a sulfonimide of the formula $—C(O)NHS(O)_2R^9$, where R⁹ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl, or R⁹ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; or R⁹ is a $C_{1-6}$ alkyl optionally substituted with up to 5 fluoro groups, $NR^6R^7$, or $(CO)OH$, or R⁹ is a heteroaromatic ring optionally substituted up to two times with halo, cyano, nitro, hydroxyl, or $C_{1-6}$ alkoxy; or Y is a carboxylic acid or pharmaceutically acceptable salt, solvate, or prodrug thereof;

R¹⁰ and R¹¹ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where R¹⁴ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or R¹⁴ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of R¹⁰ and R¹¹ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or R¹⁰ and R¹¹ are taken together with the carbon to which they are attached to form cyclopropyl, cyclobutyl, cyclopentyl, or cyclohexyl; or $R^{10}$ and $R^{11}$ are combined as O;

p=0 or 1;

$R^{12}$ and $R^{13}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl; or $R^{12}$ and $R^{13}$ are each independently $C_{1-6}$ alkyl optionally substituted with $(CH_2)_nOR^8$;

$R^{20}$ is H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, or $(CH_2)_nNR^6R^7$, $(CH_2)_nC(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro;

n=1-4;

V is selected from O, S, or NH;

when V is O or S, W is selected from O, $NR^{15}$, or $CR^{15}$; when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

the dashed line represents an optional double bond;

$R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

Section B embodiments provide compounds having the general Formula II,

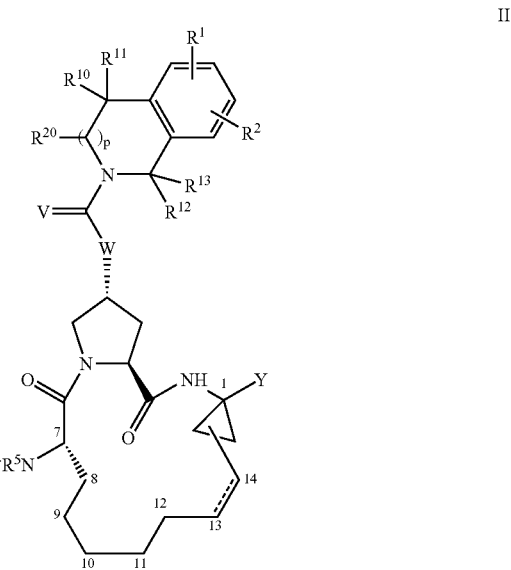

II wherein:

$R^1$ is H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^2$ is H, $O(CH_2)_nNR^6R^7$, $O(CH_2)_nR^{16}$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $R^6$ and $R^7$ in the definition of $R^2$ being each independently H, $C_{1-6}$ alkyl, $C_{3-7}$ cycloalkyl, or $C_{4-10}$ alkylcycloalkyl; or said $R^6$ and $R^7$ in the definition of $R^2$ taken together with the nitrogen to which they are attached form indolinyl, pyrrolidinyl, piperidinyl, piperazinyl, or morpholinyl;

n=1-3;

$R^4$=H;

$R^5$ is H, $C(O)NR^6R^7$ or $C(O)OR^8$, said $R^6$ and $R^7$ in the definition of $R^5$ being each independently H, $C_{1-6}$ alkyl, $C_{3-7}$ cycloalkyl, or $C_{4-10}$ alkylcycloalkyl;

$R^8$ is $C_{1-6}$ alkyl, $C_{3-7}$ cycloalkyl, or $C_{4-10}$ alkylcycloalkyl, all of which are optionally substituted from one to three times with halo, cyano, nitro, hydroxy, $C_{1-6}$ alkoxy, or phenyl; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is a sulfonimide of the formula —$C(O)NHS(O)_2R^9$, where $R^9$ is $C_{1-6}$ alkyl, $C_{3-7}$ cycloalkyl, or $C_{4-10}$ alkylcycloalkyl, all of which are optionally substituted from one to three times with halo, $C_{1-6}$ alkoxy, or phenyl;

$R^{10}$, $R^{11}$, $R^{12}$ and $R^{13}$ are H;

p=0 or 1;

V=O; and

W is selected from O, NH, or $CH_2$.

In preferred embodiments, Section B embodiments provide compounds having the general Formulas II, III, and IV, in which p may be 0. In preferred embodiments, Section B embodiments provide compounds having the general Formulas II, III, and IV, in which p may be 1.

In preferred embodiments, Section B embodiments provide compounds having the general Formulas II, III, and IV, in which either or both of $R^1$ and $R^2$ are H. In some embodiments, p is 0. In other embodiments p is 1.

In preferred embodiments, Section B embodiments provide compounds having the general Formulas II, III, and IV, in which neither $R^1$ nor $R^2$ is H. In some embodiments, p is 0. In other embodiments, p is 1.

In preferred embodiments, Section B embodiments provide compounds having the general Formulas II, III, and IV, in which $R^2$ is $O(CH_2)_nNR^6R^7$ or $O(CH_2)_nR^{16}$.

In preferred embodiments, Section B embodiments provide compounds having the general Formulas II, III, and IV in which $R^9$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl.

In preferred embodiments, Section B embodiments provide compounds having the general Formulas II, III, and IV in which $R^9$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro.

In preferred embodiments, Section B embodiments provide compounds having the general Formulas II, III, and IV in which $R^9$ is a heteroaromatic ring optionally substituted up to two times with halo, cyano, nitro, hydroxyl, or $C_{1-6}$ alkoxy.

In preferred embodiments, Section B embodiments provide compounds having the general Formulas II, III, and IV in which $R^9$ is a $C_{1-6}$ alkyl optionally substituted with up to 5 fluoro groups, $NR^6R^7$, or (CO)OH.

In preferred embodiments, Section B embodiments provide compounds having the general Formulas II, III, and IV in which the dashed line in Formula (II), (III), or (IV) represents a single bond.

Section B embodiments provide compounds having the general Formula II:

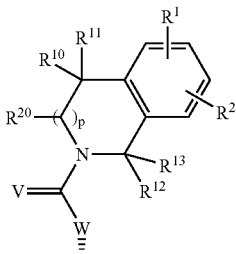

II

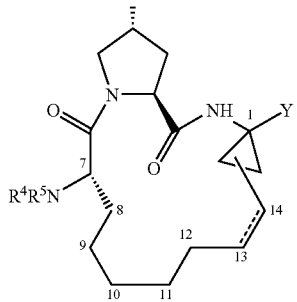

wherein:

$R^1$ and $R^2$ are each independently H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro, $C_{6\ OR\ 10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$, $NHS(O)_2R^8$, $O(CH_2)_nNR^6R^7$, or $O(CH_2)_nR^{16}$ where $R^{16}$ is imidazolyl or pyrazolyl; said thienyl, pyrimidyl, furanyl, thiazolyl and oxazolyl in the definition of $R^1$ and $R^2$ are optionally substituted by up to two halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ OR\ 10}$ aryl, pyridyl, phenoxy, and thiophenoxy in the definition of $R^1$ and $R^2$ are optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

m=0, 1, or 2;

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is a sulfonimide of the formula $—C(O)NHS(O)_2R^9$, where $R^9$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl, or $R^9$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro, or $R^9$ is a $C_{1-6}$ alkyl optionally substituted with up to 5 fluoro groups, $NR^6R^7$, or (CO)OH, or $R^9$ is a heteroaromatic ring optionally substituted up to two times with halo, cyano, nitro, hydroxyl, or $C_{1-6}$ alkoxy; or Y is a carboxylic acid or pharmaceutically acceptable salt, solvate, or prodrug thereof;

$R^{10}$ and $R^{11}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_n NR^6 R^7$, or $(CH_2)_n C(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{10}$ and $R^{11}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{10}$ and $R^{11}$ are taken together with the carbon to which they are attached to form cyclopropyl, cyclobutyl, cyclopentyl, or cyclohexyl; or $R^{10}$ and $R^{11}$ are combined as O;

p=0 or 1;

$R^{12}$ and $R^{13}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_n NR^6 R^7$, or $(CH_2)_n C(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl, or $R^{12}$ and $R^{13}$ are each independently $C_{1-6}$ alkyl optionally substituted with $(CH_2)_n OR^8$;

$R^{20}$ is H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_n NR^6 R^7$, or $(CH_2)_n C(O)OR^4$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

n=0-4;

V is selected from O, S, or NH;

when V is O or S, W is selected from O, $NR^{15}$, or $CR^{15}$; when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

the dashed line represents an optional double bond;

$R^{21}$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

Section B embodiments provide compounds having the general Formula IIa:

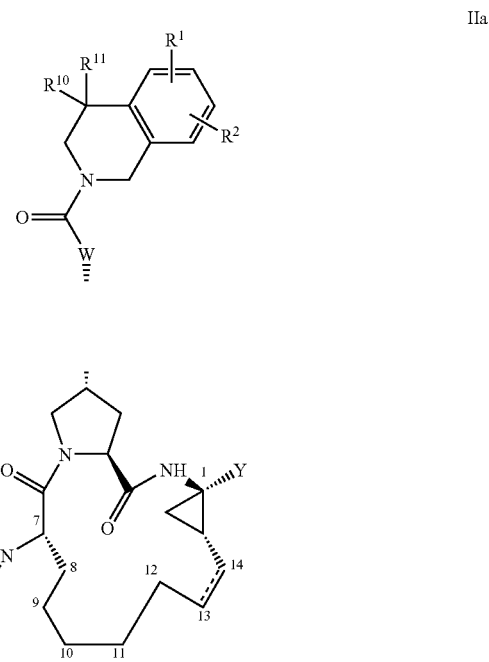

IIa wherein:

$R^1$ and $R^2$ are each independently H, halo, cyano, hydroxy, $C_{1-3}$ alkyl, or $C_{1-3}$ alkoxy;

$R^5$ is H, $C(O)NR^6 R^7$, $C(O)R^8$, or $C(O)OR^8$;

$R^6$ and $R^7$ are each independently H, $C_{1-6}$ alkyl, $C_{3-7}$ cycloalkyl, $C_{4-10}$ alkylcycloalkyl, or phenyl;

$R^8$ is $C_{1-6}$ alkyl, $C_{3-7}$ cycloalkyl, $C_{4-10}$ alkylcycloalkyl, or 3-tetrahydrofuryl. Y is a sulfonimide of the formula —C(O)NHS(O)$_2$R$^9$, where R$^9$ is $C_{1-3}$ alkyl, $C_{3-7}$ cycloalkyl, or phenyl which is optionally substituted by up to two halo, cyano, nitro, hydroxy, $C_{1-3}$ alkyl, $C_{3-7}$ cycloalkyl, or $C_{1-3}$ alkoxy, or Y is a carboxylic acid or pharmaceutically acceptable salt, solvate, or prodrug thereof;

$R^{10}$ and $R^{11}$ are each independently H or $C_{1-3}$ alkyl, or $R^{10}$ and $R^{11}$ are taken together with the carbon to which they are attached to form cyclopropyl, cyclobutyl, cyclopentyl, or cyclohexyl;

W is selected from O or NH; and the dashed line represents an optional double bond.

Section B embodiments provide compounds having the general Formula IIIa:

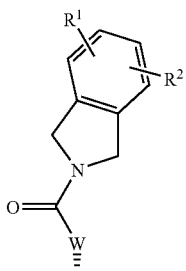

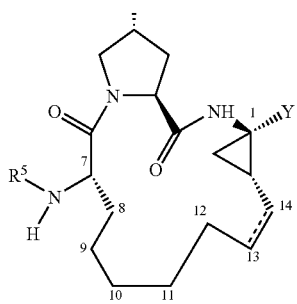

wherein:

$R^1$ and $R^2$ are each independently H, halo, cyano, hydroxy, $C_{1-3}$ alkyl, or $C_{1-3}$ alkoxy;

$R^5$ is H, $C(O)NR^6R^7$, $C(O)R^8$, or $C(O)OR^8$;

$R^8$ is $C_{1-6}$ alkyl, $C_{3-7}$ cycloalkyl, $C_{4-10}$ alkylcycloalkyl, or 3-tetrahydrofuryl.

Y is a sulfonimide of the formula $-C(O)NHS(O)_2R^9$, where $R^9$ is $C_{1-3}$ alkyl, $C_{3-7}$ cycloalkyl, or phenyl which is optionally substituted by up to two halo, cyano, nitro, hydroxy, $C_{1-3}$ alkyl, $C_{3-7}$ cycloalkyl, or $C_{1-3}$ alkoxy, or Y is a carboxylic acid or pharmaceutically acceptable salt, solvate, or prodrug thereof;

W is selected from O or NH; and the dashed line represents an optional double bond.

Section B embodiments provide compounds having the general Formula IIb:

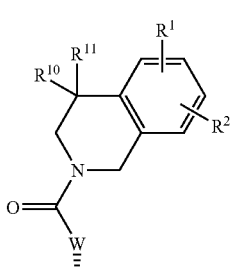

IIb

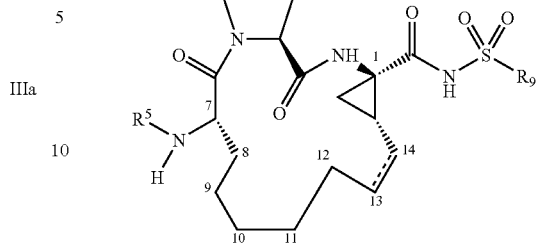

IIIa

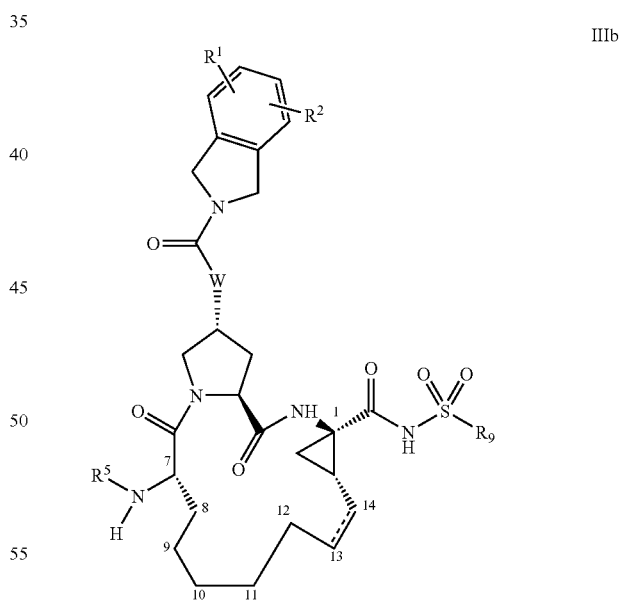

wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy;

$R^{10}$ and $R^{11}$ are each independently H or $C_{1-3}$ alkyl, or $R^{10}$ and $R^{11}$ are taken together with the carbon to which they are attached to form cyclopropyl, cyclobutyl, cyclopentyl, or cyclohexyl;

W is selected from O or NH; and the dashed line represents an optional double bond.

Section B embodiments provide compounds having the general Formula IIIb:

IIIb wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-5}$ cycloalkyl, or phenyl which is optionally substituted by up to two halo, cyano, hydroxy, $C_{1-3}$ alkyl, or $C_{1-3}$ alkoxy;

$R^{10}$ and $R^{11}$ are each independently H, $C_{1-3}$ alkyl, or $C_{4-5}$ cycloalkyl;

W is selected from O or NH; and the dashed line represents an optional double bond.

Section B embodiments provide compounds having the general Formula IIc:

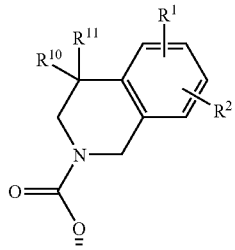

IIc

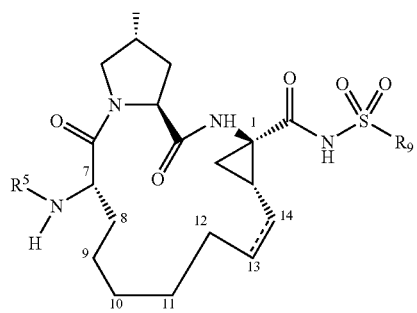

wherein:

$R^1$ and $R^2$ are each independently H, chloro, fluoro, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl or $C_{5-6}$ cycloalkyl;

$R^9$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy;

(e) $R^{10}$ and $R^{11}$ are each independently H or $C_{1-3}$ alkyl, or $R^{10}$ and $R^{11}$ are taken together with the carbon to which they are attached to form cyclopropyl or cyclobutyl; and (f) the dashed line represents an optional double bond.

Section B embodiments provide compounds having the general Formula IIIc:

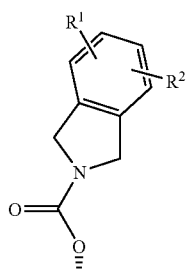

IIIc

-continued

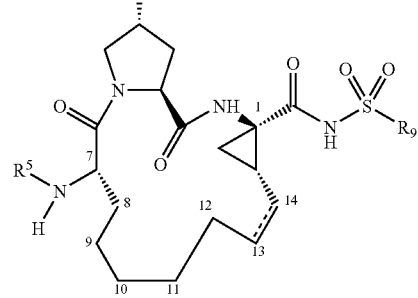

wherein:

$R^1$ and $R^2$ are each independently H, chloro, fluoro, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl or $C_{5-6}$ cycloalkyl;

$R^9$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy; and the dashed line represents an optional double bond.

Section B embodiments provide compounds having the general Formula IIId:

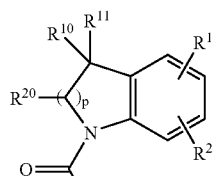

IIId

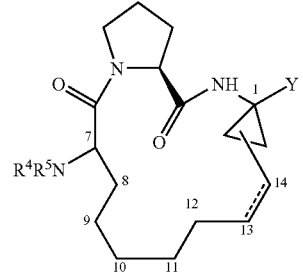

wherein:

$R^1$ and $R^2$ are each independently H, halo, cyano, hydroxy, $C_{1-3}$ alkyl, or $C_{1-3}$ alkoxy;

$R^4$ is H;

$R^5$ is H, $C(O)NR^6R^7$, $C(O)R^8$, or $C(O)OR^8$;

$R^8$ is $C_{1-6}$ alkyl, $C_{3-7}$ cycloalkyl, $C_{4-10}$ alkylcycloalkyl, or 3-tetrahydrofuryl;

Y is a sulfonimide of the formula $—C(O)NHS(O)_2R^9$, where $R^9$ is $C_{1-3}$ alkyl, $C_{3-7}$ cycloalkyl, or phenyl which is optionally substituted by up to two halo, cyano, nitro, hydroxy, $C_{1-3}$ alkyl, $C_{3-7}$ cycloalkyl, or $C_{1-3}$ alkoxy, or Y is a carboxylic acid or pharmaceutically acceptable salt, solvate, or prodrug thereof;

$R^{10}$ and $R^{11}$ are each independently H or $C_{1-3}$ alkyl, or $R^{10}$ and $R^{11}$ are taken together with the carbon to which they are attached to form cyclopropyl, cyclobutyl, cyclopentyl, or cyclohexyl;

$R^{20}$ is H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^6$, or $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

W is selected from O or NH; and the dashed line represents an optional double bond.

Section B embodiments provide compounds having the general Formula IVa:

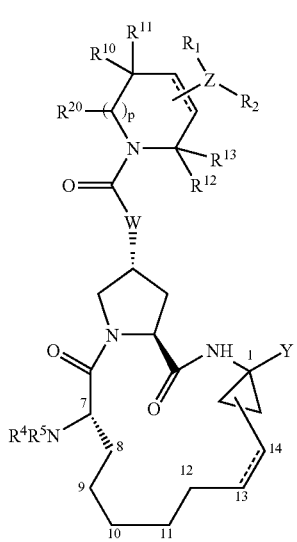

wherein:

$R^1$ and $R^2$ are each independently H, halo, cyano, hydroxy, $C_{1-3}$ alkyl, or $C_{1-3}$ alkoxy;

$R^4$ is H;

R5 is H, $C(O)NR^6R^7$, $C(O)R^8$, or $C(O)OR^8$;

$R^8$ is $C_{1-6}$ alkyl, $C_{3-7}$ cycloalkyl, $C_{4-10}$ alkylcycloalkyl, or 3-tetrahydrofuryl;

Y is a sulfonimide of the formula $-C(O)NHS(O)_2R^9$, where $R^9$ is $C_{1-3}$ alkyl, $C_{3-7}$ cycloalkyl, or phenyl which is optionally substituted by up to two halo, cyano, nitro, hydroxy, $C_{1-3}$ alkyl, $C_{3-7}$ cycloalkyl, or $C_{1-3}$ alkoxy, or Y is a carboxylic acid or pharmaceutically acceptable salt, solvate, or prodrug thereof;

$R^{10}$ and $R^{11}$ are each independently H or $C_{1-3}$ alkyl, or $R^{10}$ and $R^{11}$ are taken together with the carbon to which they are attached to form cyclopropyl, cyclobutyl, cyclopentyl, or cyclohexyl;

$R^{20}$ is H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, and $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro;

W is selected from O or NH;

the dashed line represents an optional double bond; and where Z is a fused or appended aryl or heteroaryl ring system.

Section C

Section C embodiments provide compounds having the general Formula XI.

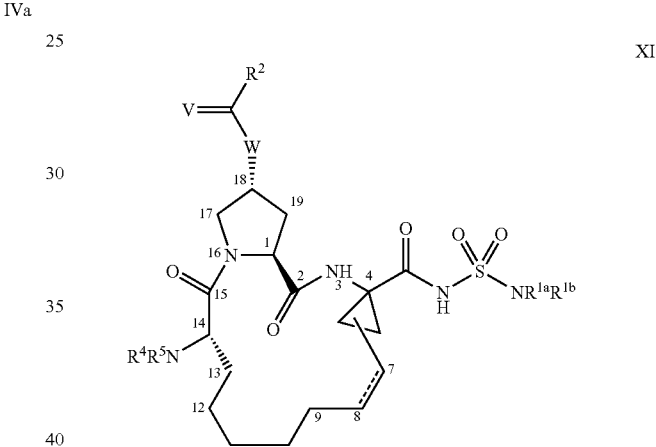

wherein:

$R^{1a}$ and $R^{1b}$ are each independently H, $C_{1-6}$ alkyl, $C_{3-7}$ cycloalkyl, or $C_{4-10}$ alkylcycloalkyl, which are all optionally substituted from one to three times with halo, cyano, nitro, $C_{1-6}$ alkoxy, amido, or phenyl;

or $R^{1a}$ and $R^{1b}$ are each independently H or $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

or $R^{1a}$ and $R^{1b}$ are each independently H or heterocycle, which is a five-, six-, or seven-membered, saturated or unsaturated heterocyclic molecule, containing from one to four heteroatoms selected from the group consisting of nitrogen, oxygen and sulfur;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

or $NR^{1a}R^{1b}$ is a heteroaryl selected from the group consisting of:

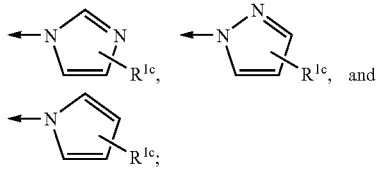

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $R^{1c}$ is $NH(CO)OR^{1e}$ wherein $R^{1e}$ is $C_{1-6}$ alkyl or $C_{3-6}$ cycloalkyl;

W is O or NH;

V is selected from O, S, or NH;

when V is O or S, W is selected from O, $NR^{15}$, or $CR^{15}$;

when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl, or $C_{1-6}$ alkyl optionally substituted with up to 5 fluoro;

$R^2$ is a bicyclic secondary amine with the structure of:

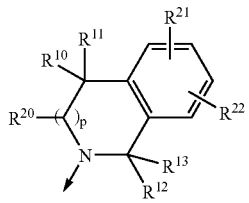

wherein $R^{21}$ and $R^{22}$ are each independently H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro, $C_{6\ OR\ 10}$ aryl, pyridyl, pyrimidyl, thienyl, furanyl, thiazolyl, oxazolyl, phenoxy, thiophenoxy, $S(O)_2NR^6R^7$, $NHC(O)NR^6R^7$, $NHC(S)NR^6R^7$, $C(O)NR^6R^7$, $NR^6R^7$, $C(O)R^8$, $C(O)OR^8$, $NHC(O)R^8$, $NHC(O)OR^8$, $SO_mR^8$ (m=0, 1 or 2), or $NHS(O)_2R^8$; said thienyl, pyrimidyl, furanyl, thiazolyl and oxazolyl in the definition of $R^{21}$ and $R^{22}$ are optionally substituted by up to two halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; said $C_{6\ OR\ 10}$ aryl, pyridyl, phenoxy, and thiophenoxy in the definition of $R^{21}$ and $R^{22}$ are optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein $R^{10}$ and $R^{11}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, or $C_{1-6}$ alkyl optionally substituted with up to 5 fluoro, $(CH_2)_nNR^6R^7$, or $(CH_2)_nC(O)OR^{14}$ where $R^{14}$ is H, $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro; said $C_{6\ or\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{10}$ and $R^{11}$ are taken together with the carbon to which they are attached to form cyclopropyl, cyclobutyl, cyclopentyl, or cyclohexyl; or $R^{10}$ and $R^{11}$ are combined as O;

wherein p=0 or 1;

wherein $R^{12}$ and $R^{13}$ are each independently H, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, $C_{1-6}$ alkyl optionally substituted with up to 5 fluoro, $(CH_2)_nNR^6R^7$, $(CH_2)_nC(O)OR^{14}$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{12}$ and $R^{13}$ are taken together with the carbon to which they are attached to form cyclopropyl, cyclobutyl, cyclopentyl, or cyclohexyl;

wherein $R^{20}$ is H, $C_{1-6}$ alkyl, $C_{3-7}$ cycloalkyl, $C_{4-10}$ alkylcycloalkyl, $C_6$ or 10 aryl, hydroxy-$C_{1-6}$ alkyl, $C_{1-6}$ alkyl optionally substituted with up to 5 fluoro, $(CH_2)_nNR^6R^7$ $(CH_2)_nC(O)OR^4$ where $R^{14}$ is H, $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^{14}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; said $C_{6\ OR\ 10}$ aryl, in the definition of $R^{12}$ and $R^{13}$ is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

wherein n=0-4;

wherein $R^6$ and $R^7$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

or $R^2$ is $R^{2a}$-$R^{2b}$ when W=NH and V=O, wherein $R^{2a}$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro;

$R^{2b}$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three $NR^{2c}R^{2d}$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, or $C_{1-6}$ alkyl optionally substituted with up to 5 fluoro, $C_{1-6}$ alkoxy optionally substituted with up to 5 fluoro;

said $R^{2c}$ and $R^{2d}$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{2c}$ and $R^{2d}$ are taken together with the nitrogen to which they are attached to form indolinyl, pyrrolidinyl, piperidinyl, piperazinyl, or morpholinyl;

$R^4$ is H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, or $S(O)_2R^8$;

$R^8$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; and the dashed line represents an optional double bond.

Section C embodiments provide compounds having the general Formula XII.

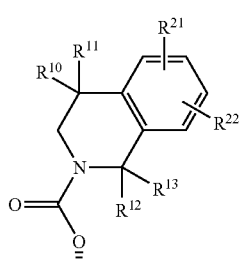

XII

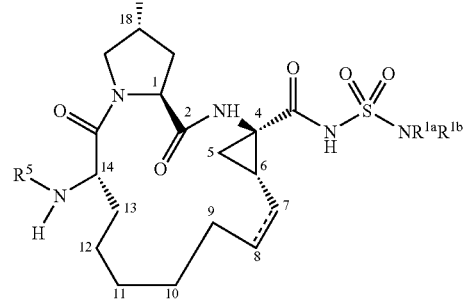

-continued wherein:

$R^{1a}$ and $R^{1b}$ are each independently H, $C_{1-6}$ alkyl, $C_{3-7}$ cycloalkyl, or $C_{4-10}$ alkylcycloalkyl, which are all optionally substituted from one to three times with halo, cyano, nitro, $C_{1-6}$ alkoxy, amido, or phenyl;

or $R^{1a}$ and $R^{1b}$ are each independently H or heteroaryl selected from a group consisting of:

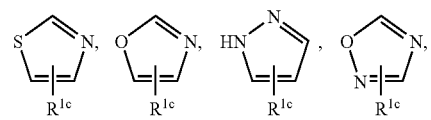

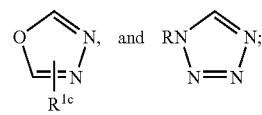

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

$R^{21}$ and $R^{22}$ are each independently H, halo, cyano, hydroxy, $C_{1-3}$ alkyl, or $C_{1-3}$ alkoxy;

$R^5$ is H, $C(O)NR^6R^7$, $C(O)R^8$, or $C(O)OR^8$ $R^6$ and $R^7$ are each independently H, $C_{1-6}$ alkyl, $C_{3-7}$ cycloalkyl, $C_{4-10}$ alkylcycloalkyl, or phenyl;

$R^8$ is $C_{1-6}$ alkyl, $C_{3-7}$ cycloalkyl, $C_{4-10}$ alkylcycloalkyl, or 3-tetrahydrofuryl;

$R^{10}$ and $R^{11}$ are each independently H, halo, or $C_{1-3}$ alkyl, or $R^{10}$ and $R^{11}$ are taken together with the carbon to which they are attached to form cyclopropyl, cyclobutyl, cyclopentyl, or cyclohexyl;

$R^{12}$ and $R^{13}$ are each independently H, halo, $C_{1-6}$ alkyl, $C_{3-7}$ cycloalkyl, $C_{4-10}$ alkylcycloalkyl, $C_{6\ OR\ 10}$ aryl, hydroxy-$C_{1-6}$ alkyl, or $C_{1-6}$ alkyl optionally substituted with up to 5 halo atoms; and the dashed line represents an optional double bond.

Section C embodiments provide compounds having the general Formula XIII.

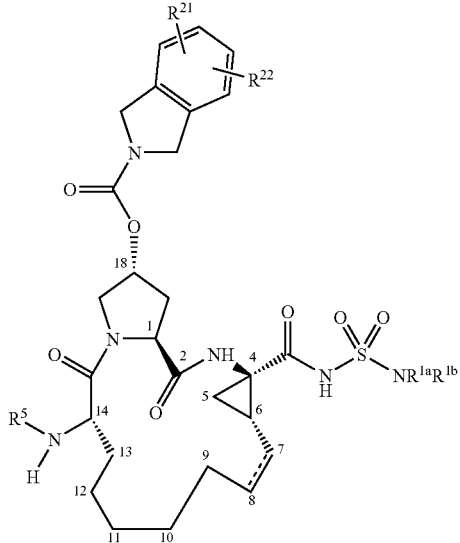

wherein:

$R^{1a}$ and $R^{1b}$ are each independently H, $C_{1-6}$ alkyl, $C_{3-7}$ cycloalkyl, $C_{4-10}$ alkylcycloalkyl, which are all optionally substituted from one to three times with halo, cyano, nitro, $C_{1-6}$ alkoxy, amido, or phenyl;

or $R^{1a}$ and $R^{1b}$ are each independently H or heteroaryl selected from a group consisting of:

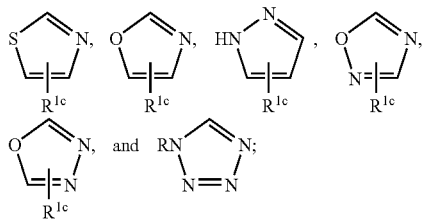

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido or phenyl;

$R^{21}$ and $R^{22}$ are each independently H, halo, cyano, hydroxy, $C_{1-3}$ alkyl, or $C_{1-3}$ alkoxy;

$R^5$ is H, $C(O)NR^6R^7$, $C(O)R^8$, or $C(O)OR^8$;

$R^6$ and $R^7$ are each independently H, $C_{1-6}$ alkyl, $C_{3-7}$ cycloalkyl, $C_{4-10}$ alkylcycloalkyl, or phenyl;

$R^8$ is $C_{1-6}$ alkyl, $C_{3-7}$ cycloalkyl, $C_{4-10}$ alkylcycloalkyl, or 3-tetrahydrofuryl; and the dashed line represents an optional double bond.

Section C embodiments provide compounds having the general Formula XIV.

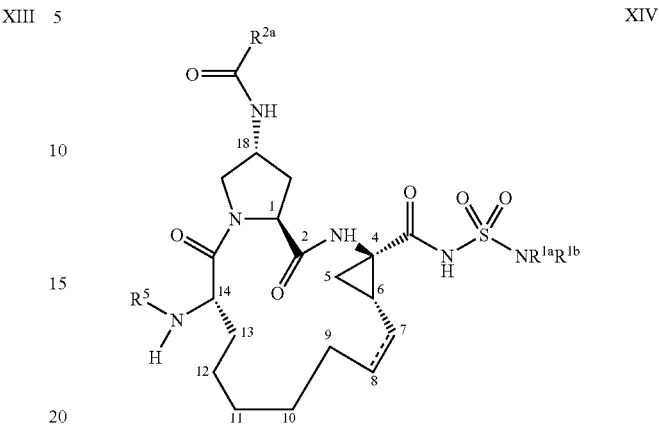

wherein:

$R^{1a}$ and $R^{1b}$ are each independently H, $C_{1-6}$ alkyl, $C_{3-7}$ cycloalkyl, $C_{4-10}$ alkylcycloalkyl, which are all optionally substituted from one to three times with halo, cyano, nitro, $C_{1-6}$ alkoxy, amido, or phenyl;

or $R^{1a}$ and $R^{1b}$ are each independently H or heteroaryl selected from a group consisting of:

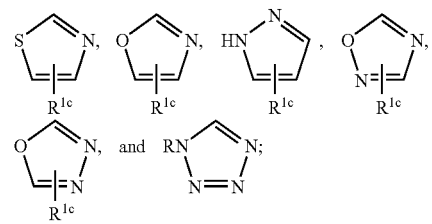

wherein $R^{1c}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{1d})_2$, $NH(CO)R^{1d}$, or $NH(CO)NHR^{1d}$, wherein each $R^{1d}$ is independently H, $C_{1-6}$ alkyl, or $C_{3-6}$ cycloalkyl;

or $NR^{1a}R^{1b}$ is a three- to six-membered alkyl cyclic secondary amine, which optionally has one to three hetero atoms incorporated in the ring, and which is optionally substituted from one to three times with halo, cyano, nitro, $C_{1-6}$ alkoxy, amido, or phenyl;

$R^{2a}$ is $C_6$ or $C_{10}$ aryl optionally substituted with up to three $NR^{2c}R^{2d}$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

said $R^{2c}$ and $R^{2d}$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^{2c}$ and $R^{2d}$ are taken together with the nitrogen to which they are attached to form indolinyl, pyrrolidinyl, piperidinyl, piperazinyl, or morpholinyl;

or $R^{2a}$ is an unsaturated five- or six-membered heteroaryl, or such defined heteroaryl fused to another cycle be it heterocycle or any other cycle;

$R^5$ is H, $C(O)NR^6R^7$, $C(O)R^8$, or $C(O)OR^8$ $R^6$ and $R^7$ are each independently H, $C_{1-6}$ alkyl, $C_{3-7}$ cycloalkyl, $C_{4-10}$ alkylcycloalkyl, or phenyl;

$R^8$ is $C_{1-6}$ alkyl, $C_{3-7}$ cycloalkyl, $C_{4-10}$ alkylcycloalkyl, or 3-tetrahydrofuryl; and the dashed line represents an optional double bond.

Section C embodiments provide compounds having the general Formula XV.

XV wherein:

$R^1$ and $R^2$ are each independently H, halo, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl, $C_{5-6}$ cycloalkyl, or 3-tetrahydrofuryl;

$R^9$ is $C_{1-3}$ alkyl, $C_{3-5}$ cycloalkyl, or phenyl which is optionally substituted by up to two halo, cyano, hydroxy, $C_{1-3}$ alkyl, or $C_{1-3}$ alkoxy;

W is selected from O or NH; and the dashed line represents an optional double bond.

Section C embodiments provide compounds having the general Formula XVI.

XVI

-continued wherein:

$R^1$ and $R^2$ are each independently H, chloro, fluoro, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl or $C_{5-6}$ cycloalkyl;

$R^9$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy;

$R^{10}$ and $R^{11}$ are each independently H or $C_{1-3}$ alkyl, or $R^{10}$ and $R^{11}$ are taken together with the carbon to which they are attached to form cyclopropyl or cyclobutyl; and the dashed line represents an optional double bond.

Section C embodiments provide compounds having the general Formula XVII.

XVII wherein:

$R^1$ and $R^2$ are each independently H, chloro, fluoro, cyano, hydroxy, $C_{1-3}$ alkyl, or $C_{1-3}$ alkoxy;

$R^5$ is H, $C(O)OR^8$ or $C(O)NHR^8$;

$R^8$ is $C_{1-6}$ alkyl or $C_{5-6}$ cycloalkyl;

$R^9$ is $C_{1-3}$ alkyl, $C_{3-4}$ cycloalkyl, or phenyl which is optionally substituted by up to two halo, cyano, hydroxy, $C_{1-3}$ alkyl, or $C_{1-3}$ alkoxy; and the dashed line represents an optional double bond.

Section D

Section D embodiments provide compounds having the general Formula XVIII:

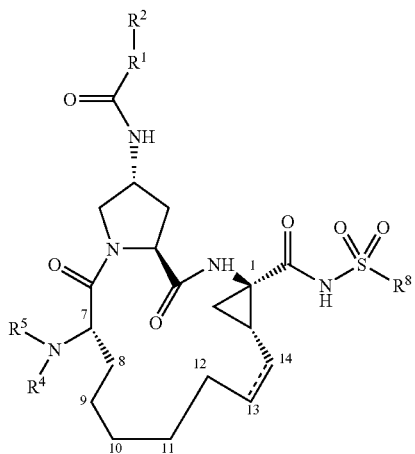

XVIII wherein:

R$^1$ is C$_{1-6}$ alkyl, C$_{3-7}$ cycloalkyl, C$_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three NR$^5$R$^6$, halo, cyano, nitro, hydroxy, C$_{1-6}$ alkyl, C$_{3-7}$ cycloalkyl, C$_{4-10}$ alkylcycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, or C$_{1-6}$ alkoxy optionally substituted with up to 5 fluoro;

R$^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, or benzimidazole, each optionally substituted with up to three NR$^5$R$^6$, halo, cyano, nitro, hydroxy, C$_{1-6}$ alkyl, C$_{3-7}$ cycloalkyl, C$_{4-10}$ alkylcycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, or C$_{1-6}$ alkoxy optionally substituted with up to 5 fluoro;

R$^3$ is H, C$_{1-6}$ alkyl, C$_{3-7}$ cycloalkyl, C$_{4-10}$ alkylcycloalkyl, or phenyl, said phenyl optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, or C$_{1-6}$ alkoxy optionally substituted with up to 5 fluoro;

R$^4$ is C$_{1-6}$ alkyl, C(O)NR$^5$R$^6$, C(S)NR$^5$R$^6$, C(O)R$^7$, C(O)OR$^7$, or S(O)$_2$R$^7$;

R$^5$ and R$^6$ are each independently H, C$_{1-6}$ alkyl, C$_{3-7}$ cycloalkyl, C$_{4-10}$ alkylcycloalkyl, or phenyl, said phenyl optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, hydroxy-C$_{1-6}$ alkyl, C$_{1-6}$ alkyl optionally substituted with up to 5 fluoro, or C$_{1-6}$ alkoxy optionally substituted with up to 5 fluoro; or R$^5$ and R$^6$ are taken together with the nitrogen to which they are attached to form indolinyl, pyrrolidinyl, piperidinyl, piperazinyl, or morpholinyl;

R$^7$ is C$_{1-6}$ alkyl, C$_{3-7}$ cycloalkyl, or C$_{4-10}$ alkylcycloalkyl, which are all optionally substituted from one to three times with halo, cyano, nitro, hydroxy, C$_{1-6}$ alkoxy, or phenyl; or R$^7$ is C$_{6\ OR\ 10}$ aryl which is optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, or C$_{1-6}$ alkoxy optionally substituted with up to 5 fluoro;

R$^8$ is C$_{1-3}$ alkyl, C$_{3-4}$ cycloalkyl, or phenyl which is optionally substituted by up to two halo, cyano, hydroxy, C$_{1-3}$ alkyl, or C$_{1-3}$ alkoxy; and the dashed line represents an optional double bond.

Section E

Section E embodiments provide compounds having the general Formula XIX:

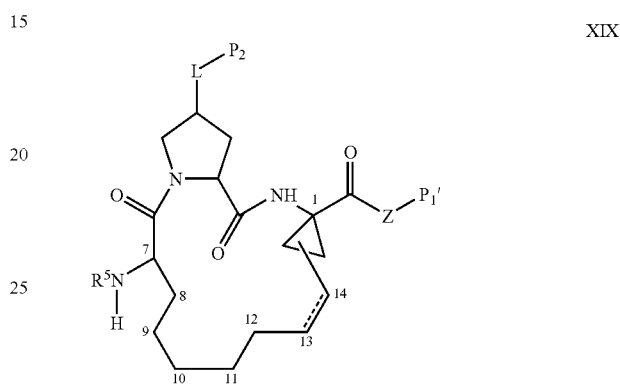

XIX wherein:

Z is a group configured to hydrogen bond to an NS3 protease His57 imidazole moiety and to hydrogen bond to a NS3 protease Gly137 nitrogen atom;

P1' is a group configured to form a non-polar interaction with at least one NS3 protease S1' pocket moiety selected from the group consisting of Lys136, Gly137, Ser139, His57, Gly58, Gln41, Ser42, and Phe43;

L is a linker group consisting of from 1 to 5 atoms selected from the group consisting of carbon, oxygen, nitrogen, hydrogen, and sulfur;

P2 is selected from the group consisting of unsubstituted aryl, substituted aryl, unsubstituted heteroaryl, substituted heteroaryl, unsubstituted heterocyclic and substituted heterocyclic; P2 being positioned by L to form a non-polar interaction with at least one NS3 protease S2 pocket moiety selected from the group consisting of His57, Arg155, Val78, Asp79, Gln80 and Asp81;

the dashed line represents an optional double bond;

R$^5$ is selected from the group consisting of C(O)NR$^6$R$^7$ and C(O)OR$^8$;

R$^6$ and R$^7$ are each independently H, C$_{1-6}$ alkyl, C$_{3-7}$ cycloalkyl, C$_{4-10}$ alkylcycloalkyl or phenyl, said phenyl optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, hydroxy-C$_{1-6}$ alkyl, C$_{1-6}$ alkyl optionally substituted with up to 5 fluoro, C$_{1-6}$ alkoxy optionally substituted with up to 5 fluoro; or R$^6$ and R$^7$ are taken together with the nitrogen to which they are attached to form indolinyl, pyrrolidinyl, piperidinyl, piperazinyl, or morpholinyl; and R$^8$ is C$_{1-6}$ alkyl, C$_{3-7}$ cycloalkyl, C$_{4-10}$ alkylcycloalkyl, which are all optionally substituted from one to three times with halo, cyano, nitro, hydroxy, C$_{1-6}$ alkoxy, or phenyl; or R$^8$ is C$_{6\ OR\ 10}$ aryl which is optionally substituted by up to three halo, cyano, nitro, hydroxy, C$_{1-6}$ alkyl, C$_{3-7}$ cycloalkyl, C$_{4-10}$ alkylcycloalkyl, C$_{2-6}$ alkenyl, C$_{1-6}$ alkoxy, hydroxy-C$_{1-6}$ alkyl, C$_{1-6}$ alkyl optionally substituted with up to 5 fluoro, $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring.

As used herein, "hydrogen bond" refers to an attractive force between an electronegative atom (such as oxygen, nitrogen, sulfur or halogen) and a hydrogen atom which is linked covalently to another electronegative atom (such as oxygen, nitrogen, sulfur or halogen). See, e.g., Stryer et. al. "Biochemistry", Fifth Edition 2002, Freeman & Co. N.Y. Typically, the hydrogen bond is between a hydrogen atom and two unshared electrons of another atom. A hydrogen bond between hydrogen and an electronegative atom not covalently bound to the hydrogen may be present when the hydrogen atom is at a distance of about 2.5 angstrom to about 3.8 angstrom from the not-covalently bound electronegative atom, and the angle formed by the three atoms (electronegative atom covalently bound to hydrogen, hydrogen, and electronegative atom not-covalently bound electronegative atom) deviates from 180 degrees by about 45 degrees or less. The distance between the hydrogen atom and the not-covalently bound electronegative atom may be referred to herein as the "hydrogen bond length," and the angle formed by the three atoms (electronegative atom covalently bound to hydrogen, hydrogen, and electronegative atom not-covalently bound electronegative atom) may be referred to herein as the "hydrogen bond angle." In some instances, stronger hydrogen bonds are formed when the hydrogen bond length is shorter; thus, in some instances, hydrogen bond lengths may range from about 2.7 angstroms to about 3.6 angstroms, or about 2.9 angstroms to about 3.4 angstroms. In some instances, stronger hydrogen bonds are formed when the hydrogenbond angle is closer to linear; thus, in some instances, hydrogen bond angles may deviate from 180 degrees by about 25 degrees or less, or by about 10 degrees or less.

As used herein, non-polar interaction refers to proximity of non-polar molecules or moieties, or proximity of molecules or moieties with low polarity, sufficient for van der Waals interaction between the moieties and/or sufficient to exclude polar solvent molecules such as water molecules. See, e.g., Stryer et. al. "Biochemistry", Fifth Edition 2002, Freeman & Co. N.Y. Typically, the distance between atoms (excluding hydrogen atoms) of non-polar interacting moieties may range from about 2.9 angstroms to about 6 angstroms. In some instances, the space separating non-polar interacting moieties is less than the space that would accommodate a water molecule. As used herein a non-polar moiety or moiety with low polarity refers to moieties with low dipolar moments (typically dipolar moments less than the dipolar moment of O—H bonds of $H_2O$ and N—H bonds of $NH_3$) and/or moieties that are not typically present in hydrogen bonding or electrostatic interactions. Exemplary moieties with low polarity are alkyl, alkenyl, and unsubstituted aryl moieties.

As used herein, an NS3 protease S1' pocket moiety refers to a moiety of the NS3 protease that interacts with the amino acid positioned one residue C-terminal to the cleavage site of the substrate polypeptide cleaved by NS3 protease (e.g., the NS3 protease moieties that interact with amino acid S in the polypeptide substrate DLEVVT-STWVLV). Exemplary moieties include, but are not limited to, atoms of the peptide backbone or side chains of amino acids Lys136, Gly137, Ser139, His57, Gly58, Gln41, Ser42, and Phe43, see Yao. et. al., Structure 1999, 7, 1353.

As used herein, an NS3 protease S2 pocket moiety refers to a moiety of the NS3 protease that interacts with the amino acid positioned two residues N-terminal to the cleavage site of the substrate polypeptide cleaved by NS3 protease (e.g., the NS3 protease moieties that interact with amino acid V in the polypeptide substrate DLEVVT-STWVLV). Exemplary moieties include, but are not limited to, atoms of the peptide backbone or side chains of amino acids His57, Arg155, Val78, Asp79, Gln80 and Asp81, see Yao. et. al., Structure 1999, 7, 1353.

As used herein, a first moiety "positioned by" a second moiety refers to the spatial orientation of a first moiety as determined by the properties of a second moiety to which the first atom or moiety is covalently bound. For example, a phenyl carbon may position an oxygen atom bonded to the phenyl carbon in a spatial position such that the oxygen atom hydrogen bonds with a hydroxyl moiety in an NS3 active site.

Also provided herein are compounds containing moieties configured to interact with particular regions, particular amino acid residues, or particular atoms of NS3 protease. Some compounds provided herein contain one or more moieties configured to form a hydrogen bond with NS3 protease at a particular region, amino acid residue, or atom. Some compounds provided herein contain one or more moieties configured to form a non-polar interaction with NS3 protease at a particular region, amino acid residue, or atom. For example, the compound having the general Formula XIX may contain one or more moieties that form a hydrogen bond with a peptide backbone atom or side chain moiety located in the substrate binding pocket of NS3 protease. In another example, the compound having the general Formula XIX may contain one or more moieties that form non-polar interactions with peptide backbone or side chain atom or atoms located in the substrate binding pocket of NS3 protease. In the compound of formula XIX, the dashed line between carbons 13 and 14 may be a single bond or a double bond.

As provided in the compound having the general formula XIX, Z may be configured to form a hydrogen bond with a peptide backbone atom or side chain moiety located in the substrate binding pocket of NS3 protease, including, but not limited to, NS3 protease His57 imidazole moiety and NS3 protease Gly137 nitrogen atom. In some instances, Z may be configured to form a hydrogen bond with both the NS3 protease His57 imidazole moiety and the NS3 protease Gly137 nitrogen atom.

The P1' group of the compound having the general formula XIX may be configured to form a non-polar interaction with peptide backbone or side chain atom or atoms located in the substrate binding pocket of NS3 protease, including, but not limited to amino acid residues that form the NS3 protease S1' pocket. For example the P1' group may form a non-polar interaction with at least one amino acid selected from Lys136, Gly137, Ser139, His57, Gly58, Gln41, Ser42, and Phe43.

The P2 group of the compound having the general formula XIX may be configured to form a non-polar interaction with peptide backbone or side chain atom or atoms located in the substrate binding pocket of NS3 protease, including, but not limited to amino acid residues that form the NS3 protease S2 pocket. For example the P2 group may form a non-polar interaction with at least one amino acid selected from His57, Arg155, Val78, Asp79, Gln80 and Asp81. The P2 group also may be configured to form a hydrogen bond with peptide backbone or side chain atom or atoms located in the substrate binding pocket of NS3 protease, including, but not limited to amino acid residues that form the NS3 protease S2 pocket. For example the P2 group may form a hydrogen bond with at least one amino acid selected from His57, Arg155, Val78, Asp79, Gln80 and Asp81. In some instances, P2 may form both a non-polar interaction and a hydrogen bond with peptide backbone or side chain moieties or atoms located in the substrate binding pocket of NS3 protease, such amino acids selected from His57, Arg155, Val78, Asp79, Gln80 and Asp81. Such hydrogen bond and non-polar interactions may occur with the same amino acid residue or with different amino acid residues in the NS3 protease S2 pocket. In some embodiments, P2 may be selected from the group consisting of unsubstituted aryl, substituted aryl, unsubstituted heteroaryl, substituted heteroaryl, unsubstituted heterocyclic and substituted heterocyclic.

In some embodiments, the position of the P2 group is determined by the linker L. For example, P2 may be positioned by linker L to form a non-polar interaction with peptide backbone or side chain atom or atoms located in the substrate binding pocket of NS3 protease, including, but not limited to amino acid residues that form the NS3 protease S2 pocket. For example the P2 group may be positioned by L to form a non-polar interaction with at least one amino acid selected from His57, Arg155, Val78, Asp79, Gln80 and Asp81. In another example, P2 may be positioned by linker L to form a hydrogen bond with peptide backbone or side chain atom or atoms located in the substrate binding pocket of NS3 protease, including, but not limited to amino acid residues that form the NS3 protease S2 pocket. For example the P2 group may be positioned by L to form a hydrogen bond with at least one amino acid selected from His57, Arg155, Val78, Asp79, Gln80 and Asp81. In some instances, P2 may be positioned to form both a non-polar interaction and a hydrogen bond peptide backbone or side chain atom or atoms located in the substrate binding pocket of NS3 protease, such as an amino acid selected from His57, Arg155, Val78, Asp79, Gln80 and Asp81. Such hydrogen bond and non-polar interactions may occur with the same amino acid residue or with different amino acid residues in the NS3 protease S2 pocket.

As provided in the compound having the general formula XIX, L may be a linker group that links P2 to the heterocyclic backbone of the compound of formula XIX. Linker L may contain any of a variety of atoms and moieties suitable for positioning P2 in the NS3 protease substrate binding pocket. In one embodiment, L may contain 1 to 5 atoms selected from the group consisting of carbon, oxygen, nitrogen, hydrogen, and sulfur. In another embodiment, L may contain 2 to 5 atoms selected from the group consisting of carbon, oxygen, nitrogen, hydrogen, and sulfur. For example, L may contain a group having the formula —W—C(=V)—, where V and W are each individually selected from O, S or NH. Specific exemplary groups for L include, but are not limited to, ester, amide, carbamate, thioester, and thioamide.

The compound of formula XIX also may contain an $R^5$ group, where the $R^5$ group may contain a carboxyl moiety. Exemplary carboxyl moieties of $R^5$ include $C(O)NR^6R^7$ and $C(O)OR^8$ where $R^6$ and $R^7$ are each independently H, $C_{1-6}$ alkyl, $C_{3-7}$ cycloalkyl, $C_{4-10}$ alkylcycloalkyl or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl; and where $R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_6$ or 10 aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring In some embodiments, several bonds of the compound of formula XIX may have a particular chirality.

Section E embodiments provide compounds wherein the C13-C14 double bond is cis. Section E embodiments provide compounds wherein the C13-C14 double bond is trans.

In preferred embodiments, Section E embodiments provide compounds having the general Formula XIX, in which L consists of from 2 to 5 atoms.

In preferred embodiments, Section E embodiments provide compounds having the general Formula XIX, in which L comprises a —W—C(=V)— group, where V and W are each individually selected from O, S or NH.

In preferred embodiments, Section E embodiments provide compounds having the general Formula XIX, in which L is selected from the group consisting of ester, amide, carbamate, thioester, and thioamide.

In preferred embodiments, Section E embodiments provide compounds having the general Formula XIX, in which P2 is further positioned by L to form a hydrogen bonding interaction with at least one NS3 protease S2 pocket moiety selected from the group consisting of His57, Arg155, Val78, Asp79, Gln80 and Asp81.

In preferred embodiments, Section E embodiments provide compounds having the formula XIXa:

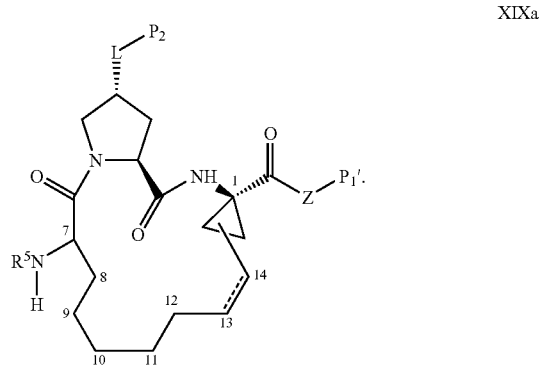

XIXa

In preferred embodiments, Section E embodiments provide compounds having the general Formula XIXa, in which L consists of from 2 to 5 atoms.

In preferred embodiments, Section E embodiments provide compounds having the general Formula XIXa, in which L comprises a —W—C(=V)— group, where V and W are each individually selected from O, S, or NH.

In preferred embodiments, Section E embodiments provide compounds having the general Formula XIXa, in which L is selected from the group consisting of ester, amide, carbamate, thioester, and thioamide.

In preferred embodiments, Section E embodiments provide compounds having the general Formula XIXa, in which P2 is further positioned by L to form a hydrogen bonding interaction with at least one NS3 protease S2 pocket moiety selected from the group consisting of His57, Arg155, Val78, Asp79, Gln80 and Asp81.

In preferred embodiments, Section E embodiments provide compounds

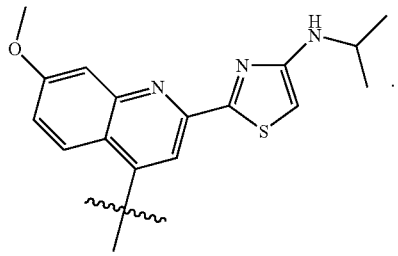

having the general Formula XIX, in which P2 is

In preferred embodiments, Section E embodiments provide compounds having the formula XIXb:

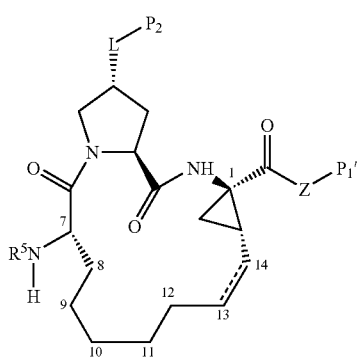

XIXb

In preferred embodiments, Section E embodiments provide compounds having the general Formula XIXb, in which L consists of from 2 to 5 atoms.

In preferred embodiments, Section E embodiments provide compounds having the general Formula XIXb, in which L comprises a —W—C(=V)— group, where V and W are each individually selected from O, S, or NH.

In preferred embodiments, Section E embodiments provide compounds having the general Formula XIXb, in which L is selected from the group consisting of ester, amide, carbamate, thioester, and thioamide.

In preferred embodiments, Section E embodiments provide compounds having the general Formula XIXb, in which P2 is further positioned by L to form a hydrogen bonding interaction with at least one NS3 protease S2 pocket moiety selected from the group consisting of His57, Arg155, Val78, Asp79, Gln80 and Asp81.

In preferred embodiments, Section E embodiments provide compounds having the general Formula XIXb, wherein the C13-C14 double bond is cis.

In preferred embodiments, Section E embodiments provide compounds having the general Formula XIXb, wherein the C13-C14 double bond is trans.

Compounds of the Formula XIX may be prepared in the same general manner as the compounds of the Formulas I-XVII.

In certain embodiments, the compounds of general Formula XIX do not include the compounds disclosed in PCT/US04/33970. For example, in certain embodiments, the compounds of general Formula I do not include the compounds of Formulas II, III, and IV in Section B above.

Pharmaceutical Compositions

The embodiments further provide compositions, including pharmaceutical compositions, comprising compounds of the general formulas I-XIX, and salts, esters, or other derivatives thereof. A subject pharmaceutical composition comprises a subject compound; and a pharmaceutically acceptable excipient. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public. Examples of suitable pharmaceutical composition embodiments and methods for making them are described in greater detail below.

Inhibiting Enzymatic Activity of a Flavivirus

In many embodiments, a subject compound inhibits the enzymatic activity of a flavirus. Whether a subject compound inhibits flavivirus may be readily determined using any known method. Flaviviral infections include those caused by flaviviruses including, but not limited to, hepatitis virus C, West Nile Virus, GB virus, Japanese Encephalitis, Dengue virus and Yellow Fever virus. In many embodiments, a subject compound inhibits the enzymatic activity of a hepatitis virus C(HCV) protease NS3. Whether a subject compound inhibits HCV NS3 may be readily determined using any known method. Typical methods involve a determination of whether an HCV polyprotein or other polypeptide comprising an NS3 recognition site is cleaved by NS3 in the presence of the agent. In many embodiments, a subject compound inhibits NS3 enzymatic activity by at least about 10%, at least about 15%, at least about 20%, at least about 25%, at least about 30%, at least about 40%, at least about 50%, at least about 60%, at least about 70%, at least about 80%, or at least about 90%, or more, compared to the enzymatic activity of NS3 in the absence of the compound.

In many embodiments, a subject compound inhibits enzymatic activity of an HCV NS3 protease with an $IC_{50}$ of less than about 50 μM, e.g., a subject compound inhibits an HCV NS3 protease with an $IC_{50}$ of less than about 40 μM, less than about 25 μM, less than about 10 μM, less than about 1 μM, less than about 100 nM, less than about 80 nM, less than about 60 nM, less than about 50 nM, less than about 25 nM, less than about 10 nM, or less than about 1 nM, or less.

In many embodiments, a subject compound inhibits HCV viral replication. For example, a subject compound inhibits HCV viral replication by at least about 10%, at least about 15%, at least about 20%, at least about 25%, at least about 30%, at least about 40%, at least about 50%, at least about 60%, at least about 70%, at least about 80%, or at least about 90%, or more, compared to HCV viral replication in the absence of the compound. Whether a subject compound inhibits HCV viral replication may be determined using methods known in the art, including an in vitro viral replication assay.

Treating a Flaviviral Infection

The methods and compositions described herein are generally useful in treatment of a flaviviral infection.

Whether a subject method is effective in treating a flaviviral infection may be determined by a reduction in viral load, a reduction in time to seroconversion (virus undetectable in patient serum), an increase in the rate of sustained viral response to therapy, a reduction of morbidity or mortality in clinical outcomes, or other indicator of disease response.

In general, an effective amount of a compound of formulas I-XIX, and optionally one or more additional antiviral agents, is an amount that is effective to reduce viral load or achieve a sustained viral response to therapy.

Whether a subject method is effective in treating a flaviviral infection may be determined by measuring viral load, or by measuring a parameter associated with a flaviviral infection, including, but not limited to, liver fibrosis, elevations in serum transaminase levels, and necroinflammatory activity in the liver. Indicators of liver fibrosis are discussed in detail below.

The method involves administering an effective amount of a compound of formulas I-XIX, optionally in combination with an effective amount of one or more additional antiviral agents. In some embodiments, an effective amount of a compound of formulas I-XIX, and optionally one or more additional antiviral agents, is an amount that is effective to reduce viral titers to undetectable levels, e.g., to about 1000 to about 5000, to about 500 to about 1000, or to about 100 to about 500 genome copies/mL serum. In some embodiments, an effective amount of a compound of formulas I-XIX, and optionally one or more additional antiviral agents, is an amount that is effective to reduce viral load to lower than 100 genome copies/mL serum.

In some embodiments, an effective amount of a compound of formulas I-XIX, and optionally one or more additional antiviral agents, is an amount that is effective to achieve a 1.5-log, a 2-log, a 2.5-log, a 3-log, a 3.5-log, a 4-log, a 4.5-log, or a 5-log reduction in viral titer in the serum of the individual.

In many embodiments, an effective amount of a compound of formulas I-XIX, and optionally one or more additional antiviral agents, is an amount that is effective to achieve a sustained viral response, e.g., no detectable HCV RNA (e.g., less than about 500, less than about 400, less than about 200, or less than about 100 genome copies per milliliter serum) is found in the patient's serum for a period of at least about one month, at least about two months, at least about three months, at least about four months, at least about five months, or at least about six months following cessation of therapy.

As noted above, whether a subject method is effective in treating a flaviviral infection may be determined by measuring a parameter associated with a flaviviral infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a compound of formulas I-XIX, and optionally one or more additional antiviral agents, is an amount effective to reduce ALT levels to less than about 45 IU/ml serum.

A therapeutically effective amount of a compound of formulas I-XIX, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

In many embodiments, an effective amount of a compound of formulas I-XIX and an additional antiviral agent is synergistic amount. As used herein, a "synergistic combination" or a "synergistic amount" of a compound of formulas I-XIX and an additional antiviral agent is a combined dosage that is more effective in the therapeutic or prophylactic treatment of an HCV infection than the incremental improvement in treatment outcome that could be predicted or expected from a merely additive combination of (i) the therapeutic or prophylactic benefit of the compound of formulas I-XIX when administered at that same dosage as a monotherapy and (ii) the therapeutic or prophylactic benefit of the additional antiviral agent when administered at the same dosage as a monotherapy.

In some embodiments, a selected amount of a compound of formulas I-XIX and a selected amount of an additional antiviral agent are effective when used in combination therapy for a disease, but the selected amount of the compound of formulas I-XIX and/or the selected amount of the additional antiviral agent is ineffective when used in monotherapy for the disease. Thus, the embodiments encompass (1) regimens in which a selected amount of the additional antiviral agent enhances the therapeutic benefit of a selected amount of the compound of formulas I-XIX when used in combination therapy for a disease, where the selected amount of the additional antiviral agent provides no therapeutic benefit when used in monotherapy for the disease (2) regimens in which a selected amount of the compound of formulas I-XIX enhances the therapeutic benefit of a selected amount of the additional antiviral agent when used in combination therapy for a disease, where the selected amount of the compound of formulas I-XIX provides no therapeutic benefit when used in monotherapy for the disease and (3) regimens in which a selected amount of the compound of formula I and a selected amount of the additional antiviral agent provide a therapeutic benefit when used in combination therapy for a disease, where each of the selected amounts of the compound of formulas I-XIX and the additional antiviral agent, respectively, provides no therapeutic benefit when used in monotherapy for the disease. As used herein, a "synergistically effective amount" of a compound of formulas I-XIX and an additional antiviral agent, and its grammatical equivalents, shall be understood to include any regimen encompassed by any of (1)-(3) above.

Treating Hepatitis Virus Infection

The methods and compositions described herein are generally useful in treatment of an HCV infection.

Whether a subject method is effective in treating an HCV infection may be determined by a reduction in viral load, a reduction in time to seroconversion (virus undetectable in patient serum), an increase in the rate of sustained viral response to therapy, a reduction of morbidity or mortality in clinical outcomes, or other indicator of disease response.

In general, an effective amount of a compound of formulas I-XIX, and optionally one or more additional antiviral agents, is an amount that is effective to reduce viral load or achieve a sustained viral response to therapy.

Whether a subject method is effective in treating an HCV infection may be determined by measuring viral load, or by measuring a parameter associated with HCV infection, including, but not limited to, liver fibrosis, elevations in serum transaminase levels, and necroinflammatory activity in the liver. Indicators of liver fibrosis are discussed in detail below.

The method involves administering an effective amount of a compound of formulas I-XIX, optionally in combination with an effective amount of one or more additional antiviral agents. In some embodiments, an effective amount of a compound of formulas I-XIX, and optionally one or more additional antiviral agents, is an amount that is effective to reduce viral titers to undetectable levels, e.g., to about 1000 to about 5000, to about 500 to about 1000, or to about 100 to about 500 genome copies/mL serum. In some embodiments, an effective amount of a compound of formulas I-XIX, and optionally one or more additional antiviral agents, is an amount that is effective to reduce viral load to lower than 100 genome copies/mL serum.

In some embodiments, an effective amount of a compound of formulas I-XIX, and optionally one or more additional antiviral agents, is an amount that is effective to achieve a 1.5-log, a 2-log, a 2.5-log, a 3-log, a 3.5-log, a 4-log, a 4.5-log, or a 5-log reduction in viral titer in the serum of the individual.

In many embodiments, an effective amount of a compound of formulas I-XIX, and optionally one or more additional antiviral agents, is an amount that is effective to achieve a sustained viral response, e.g., no detectable HCV RNA (e.g., less than about 500, less than about 400, less than about 200, or less than about 100 genome copies per milliliter serum) is found in the patient's serum for a period of at least about one month, at least about two months, at least about three months, at least about four months, at least about five months, or at least about six months following cessation of therapy.

As noted above, whether a subject method is effective in treating an HCV infection may be determined by measuring a parameter associated with HCV infection, such as liver fibrosis. Methods of determining the extent of liver fibrosis are discussed in detail below. In some embodiments, the level of a serum marker of liver fibrosis indicates the degree of liver fibrosis.

As one non-limiting example, levels of serum alanine aminotransferase (ALT) are measured, using standard assays. In general, an ALT level of less than about 45 international units is considered normal. In some embodiments, an effective amount of a compound of formulas I-XIX, and optionally one or more additional antiviral agents, is an amount effective to reduce ALT levels to less than about 45 IU/ml serum.

A therapeutically effective amount of a compound of formulas I-XIX, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Methods of measuring serum markers include immunological-based methods, e.g., enzyme-linked immunosorbent assays (ELISA), radioimmunoassays, and the like, using antibody specific for a given serum marker.

In many embodiments, an effective amount of a compound of formulas I-XIX and an additional antiviral agent is synergistic amount. As used herein, a "synergistic combination" or a "synergistic amount" of a compound of formulas I-XIX and an additional antiviral agent is a combined dosage that is more effective in the therapeutic or prophylactic treatment of an HCV infection than the incremental improvement in treatment outcome that could be predicted or expected from a merely additive combination of (i) the therapeutic or prophylactic benefit of the compound of formulas I-XIX when administered at that same dosage as a monotherapy and (ii) the therapeutic or prophylactic benefit of the additional antiviral agent when administered at the same dosage as a monotherapy.

In some embodiments, a selected amount of a compound of formulas I-XIX and a selected amount of an additional antiviral agent are effective when used in combination therapy for a disease, but the selected amount of the compound of formulas I-XIX and/or the selected amount of the additional antiviral agent is ineffective when used in monotherapy for the disease. Thus, the embodiments encompass (1) regimens in which a selected amount of the additional antiviral agent enhances the therapeutic benefit of a selected amount of the compound of formulas I-XIX when used in combination therapy for a disease, where the selected amount of the additional antiviral agent provides no therapeutic benefit when used in monotherapy for the disease (2) regimens in which a selected amount of the compound of formulas I-XIX enhances the therapeutic benefit of a selected amount of the additional antiviral agent when used in combination therapy for a disease, where the selected amount of the compound of formulas I-XIX provides no therapeutic benefit when used in monotherapy for the disease and (3) regimens in which a selected amount of the compound of formula I and a selected amount of the additional antiviral agent provide a therapeutic benefit when used in combination therapy for a disease, where each of the selected amounts of the compound of formulas I-XIX and the additional antiviral agent, respectively, provides no therapeutic benefit when used in monotherapy for the disease. As used herein, a "synergistically effective amount" of a compound of formulas I-XIX and an additional antiviral agent, and its grammatical equivalents, shall be understood to include any regimen encompassed by any of (1)-(3) above.

Treating Fibrosis

The embodiments provide methods for treating liver fibrosis (including forms of liver fibrosis resulting from, or associated with, HCV infection), generally involving administering a therapeutic amount of a compound of formulas I-XIX, and optionally one or more additional antiviral agents. Effective amounts of compounds of formulas I-XIX, with and without one or more additional antiviral agents, as well as dosing regimens, are as discussed below.

Whether treatment with a compound of formulas I-XIX, and optionally one or more additional antiviral agents, is effective in reducing liver fibrosis is determined by any of a number of well-established techniques for measuring liver fibrosis and liver function. Liver fibrosis reduction is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P—P) bridging; stage 4, Fibrous expansion of portal areas with marked bridging (P—P) as well as portal-central (P—C); stage 5, Marked bridging (P—P and/or P—C) with occasional nodules (incomplete cirrhosis); stage 6, Cirrhosis, probable or definite.

The benefit of anti-fibrotic therapy may also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

In some embodiments, a therapeutically effective amount of a compound of formula I, and optionally one or more additional antiviral agents, is an amount that effects a change of one unit or more in the fibrosis stage based on pre- and post-therapy liver biopsies. In particular embodiments, a therapeutically effective amount of a compound of formulas I-XIX, and optionally one or more additional antiviral agents, reduces liver fibrosis by at least one unit in the METAVIR, the Knodell, the Scheuer, the Ludwig, or the Ishak scoring system.

Secondary, or indirect, indices of liver function may also be used to evaluate the efficacy of treatment with a compound of formulas I-XIX. Morphometric computerized semi-automated assessment of the quantitative degree of liver fibrosis based upon specific staining of collagen and/or serum markers of liver fibrosis may also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score.

An effective amount of a compound of formulas I-XIX, and optionally one or more additional antiviral agents, is an amount that is effective to increase an index of liver function by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the index of liver function in an untreated individual, or to a placebo-treated individual. Those skilled in the art may readily measure such indices of liver function, using standard assay methods, many of which are commercially available, and are used routinely in clinical settings.

Serum markers of liver fibrosis may also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include $\alpha$-2-macroglobulin, haptoglobin, gamma globulin, apolipoprotein A, and gamma glutamyl transpeptidase.

A therapeutically effective amount of a compound of formulas I-XIX, and optionally one or more additional antiviral agents, is an amount that is effective to reduce a serum level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated individual, or to a placebo-treated individual. Those skilled in the art may readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve may also be used to assess the efficacy of treatment with an interferon receptor agonist and pirfenidone (or a pirfenidone analog). These include: indocyanine green clearance (ICG), galactose elimination capacity (GEC), aminopyrine breath test (ABT), antipyrine clearance, monoethylglycine-xylidide (MEG-X) clearance, and caffeine clearance.

As used herein, a "complication associated with cirrhosis of the liver" refers to a disorder that is a sequellae of decompensated liver disease, i.e., or occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

A therapeutically effective amount of a compound of formulas I-XIX, and optionally one or more additional antiviral agents, is an amount that is effective in reducing the incidence (e.g., the likelihood that an individual will develop) of a disorder associated with cirrhosis of the liver by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to an untreated individual, or to a placebo-treated individual.

Whether treatment with a compound of formulas I-XIX, and optionally one or more additional antiviral agents, is effective in reducing the incidence of a disorder associated with cirrhosis of the liver may readily be determined by those skilled in the art.

Reduction in liver fibrosis increases liver function. Thus, the embodiments provide methods for increasing liver function, generally involving administering a therapeutically effective amount of a compound of formulas I-XIX, and optionally one or more additional antiviral agents. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, may be assessed by measuring the level of these markers in the serum, using standard immunological and enzymatic assays. Splanchnic circulation and portal hemodynamics may be measured by portal wedge pressure and/or resistance using standard methods. Metabolic functions may be measured by measuring the level of ammonia in the serum.

Whether serum proteins normally secreted by the liver are in the normal range may be determined by measuring the levels of such proteins, using standard immunological and enzymatic assays. Those skilled in the art know the normal ranges for such serum proteins. The following are non-limiting examples. The normal level of alanine transaminase is about 45 IU per milliliter of serum. The normal range of aspartate transaminase is from about 5 to about 40 units per liter of serum. Bilirubin is measured using standard assays. Normal bilirubin levels are usually less than about 1.2 mg/dL. Serum albumin levels are measured using standard assays. Normal levels of serum albumin are in the range of from about 35 to about 55 g/L. Prolongation of prothrombin time is measured using standard assays. Normal prothrombin time is less than about 4 seconds longer than control.

A therapeutically effective amount of a compound of formulas I-XIX, and optionally one or more additional antiviral agents, is one that is effective to increase liver function by at least about 10%, at least about 20%, at least about 30%, at least about 40%, at least about 50%, at least about 60%, at least about 70%, at least about 80%, or more. For example, a therapeutically effective amount of a compound of formulas I-XIX, and optionally one or more additional antiviral agents, is an amount effective to reduce an elevated level of a serum marker of liver function by at least about 10%, at least about 20%, at least about 30%, at least about 40%, at least about 50%, at least about 60%, at least about 70%, at least about 80%, or more, or to reduce the level of the serum marker of liver function to within a normal range. A therapeutically effective amount of a compound of formulas I-XIX, and optionally one or more additional antiviral agents, is also an amount effective to increase a reduced level of a serum marker of liver function by at least about 10%, at least about 20%, at least about 30%, at least about 40%, at least about 50%, at least about 60%, at least about 70%, at least about 80%, or more, or to increase the level of the serum marker of liver function to within a normal range.

Type I Interferon Receptor Agonists

In any of the above-described methods, in some embodiments a Type I interferon receptor agonist is administered. Type I interferon receptor agonists include an IFN-α; an IFN-β; an IFN-tau; an IFN-ω; antibody agonists specific for a Type I interferon receptor; and any other agonist of Type I interferon receptor, including non-polypeptide agonists.

Interferon-Alpha

Any known IFN-α may be used in the embodiments. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2 C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon Tradename.

The term "IFN-α" also encompasses consensus IFN-α. Consensus IFN-αX (also referred to as "CIFN" and "IFN-con" and "consensus interferon") encompasses but is not limited to the amino acid sequences designated IFN-con1, IFN-con2 and IFN-con3 which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con1 is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. Use of CIFN is of particular interest.

Also suitable for use in the embodiments are fusion polypeptides comprising an IFN-α and a heterologous polypeptide. Suitable IFN-α fusion polypeptides include, but are not limited to, Albuferon-alpha™ (a fusion product of human albumin and IFN-α; Human Genome Sciences; see, e.g., Osborn et al. (2002) J. Pharmacol. Exp. Therap. 303: 540-548). Also suitable for use in the present embodiments are gene-shuffled forms of IFN-α. See., e.g., Masci et al. (2003) Curr. Oncol. Rep. 5:108-113.

PEGylated Interferon-Alpha

The term "IFN-α" also encompasses derivatives of IFN-α that are derivatized (e.g., are chemically modified) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

Any of the above-mentioned IFN-α polypeptides may be modified with one or more polyethylene glycol moieties, i.e., PEGylated. The PEG molecule of a PEGylated IFN-α polypeptide is conjugated to one or more amino acid side chains of the IFN-α polypeptide. In some embodiments, the PEGylated IFN-α contains a PEG moiety on only one amino acid. In other embodiments, the PEGylated IFN-α contains a PEG moiety on two or more amino acids, e.g., the IFN-α contains a PEG moiety attached to two, three, four, five, six, seven, eight, nine, or ten different amino acid residues.

IFN-α may be coupled directly to PEG (i.e., without a linking group) through an amino group, a sulfhydryl group, a hydroxyl group, or a carboxyl group.

In some embodiments, the PEGylated IFN-α is PEGylated at or near the amino terminus (N-terminus) of the IFN-α polypeptide, e.g., the PEG moiety is conjugated to the IFN-α polypeptide at one or more amino acid residues from amino acid 1 through amino acid 4, or from amino acid 5 through about 10.

In other embodiments, the PEGylated IFN-α is PEGylated at one or more amino acid residues from about 10 to about 28.

In other embodiments, the PEGylated IFN-α is PEGylated at or near the carboxyl terminus (C-terminus) of the IFN-α polypeptide, e.g., at one or more residues from amino acids 156-166, or from amino acids 150 to 155.

In other embodiments, the PEGylated IFN-α is PEGylated at one or more amino acid residues at one or more residues from amino acids 100-114.

The polyethylene glycol derivatization of amino acid residues at or near the receptor-binding and/or active site domains of the IFN-α protein may disrupt the functioning of these domains. In certain embodiments, amino acids at which PEGylation is to be avoided include amino acid residues from amino acid 30 to amino acid 40; and amino acid residues from amino acid 113 to amino acid 149.

In some embodiments, PEG is attached to IFN-α via a linking group. The linking group is any biocompatible linking group, where "biocompatible" indicates that the compound or group is non-toxic and may be utilized in vitro or in vivo without causing injury, sickness, disease, or death. PEG may be bonded to the linking group, for example, via an ether bond, an ester bond, a thiol bond or an amide bond. Suitable biocompatible linking groups include, but are not limited to, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl butanoate (SBA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine.

Methods for making succinimidyl propionate (SPA) and succinimidyl butanoate (SBA) ester-activated PEGs are described in U.S. Pat. No. 5,672,662 (Harris, et al.) and WO 97/03106.

Methods for attaching a PEG to an IFN-α polypeptide are known in the art, and any known method may be used. See, for example, by Park et al, Antimaycer Res., 1:373-376 (1981); Zaplipsky and Lee, Polyethylene Glycol Chemistry: Biotechnical and Biomedical Applications, J. M. Harris, ed., Plenum Press, NY, Chapter 21 (1992); U.S. Pat. No. 5,985,265; U.S. Pat. No. 5,672,662 (Harris, et al.) and WO 97/03106.

Pegylated IFN-α, and methods for making same, is discussed in, e.g., U.S. Pat. Nos. 5,382,657; 5,981,709; 5,985, 265; and 5,951,974. Pegylated IFN-α encompasses conjugates of PEG and any of the above-described IFN-α molecules, including, but not limited to, PEG conjugated to interferon alpha-2a (Roferon, Hoffman LaRoche, Nutley, N.J.), where PEGylated Roferon is known as Pegasys (Hoffman LaRoche); interferon alpha 2b (Intron, Schering-Plough, Madison, N.J.), where PEGylated Intron is known as PEG-Intron (Schering-Plough); interferon alpha-2c (Berofor Alpha, Boehringer Ingelheim, Ingelheim, Germany); and consensus interferon (CIFN) as defined by determination of a consensus sequence of naturally occurring interferon alphas (Infergen®, InterMune, Inc., Brisbane, Calif.), where PEGylated Infergen is referred to as PEG-Infergen.

In many embodiments, the PEG is a monomethoxyPEG molecule that reacts with primary amine groups on the IFN-α polypeptide. Methods of modifying polypeptides with monomethoxy PEG via reductive alkylation are known in the art. See, e.g., Chamow et al. (1994) Bioconj. Chem. 5:133-140.

In one non-limiting example, PEG is linked to IFN-α via an SPA linking group. SPA esters of PEG, and methods for making same, are described in U.S. Pat. No. 5,672,662. SPA linkages provide for linkage to free amine groups on the IFN-α polypeptide.

For example, a PEG molecule is covalently attached via a linkage that comprises an amide bond between a propionyl group of the PEG moiety and the epsilon amino group of a surface-exposed lysine residue in the IFN-α polypeptide. Such a bond may be formed, e.g., by condensation of an α-methoxy, omega propanoic acid activated ester of PEG (mPEGspa).

As one non-limiting example, one monopegylated CIFN conjugate preferred for use herein has a linear PEG moiety of about 30 kD attached via a covalent linkage to the CIFN polypeptide, where the covalent linkage is an amide bond between a propionyl group of the PEG moiety and the epsilon amino group of a surface-exposed lysine residue in the CIFN polypeptide, where the surface-exposed lysine residue is chosen from $lys^{31}$, $lys^{50}$, $lys^{71}$, $lys^{84}$, $lys^{121}$, $lys^{122}$, $lys^{134}$, $lys^{135}$, and $lys^{165}$, and the amide bond is formed by condensation of an α-methoxy, omega propanoic acid activated ester of PEG.

Polyethylene Glycol

Polyethylene glycol suitable for conjugation to an IFN-α polypeptide is soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally has from 1 to 8 carbons.

In many embodiments, PEG has at least one hydroxyl group, e.g., a terminal hydroxyl group, which hydroxyl group is modified to generate a functional group that is reactive with an amino group, e.g., an epsilon amino group of a lysine residue, a free amino group at the N-terminus of a polypeptide, or any other amino group such as an amino group of asparagine, glutamine, arginine, or histidine.

In other embodiments, PEG is derivatized so that it is reactive with free carboxyl groups in the IFN-α polypeptide, e.g., the free carboxyl group at the carboxyl terminus of the IFN-α polypeptide. Suitable derivatives of PEG that are reactive with the free carboxyl group at the carboxyl-terminus of IFN-α include, but are not limited to PEG-amine, and hydrazine derivatives of PEG (e.g., PEG-NH—NH$_2$).

In other embodiments, PEG is derivatized such that it comprises a terminal thiocarboxylic acid group, —COSH, which selectively reacts with amino groups to generate amide derivatives. Because of the reactive nature of the thio acid, selectivity of certain amino groups over others is achieved. For example, —SH exhibits sufficient leaving group ability in reaction with N-terminal amino group at appropriate pH conditions such that the ε-amino groups in lysine residues are protonated and remain non-nucleophilic. On the other hand, reactions under suitable pH conditions may make some of the accessible lysine residues to react with selectivity.

In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as neutral 6.5-7.5. For example, the N-terminal amino groups may be selectively modified under neutral pH conditions. However, if the reactivity of the reagent were extreme, accessible-NH$_2$ groups of lysine may also react.

The PEG may be conjugated directly to the IFN-α polypeptide, or through a linker. In some embodiments, a linker is added to the IFN-α polypeptide, forming a linker-modified IFN-α polypeptide. Such linkers provide various functionalities, e.g., reactive groups such sulfhydryl, amino, or carboxyl groups to couple a PEG reagent to the linker-modified IFN-α polypeptide.

In some embodiments, the PEG conjugated to the IFN-α polypeptide is linear. In other embodiments, the PEG conjugated to the IFN-α polypeptide is branched. Branched PEG derivatives such as those described in U.S. Pat. No. 5,643, 575, "star-PEG's" and multi-armed PEG's such as those described in Shearwater Polymers, Inc. catalog "Polyethylene Glycol Derivatives 1997-1998." Star PEGs are described in the art including, e.g., in U.S. Pat. No. 6,046,305.

PEG having a molecular weight in a range of from about 2 kDa to about 100 kDa, is generally used, where the term "about," in the context of PEG, indicates that in preparations of polyethylene glycol, some molecules will weigh more, some less, than the stated molecular weight. For example, PEG suitable for conjugation to IFN-α has a molecular weight of from about 2 kDa to about 5 kDa, from about 5 kDa to about 10 kDa, from about 10 kDa to about 15 kDa, from about 15 kDa to about 20 kDa, from about 20 kDa to about 25 kDa, from about 25 kDa to about 30 kDa, from about 30 kDa to about 40 kDa, from about 40 kDa to about 50 kDa, from about 50 kDa to about 60 kDa, from about 60 kDa to about 70 kDa, from about 70 kDa to about 80 kDa, from about 80 kDa to about 90 kDa, or from about 90 kDa to about 100 kDa.

Preparing PEG-IFN-α Conjugates

As discussed above, the PEG moiety may be attached, directly or via a linker, to an amino acid residue at or near the N-terminus, internally, or at or near the C-terminus of the IFN-α polypeptide. Conjugation may be carried out in solution or in the solid phase.

N-Terminal Linkage

Methods for attaching a PEG moiety to an amino acid residue at or near the N-terminus of an IFN-α polypeptide are known in the art. See, e.g., U.S. Pat. No. 5,985,265.

In some embodiments, known methods for selectively obtaining an N-terminally chemically modified IFN-α are used. For example, a method of protein modification by reductive alkylation which exploits differential reactivity of different types of primary amino groups (lysine versus the N-terminus) available for derivatization in a particular protein may be used. Under the appropriate reaction conditions, substantially selective derivatization of the protein at the N-terminus with a carbonyl group containing polymer is achieved. The reaction is performed at pH which allows one to take advantage of the pK$_a$ differences between the ε-amino groups of the lysine residues and that of the α-amino group of the N-terminal residue of the protein. By such selective derivatization attachment of a PEG moiety to the IFN-α is controlled: the conjugation with the polymer takes place predominantly at the N-terminus of the IFN-α and no significant modification of other reactive groups, such as the lysine side chain amino groups, occurs.

C-Terminal Linkage

N-terminal-specific coupling procedures such as described in U.S. Pat. No. 5,985,265 provide predominantly monoPEGylated products. However, the purification procedures aimed at removing the excess reagents and minor multiply PEGylated products remove the N-terminal blocked polypeptides. In terms of therapy, such processes lead to significant increases in manufacturing costs. For example, examination of the structure of the well-characterized Infergen® Alfacon-1 CIFN polypeptide amino acid sequence reveals that the clipping is approximate 5% at the carboxyl terminus and thus there is only one major C-terminal sequence. Thus, in some embodiments, N-terminally PEGylated IFN-α is not used; instead, the IFN-α polypeptide is C-terminally PEGylated.

An effective synthetic as well as therapeutic approach to obtain mono PEGylated Infergen product is therefore envisioned as follows:

A PEG reagent that is selective for the C-terminal may be prepared with or without spacers. For example, polyethylene glycol modified as methyl ether at one end and having an amino function at the other end may be used as the starting material.

Preparing or obtaining a water-soluble carbodiimide as the condensing agent may be carried out. Coupling IFN-α (e.g., Infergen® Alfacon-1 CIFN or consensus interferon) with a water-soluble carbodiimide as the condensing reagent is generally carried out in aqueous medium with a suitable buffer system at an optimal pH to effect the amide linkage. A high molecular weight PEG may be added to the protein covalently to increase the molecular weight.

The reagents selected will depend on process optimization studies. A non-limiting example of a suitable reagent is EDAC or 1-ethyl-3-(3-dimethylaminopropyl) carbodiimide. The water solubility of EDAC allows for direct addition to a reaction without the need for prior organic solvent dissolution. Excess reagent and the isourea formed as the by-product of the cross-linking reaction are both water-soluble and may easily be removed by dialysis or gel filtration. A concentrated solution of EDAC in water is prepared to facilitate the addition of a small molar amount to the reaction. The stock solution is prepared and used immediately in view of the water labile nature of the reagent. Most of the synthetic protocols in literature suggest the optimal reaction medium to be in pH range between 4.7 and 6.0. However the condensation reactions do proceed without significant losses in yields up to pH 7.5. Water may be used as solvent. In view of the contemplated use of Infergen, preferably the medium will be 2-(N-morpholino)ethane sulfonic acid buffer pre-titrated to pH between 4.7 and 6.0. However, 0.1M phosphate in the pH 7-7.5 may also be used in view of the fact that the product is in the same buffer. The ratios of PEG amine to the IFN-α molecule is optimized such that the C-terminal carboxyl residue(s) are selectively PEGylated to yield monoPEGylated derivative(s).

Even though the use of PEG amine has been mentioned above by name or structure, such derivatives are meant to be exemplary only, and other groups such as hydrazine derivatives as in PEG-NH—$NH_2$ which will also condense with the carboxyl group of the IFN-α protein, may also be used. In addition to aqueous phase, the reactions may also be conducted on solid phase. Polyethylene glycol may be selected from list of compounds of molecular weight ranging from 300-40000. The choice of the various polyethylene glycols will also be dictated by the coupling efficiency and the biological performance of the purified derivative in vitro and in vivo i.e., circulation times, anti viral activities etc.

Additionally, suitable spacers may be added to the C-terminal of the protein. The spacers may have reactive groups such as SH, $NH_2$ or COOH to couple with appropriate PEG reagent to provide the high molecular weight IFN-α derivatives. A combined solid/solution phase methodology may be devised for the preparation of C-terminal pegylated interferons. For example, the C-terminus of IFN-α is extended on a solid phase using a Gly-Gly-Cys-$NH_2$ spacer and then monopegylated in solution using activated dithiopyridyl-PEG reagent of appropriate molecular weights. Since the coupling at the C-terminus is independent of the blocking at the N-terminus, the envisioned processes and products will be beneficial with respect to cost (a third of the protein is not wasted as in N-terminal PEGylation methods) and contribute to the economy of the therapy to treat virus infection.

There may be a more reactive carboxyl group of amino acid residues elsewhere in the molecule to react with the PEG reagent and lead to monoPEGylation at that site or lead to multiple PEGylations in addition to the —COOH group at the C-terminus of the IFN-α. It is envisioned that these reactions will be minimal at best owing to the steric freedom at the C-terminal end of the molecule and the steric hindrance imposed by the carbodiimides and the PEG reagents such as in branched chain molecules. It is therefore the preferred mode of PEG modification for Infergen and similar such proteins, native or expressed in a host system, which may have blocked N-termini to varying degrees to improve efficiencies and maintain higher in vivo biological activity.

Another method of achieving C-terminal PEGylation is as follows. Selectivity of C-terminal PEGylation is achieved with a sterically hindered reagent which excludes reactions at carboxyl residues either buried in the helices or internally in IFN-α. For example, one such reagent could be a branched chain PEG ~40 kd in molecular weight and this agent could be synthesized as follows:

$OH_3C$—$(CH_2CH_2O)_n$—$CH_2CH_2NH_2$+Glutamic Acid i.e., HOCO—$CH_2CH_2CH(NH_2)$—COOH is condensed with a suitable agent e.g., dicyclohexyl carbodiimide or water-soluble EDC to provide the branched chain PEG agent $OH_3C$—$(CH_2CH_2O)_n$—$CH_2CH_2NHCOCH(NH_2)$ $CH_2OCH_3$—$(CH_2CH_2O)_n$—$CH_2CH_2NHCOCH_2$.

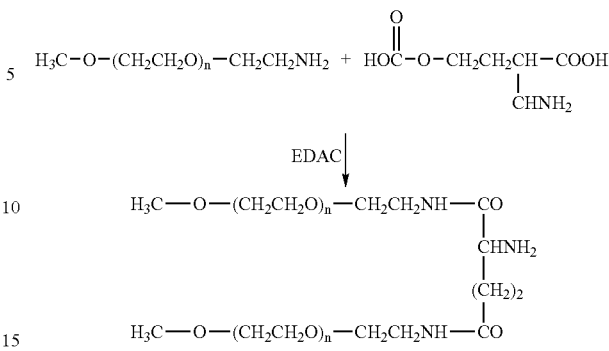

This reagent may be used in excess to couple the amino group with the free and flexible carboxyl group of IFN-α to form the peptide bond.

If desired, PEGylated IFN-α is separated from unPEGylated IFN-α using any known method, including, but not limited to, ion exchange chromatography, size exclusion chromatography, and combinations thereof. For example, where the PEG-IFN-α conjugate is a monoPEGylated IFN-α, the products are first separated by ion exchange chromatography to obtain material having a charge characteristic of monoPEGylated material (other multi-PEGylated material having the same apparent charge may be present), and then the monoPEGylated materials are separated using size exclusion chromatography.

MonoPEG (30 kD, Linear)-ylated IFN-α

PEGylated IFN-α that is suitable for use in the embodiments includes a monopegylated consensus interferon (CIFN) molecule comprised of a single CIFN polypeptide and a single polyethylene glycol (PEG) moiety, where the PEG moiety is linear and about 30 kD in molecular weight and is directly or indirectly linked through a stable covalent linkage to either the N-terminal residue in the CIFN polypeptide or a lysine residue in the CIFN polypeptide. In some embodiments, the monoPEG (30 kD, linear)-ylated IFN-α is monoPEG (30 kD, linear)-ylated consensus IFN-α.

In some embodiments, the PEG moiety is linked to either the alpha-amino group of the N-terminal residue in the CIFN polypeptide or the epsilon-amino group of a lysine residue in the CIFN polypeptide. In further embodiments, the linkage comprises an amide bond between the PEG moiety and either the alpha-amino group of the N-terminal residue or the epsilon-amino group of the lysine residue in the CIFN polypeptide. In still further embodiments, the linkage comprises an amide bond between a propionyl group of the PEG moiety and either the alpha-amino group of the N-terminal residue or the epsilon-amino group of the lysine residue in the CIFN polypeptide. In additional embodiments, the amide bond is formed by condensation of an alpha-methoxy, omega-propanoic acid activated ester of the PEG moiety and either the alpha-amino group of the N-terminal residue or the epsilon-amino group of the lysine residue in the CIFN polypeptide, thereby forming a hydrolytically stable linkage between the PEG moiety and the CIFN polypeptide.

In some embodiments, the PEG moiety is linked to the N-terminal residue in the CIFN polypeptide. In other embodiments, the PEG moiety is linked to the alpha-amino group of the N-terminal residue in the CIFN polypeptide. In further embodiments, the linkage comprises an amide bond between the PEG moiety and the alpha-amino group of the N-terminal residue in the CIFN polypeptide. In still further embodiments, the linkage comprises an amide bond between a propionyl group of the PEG moiety and the alpha-amino group of the N-terminal residue in the CIFN polypeptide. In additional embodiments, the amide bond is formed by condensation of an alpha-methoxy, omega-propanoic acid activated ester of the PEG moiety and the alpha-amino group of the N-terminal residue of the CIFN polypeptide.

In some embodiments, the PEG moiety is linked to a lysine residue in the CIFN polypeptide. In other embodiments, the PEG moiety is linked to the epsilon-amino group of a lysine residue in the CIFN polypeptide. In further embodiments, the linkage comprises an amide bond between the PEG moiety and the epsilon-amino group of the lysine group in the CIFN polypeptide. In still further embodiments, the linkage comprises an amide bond between a propionyl group of the PEG moiety and the epsilon-amino group of the lysine group in the CIFN polypeptide. In additional embodiments, the amide bond is formed by condensation of an alpha-methoxy, omega-propanoic acid activated ester of the PEG moiety and the epsilon-amino group of the lysine residue in the CIFN polypeptide.

In some embodiments, the PEG moiety is linked to a surface-exposed lysine residue in the CIFN polypeptide. In other embodiments, the PEG moiety is linked to the epsilon-amino group of a surface-exposed lysine residue in the CIFN polypeptide. In further embodiments, the linkage comprises an amide bond between the PEG moiety and the epsilon-amino group of the surface-exposed lysine residue in the CIFN polypeptide. In still further embodiments, the linkage comprises an amide bond between a propionyl group of the PEG moiety and the epsilon-amino group of the surface-exposed lysine residue in the CIFN polypeptide. In additional embodiments, the amide bond is formed by condensation of an alpha-methoxy, omega-propanoic acid activated ester of the PEG moiety and the epsilon-amino group of the surface-exposed lysine residue in the CIFN polypeptide.

In some embodiments, the PEG moiety is linked to a lysine chosen from $lys^{31}$, $lys^{50}$, $lys^{71}$, $lys^{84}$, $lys^{121}$, $lys^{121}$, $lys^{134}$, $lys^{135}$, and $lys^{165}$ of the CIFN polypeptide. In other embodiments, the PEG moiety is linked to the epsilon-amino group of a lysine chosen from $lys^{31}$, $lys^{50}$, $lys^{71}$, $lys^{84}$, $lys^{121}$, $lys^{122}$, $lys^{134}$, $lys^{135}$, and $lys^{165}$ of the CIFN polypeptide. In further embodiments, the linkage comprises an amide bond between the PEG moiety and the epsilon-amino group of the chosen lysine residue in the CIFN polypeptide. In still further embodiments, the linkage comprises an amide bond between a propionyl group of the PEG moiety and the epsilon-amino group of the chosen lysine residue in the CIFN polypeptide. In additional embodiments, the amide bond is formed by condensation of an alpha-methoxy, omega-propanoic acid activated ester of the PEG moiety and the epsilon-amino group of the chosen lysine residue in the CIFN polypeptide.

me embodiments, the PEG moiety is linked to a lysine chosen from $lys^{121}$, $lys^{134}$, $lys^{135}$, and $lys^{165}$ of the CIFN polypeptide. In other embodiments, the PEG moiety is linked to the epsilon-amino group of a lysine chosen from $lys^{121}$, $lys^{134}$, $lys^{135}$, and $lys^{165}$ of the CIFN polypeptide. In further embodiments, the linkage comprises an amide bond between the PEG moiety and the epsilon-amino group of the chosen lysine residue in the CIFN polypeptide. In still further embodiments, the linkage comprises an amide bond between a propionyl group of the PEG moiety and the epsilon-amino group of the chosen lysine residue in the CIFN polypeptide. In additional embodiments, the amide bond is formed by condensation of an alpha-methoxy, omega-propanoic acid activated ester of the PEG moiety and the epsilon-amino group of the chosen lysine residue in the CIFN polypeptide.

In connection with the above-described monopegylated CIFN molecules, the invention contemplates embodiments of each such molecule where the CIFN polypeptide is chosen from interferon alpha-$con_1$, interferon alpha-$con_2$, and interferon alpha-$con_3$, the amino acid sequences of which CIFN polypeptides are disclosed in U.S. Pat. No. 4,695,623.

Populations of IFN-α

In addition, any of the methods of the embodiments may employ a PEGylated IFN-α composition that comprises a population of monopegylated IFN-α molecules, where the population consists of one or more species of monopegylated IFN-α molecules as described above. The subject composition comprises a population of modified IFN-α polypeptides, each with a single PEG molecule linked to a single amino acid residue of the polypeptide.

In some of these embodiments, the population comprises a mixture of a first IFN-α polypeptide linked to a PEG molecule at a first amino acid residue; and at least a second IFN-α polypeptide linked to a PEG molecule at a second amino acid residue, wherein the first and second IFN-α polypeptides are the same or different, and wherein the location of the first amino acid residue in the amino acid sequence of the first IFN-α polypeptide is not the same as the location of the second amino acid residue in the second IFN-α polypeptide. As one non-limiting example, a subject composition comprises a population of PEG-modified IFN-α polypeptides, the population comprising an IFN-α polypeptide linked at its amino terminus to a linear PEG molecule; and an IFN-α polypeptide linked to a linear PEG molecule at a lysine residue.

Generally, a given modified IFN-α species represents from about 0.5% to about 99.5% of the total population of monopegylated IFNα polypeptide molecules in a population, e.g, a given modified IFN-α species represents about 0.5%, about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or about 99.5% of the total population of monopegylated IFN-α polypeptide molecules in a population. In some embodiments, a subject composition comprises a population of monopegylated IFN-α polypeptides, which population comprises at least about 70%, at least about 80%, at least about 90%, at least about 95%, or at least about 99%, IFN-α polypeptides linked to PEG at the same site, e.g., at the N-terminal amino acid.

In particular embodiments of interest, a subject composition comprises a population of monopegylated CIFN molecules, the population consisting of one or more species of molecules, where each species of molecules is characterized by a single CIFN polypeptide linked, directly or indirectly in a covalent linkage, to a single linear PEG moiety of about 30 kD in molecular weight, and where the linkage is to either a lysine residue in the CIFN polypeptide, or the N-terminal amino acid residue of the CIFN polypeptide.

The amino acid residue to which the PEG is attached is in many embodiments the N-terminal amino acid residue. In other embodiments, the PEG moiety is attached (directly or via a linker) to a surface-exposed lysine residue. In additional embodiments, the PEG moiety is attached (directly or via a linker) to a lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$ of the CIFN polypeptide. In further embodiments, the PEG moiety is attached (directly or via a linker) to a lysine residue chosen from $lys^{121}$, $lys^{134}$, $lys^{135}$, and $lys^{165}$ of the CIFN polypeptide.

As an example, a subject composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first lysine residue of a second CIFN polypeptide, where the first and second CIFN polypeptides are the same or different. A subject composition may further comprise at least one additional monopegylated CIFN polypeptide species of molecules characterized by a PEG moiety linked to a lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

In connection with each of the above-described populations of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first surface-exposed lysine residue of a second CIFN polypeptide, where the first and second CIFN polypeptides are the same or different. A subject composition may further comprise at least one additional monopegylated CIFN polypeptide species of molecules characterized by a PEG moiety linked to a surface-exposed lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another example, a subject composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first lysine residue selected from one of $lys^{31}$, $lys^{50}$, $lys^{71}$, $lys^{84}$, $lys^{121}$, $lys^{122}$, $lys^{134}$, $lys^{135}$, and $lys^{165}$ in a second CIFN polypeptide, where the first and second CIFN polypeptides are the same or different. A subject composition may further comprise a third monopegylated CIFN polypeptide species of molecules characterized by a PEG moiety linked to a second lysine residue selected from one of $lys^{31}$, $lys^{50}$, $lys^{71}$, $lys^{84}$, lys121, $lys^{122}$, $lys^{134}$, $lys^{135}$, and $lys^{165}$ in a third CIFN polypeptide, where the third CIFN polypeptide is the same or different from either of the first and second CIFN polypeptides, where the second lysine residue is located in a position in the amino acid sequence of the third CIFN polypeptide that is not the same as the position of the first lysine residue in the amino acid sequence of the second CIFN polypeptide. A subject composition may further comprise at least one additional monopegylated CIFN polypeptide species of molecules characterized by a PEG moiety linked to one of $lys^{31}$, $lys^{50}$, $lys^{71}$, $lys^{84}$, $lys^{121}$, $lys^{122}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another example, a subject composition comprises a population of monopegylated CIFN molecules, consisting of a first monopegylated CIFN polypeptide species of molecules characterized by a PEG moiety linked at the N-terminal amino acid residue of a first CIFN polypeptide, and a second monopegylated CIFN polypeptide species of molecules characterized by a PEG moiety linked to a first lysine residue selected from one of $lys^{121}$, $lys^{134}$, $lys^{135}$, and $lys^{165}$ in a second CIFN polypeptide, where the first and second CIFN polypeptides are the same or different. A subject composition may further comprise a third monopegylated CIFN polypeptide species of molecules characterized by a PEG moiety linked to a second lysine residue selected from one of $lys^{121}$, $lys^{134}$, $lys^{135}$, and $lys^{165}$ in a third CIFN polypeptide, where the third CIFN polypeptide is the same or different from either of the first and second CIFN polypeptides, where the second lysine residue is located in a position in the amino acid sequence of the third CIFN polypeptide that is not the same as the position of the first lysine residue in the amino acid sequence of the second CIFN polypeptide. A subject composition may further comprise at least one additional monopegylated CIFN polypeptide species of molecules characterized by a PEG moiety linked to one of $lys^{121}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, a subject composition comprises a population of monopegylated CIFN molecules, consisting of a first monopegylated CIFN polypeptide species of molecules characterized by a PEG moiety linked to a first lysine residue in a first CIFN polypeptide; and a second monopegylated CIFN polypeptide species of molecules characterized by a PEG moiety linked at a second lysine residue in a second CIFN polypeptide, where the first and second CIFN polypeptides are the same or different, and where the first lysine is located in a position in the amino acid sequence of the first CIFN polypeptide that is not the same as the position of the second lysine residue in the amino acid sequence of the second CIFN polypeptide. A subject composition may further comprise at least one additional monopegylated CIFN species of molecules characterized by a PEG moiety linked to a lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, a subject composition comprises a population of monopegylated CIFN molecules, consisting of a first monopegylated CIFN polypeptide species of molecules characterized by a PEG moiety linked at a first lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$ in a first CIFN polypeptide; and a second monopegylated CIFN polypeptide species of molecules characterized by a PEG moiety linked at a second lysine residue chosen from $lys^{31}$, $lys^{50}$, $lys^{71}$, $lys^{84}$, $lys^{121}$, $lys^{122}$, $lys^{134}$, $lys^{135}$, and $lys^{165}$ in a second CIFN polypeptide, where the first and second CIFN polypeptides are the same or different, and where the second lysine residue is located in a position in the amino acid sequence of the second CIFN polypeptide that is not the same as the position of the first lysine residue in the first CIFN polypeptide. The composition may further comprise at least one additional monopegylated CIFN polypeptide species of molecules characterized by a PEG moiety linked to one of $lys^{31}$, $lys^{50}$, $lys^{71}$, $lys^{84}$, $lys^{121}$, $lys^{122}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, a subject composition comprises a population of monopegylated CIFN molecules, consisting of a first monopegylated CIFN polypeptide species of molecules characterized by a PEG moiety linked at a first lysine residue chosen from $lys^{121}$, $lys^{134}$, $lys^{135}$, and $lys^{165}$ in a first CIFN polypeptide; and a second monopegylated CIFN polypeptide species of molecules characterized by a PEG moiety linked at a second lysine residue chosen from $lys^{121}$, $lys^{134}$, $lys^{135}$, and $lys^{165}$ in a second CIFN polypeptide, where the first and second CIFN polypeptides are the same or different, and where the second lysine residue is located in a position in the amino acid sequence of the second CIFN polypeptide that is not the same as the position of the first lysine residue in the first CIFN polypeptide. The composition may further comprise at least one additional monopegylated CIFN polypeptide species of molecules characterized by a PEG moiety linked to one of $lys^{121}$, $lys^{134}$, $lys^{135}$, and $lys^{165}$, where the location of the linkage site in each additional monopegylated CIFN polypeptide species is not the same as the location of the linkage site in any other species. In all species in this example, the PEG moiety is a linear PEG moiety having an average molecular weight of about 30 kD.

As another non-limiting example, a subject composition comprises a monopegylated population of CIFN molecules, consisting of a first monopegylated CIFN polypeptide species of molecules characterized by a PEG moiety linked to a first surface-exposed lysine residue in a first CIFN polypeptide; and a second monopegylated CIFN polypeptide species of molecules characterized by a PEG moiety linked at a second surface-exposed lysine residue in a second CIFN polypeptide, where the first and second CIFN polypeptides are the same or different, and where the first surface-exposed lysine is located in a position in the amino acid sequence of the first CIFN polypeptide that is not the same as the position of the second surface-exposed lysine residue in the amino acid sequence of the second CIFN polypeptide. A subject composition may further comprise at least one additional monopegylated CIFN species of molecules characterized by a PEG moiety linked to a surface-exposed lysine residue in the CIFN polypeptide, where the location of the linkage site in each additional monopegylated CIFN polypeptide species is not the same as the location of the linkage site in any other species. In all species in this example, the PEG moiety is a linear PEG moiety having an average molecular weight of about 30 kD.

In connection with each of the above-described populations of monopegylated CIFN molecules, the invention contemplates embodiments where the molecules in each such population comprise a CIFN polypeptide chosen from interferon alpha-$con_1$, interferon alpha-$con_2$, and interferon alpha-$con_3$.

Certain embodiments further feature a product that is produced by the process of reacting CIFN polypeptide with a succinimidyl ester of alpha-methoxy, omega-propionylpoly (ethylene glycol) (mPEGspa) that is linear and about 30 kD in molecular weight, where the reactants are initially present at a molar ratio of about 1:1 to about 1:5 CIFN:mPEGspa, and where the reaction is conducted at a pH of about 7 to about 9, followed by recovery of the monopegylated CIFN product of the reaction. In one embodiment, the reactants are initially present at a molar ratio of about 1:3 CIFN:mPEGspa and the reaction is conducted at a pH of about 8. In another embodiment where the product is generated by a scaled-up procedure needed for toxicological and clinical investigations, the reactants are initially present in a molar ratio of 1:2 CIFN:mPEG-spa and the reaction is conducted at a pH of about 8.0.

In connection with the above-described product-by-process, the invention contemplates embodiments where the CIFN reactant is chosen from interferon alpha-$con_1$, interferon alpha-$con_2$, and interferon alpha-$con_3$.

IFN-β

The term interferon-beta ("IFN-β") includes IFN-β polypeptides that are naturally occurring; non-naturally-occurring IFN-β polypeptides; and analogs of naturally occurring or non-naturally occurring IFN-β that retain antiviral activity of a parent naturally-occurring or non-naturally occurring IFN-β.

Any of a variety of beta interferons may be delivered by the continuous delivery method of the present embodiments. Suitable beta interferons include, but are not limited to, naturally-occurring IFN-β; IFN-β1a, e.g., Avonex® (Biogen, Inc.), and Rebif® (Serono, SA); IFN-β1b (Betaseron®; Berlex); and the like.

The IFN-β formulation may comprise an N-blocked species, wherein the N-terminal amino acid is acylated with an acyl group, such as a formyl group, an acetyl group, a malonyl group, and the like. Also suitable for use is a consensus IFN-β.

IFN-β polypeptides may be produced by any known method. DNA sequences encoding IFN-β may be synthesized using standard methods. In many embodiments, IFN-β polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-β is "recombinant IFN-β". Where the host cell is a bacterial host cell, the IFN-β is modified to comprise an N-terminal methionine.

It is to be understood that IFN-β as described herein may comprise one or more modified amino acid residues, e.g., glycosylations, chemical modifications, and the like.

IFN-tau

The term interferon-tau includes IFN-tau polypeptides that are naturally occurring; non-naturally-occurring IFN-tau polypeptides; and analogs of naturally occurring or non-naturally occurring IFN-tau that retain antiviral activity of a parent naturally-occurring or non-naturally occurring IFN-tau.

Suitable tau interferons include, but are not limited to, naturally-occurring IFN-tau; Tauferon® (Pepgen Corp.); and the like.

IFN-tau may comprise an amino acid sequence as set forth in any one of GenBank Accession Nos. P15696; P56828; P56832; P56829; P56831; Q29429; Q28595; Q28594; S08072; Q08071; Q08070; Q08053; P56830; P28169; P28172; and P28171. The sequence of any known IFN-tau polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The IFN-tau formulation may comprise an N-blocked species, wherein the N-terminal amino acid is acylated with an acyl group, such as a formyl group, an acetyl group, a malonyl group, and the like. Also suitable for use is a consensus IFN-tau.

IFN-tau polypeptides may be produced by any known method. DNA sequences encoding IFN-tau may be synthesized using standard methods. In many embodiments, IFN-tau polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-tau is "recombinant IFN-tau." Where the host cell is a bacterial host cell, the IFN-tau is modified to comprise an N-terminal methionine.

It is to be understood that IFN-tau as described herein may comprise one or more modified amino acid residues, e.g., glycosylations, chemical modifications, and the like.

IFN-ω

The term interferon-omega ("IFN-ω") includes IFN-ω polypeptides that are naturally occurring; non-naturally-occurring IFN-ω polypeptides; and analogs of naturally occurring or non-naturally occurring IFN-ω that retain antiviral activity of a parent naturally-occurring or non-naturally occurring IFN-ω.

Any known omega interferon may be delivered by the continuous delivery method of the present embodiments. Suitable IFN-ω include, but are not limited to, naturally-occurring IFN-ω; recombinant IFN-ω, e.g., Biomed 510 (BioMedicines); and the like.

IFN-ω may comprise an amino acid sequence as set forth in GenBank Accession No. NP_002168; or AAA70091. The sequence of any known IFN-ω polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

The IFN-ω formulation may comprise an N-blocked species, wherein the N-terminal amino acid is acylated with an acyl group, such as a formyl group, an acetyl group, a malonyl group, and the like. Also suitable for use is a consensus IFN-ω.

IFN-ω polypeptides may be produced by any known method. DNA sequences encoding IFN-ω may be synthesized using standard methods. In many embodiments, IFN-ω polypeptides are the products of expression of manufactured DNA sequences transformed or transfected into bacterial hosts, e.g., *E. coli*, or in eukaryotic host cells (e.g., yeast; mammalian cells, such as CHO cells; and the like). In these embodiments, the IFN-ω is "recombinant IFN-ω." Where the host cell is a bacterial host cell, the IFN-ω is modified to comprise an N-terminal methionine.

It is to be understood that IFN-ω as described herein may comprise one or more modified amino acid residues, e.g., glycosylations, chemical modifications, and the like.

Type III Interferon Receptor Agonists

In any of the above-described methods, the interferon receptor agonist is in some embodiments an agonist of a Type III interferon receptor (e.g., "a Type III interferon agonist"). Type III interferon agonists include an IL-28b polypeptide; and IL-28a polypeptide; and IL-29 polypeptide; antibody specific for a Type III interferon receptor; and any other agonist of Type III interferon receptor, including non-polypeptide agonists.

IL-28A, IL-28B, and IL-29 (referred to herein collectively as "Type III interferons" or "Type III IFNs") are described in Sheppard et al. (2003) *Nature* 4:63-68. Each polypeptide binds a heterodimeric receptor consisting of IL-10 receptor β chain and an IL-28 receptor α. Sheppard et al. (2003), supra. The amino acid sequences of IL-28A, IL-28B, and IL-29 are found under GenBank Accession Nos. NP_742150, NP_742151, and NP_742152, respectively.

The amino acid sequence of a Type III IFN polypeptide may be altered in various ways known in the art to generate targeted changes in sequence. A variant polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. Also included are modifications of glycosylation, e.g. those made by modifying the glycosylation patterns of a polypeptide during its synthesis and processing or in further processing steps; e.g. by exposing the polypeptide to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Included in the embodiments are polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) J. Biol. Chem. 275:23783-23789). Analogs may be used that include residues other than naturally occurring L-amino acids, e.g. D-amino acids or non-naturally occurring synthetic amino acids. The protein may be pegylated to enhance stability. The polypeptides may be fused to albumin.

The polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines may be used to make thioethers, histidines for linking to a metal ion complex, carboxyl groups for forming amides or esters, amino groups for forming amides, and the like.

Type II Interferon Receptor Agonists

Type II interferon receptor agonists include any naturally-occurring or non-naturally-occurring ligand of a human Type II interferon receptor which binds to and causes signal transduction via the receptor. Type II interferon receptor agonists include interferons, including naturally-occurring interferons, modified interferons, synthetic interferons, pegylated interferons, fusion proteins comprising an interferon and a heterologous protein, shuffled interferons; antibody specific for an interferon receptor; non-peptide chemical agonists; and the like.

A specific example of a Type II interferon receptor agonist is IFN-γ and variants thereof. While the present embodiments exemplify use of an IFN-γ polypeptide, it will be readily apparent that any Type II interferon receptor agonist may be used in a subject method.

Interferon-Gamma

The nucleic acid sequences encoding IFN-γ polypeptides may be accessed from public databases, e.g., Genbank, journal publications, etc. While various mammalian IFN-γ polypeptides are of interest, for the treatment of human disease, generally the human protein will be used. Human IFN-γ coding sequence may be found in Genbank, accession numbers X13274; V00543; and NM_000619. The corresponding genomic sequence may be found in Genbank, accession numbers J00219; M37265; and V00536. See, for example. Gray et al. (1982) Nature 295:501 (Genbank X13274); and Rinderknecht et al. (1984) J.B.C. 259:6790.

IFN-γ1b (Actimmune®; human interferon) is a single-chain polypeptide of 140 amino acids. It is made recombinantly in E. coli and is unglycosylated. Rinderknecht et al. (1984) J. Biol. Chem. 259:6790-6797. Recombinant IFN-γ as discussed in U.S. Pat. No. 6,497,871 is also suitable for use herein.

The IFN-γ to be used in the methods of the present embodiments may be any of natural IFN-γs, recombinant IFN-γs and the derivatives thereof so far as they have an IFN-γ activity, particularly human IFN-γ activity. Human IFN-γ exhibits the antiviral and anti-proliferative properties characteristic of the interferons, as well as a number of other immunomodulatory activities, as is known in the art. Although IFN-γ is based on the sequences as provided above, the production of the protein and proteolytic processing may result in processing variants thereof. The unprocessed sequence provided by Gray et al., supra, consists of 166 amino acids (aa). Although the recombinant IFN-γ produced in E. coli was originally believed to be 146 amino acids, (commencing at amino acid 20) it was subsequently found that native human IFN-γ is cleaved after residue 23, to produce a 143 aa protein, or 144 aa if the terminal methionine is present, as required for expression in bacteria. During purification, the mature protein may additionally be cleaved at the C terminus after reside 162 (referring to the Gray et al. sequence), resulting in a protein of 139 amino acids, or 140 amino acids if the initial methionine is present, e.g. if required for bacterial expression. The N-terminal methionine is an artifact encoded by the mRNA translational "start" signal AUG that, in the particular case of E. coli expression is not processed away. In other microbial systems or eukaryotic expression systems, methionine may be removed.

For use in the subject methods, any of the native IFN-γ peptides, modifications and variants thereof, or a combination of one or more peptides may be used. IFN-γ peptides of interest include fragments, and may be variously truncated at the carboxyl terminus relative to the full sequence. Such fragments continue to exhibit the characteristic properties of human gamma interferon, so long as amino acids 24 to about 149 (numbering from the residues of the unprocessed polypeptide) are present. Extraneous sequences may be substituted for the amino acid sequence following amino acid 155 without loss of activity. See, for example, U.S. Pat. No. 5,690,925. Native IFN-γ moieties include molecules variously extending from amino acid residues 24-150; 24-151, 24-152; 24-153, 24-155; and 24-157. Any of these variants, and other variants known in the art and having IFN-γ activity, may be used in the present methods.

The sequence of the IFN-γ polypeptide may be altered in various ways known in the art to generate targeted changes in sequence. A variant polypeptide will usually be substantially similar to the sequences provided herein, i.e., will differ by at least one amino acid, and may differ by at least two but not more than about ten amino acids. The sequence changes may be substitutions, insertions or deletions. Scanning mutations that systematically introduce alanine, or other residues, may be used to determine key amino acids. Specific amino acid substitutions of interest include conservative and non-conservative changes. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that may or may not alter the primary amino acid sequence include chemical derivatization of polypeptides, e.g., acetylation, or carboxylation; changes in amino acid sequence that introduce or remove a glycosylation site; changes in amino acid sequence that make the protein susceptible to PEGylation; and the like. One embodiment contemplates the use of IFN-γ variants with one or more non-naturally occurring glycosylation and/or pegylation sites that are engineered to provide glycosyl- and/or PEG-derivatized polypeptides with reduced serum clearance, such as the IFN-γ polypeptide variants described in International Patent Publication No. WO 01/36001. Also included are modifications of glycosylation, e.g., those made by modifying the glycosylation patterns of a polypeptide during its synthesis and processing or in further processing steps; e.g., by exposing the polypeptide to enzymes that affect glycosylation, such as mammalian glycosylating or deglycosylating enzymes. Also embraced are sequences that have phosphorylated amino acid residues, e.g., phosphotyrosine, phosphoserine, or phosphothreonine.

Included in the embodiments are polypeptides that have been modified using ordinary chemical techniques so as to improve their resistance to proteolytic degradation, to optimize solubility properties, or to render them more suitable as a therapeutic agent. For examples, the backbone of the peptide may be cyclized to enhance stability (see Friedler et al. (2000) *J. Biol. Chem.* 275:23783-23789). Analogs may be used that include residues other than naturally occurring L-amino acids, e.g., D-amino acids or non-naturally occurring synthetic amino acids. The protein may be pegylated to enhance stability.

The polypeptides may be prepared by in vitro synthesis, using conventional methods as known in the art, by recombinant methods, or may be isolated from cells induced or naturally producing the protein. The particular sequence and the manner of preparation will be determined by convenience, economics, purity required, and the like. If desired, various groups may be introduced into the polypeptide during synthesis or during expression, which allow for linking to other molecules or to a surface. Thus cysteines may be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Pirfenidone and Analogs Thereof

Pirfenidone (5-methyl-1-phenyl-2-(1H)-pyridone) and specific pirfenidone analogs are disclosed for the treatment of fibrotic conditions. A "fibrotic condition" is one that is amenable to treatment by administration of a compound having anti-fibrotic activity.

Pirfenidone

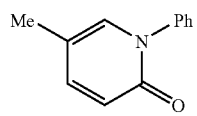

Pirfenidone analogs

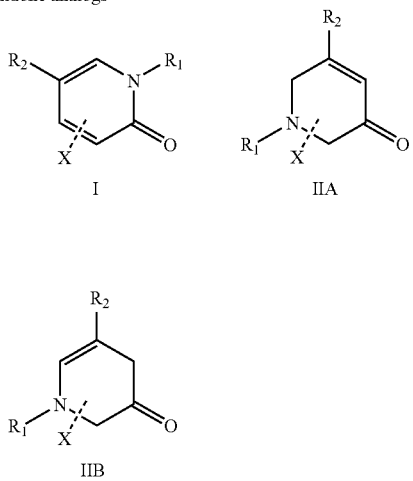

Descriptions for Substituents $R_1$, $R_2$, X $R_1$: carbocyclic (saturated and unsaturated), heterocyclic (saturated or unsaturated), alkyls (saturated and unsaturated). Examples include phenyl, benzyl, pyrimidyl, naphthyl, indolyl, pyrrolyl, furyl, thienyl, imidazolyl, cyclohexyl, piperidyl, pyrrolidyl, morpholinyl, cyclohexenyl, butadienyl, and the like.

$R_1$ may further include substitutions on the carbocyclic or heterocyclic moieties with substituents such as halogen, nitro, amino, hydroxyl, alkoxy, carboxyl, cyano, thio, alkyl, aryl, heteroalkyl, heteroaryl and combinations thereof, for example, 4-nitrophenyl, 3-chlorophenyl, 2,5-dinitrophenyl, 4-methoxyphenyl, 5-methyl-pyrrolyl, 2,5-dichlorocyclohexyl, guanidinyl-cyclohexenyl and the like.

$R_2$: alkyl, carbocyclic, aryl, heterocyclic. Examples include: methyl, ethyl, propyl, isopropyl, phenyl, 4-nitrophenyl, thienyl and the like.

X: may be any number (from 1 to 3) of substituents on the carbocyclic or heterocyclic ring. The substituents may be the same or different. Substituents may include hydrogen, alkyl, heteroalkyl, aryl, heteroaryl, halo, nitro, carboxyl, hydroxyl, cyano, amino, thio, alkylamino, haloaryl and the like.

The substituents may be optionally further substituted with 1-3 substituents from the group consisting of alkyl, aryl, nitro, alkoxy, hydroxyl and halo groups.

Examples include: methyl, 2,3-dimethyl, phenyl, p-tolyl, 4-chlorophenyl, 4-nitrophenyl, 2,5-dichlorophenyl, furyl, thienyl and the like.

Specific Examples include the compounds listed in Table 1:

TABLE 1

| IIA | IIB |
|---|---|
| 5-Methyl-1-(2'-pyridyl)-2-(1H)pyridine, | 6-Methyl-1-phenyl-3-(1H)pyridone, |
| 6-Methyl-1-phenyl-2-(1H)pyridone, | 5-Methyl-1-p-tolyl-3-(1H)pyridone, |
| 5-Methyl-3-phenyl-1-(2'-thienyl)-2-(1H)pyridone, | 5-Methyl-1-(2'-naphthyl)-3-(1H)pyridone, |
| 5-Methyl-1-(2'-naphthyl)-2-(1H)pyridone, | 5-Methyl-1-phenyl-3-(1H)pyridone, |
| 5-Methyl-1-p-tolyl-2-(1H)pyridone, | 5-Methyl-1-(5'-quinolyl)-3-(1H)pyridone, |

TABLE 1-continued

| IIA | IIB |
|---|---|
| 5-Methyl-1-(1'naphthyl)-2-(1H)pyridone, | 5-Ethyl-1-phenyl-3-(1H)pyridone, |
| 5-Ethyl-1-phenyl-2-(1H)pyridone, | 5-Methyl-1-(4'-methoxyphenyl)-3-(1H)pyridone, |
| 5-Methyl-1-(5'-quinolyl)-2-(1H)pyridone, | 4-Methyl-1-phenyl-3-(1H)pyridone, |
| 5-Methyl-1-(4'-quinolyl)-2-(1H)pyridone, | 5-Methyl-1-(3'-pyridyl)-3-(1H)pyridone, |
| 5-Methyl-1-(4'-pyridyl)-2-(1H)pyridone, | 5-Methyl-1-(2'-Thienyl)-3-(1H)pyridone, |
| 3-Methyl-1-phenyl-2-(1H)pyridone, | 5-Methyl-1-(2'-pyridyl)-3-(1H)pyridone, |
| 5-Methyl-1-(4'-methoxyphenyl)-2-(1H)pyridone, | 5-Methyl-1-(2'-quinolyl)-3-(1H)pyridone, |
| 1-Phenyl-2-(1H)pyridone, | 1-Phenyl-3-(1H)pyridine, |
| 1,3-Diphenyl-2-(1H)pyridone, | 1-(2'-Furyl)-5-methyl-3-(1H)pyridone, |
| 1,3-Diphenyl-5-methyl-2-(1H)pyridone, | 1-(4'-ChIorophenyl)-5-methyl-3-(1H)pyridine. |
| 5-Methyl-1-(3'-trifluoromethylphenyl)-2-(1H)-pyridone, | |
| 3-Ethyl-1-phenyl-2-(1H)pyridone, | |
| 5-Methyl-1-(3'-pyridyl)-2-(1H)pyridone, | |
| 5-Methyl-1-(3-nitrophenyl)-2-(1H)pyridone, | |
| 3-(4'-Chlorophenyl)-5-Methyl-1-phenyl-2-(1H)pyridone, | |
| 5-Methyl-1-(2'-Thienyl)-2-(1H)pyridone, | |
| 5-Methyl-1-(2'-thiazolyl)-2-(1H)pyridone, | |
| 3,6-Dimethyl-1-phenyl-2-(1H)pyridone, | |
| 1-(4'Chlorophenyl)-5-Methyl-2-(1H)pyridone, | |
| 1-(2'-Imidazolyl)-5-Methyl-2-(1H)pyridone, | |
| 1-(4'-Nitrophenyl)-2-(1H)pyridone, | |
| 1-(2'-Furyl)-5-Methyl-2-(1H)pyridone, | |
| 1-Phenyl-3-(4'-chlorophenyl)-2-(1H)pyridine. | |

U.S. Pat. Nos. 3,974,281; 3,839,346; 4,042,699; 4,052,509; 5,310,562; 5,518,729; 5,716,632; and 6,090,822 describe methods for the synthesis and formulation of pirfenidone and specific pirfenidone analogs in pharmaceutical compositions suitable for use in the methods of the present embodiments.

Thymosin-α

Thymosin-α (Zadaxin™; available from SciClone Pharmaceuticals, Inc., San Mateo, Calif.) is a synthetic form of thymosin alpha 1, a hormone found naturally in the circulation and produced by the thymus gland. Thymosin-α increases activity of T cells and NK cells. Zadaxin™ formulated for subcutaneous injection is a purified sterile lyophilized preparation of chemically synthesized thymosin alpha 1 identical to human thymosin alpha 1. Thymosin alpha 1 is an acetylated polypeptide with the following sequence: Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH, and having a molecular weight of 3,108 daltons. The lyophilized preparation contains 1.6 mg synthetic thymosin-α, 50 mg mannitol, and sodium phosphate buffer to adjust the pH to 6.8.

Ribavirin

Ribavirin, 1-β-D-ribofuranosyl-1H-1,2,4-triazole-3-carboxamide, is a nucleoside analog available from ICN Pharmaceuticals, Inc., Costa Mesa, Calif., and is described in the Merck Index, compound No. 8199, Eleventh Edition. Its manufacture and formulation is described in U.S. Pat. No. 4,211,771. The embodiments also contemplate use of derivatives of ribavirin (see, e.g., U.S. Pat. No. 6,277,830). The ribavirin may be administered orally in capsule or tablet form. Of course, other types of administration of ribavirin, as they become available are contemplated, such as by nasal spray, transdermally, by suppository, by sustained release dosage form, etc. Any form of administration will work so long as the proper dosages are delivered without destroying the active ingredient.

Ribavirin is generally administered in an amount ranging from about 400 mg to about 1200 mg, from about 600 mg to about 1000 mg, or from about 700 to about 900 mg per day. In some embodiments, ribavirin is administered throughout the entire course of NS3 inhibitor therapy.

Levovirin

Levovirin is the L-enantiomer of ribavirin, and exhibits the property of enhancing a Th1 immune response over a Th2 immune response. Levovirin is manufactured by ICN Pharmaceuticals.

Levovirin has the following structure:

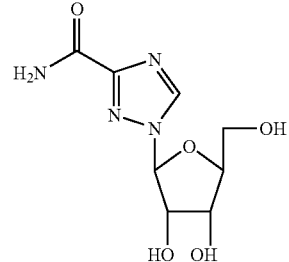

Viramidine

Viramidine is a 3-carboxamidine derivative of ribavirin, and acts as a prodrug of ribavirin. It is efficiently converted to ribavirin by adenosine deaminases.

Viramidine has the following structure:

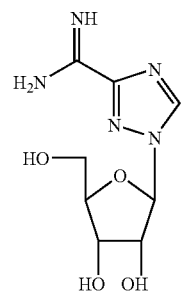

Nucleoside Analogs

Nucleoside analogs that are suitable for use in a subject combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2': 4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, $O^2,O^2$-anhydro-β-L-arabinofuranosyluracil, 2'-deoxy-β-L-uridine, 3',5'-Di-O-benzoyl-2'-deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

TNF Antagonists

In some embodiments, a subject method comprises administering an effective amount of a NS3 inhibitor and an effective amount of a tumor necrosis factor-α (TNF-α) antagonist. Suitable TNF-α antagonists for use herein include agents that decrease the level of TNF-α synthesis, agents that block or inhibit the binding of TNF-α to a TNF-α receptor (TNFR), and agents that block or inhibit TNFR-mediated signal transduction. Unless otherwise expressly stated, every reference to a "TNF-α antagonist" or "TNF antagonist" herein will be understood to mean a TNF-α antagonist other than pirfenidone or a pirfenidone analog.

As used herein, the terms "TNF receptor polypeptide" and "TNFR polypeptide" refer to polypeptides derived from TNFR (from any species) which are capable of binding TNF. Two distinct cell-surface TNFRs have described: Type II TNFR (or p75 TNFR or TNFRII) and Type I TNFR (or p55 TNFR or TNFRI). The mature full-length human p75 TNFR is a glycoprotein having a molecular weight of about 75-80 kilodaltons (kD). The mature full-length human p55 TNFR is a glycoprotein having a molecular weight of about 55-60 kD. Exemplary TNFR polypeptides are derived from TNFR Type I and/or TNFR type II. Soluble TNFR includes p75 TNFR polypeptide; fusions of p75 TNFR with heterologous fusion partners, e.g., the Fc portion of an immunoglobulin.

TNFR polypeptide may be an intact TNFR or a suitable fragment of TNFR. U.S. Pat. No. 5,605,690 provides examples of TNFR polypeptides, including soluble TNFR polypeptides, appropriate for use in the present embodiments. In many embodiments, the TNFR polypeptide comprises an extracellular domain of TNFR. In some embodiments, the TNFR polypeptide is a fusion polypeptide comprising an extracellular domain of TNFR linked to a constant domain of an immunoglobulin molecule. In other embodiments, the TNFR polypeptide is a fusion polypeptide comprising an extracellular domain of the p75 TNFR linked to a constant domain of an IgG1 molecule. In some embodiments, when administration to humans is contemplated, an Ig used for fusion proteins is human, e.g., human IgG1.

Monovalent and multivalent forms of TNFR polypeptides may be used in the present embodiments. Multivalent forms of TNFR polypeptides possess more than one TNF binding site. In some embodiments, the TNFR is a bivalent, or dimeric, form of TNFR. For example, as described in U.S. Pat. No. 5,605,690 and in Mohler et al., 1993, J. Immunol., 151:1548-1561, a chimeric antibody polypeptide with TNFR extracellular domains substituted for the variable domains of either or both of the immunoglobulin heavy or light chains would provide a TNFR polypeptide for the present embodiments. Generally, when such a chimeric TNFR:antibody polypeptide is produced by cells, it forms a bivalent molecule through disulfide linkages between the immunoglobulin domains. Such a chimeric TNFR:antibody polypeptide is referred to as TNFR:Fc.

In one embodiment, a subject method involves administration of an effective amount of the soluble TNFR ENBREL®. ENBREL® is a dimeric fusion protein consisting of the extracellular ligand-binding portion of the human 75 kilodalton (p75) TNFR linked to the Fc portion of human IgG1. The Fc component of ENBREL® contains the CH2 domain, the CH3 domain and hinge region, but not the CH1 domain of IgG1. ENBREL® is produced in a Chinese hamster ovary (CHO) mammalian cell expression system. It consists of 934 amino acids and has an apparent molecular weight of approximately 150 kilodaltons. Smith et al. (1990) *Science* 248:1019-1023; Mohler et al. (1993) *J. Immunol.* 151:1548-1561; U.S. Pat. No. 5,395,760; and U.S. Pat. No. 5,605,690.

Also suitable for use are monoclonal antibodies that bind TNF-α. Monoclonal antibodies include "humanized" mouse monoclonal antibodies; chimeric antibodies; monoclonal antibodies that are at least about 80%, at least about 90%, at least about 95%, or 100% human in amino acid sequence; and the like. See, e.g., WO 90/10077; WO 90/04036; and WO 92/02190. Suitable monoclonal antibodies include antibody fragments, such as Fv, F(ab')$_2$ and Fab; synthetic antibodies; artificial antibodies; phage display antibodies; and the like.

Examples of suitable monoclonal antibodies include Infliximab (REMICADE®, Centocor); and Adalimumab (HUMIRA™, Abbott). REMICADE® is a chimeric monoclonal anti-TNF-α antibody that includes about 25% mouse amino acid sequence and about 75% human amino acid sequence. REMICADE® comprises a variable region of a mouse monoclonal anti-TNF-α antibody fused to the constant region of a human IgG1. Elliott et al. (1993) *Arthritis Rheum.* 36:1681-1690; Elliott et al. (1994) *Lancet* 344:1105-1110; Baert et al. (1999) *Gastroenterology* 116:22-28. HUMIRA™ is a human, full-length IgG1 monoclonal antibody that was identified using phage display technology. Piascik (2003) *J. Am. Pharm. Assoc.* 43:327-328.

Also included in the term "TNF antagonist," and therefore suitable for use in a subject method, are stress-activated protein kinase (SAPK) inhibitors. SAPK inhibitors are known in the art, and include, but are not limited to 2-alkyl imidazoles disclosed in U.S. Pat. Nos. 6,548,520; 1,4,5-substituted imidazole compounds disclosed in U.S. Pat. Nos. 6,489,325; 1,4,5-substituted imidazole compounds disclosed in U.S. Pat. No. 6,569,871; heteroaryl aminophenyl ketone compounds disclosed in Published U.S. Patent Application No. 2003/0073832; pyridyl imidazole compounds disclosed in U.S. Pat. No. 6,288,089; and heteroaryl aminobenzophenones disclosed in U.S. Pat. No. 6,432,962. Also of interest are compounds disclosed in U.S. Patent Application Publication No. 2003/0149041; and U.S. Pat. No. 6,214,854. A stress-activated protein kinase is a member of a family of mitogen-activated protein kinases which are activated in response to stress stimuli. SAPK include, but are not limited to, p38 (Lee et al. (1994) *Nature* 372:739) and c-jun N-terminal kinase (JNK).

Methods to assess TNF antagonist activity are known in the art and exemplified herein. For example, TNF antagonist activity may be assessed with a cell-based competitive binding assay. In such an assay, radiolabeled TNF is mixed with serially diluted TNF antagonist and cells expressing cell membrane bound TNFR. Portions of the suspension are centrifuged to separate free and bound TNF and the amount of radioactivity in the free and bound fractions determined. TNF antagonist activity is assessed by inhibition of TNF binding to the cells in the presence of the TNF antagonist.

As another example, TNF antagonists may be analyzed for the ability to neutralize TNF activity in vitro in a bioassay using cells susceptible to the cytotoxic activity of TNF as target cells. In such an assay, target cells, cultured with TNF, are treated with varying amounts of TNF antagonist and subsequently are examined for cytolysis. TNF antagonist activity is assessed by a decrease in TNF-induced target cell cytolysis in the presence of the TNF antagonist.

NS5B Inhibitors

Some embodiments provides a method comprising administering an effective amount of a subject NS3 inhibitor and an effective amount of an HCV non-structural protein-5 (NS5; RNA-dependent RNA polymerase) inhibitor to an HCV patient in need thereof. Suitable NS5B inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) *Antimicrob. Agents Chemother.* 47:2674-2681; a benzothiadiazine compound as disclosed in Dhanak et al. (2002) *J. Biol. Chem.* 277(41):38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

Of particular interest in many embodiments are NS5 inhibitors that are specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

Additional Antiviral Agents

Additional antiviral therapeutic agents that may be administered in combination with a subject NS3 inhibitor compound include, but are not limited to, inhibitors of inosine monophosphate dehydrogenase (IMPDH); ribozymes that are complementary to viral nucleotide sequences; antisense RNA inhibitors; and the like.

IMPDH Inhibitors

IMPDH inhibitors that are suitable for use in a subject combination therapy include, but are not limited to, VX-497 ((S)—N-3-[3-(3-methoxy-4-oxazol-5-yl-phenyl)-ureido]-benzyl-carbamic acid tetrahydrofuran-3-yl-ester); Vertex Pharmaceuticals; see, e.g., Markland et al. (2000) *Antimicrob. Agents Chemother.* 44:859-866); ribavirin; levovirin (Ribapharm; see, e.g., Watson (2002) *Curr Opin Investig Drugs* 3(5):680-3); viramidine (Ribapharm); and the like.

Ribozyme and Antisense

Ribozyme and antisense antiviral agents that are suitable for use in a subject combination therapy include, but are not limited to, ISIS14803 (ISIS Pharmaceuticals/Elan Corporation; see, e.g., Witherell (2001) *Curr Opin Investig Drugs.* 2(11):1523-9); Heptazyme™; and the like.

In some embodiments, an additional antiviral agent is administered during the entire course of NS3 inhibitor compound treatment. In other embodiments, an additional antiviral agent is administered for a period of time that is overlapping with that of the NS3 inhibitor compound treatment, e.g., the additional antiviral agent treatment may begin before the NS3 inhibitor compound treatment begins and end before the NS3 inhibitor compound treatment ends; the additional antiviral agent treatment may begin after the NS3 inhibitor compound treatment begins and end after the NS3 inhibitor compound treatment ends; the additional antiviral agent treatment may begin after the NS3 inhibitor compound treatment begins and end before the NS3 inhibitor compound treatment ends; or the additional antiviral agent treatment may begin before the NS3 inhibitor compound treatment begins and end after the NS3 inhibitor compound treatment ends.

Dosages, Formulations, and Routes of Administration

In the subject methods, the active agent(s) (e.g., compound of formula I, and optionally one or more additional antiviral agents) may be administered to the host using any convenient means capable of resulting in the desired therapeutic effect. Thus, the agent may be incorporated into a variety of formulations for therapeutic administration. More particularly, the agents of the present embodiments may be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations

The above-discussed active agent(s) may be formulated using well-known reagents and methods. Compositions are provided in formulation with a pharmaceutically acceptable excipient(s). A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3 ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an agent is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations may be stored over extended periods of time, even at ambient temperatures.

As such, administration of the agents may be achieved in various ways, including oral, buccal, rectal, parenteral, intraperitoneal, intradermal, subcutaneous, intramuscular, transdermal, intratracheal, etc., administration. In many embodiments, administration is by bolus injection, e.g., subcutaneous bolus injection, intramuscular bolus injection, and the like.

The pharmaceutical compositions of the present embodiments may be administered orally, parenterally or via an implanted reservoir. Oral administration or administration by injection are preferred.

Subcutaneous administration of a pharmaceutical composition of the present embodiments is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a pharmaceutical composition of the embodiments to a patient through the port is referred to herein as "a subcutaneous injection port delivery system." In many embodiments, subcutaneous administration is achieved by bolus delivery by needle and syringe.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents may be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the agents may be made into suppositories by mixing with a variety of bases such as emulsifying bases or water-soluble bases. The compounds of the present embodiments may be administered rectally via a suppository. The suppository may include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the embodiments calculated in an amount sufficient to produce the desired effect in association with a pharmaceutically acceptable diluent, carrier or vehicle. The specifications for the novel unit dosage forms of the present embodiments depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Other Antiviral Agents

As discussed above, a subject method will in some embodiments be carried out by administering an NS3 inhibitor that is a compound of formulas I-XIX, and optionally one or more additional antiviral agent(s).

In some embodiments, the method further includes administration of one or more interferon receptor agonist(s). Interferon receptor agonists are described above.

In other embodiments, the method further includes administration of pirfenidone or a pirfenidone analog. Pirfenidone and pirfenidone analogs are described above.

Additional antiviral agents that are suitable for use in combination therapy include, but are not limited to, nucleotide and nucleoside analogs. Non-limiting examples include azidothymidine (AZT) (zidovudine), and analogs and derivatives thereof; 2',3'-dideoxyinosine (DDI) (didanosine), and analogs and derivatives thereof; 2',3'-dideoxycytidine (DDC) (dideoxycytidine), and analogs and derivatives thereof; 2'3,'-didehydro-2',3'-dideoxythymidine (D4T) (stavudine), and analogs and derivatives thereof; combivir; abacavir; adefovir dipoxil; cidofovir; ribavirin; ribavirin analogs; and the like.

In some embodiments, the method further includes administration of ribavirin. Ribavirin, 1-β-D-ribofuranosyl-1H-1,2, 4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The embodiments also contemplate use of derivatives of ribavirin (see, e.g., U.S. Pat. No. 6,277,830). The ribavirin may be administered orally in capsule or tablet form, or in the same or different administration form and in the same or different route as the interferon receptor agonist. Of course, other types of administration of both medicaments, as they become available are contemplated, such as by nasal spray, transdermally, intravenously, by suppository, by sustained release dosage form, etc. Any form of administration will work so long as the proper dosages are delivered without destroying the active ingredient.

In some embodiments, an additional antiviral agent is administered during the entire course of NS3 inhibitor compound treatment. In other embodiments, an additional antiviral agent is administered for a period of time that is overlapping with that of the NS3 inhibitor compound treatment, e.g., the additional antiviral agent treatment may begin before the NS3 inhibitor compound treatment begins and end before the NS3 inhibitor compound treatment ends; the additional antiviral agent treatment may begin after the NS3 inhibitor compound treatment begins and end after the NS3 inhibitor compound treatment ends; the additional antiviral agent treatment may begin after the NS3 inhibitor compound treatment begins and end before the NS3 inhibitor compound treatment ends; or the additional antiviral agent treatment may begin before the NS3 inhibitor compound treatment begins and end after the NS3 inhibitor compound treatment ends.

The NS3 inhibitor compounds of the embodiments are suitable for use in formulations that require good solubility in water. For example, the compounds of the embodiments may be used in formulations that are free of sugar alcohols and polyols, such as trihydric or higher sugar alcohols, e.g., glycerin, erythritol, glycerol, arabitol, xylitol, sorbitol, and mannitol, and free of other alcohols, such as propylene glycol and poly (ethylene glycol) (PEG), or other agent used to compensate for inadequate solubility in water. In one aspect, the embodiments provide the subject NS3 inhibitor compound in a capsule, tablet or caplet formulation, where the capsule, tablet or caplet formulation provides an adequate bioavailability because of the superior water solubility of the compound. In some embodiments, the solubility of the subject compound permits the administration of dosages equal to or greater than 1 mg of drug compound/kg of patient body weight.

Methods of Treatment

Monotherapies

The NS3 inhibitor compound of the embodiments may be used in acute or chronic therapy for HCV disease. In many embodiments, the NS3 inhibitor compound is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The NS3 inhibitor compound may be administered 5 times per day, 4 times per day, tid, bid, qd, qod, biw, tiw, qw, qow, three times per month, or once monthly. In other embodiments, the NS3 inhibitor compound is administered as a continuous infusion.

In many embodiments, an NS3 inhibitor compound of the embodiments is administered orally.

In connection with the above-described methods for the treatment of HCV disease in a patient, an NS3 inhibitor compound of the embodiments may be administered to the patient at a dosage from about 0.01 mg to about 100 mg/kg patient bodyweight per day, in 1 to 5 divided doses per day. In some embodiments, the NS3 inhibitor compound is administered at a dosage of about 0.5 mg to about 75 mg/kg patient bodyweight per day, in 1 to 5 divided doses per day.

The amount of active ingredient that may be combined with carrier materials to produce a dosage form may vary depending on the host to be treated and the particular mode of administration. A typical pharmaceutical preparation may contain from about 5% to about 95% active ingredient (w/w). In other embodiments, the pharmaceutical preparation may contain from about 20% to about 80% active ingredient.

Those of skill will readily appreciate that dose levels may vary as a function of the specific NS3 inhibitor compound, the severity of the symptoms and the susceptibility of the subject to side effects. Preferred dosages for a given NS3 inhibitor compound are readily determinable by those of skill in the art by a variety of means. A preferred means is to measure the physiological potency of a given interferon receptor agonist.

In many embodiments, multiple doses of NS3 inhibitor compound are administered. For example, an NS3 inhibitor compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapies with Ribavirin

In some embodiments, the methods provide for combination therapy comprising administering an NS3 inhibitor compound as described above, and an effective amount of ribavirin. Ribavirin may be administered in dosages of about 400 mg, about 800 mg, about 1000 mg, or about 1200 mg per day.

One embodiment provides any of the above-described methods modified to include co-administering to the patient a therapeutically effective amount of ribavirin for the duration of the desired course of NS3 inhibitor compound treatment.

Another embodiment provides any of the above-described methods modified to include co-administering to the patient about 800 mg to about 1200 mg ribavirin orally per day for the duration of the desired course of NS3 inhibitor compound treatment.

Another embodiment provides any of the above-described methods modified to include co-administering to the patient (a) 1000 mg ribavirin orally per day if the patient has a body weight less than 75 kg or (b) 1200 mg ribavirin orally per day if the patient has a body weight greater than or equal to 75 kg, where the daily dosage of ribavirin is optionally divided into to 2 doses for the duration of the desired course of NS3 inhibitor compound treatment.

Combination Therapies with Levovirin

In some embodiments, the methods provide for combination therapy comprising administering an NS3 inhibitor compound as described above, and an effective amount of levovirin. Levovirin is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, levovirin is administered orally in dosages of about 400, about 800, about 1000, or about 1200 mg per day for the desired course of NS3 inhibitor compound treatment.

Combination Therapies with Viramidine

In some embodiments, the methods provide for combination therapy comprising administering an NS3 inhibitor compound as described above, and an effective amount of viramidine. Viramidine is generally administered in an amount ranging from about 30 mg to about 60 mg, from about 60 mg to about 125 mg, from about 125 mg to about 200 mg, from about 200 mg to about 300 gm, from about 300 mg to about 400 mg, from about 400 mg to about 1200 mg, from about 600 mg to about 1000 mg, or from about 700 to about 900 mg per day, or about 10 mg/kg body weight per day. In some embodiments, viramidine is administered orally in dosages of about 800, or about 1600 mg per day for the desired course of NS3 inhibitor compound treatment.

Combination Therapies with Thymosin-α

In some embodiments, the methods provide for combination therapy comprising administering an NS3 inhibitor compound as described above, and an effective amount of thymosin-α. Thymosin-α (Zadaxin™) is generally administered by subcutaneous injection. Thymosin-α may be administered tid, bid, qd, qod, biw, tiw, qw, qow, three times per month, once monthly, substantially continuously, or continuously for the desired course of NS3 inhibitor compound treatment. In many embodiments, thymosin-α is administered twice per week for the desired course of NS3 inhibitor compound treatment.

Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

Thymosin-α may be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In one emobidment, thymosin-α is administered for the desired course of NS3 inhibitor compound treatment.

Combination Therapies with Interferon(s)

In many embodiments, the methods provide for combination therapy comprising administering an NS3 inhibitor compound as described above, and an effective amount of an interferon receptor agonist. In some embodiments, a compound of formula I and a Type I or III interferon receptor agonist are co-administered in the treatment methods of the embodiments. Type I interferon receptor agonists suitable for use herein include any interferon-α (IFN-α). In certain embodiments, the interferon-α is a PEGylated interferon-α. In certain other embodiments, the interferon-α is a consensus interferon, such as INFERGEN® interferon alfacon-1. In still other embodiments, the interferon-α is a monoPEG (30 kD, linear)-ylated consensus interferon.

Effective dosages of an IFN-α range from about 3 μg to about 27 μg, from about 3 MU to about 10 MU, from about 90 μg to about 180 μg, or from about 18 μg to about 90 μg. Effective dosages of Infergen® consensus IFN-α include about 3 μg, about 6 μg, about 9 μg, about 12 μg, about 15 μg, about 18 μg, about 21 μg, about 24 μg, about 27 μg, or about 30 μg, of drug per dose. Effective dosages of IFN-α2a and IFN-α2b range from 3 million Units (MU) to 10 MU per dose. Effective dosages of PEGASYS®PEGylated IFN-α2a contain an amount of about 90 μg to 270 μg, or about 180 μg, of drug per dose. Effective dosages of PEG-INTRON®PEGylated IFN-α2b contain an amount of about 0.5 μg to 3.0 μg of drug per kg of body weight per dose.

Effective dosages of PEGylated consensus interferon (PEG-CIFN) contain an amount of about 18 μg to about 90 μg, or from about 27 μg to about 60 μg, or about 45 μg, of CIFN amino acid weight per dose of PEG-CIFN. Effective dosages of monoPEG (30 kD, linear)-ylated CIFN contain an amount of about 45 μg to about 270 μg, or about 60 μg to about 180 μg, or about 90 μg to about 120 μg, of drug per dose. IFN-α may be administered daily, every other day, once a week, three times a week, every other week, three times per month, once monthly, substantially continuously or continuously.

In many embodiments, the Type I or Type III interferon receptor agonist and/or the Type II interferon receptor agonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. Dosage regimens may include tid, bid, qd, qod, biw, tiw, qw, qow, three times per month, or monthly administrations. Some embodiments provide any of the above-described methods in which the desired dosage of IFN-α is administered subcutaneously to the patient by bolus delivery qd, qod, tiw, biw, qw, qow, three times per month, or monthly, or is administered subcutaneously to the patient per day by substantially continuous or continuous delivery, for the desired treatment duration. Other embodiments provide any of the above-described methods in which the desired dosage of PEGylated IFN-α (PEG-IFN-α) is administered subcutaneously to the patient by bolus delivery qw, qow, three times per month, or monthly for the desired treatment duration.

In other embodiments, an NS3 inhibitor compound and a Type II interferon receptor agonist are co-administered in the treatment methods of the embodiments. Type II interferon receptor agonists suitable for use herein include any interferon-γ (IFN-γ).

Effective dosages of IFN-γ may range from about 0.5 μg/m2 to about 500 g/m$^2$, usually from about 1.5 μg/m$^2$ to 200 μg/m$^2$, depending on the size of the patient. This activity is based on 106 international units (U) per 50 μg of protein. IFN-γ may be administered daily, every other day, three times a week, or substantially continuously or continuously.

In specific embodiments of interest, IFN-γ is administered to an individual in a unit dosage form of from about 25 μg to about 500 μg, from about 50 μg to about 400 μg, or from about 100 μg to about 300 μg. In particular embodiments of interest, the dose is about 200 μg IFN-γ. In many embodiments of interest, IFN-γ1b is administered.

Where the dosage is 200 μg IFN-γ per dose, the amount of IFN-γ per body weight (assuming a range of body weights of from about 45 kg to about 135 kg) is in the range of from about 4.4 μg IFN-γ per kg body weight to about 1.48 μg IFN-γ per kg body weight.

The body surface area of subject individuals generally ranges from about 1.33 m to about 2.50 m$^2$. Thus, in many embodiments, an IFN-γ dosage ranges from about 150 μg/m2 to about 20 μg/m$^2$. For example, an IFN-γ dosage ranges from about 20 μg/m2 to about 30 μg/m$^2$, from about 30 μg/m$^2$ to about 40 μg/m$^2$, from about 40 μg/m$^2$ to about 50 μg/m$^2$, from about 50 μg/m$^2$ to about 60 μg/m$^2$, from about 60 μg/m$^2$ to about 70 μg/m$^2$, from about 70 μg/m$^2$ to about 80 μg/m$^2$, from about 80 μg/m$^2$ to about 90 μg/m$^2$, from about 90 μg/m$^2$ to about 100 μg/m$^2$, from about 100 μg/m$^2$ to about 110 μg/m$^2$, from about 110 μg/m$^2$ to about 120 μg/m$^2$, from about 120 μg/m$^2$ to about 130 μg/m$^2$, from about 130 μg/m$^2$ to about 140 μg/m$^2$, or from about 140 μg/m$^2$ to about 150 μg/m$^2$. In some embodiments, the dosage groups range from about 25 µg/m² to about 100 µg/m². In other embodiments, the dosage groups range from about 25 µg/m² to about 50 µg/m².

In some embodiments, a Type I or a Type III interferon receptor agonist is administered in a first dosing regimen, followed by a second dosing regimen. The first dosing regimen of Type I or a Type III interferon receptor agonist (also referred to as "the induction regimen") generally involves administration of a higher dosage of the Type I or Type III interferon receptor agonist. For example, in the case of Infergen® consensus IFN-α (CIFN), the first dosing regimen comprises administering CIFN at about 9 µg, about 15 µg. about 18 µg, or about 27 µg. The first dosing regimen may encompass a single dosing event, or at least two or more dosing events. The first dosing regimen of the Type I or Type III interferon receptor agonist may be administered daily, every other day, three times a week, every other week, three times per month, once monthly, substantially continuously or continuously.

The first dosing regimen of the Type I or Type III interferon receptor agonist is administered for a first period of time, which time period may be at least about 4 weeks, at least about 8 weeks, or at least about 12 weeks.

The second dosing regimen of the Type I or Type III interferon receptor agonist (also referred to as "the maintenance dose") generally involves administration of a lower amount of the Type I or Type III interferon receptor agonist. For example, in the case of CIFN, the second dosing regimen comprises administering CIFN at a dose of at least about 3 µg, at least about 9 g, at least about 15 µg, or at least about 18 µg. The second dosing regimen may encompass a single dosing event, or at least two or more dosing events.

The second dosing regimen of the Type I or Type III interferon receptor agonist may be administered daily, every other day, three times a week, every other week, three times per month, once monthly, substantially continuously or continuously.

In some embodiments, where an "induction"/"maintenance" dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase.

In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, the Type II interferon receptor agonist treatment is discontinued once Type I or a Type III interferon receptor agonist treatment begins.

In other embodiments, the Type I or Type III interferon receptor agonist is administered in single dosing regimen. For example, in the case of CIFN, the dose of CIFN is generally in a range of from about 3 µg to about 15 µg, or from about 9 µg to about 15 µg. The dose of Type I or a Type III interferon receptor agonist is generally administered daily, every other day, three times a week, every other week, three times per month, once monthly, or substantially continuously. The dose of the Type I or Type III interferon receptor agonist is administered for a period of time, which period may be, for example, from at least about 24 weeks to at least about 48 weeks, or longer.

In some embodiments, where a single dosing regimen of a Type I or a Type III interferon receptor agonist is administered, a "priming" dose of a Type II interferon receptor agonist (e.g., IFN-γ) is included. In these embodiments, IFN-γ is administered for a period of time from about 1 day to about 14 days, from about 2 days to about 10 days, or from about 3 days to about 7 days, before the beginning of treatment with the Type I or Type III interferon receptor agonist. This period of time is referred to as the "priming" phase. In some of these embodiments, the Type II interferon receptor agonist treatment is continued throughout the entire period of treatment with the Type I or Type III interferon receptor agonist. In other embodiments, the Type II interferon receptor agonist treatment is discontinued before the end of treatment with the Type I or Type III interferon receptor agonist. In these embodiments, the total time of treatment with the Type II interferon receptor agonist (including the "priming" phase) is from about 2 days to about 30 days, from about 4 days to about 25 days, from about 8 days to about 20 days, from about 10 days to about 18 days, or from about 12 days to about 16 days. In still other embodiments, Type II interferon receptor agonist treatment is discontinued once Type I or a Type III interferon receptor agonist treatment begins.

In additional embodiments, an NS3 inhibitor compound, a Type I or III interferon receptor agonist, and a Type II interferon receptor agonist are co-administered for the desired duration of treatment in the methods of the embodiments. In some embodiments, an NS3 inhibitor compound, an interferon-α, and an interferon-γ are co-administered for the desired duration of treatment in the methods of the embodiments.

Some embodiments provide methods using an amount of a Type I or Type III interferon receptor agonist, a Type II interferon receptor agonist, and an NS3 inhibitor compound, effective for the treatment of HCV infection in a patient. In some embodiments, the embodiments provide methods using an effective amount of an IFN-α, IFN-γ, and an NS3 inhibitor compound in the treatment of HCV infection in a patient. One embodiment provides a method using an effective amount of a consensus IFN-α, IFN-γ and an NS3 inhibitor compound in the treatment of HCV infection in a patient.

In general, an effective amount of a consensus interferon (CIFN) and IFN-γ suitable for use in the methods of the embodiments is provided by a dosage ratio of 1 µg CIFN: 10 µg IFN-γ, where both CIFN and IFN-γ are unPEGylated and unglycosylated species.

One embodiment provides any of the above-described methods modified to use an effective amount of INFERGEN® consensus IFN-α and IFN-γ in the treatment of HCV infection in a patient comprising administering to the patient a dosage of INFERGEN® containing an amount of about 1 µg to about 30 µg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 µg to about 300 µg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of virus infection in a patient comprising administering to the patient a dosage of INFERGEN® containing an amount of about 1 µg to about 9 µg, of drug per dose of INFERGEN®, subcutaneously qd, qod, tiw, biw, qw, qow, three times per month, once monthly, or per day substantially continuously or continuously, in combination with a dosage of IFN-γ containing an amount of about 10 µg to about 100 µg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of virus infection in a patient comprising administering to the patient a dosage of INFERGEN® containing an amount of about 1 µg of drug per dose of INFERGEN®, subcutaneously qd, qod, tiw, biw, qw, qow, three times per month, once monthly, or per day substantially continuously or continuously, in combination with a dosage of IFN-γ containing an amount of about 10 µg to about 50 µg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of a virus infection in a patient comprising administering to the patient a dosage of INFERGEN® containing an amount of about 9 µg of drug per dose of INFERGEN®, subcutaneously qd, qod, tiw, biw, qw, qow, three times per month, once monthly, or per day substantially continuously or continuously, in combination with a dosage of IFN-γ containing an amount of about 90 µg to about 100 µg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of INFERGEN® consensus IFN-α and IFN-γ in the treatment of a virus infection in a patient comprising administering to the patient a dosage of INFERGEN® containing an amount of about 30 µg of drug per dose of INFERGEN®, subcutaneously qd, qod, tiw, biw, qw, qow, three times per month, once monthly, or per day substantially continuously or continuously, in combination with a dosage of IFN-γ containing an amount of about 200 µg to about 300 µg of drug per dose of IFN-γ, subcutaneously qd, qod, tiw, biw, qw, qow, three times per month, once monthly, or per day substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 4 µg to about 60 µg of CIFN amino acid weight per dose of PEG-CIFN, subcutaneously qw, qow, three times per month, or monthly, in combination with a total weekly dosage of IFN-γ containing an amount of about 30 µg to about 1,000 µg of drug per week in divided doses administered subcutaneously qd, qod, tiw, biw, or administered substantially continuously or continuously, for the desired duration of treatment with an NS3 inhibitor compound.

Another embodiment provides any of the above-described methods modified to use an effective amount of PEGylated consensus IFN-α and IFN-γ in the treatment of a virus infection in a patient comprising administering to the patient a dosage of PEGylated consensus IFN-α (PEG-CIFN) containing an amount of about 18 µg to about 24 µg of CIFN amino acid weight per dose of PEG-CIFN, subcutaneously qw, qow, three times per month, or monthly, in combination with a total weekly dosage of IFN-γ containing an amount of about 100 µg to about 300 µg of drug per week in divided doses administered subcutaneously qd, qod, tiw, biw, or substantially continuously or continuously, for the desired duration of treatment with an NS3 inhibitor compound.

In general, an effective amount of IFN-α 2a or 2b or 2c and IFN-γ suitable for use in the methods of the embodiments is provided by a dosage ratio of 1 million Units (MU) IFN-α 2a or 2b or 2c: 30 µg IFN-γ, where both IFN-α 2a or 2b or 2c and IFN-γ are unPEGylated and unglycosylated species.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 1 MU to about 20 MU of drug per dose of IFN-α 2a, 2b or 2c subcutaneously qd, qod, tiw, biw, or per day substantially continuously or continuously, in combination with a dosage of IFN-γ containing an amount of about 30 µg to about 600 µg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 3 MU of drug per dose of IFN-α 2a, 2b or 2c subcutaneously qd, qod, tiw, biw, or per day substantially continuously or continuously, in combination with a dosage of IFN-γ containing an amount of about 100 µg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of IFN-α 2a or 2b or 2c and IFN-γ in the treatment of a virus infection in a patient comprising administering to the patient a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of IFN-γ containing an amount of about 300 µg of drug per dose of IFN-γ, subcutaneously qd, qod, tiw, biw, or per day substantially continuously or continuously, for the desired duration of treatment with an NS3 inhibitor compound.

Another embodiment provides any of the above-described methods modified to use an effective amount of PEGASYS®PEGylated IFN-α 2a and IFN-γ in the treatment of a virus infection in a patient comprising administering to the patient a dosage of PEGASYS® containing an amount of about 90 µg to about 360 µg, of drug per dose of PEGASYS®, subcutaneously qw, qow, three times per month, or monthly, in combination with a total weekly dosage of IFN-γ containing an amount of about 30 µg to about 1,000 µg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEGASYS®PEGylated IFN-α2a and IFN-γ in the treatment of a virus infection in a patient comprising administering to the patient a dosage of PEGASYS® containing an amount of about 180 μg of drug per dose of PEGASYS®, subcutaneously qw, qow, three times per month, or monthly, in combination with a total weekly dosage of IFN-γ containing an amount of about 100 μg to about 300 μg, of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON®PEGylated IFN-α2b and IFN-γ in the treatment of a virus infection in a patient comprising administering to the patient a dosage of PEG-INTRON® containing an amount of about 0.75 μg to about 3.0 μg of drug per kilogram of body weight per dose of PEG-INTRON®, subcutaneously qw, qow, three times per month, or monthly, in combination with a total weekly dosage of IFN-γ containing an amount of about 30 μg to about 1,000 μg of drug per week administered in divided doses subcutaneously qd, qod, tiw, or biw, or administered substantially continuously or continuously, for the desired duration of treatment with an NS3 inhibitor compound.

Another embodiment provides any of the above-described methods modified to use an effective amount of PEG-INTRON®PEGylated IFN-α 2b and IFN-γ in the treatment of a virus infection in a patient comprising administering to the patient a dosage of PEG-INTRON® containing an amount of about 1.5 μg of drug per kilogram of body weight per dose of PEG-INTRON®, subcutaneously qw, qow, three times per month, or monthly, in combination with a total weekly dosage of IFN-γ containing an amount of about 100 μg to about 300 μg of drug per week administered in divided doses subcutaneously qd, qod, tiw, or biw, or administered substantially continuously or continuously, for the desired duration of treatment with an NS3 inhibitor compound.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 25 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; 200 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 25 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 9 μg INFERGEN® consensus IFN-α administered subcutaneously qd or tiw; and 200 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 100 μg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 μg monoPEG(30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 μg monoPEG(30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 100 μg monoPEG(30 kD, linear)-ylated consensus IFN-α administered subcutaneously every 10 days or qw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 100 μg monoPEG(30 kD, linear)-ylated consensus IFN-α administered subcutaneously every 10 days or qw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 150 μg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 μg monoPEG(30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 μg monoPEG(30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 150 μg monoPEG(30 kD, linear)-ylated consensus IFN-α administered subcutaneously every 10 days or qw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 150 μg monoPEG(30 kD, linear)-ylated consensus IFN-α administered subcutaneously every 10 days or qw; and 100 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 μg monoPEG(30 kD, linear)-ylated consensus IFN-α administered subcutaneously every 10 days or qw, and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 μg monoPEG(30 kD, linear)-ylated consensus IFN-α administered subcutaneously every 10 days or qw; 50 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 μg monoPEG(30 kD, linear)-ylated consensus IFN-α administered subcutaneously every 10 days or qw; 100 μg Actimmune® human IFN-γ1b administered subcutaneously tiw; and ribavirin administered orally qd, where the duration of therapy is 48 weeks. In this embodiment, ribavirin is administered in an amount of 1000 mg for individuals weighing less than 75 kg, and 1200 mg for individuals weighing 75 kg or more.

One embodiment provides any of the above-described methods modified to comprise administering to an individual having an HCV infection an effective amount of an NS3 inhibitor; and a regimen of 200 μg monoPEG(30 kD, linear)-ylated consensus IFN-α administered subcutaneously every 10 days or qw; and 50 μg Actimmune® human IFN-γ1b administered subcutaneously tiw, where the duration of therapy is 48 weeks.

One embodiment provides any of the above-described methods modified to comprise administering to an individual having an HCV infection an effective amount of an NS3 inhibitor; and a regimen of 200 μg monoPEG(30 kD, linear)-ylated consensus IFN-α administered subcutaneously every 10 days or qw; and 100 μg Actimmune® human IFN-γ1b administered subcutaneously tiw, where the duration of therapy is 48 weeks.

Any of the above-described methods involving administering an NS3 inhibitor, a Type I interferon receptor agonist (e.g., an IFN-α), and a Type II interferon receptor agonist (e.g., an IFN-γ), may be augmented by administration of an effective amount of a TNF-α antagonist (e.g., a TNF-α antagonist other than pirfenidone or a pirfenidone analog). Exemplary, non-limiting TNF-α antagonists that are suitable for use in such combination therapies include ENBREL®, REMICADE®, and HUMIRA™.

One embodiment provides a method using an effective amount of ENBREL®; an effective amount of IFN-α; an effective amount of IFN-γ; and an effective amount of an NS3 inhibitor in the treatment of an HCV infection in a patient, comprising administering to the patient a dosage ENBREL® containing an amount of from about 0.1 µg to about 23 mg per dose, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment.

One embodiment provides a method using an effective amount of REMICADE®, an effective amount of IFN-α with or without an effective amount of IFN-γ; and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment.

One embodiment provides a method using an effective amount of HUMIRA™, an effective amount of IFN-α; an effective amount of IFN-γ; and an effective amount of an NS3 inhibitor in the treatment of an HCV infection in a patient, comprising administering to the patient a dosage of HUMIRA™ containing an amount of from about 0.1 µg to about 35 mg, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment.

Combination Therapies with Pirfenidone

In many embodiments, the methods provide for combination therapy comprising administering an NS3 inhibitor compound as described above, and an effective amount of pirfenidone or a pirfenidone analog. In some embodiments, an NS3 inhibitor compound, one or more interferon receptor agonist(s), and pirfenidone or pirfenidone analog are co-administered in the treatment methods of the embodiments. In certain embodiments, an NS3 inhibitor compound, a Type I interferon receptor agonist, and pirfenidone (or a pirfenidone analog) are co-administered. In other embodiments, an NS3 inhibitor compound, a Type I interferon receptor agonist, a Type II interferon receptor agonist, and pirfenidone (or a pirfenidone analog) are co-administered. Type I interferon receptor agonists suitable for use herein include any IFN-α, such as interferon alfa-2a, interferon alfa-2b, interferon alfacon-1, and PEGylated IFN-α's, such as peginterferon alfa-2a, peginterferon alfa-2b, and PEGylated consensus interferons, such as monoPEG (30 kD, linear)-ylated consensus interferon. Type II interferon receptor agonists suitable for use herein include any interferon-γ.

Pirfenidone or a pirfenidone analog may be administered once per month, twice per month, three times per month, once per week, twice per week, three times per week, four times per week, five times per week, six times per week, daily, or in divided daily doses ranging from once daily to 5 times daily over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Effective dosages of pirfenidone or a specific pirfenidone analog include a weight-based dosage in the range from about 5 mg/kg/day to about 125 mg/kg/day, or a fixed dosage of about 400 mg to about 3600 mg per day, or about 800 mg to about 2400 mg per day, or about 1000 mg to about 1800 mg per day, or about 1200 mg to about 1600 mg per day, administered orally in one to five divided doses per day. Other doses and formulations of pirfenidone and specific pirfenidone analogs suitable for use in the treatment of fibrotic diseases are described in U.S. Pat. Nos. 5,310,562; 5,518,729; 5,716,632; and 6,090,822.

One embodiment provides any of the above-described methods modified to include co-administering to the patient a therapeutically effective amount of pirfenidone or a pirfenidone analog for the duration of the desired course of NS3 inhibitor compound treatment.

Combination Therapies with TNF-α Antagonists

In many embodiments, the methods provide for combination therapy comprising administering an effective amount of an NS3 inhibitor compound as described above, and an effective amount of TNF-α antagonist, in combination therapy for treatment of an HCV infection.

Effective dosages of a TNF-α antagonist range from 0.1 µg to 40 mg per dose, e.g., from about 0.1 µg to about 0.5 µg per dose, from about 0.5 µg to about 1.0 µg per dose, from about 1.0 µg per dose to about 5.0 µg per dose, from about 5.0 µg to about 10 µg per dose, from about 10 µg to about 20 µg per dose, from about 20 µg per dose to about 30 µg per dose, from about 30 µg per dose to about 40 µg per dose, from about 40 µg per dose to about 50 µg per dose, from about 50 µg per dose to about 60 µg per dose, from about 60 µg per dose to about 70 µg per dose, from about 70 µg to about 80 µg per dose, from about 80 µg per dose to about 100 µg per dose, from about 100 µg to about 150 µg per dose, from about 150 µg to about 200 µg per dose, from about 200 µg per dose to about 250 µg per dose, from about 250 µg to about 300 µg per dose, from about 300 µg to about 400 µg per dose, from about 400 µg to about 500 µg per dose, from about 500 µg to about 600 µg per dose, from about 600 µg to about 700 µg per dose, from about 700 µg to about 800 µg per dose, from about 800 µg to about 900 µg per dose, from about 900 µg to about 1000 µg per dose, from about 1 mg to about 10 mg per dose, from about 10 mg to about 15 mg per dose, from about 15 mg to about 20 mg per dose, from about 20 mg to about 25 mg per dose, from about 25 mg to about 30 mg per dose, from about 30 mg to about 35 mg per dose, or from about 35 mg to about 40 mg per dose.

In some embodiments, effective dosages of a TNF-α antagonist are expressed as mg/kg body weight. In these embodiments, effective dosages of a TNF-α antagonist are from about 0.1 mg/kg body weight to about 10 mg/kg body weight, e.g., from about 0.1 mg/kg body weight to about 0.5 mg/kg body weight, from about 0.5 mg/kg body weight to about 1.0 mg/kg body weight, from about 1.0 mg/kg body weight to about 2.5 mg/kg body weight, from about 2.5 mg/kg body weight to about 5.0 mg/kg body weight, from about 5.0 mg/kg body weight to about 7.5 mg/kg body weight, or from about 7.5 mg/kg body weight to about 10 mg/kg body weight.

In many embodiments, a TNF-α antagonist is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The TNF-α antagonist may be administered tid, bid, qd, qod, biw, tiw, qw, qow, three times per month, once monthly, substantially continuously, or continuously.

In many embodiments, multiple doses of a TNF-α antagonist are administered. For example, a TNF-α antagonist is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid), substantially continuously, or continuously, over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A TNF-α antagonist and an NS3 inhibitor are generally administered in separate formulations. A TNF-α antagonist and an NS3 inhibitor may be administered substantially simultaneously, or within about 30 minutes, about 1 hour, about 2 hours, about 4 hours, about 8 hours, about 16 hours, about 24 hours, about 36 hours, about 72 hours, about 4 days, about 7 days, or about 2 weeks of one another.

One embodiment provides a method using an effective amount of a TNF-α antagonist and an effective amount of an NS3 inhibitor in the treatment of an HCV infection in a patient, comprising administering to the patient a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

One embodiment provides a method using an effective amount of ENBREL® and an effective amount of an NS3 inhibitor in the treatment of an HCV infection in a patient, comprising administering to the patient a dosage ENBREL® containing an amount of from about 0.1 µg to about 23 mg per dose, from about 0.1 µg to about 1 µg, from about 1 µg to about 10 µg, from about 10 µg to about 100 µg, from about 100 µg to about 1 mg, from about 1 mg to about 5 mg, from 5 mg to about 10 mg, from about 10 mg to about 15 mg, from about 15 mg to about 20 mg, or from about 20 mg to about 23 mg of ENBREL®, subcutaneously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of REMICADE® and an effective amount of an NS3 inhibitor in the treatment of an HCV infection in a patient, comprising administering to the patient a dosage of REMICADE® containing an amount of from about 0.1 mg/kg to about 4.5 mg/kg, from about 0.1 mg/kg to about 0.5 mg/kg, from about 0.5 mg/kg to about 1.0 mg/kg, from about 1.0 mg/kg to about 1.5 mg/kg, from about 1.5 mg/kg to about 2.0 mg/kg, from about 2.0 mg/kg to about 2.5 mg/kg, from about 2.5 mg/kg to about 3.0 mg/kg, from about 3.0 mg/kg to about 3.5 mg/kg, from about 3.5 mg/kg to about 4.0 mg/kg, or from about 4.0 mg/kg to about 4.5 mg/kg per dose of REMICADE®, intravenously qd, qod, tiw, biw, qw, qow, three times per month, once monthly, or once every other month, or per day substantially continuously or continuously, for the desired duration of treatment with an NS3 inhibitor compound.

One embodiment provides a method using an effective amount of HUMIRA™ and an effective amount of an NS3 inhibitor in the treatment of an HCV infection in a patient, comprising administering to the patient a dosage of HUMIRA™ containing an amount of from about 0.1 µg to about 35 mg, from about 0.1 µg to about 1 µg, from about 1 µg to about 10 µg, from about 10 µg to about 100 µg, from about 100 µg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, or from about 30 mg to about 35 mg per dose of a HUMIRA™, subcutaneously qd, qod, tiw, biw, qw, qow, three times per month, once monthly, or once every other month, or per day substantially continuously or continuously, for the desired duration of treatment with an NS3 inhibitor compound.

Combination Therapies with Thymosin-α

In many embodiments, the methods provide for combination therapy comprising administering an effective amount of an NS3 inhibitor compound as described above, and an effective amount of thymosin-α, in combination therapy for treatment of an HCV infection.

Effective dosages of thymosin-α range from about 0.5 mg to about 5 mg, e.g., from about 0.5 mg to about 1.0 mg, from about 1.0 mg to about 1.5 mg, from about 1.5 mg to about 2.0 mg, from about 2.0 mg to about 2.5 mg, from about 2.5 mg to about 3.0 mg, from about 3.0 mg to about 3.5 mg, from about 3.5 mg to about 4.0 mg, from about 4.0 mg to about 4.5 mg, or from about 4.5 mg to about 5.0 mg. In particular embodiments, thymosin-α is administered in dosages containing an amount of 1.0 mg or 1.6 mg.

One embodiment provides a method using an effective amount of ZADAXIN™ thymosin-α and an effective amount of an NS3 inhibitor in the treatment of an HCV infection in a patient, comprising administering to the patient a dosage of ZADAXIN™ containing an amount of from about 1.0 mg to about 1.6 mg per dose, subcutaneously twice per week for the desired duration of treatment with the NS3 inhibitor compound.

Combination Therapies with a TNF-α Antagonist and an Interferon

Some embodiments provide a method of treating an HCV infection in an individual having an HCV infection, the method comprising administering an effective amount of an NS3 inhibitor, and effective amount of a TNF-α antagonist, and an effective amount of one or more interferons.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 μg to about 300 μg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of IFN-γ and an effective amount of a TNF-α antagonist in the treatment of HCV infection in a patient comprising administering to the patient a dosage of IFN-γ containing an amount of about 10 μg to about 100 μg of drug per dose of IFN-γ, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 30 μg to about 1,000 μg of drug per week in divided doses administered subcutaneously qd, qod, tiw, biw, or administered substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-γ and an effective amount of a TNF-α antagonist in the treatment of a virus infection in a patient comprising administering to the patient a total weekly dosage of IFN-γ containing an amount of about 100 μg to about 300 μg of drug per week in divided doses administered subcutaneously qd, qod, tiw, biw, or administered substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 μg to about 30 μg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

One embodiment provides any of the above-described methods modified to use an effective amount of INFERGEN® consensus IFN-α and a TNF-α antagonist in the treatment of HCV infection in a patient comprising administering to the patient a dosage of INFERGEN® containing an amount of about 1 μg to about 9 μg, of drug per dose of INFERGEN®, subcutaneously qd, qod, tiw, biw, qw, qow, three times per month, once monthly, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 4 μg to about 60 μg of CIFN amino acid weight per dose of PEG-CIFN, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGylated consensus IFN-α and an effective amount of a TNF-α antagonist in the treatment of a virus infection in a patient comprising administering to the patient a dosage of PEGylated consensus IFN-α (PEG-CIFN) containing an amount of about 18 μg to about 24 μg of CIFN amino acid weight per dose of PEG-CIFN, subcutaneously qw, qow, three times per month, or monthly, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α2a, 2b or 2c containing an amount of about 1 MU to about 20 MU of drug per dose of IFN-α2a, 2b or 2c subcutaneously qd, qod, tiw, biw, or per day substantially continuously or continuously, in combination with a dosage of a TNF-α antagonist containing an amount of from about 0.1 μg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α2a or 2b or 2c and an effective amount of a TNF-α antagonist in the treatment of a virus infection in a patient comprising administering to the patient a dosage of IFN-α2a, 2b or 2c containing an amount of about 3 MU of drug per dose of IFN-α2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of IFN-α 2a or 2b or 2c and an effective amount of a TNF-α antagonist in the treatment of a virus infection in a patient comprising administering to the patient a dosage of IFN-α 2a, 2b or 2c containing an amount of about 10 MU of drug per dose of IFN-α 2a, 2b or 2c subcutaneously qd, qod, tiw, biw, or per day substantially continuously or continuously, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS®PEGylated IFN-α2a and an effective amount of a TNF-α antagonist in the treatment of a virus infection in a patient comprising administering to the patient a dosage of PEGASYS® containing an amount of about 90 µg to about 360 µg, of drug per dose of PEGASYS®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEGASYS®PEGylated IFN-α2a and an effective amount of a TNF-α antagonist in the treatment of a virus infection in a patient comprising administering to the patient a dosage of PEGASYS® containing an amount of about 180 µg, of drug per dose of PEGASYS®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON®PEGylated IFN-α2b and an effective amount of a TNF-α antagonist in the treatment of a virus infection in a patient comprising administering to the patient a dosage of PEG-INTRON® containing an amount of about 0.75 µg to about 3.0 µg of drug per kilogram of body weight per dose of PEG-INTRON®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Another embodiment provides any of the above-described methods modified to use an effective amount of PEG-INTRON®PEGylated IFN-α 2b and an effective amount of a TNF-α antagonist in the treatment of a virus infection in a patient comprising administering to the patient a dosage of PEG-INTRON® containing an amount of about 1.5 µg of drug per kilogram of body weight per dose of PEG-INTRON®, subcutaneously qw, qow, three times per month, or monthly, in combination with a dosage of a TNF-α antagonist containing an amount of from about 0.1 µg to about 40 mg per dose of a TNF-α antagonist, subcutaneously qd, qod, tiw, or biw, or per day substantially continuously or continuously, for the desired duration of treatment with an NS3 inhibitor compound.

Combination Therapies with Other Antiviral Agents

Other agents such as inhibitors of HCV NS3 helicase are also attractive drugs for combinational therapy, and are contemplated for use in combination therapies described herein. Ribozymes such as Heptazyme™ and phosphorothioate oligonucleotides which are complementary to HCV protein sequences and which inhibit the expression of viral core proteins are also suitable for use in combination therapies described herein.

In some embodiments, the additional antiviral agent(s) is administered during the entire course of treatment with the NS3 inhibitor compound of the embodiments, and the beginning and end of the treatment periods coincide. In other embodiments, the additional antiviral agent(s) is administered for a period of time that is overlapping with that of the NS3 inhibitor compound treatment, e.g., treatment with the additional antiviral agent(s) begins before the NS3 inhibitor compound treatment begins and ends before the NS3 inhibitor compound treatment ends; treatment with the additional antiviral agent(s) begins after the NS3 inhibitor compound treatment begins and ends after the NS3 inhibitor compound treatment ends; treatment with the additional antiviral agent(s) begins after the NS3 inhibitor compound treatment begins and ends before the NS3 inhibitor compound treatment ends; or treatment with the additional antiviral agent(s) begins before the NS3 inhibitor compound treatment begins and ends after the NS3 inhibitor compound treatment ends.

The NS3 inhibitor compound may be administered together with (i.e., simultaneously in separate formulations; simultaneously in the same formulation; administered in separate formulations and within about 48 hours, within about 36 hours, within about 24 hours, within about 16 hours, within about 12 hours, within about 8 hours, within about 4 hours, within about 2 hours, within about 1 hour, within about 30 minutes, or within about 15 minutes or less) one or more additional antiviral agents.

As non-limiting examples, any of the above-described methods featuring an IFN-α regimen may be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 100 µg of drug per dose, subcutaneously once weekly, once every 8 days, or once every 10 days for the desired treatment duration with an NS3 inhibitor compound.

As non-limiting examples, any of the above-described methods featuring an IFN-α regimen may be modified to replace the subject IFN-α regimen with a regimen of monoPEG (30 kD, linear)-ylated consensus IFN-α comprising administering a dosage of monoPEG (30 kD, linear)-ylated consensus IFN-α containing an amount of 150 µg of drug per dose, subcutaneously once weekly, once every 8 days, or once every 10 days for the desired treatment duration with an NS3 inhibitor compound.

As non-limiting examples, any of the above-described methods featuring an IFN-α regimen may be modified to replace the subject IFN-α regimen with a regimen of monoPEG (30 kD, linear)-ylated consensus IFN-α comprising administering a dosage of monoPEG (30 kD, linear)- ylated consensus IFN-α containing an amount of 200 μg of drug per dose, subcutaneously once weekly, once every 8 days, or once every 10 days for the desired treatment duration with an NS3 inhibitor compound.

As non-limiting examples, any of the above-described methods featuring an IFN-α regimen may be modified to replace the subject IFN-α regimen with a regimen of INFERGEN® interferon alfacon-1 comprising administering a dosage of INFERGEN® interferon alfacon-1 containing an amount of 9 μg of drug per dose, subcutaneously once daily or three times per week for the desired treatment duration with an NS3 inhibitor compound.

As non-limiting examples, any of the above-described methods featuring an IFN-α regimen may be modified to replace the subject IFN-α regimen with a regimen of INFERGEN® interferon alfacon-1 comprising administering a dosage of INFERGEN® interferon alfacon-1 containing an amount of 15 μg of drug per dose, subcutaneously once daily or three times per week for the desired treatment duration with an NS3 inhibitor compound.

As non-limiting examples, any of the above-described methods featuring an IFN-γ regimen may be modified to replace the subject IFN-γ regimen with a regimen of IFN-γ comprising administering a dosage of IFN-γ containing an amount of 25 μg of drug per dose, subcutaneously three times per week for the desired treatment duration with an NS3 inhibitor compound.

As non-limiting examples, any of the above-described methods featuring an IFN-γ regimen may be modified to replace the subject IFN-γ regimen with a regimen of IFN-γ comprising administering a dosage of IFN-γ containing an amount of 50 μg of drug per dose, subcutaneously three times per week for the desired treatment duration with an NS3 inhibitor compound.

As non-limiting examples, any of the above-described methods featuring an IFN-γ regimen may be modified to replace the subject IFN-γ regimen with a regimen of IFN-γ comprising administering a dosage of IFN-γ containing an amount of 100 μg of drug per dose, subcutaneously three times per week for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-(and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring a TNF antagonist regimen may be modified to replace the subject TNF antagonist regimen with a TNF antagonist regimen comprising administering a dosage of a TNF antagonist selected from the group of: (a) etanercept in an amount of 25 mg of drug per dose subcutaneously twice per week, (b) infliximab in an amount of 3 mg of drug per kilogram of body weight per dose intravenously at weeks 0, 2 and 6, and every 8 weeks thereafter, or (c) adalimumab in an amount of 40 mg of drug per dose subcutaneously once weekly or once every 2 weeks; for the desired treatment duration with an NS3 inhibitor compound.

As non-limiting examples, any of the above-described methods featuring an IFN-α and IFN-γ combination regimen can be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 100 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 150 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of monoPEG (30 kD, linear)-ylated consensus IFN-α containing an amount of 200 μg of drug per dose, subcutaneously once weekly, once every 8 days, or once every 10 days; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 25

μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 9 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously three times per week; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 25 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 50 μg of drug per dose, subcutaneously three times per week; for the desired treatment duration with an NS3 inhibitor compound.

As non-limiting examples, any of the above-described methods featuring an IFN-α and IFN-γ combination regimen may be modified to replace the subject IFN-α and IFN-γ combination regimen with an IFN-α and IFN-γ combination regimen comprising: (a) administering a dosage of INFERGEN® interferon alfacon-1 containing an amount of 15 μg of drug per dose, subcutaneously once daily; and (b) administering a dosage of IFN-γ containing an amount of 100 μg of drug per dose, subcutaneously three times per week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 100 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 150 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of monoPEG (30 kD, linear)-ylated consensus IFN-α containing an amount of 200 μg of drug per dose, subcutaneously once weekly, once every 8 days, or once every 10 days; (b) administering a dosage of IFN-γ containing an amount of 100 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 25 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 μg of drug per dose, subcutaneously three times per week; (b) administering a dosage of IFN-γ containing an amount of 50 μg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 µg of drug per dose, subcutaneously three times per week; (b) administering a dosage of IFN-γ containing an amount of 100 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 µg of drug per dose, subcutaneously once daily; (b) administering a dosage of IFN-γ containing an amount of 25 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 µg of drug per dose, subcutaneously once daily; (b) administering a dosage of IFN-γ containing an amount of 50 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 9 µg of drug per dose, subcutaneously once daily; (b) administering a dosage of IFN-γ containing an amount of 100 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 µg of drug per dose, subcutaneously three times per week; (b) administering a dosage of IFN-γ containing an amount of 25 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 µg of drug per dose, subcutaneously three times per week; (b) administering a dosage of IFN-γ containing an amount of 50 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 µg of drug per dose, subcutaneously three times per week; (b) administering a dosage of IFN-γ containing an amount of 100 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 µg of drug per dose, subcutaneously once daily; (b) administering a dosage of IFN-γ containing an amount of 25 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 µg of drug per dose, subcutaneously once daily; (b) administering a dosage of IFN-γ containing an amount of 50 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α, IFN-γ and TNF antagonist combination regimen may be modified to replace the subject IFN-α, IFN-γ and TNF antagonist combination regimen with an IFN-α, IFN-γ and TNF antagonist combination regimen comprising: (a) administering a dosage of INFERGEN® interferon alfacon-1 containing an amount of 15 µg of drug per dose, subcutaneously once daily; (b) administering a dosage of IFN-γ containing an amount of 100 µg of drug per dose, subcutaneously three times per week; and (c) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen may be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 100 µg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen may be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 150 µg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen may be modified to replace the subject IFN-α and TNF antagonist combination regimen with an IFN-α and TNF antagonist combination regimen comprising: (a) administering a dosage of monoPEG (30 kD, linear)-ylated consensus IFN-α containing an amount of 200 µg of drug per dose, subcutaneously once weekly, once every 8 days, or once every 10 days; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen may be modified to replace the subject IFN-α and TNF antagonist combination regimen with an IFN-α and TNF antagonist combination regimen comprising: (a) administering a dosage of INFERGEN® interferon alfacon-1 containing an amount of 9 µg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-α and TNF antagonist combination regimen may be modified to replace the subject IFN-α and TNF antagonist combination regimen with an IFN-α and TNF antagonist combination regimen comprising: (a) administering a dosage of INFERGEN® interferon alfacon-1 containing an amount of 15 µg of drug per dose, subcutaneously once daily or three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen may be modified to replace the subject IFN-γ and TNF antagonist combination regimen with an IFN-γ and TNF antagonist combination regimen comprising: (a) administering a dosage of IFN-γ containing an amount of 25 µg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen may be modified to replace the subject IFN-γ and TNF antagonist combination regimen with an IFN-γ and TNF antagonist combination regimen comprising: (a) administering a dosage of IFN-γ containing an amount of 50 µg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods featuring an IFN-γ and TNF antagonist combination regimen may be modified to replace the subject IFN-γ and TNF antagonist combination regimen with an IFN-γ and TNF antagonist combination regimen comprising: (a) administering a dosage of IFN-γ containing an amount of 100 µg of drug per dose, subcutaneously three times per week; and (b) administering a dosage of a TNF antagonist selected from (i) etanercept in an amount of 25 mg subcutaneously twice per week, (ii) infliximab in an amount of 3 mg of drug per kilogram of body weight intravenously at weeks 0, 2 and 6, and every 8 weeks thereafter or (iii) adalimumab in an amount of 40 mg subcutaneously once weekly or once every other week; for the desired treatment duration with an NS3 inhibitor compound.

As non-limiting examples, any of the above-described methods that includes a regimen of monoPEG (30 kD, linear)-ylated consensus IFN-α may be modified to replace the regimen of monoPEG (30 kD, linear)-ylated consensus IFN-α with a regimen of peginterferon alfa-2a comprising administering a dosage of peginterferon alfa-2a containing an amount of 180 µg of drug per dose, subcutaneously once weekly for the desired treatment duration with an NS3 inhibitor compound.

As non-limiting examples, any of the above-described methods that includes a regimen of monoPEG (30 kD, linear)-ylated consensus IFN-α may be modified to replace the regimen of monoPEG (30 kD, linear)-ylated consensus IFN-α with a regimen of peginterferon alfa-2b comprising administering a dosage of peginterferon alfa-2b containing an amount of 1.0 µg to 1.5 µg of drug per kilogram of body weight per dose, subcutaneously once or twice weekly for the desired treatment duration with an NS3 inhibitor compound.

As non-limiting examples, any of the above-described methods may be modified to include administering a dosage of ribavirin containing an amount of 400 mg, 800 mg, 1000 mg or 1200 mg of drug orally per day, optionally in two or more divided doses per day, for the desired treatment duration with an NS3 inhibitor compound.

As non-limiting examples, any of the above-described methods may be modified to include administering a dosage of ribavirin containing (i) an amount of 1000 mg of drug orally per day for patients having a body weight of less than 75 kg or (ii) an amount of 1200 mg of drug orally per day for patients having a body weight of greater than or equal to 75 kg, optionally in two or more divided doses per day, for the desired treatment duration with an NS3 inhibitor compound.

As non-limiting examples, any of the above-described methods may be modified to replace the subject NS3 inhibitor regimen with an NS3 inhibitor regimen comprising administering a dosage of 0.01 mg to 0.1 mg of drug per kilogram of body weight orally daily, optionally in two or more divided doses per day, for the desired treatment duration with the NS3 inhibitor compound.

As non-limiting examples, any of the above-described methods may be modified to replace the subject NS3 inhibitor regimen with an NS3 inhibitor regimen comprising administering a dosage of 0.1 mg to 1 mg of drug per kilogram of body weight orally daily, optionally in two or more divided doses per day, for the desired treatment duration with the NS3 inhibitor compound.

As non-limiting examples, any of the above-described methods may be modified to replace the subject NS3 inhibitor regimen with an NS3 inhibitor regimen comprising administering a dosage of 1 mg to 10 mg of drug per kilogram of body weight orally daily, optionally in two or more divided doses per day, for the desired treatment duration with the NS3 inhibitor compound.

As non-limiting examples, any of the above-described methods may be modified to replace the subject NS3 inhibitor regimen with an NS3 inhibitor regimen comprising administering a dosage of 10 mg to 100 mg of drug per kilogram of body weight orally daily, optionally in two or more divided doses per day, for the desired treatment duration with the NS3 inhibitor compound.

As non-limiting examples, any of the above-described methods featuring an NS5B inhibitor regimen may be modified to replace the subject NS5B inhibitor regimen with an NS5B inhibitor regimen comprising administering a dosage of 0.01 mg to 0.1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen may be modified to replace the subject NS5B inhibitor regimen with an NS5B inhibitor regimen comprising administering a dosage of 0.1 mg to 1 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen may be modified to replace the subject NS5B inhibitor regimen with an NS5B inhibitor regimen comprising administering a dosage of 1 mg to 10 mg of drug per kilogram of body weight orally daily, optionally in two or more divided doses per day, for the desired treatment duration with an NS3 inhibitor compound.

As non-limiting examples, any of the above-described methods featuring an NS5B inhibitor regimen may be modified to replace the subject NS5B inhibitor regimen with an NS5B inhibitor regimen comprising administering a dosage of 10 mg to 100 mg of drug per kilogram of body weight orally daily, optionally in two or more divided doses per day, for the desired treatment duration with an NS3 inhibitor compound.

Patient Identification

In certain embodiments, the specific regimen of drug therapy used in treatment of the HCV patient is selected according to certain disease parameters exhibited by the patient, such as the initial viral load, genotype of the HCV infection in the patient, liver histology and/or stage of liver fibrosis in the patient.

Thus, some embodiments provide any of the above-described methods for the treatment of HCV infection in which the subject method is modified to treat a treatment failure patient for a duration of 48 weeks.

Other embodiments provide any of the above-described methods for HCV in which the subject method is modified to treat a non-responder patient, where the patient receives a 48 week course of therapy.

Other embodiments provide any of the above-described methods for the treatment of HCV infection in which the subject method is modified to treat a relapser patient, where the patient receives a 48 week course of therapy.

Other embodiments provide any of the above-described methods for the treatment of HCV infection in which the subject method is modified to treat a naïve patient infected with HCV genotype 1, where the patient receives a 48 week course of therapy.

Other embodiments provide any of the above-described methods for the treatment of HCV infection in which the subject method is modified to treat a naïve patient infected with HCV genotype 4, where the patient receives a 48 week course of therapy.

Other embodiments provide any of the above-described methods for the treatment of HCV infection in which the subject method is modified to treat a naïve patient infected with HCV genotype 1, where the patient has a high viral load (HVL), where "HVL" refers to an HCV viral load of greater than $2\times10^6$ HCV genome copies per mL serum, and where the patient receives a 48 week course of therapy.

One embodiment provide any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having advanced or severe stage liver fibrosis as measured by a Knodell score of 3 or 4 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 1 infection and an initial viral load of greater than 2 million viral genome copies per ml of patient serum and no or early stage liver fibrosis as measured by a Knodell score of 0, 1, or 2 and then (2) administering to the patient the drug therapy of the subject method for a time period of about 40 weeks to about 50 weeks, or about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 1 infection and an initial viral load of less than or equal to 2 million viral genome copies per ml of patient serum and then (2) administering to the patient the drug therapy of the subject method for a time period of about 24 weeks to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 50 weeks, or about 24 weeks to about 48 weeks, or about 30 weeks to about 40 weeks, or up to about 20 weeks, or up to about 24 weeks, or up to about 30 weeks, or up to about 36 weeks, or up to about 48 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of about 20 weeks to about 24 weeks.

Another embodiment provides any of the above-described methods for the treatment of an HCV infection, where the subject method is modified to include the steps of (1) identifying a patient having an HCV genotype 2 or 3 infection and then (2) administering to the patient the drug therapy of the subject method for a time period of at least about 24 weeks.

Another embodiment provides any of the above-described methods for the treatment of an HCV infection, where the subject method is modified to include the steps of (1) identifying a patient having an HCV genotype 1 or 4 infection and then (2) administering to the patient the drug therapy of the subject method for a time period of about 24 weeks to about 60 weeks, or about 30 weeks to about one year, or about 36 weeks to about 50 weeks, or about 40 weeks to about 48 weeks, or at least about 24 weeks, or at least about 30 weeks, or at least about 36 weeks, or at least about 40 weeks, or at least about 48 weeks, or at least about 60 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of about 20 weeks to about 50 weeks.

Another embodiment provides any of the above-described methods for the treatment of an HCV infection, where the subject method is modified to include the steps of (1) identifying a patient having an HCV infection characterized by any of HCV genotypes 5, 6, 7, 8 and 9 and then (2) administering to the patient the drug therapy of the subject method for a time period of at least about 24 weeks and up to about 48 weeks.

Subjects Suitable for Treatment

Any of the above treatment regimens may be administered to individuals who have been diagnosed with an HCV infection. Individuals who are infected with HCV are identified as having HCV RNA in their blood, and/or having anti-HCV antibody in their serum. Any of the above treatment regimens may be administered to individuals who have failed previous treatment for HCV infection ("treatment failure patients," including non-responders and relapsers).

Individuals who have been clinically diagnosed as infected with HCV are of particular interest in many embodiments. Individuals who are infected with HCV are identified as having HCV RNA in their blood, and/or having anti-HCV antibody in their serum. Such individuals include anti-HCV ELISA-positive individuals, and individuals with a positive recombinant immunoblot assay (RIBA). Such individuals may also, but need not, have elevated serum ALT levels.

Individuals who are clinically diagnosed as infected with HCV include naïve individuals (e.g., individuals not previously treated for HCV, particularly those who have not previously received IFN-α-based and/or ribavirin-based therapy) and individuals who have failed prior treatment for HCV ("treatment failure" patients). Treatment failure patients include non-responders (i.e., individuals in whom the HCV titer was not significantly or sufficiently reduced by a previous treatment for HCV, e.g., a previous IFN-α monotherapy, a previous IFN-α and ribavirin combination therapy, or a previous pegylated IFN-α and ribavirin combination therapy); and relapsers (i.e., individuals who were previously treated for HCV, e.g., who received a previous IFN-α monotherapy, a previous IFN-α and ribavirin combination therapy, or a previous pegylated IFN-α and ribavirin combination therapy, whose HCV titer decreased, and subsequently increased).

In particular embodiments of interest, individuals have an HCV titer of at least about $10^5$, at least about $5 \times 10^5$, or at least about $10^6$, or at least about $2 \times 10^6$, genome copies of HCV per milliliter of serum. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also of interest are HCV-positive individuals (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment with IFN-α-based therapies or who cannot tolerate IFN-α-based therapies, or who have a contraindication to such therapies. In particular embodiments of interest, HCV-positive individuals with stage 3 or 4 liver fibrosis according to the METAVIR scoring system are suitable for treatment with the methods of the present embodiments. In other embodiments, individuals suitable for treatment with the methods of the embodiments are patients with decompensated cirrhosis with clinical manifestations, including patients with far-advanced liver cirrhosis, including those awaiting liver transplantation. In still other embodiments, individuals suitable for treatment with the methods of the embodiments include patients with milder degrees of fibrosis including those with early fibrosis (stages 1 and 2 in the METAVIR, Ludwig, and Scheuer scoring systems; or stages 1, 2, or 3 in the Ishak scoring system.).

Preparation of Section a Viral Inhibitors

Compounds of the general Formula I may be synthesized in the same general manner as described below for compounds of the general Formulas II-XIX. The syntheses of various specific compounds of the general Formula I are described in the Examples below. Those skilled in the art will appreciate variations in the sequence and, further, will recognize variations in the appropriate reaction conditions from the analogous reactions shown or otherwise known which may be appropriately used in the processes described below to make the compounds of formula I.

The products of the reactions described herein are isolated by conventional means such as extraction, distillation, chromatography, and the like.

The salts of the compounds of formula described above are prepared by reacting the appropriate base or acid with a stoichiometric equivalent of the compounds of formula I.

Preparation of Section B Viral Inhibitors

The meanings of the terms and structural names used within this section are the same as those in Section B above. Any references within this section to a particular number or label should be understood in the context of the corresponding numbering or labeling scheme used within this section or Section B above, rather than in the context of a possibly similar or identical numbering or labeling scheme used elsewhere herein, unless otherwise indicated.

The compounds of formulas II-X may be synthesized according to the methods described below.

Methodology

Preparation of Compounds

Two methods were used in preparing compounds with formulas II-X. In both methods, intermediates 1 and 4 were prepared according to the procedures disclosed in International Application PCT/CA00/00353 (Publication No. WO 00/59929). Intermediate 4 was also purchased from RSP Amino Acids.

Example 1-1

Synthesis of Compound # 101 (Compound AR00220042) by Method A

Compound #101 (Compound AR00220042)

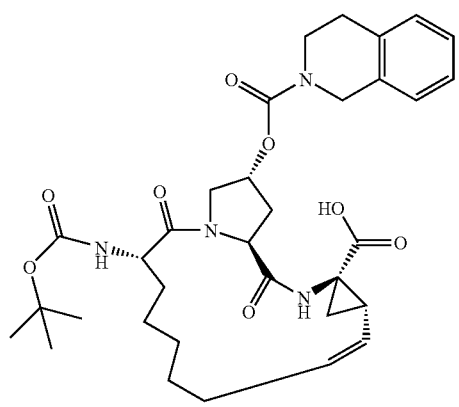

Method A:

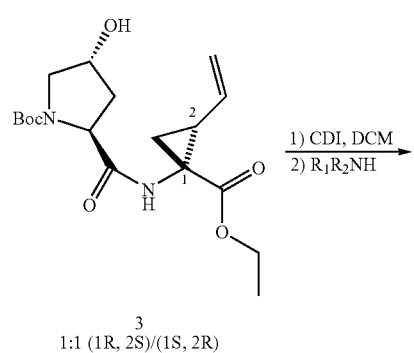

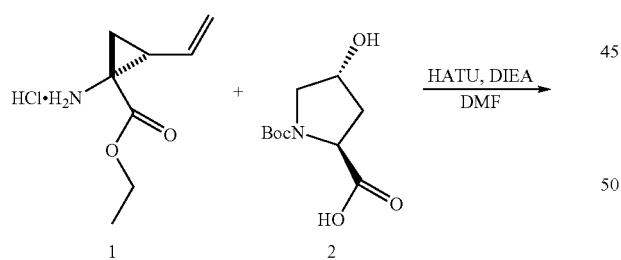
3
1:1 (1R, 2S)/(1S, 2R)

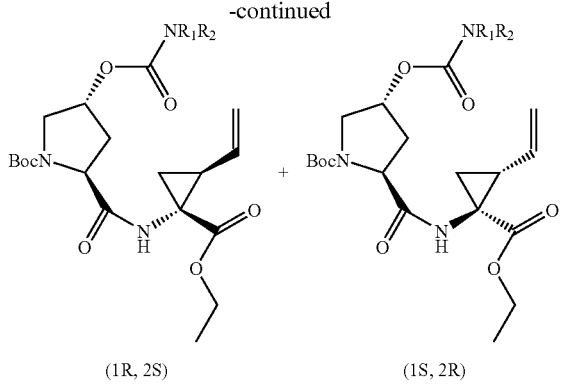
(1R, 2S)          (1S, 2R)

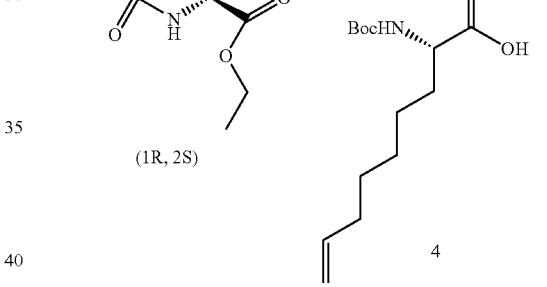

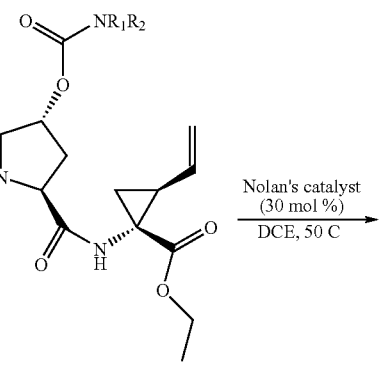

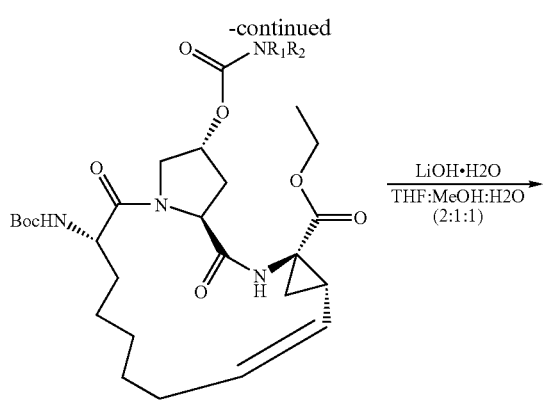

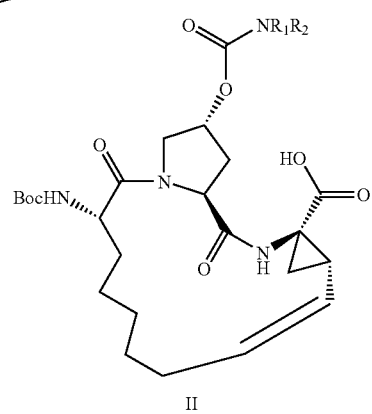

Step 1: Synthesis of 2S-(1-Ethoxycarbonyl-2-vinyl-cyclopropylcarbamoyl)-4R-hydroxy-pyrrolidine-1-carboxylic acid tert-butyl ester (3)

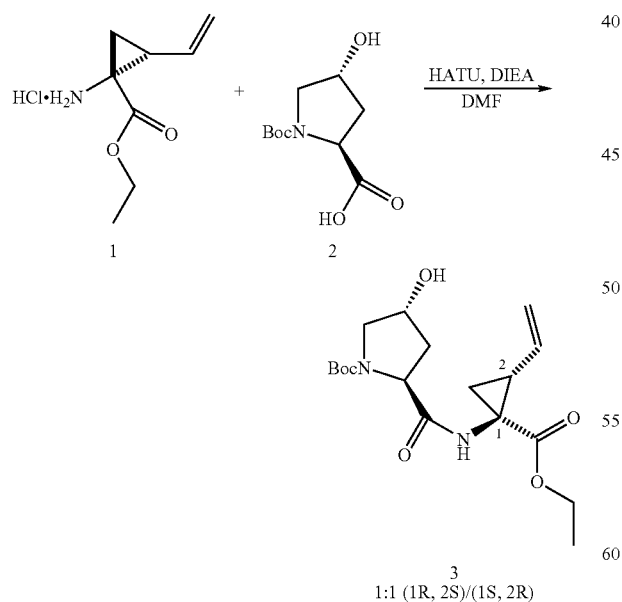

To a flask charged with ethyl-(1R,2S)/(1S,2R)-1-amino-2-vinylcyclopropyl carboxylate (1, 1.0 g, 5.2 mmol), trans-N-(tert-Butoxycarbonyl)-4-hydroxy-L-proline (2, 1.3 g, 1.1 equiv), and HATU (2.7 g, 1.1 equiv) were added 30 mL DMF to make a solution. It was cooled to 0° C. in an ice-water bath, followed by slow addition of a solution of DIEA (4.4 mL, 4 equiv) in DMF (15 mL) while stirring. The reaction was allowed to warm up to rt and stirred overnight After 16 h, the reaction was complete as monitored by HPLC. It was diluted with EtOAc (100 mL), washed with water (3×40 mL), sat. NaHCO$_3$ (2×40 mL), and brine (2×40 mL), then dried over Na$_2$SO$_4$ and concentrated down to give a dark copper colored oil. The crude was purified on silica gel (eluent: acetone/hexanes 3:7), giving pure 3 as tan foamy powder (770 mg, 32%).

Step 2: Syntheses of 3,4-Dihydro-1H-isoquinoline-2-carboxylic acid 1-tert-butoxycarbonyl-5-(1R-ethoxy-carbonyl-2S-vinyl-cyclopropylcarbamoyl)-pyrrolidin-3R-yl ester (5), and 3,4-Dihydro-1H-isoquinoline-2-carboxylic acid 1-tert-butoxycarbonyl-5-(1S-ethoxycarbonyl-2R-vinyl-cyclopropylcarbamoyl)-pyrrolidin-3R-yl ester (6)

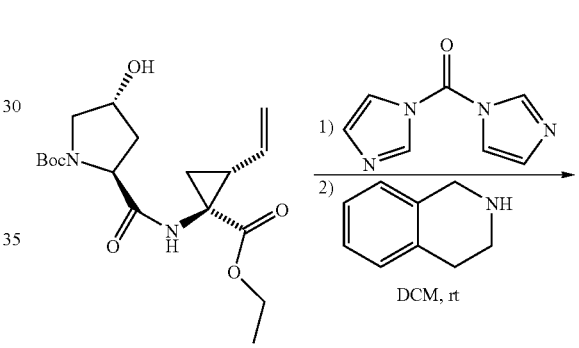

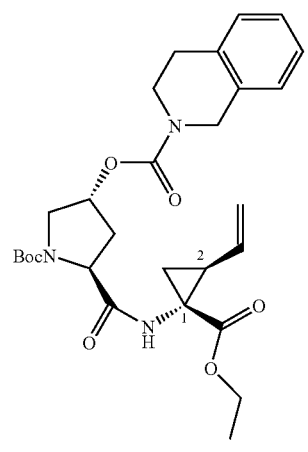

135

-continued

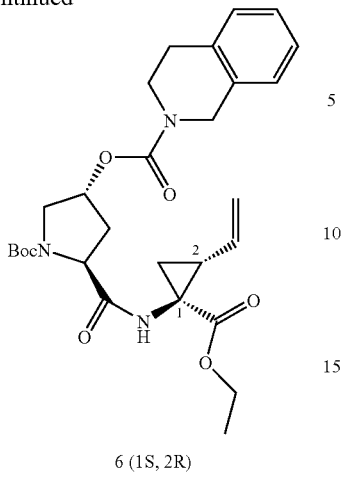

6 (1S, 2R)

136

-continued

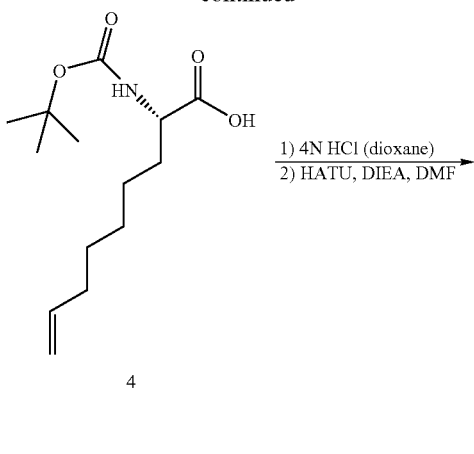

4

1) 4N HCl (dioxane)
2) HATU, DIEA, DMF

The dipeptide 3 (300 mg, 0.81 mmol) was dissolved in DCM (8 mL), followed by addition of CDI (163 mg, 1.2 equiv) in one portion. The reaction was stirred at rt overnight. After 15 h, the reaction was complete as monitored by TLC (DCM/MeOH 9:1). 1,2,3,4-tetrahydroisoquinoline (0.32 mL, 3 equiv) was added to the reaction portion-wise, and the reaction was stirred at rt for overnight.

After 22 h, TLC showed reaction complete. The reaction was diluted with DCM (15 mL) and washed with 1N aq. HCl (15 mL), brine (15 mL), dried (Na$_2$SO$_4$), and concentrated down. The crude was purified on silica gel (eluent: DCM/Et$_2$O/acetone 30:10:1). The top spot isolated (5) was white foamy powder (169 mg, 40%), and the bottom spot (6) was white solid (156 mg, 38%). MS m/e 550 (M$^+$+Na).

Step 3: Synthesis of 3,4-Dihydro-1H-isoquinoline-2-carboxylic acid 1-(2S-tert-butoxycarbonylamino-non-8-enoyl)-5-(1R-ethoxycarbonyl-2S-vinyl-cyclopropylcarbamoyl)-pyrrolidin-3R-yl ester (7)

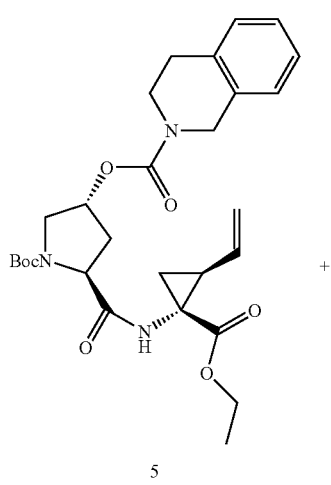

5

+

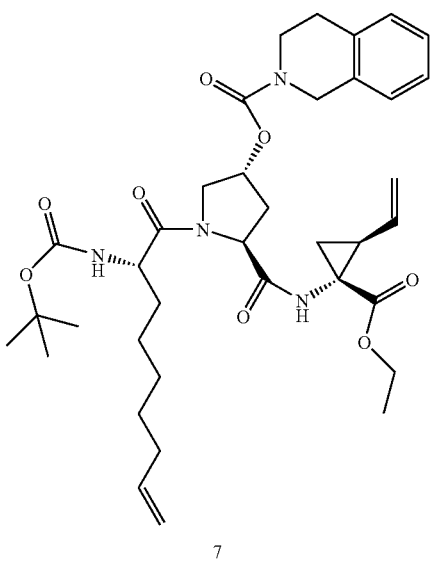

7

The top isomer 5 (118 mg, 0.22 mmol) was dissolved in 4N HCl (dioxane, 8 mL) and left at rt for 90 min to remove the BOC protective group. It was then concentrated down, taken up in acetonitrile and concentrated down again twice. To this light brownish residue was added 4 (66.8 mg, 1.1 equiv) and HATU (93.5 mg, 1.1 equiv), followed by 2 mL DMF under nitrogen. The reaction was cooled on ice-water bath for 15 min, after which a 0.5 mL DMF solution of DIEA (0.13 mL, 4 equiv) was added to the reaction drop-wise while stirring. The ice bath was left to slowly rise to rt and the reaction stirred for overnight.

After 24 h, the reaction has turned dark brownish. Its aliquot TLC shows reaction complete. The reaction was diluted with EtOAc (30 mL) and washed with water (3×15 mL), sat. NaHCO$_3$ (2×15 mL), brine (15 mL), dried (Na$_2$SO$_4$), and concentrated to give 7 as an orange oily residue (156 mg). It was directly used in the next step without further purification. MS m/e 703 (M$^+$+Na).

Step 4: Synthesis of (1S,4R,6S,14S,18R)-14-tert-Butoxycarbonylamino-18-(3,4-dihydro-1H-isoquinoline-2-carbonyloxy)-2,15-dioxo-3,16-diaza-tricyclo[14.3.0.0$^{4,6}$]nonadec-7-ene-4-carboxylic acid ethyl ester (8)
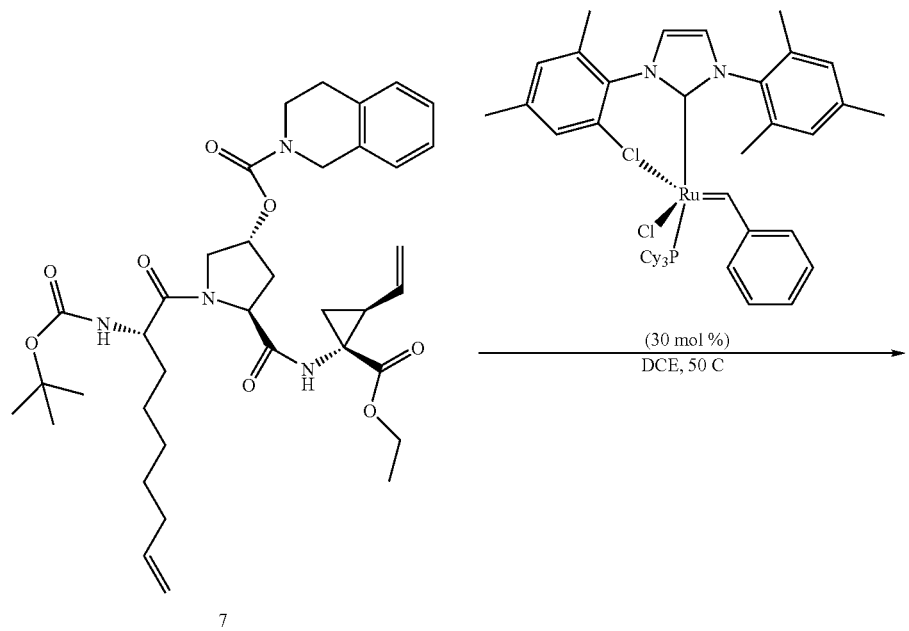
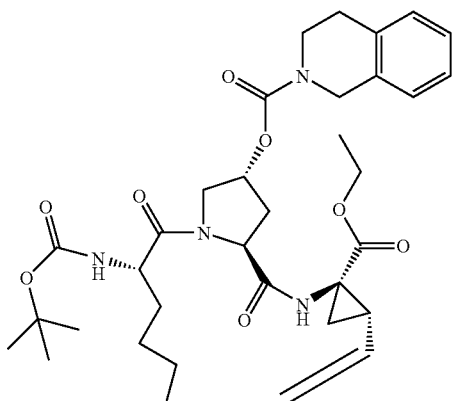

The crude 7 (135 mg, 0.2 mmol) was dissolved in 20 mL DriSolve DCE to make a solution, followed by addition of the Nolan's catalyst (5 mg, 0.3 equiv) at rt under nitrogen. The solution turned purplish. The reaction was put on a pre-heated oil bath (50 C) and stirred for overnight.

After 10 h, the reaction had turned dark brownish. TLC (DCM/EtOAc 1:1) showed clean conversion to a new spot with slightly lower R$_f$. The reaction was concentrated down and purified on silica gel (eluent: DCM/EtOAc gradient from 5:1 to 2:1), giving product 8 as a tan foamy powder (75 mg, 58%). MS m/e 653.1 (M$^+$+1).

Step 5: Synthesis of (1S,4R,6S,14S,18R)-14-tert-Butoxycarbonylamino-18-(3,4-dihydro-1H-isoquino-line-2-carbonyloxy)-2,15-dioxo-3,16-diaza-tricyclo [14.3.0.0$^{4,6}$]nonadec-7-ene-4-carboxylic acid (Compound# 101)

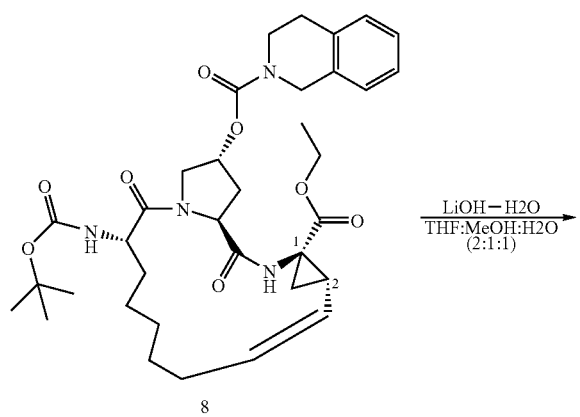

The macrocyclic ester 8 (60 mg, 0.092 mmol) was dissolved in 0.9 mL of a mixed solvent (THF/MeOH/H2O 2:1:1), followed by addition of LiOH—H$_2$O (23 mg, 6 equiv). The mixture was stirred at rt for overnight. After 18 h, TLC (DCM/MeOH 9:1) showed a clean new spot with a lower Rf. The reaction was concentrated down to almost dryness and partitioned between 1N aq. HCl (15 mL) and DCM (20 mL). The aqueous layer was extracted with DCM (2×10 mL). The organic layers were combined, dried over Na$_2$SO$_4$ and concentrated down, giving compound # 101 as a light brownish foamy powder (50 mg, 87%). $^1$H NMR (CD$_3$OD, 400 MHz) δ 1.20-1.67 (m, 21H), 1.70-1.83 (m, 1H), 1.88-2.10 (m, 1H), 2.12-2.58 (m, 4H), 2.82 (m, 2H), 3.60-3.80 (m, 2H), 3.86 (m, 1H), 4.20 (m, 1H), 4.35 (m, 1H), 4.54 (s, 7H), 4.58 (m, 3H), 5.29-5.41 (m, 2H), 5.57 (m, 1H), 7.0-7.24 (m, 4H). MS m/e 625.1 (M$^+$+1).

Example 1-1a

Compound AR00220122

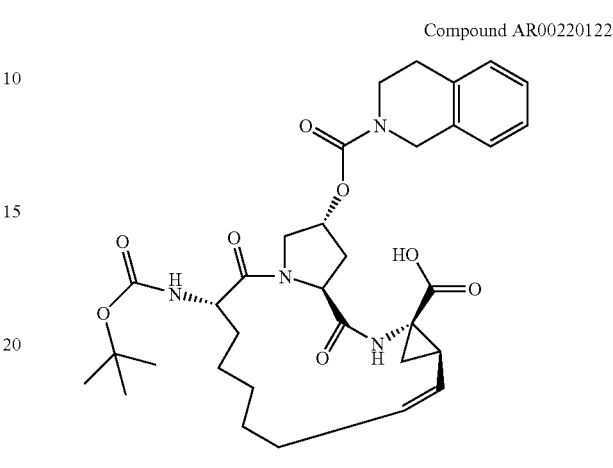

(1S,4S,6R,14S,18R)-14-tert-Butoxycarbonylamino-18-(3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00220122) was prepared similarly according to procedures described in Example 1-1, substituting compound 5 with 6 in Step 3. MS m/e 625 (M$^+$+1).

Example 1-2

Synthesis of Compound# 101 (Compound AR00220042) by Method B

Method B:

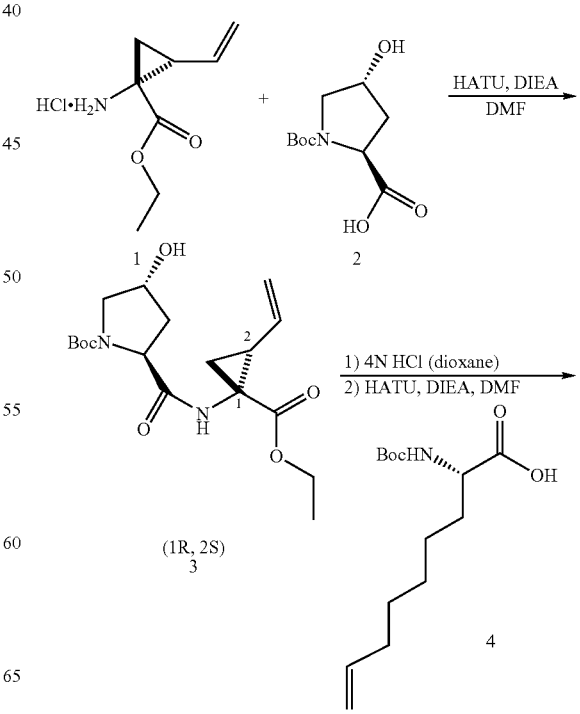

141

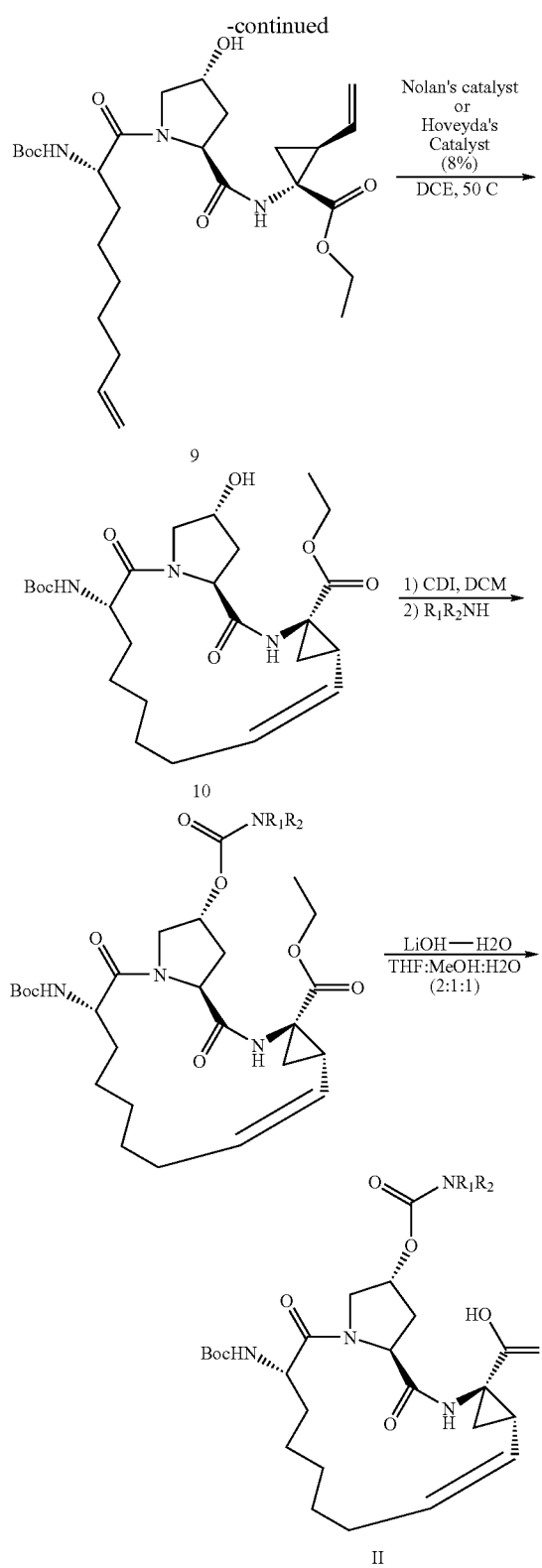

Compound# 101 was also prepared according to the above procedure. The synthesis of the macrocyclic intermediate 10 described here is similar to that described in International Application PCT/CA00/00353 (Publication No. WO 00/59929).

142

Step 1: Synthesis of 2S-(1-Ethoxycarbonyl-2-vinyl-cyclopropylcarbamoyl)-4R-hydroxy-pyrrolidine-1-carboxylic acid tert-butyl ester (3)

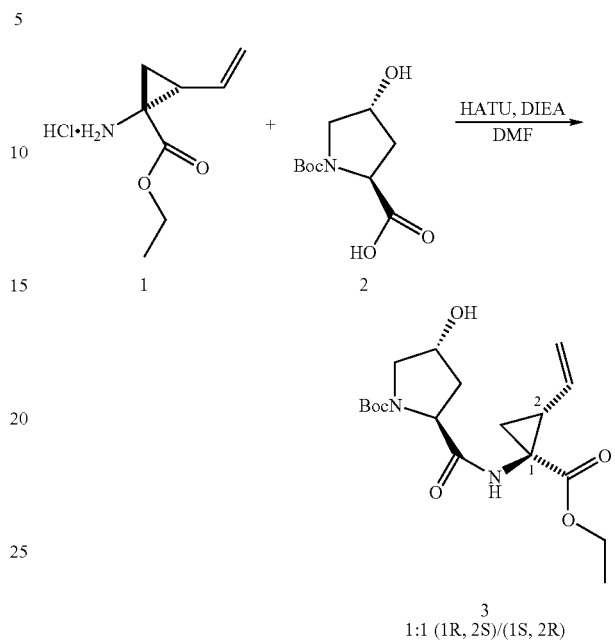

To a flask charged with ethyl-(1R,2S)/(1S,2R)-1-amino-2-vinylcyclopropyl carboxylate (1, 1.0 g, 5.2 mmol), trans-N-(tert-Butoxycarbonyl)-4-hydroxy-L-proline (2, 1.3 g, 1.1 equiv), and HATU (2.7 g, 1.1 equiv) were added 30 mL DMF to make a solution. It was cooled to 0° C. in an ice-water bath, followed by slow addition of a solution of DIEA (4.4 mL, 4 equiv) in DMF (15 mL) while stirring. The reaction was allowed to warm up to rt and stirred overnight.

After 16 h, the reaction was complete as monitored by HPLC. It was diluted with EtOAc (100 mL), washed with water (3×40 mL), sat. NaHCO$_3$ (2×40 mL), and brine (2×40 mL), then dried over Na$_2$SO$_4$ and concentrated down to give a dark copper colored oil. The crude was purified on silica gel (eluent: acetone/hexanes 3:7), giving pure 3 as tan foamy powder (770 mg, 32%).

Step 2: Synthesis of 1R-{[1-(2S-tert-Butoxycarbonylamino-non-8-enoyl)-4R-hydroxy-pyrrolidine-2S-carbonyl]-amino}-2S-vinyl-cyclopropanecarboxylic acid ethyl ester (9)

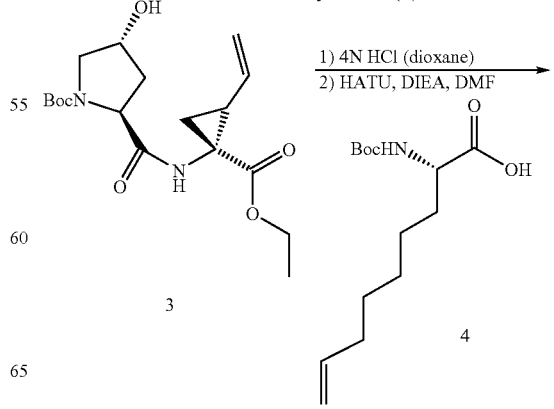

-continued

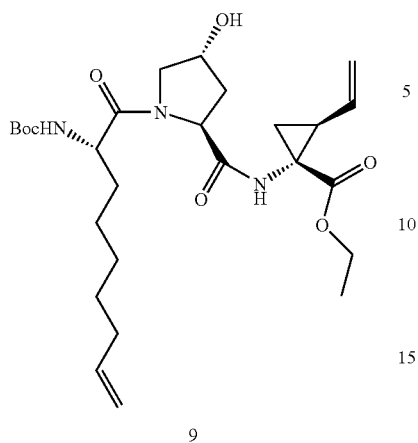

9

Compound 3 (2.85 g, 7.7 mmol) was dissolved in 10 mL 4N HCl (dioxane) and left at rt for 90 min to remove the Boc protective group. It was then concentrated down, taken up in acetonitrile and concentrated down again twice. To this light brownish residue was added 4 (2.2 g, 8.1 mmol) and HATU (3.2 g, 8.5 mmol), followed by 80 mL DMF under nitrogen. The reaction was cooled on ice-water bath for 15 min, after which a 5 mL DMF solution of DIEA (5.4 mL, 30.9 mmol) was added to the reaction drop-wise while stirring. The ice bath was left to slowly rise to rt and the reaction stirred for overnight.

After 18 h, TLC showed reaction complete. The reaction was diluted with EtOAc (300 mL) and washed with water (3×150 mL), sat. NaHCO$_3$ (2×150 mL), brine (150 mL), dried (Na$_2$SO$_4$), and solvent removed. The crude was purified by silica gel flash chromatography on Biotage 40M (eluent=3% to 5% MeOH in DCM) to give 9 as a brownish foamy solid (3.5 g, 87%).

Step 3: Synthesis of (1S,4R,6S,14S,18R)-14-tert-Butoxycarbonylamino-18-hydroxy-2,15-dioxo-3,16-diaza-tricyclo[14.3.0.0$^{4,6}$]nonadec-7-ene-4-carboxylic acid ethyl ester (10)

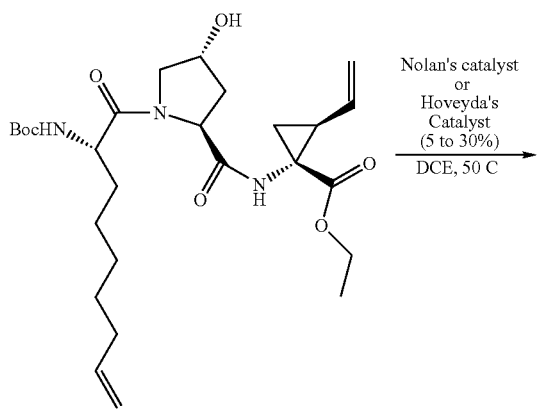

9

-continued

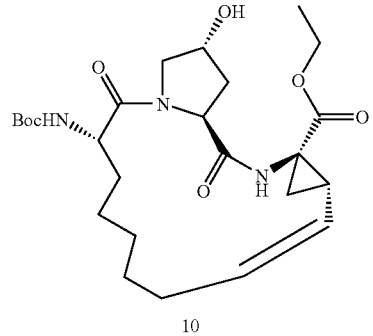

10

Compound 9 (2.6 g, 5.0 mmol) was dissolved in 500 mL DriSolve DCE in a 1 L round-bottomed flask to make a solution. It was degassed by bubbling nitrogen through for 1 h. Then the Hoveyda catalyst (0.25 equiv) was added at rt under nitrogen. The reaction was put on a pre-heated oil bath (50 C) and stirred for overnight. After 16 h, the reaction had turned dark brownish. TLC (DCM/EtOAc 1:1) showed clean conversion to a new spot with slightly lower R$_f$. The reaction was concentrated down and purified on silica gel (Biotage 40 M, eluent=DCM/EtOAc gradient from 1:1 to 1:2), giving product 10 as a tan foamy powder (0.64 g, 52%). $^1$H NMR (CDCl$_3$, 400 MHz) δ 1.21 (t, J=7.0 Hz, 3H), 1.43 (s, 9H), 1.20-1.50 (m, 6H), 1.53-1.68 (m, 2H), 1.83-1.96 (m, 2H), 1.98-2.28 (m, 4H), 2.60 (m, 1H), 3.13 (brs, 1H), 3.68 (m, 1H), 3.94 (m, 1H), 4.01-4.19 (m, 2H), 4.48 (m, 1H), 4.56 (brs, 1H), 4.79 (m, 1H), 5.26 (t, J=9.4 Hz, 1H), 5.36 (d, J=7.8 Hz, 1H), 5.53 (m, 1H), 7.19 (brs, 1H). MS m/e 494.0 (M$^+$+1).

Step 4: Synthesis of (1S,4R,6S,14S,18R)-14-tert-Butoxycarbonylamino-18-(3,4-dihydro-1H-isoquinoline-2-carbonyloxy)-2,15-dioxo-3,16-diaza-tricyclo[14.3.0.0$^{4,6}$]nonadec-7-ene-4-carboxylic acid ethyl ester (11)

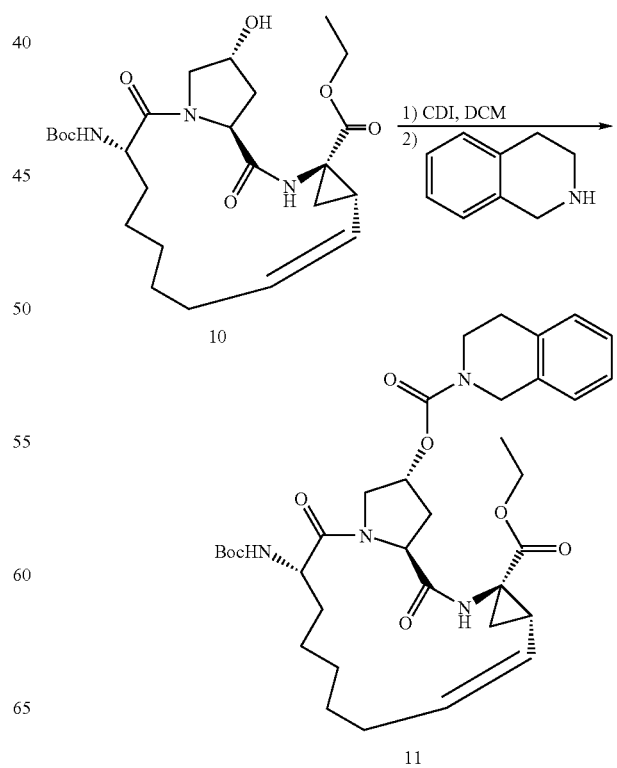

11

The macrocyclic intermediate 10 (110 mg, 0.22 mmol) was dissolved in DCM (2.2 mL), followed by addition of CDI (45 mg, 0.27 mmol) in one portion. The reaction was stirred at rt overnight. After 15 h, the reaction was complete as monitored by TLC (DCM/MeOH 9:1). 1,2,3,4-tetrahydroisoquinoline (0.14 mL, 1.1 mmol) was added to the reaction drop-wise, and the reaction was stirred at rt for overnight. After 22 h, TLC showed reaction complete. The reaction was diluted with DCM (6 mL) and washed with 1N aq. HCl (2×2 mL), sat. sodium bicarbonate (2 mL), brine (2 mL), dried (Na$_2$SO$_4$), and concentrated down. The crude was purified on silica gel (Biotage 40S, eluent: 2 to 4% MeOH in DCM), giving 11 as a pale yellowish foamy powder (131 mg, 90%).

Step 5: Compound 11 was Hydrolyzed in the Same Fashion as Described in the Step 5 of Example 1-1 to Give Compound# 101

The following compounds were also prepared according to Method B described above, with 1,2,3,4-tetrahydroisoquinoline being substituted by various other secondary amines. Most of these amines were either purchased from commercial sources, or are known literature compounds, therefore were prepared using the procedures listed here (1. Stokker, G E. *Tetrahedron Lett.* 1996, 37(31), 5453-5456. 2. Chan, N W. *Bioorganic & Medicinal Chemistry* 2000, 8, 2085-2094. 3. Vecchietti, V. et al, *J. Med. Chem.* 1991, 34, 2624-2633.) For those amine inputs that were not directly prepared according to literature procedures, or the specific input has not been reported in literature before at our best knowledge, their syntheses are given within each example.

Example 1-3

Compound AR00226824

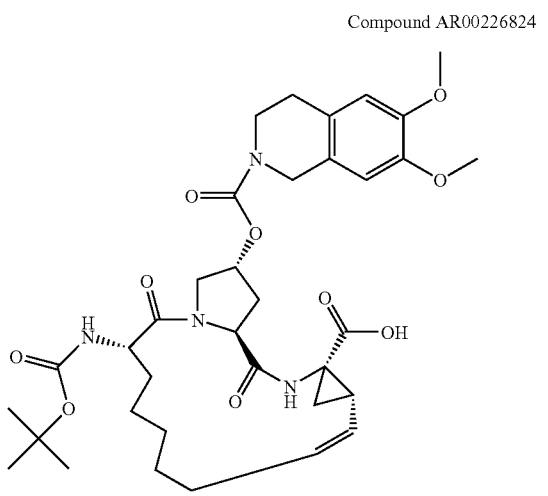

(1S,4R,6S,14S,18R)-14-tert-Butoxycarbonylamino-18-(6,7-dimethoxy-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00226824) was synthesized according to Method B, except 6,7-dimethoxy-1,2,3,4-tetrahydro-isoquinoline was used in Step 4 instead. MS m/e 585.2 (M$^+$+1−100).

Example 1-4

Compound AR00226825

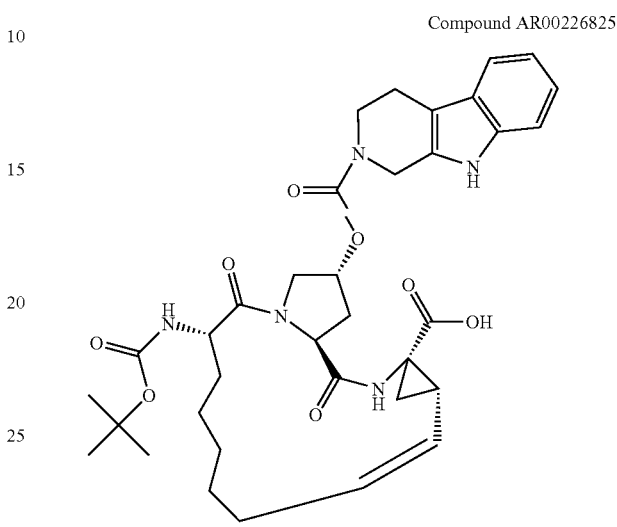

(1S,4R,6S,14S,18R)-14-tert-Butoxycarbonylamino-2,15-dioxo-18-(1,3,4,9-tetrahydro-b-carboline-2-carbonyloxy)-3,16-diaza-tricyclo[14.3.0.0$^{4,6}$]nonadec-7-ene-4-carboxylic acid (compound AR00226825) was synthesized according to Method B, except 2,3,4,9-Tetrahydro-1H-b-carboline was used in Step 4 instead. MS m/e 564.2 (M$^+$+1−100).

Example 1-5

Compound AR00291871

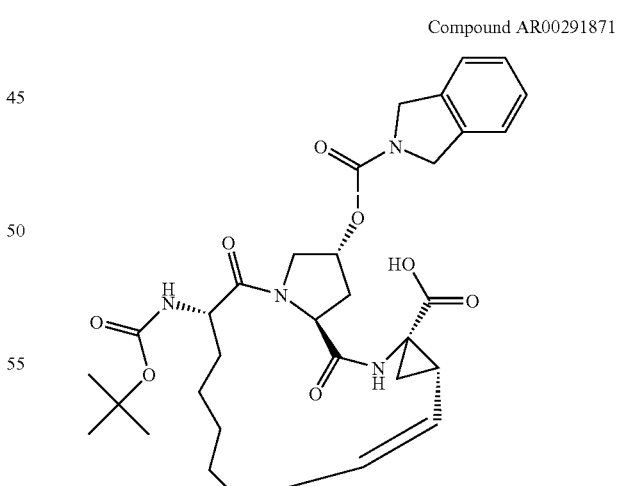

(1S,4R,6S,14S,18R)-14-tert-Butoxycarbonylamino-18-(1,3-dihydro-isoindole-2-carbonyloxy)-2,15-dioxo-3,16-diaza-tricyclo[14.3.0.0$^{4,6}$]nonadec-7-ene-4-carboxylic acid (compound AR00291871) was synthesized according to Method B, except 2,3-Dihydro-1H-isoindole was used in Step 4 instead. $^1$H NMR (CDCl$_3$, 500 MHz) δ 1.21-1.44 (m, 8H), 1.32 (s, 9H), 1.54-1.62 (m, 2H), 1.78-1.88 (m, 2H), 2.04-2.13 (m, 1H), 2.16-2.23 (m, 1H), 2.24-2.36 (m, 2H), 2.66-2.74 (m, 1H), 3.87-3.90 (m, 1H), 4.15 (d, J=11.0 Hz, 1H), 4.37-4.43 (m, 1H), 4.61-4.77 (m, 5H), 5.18 (t, J=10.3 Hz, 1H), 5.24-5.31 (m, 1H), 5.40-5.45 (m, 1H), 5.58-5.66 (m, 1H), 7.11-7.30 (m, 4H). MS m/e 611.0 (M$^+$+1).

Example 1-6

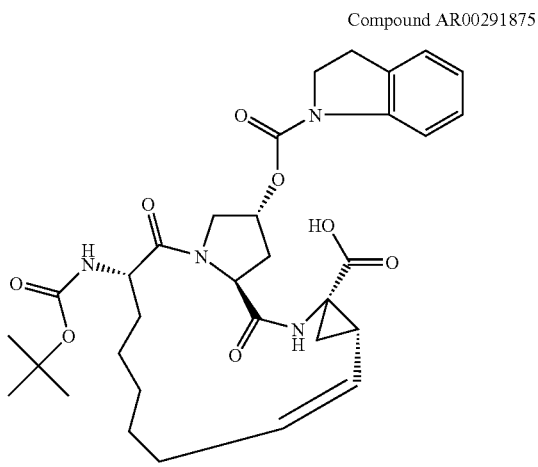

Compound AR00291875

(1S,4R,6S,14S,18R)-14-tert-Butoxycarbonylamino-18-(2,3-dihydro-indole-1-carbonyloxy)-2,15-dioxo-3,16-diaza-tricyclo[14.3.0.0$^{4,6}$]nonadec-7-ene-4-carboxylic acid (compound AR00291875) was synthesized according to Method B, except 2,3-Dihydro-1H-indole was used in Step 4 instead. MS m/e 610.9 (M$^+$+1).

Example 1-7

Compound AR00294382

(1S,4R,6S,14S,18R)-14-tert-Butoxycarbonylamino-2,15-dioxo-18-(8-trifluoromethyl-3,4-dihydro-1H-isoquinoline-2-carbonyloxy)-3,16-diaza-tricyclo[14.3.0.0$^{4,6}$]nonadec-7-ene-4-carboxylic acid (compound AR00294382) was synthesized according to Method B, except 8-Trifluoromethyl-1,2,3,4-tetrahydro-isoquinoline was used in Step 4 instead. MS m/e 693.0 (M$^+$)

Example 1-8

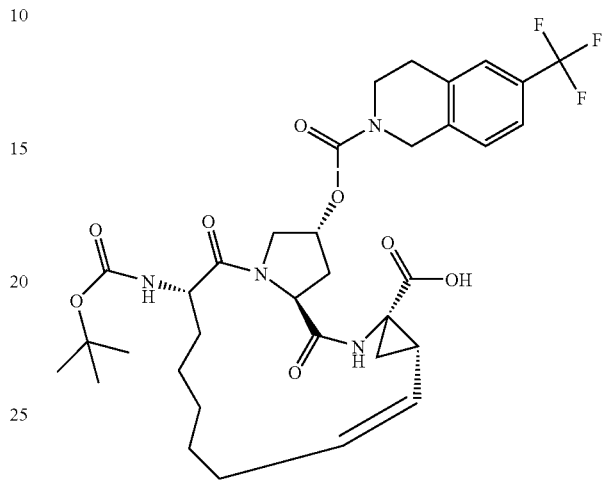

Compound AR00294383

(1S,4R,6S,14S,18R)-14-tert-Butoxycarbonylamino-2,15-dioxo-18-(6-trifluoromethyl-3,4-dihydro-1H-isoquinoline-2-carbonyloxy)-3,16-diaza-tricyclo[14.3.0.0$^{4,6}$]nonadec-7-ene-4-carboxylic acid (compound AR00294383) was synthesized according to Method B, except 6-Trifluoromethyl-1,2,3,4-tetrahydro-isoquinoline was used in Step 4 instead. $^1$H NMR (500 MHz, CDCl$_3$): δ 7.46-7.38 (m, 2H), 7.26-7.18 (m, 1H), 6.98 (s, 1H), 5.62 (q, 1H), 5.42 (s, 1H), 5.21-5.15 (m, 2H), 4.78-4.60 (m, 3H), 4.40 (s, 1H), 4.16-4.00 (m, 1H), 3.92-3.81 (m, 1H), 3.80-3.60 (m, 2H), 3.00-2.85 (m, 2H), 2.72-2.64 (br s, 1H), 2.40-1.18 (m, 20H). MS: m/e 693.0 (M$^+$).

Example 1-9

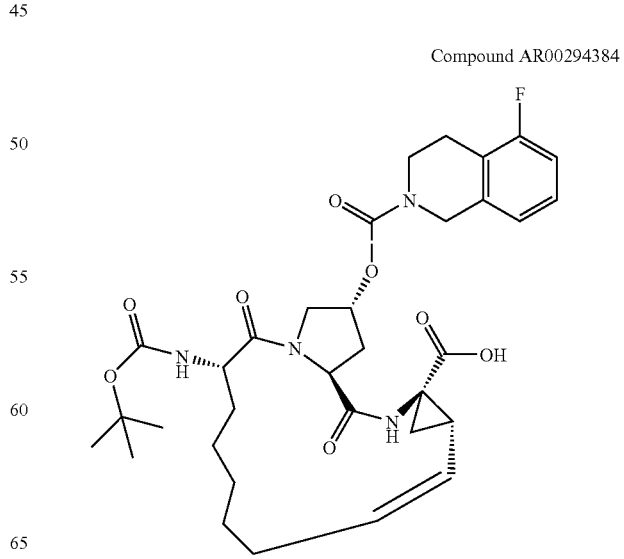

Compound AR00294384

(1S,4R,6S,14S,18R)-14-tert-Butoxycarbonylamino-18-(5-fluoro-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00294384) was synthesized according to Method B, except 5-fluoromethyl-1,2,3,4-tetrahydro-isoquinoline was used in Step 4 instead. $^1$H NMR (500 MHz, CDCl$_3$): δ 7.19-7.11 (m, 1H), 7.05 (m, 1H), 6.91 (t, 2H), 5.62 (q, 1H), 5.40 (s, 1H), 5.24 (d, 1H), 5.20 (t, 1H), 4.78 (s, 1H), 4.64-4.56 (m, 2H), 4.42 (s, 1H), 4.12-4.02 (m, 1H), 3.92-3.81 (m, 1H), 3.78-3.61 (m, 2H), 2.84-2.80 (m, 2H), 2.74-2.64 (m, 1H), 2.36-2.18 (m, 2H), 1.91-1.81 (m, 2H), 1.64-1.54 (m, 2H), 1.48-1.10 (m, 15H). MS: m/e 643.0 (M$^+$)

Example 1-10

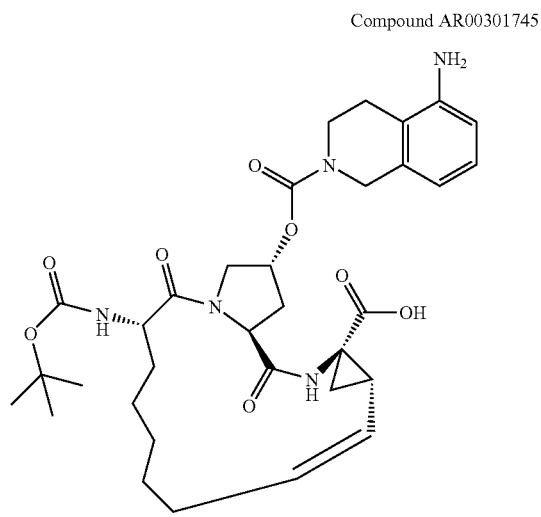

Compound AR00301745

(1S,4R,6S,14S,18R)-18-(5-Amino-3,4-dihydro-1H-isoquinoline-2-carbonyloxy)-14-tert-butoxycarbonylamino-2,15-dioxo-3,16-diaza-tricyclo[14.3.0.0$^{4,6}$]nonadec-7-ene-4-carboxylic acid (compound AR00301745) was synthesized according to Method B, except 5-amino-1,2,3,4-tetrahydro-isoquinoline was used in Step 4 instead. MS: m/e 640.1 (M$^+$)

Example 1-11

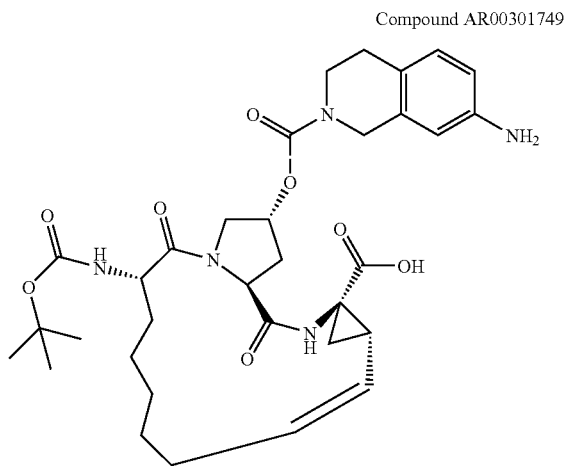

Compound AR00301749

(1S,4R,6S,14S,18R)-18-(7-Amino-3,4-dihydro-1H-isoquinoline-2-carbonyloxy)-14-tert-butoxycarbonylamino-2,15-dioxo-3,16-diaza— tricyclo[14.3.0.0$^{4,6}$]nonadec-7-ene-4-carboxylic acid (compound AR00301749) was synthesized according to Method B, except 7-amino-1,2,3,4-tetrahydro-isoquinoline was used in Step 4 instead. MS: m/e 640.1 (M$^+$), 641.1 (M$^+$+1)

Example 1-12

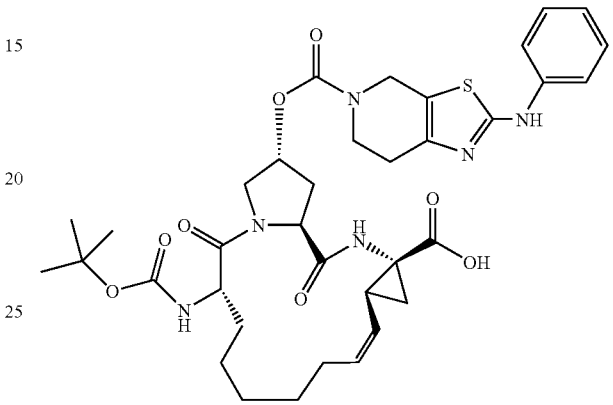

Compound AR00304000

(1S,4R,6S,14S,18R)-14-tert-Butoxycarbonylamino-2,15-dioxo-18-(2-phenylamino-6,7-dihydro-4H-thiazolo[5,4-c]pyridine-5-carbonyloxy)-3,16-diaza-tricyclo[14.3.0.0$^{4,6}$]nonadec-7-ene-4-carboxylic acid (compound AR00304000) was synthesized according to Method B, except Phenyl-(4,5,6,7-tetrahydro-thiazolo[5,4-c]pyridin-2-yl)-amine was used in Step 4 instead. MS m/e 721.2 (M−1).

Example 1-13

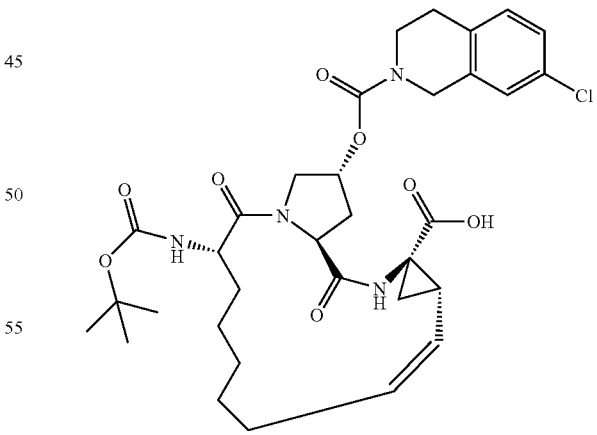

Compound AR00304062

(1S,4R,6S,14S,18R)-14-tert-Butoxycarbonylamino-18-(7-chloro-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00304062) was synthesized according to Method B, except 7-Chloro-1,2,3,4-tetrahydro-isoquinoline was used in Step 4 instead. MS m/e 659.0 (M$^+$), 661.0 (M$^+$+2)

Example 1-14

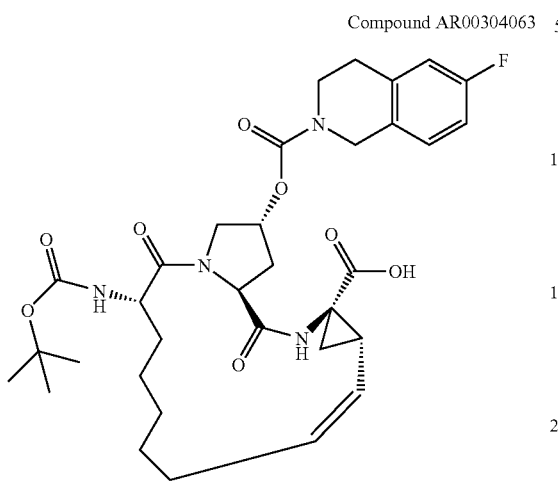

Compound AR00304063

(1S,4R,6S,14S,18R)-14-tert-Butoxycarbonylamino-18-(6-fluoro-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00304063) was synthesized according to Method B, except 6-fluoro-1,2,3,4-tetrahydro-isoquinoline was used in Step 4 instead. MS m/e 643.0 (M$^+$), 644.0 (M$^+$+1)

Example 1-15

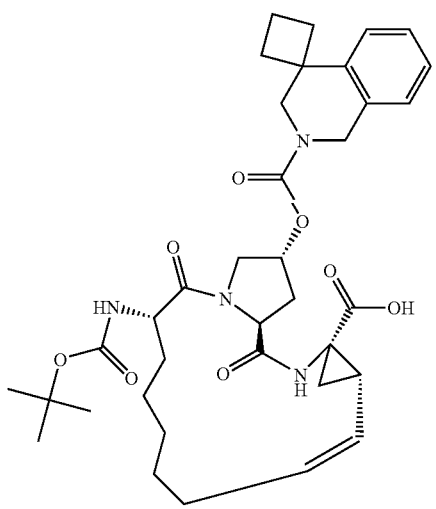

Compound AR00304065

(1S,4R,6S,14S,18R)-14-tert-Butoxycarbonylamino-18-(4,4-spirocyclobutyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00304065) was synthesized according to Method B, except 4,4-siprocyclobutyl-1,2,3,4-tetrahydro-isoquinoline was used in Step 4 instead. $^1$H NMR (400 MHz, d$_6$-acetone) δ 7.99 (d, 1H), 7.57-7.66 (m, 1H), 7.27 (t, 1H), 7.09-7.22 (m, 2H), 5.99 (bs, 1H), 5.56 (dd, 1H), 5.42 (bs, 1H), 5.19-5.30 (m, 1H), 4.52-4.70 (m, 1H), 4.27-4.42 (m, 1H), 4.17-4.27 (m, 1H), 3.91 (dd, 1H), 3.63-3.82 (m, 2H), 2.22-2.51 (m, 6H), 1.93-2.20 (m, 3H), 1.79-1.91 (m, 1H), 1.52-1.66 (m, 1H), 1.16-1.50 (m, 19H). MS m/z 665.1 (M$^+$+1)

Example 1-15a

Preparation of 4,4-siprocyclobutyl-1,2,3,4-tetrahydro-isoquinoline

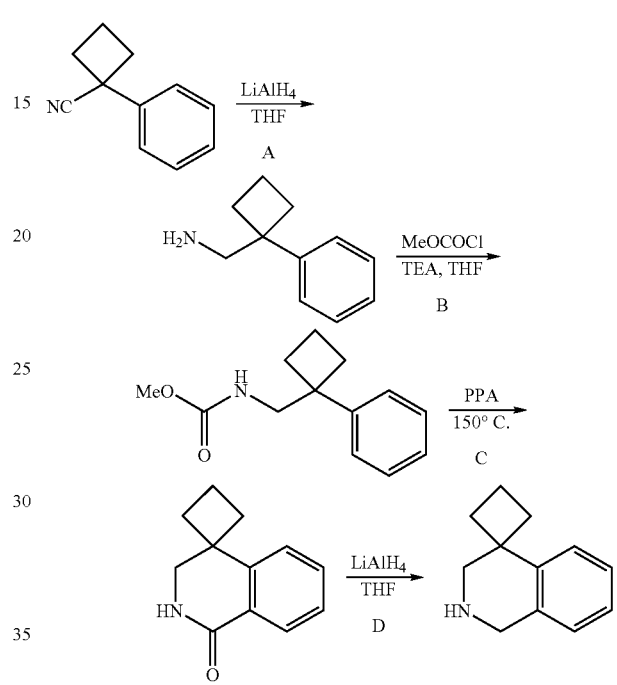

A: To a solution of 1-phenyl-1-cyclopropane carbonitrile (2.00 g, 12.7 mmol) in 100 ml THF was added a 1.0 M solution of LiAlH (19.1 ml, 19.1 mmol) dropwise at r.t. The reaction was stirred at r.t. for 15 hours, then quenched slowly at 0° C. with 10 ml H$_2$O and then 10 ml 1.0N NaOH and stirred at r.t. for 1.5 hours. The solution was filtered, and the THF was removed by rotary evaporation. The aqueous was extracted with EtOAc, and the organic extract was washed with H$_2$O and brine, dried over Na$_2$SO$_4$, and concentrated to give 0.70 g (34%) of a clear oil which was used in the next step without further purification.

B: To a solution of C-(1-Phenyl-cyclobutyl)-methylamine (0.70 g, 4.34 mmol) and TEA (0.67 ml, 4.78 mmol) in 40 ml THF at 0° C. was added methyl chloroformate dropwise. The reaction was stirred at r.t. for 15 hours. The next day water and EtOAc were added and the organic layer was separated and washed with 1N HCl and brine, dried over Na$_2$SO$_4$, concentrated to an oil, and used directly in the next step without further purification.

C: A mixture of (1-Phenyl-cyclobutylmethyl)-carbamic acid methyl ester (0.95 g, 4.34 mmol) and PPA (20 ml) were added to a sand bath preheated to 150° C. After 30 minutes the reaction was cooled to room temperature (r.t.). After cooling, water was added dropwise and the solution was extracted twice with DCM. The organic extracts were washed with brine, dried over Na$_2$SO$_4$, and concentrated to a clear oil which was used directly in the in the next step without further purification.

D: To a solution of the 3,4-dihydro-2H-isoquinolin-1-one (0.406 g, 2.17 mmol) in 20 ml THF at 0° C. was added a 1.0 M solution of LiAlH (3.26 ml, 3.26 mmol) dropwise. The reaction was allowed to warm to r.t. and was stirred for 15 hours, then quenched slowly at 0° C. with 5 ml H₂O and then 5 ml 1.0N NaOH and stirred at r.t. for 1.5 hours. The solution was filtered, and the THF was removed by rotary evaporation. The aqueous was extracted with EtOAc, and the organic extract was washed with H₂O and brine, dried over Na$_2$SO$_4$, and concentrated to give 0.21 g (56%) of a clear oil which was used in the next step without further purification.

Example 1-16

Compound AR00304066

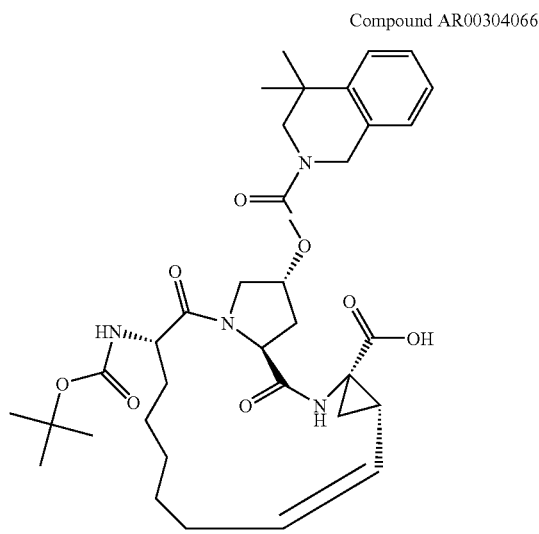

(1S,4R,6S,14S,18R)-14-tert-Butoxycarbonylamino-18-(4,4-dimethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00304066) was synthesized according to Method B, except 4,4-Dimethyl-1,2,3,4-tetrahydro-isoquinoline was used in Step 4 instead. $^1$H NMR (400 MHz, d$_6$-acetone) δ 7.98 (d, 1H), 7.39 (bs, 1H), 7.09-7.24 (m, 3H), 5.99 (bs, 1H), 5.57 (dd, 1H), 5.37-5.46 (bs, 1H), 5.24 (dd, 1H), 4.55-4.69 (m, 1H), 4.26-4.36 (m, 1H), 4.16-4.26 (m, 1H), 3.90 (dd, 1H), 3.40-3.49 (m, 1H), 2.28-2.50 (m, 4H), 1.98-2.09 (2H), 1.79-1.92 (m, 1H), 1.52-1.65 (m, 3H), 1.16-1.51 (m, 22H). MS m/z 653.0 (M$^+$+1)

Example 1-16a

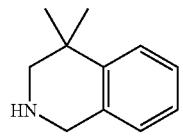

4,4-dimethyl-1,2,3,4-tetrahydroisoquinoline was prepared following the experimental of steps A through D in Example 1-15a, 2-Methyl-2-phenyl-propionitrile (prepared according to Caron, S.; Vazquez, E.; Wojcik, J. M. *J. Am. Chem. Soc.* 2000, 122, 712-713) was converted to the title compound.

Example 1-17

Compound AR00304067

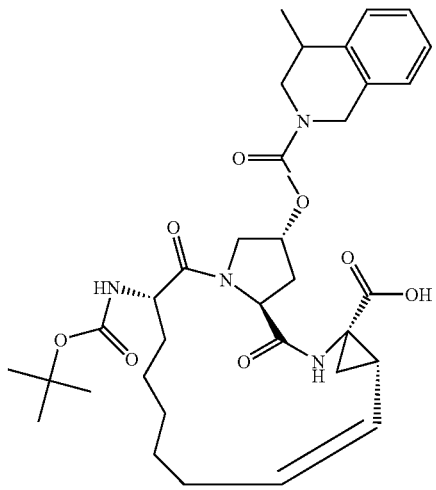

(1S,4R,6S,14S,18R)-14-tert-Butoxycarbonylamino-18-(4-methyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (compound AR00304067) was synthesized according to Method B, except 4-methyl-1,2,3,4-tetrahydro-isoquinoline was used in Step 4 instead. $^1$H NMR (400 MHz, d$_6$-acetone) δ 7.93-8.03 (m, 1H), 7.04-7.28 (m, 4H), 6.02 (bs, 1H), 5.56 (dd, 1H), 5.40 (m, 1H), 5.23 (dd, 1H), 4.66-4.85 (m, 1H), 4.54-4.64 (m, 1H), 4.34-4.54 (m, 1H), 4.17-4.34 (m, 1H), 3.91 (dd, 1H), 3.57-3.78 (m, 1H), 3.42-3.57 (m, 1H), 2.26-2.52 (m, 4H), 1.96-2.09 (m, 2.0), 1.77-1.92 (m, 1.0), 1.50-1.64 (m, 3.0), 1.13-1.50 (m, 17h). MS m/z 639.0 (M$^+$+1)

Example 1-17a

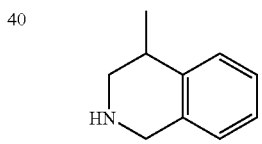

4-methyl-1,2,3,4-tetrahydroisoquinoline was prepared from 2-phenyl-propylamine according to Grunewald, G. L.; Sall, D. J.; Monn, J. A. *J. Med. Chem.* 1988, 31, 433-444.

Example 1-18

Compound AR00304103

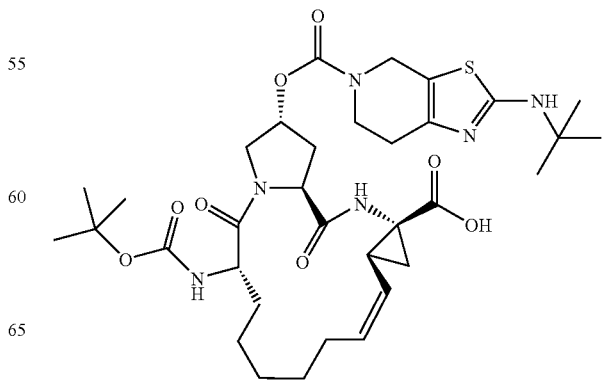

(1S,4R,6S,14S,18R)-14-tert-Butoxycarbonylamino-18-(2-tert-butylamino-6,7-dihydro-4H-thiazolo[5,4-c]pyridine-5-carbonyloxy)-2,15-dioxo-3,16-diaza-tricyclo[14.3.0.0$^{4,6}$]nonadec-7-ene-4-carboxylic acid (compound AR00304103) was synthesized according to Method B, except tert-Butyl-(4,5,6,7-tetrahydro-thiazolo[5,4-c]pyridin-2-yl)-amine was used in Step 4 instead. MS m/e 731.2 (M$^+$+1).

Example 1-19

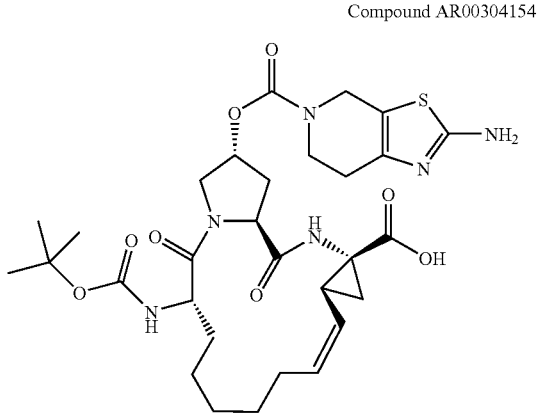

Compound AR00304154

(1S,4R,6S,14S,18R)-18-(2-Amino-6,7-dihydro-4H-thiazolo[5,4-c]pyridine-5-carbonyloxy)-14-tert-butoxycarbonylamino-2,15-dioxo-3,16-diaza-tricyclo[14.3.0.0$^{4,6}$]nonadec-7-ene-4-carboxylic acid (compound AR00304154) was synthesized according to Method B, except 4,5,6,7-Tetrahydro-thiazolo[5,4-c]pyridin-2-ylamine was used in Step 4 instead. MS m/e 675.1 (M$^+$+1).

Example 1-20

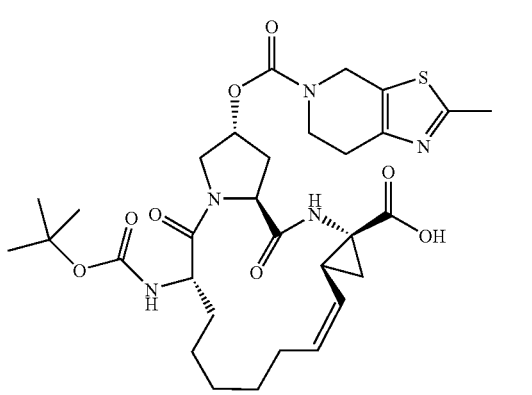

Compound AR00304158

(1S,4R,6S,14S,18R)-14-tert-Butoxycarbonylamino-18-(2-methyl-6,7-dihydro-4H-thiazolo[5,4-c]pyridine-5-carbonyloxy)-2,15-dioxo-3,16-diaza-tricyclo[14.3.0.0$^{4,6}$]nonadec-7-ene-4-carboxylic acid (compound AR00304158) was synthesized according to Method B, except 2-Methyl-4,5,6,7-tetrahydro-thiazolo[5,4-c]pyridine was used in Step 4 instead. MS m/e 546.2 (M$^+$+1–100).

Example 1-21

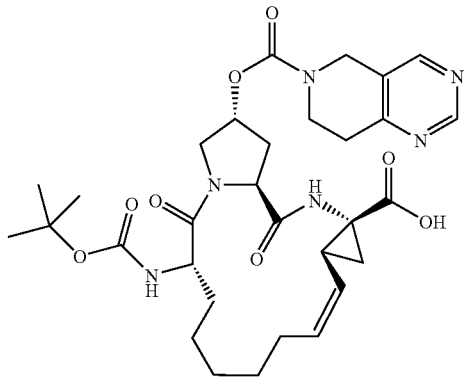

Compound AR00304183

(1S,4R,6S,14S,18R)-14-tert-Butoxycarbonylamino-18-(7,8-dihydro-5H-pyrido[4,3-d]pyrimidine-6-carbonyloxy)-2,15-dioxo-3,16-diaza-tricyclo[14.3.0.0$^{4,6}$]nonadec-7-ene-4-carboxylic acid (Compound AR00304183) was synthesized according to Method B, except 5,6,7,8-Tetrahydro-pyrido[4,3-d]pyrimidine was used in Step 4 instead. MS m/e 625.2 (M–1).

Example 1-22

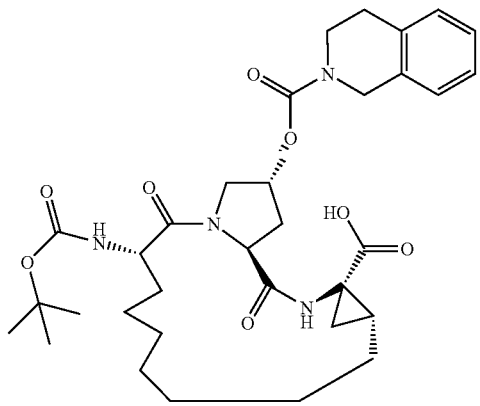

Compound AR00312023

(1S,4R,6S,14S,18R)-14-tert-Butoxycarbonylamino-18-(3,4-dihydro-1H-isoquinoline-2-carbonyloxy)-2,15-dioxo-3,16-diaza-tricyclo[14.3.0.0$^{4,6}$]nonadecane-4-carboxylic acid (Compound AR00312023) was synthesized according to Method B, except that the ring-closing metathesis product 10 from step 3 was further reduced with H$_2$/Rh—Al$_2$O$_3$ before the next coupling step (WO 0059929, p.p. 76-77). MS m/e 625.3 (M–1).

Example 1-23

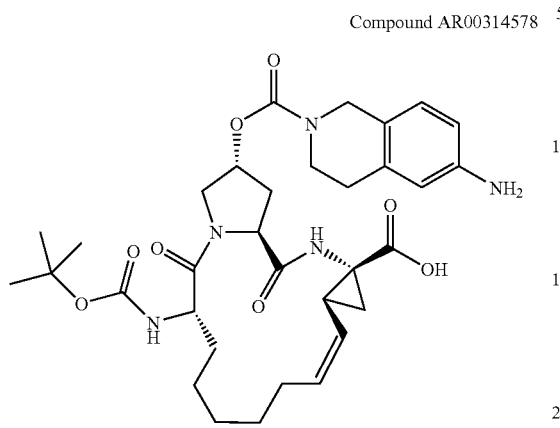
Compound AR00314578

(1S,4R,6S,14S,18R)-18-(6-Amino-3,4-dihydro-1H-isoquinoline-2-carbonyloxy)-14-tert-butoxycarbonylamino-2,15-dioxo-3,16-diaza-tricyclo[14.3.0.0$^{4,6}$]nonadec-7-ene-4-carboxylic acid (Compound AR00314578) was synthesized according to Method B, except 1,2,3,4-Tetrahydro-isoquinolin-6-ylamine was used in Step 4 instead. MS (POS ESI) m/z 540.2 [parent, (M$^+$+1)–100 (Boc group)].

Example 1-24

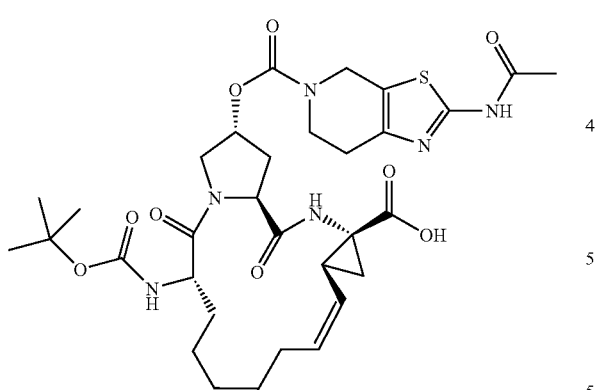
Compound AR00314685

(1S,4R,6S,14S,18R)-18-(2-Acetylamino-6,7-dihydro-4H-thiazolo[5,4-c]pyridine-5-carbonyloxy)-14-tert-butoxycarbonylamino-2,15-dioxo-3,16-diaza-tricyclo[14.3.0.0$^{4,6}$]nonadec-7-ene-4-carboxylic acid (Compound AR00314685) was synthesized according to Method B, except N-(4,5,6,7-Tetrahydro-thiazolo[5,4-c]pyridin-2-yl)-acetamide was used in Step 4 instead. MS m/e 589.2 (M$^+$+1–100).

Example 1-25

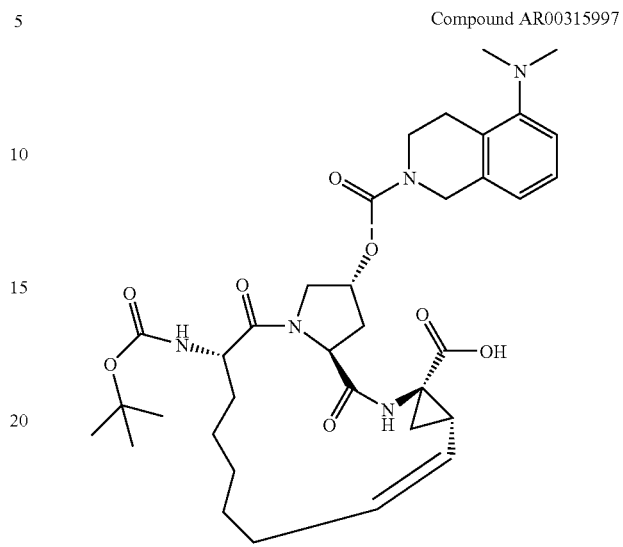
Compound AR00315997

(1S,4R,6S,14S,18R)-14-tert-Butoxycarbonylamino-18-(5-dimethylamino-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00315997) was synthesized according to Method B, except Dimethyl-(1,2,3,4-tetrahydro-isoquinolin-5-yl)-amine (Example 1-25a) was used in Step 4 instead. MS m/e 668.0 (M$^+$).

Example 1-25a

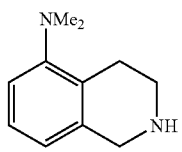

The synthesis of dimethyl-(1,2,3,4-tetrahydro-isoquinolin-5-yl)-amine is described in the following scheme:

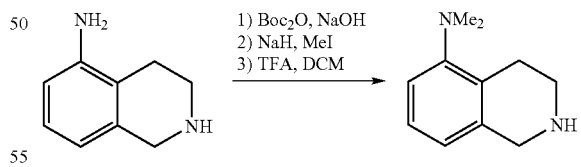

To a solution of 5-aminotetrahydroisoquinoline (3.68 g, 24.8 mmol) in 1,4-dioxane (100 mL) was added 3 N NaOH (8.27 mL, 24.8 mmol). After cooling to 0° C., (Boc)$_2$O (5.42 g, 24.8 mmol) in 1,4-dioxane (10 mL) was added drop-wise and stirred for overnight at room temperature. The reaction mixture was poured into water and extracted with EtOAc (2×). The combined organic layers was washed with sat. aq. NaHCO$_3$ solution, water, and brine, then dried and concentrated. The residue was purified by silica gel column chromatography to give 5.44 g (88%) of the desired Boc-protected product as a white solid.

To a solution of the product from the previous step described above (0.2 g, 0.81 mmol) in THF (5 mL) was added NaH at 0° C. After 15 minutes, CH₃I was added and the stirring continued for overnight at room temperature. After completion the reaction mixture was quenched with ice water, extracted with EtOAc (25 mL), dried (Na₂SO₄) and concentrated. The Boc group was removed with 60% TFA-DCM (2 mL) at 0° C. to give 110 mg (77.5%) of the final product as a light greenish solid. MS: 177.1 (MH⁺).

Example 1-26

Compound AR00315998

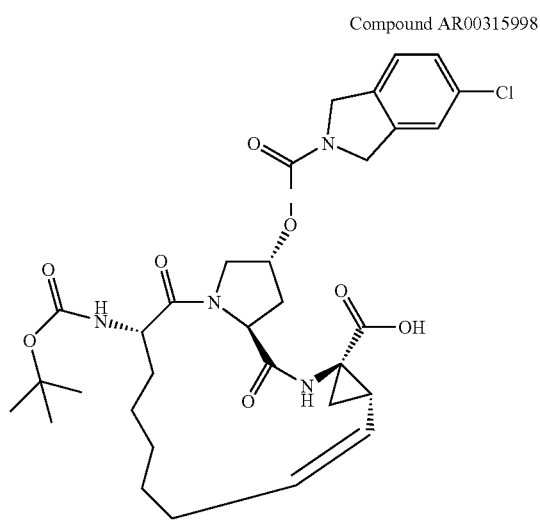

(1S,4R,6S,14S,18R)-14-tert-Butoxycarbonylamino-18-(5-chloro-1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00315998) was synthesized according to Method B, except 5-Chloro-2,3-dihydro-1H-isoindole was used in Step 4 instead. $^{1}$H NMR (400 MHz, CDCl₃): δ 7.24-7.02 (m, 3H), 6.82 (s, 1H), 5.68-5.51 (m, 1H), 5.36 (s, 1H), 5.11-4.96 (m, 2H), 4.67-4.44 (m, 5H), 4.29-4.20 (m, 1H), 4.20-4.11 (m, 1H), 3.82-3.74 (m, 1H), 2.69-2.55 (m, 1H), 2.31-2.15 (m, 1H), 2.14-2.06 (m, 1H), 2.03 (s, 1H), 2.01-1.86 (m, 1H), 1.86-1.24 (m, 11H), 1.22 (s, 9H). MS: m/e 644.9 (M⁺), 646.9 (M⁺+2)

Example 1-27

Compound AR00315999

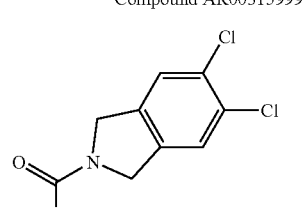

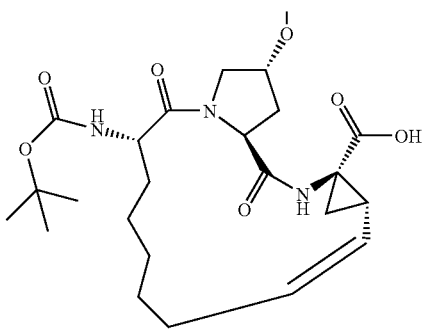

(1S,4R,6S,14S,18R)-14-tert-Butoxycarbonylamino-18-(5,6-dichloro-1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00315999) was synthesized according to Method B, except 5,6-Dichloro-2,3-dihydro-1H-isoindole was used in Step 4 instead. $^{1}$H NMR (400 MHz, CDCl₃): δ 7.29 (s, 1H), 7.22 (s, 1H), 7.06 (s, 1H), 5.57-5.50 (m, 1H), 5.33 (s, 1H), 5.23-5.09 (m, 2H), 4.73-4.65 (m, 1H), 4.64-4.48 (m, 5H), 4.33-4.29 (m, 1H), 4.11-4.02 (m, 1H), 3.82-3.74 (m, 1H), 2.73-2.61 (m, 1H), 2.29-2.08 (m, 3H), 2.01 (s, 1H), 1.83-1.65 (m, 2H), 1.63-1.46 (m, 2H), 1.40-1.12 (m, 15H). MS: m/e 678.9 (M⁺), 681 (M⁺+2)

Example 1-28

Compound AR00320122

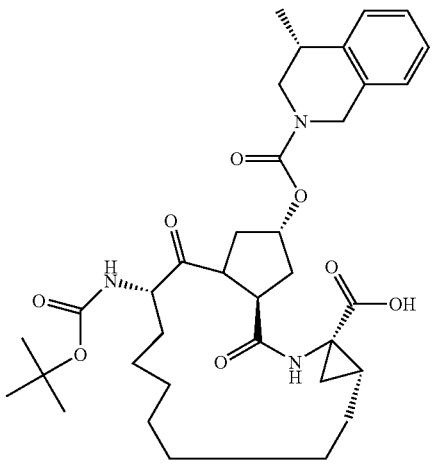

(1S,4R,6S,14S,18R)-14-tert-Butoxycarbonylamino-18-(4R-methyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00320122) was synthesized according to Method B, except 4R-Methyl-1,2,3,4-tetrahydro-isoquinoline was used in Step 4 instead. $^{1}$H NMR (400 MHz, CD₃OD) δ 7.02-7.24 (m, 3H), 5.59 (dd, 1H), 5.30-5.44 (m, 2H), 4.66-4.81 (m, 1H), 4.14-4.64 (m, 3H), 3.83-3.92 (m, 1H), 3.58-3.81 (m, 1H), 3.44-3.56 (m, 1H), 2.86-3.86 (m, 1H), 2.23-2.58 (m, 4H), 1.87-2.13 (m, 2H), 1.70-1.87 (m, 1H), 1.50-1.70 (m, 3H), 1.07-1.51 (m, 19H), 0.80-0.96 (m, 2H). MS m/z 639.0 (M⁺+1)

Example 1-29

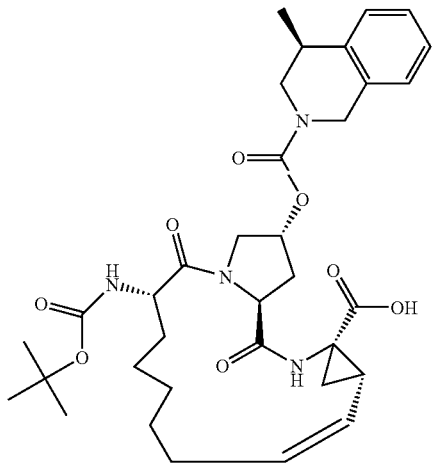

Compound AR00320123

(1S,4R,6S,14S,18R)-14-tert-Butoxycarbonylamino-18-(4S-methyl-3,4-dihydro-1H-isoquinoline-2-carbonyloxy)-2,15-dioxo-3,16-diaza-tricyclo[14.3.0.0⁴,⁶]nonadec-7-ene-4-carboxylic acid (Compound AR00320123) was synthesized according to Method B, except 4S-Methyl-1,2,3,4-tetrahydro-isoquinoline was used in Step 4 instead. ¹H NMR (400 MHz, CD₃OD) δ 7.01-7.23 (m, 3H), 5.58 (dd, 1H), 5.32-5.45 (m, 2H), 4.66-4.82 (m, 1H), 4.12-4.64 (m, 3H), 3.86-3.94 (m, 1H), 3.52-3.74 (m, 1H), 3.43-3.56 (m, 1H), 2.88-3.85 (m, 1H), 2.24-2.60 (m, 4H), 1.87-2.15 (m, 2H), 1.71-1.87 (m, 1H), 1.52-1.70 (m, 3H), 1.07-1.52 (m, 19H), 0.80-0.96 (m, 2H). MS m/z 639.0 (M⁺+1)

Example 1-30

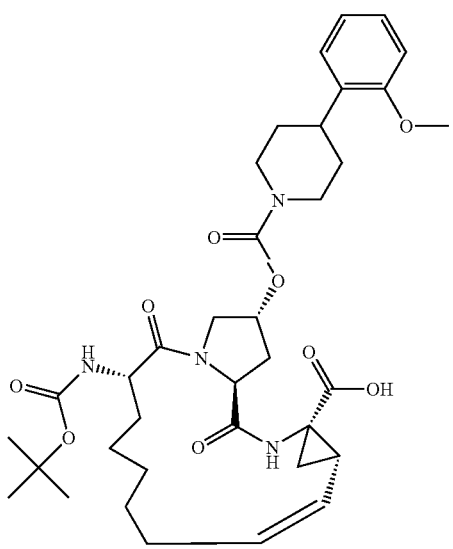

Compound AR00320576

(1S,4R,6S,14S,18R)-14-tert-Butoxycarbonylamino-18-[4-(2-methoxy-phenyl)-piperidine-1-carbonyloxy]-2,15-dioxo-3,16-diaza-tricyclo[14.3.0.0⁴,⁶]nonadec-7-ene-4-carboxylic acid (Compound AR00320576) was synthesized according to Method B, except 4-(2-Methoxy-phenyl)-piperidine was used in Step 4 instead. MS m/e 583.3 (M⁺+1−100).

Example 1-31

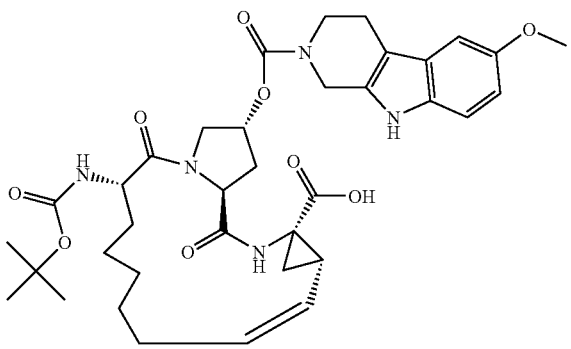

Compound AR00320577

(1S,4R,6S,14S,18R)-14-tert-Butoxycarbonylamino-18-(6-methoxy-1,3,4,9-tetrahydro-b-carboline-2-carbonyloxy)-2,15-dioxo-3,16-diaza-tricyclo[14.3.0.0⁴,⁶]nonadec-7-ene-4-carboxylic acid (Compound AR00320577) was synthesized according to Method B, except 6-Methoxy-2,3,4,9-tetrahydro-1H-b-carboline was used in Step 4 instead. MS m/e 594.2 (M⁺+1−100).

Example 1-32

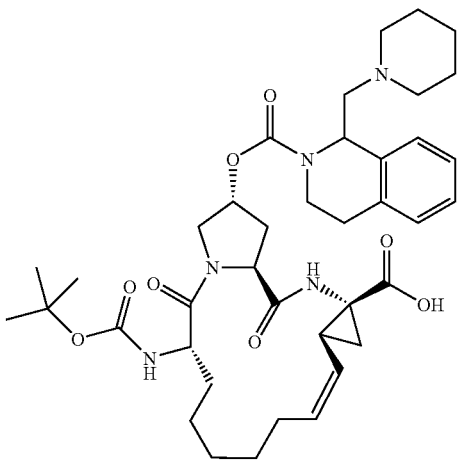

Compound AR00301383

(1S,4R,6S,14S,18R)-14-tert-Butoxycarbonylamino-2,15-dioxo-18-(1-piperidin-1-ylmethyl-3,4-dihydro-1H-isoquinoline-2-carbonyloxy)-3,16-diaza-tricyclo[14.3.0.0$^{4,6}$]nonadec-7-ene-4-carboxylic acid (Compound AR00301383) was synthesized according to Method B, except 1-Piperidin-1-ylmethyl-1,2,3,4-tetrahydro-isoquinoline was used in Step 4 instead. $^1$H NMR (500 MHz, CD$_3$OD) δ 7.33-7.24 (m, 4H), 7.20 (br s, 1H), 6.61 (br s, 1H), 5.75-5.52 (m, 2H), 5.50-5.33 (m, 2H), 4.63-4.43 (m, 2H), 4.42-4.07 (m, 4H), 3.96 (br s, 1H), 3.67-3.11 (m, 5H), 3.06-2.88 (m, 2H), 2.86-2.74 (m, 2H), 2.56-2.35 (m, 3H), 2.23 (q, 1H), 2.04-1.90 (m, 2H), 1.89-1.52 (m, 10H), 1.51-1.32 (m, 12H); MS (POS APCI) m/z 722.3 (M$^+$+1).

Example 1-33

Compound AR00333842

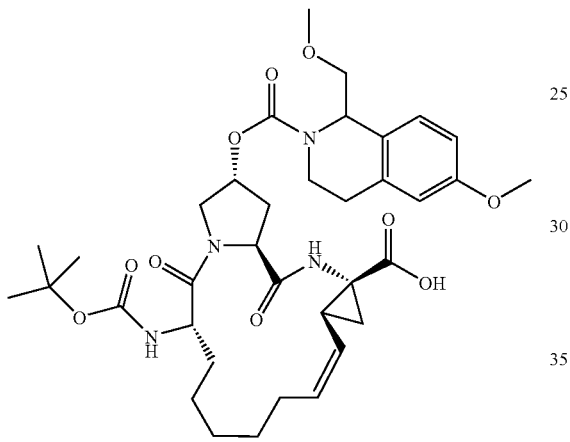

(1S,4R,6S,14S,18R)-14-tert-Butoxycarbonylamino-18-(6-methoxy-1-methoxymethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00333842) was synthesized according to the procedures described in Example 1-2, except that 6-methoxy-1-methoxymethyl-1,2,3,4-tetrahydro-isoquinolinium chloride was used to replace 1,2,3,4-Tetrahydro-isoquinoline in Step 4 instead. MS (APCI−): m/z 697.2 (M−1).

Example 1-34

Compound AR00365349

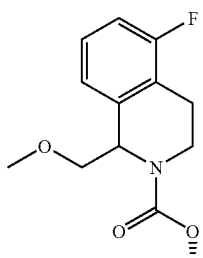

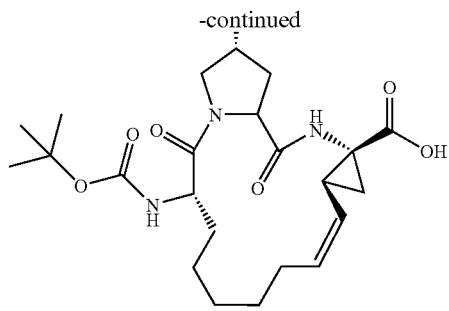

(1S,4R,6S,14S,18R)-14-tert-Butoxycarbonylamino-18-(5-fluoro-1-methoxymethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00365349) was synthesized according to the procedures described in Example 1-2, except that 5-fluoro-1-methoxymethyl-1,2,3,4-tetrahydro-isoquinolinium chloride was used to replace 1,2,3,4-Tetrahydro-isoquinoline in Step 4 instead. MS (APCI−): m/z 685.3 (M−1).

Example 1-35

Compound AR00333224

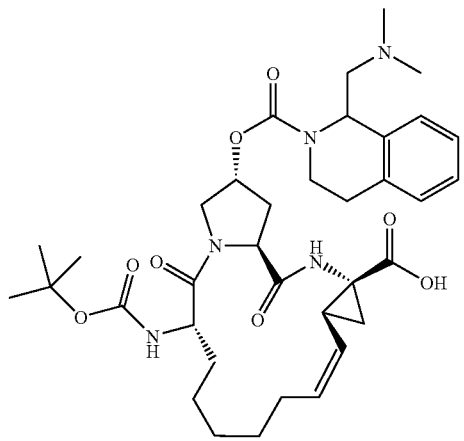

(1S,4R,6S,14S,18R)-14-tert-Butoxycarbonylamino-18-(1-dimethylaminomethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00333224) was synthesized according to the procedures described in Example 1-2, except that dimethyl-(1,2,3,4-tetrahydro-isoquinolin-1-ylmethyl)-amine (synthesized according to Example 1-35a) was used to replace 1,2,3,4-Tetrahydro-isoquinoline in Step 4 instead. MS (APCI+): m/z 582.3 (MH$^+$−Boc).

Example 1-35a

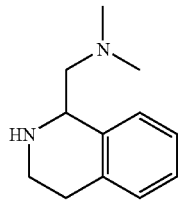

Dimethyl-(1,2,3,4-tetrahydro-isoquinolin-1-ylmethyl)-amine was synthesized by a similar fashion as shown in Example 3-76a, except that in Step 1, phenethylamine was used to replace 2-(3-methoxy-phenyl)-ethylamine, and that in the first part of Step 3, dimethyl-amine was used to replace sodium methoxide as the nucleophile. The crude product was used directly in the next coupling step without further purification.

Example 1-36

Compound AR00333225

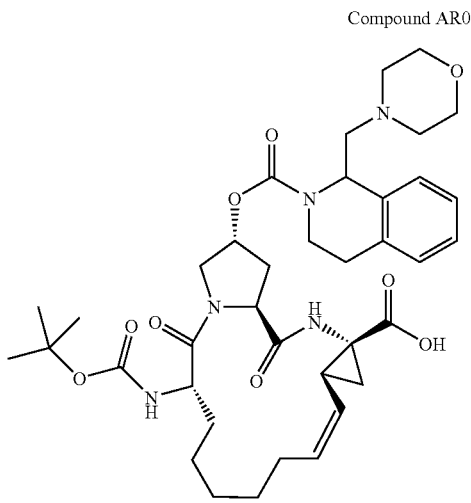

(1S,4R,6S,14S,18R)-14-tert-Butoxycarbonylamino-18-(1-morpholin-4-ylmethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00333225) was synthesized according to the procedures described in Example 1-2, except that 1-morpholin-4-ylmethyl-1,2,3,4-tetrahydro-isoquinoline (synthesized according to Example 1-36a) was used to replace 1,2,3,4-Tetrahydro-isoquinoline in Step 4 instead. MS (APCI–): m/z 722.3 (M–1).

Example 1-36a

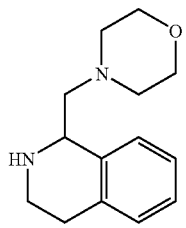

1-Morpholin-4-ylmethyl-1,2,3,4-tetrahydro-isoquinoline was synthesized by a similar fashion as shown in Example 3-76a, except that in Step 1, phenethylamine was used to replace 2-(3-methoxy-phenyl)-ethylamine, and that in the first part of Step 3, morpholin was used to replace sodium methoxide as the nucleophile. The crude product was used directly in the next coupling step without further purification.

Example 1-37

Compound AR00333248

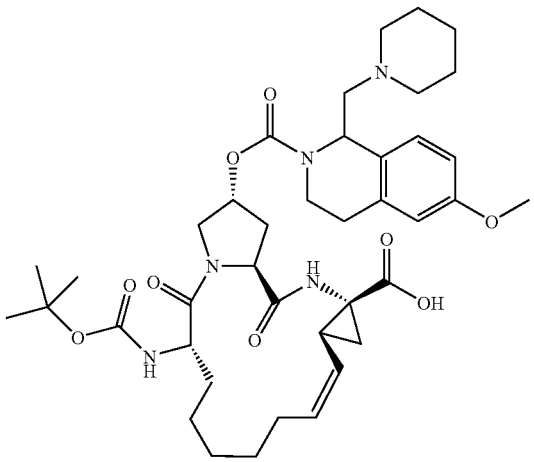

(1S,4R,6S,14S,18R)-14-tert-Butoxycarbonylamino-18-(6-methoxy-1-piperidin-1-ylmethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00333248) was synthesized according to the procedures described in Example 1-2, except that 6-methoxy-1-piperidin-1-ylmethyl-1,2,3,4-tetrahydro-isoquinoline (synthesized according to Example 1-37a) was used to replace 1,2,3,4-Tetrahydro-isoquinoline in Step 4 instead. MS (APCI–): m/z 750.4 (M–1).

Example 1-37a

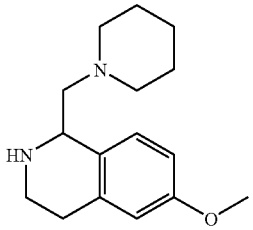

6-Methoxy-1-piperidin-1-ylmethyl-1,2,3,4-tetrahydro-isoquinoline was synthesized by a similar fashion as shown in Example 3-76a, except that in the first part of Step 3, piperidine was used to replace sodium methoxide as the nucleophile. The crude product was used directly in the next coupling step without further purification.

Example 1-38

Compound AR00333276

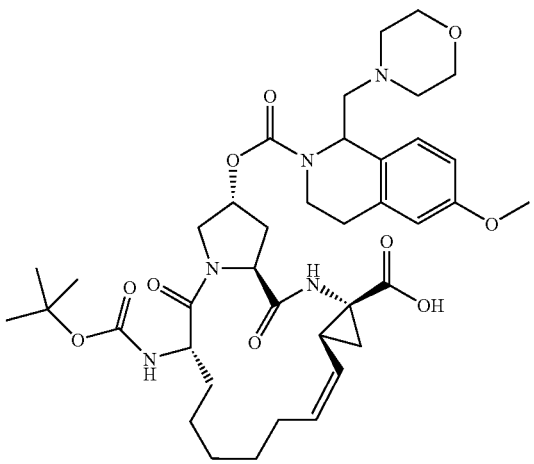

(1S,4R,6S,14S,18R)-14-tert-Butoxycarbonylamino-18-(6-methoxy-1-morpholin-4-ylmethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00333276) was synthesized according to the procedures described in Example 1-2, except that 6-methoxy-1-morpholin-4-ylmethyl-1,2,3,4-tetrahydro-isoquinoline (synthesized according to Example 1-38a) was used to replace 1,2,3,4-Tetrahydro-isoquinoline in Step 4 instead. MS (APCI−): m/z 750.3 (M−1).

Example 1-38a

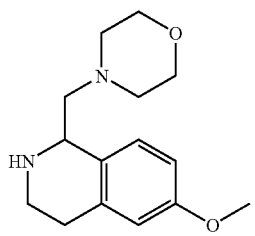

6-Methoxy-1-morpholin-4-ylmethyl-1,2,3,4-tetrahydro-isoquinoline was synthesized by a similar fashion as shown in Example 3-76a, except that in the first part of Step 3, morpholin was used to replace sodium methoxide as the nucleophile. The crude product was used directly in the next coupling step without further purification.

Example 1-39

Compound AR00333277

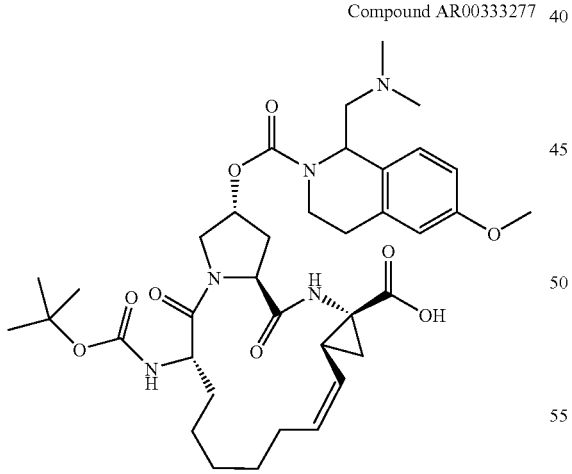

(1S,4R,6S,14S,18R)-14-tert-Butoxycarbonylamino-18-(1-dimethylaminomethyl-6-methoxy-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00333277) was synthesized according to the procedures described in Example 1-2, except that (6-methoxy-1,2,3,4-tetrahydro-isoquinolin-1-ylmethyl)-dimethyl-amine (synthesized according to Example 1-39a) was used to replace 1,2,3,4-Tetrahydro-isoquinoline in Step 4 instead. MS (APCI+): m/z 712.3 (MH+).

Example 1-39a

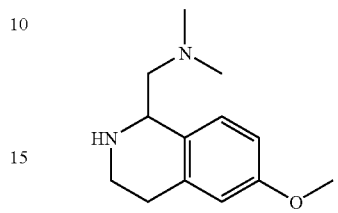

6-Methoxy-1,2,3,4-tetrahydro-isoquinolin-1-ylmethyl)-dimethyl-amine was synthesized by a similar fashion as shown in Example 3-76a, except that in the first part of Step 3, dimethylamine was used to replace sodium methoxide as the nucleophile. The crude product was used directly in the next coupling step without further purification.

Example 1-40

Compound AR00365369

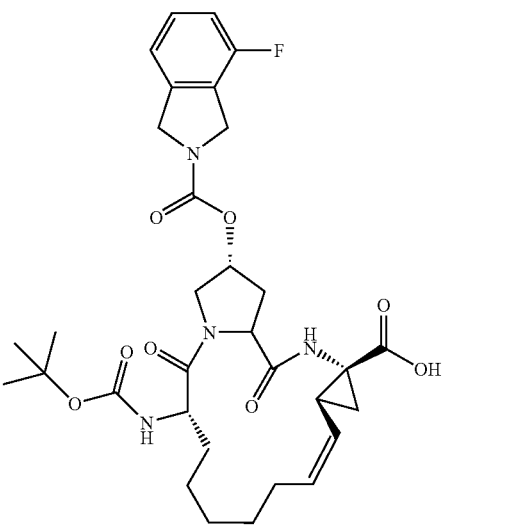

(1S,4R,6S,14S,18R)-14-tert-Butoxycarbonylamino-18-(4-fluoro-1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00365369) was synthesized according to the procedures described in Example 1-2, except that 4-fluoro-2,3-dihydro-1H-isoindole (synthesized according to Example 3-55a) was used to replace 1,2,3,4-tetrahydro-isoquinoline in Step 4 instead. $^1$H NMR (500 MHz, DMSO) δ 12.21 (br s, 1H), 8.66 (br s, 1H), 7.35 (q, 1H), 7.19 (d, 1H), 7.11 (q, 2H), 7.03 (br s, 1H), 5.51 (q, 1H), 5.33-5.21 (m, 2H), 4.66 (s, 4H), 4.22 (q, 1H), 4.24 (t, 1H), 3.99-3.89 (m, 1H), 3.73-3.64 (m, 1H), 2.65-2.55 (m, 1H), 2.28-2.08 (m, 3H), 1.77-1.61 (m, 2H), 1.54-1.42 (m, 1H), 1.42-1.03 (m, 16H); MS (APCI−): m/z 627.3 (M−1).

Example 1-41

Compound AR00371946

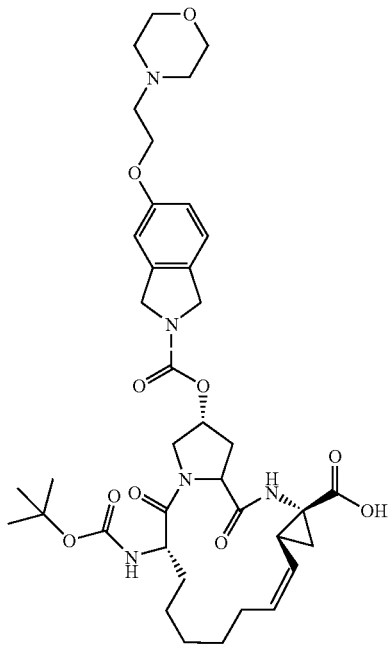

(1S,4R,6S,14S,18R)-14-tert-Butoxycarbonylamino-18-[5-(2-morpholin-4-yl-ethoxy)-1,3-dihydro-isoindole-2-carbonyloxy]-2,15-dioxo-3,16-diaza-tricyclo[14.3.0.0$^{4,6}$]nonadec-7-ene-4-carboxylic acid (Compound AR00371946) was synthesized according to the procedures described in Example 1-2, except that 5-(2-Morpholin-4-yl-ethoxy)-2,3-dihydro-1H-isoindole (prepared according to the procedures described in J. Med. Chem. 2002, Vol. 45, No. 26, 5771, preparation method D, and in Bioorg. Med. Chem. Lett. 11 (2001) 685-688. For the N-Boc protected amine input: $^1$H NMR (500 MHz, CDCl$_3$) δ 7.13 (dd, 1H), 6.85-6.74 (m, 2H), 4.61 (t, 4H), 4.10 (t, 2H), 3.73 (t, 4H), 2.81 (t, 2H), 2.61-2.54 (m, 4H), 1.51 (s, 9H); MS (APCI+): m/z 349.1 (M+1)) was used to replace 1,2,3,4-tetrahydro-isoquinoline in Step 4 instead. MS (APCI+): m/z 640.3 [(M+1)−Boc].

Example 1-42

Compound AR00371947

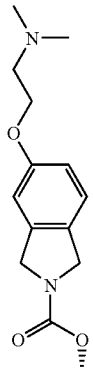

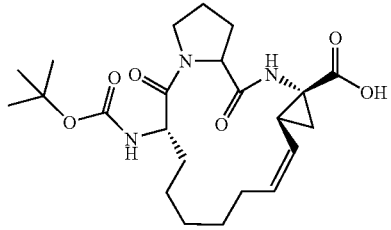

(1S,4R,6S,14S,18R)-14-tert-Butoxycarbonylamino-18-[5-(2-dimethylamino-ethoxy)-1,3-dihydro-isoindole-2-carbonyloxy]-2,15-dioxo-3,16-diaza-tricyclo[14.3.0.0$^{4,6}$]nonadec-7-ene-4-carboxylic acid (Compound AR00371947) was synthesized according to the procedures described in Example 1-2, except that [2-(2,3-Dihydro-1H-isoindol-5-yloxy)-ethyl]-dimethyl-amine (prepared according to the procedures described in J. Med. Chem. 2002, Vol. 45, No. 26, 5771, preparation method D, and in Bioorg. Med. Chem. Lett. 11 (2001) 685-688. For the N-Boc protected amine input: $^1$H NMR (500 MHz, CDCl$_3$) δ 7.14 (dd, 1H), 6.88-6.76 (m, 2H), 4.61 (t, 4H), 4.04 (t, 2H), 2.72 (t, 2H), 2.34 (s, 6H), 1.50 (s, 9H); MS (APCI+): m/z 307.1 (M+1)) was used to replace 1,2,3,4-tetrahydro-isoquinoline in Step 4 instead. MS (APCI+): m/z 698.2 (M+1).

Example 1-43

Compound AR00371948

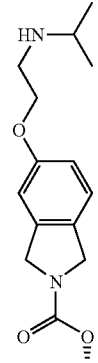

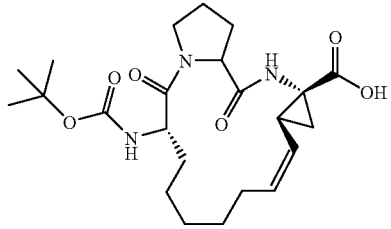

(1S,4R,6S,14S,18R)-14-tert-Butoxycarbonylamino-18-[5-(2-isopropylamino-ethoxy)-1,3-dihydro-isoindole-2-carbonyloxy]-2,15-dioxo-3,16-diaza-tricyclo[14.3.0.0$^{4,6}$]nonadec-7-ene-4-carboxylic acid (Compound AR00371948) was synthesized according to the procedures described in Example 1-2, except that [2-(2,3-Dihydro-1H-isoindol-5-yloxy)-ethyl]-isopropyl-amine (prepared according to the procedures described in J. Med. Chem. 2002, Vol. 45, No. 26, 5771, preparation method D, and in Bioorg. Med. Chem. Lett. 11 (2001) 685-688. For the N-Boc protected amine input: $^1$H NMR (500 MHz, CDCl₃) δ 7.13 (dd, 1H), 6.86-6.75 (m, 2H), 4.62 (t, 4H), 4.06 (t, 2H), 2.99 (t, 2H), 2.88 (septuplet, 1H), 1.62 (br s, 1H), 1.51 (s, 9H), 1.10 (d, 6H); MS (APCI+): m/z 321.2 (M+1)) was used to replace 1,2,3,4-tetrahydro-isoquinoline in Step 4 instead. MS (APCI−): m/z 710.3 (M−1).

Preparation of Compounds with General Structure III

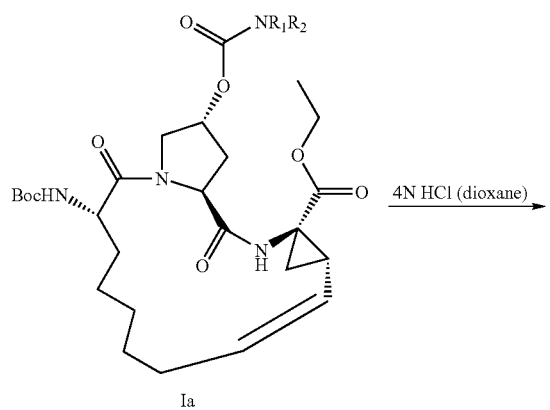

Ia

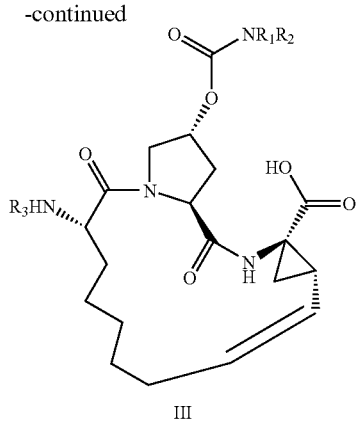

III

Compounds with general structure II were prepared according to the general scheme shown above. A compound with structure Ia was first removed of its Boc protective group, followed by nucleophillic attack of the amino group on an electrophile, to form a carbamate, amide, or urea.

Example 2-1

Compound AR00247310

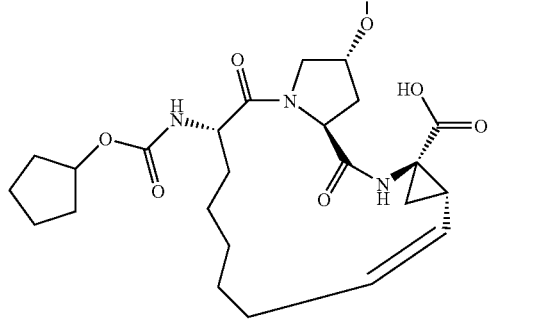

Step 1: Preparation of (1S,4R,6S,14S,18R)-14-Amino-18-(3,4-dihydro-1H-isoquinoline-2-carbonyloxy)-2,15-dioxo-3,16-diaza-tricyclo[14.3.0.0⁴,⁶] nonadec-7-ene-4-carboxylic acid ethyl ester

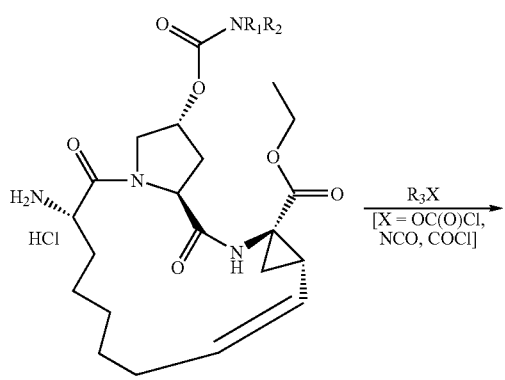

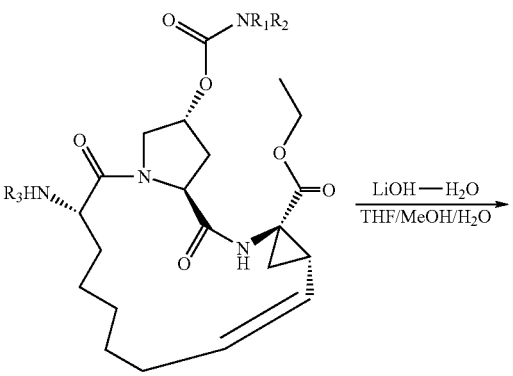

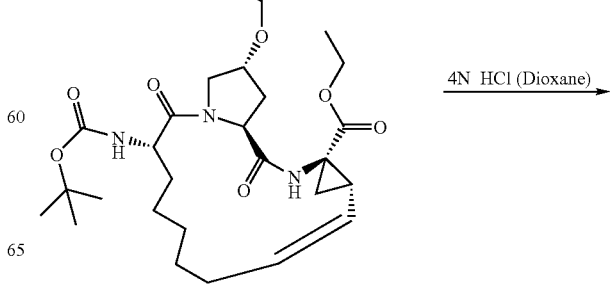

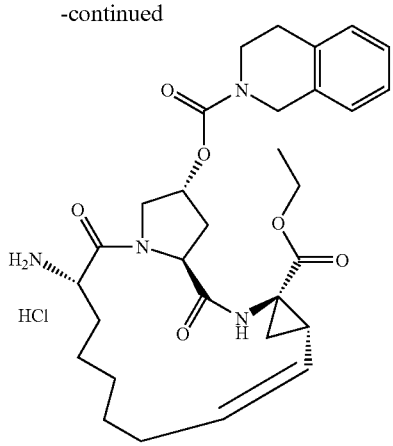

The N-Boc protected starting material (102 mg, 0.16 mmol) was dissolved in 6 mL 4N HCl (dioxane), and left at rt for 90 min. HPLC showed complete removal of the Boc protective group. The reaction mixture was then concentrated down, taken up in acetonitrile and concentrated down again twice. The resulting light brownish foamy powder was carried out to the next step.

Step 2: Preparation of (1S,4R,6S,14S,18R)-14-Cyclopentyloxycarbonylamino-18-(3,4-dihydro-1H-isoquinoline-2-carbonyloxy)-2,15-dioxo-3,16-diazatricyclo[14.3.0.0$^{4,6}$]nonadec-7-ene-4-carboxylic acid ethyl ester.

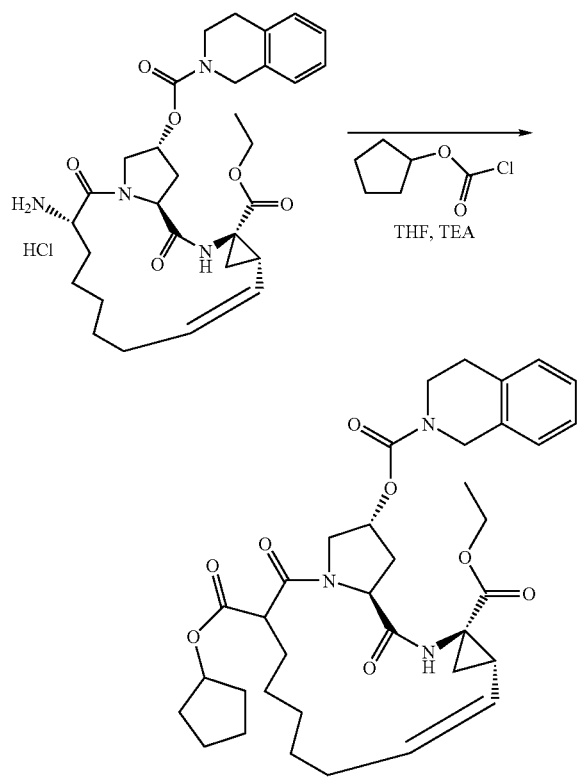

To a solution of cyclopentanol (42 mg, 0.48 mmol) in THF (16 mL), a toluene solution of phosgene (0.42 mL, 1.9 M, 0.80 mmol) was added drop-wise. The mixture was stirred at rt for 2 h to form the cyclopentyl chloroformate reagent. The reaction was then concentrated down to about half the volume. It was then diluted with DCM to the original volume, and concentrated down again to half the volume, in order to completely remove excess phosgene. This solution of the cyclopentyl chloroformate was further diluted with THF (16 mL), cooled to 0° C., and added to the solid residue (0.16 mmol) from Step 1 above at 0° C. TEA (0.11 mL, 0.81 mmol) was then added to the reaction mixture, and the reaction was stirred at 0° C. for 2 h. The reaction was complete by HPLC. It was concentrated down, taken up in EtOAc (15 mL), and then washed with water, sat. sodium bicarbonate, water, and brine (10 mL each), dried over Na$_2$SO$_4$ and concentrated down. The crude yellowish thick oil residue was purified by flash chromatography on Biotage 40S (eluent=hexanes/ EtOAc 1:1), giving the desired product as a white crispy foamy powder (65.2 mg, 63%). MS (MH$^+$ 665.2)

Step 3: Preparation of (1S,4R,6S,14S,18R)-14-Cyclopentyloxycarbonylamino-18-(3,4-dihydro-1H-isoquinoline-2-carbonyloxy)-2,15-dioxo-3,16-diazatricyclo[14.3.0.0$^{4,6}$]nonadec-7-ene-4-carboxylic acid (Compound AR00247310).

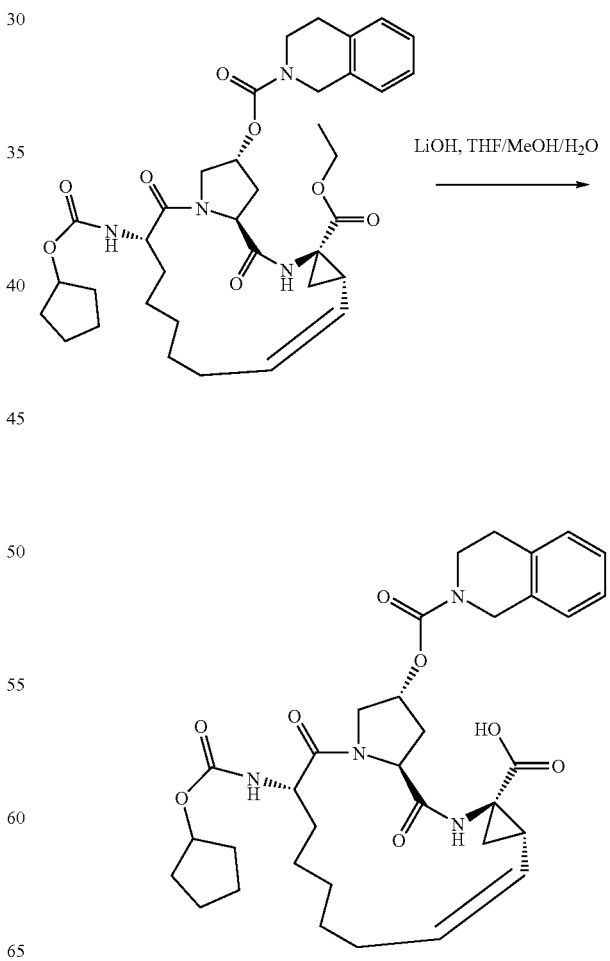

Followed the same hydrolysis procedures as in Step 5 of Example 1-1.

The following compounds were also prepared following the same procedures as aforementioned in Example 2-1, with either the cyclopentyl chloroformate being substituted by other electrophiles, and/or the P2-tetrahydroisoquinoline being substituted by other amine inputs as illustrated in Step 4 of Method B in Example 1-2.

Example 2-2

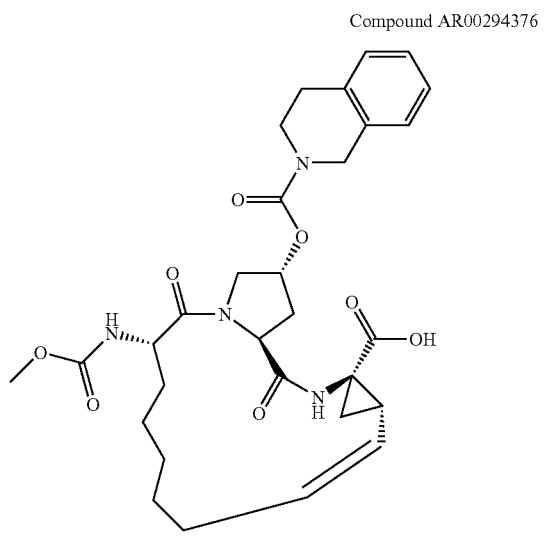

Compound AR00294376

(1S,4R,6S,14S,18R)-18-(3,4-Dihydro-1H-isoquinoline-2-carbonyloxy)-14-methoxycarbonylamino-2,15-dioxo-3,16-diaza-tricyclo[14.3.0.0$^{4,6}$]nonadec-7-ene-4-carboxylic acid (Compound AR00294376) was synthesized according to the procedures described in Example 2-1, except that methyl chloroformate was used in Step 2 instead.

Example 2-3

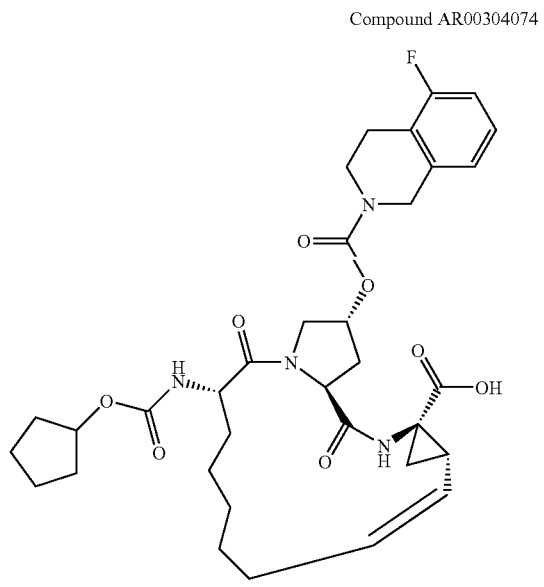

Compound AR00304074

(1S,4R,6S,14S,18R)-14-Cyclopentyloxycarbonylamino-18-(5-fluoro-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00304074) was synthesized according to the procedures described in Examples 1-2 and 2-1, except that 5-Fluoro-1,2,3,4-tetrahydro-isoquinoline was used instead in Step 4 of Example 1-2. MS m/e 583.2 (M$^+$+1).

Example 2-4

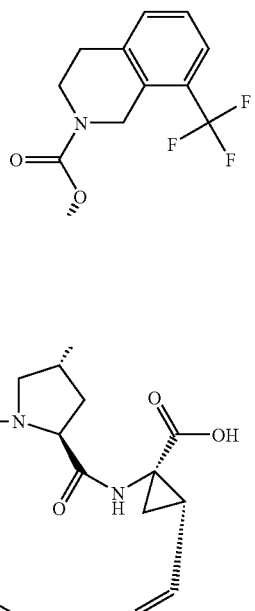

Compound AR00304075

(1S,4R,6S,14S,18R)-14-Cyclopentyloxycarbonylamino-2,15-dioxo-18-(8-trifluoromethyl-3,4-dihydro-1H-isoquinoline-2-carbonyloxy)-3,16-diaza-tricyclo[14.3.0.0$^{4,6}$]nonadec-7-ene-4-carboxylic acid (Compound AR00304075) was synthesized according to the procedures described in Examples 1-2 and 2-1, except that 8-trifluoromethyl-1,2,3,4-tetrahydro-isoquinoline was used instead in Step 4 of Example 1-2. MS m/e 705.1 (M$^+$+1).

Example 2-5

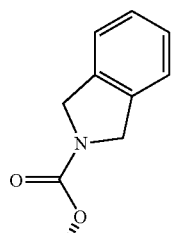

Compound AR00304076

-continued

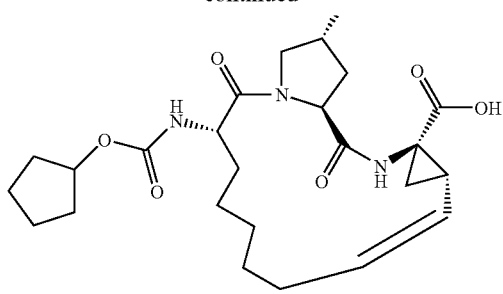

(1S,4R,6S,14S,18R)-14-Cyclopentyloxycarbonylamino-18-(1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00304076) was synthesized according to the procedures described in Examples 1-2 and 2-1, except that 2,3-Dihydro-1H-isoindole was used instead in Step 4 of Example 1-2. MS m/e 623.2 (M$^+$+1).

Example 2-6

Compound AR00304125

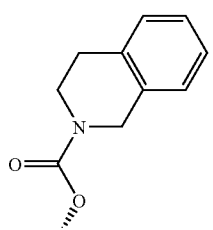

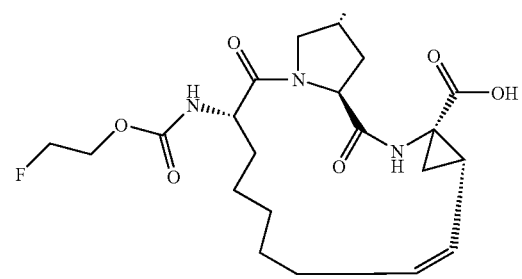

(1S,4R,6S,14S,18R)-18-(3,4-Dihydro-1H-isoquinoline-2-carbonyloxy)-14-(2-fluoro-ethoxycarbonylamino)-2,15-dioxo-3,16-diaza-tricyclo[14.3.0.0$^{4,6}$]nonadec-7-ene-4-carboxylic acid (Compound AR00304125) was synthesized according to the procedures described in Example 2-1, except that 2-fluoroethanol was used to form the chloroformate reagent in Step 2 instead of cyclopentanol. MS m/e 615.1 (M$^+$+1).

Example 2-7

Compound AR00304126

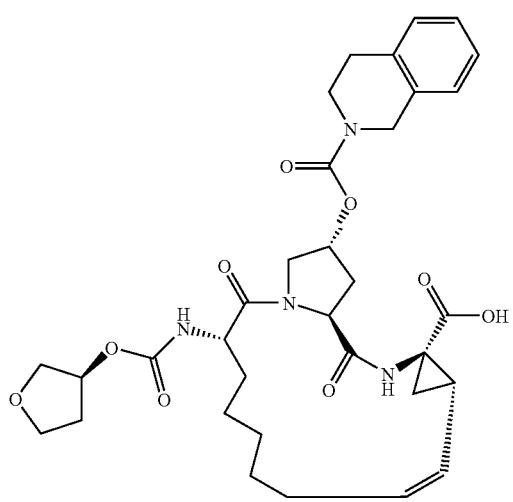

(1S,4R,6S,14S,18R)-18-(3,4-Dihydro-1H-isoquinoline-2-carbonyloxy)-2,15-dioxo-14-(tetrahydro-furan-3S-yloxycarbonylamino)-3,16-diaza-tricyclo[14.3.0.0$^{4,6}$]nonadec-7-ene-4-carboxylic acid (Compound AR00304126) was synthesized according to the procedures described in Example 2-1, except that tetrahydro-furan-3S-ol was used to form the chloroformate reagent in Step 2 instead of cyclopentanol. MS m/e 639.2 (M$^+$+1).

Example 2-8

Compound AR00304127

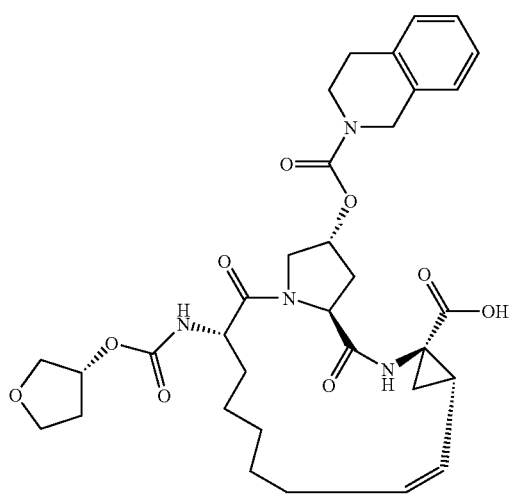

(1S,4R,6S,14S,18R)-18-(3,4-Dihydro-1H-isoquinoline-2-carbonyloxy)-2,15-dioxo-14-(tetrahydro-furan-3R-yloxycarbonylamino)-3,16-diaza-tricyclo[14.3.0.0$^{4,6}$]nonadec-7-ene-4-carboxylic acid (Compound AR00304127) was synthesized according to the procedures described in Example 2-1, except that tetrahydro-furan-3R-ol was used to form the chloroformate reagent in Step 2 instead of cyclopentanol. MS m/e 639.2 (M$^+$+1).

Example 2-9

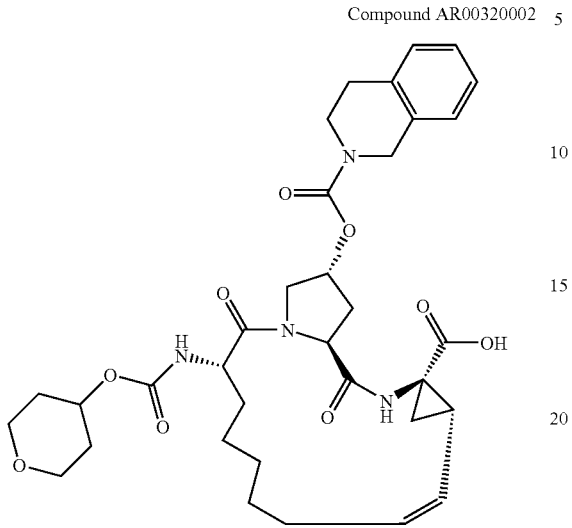

Compound AR00320002

(1S,4R,6S,14S,18R)-18-(3,4-Dihydro-1H-isoquinoline-2-carbonyloxy)-2,15-dioxo-14-(tetrahydro-pyran-4-yloxycarbonylamino)-3,16-diaza-tricyclo[14.3.0.0$^{4,6}$]nonadec-7-ene-4-carboxylic acid (Compound AR00320002) was synthesized according to the procedures described in Example 2-1, except that tetrahydro-pyran-4-ol was used to form the chloroformate reagent in Step 2 instead of cyclopentanol. MS m/e 653.2 (M$^+$+1).

Example 2-10

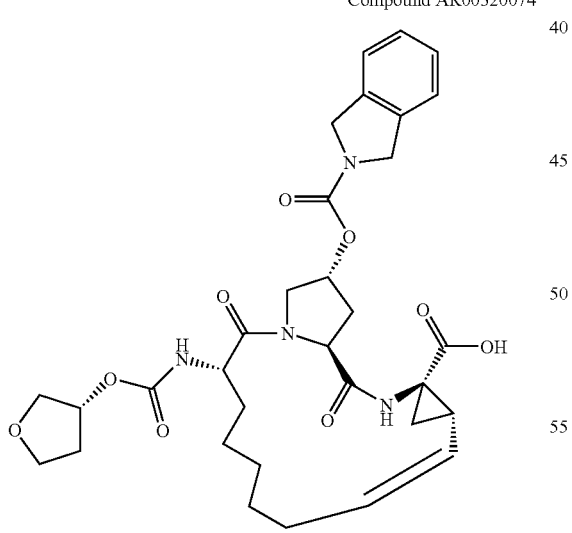

Compound AR00320074

(1S,4R,6S,14S,18R)-18-(1,3-Dihydro-isoindole-2-carbonyloxy)-2,15-dioxo-14-(tetrahydro-furan-3R-yloxycarbonylamino)-3,16-diaza-tricyclo[14.3.0.0$^{4,6}$]nonadec-7-ene-4-carboxylic acid (Compound AR00320074) was synthesized according to the procedures described in Examples 1-2 and 2-1, except that 2,3-Dihydro-1H-isoindole was used instead in Step 4 of Example 1-2, and that tetrahydro-furan-3R-ol was used to form the chloroformate reagent in Step 2 of Example 2-1 instead of cyclopentanol. MS m/e 625.2 (M$^+$+1).

Example 2-11

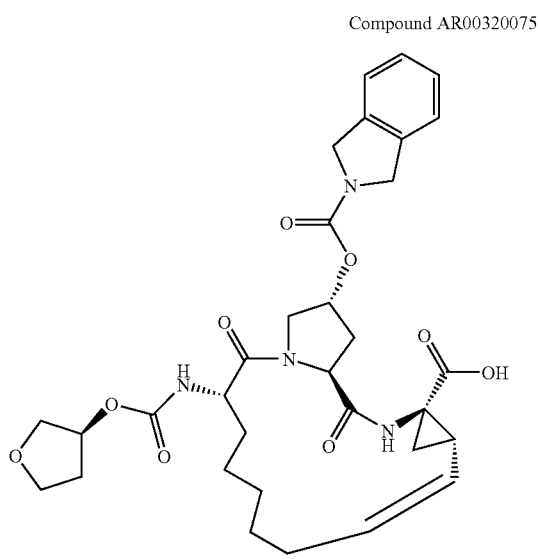

Compound AR00320075

(1S,4R,6S,14S,18R)-18-(1,3-Dihydro-isoindole-2-carbonyloxy)-2,15-dioxo-14-(tetrahydro-furan-3S-yloxycarbonylamino)-3,16-diaza-tricyclo[14.3.0.0$^{4,6}$]nonadec-7-ene-4-carboxylic acid (Compound AR00320075) was synthesized according to the procedures described in Examples 1-2 and 2-1, except that 2,3-Dihydro-1H-isoindole was used instead in Step 4 of Example 1-2, and that tetrahydro-furan-3S-ol was used to form the chloroformate reagent in Step 2 of Example 2-1 instead of cyclopentanol. MS m/e 625.2 (M$^+$+1).

Example 2-12

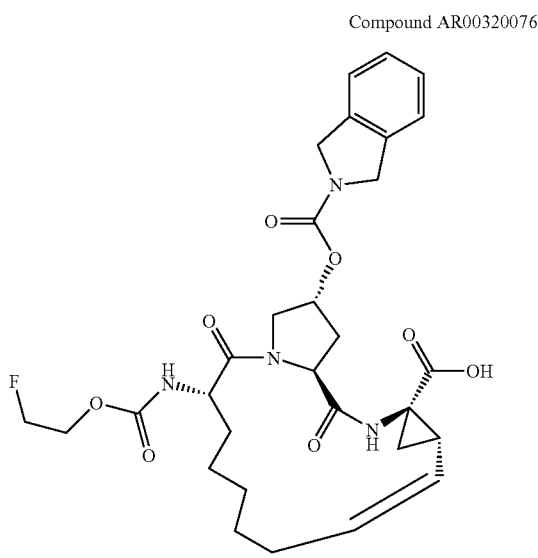

Compound AR00320076

(1S,4R,6S,14S,18R)-18-(1,3-Dihydro-isoindole-2-carbonyloxy)-2,15-dioxo-14-(2-fluoro-ethoxycarbonylamino)-3,16-diaza-tricyclo[14.3.0.0^{4,6}]nonadec-7-ene-4-carboxylic acid (Compound AR00320076) was synthesized according to the procedures described in Examples 1-2 and 2-1, except that 2,3-Dihydro-1H-isoindole was used instead in Step 4 of Example 1-2, and that 2-fluoroethanol was used to form the chloroformate reagent in Step 2 of Example 2-1 instead of cyclopentanol. MS m/e 601.1 (M$^+$+1).

Compound AR00320077

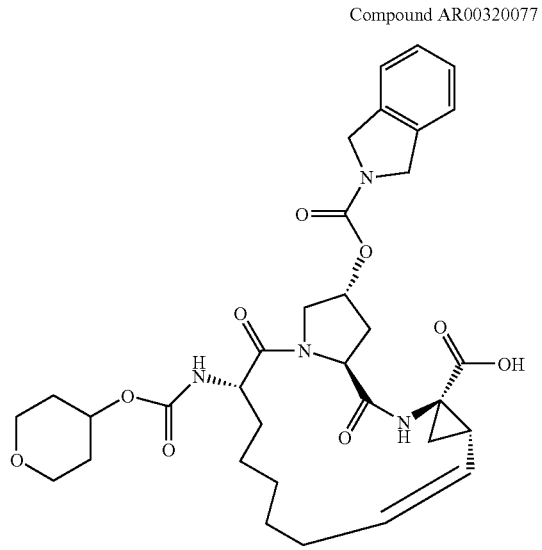

Example 2-13

(1S,4R,6S,14S,18R)-18-(1,3-Dihydro-isoindole-2-carbonyloxy)-2,15-dioxo-14-(tetrahydro-pyran-4-yloxycarbonylamino)-3,16-diaza-tricyclo[14.3.0.0^{4,6}]nonadec-7-ene-4-carboxylic acid (Compound AR00320077) was synthesized according to the procedures described in Examples 1-2 and 2-1, except that 2,3-Dihydro-1H-isoindole was used instead in Step 4 of Example 1-2, and that tetrahydro-pyran-4-ol was used to form the chloroformate reagent in Step 2 of Example 2-1 instead of cyclopentanol. MS m/e 601.1 (M$^+$+1).

Example 2-14

Compound AR00320445

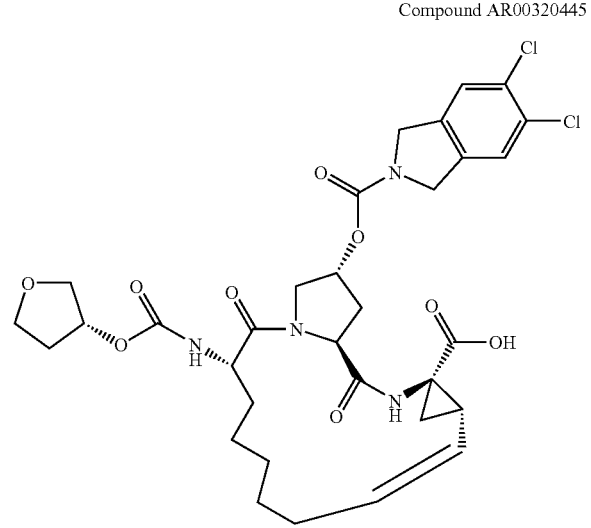

(1S,4R,6S,14S,18R)-18-(5,6-Dichloro-1,3-dihydro-isoindole-2-carbonyloxy)-2,15-dioxo-14-(tetrahydro-furan-3R-yloxycarbonylamino)-3,16-diaza-tricyclo[14.3.0.0^{4,6}]nonadec-7-ene-4-carboxylic acid (Compound AR00320445) was synthesized according to the procedures described in Examples 1-2 and 2-1, except that 5,6-dichloro-2,3-dihydro-1H-isoindole was used instead in Step 4 of Example 1-2, and that tetrahydro-furan-3R-ol was used to form the chloroformate reagent in Step 2 of Example 2-1 instead of cyclopentanol. MS: m/e 693.0 (M$^+$), 695.1 (M$^+$+2).

Example 2-15

Compound AR00320448

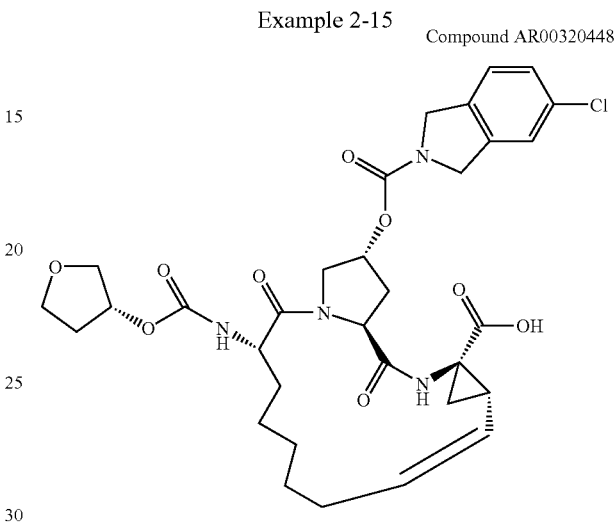

(1S,4R,6S,14S,18R)-18-(5-Chloro-1,3-dihydro-isoindole-2-carbonyloxy)-2,15-dioxo-14-(tetrahydro-furan-3R-yloxycarbonylamino)-3,16-diaza-tricyclo[14.3.0.0^{4,6}]nonadec-7-ene-4-carboxylic acid (Compound AR00320448) was synthesized according to the procedures described in Examples 1-2 and 2-1, except that 5-dichloro-2,3-dihydro-1H-isoindole was used instead in Step 4 of Example 1-2, and that tetrahydro-furan-3R-ol was used to form the chloroformate reagent in Step 2 of Example 2-1 instead of cyclopentanol. $^1$H NMR (500 MHz, CD$_3$OD): δ 7.38 (s, 1H), 7.32-7.28 (m, 2H), 7.22 (d, 1H), 7.10 (br s, 1H), 5.56-5.50 (q, 1H), 5.42-5.38 (t, 1H), 5.35 (br s, 1H), 4.80-4.48 (m, 6H), 4.44 (m, 1H), 4.16 (d, 1H), 3.84 (dd, 1H), 3.78-3.69 (m, 1H), 3.68-3.60 (m, 1H), 3.50 (t, 1H), 2.55-2.36 (m, 3H), 2.21-2.12 (m, 1H), 1.98-1.85 (m, 1H), 1.72-1.62 (m, 2H), 1.61-1.51 (m, 2H), 1.50-1.20 (m, 9H). MS: m/e 659.1 (M$^+$), 661.1 (M$^+$+2)

Example 2-16

Compound AR00248689

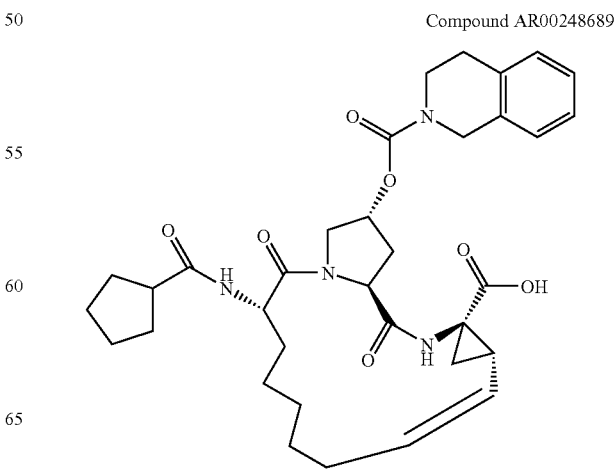

Synthesis of (1S,4R,6S,14S,18R)-14-(Cyclopentan-ecarbonyl-amino)-18-(3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR248689)

Cyclopentyl carboxylic acid was first loaded on PS-TFP resin (purchased from Argonaut Technologies) to form an active ester. The activated ester on resin (26 mg, 1.16 mmol/g, 0.03 mmol) was swelled in 0.5 mL chloroform first, followed by addition of MP-carbonate resin (purchased from Argonaut Technologies, 300 mg, 2.5 mmol/g, 0.75 mmol). To this resin mixture was then added 0.5 M chloroform solution of the macrocyclic material (15 mg, 0.02 mmol), and the reaction was shaken for overnight at rt. The reaction was complete by HPLC after 16 h. It was then filtered and concentrated down, giving clean N-acylated product. It was then hydrolyzed following the same hydrolysis procedures as in Step 5 of Example 1-1, giving the desired product AR248689 as a white solid (12.5 mg, 88%). MS (APCI+): m/z 621.3 (MH$^+$).

except that tert-butyl carboxylic acid was first loaded on PS-TFP resin instead. MS (APCI+): m/z 609.3 (MH$^+$).

Example 2-18

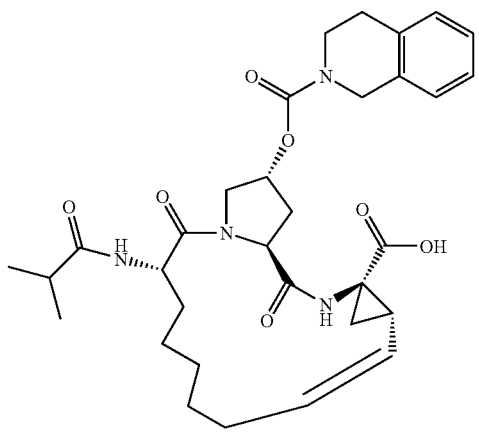

Compound AR00248688

(1S,4R,6S,14S,18R)-18-(3,4-Dihydro-1H-isoquinoline-2-carbonyloxy)-14-isobutyrylamino-2,15-dioxo-3,16-diaza-tricyclo[14.3.0.0$^{4,6}$]nonadec-7-ene-4-carboxylic acid (Compound AR00248688) was synthesized following the same procedures as described in Example 2-16, except that isopropyl carboxylic acid was first loaded on PS-TFP resin instead. MS (APCI+): m/z 595.3 (MH$^+$).

Example 2-17

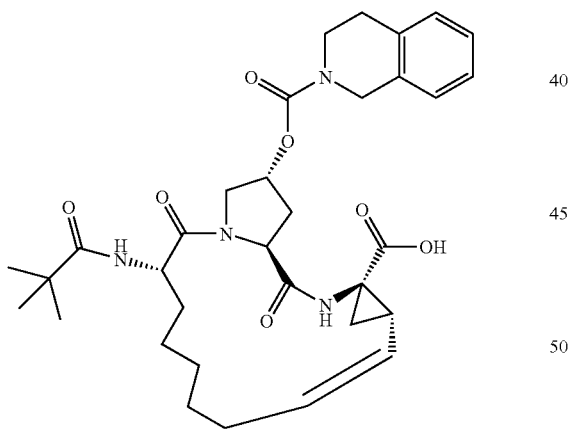

Compound AR00248687

(1S,4R,6S,14S,18R)-18-(3,4-Dihydro-1H-isoquinoline-2-carbonyloxy)-14-(2,2-dimethyl-propionylamino)-2,15-dioxo-3,16-diaza-tricyclo[14.3.0.0$^{4,6}$]nonadec-7-ene-4-carboxylic acid (Compound AR00248687) was synthesized following the same procedures as described in Example 2-16, Example 2-19

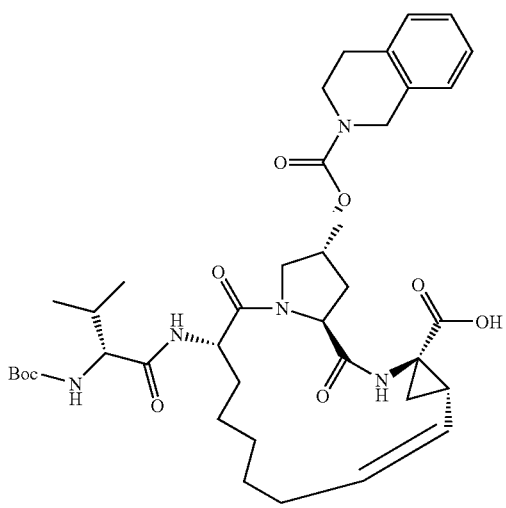

Compound AR00298989

Synthesis of (1S,4R,6S,14S,18R)-14-(2-tert-Butoxy-carbonylamino-3-methyl-butyrylamino)-18-(3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR298989)

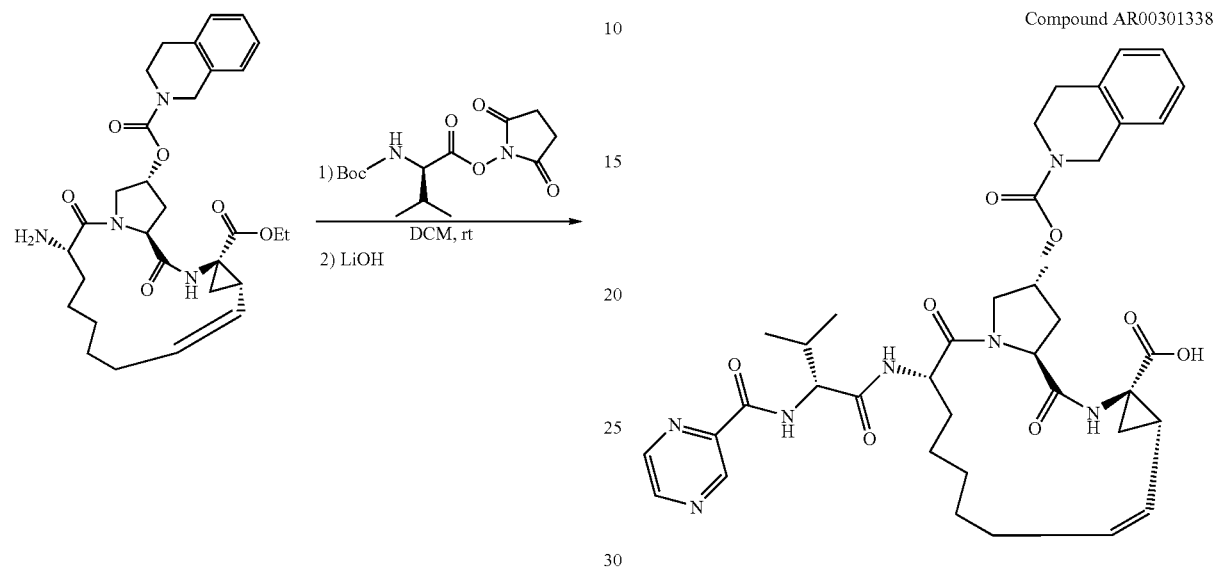

14-Amino-18-(3,4-dihydro-1H-isoquinoline-2-carbonyloxy)-2,15-dioxo-3,16-diaza-tricyclo[14.3.0.04,6]nonadec-7-ene-4-carboxylic acid ethyl ester (120 mg, 217 umol) and N-α-t-Boc-L-valine N-hydroxysuccinamide ester (96 mg, 300 umol) were stirred together in 1.1 mL dichloromethane for 14 hours. The solvent was removed in vacuo and 1 mL each of water and ethyl acetate were added. The phases were separated and the aqueous layer was washed twice with 500 uL of ethyl acetate. The combined organics were dried over MgSO4 and the solvents removed in vacuo to provide the desired compound as a white solid (132 mg, 81%). MS m/z 752.2 (MH+).

Example 2-20

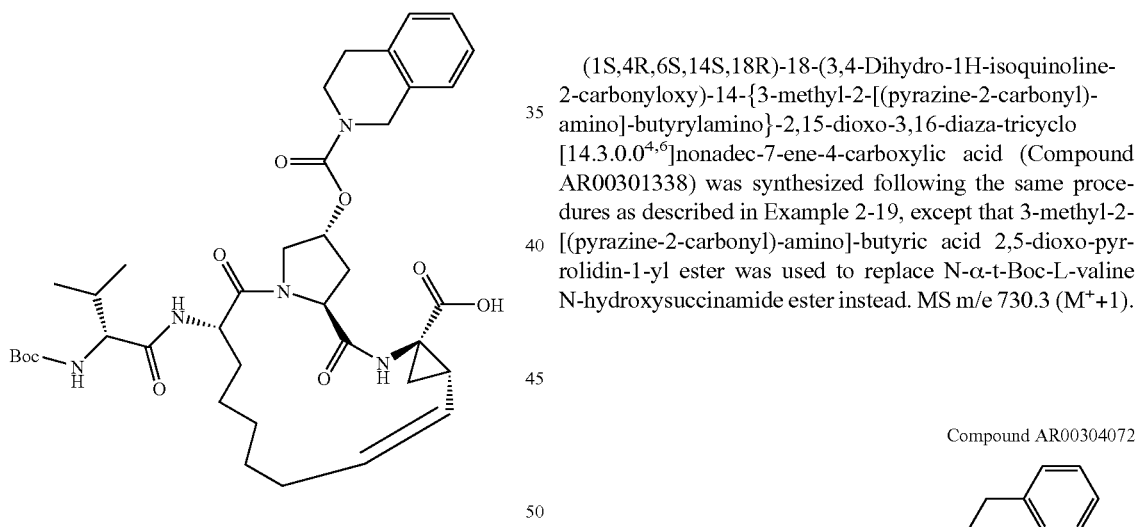

(1S,4R,6S,14S,18R)-18-(3,4-Dihydro-1H-isoquinoline-2-carbonyloxy)-14-{3-methyl-2-[(pyrazine-2-carbonyl)-amino]-butyrylamino}-2,15-dioxo-3,16-diaza-tricyclo[14.3.0.0$^{4,6}$]nonadec-7-ene-4-carboxylic acid (Compound AR00301338) was synthesized following the same procedures as described in Example 2-19, except that 3-methyl-2-[(pyrazine-2-carbonyl)-amino]-butyric acid 2,5-dioxo-pyrrolidin-1-yl ester was used to replace N-α-t-Boc-L-valine N-hydroxysuccinamide ester instead. MS m/e 730.3 (M$^+$+1).

Example 2-21

(1S,4R,6S,14S,18R)-18-(3,4-Dihydro-1H-isoquinoline-2-carbonyloxy)-14-{2-[(6-dimethylamino-pyridine-3-carbonyl)-amino]-3-methyl-butyrylamino}-2,15-dioxo-3,16-diaza-tricyclo[14.3.0.0$^{4,6}$]nonadec-7-ene-4-carboxylic acid (Compound AR00304072) was synthesized following the same procedures as described in Example 2-19, except that 2-[(6-Dimethylamino-pyridine-3-carbonyl)-amino]-3-methyl-butyric acid 2,5-dioxo-pyrrolidin-1-yl ester was used to replace N-α-t-Boc-L-valine N-hydroxysuccinamide ester instead. $^1$H NMR (CD$_3$OD, 500 MHz): δ 8.69 (s, 1H), 8.46 (s, 1H), 8.37-8.39 (m, 1H), 8.14-8.21 (m, 2H), 7.07-7.18 (m, 5H), 5.63 (q, 1H), 5.36-5.42 (m, 2H), 4.49-4.56 (m, 3H), 4.42-4.45 (m, 1H), 4.31-4.32 (m, 1H), 3.92-3.95 (m, 1H), 3.65-3.72 (m, 2H), 2.85-2.91 (m, 2H), 2.33-2.55 (m, 4H), 1.93-2.03 (m, 3H), 1.61-1.68 (m, 3H), 1.27-1.52 (m, 12H), 0.86-0.96 (m, 8H). MS m/e 770.4 (M−1).

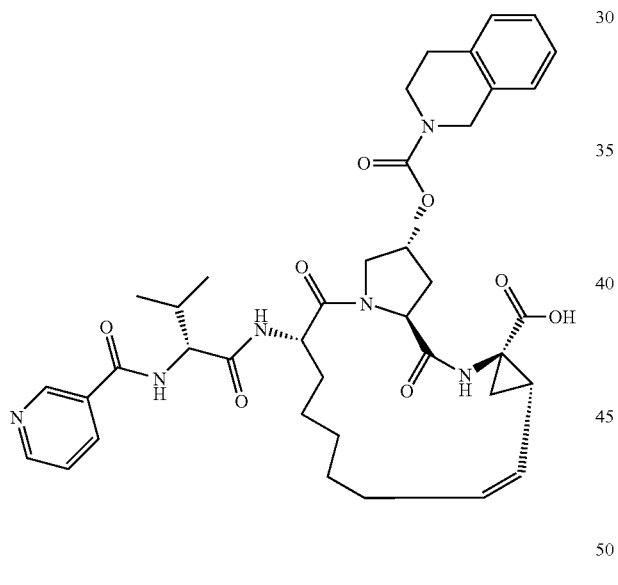

Compound AR00304073

Example 2-22

(1S,4R,6S,14S,18R)-18-(3,4-Dihydro-1H-isoquinoline-2-carbonyloxy)-14-{3-methyl-2-[(pyridine-3-carbonyl)-amino]-butyrylamino}-2,15-dioxo-3,16-diaza-tricyclo[14.3.0.0$^{4,6}$]nonadec-7-ene-4-carboxylic acid (Compound AR00304073) was synthesized following the same procedures as described in Example 2-19, except that 3-Methyl-2-[(pyridine-3-carbonyl)-amino]-butyric acid 2,5-dioxo-pyrrolidin-1-yl ester was used to replace N-α-t-Boc-L-valine N-hydroxysuccinamide ester instead. MS m/e 729.2 (M$^+$+1).

Example 2-23

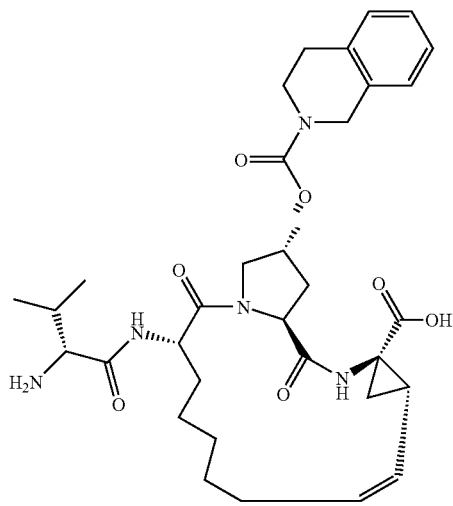

Compound AR00298990

(1S,4R,6S,14S,18R)-14-(2-Amino-3-methyl-butyrylamino)-18-(3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00298990) was prepared by following the same procedures as the Step 1 of Example 2-1. MS m/e 624.2 (M$^+$+1).

Example 2-24

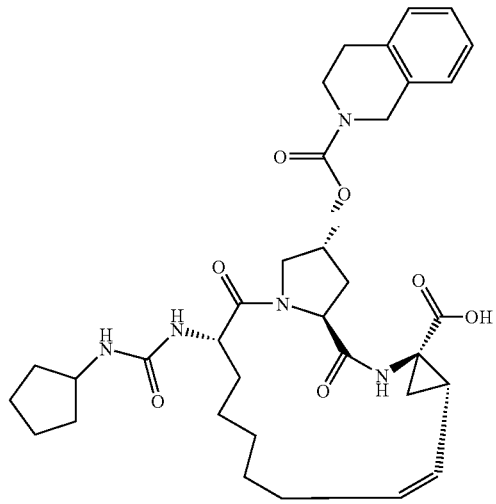

Compound AR00294378

Synthesis of (1S,4R,6S,14S,18R)-14-(3-Cyclopentyl-ureido)-18-(3,4-dihydro-1H-isoquinoline-2-carbonyloxy)-2,15-dioxo-3,16-diaza-tricyclo[14.3.0.0^{4,6}]nonadec-7-ene-4-carboxylic acid (Compound AR294378)

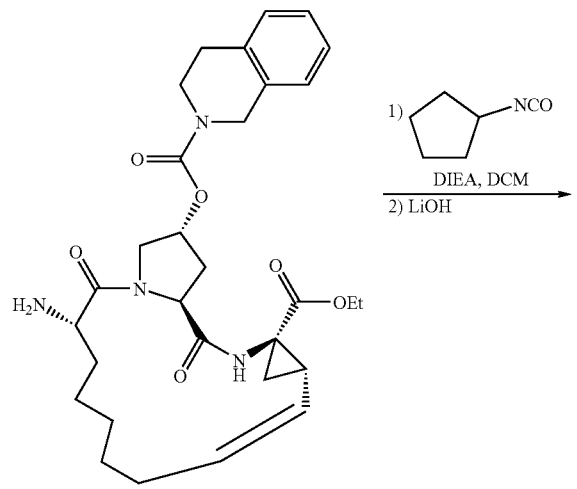

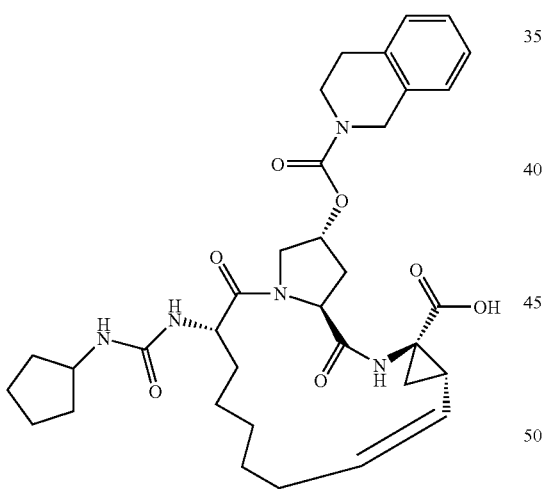

14-Amino-2,15-dioxo-18-(8-trifluoromethyl-3,4-dihydro-1H-isoquinoline-2-carbonyloxy)-3,16-diaza-tricyclo[14.3.0.0^{4,6}]nonadec-7-ene-4-carboxylic acid ethyl ester hydrochloride salt (49 mg, 74 umol), diisopropylethylamine (29 mg, 222 umol), and cyclopentyl isocyanate (25 mg, 222 umol) were taken up in 375 uL dichloromethane and stirred at 19 C for 1 hour. The reaction was loaded directly onto a C18 flash column and eluted with water/acetonitrile (10 to 100%) containing 0.1% TFA to provide the title product as a white solid (42 mg, 77%). MS m/z 732.2 (MH+).

Example 2-25

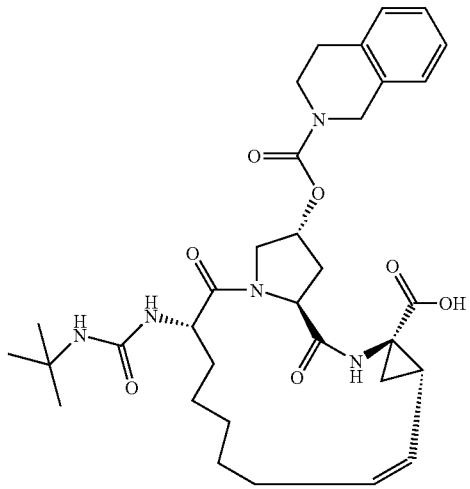

Compound AR00294377

(1S,4R,6S,14S,18R)-14-(3-tert-Butyl-ureido)-18-(3,4-dihydro-1H-isoquinoline-2-carbonyloxy)-2,15-dioxo-3,16-diaza-tricyclo[14.3.0.0^{4,6}]nonadec-7-ene-4-carboxylic acid (Compound AR00294377) was synthesized according to the procedures described in Examples 1-2 and 2-24, except that tert-butyl isocyanate was used to replace cyclopentyl isocyanate in the Example 2-24 procedures. MS m/e 624.1 (M++1).

Example 2-26

Compound AR00304077

(1S,4R,6S,14S,18R)-14-(3-Cyclopentyl-ureido)-18-(5-fluoro-3,4-dihydro-1H-isoquinoline-2-carbonyloxy)-2,15-dioxo-3,16-diaza-tricyclo[14.3.0.0^{4,6}]nonadec-7-ene-4-carboxylic acid (Compound AR00304077) was synthesized according to the procedures described in Examples 1-2 and 2-24, except that 5-Fluoro-1,2,3,4-tetrahydro-isoquinoline was used to replace 1,2,3,4-tetrahydro-isoquinoline in Step 4 of Example 1-2. MS m/e 654.2 (M$^+$+1).

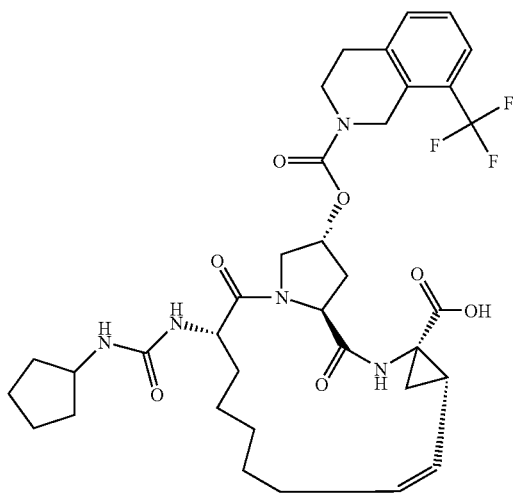

Example 2-27

(1S,4R,6S,14S,18R)-14-(3-Cyclopentyl-ureido)-2,15-dioxo-18-(8-trifluoromethyl-3,4-dihydro-1H-isoquinoline-2-carbonyloxy)-3,16-diaza-tricyclo[14.3.0.0$^{4,6}$]nonadec-7-ene-4-carboxylic acid (Compound AR00304078) was synthesized according to the procedures described in Examples 1-2 and 2-24, except that 8-trifluoromethyl-1,2,3,4-tetrahydro-isoquinoline was used to replace 1,2,3,4-tetrahydro-isoquinoline in Step 4 of Example 1-2. MS m/e 704.1 (M$^+$+1).

Example 2-28

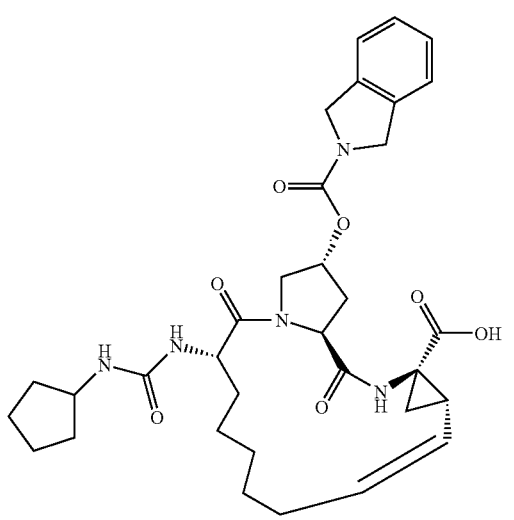

(1S,4R,6S,14S,18R)-14-(3-Cyclopentyl-ureido)-18-(1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00304079) was synthesized according to the procedures described in Examples 1-2 and 2-24, except that 2,3-dihydro-1H-isoindole was used to replace 1,2,3,4-tetrahydro-isoquinoline in Step 4 of Example 1-2. MS m/e 622.2 (M$^+$+1).

Example 2-29

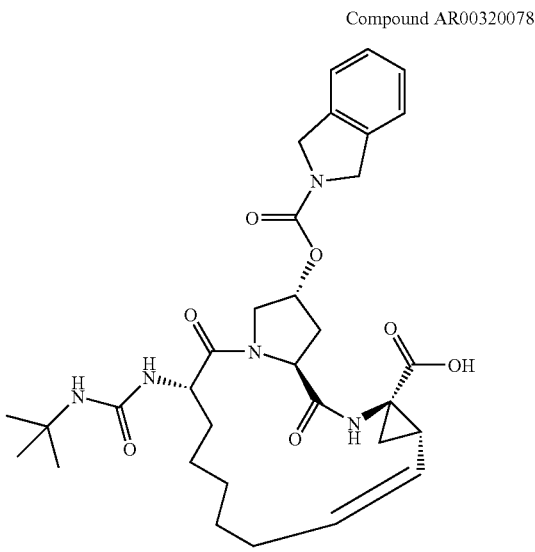

(1S,4R,6S,14S,18R)-14-(3-tert-Butyl-ureido)-18-(1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00320078) was synthesized according to the procedures described in Examples 1-2 and 2-24, except that 2,3-dihydro-1H-isoindole was used to replace 1,2,3,4-tetrahydro-isoquinoline in Step 4 of Example 1-2, and that tert-butyl isocyanate was used to replace cyclopentyl isocyanate in the Example 2-24 procedures. MS m/e 610.1 (M$^+$+1).

Example 2-30

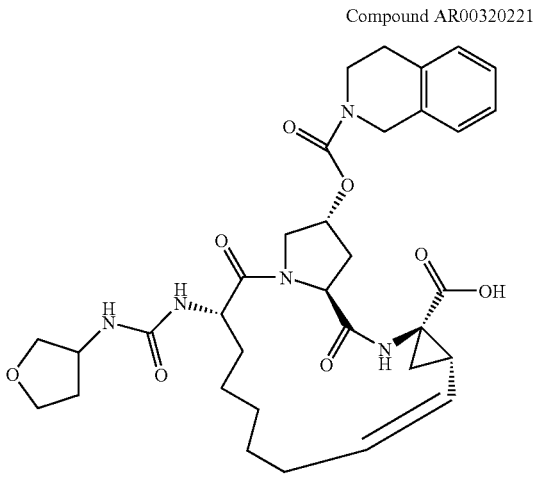

(1S,4R,6S,14S,18R)-18-(3,4-Dihydro-1H-isoquinoline-2-carbonyloxy)-2,15-dioxo-14-[3-(tetrahydro-furan-3-yl)- ureido]-3,16-diaza-tricyclo[14.3.0.0^{4,6}]nonadec-7-ene-4-carboxylic acid (Compound AR00320221) was synthesized according to the procedures described in Examples 1-2 and 2-24, except that 3-isocyanato-tetrahydro-furan was used to replace cyclopentyl isocyanate in the Example 2-24 procedures. MS m/e 638.2 (M$^+$+1).

Example 2-31

Compound AR00320449

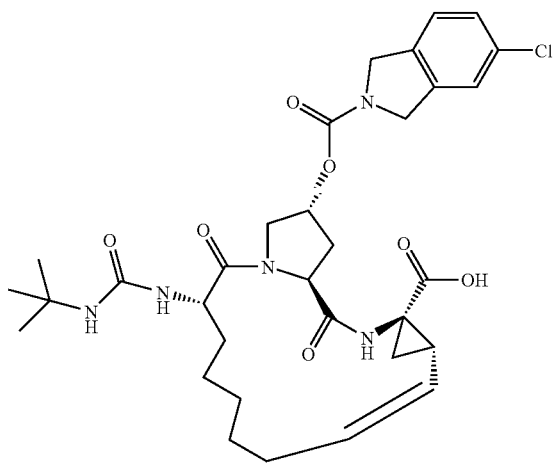

(1S,4R,6S,14S,18R)-14-(3-tert-Butyl-ureido)-18-(5-chloro-1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00320449) was synthesized according to the procedures described in Examples 1-2 and 2-24, except that 5-chloro-2,3-dihydro-1H-isoindole was used to replace 1,2,3,4-tetrahydro-isoquinoline in Step 4 of Example 1-2, and that tert-butyl isocyanate was used to replace cyclopentyl isocyanate in the Example 2-24 procedures. $^1$H NMR (500 MHz, CD$_3$OD): δ7.34 (s, 1H), 7.28-7.25 (m, 2H), 7.24 (s, 1H), 7.20 (s, 1H), 5.51 (m, 2H), 5.40 (s, 1H), 4.73-4.60 (m, 3H), 4.53 (t, 1H), 4.38 (d, 1H), 4.28 (d, 1H), 3.98 (dd, 1H), 2.43 (m, 2H), 2.38-2.30 (m, 1H), 2.12-2.00 (m, 2H), 1.81-1.70 (m, 1H), 1.64-1.56 (m, 3H), 1.48-1.20 (m, 8H), 1.18 (s, 9H). MS: m/e 644.0 (M$^+$), 645.9 (M$^+$+2)

Example 2-32

Compound AR00320450

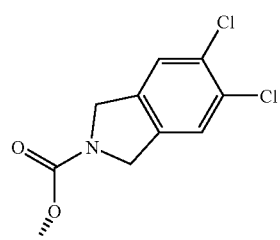

-continued

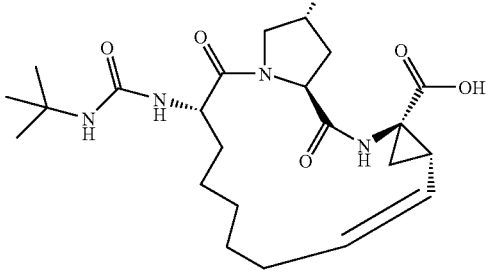

(1S,4R,6S,14S,18R)-14-(3-tert-Butyl-ureido)-18-(5,6-dichloro-1,3-dihydro-isoindole-2-carbonyloxy)-2,15-dioxo-3,16-diaza-tricyclo[14.3.0.0$^{4,6}$]nonadec-7-ene-4-carboxylic acid (Compound AR00320450) was synthesized according to the procedures described in Examples 1-2 and 2-24, except that 5,6-dichloro-2,3-dihydro-1H-isoindole was used to replace 1,2,3,4-tetrahydro-isoquinoline in Step 4 of Example 1-2, and that tert-butyl isocyanate was used to replace cyclopentyl isocyanate in the Example 2-24 procedures. $^1$H NMR (500 MHz, CD$_3$OD): δ7.50 (s, 1H), 7.38 (s, 1H), 5.56 (q, 1H), 5.42-5.38 (m, 2H), 4.72-4.61 (m, 4H), 4.55 (t, 1H), 4.34 (dd, 1H), 4.28 (d, 1H), 3.92 (dd, 1H), 2.45-2.32 (m, 2H), 2.32-2.18 (m, 1H), 2.08-2.00 (m, 1H), 1.75-1.68 (m, 1H), 1.63-1.54 (m, 3H), 1.50-1.22 (m, 8H), 1.18 (s, 9H). MS: m/e 678.0 (M$^+$), 680.0 (M$^+$+2).

Example 2-33

Compound AR00365381

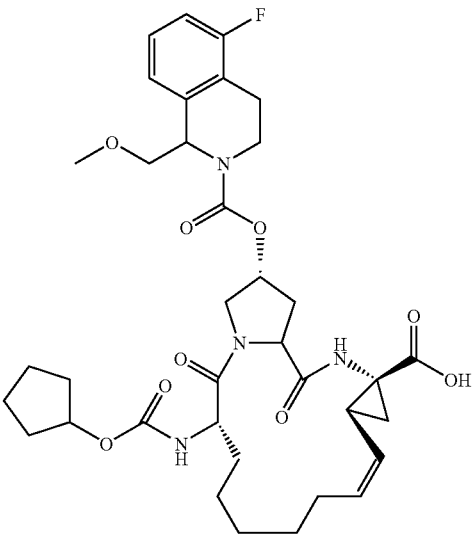

(1S,4R,6S,14S,18R)-14-Cyclopentyloxycarbonylamino-18-(5-fluoro-1-methoxymethyl-3,4-dihydro-1H-isoquinoline-2-carbonyloxy)-2,15-dioxo-3,16-diaza-tricyclo[14.3.0.0$^{4,6}$]nonadec-7-ene-4-carboxylic acid (Compound AR00365381) was synthesized according to the procedures described in Examples 1-2 and 2-1, except that 5-fluoro-1-methoxymethyl-1,2,3,4-tetrahydro-isoquinolinium chloride was used to replace 1,2,3,4-Tetrahydro-isoquinoline in Step 4 of Example 1-2 instead. MS (APCI−): m/z 697.4 (M−1).

Preparation of Compounds with General Structure IV

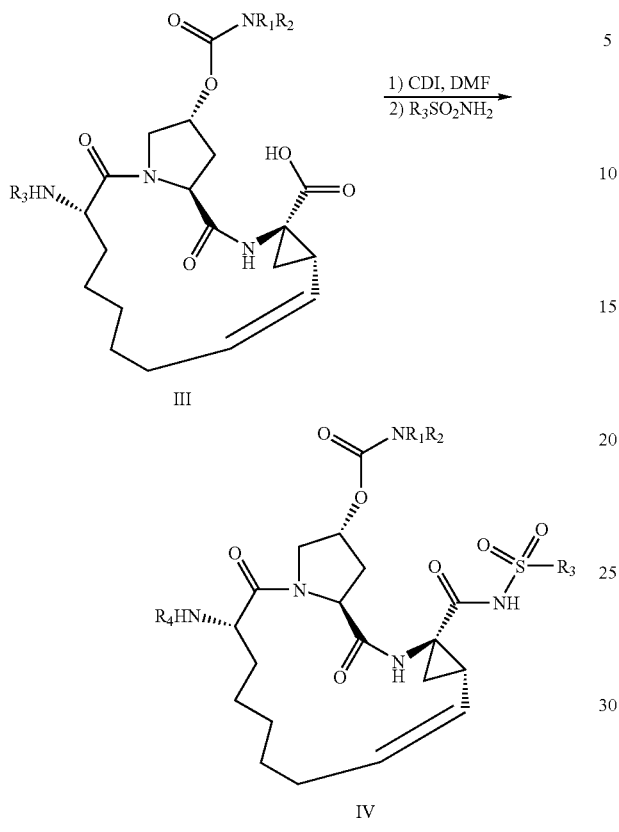

Compounds with general structure IV were prepared according to the scheme shown above (1. Khan et al, Bioorg. & Med. Chem. Lett., 1997, 7 (23), 3017-3022. 2. International Application PCT/US02/39926, WO 03/053349).

Example 3-1

Compound AR00261408

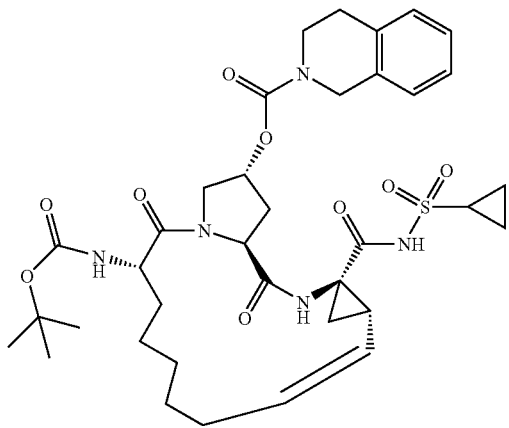

Synthesis of (1S,4R,6S,14S,18R)-3,4-Dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (AR00261408)

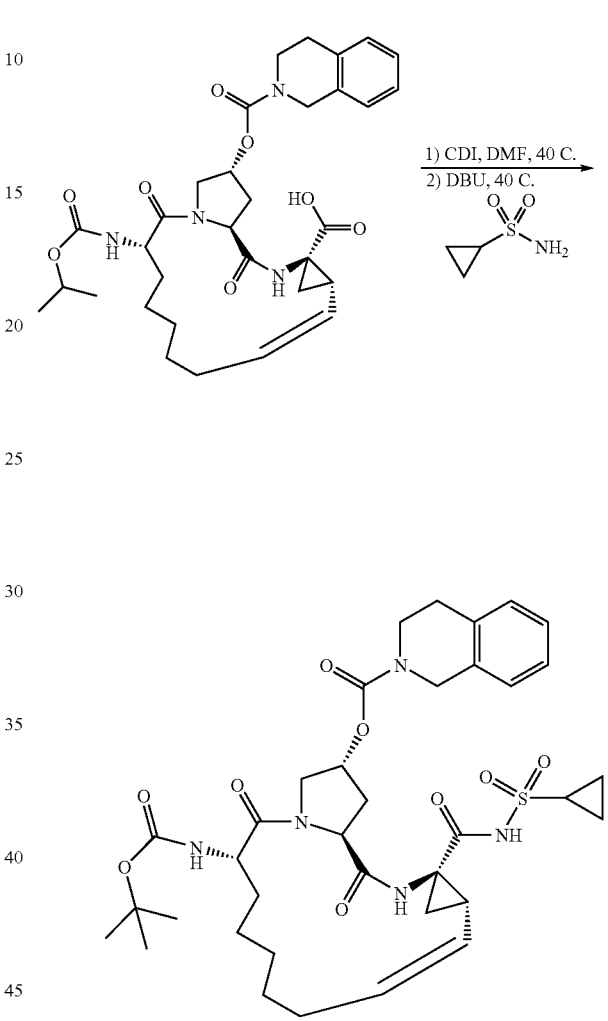

The macrocyclic acid compound# 101 (7 mg, 0.011 mmol) was dissolved in 0.1 mL DMF, followed by addition of CDI (1.8 mg, 0.011 mmol). The mixture was stirred in a 40° C. oil bath for 1 h. Then cyclopropylsulfonamide (2.0 mg, 0.017 mmol) was added to the reaction, followed by DBU (1.7 mg, 0.011 mmol). The reaction was stirred at 40° C. for overnight. After 14 h, LCMS showed reaction complete. The reaction was cooled to rt, partitioned between 2 mL EA and 2 mL 5% HCl (aq). The organic layer was washed with water, bicarb (2 mL ea), then dried (Na$_2$SO$_4$). The crude was flashed on Biotage 12M (eluent=DCM:MeOH 20:1), giving AR00261408 (4.2 mg, 52%) $^1$H NMR (CDCl$_3$, 500 MHz): δ 0.80-2.10 (m, 25H), 2.20-2.27 (m, 1H), 2.37-2.59 (m, 3H), 2.84 (m, 1H), 3.60-3.70 (m, 1H), 3.82-3.90 (m, 1H), 4.20-4.30 (m, 2H), 4.45-4.70 (m, 5H), 4.95-5.05 (m, 2H), 5.30-5.48 (m, 2H), 5.74 (m, 1H), 6.74 (m, 1H), 7.0-7.23 (m, 4H). MS m/e 728.0 (M$^+$+H).

Example 3-2

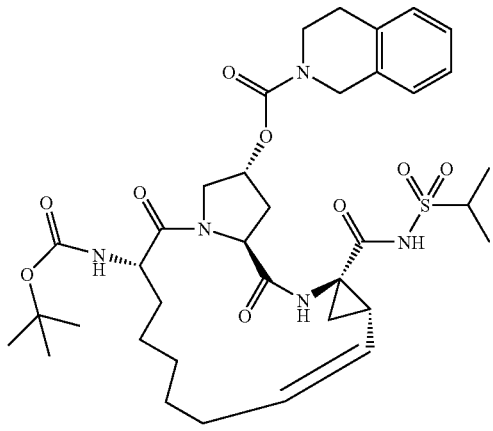

Compound AR00261407

(1S,4R,6S,14S,18R)-3,4-Dihydro-1H-isoquinoline-2-carboxylic acid 14-tert-butoxycarbonylamino-2,15-dioxo-4-(propane-2-sulfonylaminocarbonyl)-3,16-diaza-tricyclo[14.3.0.0$^{4,6}$]nonadec-7-en-18-yl ester (Compound AR00261407) was synthesized according to the procedures described in Example 3-1, except that isopropyl sulfonamide was used to replace cyclopropyl sulfonamide in the coupling step. MS m/e 728.4 (M−1).

Example 3-3

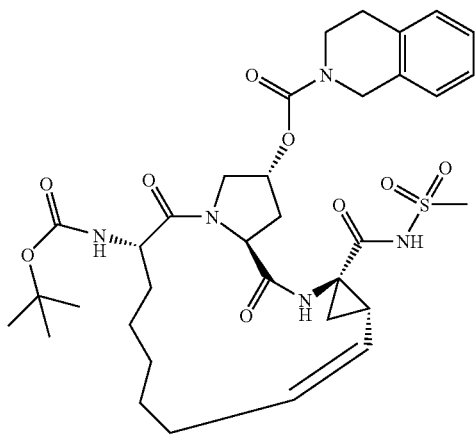

Compound AR00254906

(1S,4R,6S,14S,18R)-3,4-Dihydro-1H-isoquinoline-2-carboxylic acid 14-tert-butoxycarbonylamino-4-methanesulfonylaminocarbonyl-2,15-dioxo-3,16-diaza-tricyclo[14.3.0.0$^{4,6}$]nonadec-7-en-18-yl ester (Compound AR00254906) was synthesized according to the procedures described in Example 3-1, except that methyl sulfonamide was used to replace cyclopropyl sulfonamide in the coupling step. $^1$H NMR (CDCl$_3$, 500 MHz): δ 1.20-1.52 (m, 16H), 1.54-1.98 (m, 5H), 2.20-2.30 (m, 1H), 2.38-2.46 (m, 1H), 2.47-2.59 (m, 3H), 2.84 (m, 1H), 3.18 (s, 3H), 3.56-3.70 (m, 1H), 3.82-3.90 (m, 1H), 4.22-4.33 (m, 2H), 4.47-4.69 (m, 4H), 4.90-5.10 (m, 2H), 5.47 (brs, 1H), 5.74 (m, 1H), 6.74 (m, 1H), 7.03-7.23 (m, 4H). MS m/e 701.9 (M$^+$), 602.2 (parent, MH$^+$−Boc group).

Example 3-4

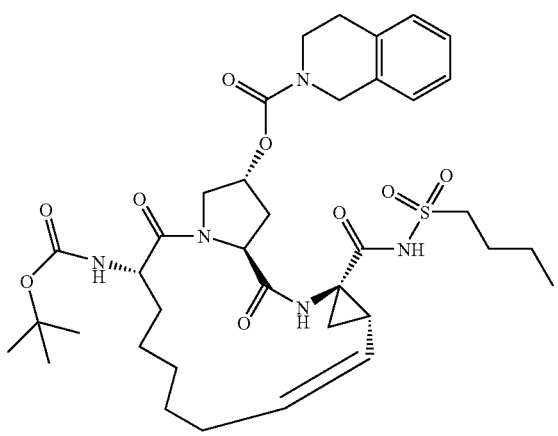

Compound AR00261409

(1S,4R,6S,14S,18R)-3,4-Dihydro-1H-isoquinoline-2-carboxylic acid 4-(butane-1-sulfonylaminocarbonyl)-14-tert-butoxycarbonylamino-2,15-dioxo-3,16-diaza-tricyclo[14.3.0.0$^{4,6}$]nonadec-7-en-18-yl ester (Compound AR00261409) was synthesized according to the procedures described in Example 3-1, except that n-butyl sulfonamide was used to replace cyclopropyl sulfonamide in the coupling step. $^1$H NMR (CDCl$_3$, 500 MHz): δ 0.80-1.03 (m, 7H), 1.20-2.10 (m, 22H), 2.20-2.60 (m, 4H), 2.84 (m, 1H), 3.20 (m, 1H), 3.44 (m, 1H), 3.65 (m, 1H), 3.80-3.95 (m, 1H), 4.20-4.34 (m, 2H), 4.50-4.65 (m, 4H), 4.95-5.05 (m, 1H), 5.30-5.39 (m, 1H), 5.44-5.49 (m, 1H), 5.74 (m, 1H), 6.74 (m, 1H), 7.0-7.23 (m, 4H). MS m/e 743.3 (M$^+$, APCI−).

Example 3-5

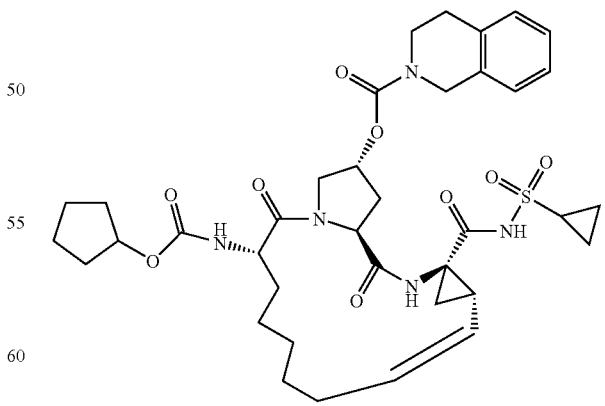

Compound AR00282131

(1S,4R,6S,14S,18R)-3,4-Dihydro-1H-isoquinoline-2-carboxylic acid 14-cyclopentyloxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00282131) was synthesized according to the procedures described in Examples 2-1 and 3-1. MS m/e 738.4 (M−1).

Example 3-6

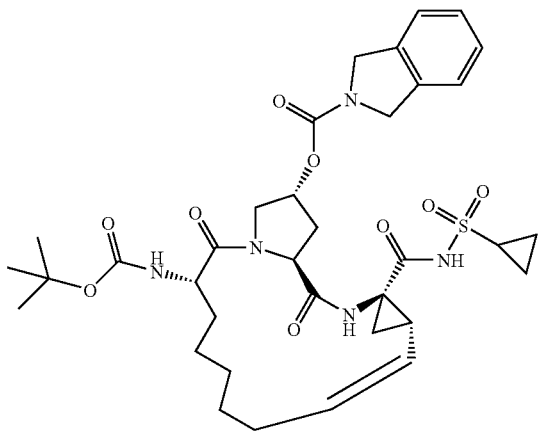

Compound AR00294381

(1S,4R,6S,14S,18R)-1,3-Dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00294381) was synthesized according to the procedures described in Examples 1-5 and 3-1. $^1$H NMR (CDCl$_3$, 500 MHz): δ 0.89-2.08 (m, 25H), 2.21-2.28 (m, 1H), 2.41-2.49 (m, 1H), 2.51-2.61 (m, 2H), 2.91 (m, 1H), 3.83 (m, 1H), 4.21 (m, 1H), 4.40 (d, J=11.7 Hz, 1H), 4.53-4.80 (m, 5H), 4.95-5.04 (m, 2H), 5.47 (brs, 1H), 5.72 (m, 1H), 6.77 (m, 1H), 7.16 (m, 1H), 7.23-7.31 (m, 3H). MS m/e 712.3 (APCI−, M−H).

Example 3-7

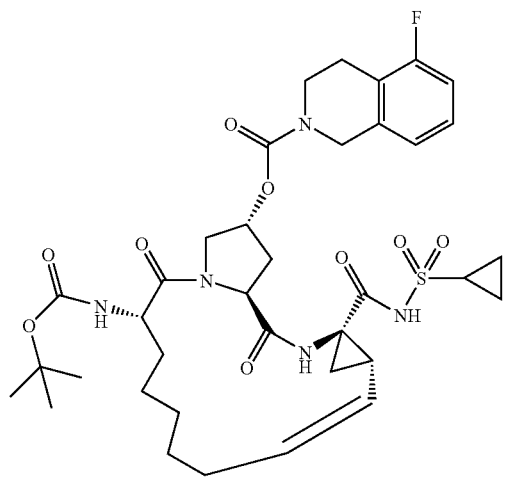

Compound AR00298996

(1S,4R,6S,14S,18R)-5-Fluoro-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00298996) was synthesized according to the procedures described in Examples 1-2 and 3-1, except that 5-Fluoro-1,2,3,4-tetrahydro-isoquinoline was used to replace 1,2,3,4-tetrahydro-isoquinoline in Step 4 of Example 1-2. $^1$H NMR (400 MHz, CDCl$_3$): δ10.05 (s, 1H), 8.12 (s, 1H), 7.04 (s, 1H), 6.84-6.73 (m, 2H), 6.70 (s, 1H), 5.65 (q, 1H), 5.40 (s, 1H), 4.59 (m, 2H), 4.54-4.40 (m, 3H), 4.30-4.10 (m, 2H), 3.82-3.74 (m, 1H), 3.72-3.51 (m, 2H), 2.92-2.68 (m, 3H), 2.55-2.30 (m, 3H), 2.21-2.15 (m, 1H), 2.00-1.60 (m, 3H), 1.40-0.75 (m, 18H). MS: m/e 746.0 (M$^+$).

Example 3-8

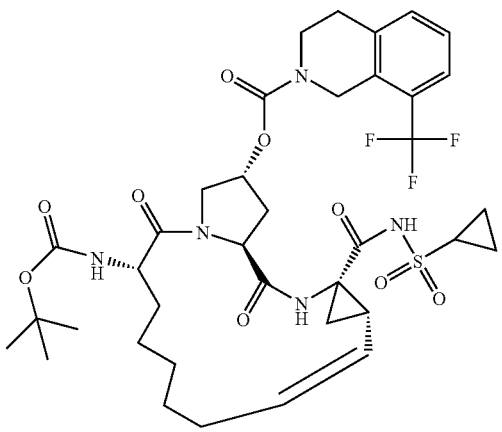

Compound AR00298997

(1S,4R,6S,14S,18R)-8-Trifluoromethyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00298997) was synthesized according to the procedures described in Examples 1-2 and 3-1, except that 8-trifluoromethyl-1,2,3,4-tetrahydro-isoquinoline was used to replace 1,2,3,4-tetrahydro-isoquinoline in Step 4 of Example 1-2. $^1$H NMR (500 MHz, CD$_3$OD): δ 7.55 (dd, 1H), 7.42 (dd, 1H), 7.35 (t, 1H), 5.71-5.61 (m, 1H), 5.40 (m, 1H), 4.60 (s, 1H), 4.52 (m, 1H), 4.42 (m, 1H), 4.15 (m, 1H), 3.91 (m, 1H), 3.78-3.62 (m, 2H), 3.00-2.82 (m, 3H), 2.58-2.52 (m, 3H), 2.51-2.32 (m, 2H), 1.86-1.56 (m, 3H), 1.41 (m, 2H), 1.32-1.21 (m, 5H), 1.04-0.98 (m, 14H). MS: m/e 795.9 (M$^+$).

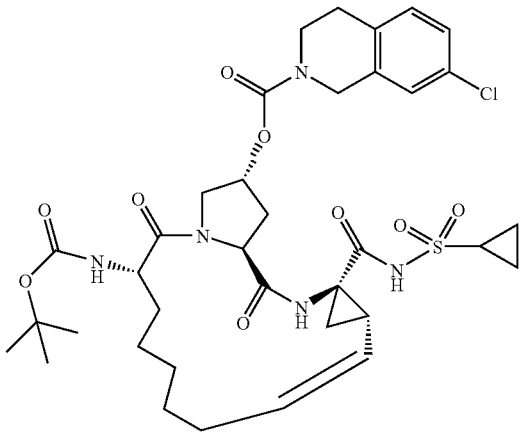

Compound AR00301746

Example 3-9

(1S,4R,6S,14S,18R)-7-Chloro-3,4-dihydro-1H-isoquinoline-2-carboxylic acid 14-tert-butoxycarbonylamino-4-cyclopropanesulfonylaminocarbonyl-2,15-dioxo-3,16-diazatricyclo[14.3.0.0$^{4,6}$]nonadec-7-en-18-yl ester (Compound AR00301746) was synthesized according to the procedures described in Examples 1-2 and 3-1, except that 7-chloro-1,2,3,4-tetrahydro-isoquinoline was used to replace 1,2,3,4-tetrahydro-isoquinoline in Step 4 of Example 1-2. $^1$H NMR (400 MHz, CDCl$_3$): δ 10.10 (s, 1H), 7.08 (d, 1H), 7.02-6.96 (m, 2H), 6.60 (d, 1H), 5.64 (q, 1H), 5.40 (s, 1H), 4.92-4.41 (m, 2H), 4.55-4.40 (m, 3H), 4.28-4.12 (m, 2H), 3.82-3.75 (m, 1H), 3.65-3.46 (m, 3H), 2.88-2.80 (m, 1H), 2.78-2.56 (m, 2H), 2.52-2.42 (m, 1H), 2.38-2.30 (m, 1H), 2.21-2.12 (q, 1H), 1.82-1.74 (m, 2H), 1.45-1.12 (m, 16H), 1.10-0.98 (m, 2H), 0.90-0.75 (m, 2H). MS m/e 761.9 (M$^+$)

Example 3-10

Compound AR00301747

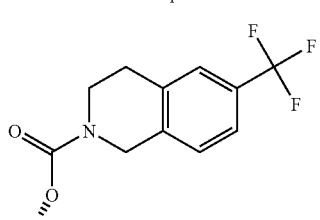

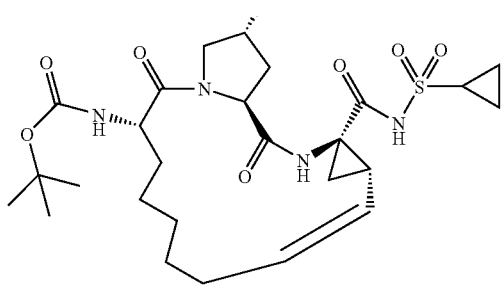

(1S,4R,6S,14S,18R)-6-Trifluoromethyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00301747) was synthesized according to the procedures described in Examples 1-2 and 3-1, except that 6-trifluoromethyl-1,2,3,4-tetrahydro-isoquinoline was used to replace 1,2,3,4-tetrahydro-isoquinoline in Step 4 of Example 1-2. $^1$H NMR (500 MHz, CD$_3$OD): δ 7.44 (m, 2H), 7.38-7.30 (m, 1H), 7.28-7.24 (m, 1H), 5.65 (q, 1H), 5.40 (m, 1H), 5.08 (m, 1H), 4.56 (brs, 2H), 4.60-4.50 (m, 1H), 4.48 (m, 1H), 4.15 (d, 1H), 3.88 (d, 1H), 3.75-3.67 (m, 2H), 2.93-2.82 (m, 3H), 2.66-2.54 (m, 1H), 2.52-2.44 (m, 1H), 2.42-2.40 (m, 2H), 1.91-1.76 (m, 2H), 1.74-1.70 (dd, 1H), 1.64-1.58 (m, 1H), 1.54-1.36 (m, 4H), 1.34-1.25 (m, 12H), 1.50-1.20 (m, 2H), 1.00-0.70 (m, 1H), 0.52-0.34 (m, 1H). MS: m/e 795.9 (M$^+$)

Example 3-11

Compound AR00301751

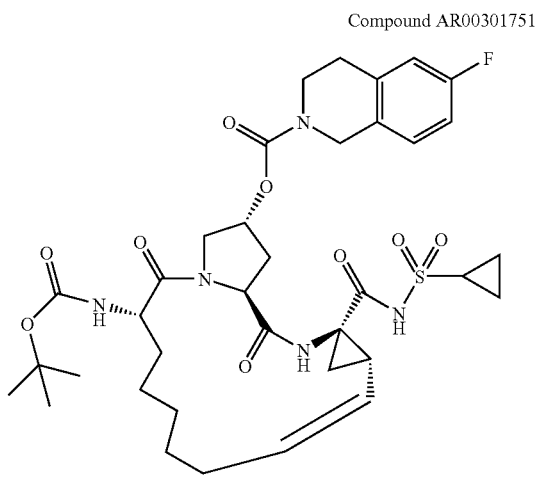

(1S,4R,6S,14S,18R)-6-Fluoro-3,4-dihydro-1H-isoquinoline-2-carboxylic acid 14-tert-butoxycarbonylamino-4-cyclopropanesulfonylaminocarbonyl-2,15-dioxo-3,16-diazatricyclo[14.3.0.0$^{4,6}$]nonadec-7-en-18-yl ester (Compound AR00301751) was synthesized according to the procedures described in Examples 1-2 and 3-1, except that 6-fluoro-1,2,3,4-tetrahydro-isoquinoline was used to replace 1,2,3,4-tetrahydro-isoquinoline in Step 4 of Example 1-2. $^1$H NMR (500 MHz, CD$_3$OD): δ 7.21-7.02 (m, 1H), 6.92 (m, 2H), 6.92 (m, 2H), 5.68 (q, 1H), 5.40 (m, 1H), 5.08 (t, 1H), 4.58 (m, 2H), 4.45 (m, 1H), 4.12 (d, 1H), 3.88 (d, 1H), 3.78-3.60 (m, 3H), 2.86-2.72 (m, 3H), 2.71-2.61 (m, 1H), 2.52-2.42 (m, 1H), 2.41-2.34 (m, 1H), 1.88-1.76 (m, 2H), 1.74-1.70 (m, 1H), 1.64-1.58 (m, 1H), 1.56-1.38 (m, 2H), 1.37-1.24 (m, 14H), 1.13-1.04 (m, 2H), 1.02-0.89 (m, 1H), 0.88-0.82 (m, 1H). MS: m/e 746.0 (M$^+$). MS m/e 757.2 (M$^+$+1).

Example 3-12

Compound AR00304080

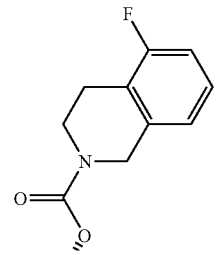

-continued

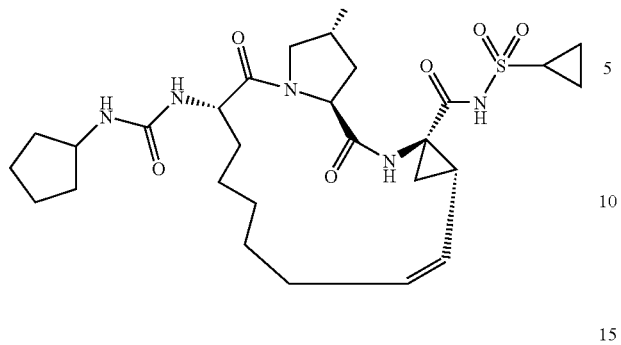

(1S,4R,6S,14S,18R)-5-Fluoro-3,4-dihydro-1H-isoquinoline-2-carboxylic acid 14-(3-cyclopentyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00304080) was synthesized according to the procedures described in Examples 1-2, 2-24 and 3-1, except that 5-fluoro-1,2,3,4-tetrahydro-isoquinoline was used to replace 1,2,3,4-tetrahydro-isoquinoline in Step 4 of Example 1-2.

Example 3-13

Compound AR00304081

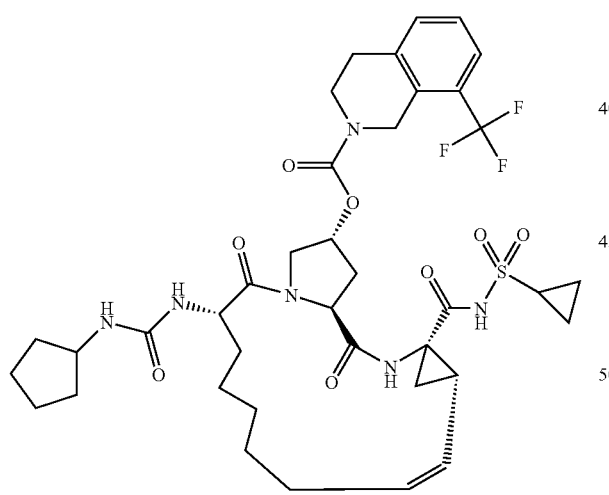

(1S,4R,6S,14S,18R)-8-Trifluoromethyl-3,4-dihydro-1H-isoquinoline-2-carboxylic acid 14-(3-cyclopentyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00304081) was synthesized according to the procedures described in Examples 1-2, 2-24 and 3-1, except that 8-trifluoromethyl-1,2,3,4-tetrahydro-isoquinoline was used to replace 1,2,3,4-tetrahydro-isoquinoline in Step 4 of Example 1-2. MS m/e 807.2 (M$^+$+1).

Example 3-14

Compound AR00304082

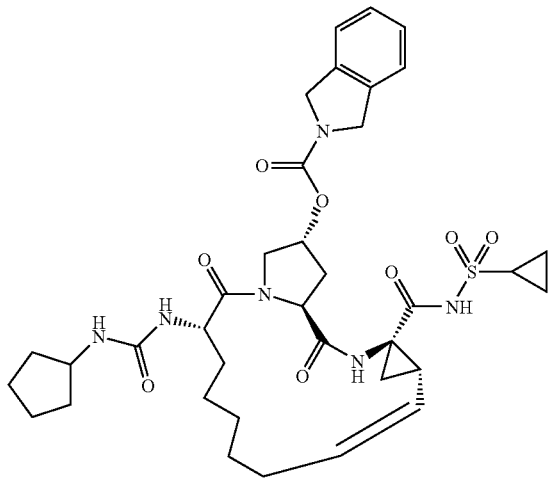

(1S,4R,6S,14S,18R)-1,3-Dihydro-isoindole-2-carboxylic acid 14-(3-cyclopentyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00304082) was synthesized according to the procedures described in Examples 1-2, 2-24 and 3-1, except 2,3-Dihydro-1H-isoindole was used to replace 1,2,3,4-tetrahydro-isoquinoline in Step 4 of Example 1-2. MS m/e 725.2 (M$^+$+1).

Example 3-15

Compound AR00304161

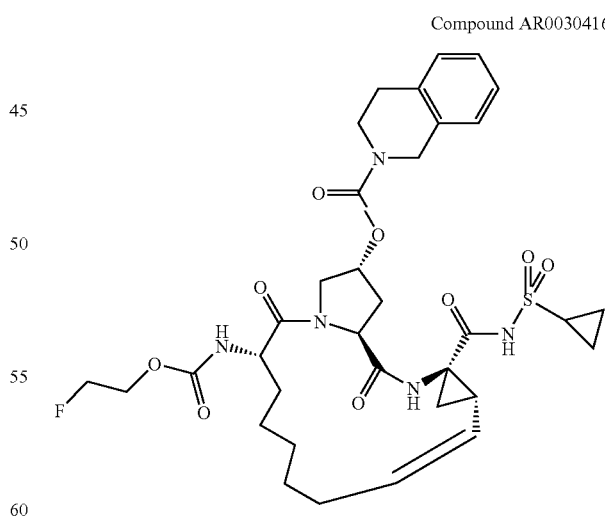

(1S,4R,6S,14S,18R)-3,4-Dihydro-1H-isoquinoline-2-carboxylic acid 4-cyclopropanesulfonylaminocarbonyl-14-(2-fluoro-ethoxycarbonylamino)-2,15-dioxo-3,16-diaza-tricyclo[14.3.0.0$^{4,6}$]nonadec-7-en-18-yl ester (Compound AR00304161) was synthesized according to the procedures described in Examples 1-2, 2-1 and 3-1, except that 2-fluoroethanol was used to form the chloroformate reagent in Step 2 of Example 2-1, instead of cyclopentanol. MS m/e 718.1 (M⁺+1).

Example 3-16

Compound AR00304162

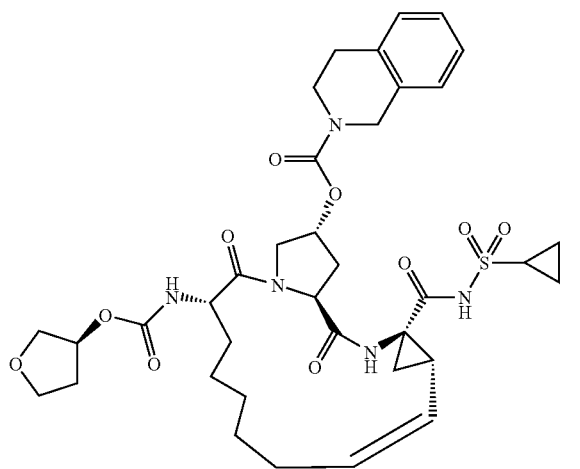

(1S,4R,6S,14S,18R)-3,4-Dihydro-1H-isoquinoline-2-carboxylic acid 4-cyclopropanesulfonylaminocarbonyl-2,15-dioxo-14-(tetrahydro-furan-3-yloxycarbonylamino)-3,16-diaza-tricyclo[14.3.0.0$^{4,6}$]nonadec-7-en-18-yl ester (Compound AR00304162) was synthesized according to the procedures described in Examples 1-2, 2-1 and 3-1, except that tetrahydro-furan-3S-ol was used to form the chloroformate reagent in Step 2 of Example 2-1, instead of cyclopentanol. MS m/e 742.1 (M⁺+1).

Example 3-17

Compound AR00304163

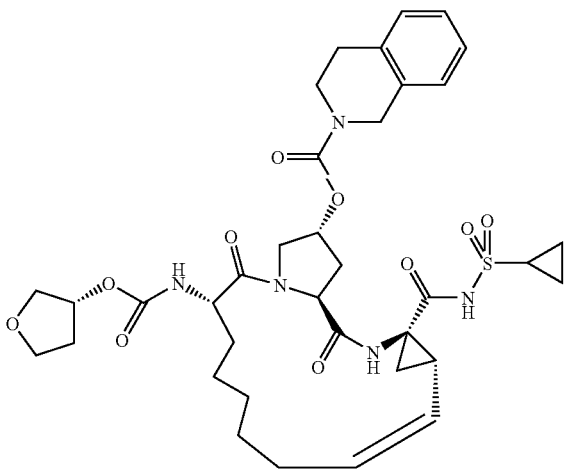

(1S,4R,6S,14S,18R)-3,4-Dihydro-1H-isoquinoline-2-carboxylic acid 4-cyclopropanesulfonylaminocarbonyl-2,15-dioxo-14-(tetrahydro-furan-3R-yloxycarbonylamino)-3,16-diaza-tricyclo[14.3.0.0$^{4,6}$]nonadec-7-en-18-yl ester (Compound AR00304163) was synthesized according to the procedures described in Examples 1-2, 2-1 and 3-1, except that tetrahydro-furan-3R-ol was used to form the chloroformate reagent in Step 2 of Example 2-1, instead of cyclopentanol. $^1$H NMR (d 6-Benzene, 500 MHz): δ 10.53 (s, 1H), 6.78-6.96 (m, 4H), 5.83-5.90 (m, 1H), 5.66 (q, 1H), 5.18-5.21 (m, 1H), 5.13 (brs, 1H), 5.04 (brs, 1H), 4.41-4.87 (m, 3H), 3.85-4.05 (m, 4H), 3.67-3.74 (m, 1H), 3.46-3.53 (m, 3H), 3.23-3.34 (m, 1H), 2.80-2.85 (m, 1H), 2.34-2.59 (m, 4H), 1.84-1.99 (m, 4H), 0.98-1.60 (m, 14H), 0.42-0.47 (m, 1H), 0.27-0.32 (m, 1H). MS m/e 741.2 (M−1).

Example 3-18

Compound AR00311814

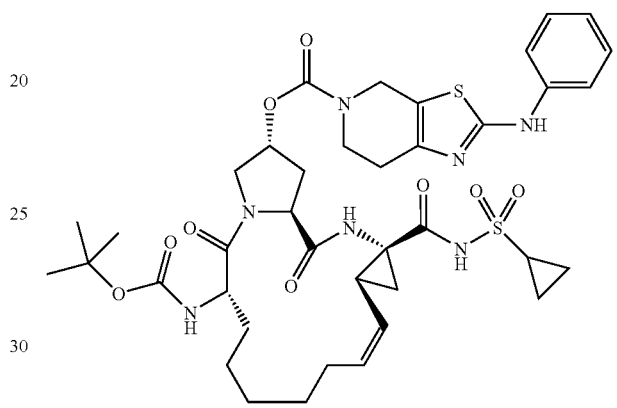

(1S,4R,6S,14S,18R)-2-Phenylamino-6,7-dihydro-4H-thiazolo[5,4-c]pyridine-5-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00311814) was synthesized according to the procedures described in Examples 1-2 and 3-1, except that phenyl-(4,5,6,7-tetrahydro-thiazolo[5,4-c]pyridin-2-yl)-amine was used to replace 1,2,3,4-tetrahydro-isoquinoline in Step 4 of Example 1-2. MS m/e 826.2 (M⁺+1).

Example 3-19

Compound AR00311815

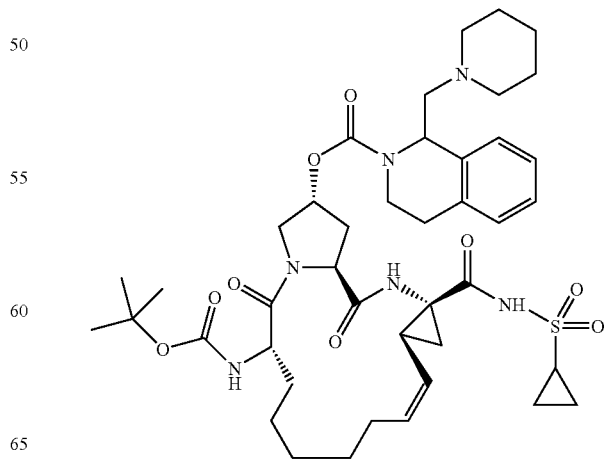

(1S,4R,6S,14S,18R)-1-Piperidin-1-ylmethyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00311815) was synthesized according to the procedures described in Examples 1-2 and 3-1, except that 1-Piperidin-1-ylmethyl-1,2,3,4-tetrahydro-isoquinoline was used to replace 1,2,3,4-tetrahydro-isoquinoline in Step 4 of Example 1-2. $^1$H NMR (500 MHz, CD$_3$OD) δ 8.94 (d, 1H), 7.59 (s, 1H), 7.31-7.23 (m, 3H), 7.22-7.15 (m, 2H), 5.74-5.64 (m, 2H), 5.47 (br s, 1H), 5.06 (t, 1H), 4.54 (dt, 1H), 4.40-4.17 (m, 4H), 4.11-4.04 (m, 1H), 3.96-3.88 (m, 1H), 3.75-3.40 (m, 5H), 3.14-2.32 (m, 7H), 2.05 (dd, 1H), 1.99-1.68 (m, 5H), 1.65-0.95 (m, 24H); MS (POS ESI) m/z 825.4 (M$^+$).

Example 3-20

Compound AR00312024

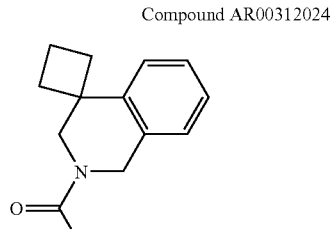

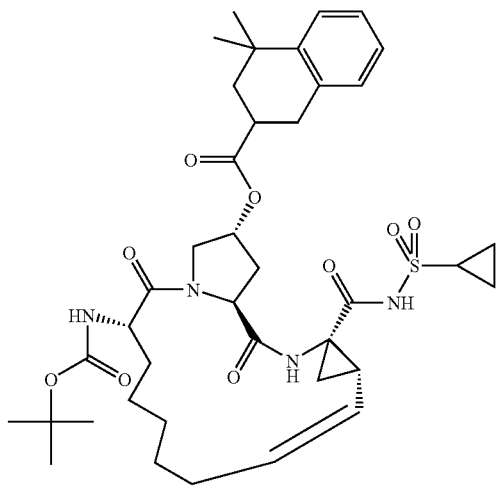

(1S,4R,6S,14S,18R)-4,4-Spirocyclobutyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00312024) was synthesized according to the procedures described in Examples 1-2 and 3-1, except that 4,4-spirocyclobutyl-1,2,3,4-tetrahydro-isoquinoline was used to replace 1,2,3,4-tetrahydro-isoquinoline in Step 4 of Example 1-2. $^1$H NMR (400 MHz, CD$_3$OD) δ 7.54-7.60 (m, 1H), 7.26 (dd, 1H), 6.97-7.21 (m, 1H), 5.66 (dd, 1H), 5.37-5.48 (m, 1H), 5.11 (dd, 1H), 4.58 (s, 2H), 4.39 (t, 3H), 4.11-4.26 (m, 1H), 3.77-3.96 (m, 1H), 3.87 (t, 3H), 3.60-3.70 (m, 1H), 2.83-2.93 (m, 1H), 2.23-2.68 (m, 6H), 1.70-2.23 (m, 7H), 1.18-1.69 (m, 18H), 0.81-1.12 (m, 3H). MS m/z 767.9 (M$^+$+1)

Example 3-21

Compound AR00312025

(1S,4R,6S,14S,18R)-4,4-Dimethyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00312025) was synthesized according to the procedures described in Examples 1-2 and 3-1, except that 4,4-dimethyl-1,2,3,4-tetrahydro-isoquinoline was used to replace 1,2,3,4-tetrahydro-isoquinoline in Step 4 of Example 1-2. $^1$H NMR (400 MHz, CD$_3$OD) δ 7.31-7.40 (m, 1H), 6.97-7.23 (m, 3H), 5.67 (dd, 1H), 5.34-5.49 (m, 1H), 5.09 (dd, 1H), 4.64 (s, 1H), 4.50-4.61 (m, 1H), 4.33-4.44 (m, 3H), 4.11-4.24 (m, 1.0), 3.82-3.95 (m, 3H), 3.36-3.55 (m, 2H), 2.84-2.94 (m, 1H), 2.25-2.69 (m, 4H), 1.68-2.24 (m, 4H), 1.15-1.68 (m, 23H), 0.81-1.15 (m, 3H). MS m/z 756.0 (M$^+$+1)

Example 3-22

Compound AR00312026

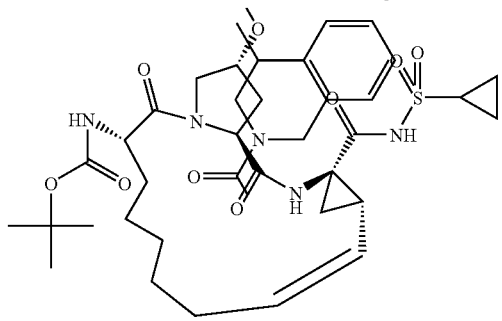

(1S,4R,6S,14S,18R)-4-Methyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00312026) was synthesized according to the procedures described in Examples 1-2 and 3-1, except that 4-methyl-1,2,3,4-tetrahydro-isoquinoline was used to replace 1,2,3,4-tetrahydro-isoquinoline in Step 4 of Example 1-2. $^1$H NMR (400 MHz, CD$_3$OD) δ 7.76 (s, 1H), 6.98-7.24 (m, 3H), 5.67 (dd, 1H), 5.2-5.51 (m, 1H), 5.04-5.15 (dd, 1H), 4.28-4.63 (m, 5H), 4.10-4.24 (m, 1H), 3.81-3.96 (m, 3H), 3.37-3.78 (m, 2H), 2.83-3.06 (m, 2H), 2.54-2.71 (m, 1H), 2.25-2.54 (m, 3H), 1.69-1.94 (m, 3H), 1.16-1.69 (m, 20H), 0.81-1.15 (3H). MS m/z 742.0 (M$^+$+1)

Example 3-23

Compound AR00314635

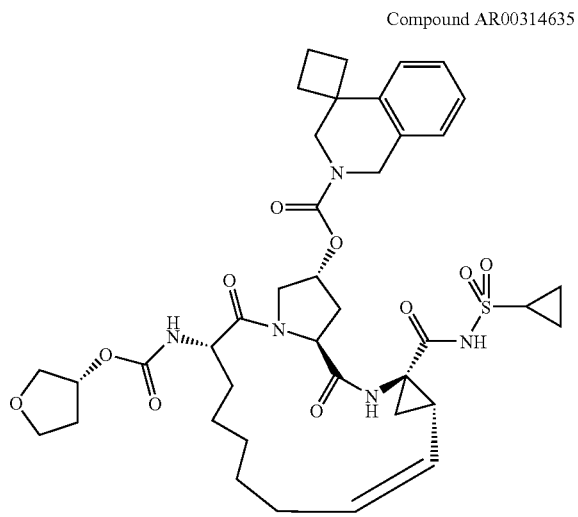

(1S,4R,6S,14S,18R)-4,4-Spirocyclobutyl-3,4-dihydro-1H-isoquinoline-2-carboxylic acid 4-cyclopropanesulfonylaminocarbonyl-2,15-dioxo-14-(tetrahydro-furan-3-yloxycarbonylamino)-3,16-diaza-tricyclo[14.3.0.0$^{4,6}$]nonadec-7-en-18-yl ester (Compound AR00314635) was synthesized according to the procedures described in Examples 1-2, 2-1 and 3-1, except that 4,4-spirocyclobutyl-1,2,3,4-tetrahydro-isoquinoline was used to replace 1,2,3,4-tetrahydro-isoquinoline in Step 4 of Example 1-2, and tetrahydro-furan-3R-ol was used to replace cyclopentanol in Step 2 of Example 2-1 to form the chloroformate reagent. $^1$H NMR (500 MHz, CD$_2$Cl$_2$) δ 10.24-10.29 (s, 1H), 7.49-7.55 (m, 1H), 7.24 (dd, 1H), 7.14 (dd, 1H), 7.04 (dd, 1H), 6.81 (d 1H), 5.71 (dd, 1H), 4.95 (dd, 1H), 4.90 (bs, 1H), 4.48-4.59 (m, 3H), 4.17-4.30 (m, 2H), 3.51-3.74 (m, 3H), 3.51-3.72 (6H), 2.80-2.86 (m, 1H), 2.36-2.54 (m, 3H), 2.10-2.33 (m, 4H), 1.80-2.10 (m, 6H), 1.24-1.80 (m, 7H), 0.65-1.24 (m, 10H). MS m/z 741.2 (M$^+$+1)

Example 3-24

Compound AR00314654

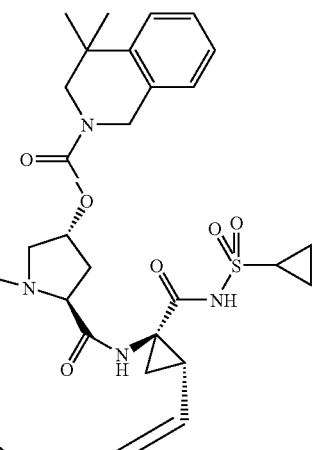

(1S,4R,6S,14S,18R)-4,4-Dimethyl-3,4-dihydro-1H-isoquinoline-2-carboxylic acid 4-cyclopropanesulfonylaminocarbonyl-2,15-dioxo-14-(tetrahydro-furan-3S-yloxycarbonylamino)-3,16-diaza-tricyclo[14.3.0.0$^{4,6}$]nonadec-7-en-18-yl ester (Compound AR00314654) was synthesized according to the procedures described in Examples 1-2, 2-1 and 3-1, except that 4,4-dimethyl-1,2,3,4-tetrahydro-isoquinoline was used to replace 1,2,3,4-tetrahydro-isoquinoline in Step 4 of Example 1-2, and tetrahydro-furan-3S-ol was used to replace cyclopentanol in Step 2 of Example 2-1 to form the chloroformate reagent. $^1$H NMR (500 MHz, CD$_2$Cl$_2$) δ 8.51-8.64 (bs, 1H), 7.26-7.36 (m, 1H), 7.09-7.19 (m, 2H), 6.98-7.08 (m, 1H), 5.70 (dd, 1H), 4.95 (dd, 1H), 4.83 (d, 1H), 4.44-4.72 (m, 3H), 4.17-4.30 (m, 2H), 3.25-3.91 (m, 9H), 2.80-2.86 (m, 1H), 2.35-2.55 (m, 4H), 2.13-2.34 (m, 4H), 1.91-2.07 (m, 2H), 1.80-1.90 (m, 2H), 1.66-1.80 (m, 2H), 1.51-1.63 (m, 2H), 1.30-1.51 (m, 2H), 0.96-1.15 (m, 3H), 0.65-0.95 (m, 9H). MS m/z 770.1 (M$^+$+1)

Example 3-25

Compound AR00314656

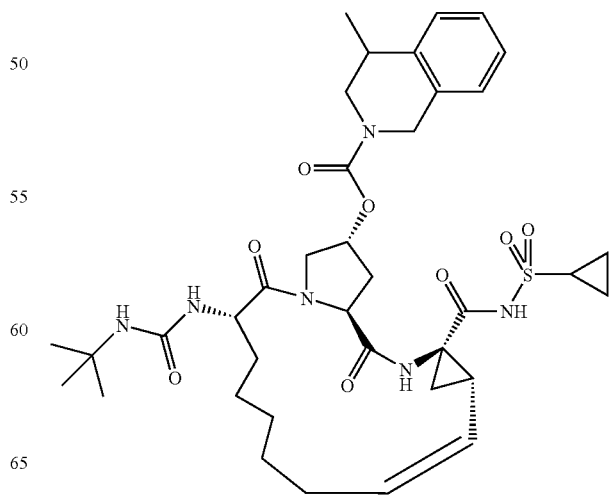

(1S,4R,6S,14S,18R)-4-Methyl-3,4-dihydro-1H-isoquinoline-2-carboxylic acid 14-(3-tert-butyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00314656) was synthesized according to the procedures described in Examples 1-2, 2-24 and 3-1, except that 4-methyl-1,2,3,4-tetrahydro-isoquinoline was used to replace 1,2,3,4-tetrahydro-isoquinoline in Step 4 of Example 1-2, and t-butyl isocyanate was used to replace cyclopentyl isocyanate in Example 2-24. $^1$H NMR (500 MHz, CD$_2$Cl$_2$) δ 7.60-7.72 (m, 1H), 7.06-7.48 (m, 4H), 5.73 (dd, 1H), 5.39-5.48 (m 1H), 5.18-5.27 (bs 1H), 4.98 (dd, 1H), 4.79-4.90 (bs, 1H), 4.30-4.72 (m, 4H), 3.40-3.77 (m, 5H), 2.97 (d, 1H), 2.83-2.90 (m, 1H), 2.37-2.58 (m, 3H), 2.17-2.30 (dt, 1H), 2.22-2.35 (dt, 1H), 1.97-2.07 (m, 1H), 1.82-1.95 (m, 2H), 1.68-1.79 (m, 1H), 1.55-1.66 (m, 2H), 1.05-1.55 (m, 15H), 0.83-0.98 (m, 3H). MS m/z 741.2 (M$^+$+1)

Example 3-26

Compound AR00314719

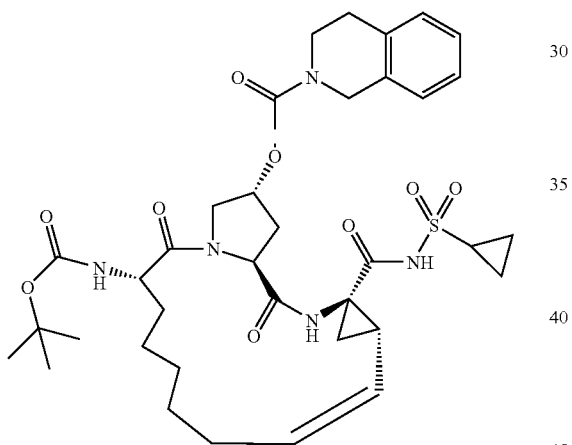

(1S,4R,6S,14S,18R)-3,4-Dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-18-yl ester (Compound AR00314719) was synthesized according to the procedures described in Examples 1-22 and 3-1. MS m/e 630.2 (M$^+$+1−100).

Example 3-27

Compound AR00320001

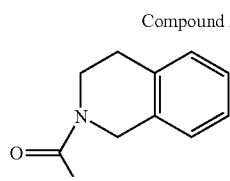

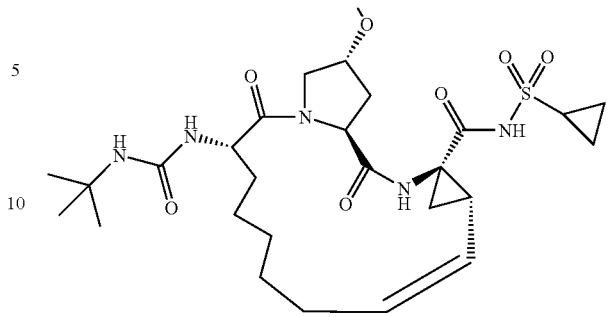

(1S,4R,6S,14S,18R)-3,4-Dihydro-1H-isoquinoline-2-carboxylic acid 14-(3-tert-butyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00320001) was synthesized according to the procedures described in Examples 1-2, 2-24 and 3-1, except that t-butyl isocyanate was used to replace cyclopentyl isocyanate in Example 2-24. MS m/e 725.7 (M−1).

Example 3-28

Compound AR00320073

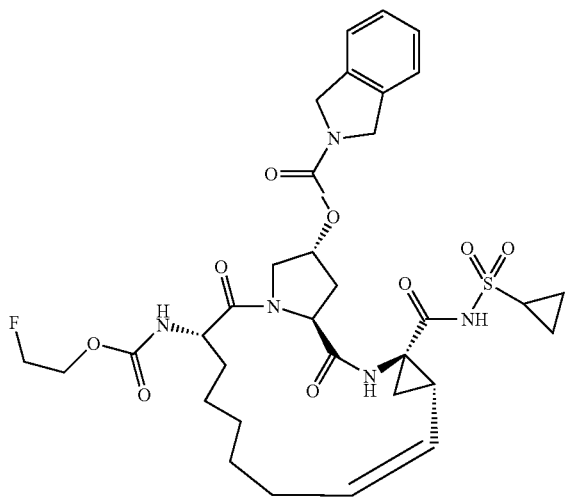

(1S,4R,6S,14S,18R)-1,3-Dihydro-isoindole-2-carboxylic acid 4-cyclopropanesulfonylaminocarbonyl-14-(2-fluoroethoxycarbonylamino)-2,15-dioxo-3,16-diaza-tricyclo[14.3.0.0$^{4,6}$]nonadec-7-en-18-yl ester (Compound AR00320073) was synthesized according to the procedures described in Examples 1-2, 2-1 and 3-1, except that 2,3-dihydro-1H-isoindole was used to replace 1,2,3,4-tetrahydro-isoquinoline in Step 4 of Example 1-2, and 2-fluoroethanol was used to replace cyclopentanol in Step 2 of Example 2-1 to form the chloroformate reagent. MS m/e 704.0 (M$^+$+1).

Example 3-29

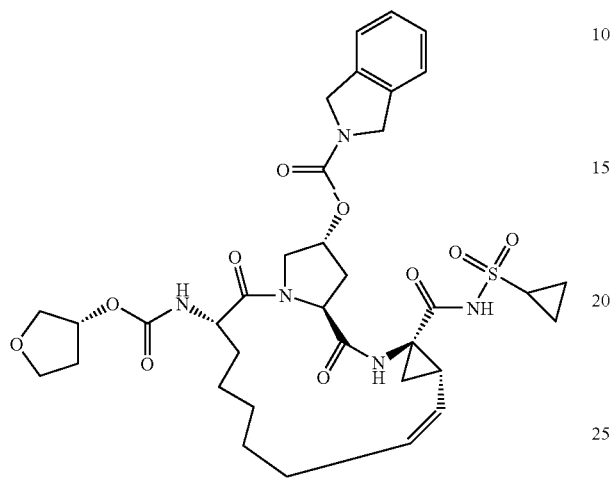

Compound AR00320079

(1S,4R,6S,14S,18R)-1,3-Dihydro-isoindole-2-carboxylic acid 4-cyclopropanesulfonylaminocarbonyl-2,15-dioxo-14-(tetrahydro-furan-3-yloxycarbonylamino)-3,16-diaza-tricyclo[14.3.0.0$^{4,6}$]nonadec-7-en-18-yl ester (Compound AR00320079) was synthesized according to the procedures described in Examples 1-2, 2-1 and 3-1, except that 2,3-dihydro-1H-isoindole was used to replace 1,2,3,4-tetrahydro-isoquinoline in Step 4 of Example 1-2, and tetrahydro-furan-3R-ol was used to replace cyclopentanol in Step 2 of Example 2-1 to form the chloroformate reagent. MS m/e 728.1 (M$^+$+1).

Example 3-30

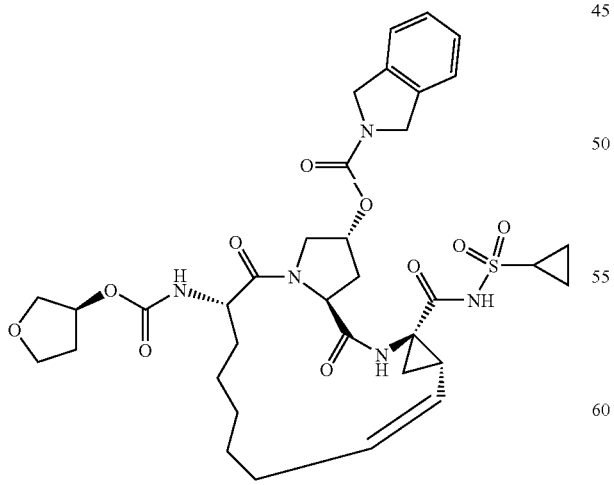

Compound AR00320080

(1S,4R,6S,14S,18R)-1,3-Dihydro-isoindole-2-carboxylic acid 4-cyclopropanesulfonylaminocarbonyl-2,15-dioxo-14-(tetrahydro-furan-3S-yloxycarbonylamino)-3,16-diaza-tricyclo[14.3.0.0$^{4,6}$]nonadec-7-en-18-yl ester (Compound AR00320080) was synthesized according to the procedures described in Examples 1-2, 2-1 and 3-1, except that 2,3-dihydro-1H-isoindole was used to replace 1,2,3,4-tetrahydro-isoquinoline in Step 4 of Example 1-2, and tetrahydro-furan-3S-ol was used to replace cyclopentanol in Step 2 of Example 2-1 to form the chloroformate reagent. MS m/e 728.1 (M$^+$+1).

Example 3-31

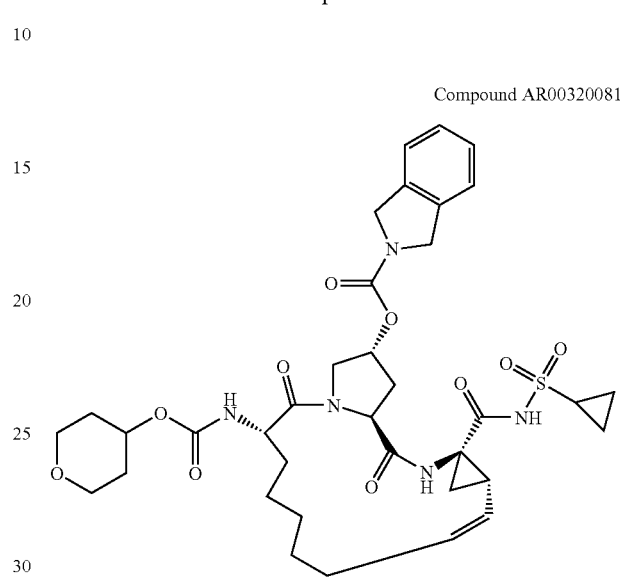

Compound AR00320081

(1S,4R,6S,14S,18R)-1,3-Dihydro-isoindole-2-carboxylic acid 4-cyclopropanesulfonylaminocarbonyl-2,15-dioxo-14-(tetrahydro-pyran-4-yloxycarbonylamino)-3,16-diaza-tricyclo[14.3.0.0$^{4,6}$]nonadec-7-en-18-yl ester (Compound AR00320081) was synthesized according to the procedures described in Examples 1-2, 2-1 and 3-1, except that 2,3-dihydro-1H-isoindole was used to replace 1,2,3,4-tetrahydro-isoquinoline in Step 4 of Example 1-2, and tetrahydro-pyran-4-ol was used to replace cyclopentanol in Step 2 of Example 2-1 to form the chloroformate reagent. MS m/e 742.1 (M$^+$+1).

Example 3-32

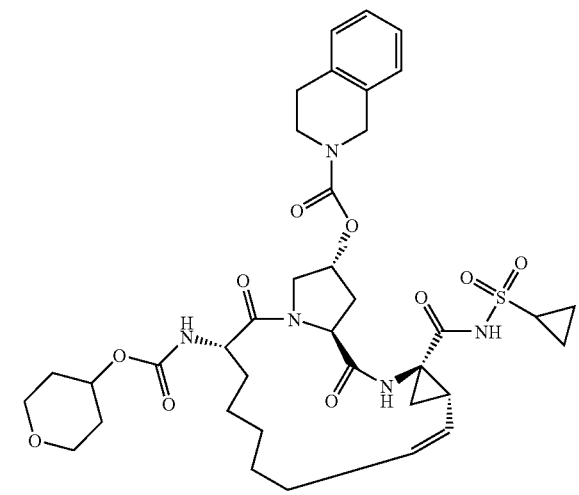

Compound AR00320082

(1S,4R,6S,14S,18R)-3,4-Dihydro-1H-isoquinoline-2-carboxylic acid 4-cyclopropanesulfonylaminocarbonyl-2,15-dioxo-14-(tetrahydro-pyran-4-yloxycarbonylamino)-3,16-diaza-tricyclo[14.3.0.0$^{4,6}$]nonadec-7-en-18-yl ester (Compound AR00320082) was synthesized according to the procedures described in Examples 1-2, 2-1 and 3-1, except that tetrahydro-pyran-4-ol was used to replace cyclopentanol in Step 2 of Example 2-1 to form the chloroformate reagent. MS m/e 756.1 (M$^+$+1).

Example 3-33

Compound AR00320119

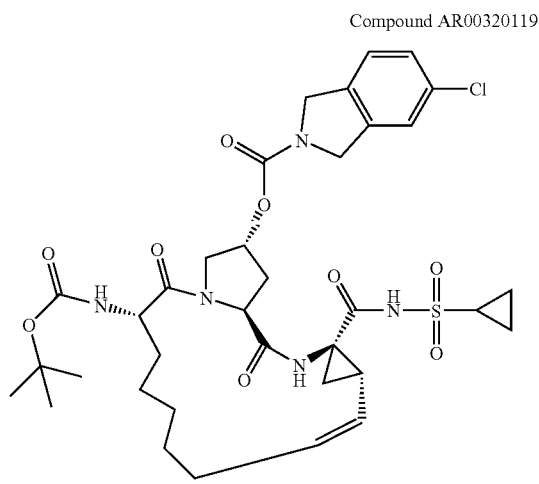

(1S,4R,6S,14S,18R)-5-Chloro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00320119) was synthesized according to the procedures described in Examples 1-2 and 3-1, except that 5-chloro-2,3-dihydro-1H-isoindole was used to replace 1,2,3,4-tetrahydro-isoquinoline in Step 4 of Example 1-2. $^1$H NMR (500 MHz, CD$_3$OD): δ 7.36 (s, 1H), 7.30 (s, 1H), 7.28 (s, 1H), 7.22 (s, 1H), 7.12-7.20 (m, 1H), 6.64 (br s, 1H), 5.72-5.64 (m, 1H), 5.41 (s, 1H), 5.14-5.04 (m, 1H), 4.80-4.62 (m, 2H), 4.61-4.56 (t, 1H), 4.54-4.48 (m, 1H), 4.10 (d, 1H), 3.85 (d, 1H), 2.90 (m, 1H), 2.65 (br s, 1H), 2.54-2.48 (m, 1H), 2.46-2.32 (m, 2H), 1.91-1.72 (m, 2H), 1.64-1.56 (m, 2H), 1.56-1.21 (m, 8H), 1.18 (s, 9H), 1.12-1.05 (m, 1H) 1.00 (m, 1H), 0.94-0.82 (m, 2H). MS m/e 747.9 (M$^+$)

Example 3-34

Compound AR00320120

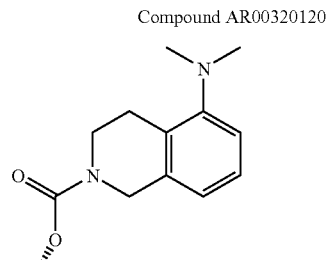

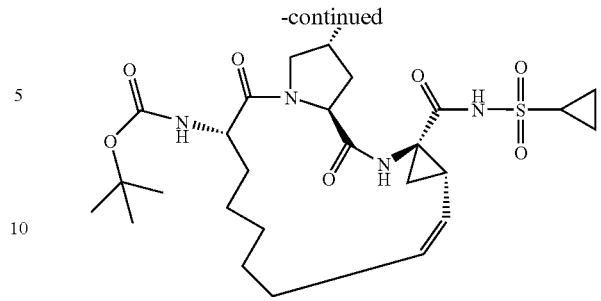

(1S,4R,6S,14S,18R)-5-Dimethylamino-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00320120) was synthesized according to the procedures described in Examples 1-2 and 3-1, except that dimethyl-(1,2,3,4-tetrahydro-isoquinolin-5-yl)-amine (Example 1-25a) was used to replace 1,2,3,4-tetrahydro-isoquinoline in Step 4 of Example 1-2. $^1$H NMR (400 MHz, CDCl$_3$): δ 10.08 (s, 1H), 7.13-7.05 (m, 1H), 6.88-6.81 (d, 1H), 6.77 (d, 1H), 6.68 (d, 1H), 6.61-6.53 (s, 1H), 5.71-5.60 (q, 1H), 5.40 (s, 1H), 5.00-4.88 (m, 2H), 4.55-4.38 (m, 3H), 4.24-4.16 (m, 2H), 3.88-3.77 (d, 1H), 3.64-3.41 (m, 3H), 2.91-2.69 (m, 3H), 2.61 (s, 6H), 2.53-2.41 (m, 2H), 2.40-2.39 (m, 1H), 2.22-2.11 (m, 1H), 1.89-1.72 (m, 1H), 1.61-1.22 (m, 10H), 1.18 (s, 9H), 1.09-0.97 (m, 2H), 0.91-0.76 (m, 2H). MS: 771.1 (M$^+$), 772.1 (M$^+$+1), 773.1 (M$^+$+2)

Example 3-35

Compound AR00320121

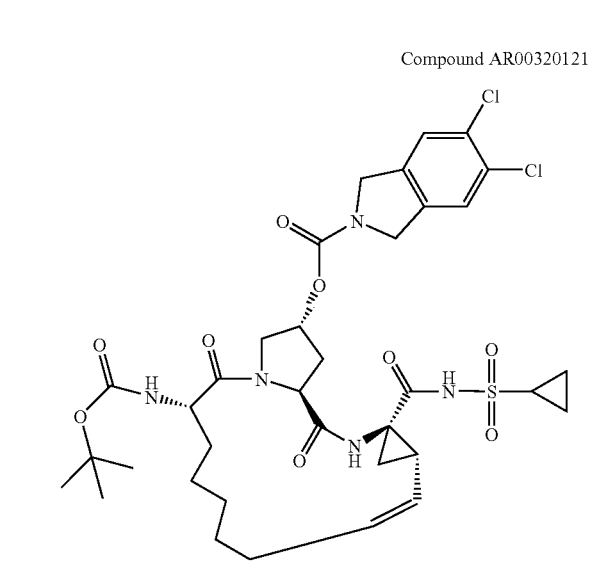

(1S,4R,6S,14S,18R)-5,6-Dichloro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00320121) was synthesized according to the procedures described in Examples 1-2 and 3-1, except that 5,6-Dichloro-2,3-dihydro-1H-isoindole was used to replace 1,2,3,4-tetrahydro-isoquinoline in Step 4 of Example 1-2. $^1$H NMR (500 MHz, CD$_3$OD): δ7.52 (s, 1H), 7.38 (s, 1H), 6.61 (br s, 1H), 5.72-5.65 (q, 1H), 5.40 (s, 1H), 5.08 (t, 1H), 4.78-4.62 (m, 3H), 4.63-4.57 (t, 1H), 4.50 (d, 1H), 4.20 (d, 1H), 3.65 (d, 1H), 2.90 (m, 1H), 2.55 (m, 1H), 2.52-2.45 (m, 1H), 2.46-2.31 (m, 2H), 1.91-1.75 (m, 3H), 1.67-1.60 (m, 1H), 1.58-1.25 (m, 8H), 1.18 (s, 9H), 1.12-1.05 (m, 2H), 1.04-0.81 (m, 2H). MS: m/e 781.9 (M$^+$)

Example 3-36

Compound AR00320220

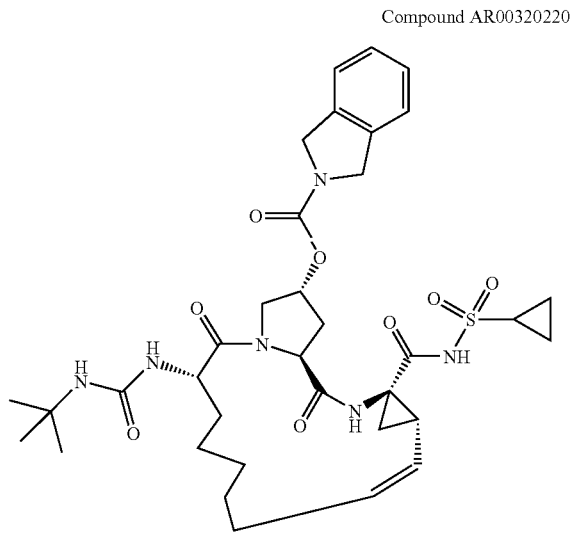

(1S,4R,6S,14S,18R)-1,3-Dihydro-isoindole-2-carboxylic acid 14-(3-tert-butyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00320220) was synthesized according to the procedures described in Examples 1-2, 2-24 and 3-1, except that 2,3-Dihydro-1H-isoindole was used to replace 1,2,3,4-tetrahydro-isoquinoline in Step 4 of Example 1-2, and that t-butyl isocyanate was used to replace cyclopentyl isocyanate in Example 2-24. MS m/e 713.1 (M$^+$+1).

Example 3-37

Compound AR00320222

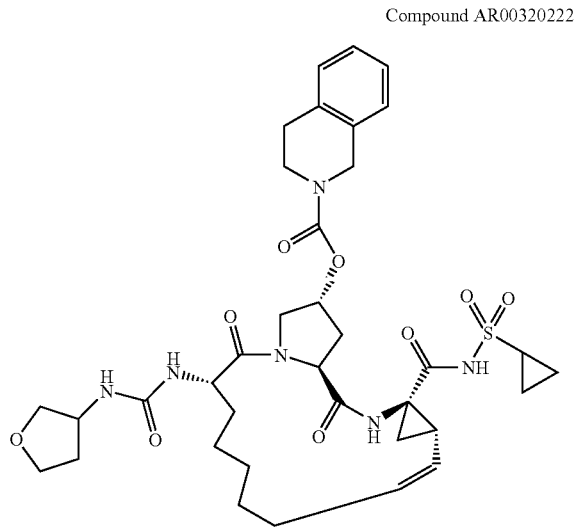

(1S,4R,6S,14S,18R)-3,4-Dihydro-1H-isoquinoline-2-carboxylic acid 4-cyclopropanesulfonylaminocarbonyl-2,15-dioxo-14-[3-(tetrahydro-furan-3-yl)-ureido]-3,16-diaza-tricyclo[14.3.0.0$^{4,6}$]nonadec-7-en-18-yl ester (Compound AR00320222) was synthesized according to the procedures described in Examples 1-2, 2-24 and 3-1, except that 3-Isocyanato-tetrahydro-furan was used to replace cyclopentyl isocyanate in Example 2-24. MS m/e 740.8 (M$^+$+1).

Example 3-38

Compound AR00320403

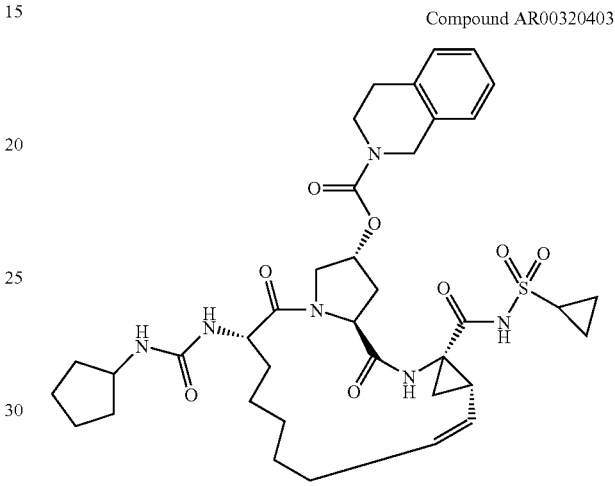

(1S,4R,6S,14S,18R)-3,4-Dihydro-1H-isoquinoline-2-carboxylic acid 14-(3-cyclopentyl-ureido)-4-cyclopropanesulfonylaminocarbonyl-2,15-dioxo-3,16-diaza-tricyclo [14.3.0.0$^{4,6}$]nonadec-7-en-18-yl ester (Compound AR00320403) was synthesized according to the procedures described in Examples 1-2, 2-24 and 3-1. MS m/e 739.2 (M$^+$+1).

Example 3-39

Compound AR00320446

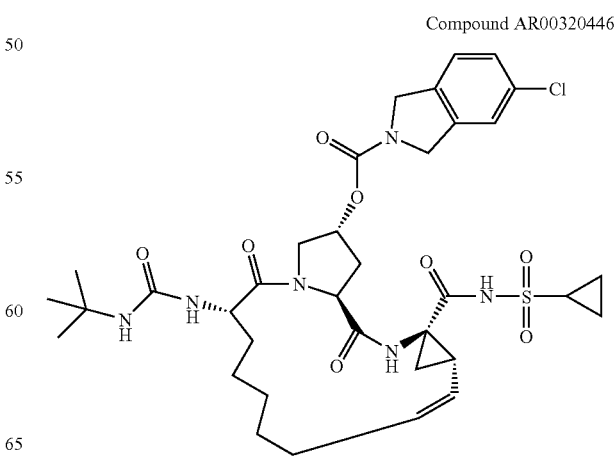

(1S,4R,6S,14S,18R)-5-Chloro-1,3-dihydro-isoindole-2-carboxylic acid 14-(3-tert-butyl-ureido)-4-cyclopropane-sulfonylaminocarbonyl-2,15-dioxo-3,16-diaza-tricyclo[14.3.0.0$^{4,6}$]nonadec-7-en-18-yl ester (Compound AR00320446) was synthesized according to the procedures described in Examples 1-2, 2-24 and 3-1, except that 5-chloro-2,3-Dihydro-1H-isoindole was used to replace 1,2,3,4-tetrahydro-isoquinoline in Step 4 of Example 1-2, and that t-butyl isocyanate was used to replace cyclopentyl isocyanate in Example 2-24. $^1$H NMR (500 MHz, CD$_3$OD): δ7.35 (s, 1H), 7.28 (s, 1H), 7.26 (s, 1H), 7.02 (s, 1H), 7.18 (s, 1H), 5.65-5.72 (q, 1H), 5.45 (s, 1H), 5.06 (t, 1H), 4.74-4.60 (m, 4H), 4.56 (t, 1H), 4.46 (m, 1H), 4.22 (d, 1H), 3.87-3.91 (dd, 1H), 2.86-2.94 (m, 1H), 2.65-2.54 (m, 1H), 2.52-2.45 (m, 1H), 2.42-2.34 (m, 2H), 1.92-1.83 (m, 1H), 1.78-1.70 (m, 2H), 1.62-1.56 (m, 1H), 1.54-3.92 (m, 4H), 1.39-1.23 (m, 7H), 1.12 (s, 9H), 1.02-0.98 (m, 1H), 0.94-0.86 (m, 1H). MS: m/e 747.1 (M$^+$), 749.1 (M$^+$+2)

Example 3-40

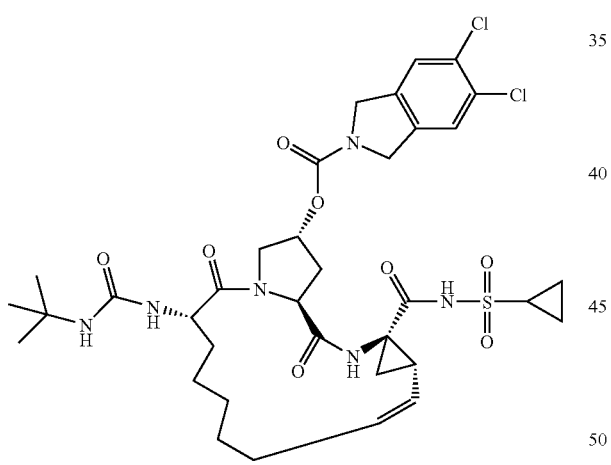

Compound AR00320447

(1S,4R,6S,14S,18R)-5,6-Dichloro-1,3-dihydro-isoindole-2-carboxylic acid 14-(3-tert-butyl-ureido)-4-cyclopropane-sulfonylaminocarbonyl-2,15-dioxo-3,16-diaza-tricyclo[14.3.0.0$^{4,6}$]nonadec-7-en-18-yl ester (Compound AR00320447) was synthesized according to the procedures described in Examples 1-2, 2-24 and 3-1, except that 5,6-dichloro-2,3-Dihydro-1H-isoindole was used to replace 1,2,3,4-tetrahydro-isoquinoline in Step 4 of Example 1-2, and that t-butyl isocyanate was used to replace cyclopentyl isocyanate in Example 2-24. MS: m/e 781.1 (M$^+$). 783.1 (M$^+$+2)

Example 3-41

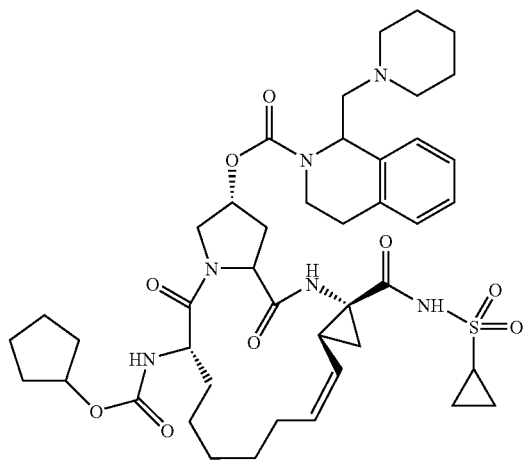

Compound AR00320506

(1S,4R,6S,14S,18R)-1-Piperidin-1-ylmethyl-3,4-dihydro-1H-isoquinoline-2-carboxylic acid 14-cyclopentyloxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00320506) was synthesized according to the procedures described in Examples 1-2, 2-1 and 3-1, except that 1-Piperidin-1-ylmethyl-1,2,3,4-tetrahydro-isoquinoline was used to replace 1,2,3,4-tetrahydro-isoquinoline in Step 4 of Example 1-2. MS (POS ESI) m/z 837.4 (M$^+$).

Example 3-42

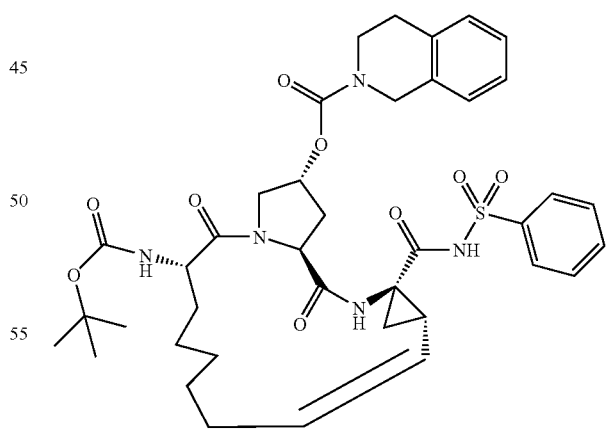

Compound AR00320547

(1S,4R,6S,14S,18R)-3,4-Dihydro-1H-isoquinoline-2-carboxylic acid 4-benzenesulfonylaminocarbonyl-14-tert-butoxycarbonylamino-2,15-dioxo-3,16-diaza-tricyclo[14.3.0.0$^{4,6}$]nonadec-7-en-18-yl ester (Compound AR00320547) was synthesized according to the procedures described in Examples 1-2 and 3-1, except that benzenesulfonamide was used to replace cyclopropylsulfonamide in the coupling step of Example 3-1. MS m/e 762.3 (M−1).

Example 3-43

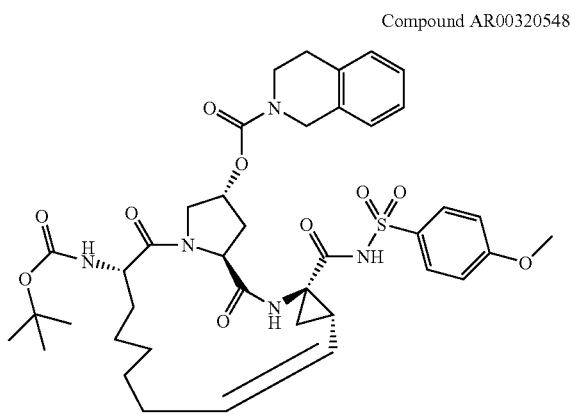

Compound AR00320548

(1S,4R,6S,14S,18R)-3,4-Dihydro-1H-isoquinoline-2-carboxylic acid 14-tert-butoxycarbonylamino-4-(4-methoxy-benzenesulfonylaminocarbonyl)-2,15-dioxo-3,16-diaza-tricyclo[14.3.0.0$^{4,6}$]nonadec-7-en-18-yl ester (Compound AR00320548) was synthesized according to the procedures described in Examples 1-2 and 3-1, except that 4-methoxy-benzenesulfonamide was used to replace cyclopropylsulfonamide in the coupling step of Example 3-1. MS m/e 792.3 (M−1).

Example 3-44

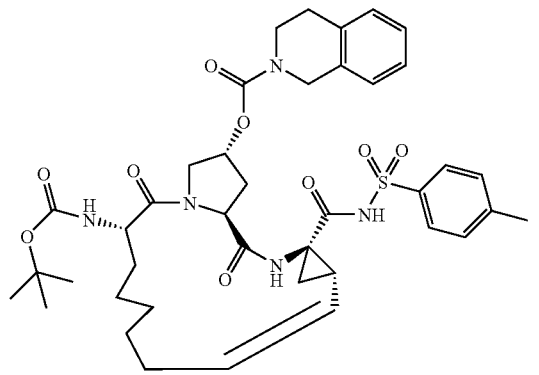

Compound AR00320549

(1S,4R,6S,14S,18R)-3,4-Dihydro-1H-isoquinoline-2-carboxylic acid 14-tert-butoxycarbonylamino-2,15-dioxo-4-(toluene-4-sulfonylaminocarbonyl)-3,16-diaza-tricyclo [14.3.0.0$^{4,6}$]nonadec-7-en-18-yl ester (Compound AR00320549) was synthesized according to the procedures described in Examples 1-2 and 3-1, except that 4-methyl-benzenesulfonamide was used to replace cyclopropylsulfonamide in the coupling step of Example 3-1. MS m/e 776.3 (M$^+$+1).

Example 3-45

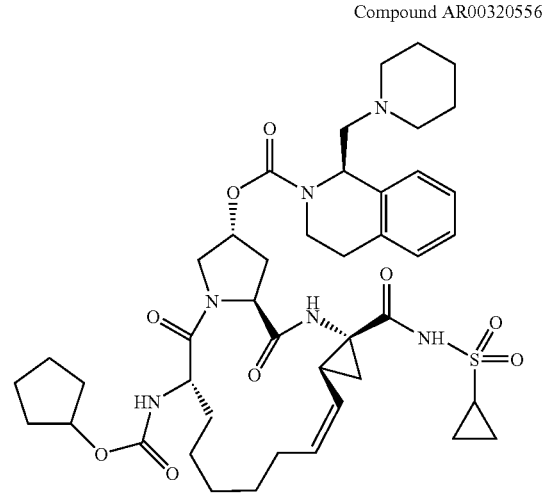

Compound AR00320556

(1S,4R,6S,14S,18R)-1-Piperidin-1R-ylmethyl-3,4-dihydro-1H-isoquinoline-2-carboxylic acid 14-cyclopentyloxycarbonylamino-4-cyclopropanesulfonylaminocarbonyl-2, 15-dioxo-3,16-diaza-tricyclo[14.3.0.0$^{4,6}$]nonadec-7-en-18-yl ester (Compound AR00320556) was synthesized according to the procedures described in Examples 1-2, 2-1 and 3-1, except that 1-Piperidin-1R-ylmethyl-1,2,3,4-tetrahydro-isoquinoline was used to replace 1,2,3,4-tetrahydro-isoquinoline in Step 4 of Example 1-2. $^1$H NMR (500 MHz, CD$_3$OD) δ 8.99 (br s, 1H), 7.34-7.13 (m, 6H), 5.75-5.65 (m, 2H), 5.44 (br s, 1H), 5.06 (t, 1H), 4.60 (t, 1H), 4.51 (d, 1H), 4.44-4.16 (m, 2H), 4.12-3.97 (m, 2H), 3.86 (d, 1H), 3.75-3.38 (m, 2H), 3.07 (t, 2H), 2.96-2.86 (m, 1H), 2.78 (d, 1H), 2.66 (br s, 1H), 2.56-2.26 (m, 3H), 2.06 (d, 1H), 1.99-1.66 (m, 10H), 1.65-1.21 (m, 18H), 1.15-0.95 (m, 3H); MS (POS ESI) m/z 837.4 (M$^+$).

Example 3-46

Compound AR00320557

(1S,4R,6S,14S,18R)-1-Piperidin-1S-ylmethyl-3,4-dihydro-1H-isoquinoline-2-carboxylic acid 14-cyclopentyloxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00320557) was synthesized according to the procedures described in Examples 1-2, 2-1 and 3-1, except that 1-Piperidin-1S-ylmethyl-1,2,3,4-tetrahydro-isoquinoline was used to replace 1,2,3,4-tetrahydro-isoquinoline in Step 4 of Example 1-2. $^1$H NMR (500 MHz, CD$_3$OD) δ 7.32-7.14 (m, 6H), 6.87 (br s, 1H), 5.72-5.60 (m, 2H), 5.47-5.39 (m, 1H), 5.11 (br s, 1H), 4.58 (t, 1H) 4.53-3.86 (m, 8H), 3.67-3.40 (m, 2H), 3.08-2.85 (m, 1H), 2.78 (d, 1H), 2.65-2.24 (m, 4H), 2.10-1.22 (m, 27H), 1.19 (dt, 1H), 1.10-1.02 (m, 2H), 1.01-0.93 (m, 1H), 0.89 (q, 1H); MS (POS ESI) m/z 837.4 (M$^+$).

Example 3-47

Compound AR00320574

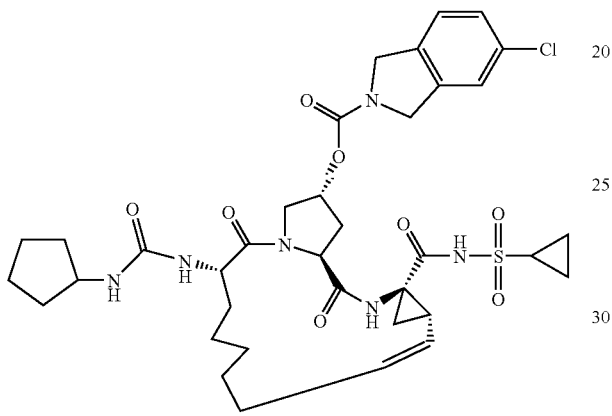

(1S,4R,6S,14S,18R)-5-Chloro-1,3-dihydro-isoindole-2-carboxylic acid 14-(3-cyclopentyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00320574) was synthesized according to the procedures described in Examples 1-2, 2-24 and 3-1, except that 5-chloro-2,3-Dihydro-1H-isoindole was used to replace 1,2,3,4-tetrahydro-isoquinoline in Step 4 of Example 1-2. MS: m/e 759.1 (M$^+$), 761.1 (M$^+$+2)

Example 3-48

Compound AR00320575

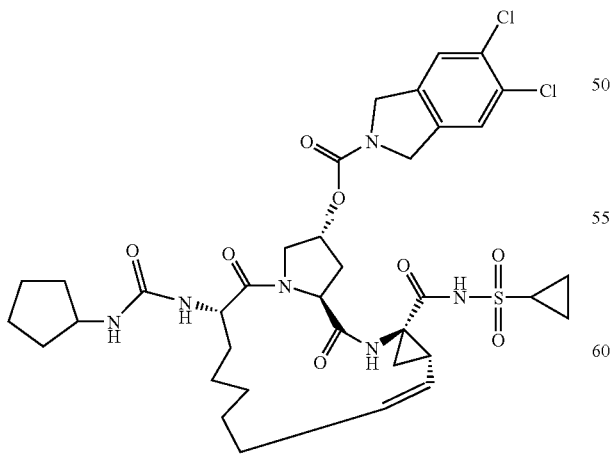

(1S,4R,6S,14S,18R)-5,6-Dichloro-1,3-dihydro-isoindole-2-carboxylic acid 14-(3-cyclopentyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00320575) was synthesized according to the procedures described in Examples 1-2, 2-24 and 3-1, except that 5,6-dichloro-2,3-Dihydro-1H-isoindole was used to replace 1,2,3,4-tetrahydro-isoquinoline in Step 4 of Example 1-2. MS: m/e 793.1 (M$^+$)

Example 3-49

Compound AR00320578

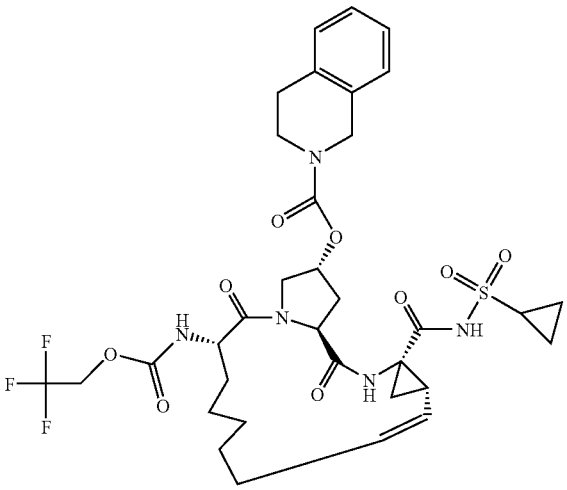

(1S,4R,6S,14S,18R)-3,4-Dihydro-1H-isoquinoline-2-carboxylic acid 4-cyclopropanesulfonylaminocarbonyl-2,15-dioxo-14-(2,2,2-trifluoro-ethoxycarbonylamino)-3,16-diaza-tricyclo[14.3.0.0$^{4,6}$]nonadec-7-en-18-yl ester (Compound AR00320578) was synthesized according to the procedures described in Examples 1-2, 2-1 and 3-1, except that 2,2,2-trifluoro-ethanol was used to replace cyclopentanol in Step 2 of Example 2-1 to form the chloroformate reagent. MS m/e 754.0 (M$^+$+1).

Example 3-50

Compound AR00320579

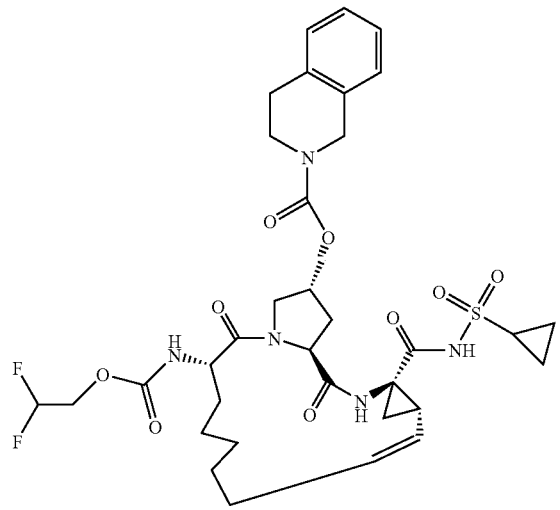

(1S,4R,6S,14S,18R)-3,4-Dihydro-1H-isoquinoline-2-carboxylic acid 4-cyclopropanesulfonylaminocarbonyl-14-(2,2-difluoro-ethoxycarbonylamino)-2,15-dioxo-3,16-diaza-tricyclo[14.3.0.0$^{4,6}$]nonadec-7-en-18-yl ester (Compound AR00320579) was synthesized according to the procedures described in Examples 1-2, 2-1 and 3-1, except that 2,2-Difluoro-ethanol was used to replace cyclopentanol in Step 2 of Example 2-1 to form the chloroformate reagent. MS m/e 736.0 (M$^+$+1).

Example 3-51

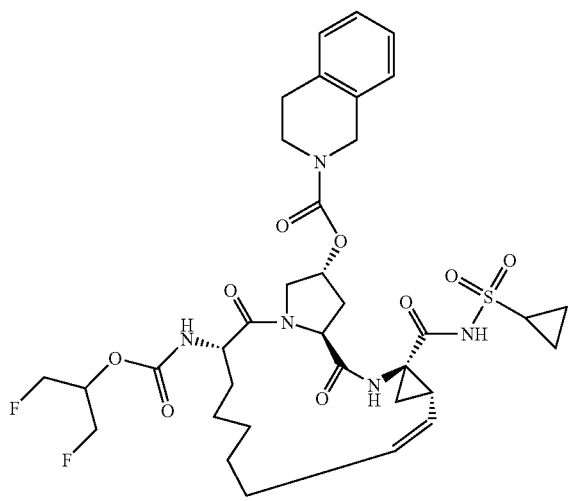

Compound AR00320580

(1S,4R,6S,14S,18R)-3,4-Dihydro-1H-isoquinoline-2-carboxylic acid 4-cyclopropanesulfonylaminocarbonyl-14-(2-fluoro-1-fluoromethyl-ethoxycarbonylamino)-2,15-dioxo-3,16-diaza-tricyclo[14.3.0.0$^{4,6}$]nonadec-7-en-18-yl ester (Compound AR00320580) was synthesized according to the procedures described in Examples 1-2, 2-1 and 3-1, except that 1,3-Difluoro-propan-2-ol was used to replace cyclopentanol in Step 2 of Example 2-1 to form the chloroformate reagent. MS m/e 750.1 (M$^+$+1).

Example 3-52

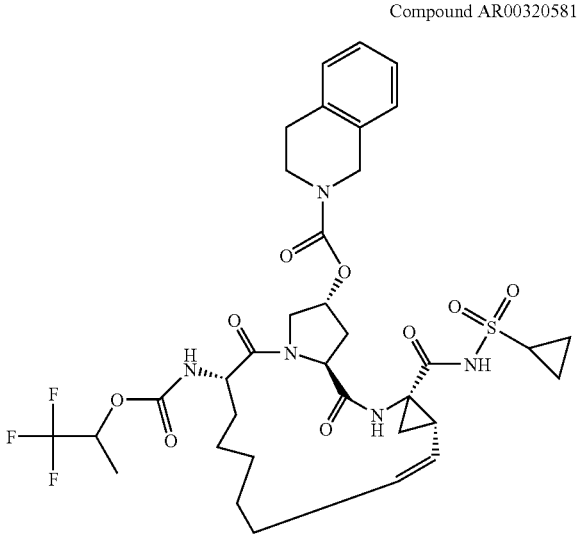

Compound AR00320581

(1S,4R,6S,14S,18R)-3,4-Dihydro-1H-isoquinoline-2-carboxylic acid 4-cyclopropanesulfonylaminocarbonyl-2,15-dioxo-14-(2,2,2-trifluoro-1-methyl-ethoxycarbonylamino)-3,16-diaza-tricyclo[14.3.0.0$^{4,6}$]nonadec-7-en-18-yl ester (Compound AR00320581) was synthesized according to the procedures described in Examples 1-2, 2-1 and 3-1, except that 1,1,1-Trifluoro-propan-2-ol was used to replace cyclopentanol in Step 2 of Example 2-1 to form the chloroformate reagent. MS m/e 768.1 (M$^+$+1).

Example 3-53

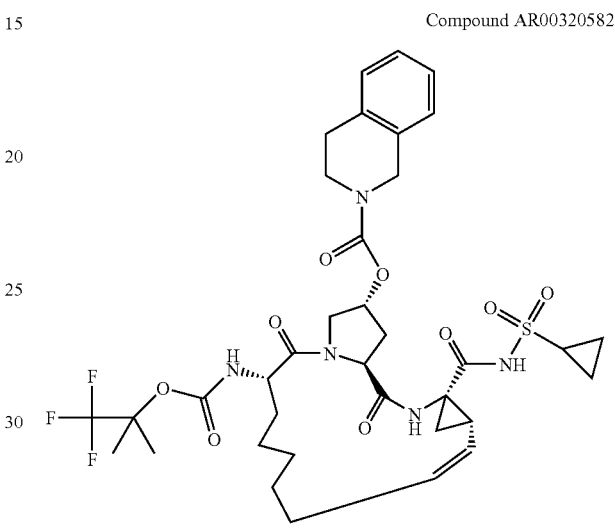

Compound AR00320582

(1S,4R,6S,14S,18R)-3,4-Dihydro-1H-isoquinoline-2-carboxylic acid 4-cyclopropanesulfonylaminocarbonyl-2,15-dioxo-14-(2,2,2-trifluoro-1,1-dimethyl-ethoxycarbonylamino)-3,16-diaza-tricyclo[14.3.0.0$^{4,6}$]nonadec-7-en-18-yl ester (Compound AR00320582) was synthesized according to the procedures described in Examples 1-2, 2-1 and 3-1, except that 1,1,1-Trifluoro-2-methyl-propan-2-ol was used to replace cyclopentanol in Step 2 of Example 2-1 to form the chloroformate reagent. MS m/e 782.1 (M$^+$+1).

Example 3-54

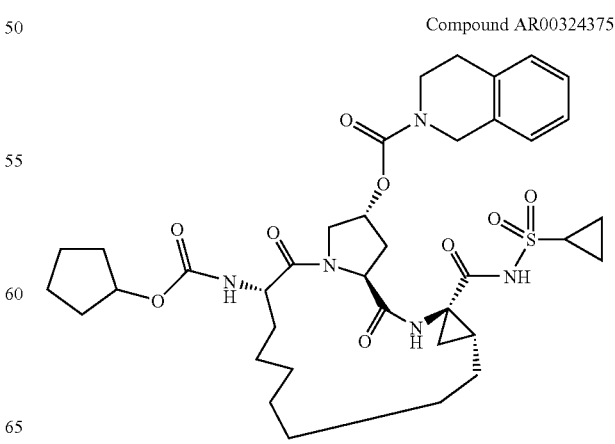

Compound AR00324375

(1S,4R,6S,14S,18R)-3,4-Dihydro-1H-isoquinoline-2-carboxylic acid 14-cyclopentyloxycarbonylamino-4-cyclopropanesulfonylaminocarbonyl-2,15-dioxo-3,16-diaza-tricyclo[14.3.0.0^{4,6}]nonadec-18-yl ester (Compound AR00324375) was synthesized according to the procedures described in Examples 1-22, 2-1 and 3-1. MS m/e 740.5 (M$^+$+1).

Example 3-55

Compound AR00334191

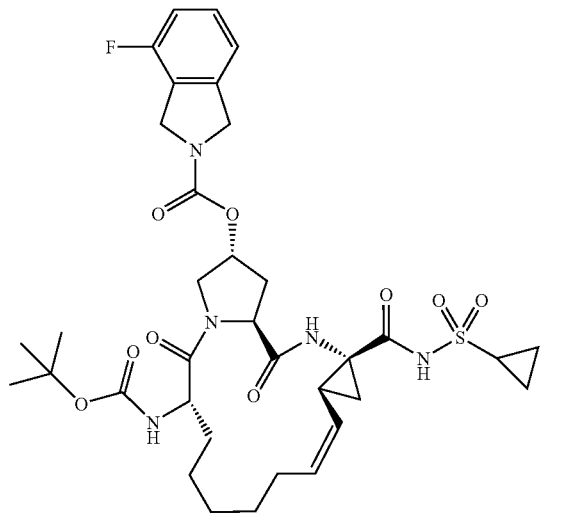

(1S,4R,6S,14S,18R)-4-Fluoro-1,3-dihydro-isoindole-2-carboxylic acid 14-tert-butoxycarbonylamino-4-cyclopropanesulfonylaminocarbonyl-2,15-dioxo-3,16-diaza-tricyclo [14.3.0.0$^{4,6}$]nonadec-7-en-18-yl ester (Compound AR00334191) was synthesized according to the procedures described in Examples 1-2 and 3-1, except that in Step 4 of Example 1-2, 4-Fluoro-2,3-dihydro-1H-isoindole was used in substitution of 1,2,3,4-Tetrahydro-isoquinoline. $^1$H NMR (500 MHz, d$_6$-acetone) δ 10.70 (br s, 1H), 8.34 (d, 1H), 7.39-7.33 (m, 1H), 7.20 (d, 1H), 7.10-7.02 (m, 2H), 6.13 (d, 1H), 5.70 (q, 1H), 5.44 (br s, 1H), 4.99 (t, 1H), 4.78-4.59 (m, 5H), 4.18-4.08 (m, 1H), 3.88-3.81 (m, 1H), 2.86-2.78 (m, 3H), 2.71-2.60 (m, 1H), 2.52-2.35 (m, 3H), 1.92-1.81 (m, 2H), 1.75 (t, 1H), 1.61-1.14 (m, 17H), 1.04-0.95 (m, 2H); −APCI MS m/z 730.4 (M−1).

Example 3-55a 4-Fluoro-2,3-dihydro-1H-isoindole used in Example 3-55 was prepared in the following two steps Step 1:

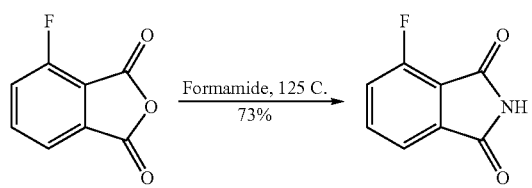

The best result occurs when the starting material is run 0.5 M in formamide and heated to 125° C. for 1 to 5 h depending on scale. Starting material is not soluble in formamide until the temperature is >60° C. Upon completion of reaction as monitored by LC/MS (apcineg), the heat is removed and 3 times the volume of the reaction of water is added. Next, the reaction is allowed to warm to room temperature and stirred until a pale yellow precipitate has formed. The yellow solid product is filtered off and washed with water before drying overnight to give yields between 70-77%.

Step 2:

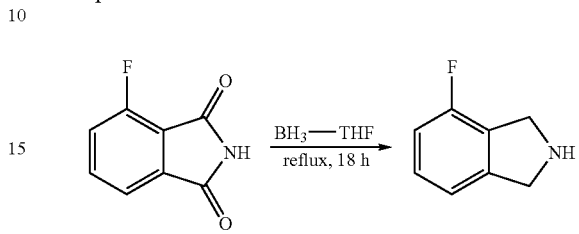

To the starting material in a round bottom flask was added 4 equivalents of 1 M BH$_3$-THF drop wise using an addition funnel to form a golden solution which upon heating and stirring turned copper in color. The reaction was then heated at reflux for 18 h.

The reaction is then cooled to room temperature (rt) and then to 0° C. in an ice bath. 4 equivalents of MeOH are added drop wise and the ice bath removed so quenched reaction can warm to rt. Reaction color turns dark during this warming process. Next, 6 N HCl was added drop wise at rt until pH paper showed reaction to be acidic and the reaction refluxed (63° C.) for 1 h. The reaction was then cooled to rt. At this point the reaction was concentrated and washed with Et$_2$O (2×) and DCM (2×). The aqueous layer was then brought to pH=11 with NaOH pellets. More water was added and the aqueous layer was extracted with ether (4×). The combined extracts were dried over Na$_2$SO$_4$ and concentrated to give a light tan colored oil product, which was used directly. Mass recovery is always slightly higher than theoretical, but material is used crude like this to give >80% yield in the next step.

Example 3-56

Compound AR00333833

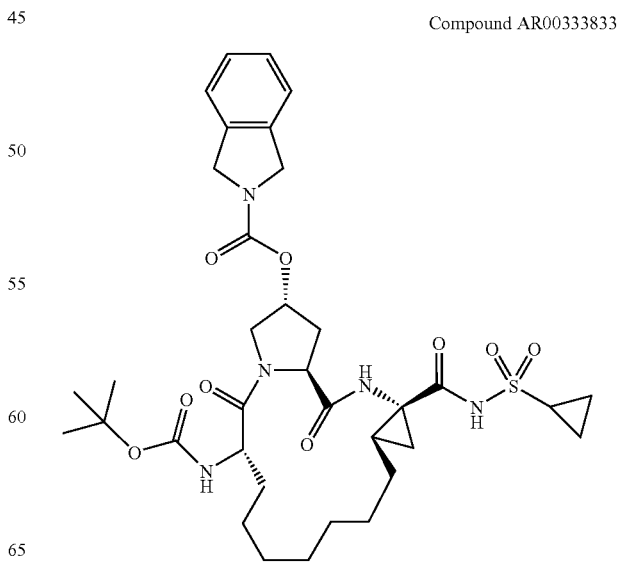

(1S,4R,6S,14S,18R)-1,3-Dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-18-yl ester (Compound AR00333833) was synthesized according to Examples 1-2 and 3-1, except that in the analogous Example 1-2 steps, 2,3-Dihydro-1H-isoindole was used in Step 4 instead, and the ring-closing metathesis product 10 from step 3 of Example 1-2 was further reduced with H$_2$/Rh—Al$_2$O$_3$ before the next coupling step according to a literature procedure (WO 0059929, p.p. 76-77). $^1$H NMR (400 MHz, CD$_3$SOCD$_3$) δ 11.11 (s, 1H), 8.89 (s, 1H), 7.16-7.29 (m, 4H), 6.95 (d, 1H), 5.25 (bs, 1H), 4.50-4.60 (bs, 4H), 4.40 (dd, 1H), 4.23 (d, 1H), 3.93 (m, 1H), 3.68 (d, 1H), 2.92 (m, 1H), 2.32 (dd, 1H), 2.11 (m. 1H), 1.40-1.68 (m, 2H), 0.92-1.40 (m, 19H). MS m/z 717.0 (M+1).

-continued

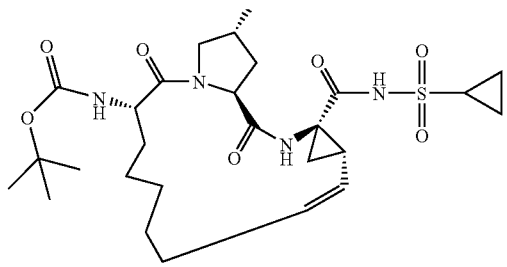

Example 3-57

Compound AR00334286

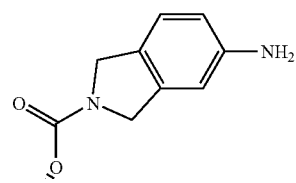

(1S,4R,6S,14S,18R)-5-Amino-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334286) was synthesized according to the procedures shown in the following scheme.

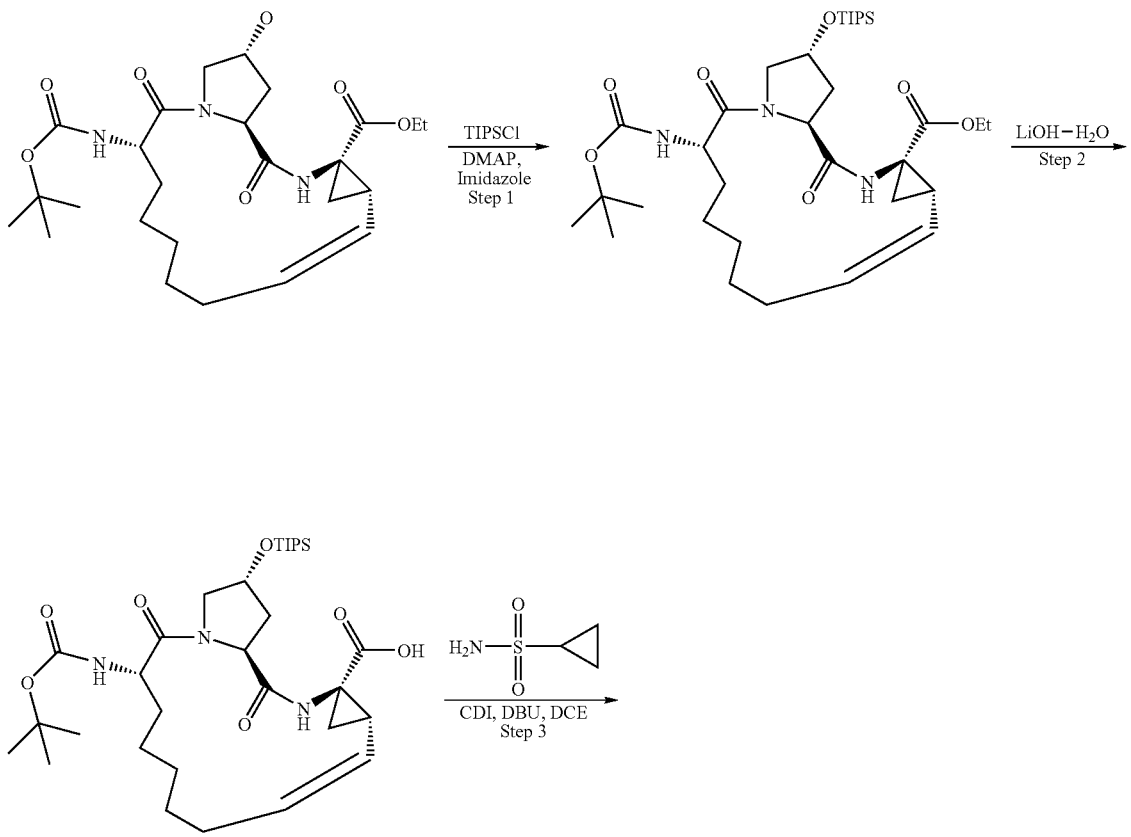

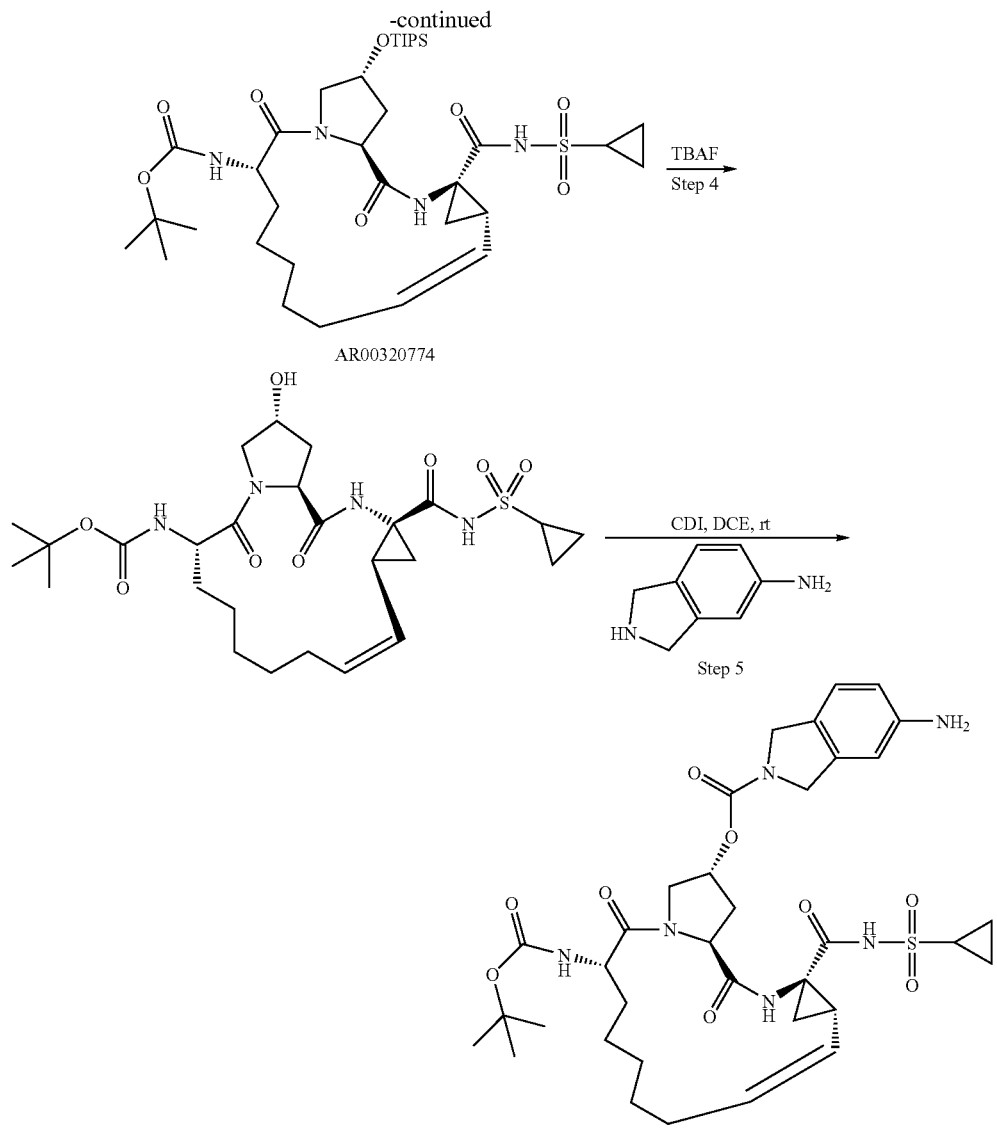

Step 1. Synthesis of (1S,4R,6S,14S,18R)-14-tert-Butoxycarbonylamino-2,15-dioxo-18-triisopropylsilanyloxy-3,16-diaza-tricyclo[14.3.0.0$^{4,6}$]nonadec-7-ene-4-carboxylic acid ethyl ester. To a solution of the free hydroxymacrocycle intermediate (compound 10 of Example 1-2, 5.0 g, 10.1 mmol) in DriSolve DCM (30 ml) was added imidazole (827 mg, 1.2 equiv) and TIPSCl (2.15 g, 1.1 equiv). The reaction mixture was stirred at RT for 18 h. TLC (5% MeOH-DCM) showed considerable amount of SM still remaining. To this reaction mixture was added more imidazole (410 mg), TIPSCl (1 g) and DMAP (121 mg). After stirring for overnight, reaction mixture showed small amount of SM left. The reaction mixture was washed with water (2×25 ml). The combined aqueous layer was backwashed with DCM (25 ml). The combined organic layers was dried and concentrated to give a light yellowish oil. The crude material was used in the next step without further purification.

Step 2. Synthesis of (1S,4R,6S,14S,18R)-14-tert-Butoxycarbonylamino-2,15-dioxo-18-triisopropylsilanyloxy-3,16-diaza-tricyclo[14.3.0.0$^{4,6}$]nonadec-7-ene-4-carboxylic acid. The ester SM from Step 1 was first dissolved in a mixture of THF (20 ml) and MeOH (20 ml). To this mixture was then added LiOH—H$_2$O (2.1 g, 50 mmol) in water (10 ml) and stirred for 12 h at RT. LCMS showed reaction complete. The reaction mixture was concentrated to almost dryness. The solid residue was then dissolved in 50 mL water, acidified with 2N HCl, and extracted with EtOAc (2×50 ml). The combined organic layers was dried over anhydrous Na$_2$SO$_4$ and concentrated. The crude material was used in the next step without further purification.

Step 3. Synthesis of (1S,4R,6S,14S,18R)-(4-Cyclopropanesulfonylaminocarbonyl-2,15-dioxo-18-triisopropylsilanyloxy-3,16-diaza-tricyclo[14.3.0.0$^{4,6}$]nonadec-7-en-14-yl)-carbamic acid tert-butyl ester. The acid SM from Step 2 above was first dissolved in 25 mL DriSolve1,2-dichloroethane. To this solution was added CDI (2.2 g, 13.8 mmol) in one portion and the reaction was stirred at 50° C. for 3 h. Then cyclopropyl sulfonamide (3.3 g, 27.5 mmol) was added to the reaction, followed by DBU (4.2 g, 27.5 mmol), and the reaction was stirred at 50° C. for 4 h. LCMS showed reaction complete. For work-up, the reaction mixture was washed with water (2×50 mL), and the organic layer was dried (anhyd. Na$_2$SO$_4$) and concentrated. The crude material was used in the next step without further purification.

Step 4. Synthesis of (1S,4R,6S,14S,18R)-(4-Cyclopropanesulfonylaminocarbonyl-18-hydroxy-2,15-dioxo-3,16-diaza-tricyclo[14.3.0.0$^{4,6}$]nonadec-7-en-14-yl)-carbamic acid tert-butyl ester. The crude product from Step 3 above was first dissolved in THF (40 mL). To this solution was then added TBAF (3.6 g, 13.7 mmol, 1.5 equiv) and stirred for 2 h at RT. TLC showed reaction complete. The reaction mixture was then concentrated down to dryness, re-dissolved in EtOAc and washed with water. The organic layer was dried (anhyd. Na$_2$SO$_4$) and concentrated. For purification, the crude product was dissolved in DCM (50 mL) and washed with 3N NaOH solution. The aq. layer was neutralized with 2N HCl and extracted with DCM (2×25 mL). The combined organic layers was dried (Na$_2$SO$_4$) and concentrated to give pure white solid (2.4 g, 46%). MS m/z (APCI+) 469.1 (MH$^+$–Boc).

Step 5. Synthesis of (1S,4R,6S,14S,18R)-5-Amino-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334286). To a DCE solution of the product from Step 4 above (19 mg, 33 µmol) was added CDI (7 mg, 1.3 equiv), and the reaction was stirred at RT for overnight. LCMS indicated reaction complete. 2,3-Dihydro-1H-isoindol-5-ylamine (18 mg, 4 equiv) was then added. After 4 h at RT, LCMS showed reaction complete. The reaction mixture was directly loaded onto silica gel and eluted with 1 to 5% methanol/DCM. The pure product was isolated as a white solid. MS m/z (APCI+): 629.2 (MH$^+$–Boc).

Example 3-58

Compound AR00334385

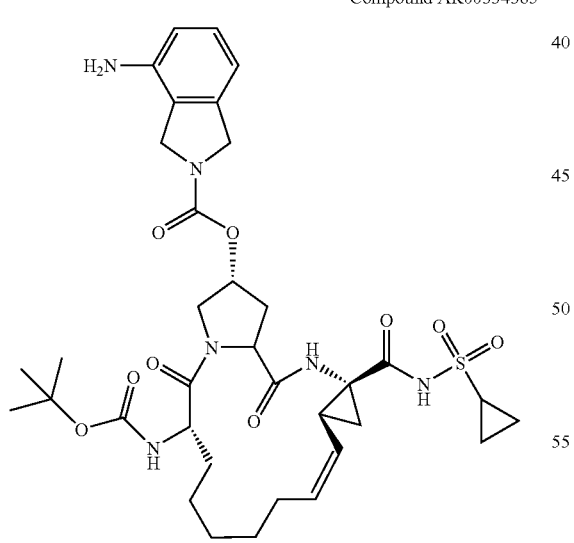

(1S,4R,6S,14S,18R)-4-Amino-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334385) was synthesized by a similar fashion as that described in Example 3-57, substituting 2,3-Dihydro-1H-isoindol-5-ylamine in Step 5 with 2,3-Dihydro-1H-isoindol-4-ylamine instead. Also, the final product purification was carried out on reverse phase column chromatography (eluent=5 to 100% acetonitrile in water), yielding the final product as a beige foamy solid. MS m/z (APCI–): 728.2 (M$^+$).

Example 3-59

Compound AR00340479

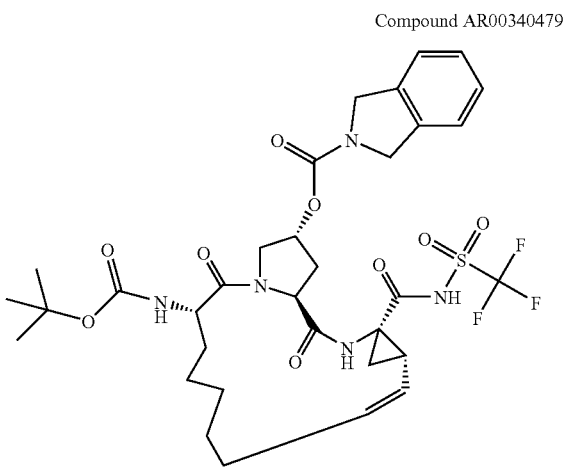

(1S,4R,6S,14S,18R)-1,3-Dihydro-isoindole-2-carboxylic acid 14-tert-butoxycarbonylamino-2,15-dioxo-4-trifluoromethanesulfonylaminocarbonyl-3,16-diaza-tricyclo [14.3.0.0$^{4,6}$]nonadec-7-en-18-yl ester (Compound AR00340479) was synthesized according to the procedures described in Example 3-6, except that trifluoro-methanesulfonamide was used to replace cyclopropanesulfonamide. $^1$H NMR (400 MHz, d$^6$-Acetone): δ 7.98 (brs, 1H), 7.23-7.35 (m, 4H), 6.13 (brd, 1H), 5.70 (q, 1H), 5.44 (brs 1H), 4.98-5.02 (m, 1H), 4.61-4.72 (m, 5H), 4.49 (d, 1H), 4.16-4.18 (m, 1H), 3.87-3.90 (m, 1H), 2.57-2.59 (m, 2H), 2.38-2.51 (m, 2H), 1.82-1.92 (m, 2H), 1.72-1.79 (m, 2H), 1.21-1.59 (m, 8H), 1.21 (s, 9H). MS m/z (APCI–): 741.1 (M$^+$).

Example 3-60

Compound AR00365387

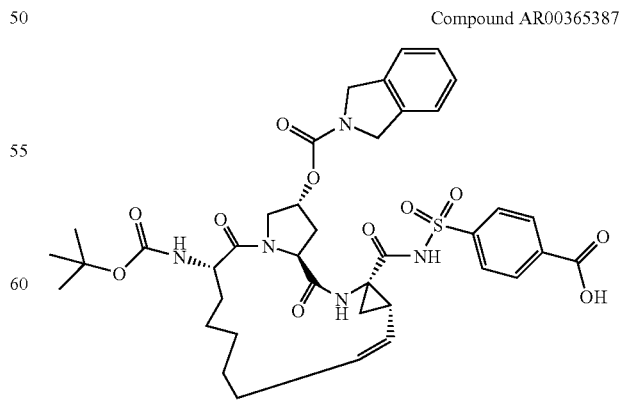

(1S,4R,6S,14S,18R)-1,3-Dihydro-isoindole-2-carboxylic acid 14-tert-butoxycarbonylamino-4-(4-carboxy-benzenesulfonylaminocarbonyl)-2,15-dioxo-3,16-diaza-tricyclo[14.3.0.0$^{4,6}$]nonadec-7-en-18-yl ester (Compound AR00365387) was synthesized according to the procedures described in Example 3-6, except that 4-sulfamoyl-benzoic acid was used to replace cyclopropanesulfonamide. MS m/z (APCI–): 792.3 (M–1).

Example 3-61

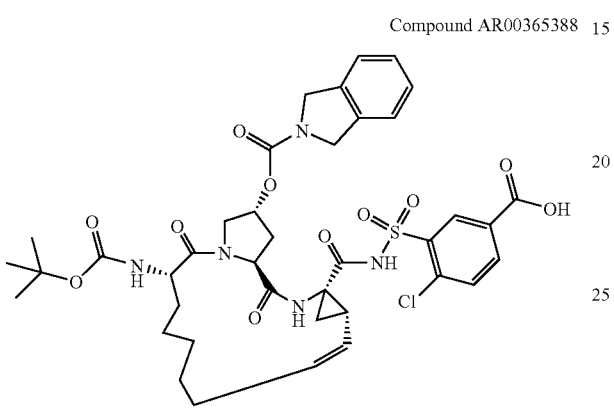

Compound AR00365388

(1S,4R,6S,14S,18R)-1,3-Dihydro-isoindole-2-carboxylic acid 14-tert-butoxycarbonylamino-4-(5-carboxy-2-chloro-benzenesulfonylaminocarbonyl)-2,15-dioxo-3,16-diaza-tricyclo[14.3.0.0$^{4,6}$]nonadec-7-en-18-yl ester (Compound AR00365388) was synthesized according to the procedures described in Example 3-6, except that 4-chloro-3-sulfamoyl-benzoic acid was used to replace cyclopropanesulfonamide. MS m/z (APCI–): 826.2 (M–2).

Example 3-62

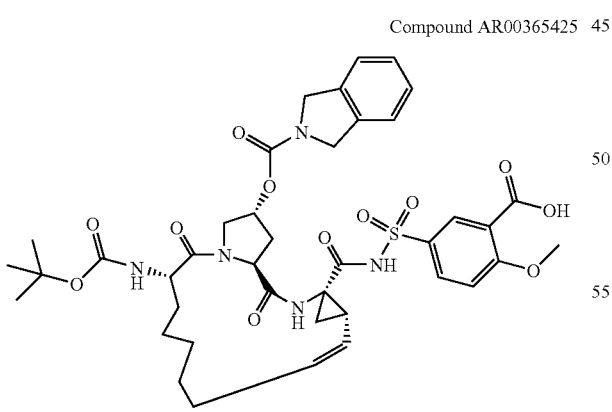

Compound AR00365425

(1S,4R,6S,14S,18R)-1,3-Dihydro-isoindole-2-carboxylic acid 14-tert-butoxycarbonylamino-4-(3-carboxy-4-methoxy-benzenesulfonylaminocarbonyl)-2,15-dioxo-3,16-diaza-tricyclo[14.3.0.0$^{4,6}$]nonadec-7-en-18-yl ester (Compound AR00365425) was synthesized according to the procedures described in Example 3-6, except that 2-methoxy-5-sulfamoyl-benzoic acid was used to replace cyclopropanesulfonamide. MS m/z (APCI–): 822.3 (M–1).

Example 3-63

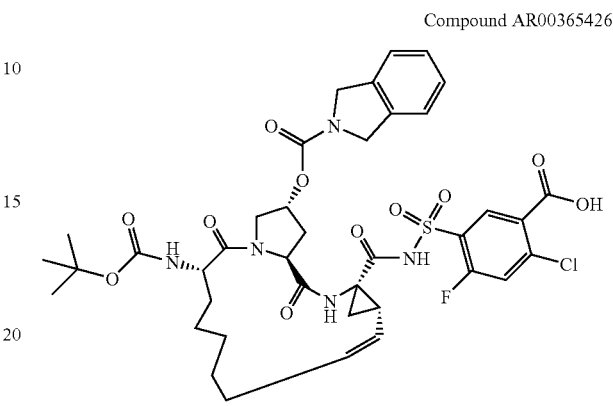

Compound AR00365426

(1S,4R,6S,14S,18R)-1,3-Dihydro-isoindole-2-carboxylic acid 14-tert-butoxycarbonylamino-4-(5-carboxy-4-chloro-2-fluoro-benzenesulfonylaminocarbonyl)-2,15-dioxo-3,16-diaza-tricyclo[14.3.0.0$^{4,6}$]nonadec-7-en-18-yl ester (Compound AR00365426) was synthesized according to the procedures described in Example 3-6, except that 2-chloro-4-fluoro-5-sulfamoyl-benzoic acid was used to replace cyclopropanesulfonamide. MS m/z (APCI–): 844.2 (M–2).

Example 3-64

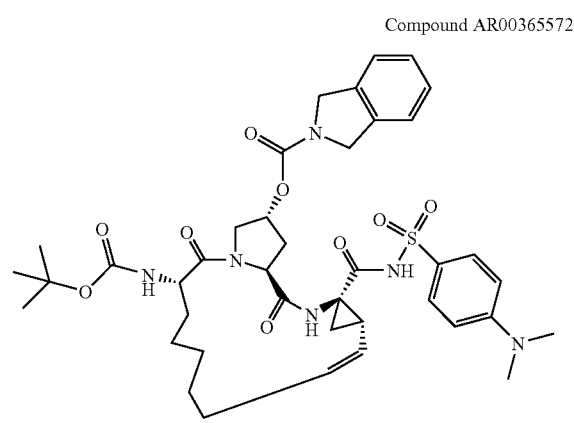

Compound AR00365572

(1S,4R,6S,14S,18R)-1,3-Dihydro-isoindole-2-carboxylic acid 14-tert-butoxycarbonylamino-4-(4-dimethylamino-benzenesulfonylaminocarbonyl)-2,15-dioxo-3,16-diaza-tricyclo[14.3.0.0$^{4,6}$]nonadec-7-en-18-yl ester (Compound AR00365572) was synthesized according to the procedures described in Example 3-6, except that 4-dimethylamino-benzenesulfonamide was used to replace cyclopropanesulfonamide. MS m/z (APCI−): 791.3 (M−1).

Example 3-65

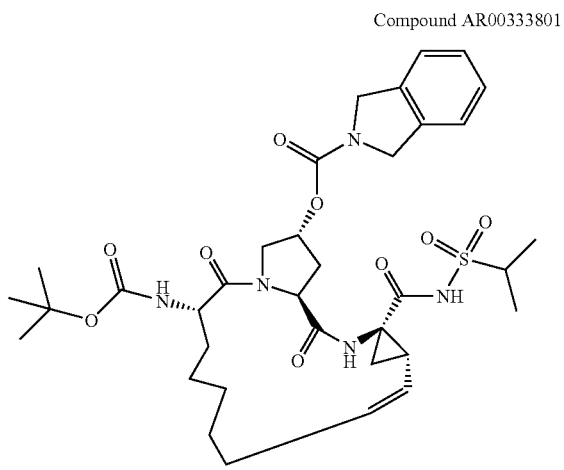

Compound AR00333801

(1S,4R,6S,14S,18R)-1,3-Dihydro-isoindole-2-carboxylic acid 14-tert-butoxycarbonylamino-2,15-dioxo-4-(propane-2-sulfonylaminocarbonyl)-3,16-diaza-tricyclo[14.3.0.0$^{4,6}$]nonadec-7-en-18-yl ester (Compound AR00333801) was synthesized according to the procedures described in Example 3-6, except that propane-2-sulfonic acid amide was used to replace cyclopropanesulfonamide. MS m/z (APCI−): 714.4 (M−1).

Example 3-66

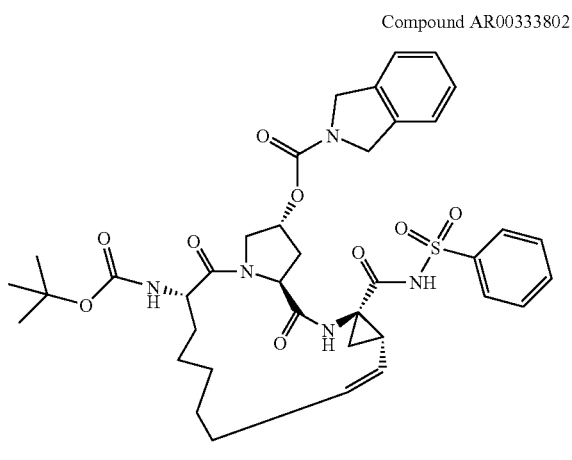

Compound AR00333802

(1S,4R,6S,14S,18R)-1,3-Dihydro-isoindole-2-carboxylic acid 4-benzenesulfonylaminocarbonyl-14-tert-butoxycarbonylamino-2,15-dioxo-3,16-diaza-tricyclo[14.3.0.0$^{4,6}$]nonadec-7-en-18-yl ester (Compound AR00333802) was synthesized according to the procedures described in Example 3-6, except that benzenesulfonamide was used to replace cyclopropanesulfonamide. MS m/z (APCI−): 748.3 (M−1).

Example 3-67

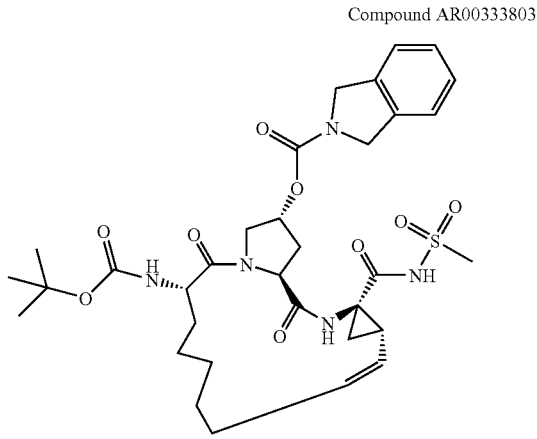

Compound AR00333803

(1S,4R,6S,14S,18R)-1,3-Dihydro-isoindole-2-carboxylic acid 14-tert-butoxycarbonylamino-4-methanesulfonylaminocarbonyl-2,15-dioxo-3,16-diaza-tricyclo[14.3.0.0$^{4,6}$] nonadec-7-en-18-yl ester (Compound AR00333803) was synthesized according to the procedures described in Example 3-6, except that methanesulfonamide was used to replace cyclopropanesulfonamide. MS m/z (APCI−): 686.4 (M−1).

Example 3-68

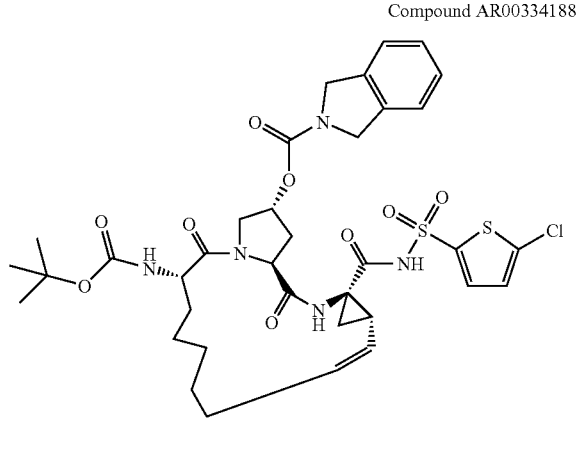

Compound AR00334188

(1S,4R,6S,14S,18R)-1,3-Dihydro-isoindole-2-carboxylic acid 14-tert-butoxycarbonylamino-4-(5-chloro-thiophene-2-sulfonylaminocarbonyl)-2,15-dioxo-3,16-diaza-tricyclo [14.3.0.0$^{4,6}$]nonadec-7-en-18-yl ester (Compound AR00334188) was synthesized according to the procedures described in Example 3-6, except that 5-chloro-thiophene-2- sulfonic acid amide was used to replace cyclopropanesulfonamide. MS m/z (APCI–): 788.3 (M–2).

Example 3-69

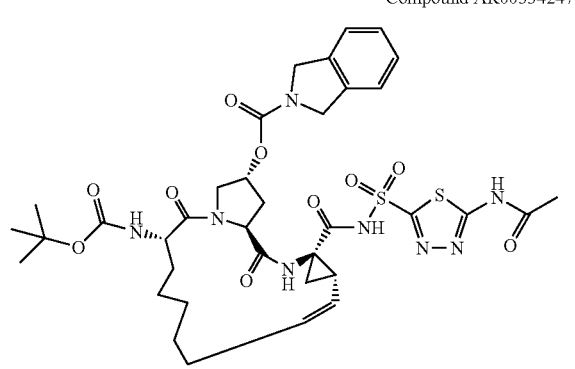

Compound AR00334247

(1S,4R,6S,14S,18R)-1,3-Dihydro-isoindole-2-carboxylic acid 4-(5-acetylamino-[1,3,4]thiadiazole-2-sulfonylaminocarbonyl)-14-tert-butoxycarbonylamino-2,15-dioxo-3,16-diaza-tricyclo[14.3.0.0$^{4,6}$]nonadec-7-en-18-yl ester (Compound AR00334247) was synthesized according to the procedures described in Example 3-6, except that N-(5-Sulfamoyl-[1,3,4]thiadiazol-2-yl)-acetamide was used to replace cyclopropanesulfonamide. $^1$H NMR (400 MHz, d$^6$-Acetone): δ 7.24-7.31 (m, 4H), 5.96 (brd, 1H), 5.42 (brs 1H), 5.28 (m, 1H), 5.15 (m, 1H), 4.68 (m, 6H), 4.49 (m, 1H), 4.14 (m, 2H), 2.60 (m, 1H), 2.25-2.36 (m, 5H), 1.70-2.19 (m, 8H), 1.19-1.48 (m, 4H), 1.30 (s, 9H). MS m/z (APCI–): 813.3 (M–1).

Example 3-70

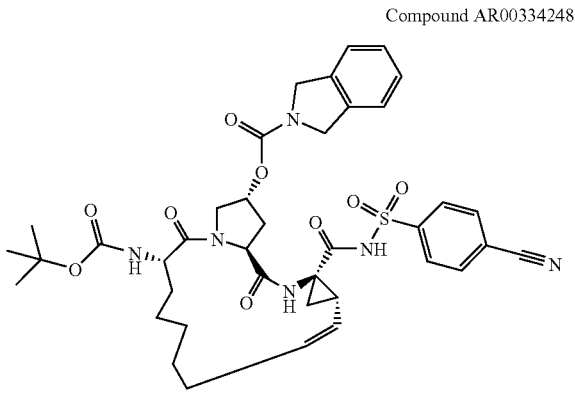

Compound AR00334248

(1S,4R,6S,14S,18R)-1,3-Dihydro-isoindole-2-carboxylic acid 14-tert-butoxycarbonylamino-4-(4-cyano-benzenesulfonylaminocarbonyl)-2,15-dioxo-3,16-diaza-tricyclo [14.3.0.0$^{4,6}$]nonadec-7-en-18-yl ester (Compound AR00334248) was synthesized according to the procedures described in Example 3-6, except that 4-cyano-benzenesulfonamide was used to replace cyclopropanesulfonamide. $^1$H NMR (400 MHz, d$^6$-Acetone): δ 11.32 (brs, 1H), 8.36 (brs, 1H), 8.04-8.15 (m, 4H), 7.22-7.35 (m, 4H), 6.12 (brd, 1H), 5.47 (brs 1H), 5.28 (q, 1H), 4.60-4.72 (m, 5H), 4.48-4.54 (m, 2H), 4.14-4.17 (m, 1H), 3.86-3.90 (m, 1H), 2.37-2.52 (m, 4H), 1.72-1.85 (m, 2H), 1.59-1.62 (m, 1H), 1.20-1.55 (m, 8H), 1.20 (s, 9H). MS m/z (APCI–): 773.3 (M–1).

Example 3-71

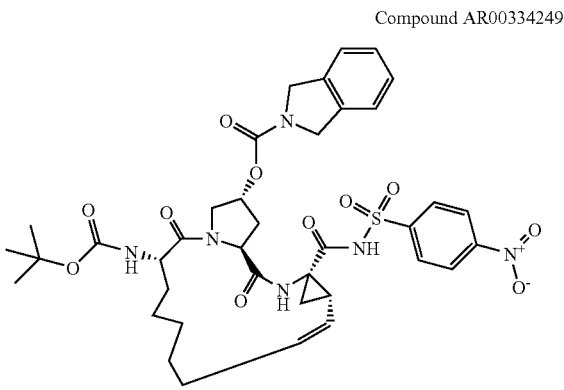

Compound AR00334249

(1S,4R,6S,14S,18R)-1,3-Dihydro-isoindole-2-carboxylic acid 14-tert-butoxycarbonylamino-4-(4-nitro-benzenesulfonylaminocarbonyl)-2,15-dioxo-3,16-diaza-tricyclo [14.3.0.0$^{4,6}$]nonadec-7-en-18-yl ester (Compound AR00334249) was synthesized according to the procedures described in Example 3-6, except that 4-nitro-benzenesulfonamide was used to replace cyclopropanesulfonamide. $^1$H NMR (400 MHz, d$^6$-Acetone): δ 11.39 (brs, 1H), 8.46 (d, 2H), 8.35 (brs, 1H), 8.23 (d, 2H), 7.23-7.36 (m, 4H), 6.11 (brd, 1H), 5.47 (brs 1H), 5.23 (q, 1H), 4.59-4.72 (m, 5H), 4.49-4.54 (m, 2H), 4.15 (m, 1H), 3.86-3.90 (m, 1H), 2.40-2.53 (m, 4H), 1.72-1.85 (m, 2H), 1.59-1.62 (m, 1H), 1.20-1.56 (m, 8H), 1.20 (s, 9H). MS m/z (APCI–): 793.3 (M–1).

Example 3-72

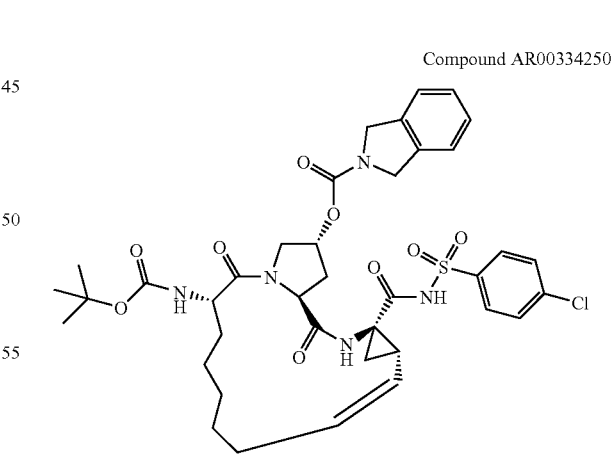

Compound AR00334250

(1S,4R,6S,14S,18R)-1,3-Dihydro-isoindole-2-carboxylic acid 14-tert-butoxycarbonylamino-4-(4-chloro-benzenesulfonylaminocarbonyl)-2,15-dioxo-3,16-diaza-tricyclo [14.3.0.0$^{4,6}$]nonadec-7-en-18-yl ester (Compound AR00334250) was synthesized according to the procedures described in Example 3-6, except that 4-chloro-benzenesulfonamide was used to replace cyclopropanesulfonamide.

$^1$H NMR (400 MHz, d$^6$-Acetone): δ 11.16 (brs, 1H), 8.34 (brs, 1H), 7.96 (d, 2H), 7.65 (d, 2H), 7.22-7.36 (m, 4H), 6.13 (brd, 1H), 5.46 (brs 1H), 5.27 (q, 1H), 4.59-4.71 (m, 5H), 4.48-4.54 (m, 2H), 4.14-4.18 (m, 1H), 3.87-3.89 (m, 1H), 2.35-2.52 (m, 4H), 1.75-1.85 (m, 2H), 1.58-1.61 (m, 1H), 1.20-1.53 (m, 8H), 1.20 (s, 9H). MS m/z (APCI−): 782.3 (M−2).

Example 3-73

Compound AR00334341

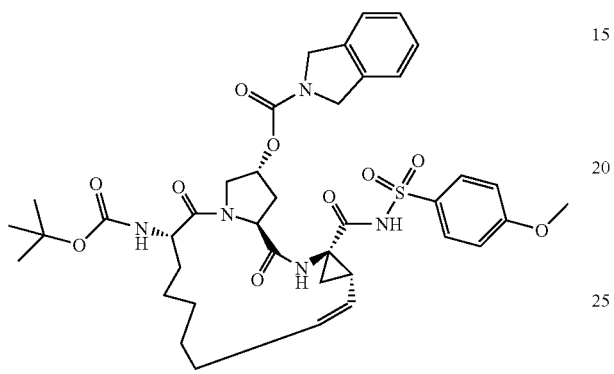

(1S,4R,6S,14S,18R)-1,3-Dihydro-isoindole-2-carboxylic acid 14-tert-butoxycarbonylamino-4-(4-methoxy-benzene-sulfonylaminocarbonyl)-2,15-dioxo-3,16-diaza-tricyclo[14.3.0.0$^{4,6}$]nonadec-7-en-18-yl ester (Compound AR00334341) was synthesized according to the procedures described in Example 3-6, except that 4-methoxy-benzene-sulfonamide was used to replace cyclopropanesulfonamide. $^1$H NMR (400 MHz, d$^6$-Acetone): δ 8.26 (brs, 1H), 7.84 (d, 2H), 7.19-7.32 (m, 4H), 7.05 (d, 2H), 6.08 (brd, 1H), 5.43 (brs 1H), 5.25 (q, 1H), 4.55-4.67 (m, 5H), 4.48 (q, 2H), 4.10-4.14 (m, 1H), 3.87 (s, 3H), 3.82-3.87 (m, 1H), 2.29-2.47 (m, 4H), 1.74-1.84 (m, 2H), 1.51-1.55 (m, 1H), 1.37-1.47 (m, 4H), 1.20-1.32 (m, 5H), 1.17 (s, 9H). MS m/z (APCI−): 779.1 (M−1).

Example 3-74

Compound AR00364266

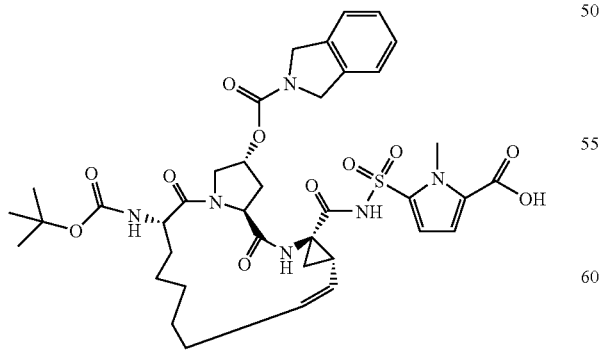

(1S,4R,6S,14S,18R)-1,3-Dihydro-isoindole-2-carboxylic acid 14-tert-butoxycarbonylamino-4-(5-carboxy-1-methyl-1H-pyrrole-2-sulfonylaminocarbonyl)-2,15-dioxo-3,16-diaza-tricyclo[14.3.0.0$^{4,6}$]nonadec-7-en-18-yl ester (Compound AR00364266) was synthesized according to the procedures described in Example 3-6, except that 1-methyl-5-sulfamoyl-1H-pyrrole-2-carboxylic acid was used to replace cyclopropanesulfonamide. $^1$H NMR (400 MHz, d$^6$-Acetone): δ 10.84 (brs, 1H), 8.27 (brs, 1H), 7.59 (d, 1H), 7.24-7.35 (m, 4H), 7.18 (d, 1H), 6.10 (brd, 1H), 5.50 (br, 1H), 5.46 (m 1H), 5.36 (q, 1H), 4.59-4.71 (m, 6H), 4.48 (d, 1H), 4.13-4.17 (m, 1H), 4.00 (s, 3H), 3.85-3.89 (m, 1H), 2.35-2.59 (m, 4H), 1.71-1.90 (m, 2H), 1.62-1.65 (m, 1H), 1.20-1.51 (m, 8H), 1.20 (s, 9H). MS m/z (APCI−): 795.4 (M−1).

Example 3-75

Compound AR00365427

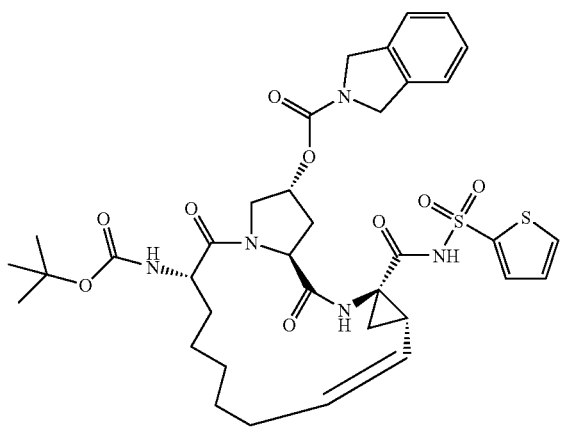

(1S,4R,6S,14S,18R)-1,3-Dihydro-isoindole-2-carboxylic acid 14-tert-butoxycarbonylamino-2,15-dioxo-4-(thiophene-2-sulfonylaminocarbonyl)-3,16-diaza-tricyclo[14.3.0.0$^{4,6}$]nonadec-7-en-18-yl ester (Compound AR00365427) was synthesized according to the procedures described in Example 3-6, except that thiophene-2-sulfonic acid amide was used to replace cyclopropanesulfonamide. MS m/z (APCI−): 754.4 (M−1).

Example 3-76

Compound AR00334339

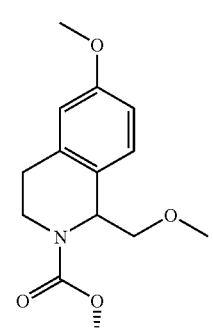

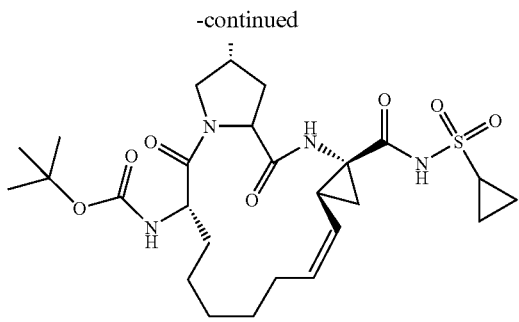

(1S,4R,6S,14S,18R)-6-Methoxy-1-methoxymethyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334339) was synthesized according to the procedures described in Example 3-6, except that 6-methoxy-1-methoxymethyl-1,2,3,4-tetrahydro-isoquinoline (for synthesis see Example 3-76a) was used to replace 2,3-dihydro-1H-isoindole. MS m/z (APCI−): 800.5 (M−1).

Example 3-76a

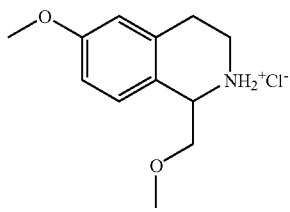

The synthesis of 6-Methoxy-1-methoxymethyl-1,2,3,4-tetrahydro-isoquinolinium chloride is depicted in the following scheme:

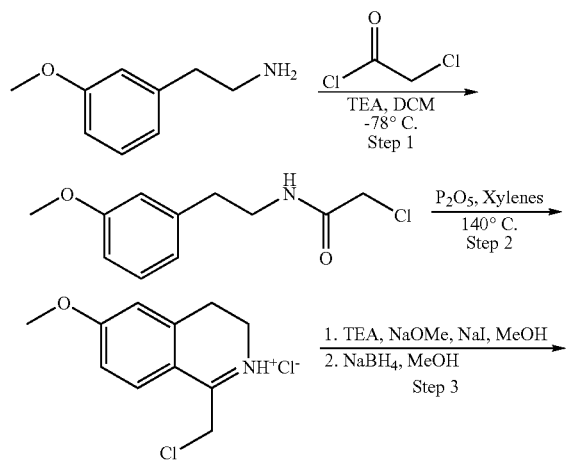

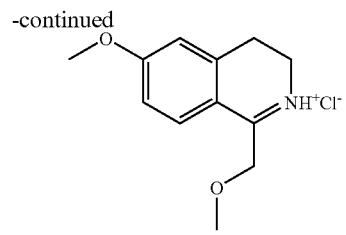

Step 1: Synthesis of 2-Chloro-N-[2-(3-methoxy-phenyl)-ethyl]-acetamide. The amine, 2-(3-Methoxy-phenyl)-ethylamine, was taken up as a 0.6 M solution in DCM, followed by addition of TEA (2 equiv.). The mixture was then cooled in an IPA/dry ice bath. When the reaction temperature reached −60° C., a solution of chloroacetylchloride in DCM (2.6 M) was added dropwise so as to keep the temperature below −60° C. After complete addition, the reaction was stirred at −60° C. for 1 h. The reaction was then warmed to −20° C. and filtered over GF filter paper to remove some of the TEA —HCl salt. The filtrate was warmed the rest of the way to rt and transferred to a separatory funnel where it was washed with 1 N HCl (2×) and brine. The organic layer was dried over MgSO$_4$ and concentrated to give a dark purple solid. This crude product was directly used in the next step without further purification.

Step 2: Synthesis of 1-Chloromethyl-6-methoxy-3,4-dihydro-isoquinolinium chloride. Two equiv. of P$_2$O$_5$ (12.9 g) was boiled in xylenes (180 mL) as a 0.25 M solution. The crude product from Step 1 above was also first boiled in xylenes (45 mL) to make a 0.5 M solution, and it was then added dropwise via an addition funnel to the P$_2$O$_5$ solution. The mixture was stirred and heated at reflux for 1 h. The reaction was then cooled to RT and the xylenes decanted off at this point. The flask was then placed in an ice bath and stirred while ice, water, EtOAc, and finally 4 M NaOH were added carefully until the pH>12. Reaction was kept <25° C. until pH=12 was reached. The reaction was then extracted with EtOAc (3×). The combined organic extracts were dried over MgSO$_4$ and concentrated to give a dark solution. This was cooled in an ice bath while 400 mL of cold Et$_2$O was added followed by 100 mL of cold HCl/Et$_2$O. A precipitate formed and was filtered away, washing with Et$_2$O. The solid was immediately placed on high vac for 2 h to give the target product as a colored foamy solid. This crude product was directly used in the next step without further purification.

Step 3: Synthesis of 6-Methoxy-1-methoxymethyl-1,2,3,4-tetrahydro-isoquinolinium chloride. The crude product from Step 2 above was added in one portion to TEA (5 equiv.) and NaI (0.1 equiv.) in MeOH at 0° C. Next, 2.2 equiv. of NaOMe was added and the homogeneous reaction became turbid. The reaction was then stirred at 0° C. for 1 h. LC/MS showed the imine completely freebased.

The reaction was then cooled again to 0° C. in an ice bath and NaBH$_4$ (1.5 equiv.) was added carefully. The reaction was then warmed to RT again and stirred for 2 h. After the reaction reached completion as monitored by LC/MS, it was concentrated, treated with 1 N NaOH and extracted with EtOAc. The organic layer was dried over MgSO$_4$ and concentrated. The resulting residue was taken up in MeOH and cooled in an ice bath. HCl gas was bubbled through it for 10 min. The reaction mixture was concentrated and re-dissolved in MeOH. After concentrating a second time the reaction was put on the high vac for overnight. The crude material was then triturated with EtOAc (3×) to give the product as a brownish foamy solid upon sitting overnight on the high vac. This crude product was directly used in the next step without further purification. MS m/z (POSESI): 208.1 (MH+).

Example 3-77

Compound AR00365193

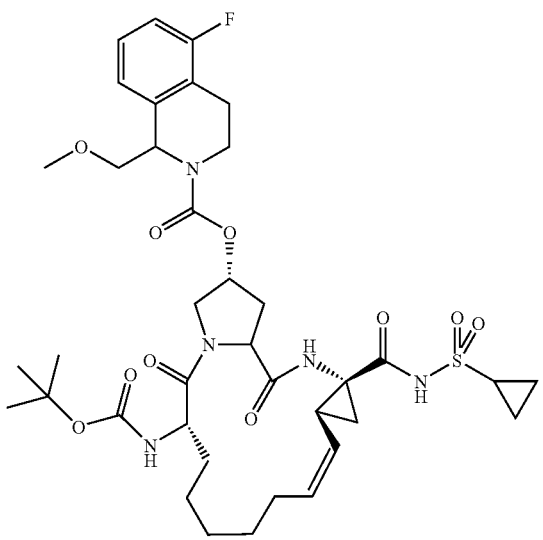

(1S,4R,6S,14S,18R)-5-Fluoro-1-methoxymethyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00365193) was synthesized according to the procedures described in Example 3-76, except that 5-fluoro-1-methoxymethyl-1,2,3,4-tetrahydro-isoquinolinium chloride (for synthesis see Example 3-77a) was used to replace 6-methoxy-1-methoxymethyl-1,2,3,4-tetrahydro-isoquinolinium chloride. $^1$H NMR (500 MHz, CD$_3$OD) δ 8.99-8.91 (m, 1H), 7.23-7.15 (m, 1H), 7.13-6.99 (m, 2H), 6.99-6.90 (m, 1H), 5.68 (q, 1H), 5.41 (br s, 1H), 5.35-5.21 (m, 1H), 5.06 (t, 1H), 4.60-4.31 (m, 3H), 4.30-4.05 (m, 3H), 3.96-3.81 (m, 1H), 3.80-3.56 (m, 3H), 3.35 (d, 3H), 2.98-2.30 (m, 9H), 1.91-1.68 (m, 4H), 1.64-0.95 (m, 16H); MS (APCI-) m/z 788.3 (M-1).

Example 3-77a

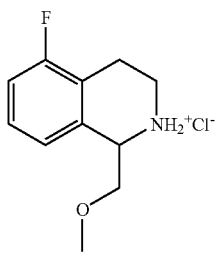

Synthesis of 5-fluoro-1-methoxymethyl-1,2,3,4-tetrahydro-isoquinolinium chloride was carried out in a similar fashion as depicted in Example 3-76a, except that in Step 1, 2-(2-Fluoro-phenyl)-ethylamine was used to replace 2-(3-Methoxy-phenyl)-ethylamine.

Example 3-78

Compound AR00365438

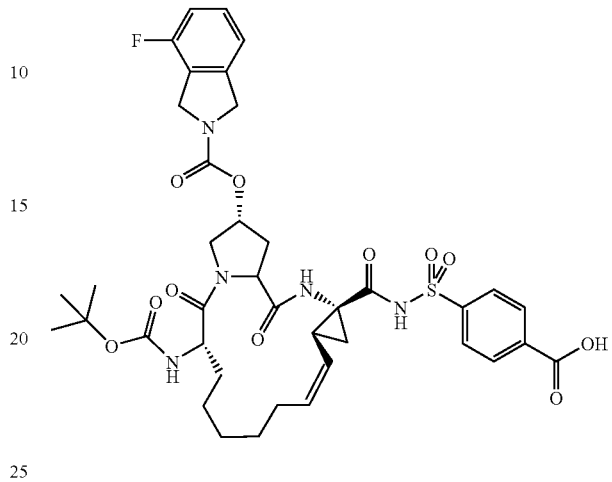

(1S,4R,6S,14S,18R)-4-Fluoro-1,3-dihydro-isoindole-2-carboxylic acid 14-tert-butoxycarbonylamino-4-(4-carboxy-benzenesulfonylaminocarbonyl)-2,15-dioxo-3,16-diaza-tricyclo[14.3.0.0$^{4,6}$]nonadec-7-en-18-yl ester (Compound AR00365438) was synthesized according to the procedures described in Example 3-55, except that 4-sulfamoyl-benzoic acid was used to replace cyclopropanesulfonamide. $^1$H-NMR (500 MHz, CD$_3$OD) δ 8.92 (d, 1H), 8.25-8.19 (m, 1H), 8.15 (d, 2H), 8.04 (d, 2H), 7.36-7.27 (m, 1H), 7.14 (d, 1H), 7.05-6.95 (m, 2H), 5.42 (br s, 1H), 5.26 (q, 1H), 4.82-4.50 (m, 8H), 4.10-4.00 (m, 1H), 3.85 (d, 1H), 3.75-3.69 (m, 1H), 2.60-2.39 (m, 4H), 2.26 (p, 2H), 1.89-1.84 (m, 1H), 1.81-1.05 (m, 15H); MS (APCI-): m/z 810.2 (M-1).

Example 3-79

Compound AR00340303

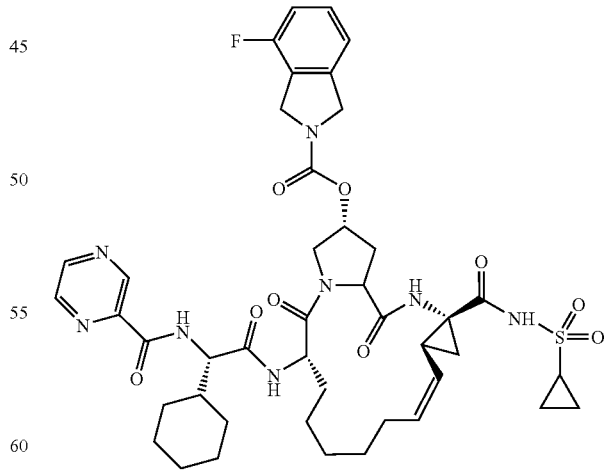

Synthesis of (1S,4R,6S,14S,18R)-4-Fluoro-1,3-dihydro-isoindole-2-carboxylic acid 14-{2-cyclohexyl-2-[(pyrazine-2-carbonyl)-amino]-acetylamino}-4-cyclopropanesulfonylaminocarbonyl-2,15-dioxo-3,16-diaza-tricyclo[14.3.0.0$^{4,6}$]nonadec-7-en-18-yl ester (Compound AR00340303).

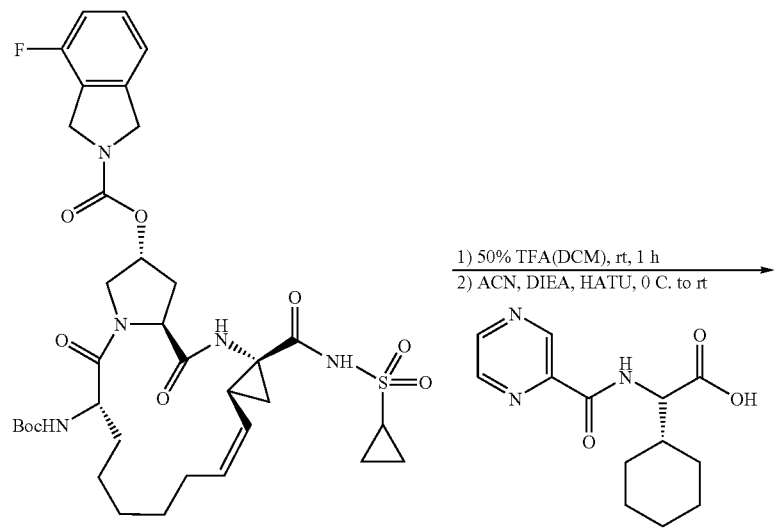
1) 50% TFA(DCM), rt, 1 h
2) ACN, DIEA, HATU, 0 C. to rt
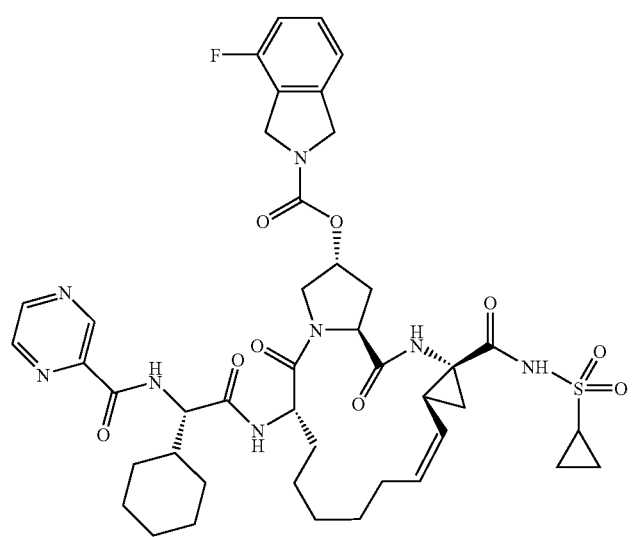

The starting material (AR00334191, Example 3-55, 10 mg, 13.7 μmol) was dissolved in 1 mL of 50% TFA (DCM) and stirred at RT for 1 h. The reaction mixture was then concentrated to dryness, taken up in acetonitrile and concentrated again. Repeat the above process once more to remove any excess TFA. The resulting solid residue was then dissolved in DCE (137 μL), cooled to 0° C. in an ice bath, followed by addition of the amino acid, cyclohexyl-[(pyrazine-2-carbonyl)-amino]-acetic acid (1.05 equiv), HATU (10 mg) and DIEA (4 drps). The mixture was let slowly warm up to RT and stir for overnight. For work-up, the reaction mixture was directly loaded onto a C-18 column and purified with reverse-phase column chromatography, giving the target compound as a white solid. MS (APCI−): m/z 876.1 (M−1).

Example 3-80

(1S,4R,6S,14S,18R)-4-Fluoro-1,3-dihydro-isoindole-2-carboxylic acid 14-(2-acetylamino-2-cyclohexyl-acetylamino)-4-cyclopropanesulfonylaminocarbonyl-2,15-dioxo-3,16-diaza-tricyclo[14.3.0.0$^{4,6}$]nonadec-7-en-18-yl ester (Compound AR00340122) was synthesized according to the procedures described in Example 3-79, except that acetylamino-cyclohexyl-acetic acid was used to replace cyclohexyl-[(pyrazine-2-carbonyl)-amino]-acetic acid. MS (APCI−): m/z 811.3 (M−1).

Example 3-81

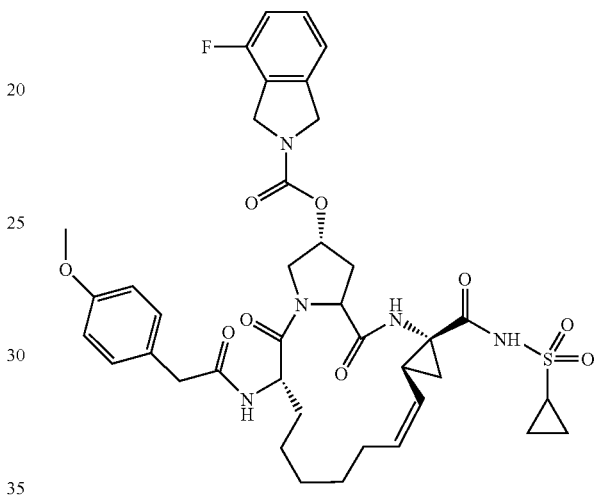

Compound AR00340156

Synthesis of (1S,4R,6S,14S,18R)-4-Fluoro-1,3-dihydro-isoindole-2-carboxylic acid 4-cyclopropanesulfonylaminocarbonyl-14-[2-(4-methoxy-phenyl)-acetylamino]-2,15-dioxo-3,16-diaza-tricyclo[14.3.0.0$^{4,6}$]nonadec-7-en-18-yl ester (Compound AR00340156).

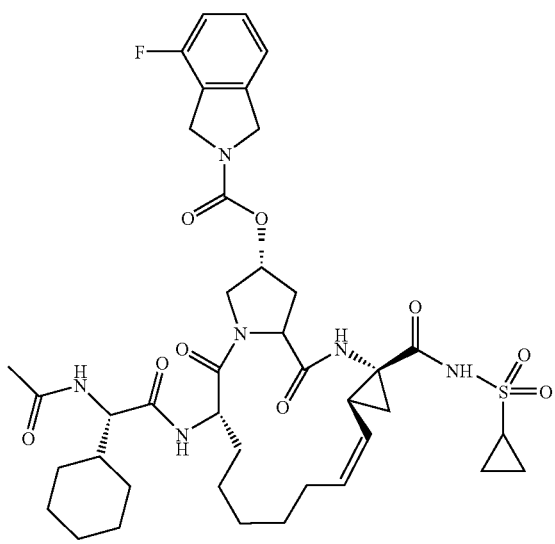

Compound AR00340122

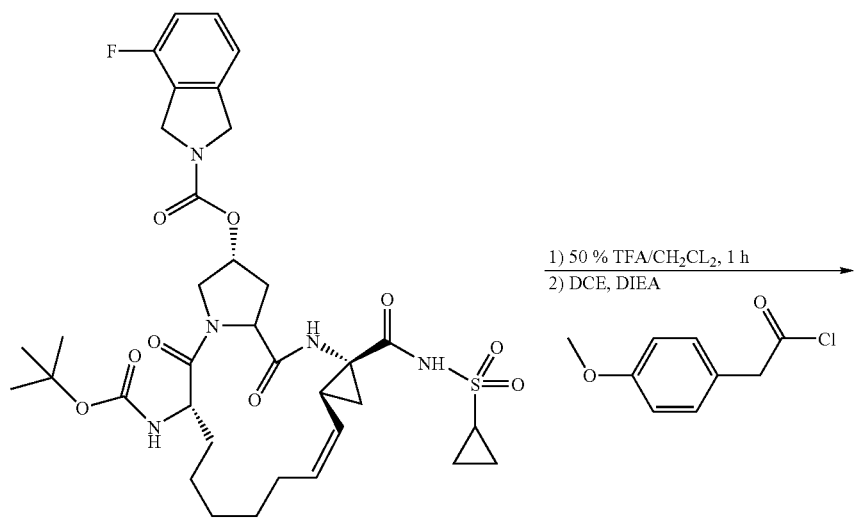

1) 50 % TFA/CH$_2$CL$_2$, 1 h
2) DCE, DIEA

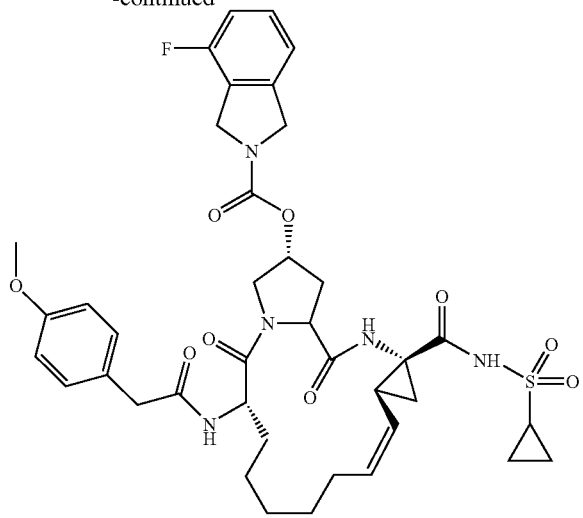

The starting material (AR00334191, Example 3-55, 10 mg, 13.7 μmol) was dissolved in 1 mL of 50% TFA (DCM) and stirred at RT for 1 h. The reaction mixture was then concentrated to dryness, taken up in acetonitrile and concentrated again. Repeat the above process once more to remove any excess TFA. The resulting solid residue was then dissolved in DCE (137 μL), followed by addition of the acid chloride, (4-Methoxy-phenyl)-acetyl chloride (2 drps) and DIEA (4 drps). The mixture was stirred ar RT for overnight. After completion, the reaction was directly loaded onto a C-18 column and purified with reverse-phase column chromatography. The compound was further purified on normal phase silica gel chromatography (eluent=40% EtOAc/hexanes with 1% formic acid) to give the target compound as a white solid. $^1$H NMR (500 MHz, CD$_3$OD) δ 7.33 (p, 1H), 7.15 (d, 1H), 7.05-6.92 (m, 3H), 6.65 (dd, 2H), 5.68 (q, 1H), 5.40 (br s, 1H), 5.09 (t, 1H), 4.78-4.46 (m, 7H), 4.43-4.24 (m, 2H), 3.89-3.80 (m, 1H), 3.68 (d, 3H), 3.21 (d, 1H), 2.69-2.57 (m, 1H), 2.52-2.30 (m, 5H), 2.06-0.80 (m, 15H); MS (APCI−): m/z 778.3 (M−1).

Example 3-82

Compound AR00340178

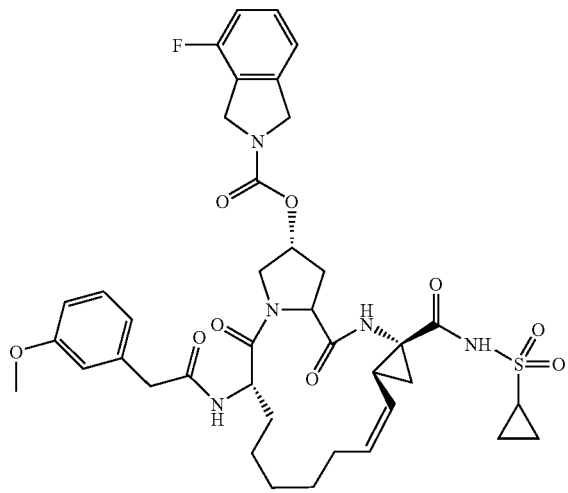

(1S,4R,6S,14S,18R)-4-Fluoro-1,3-dihydro-isoindole-2-carboxylic acid 4-cyclopropanesulfonylaminocarbonyl-14-[2-(3-methoxy-phenyl)-acetylamino]-2,15-dioxo-3,16-diaza-tricyclo[14.3.0.0$^{4,6}$]nonadec-7-en-18-yl ester (Compound AR00340178) was synthesized according to the procedures described in Example 3-81, except that (3-Methoxy-phenyl)-acetyl chloride was used to replace (4-Methoxy-phenyl)-acetyl chloride. $^1$H NMR (500 MHz, CD$_3$OD) δ 7.32 (p, 1H), 7.14 (d, 1H), 7.05-6.92 (m, 3H), 6.76-6.58 (m, 2H), 5.68 (q, 1H), 5.41 (br s, 1H), 5.09 (t, 1H), 4.76-4.46 (m, 7H), 4.43-4.26 (m, 2H), 3.91-3.82 (m, 1H), 3.69 (d, 3H), 2.94-2.85 (m, 1H), 2.70-2.57 (m, 1H), 2.52-2.30 (m, 5H), 2.06-0.80 (m, 15H); MS (APCI−) m/z 778.3 (M−1).

Example 3-83

Compound AR00340188

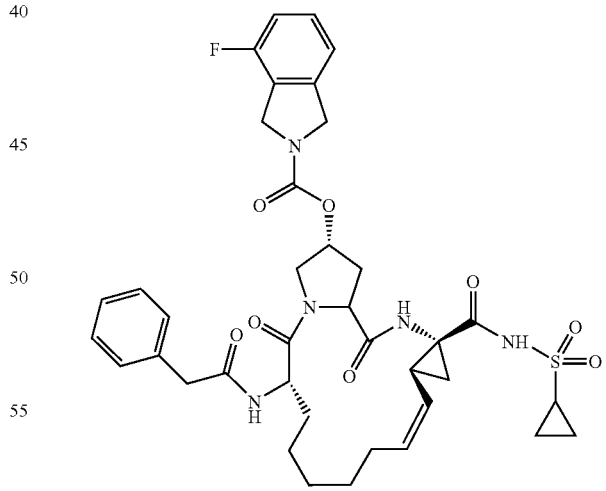

(1S,4R,6S,14S,18R)-4-Fluoro-1,3-dihydro-isoindole-2-carboxylic acid 4-cyclopropanesulfonylaminocarbonyl-2,15-dioxo-14-phenylacetylamino-3,16-diaza-tricyclo[14.3.0.0$^{4,6}$]nonadec-7-en-18-yl ester (Compound AR00340188) was synthesized according to the procedures described in Example 3-81, except that phenyl-acetyl chloride was used to replace (4-methoxy-phenyl)-acetyl chloride. MS (APCI−) m/z 748.4 (M−1).

Example 3-84

Compound AR00334314

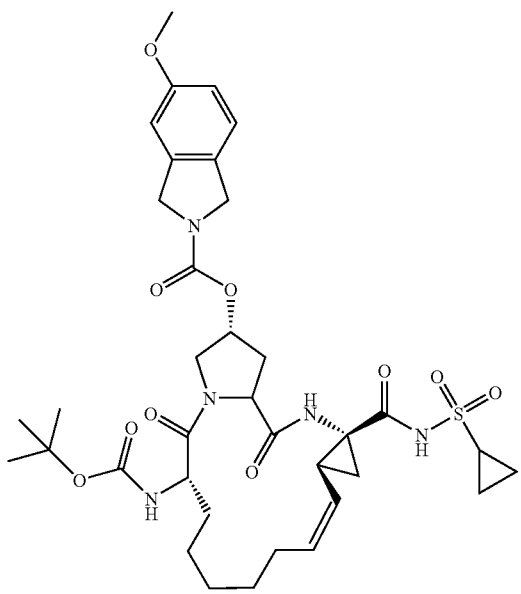

(1S,4R,6S,14S,18R)-5-Methoxy-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334314) was synthesized according to the procedures described in Example 3-6, except that 5-methoxy-2,3-dihydro-1H-isoindole (prepared by a similar fashion as described in: JOC, Vol. 53, No. 22, 1988, pp. 5381-5383) was used to replace 2,3-dihydro-1H-isoindole. MS m/z (APCI−): 742.3 (M−1).

Example 3-85

Compound AR00334399

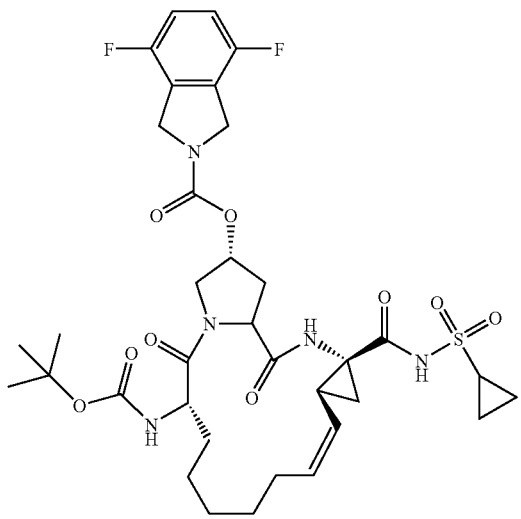

(1S,4R,6S,14S,18R)-4,7-Difluoro-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334399) was synthesized according to the procedures described in Example 3-6, except that 4,7-Difluoro-2,3-dihydro-1H-isoindole (prepared by a similar fashion as described in: JOC, Vol. 53, No. 22, 1988, pp. 5381-5383) was used to replace 2,3-dihydro-1H-isoindole. $^1$H NMR (500 MHz, CD$_3$OD) δ 8.97 (s, 1H), 6.99-6.85 (m, 2H), 5.69 (q, 1H), 5.42 (br s, 1H), 5.07 (t, 1H), 4.83-4.57 (m, 6H), 4.51 (d, 1H), 4.13-4.02 (m, 1H), 3.85 (t, 1H), 2.94-2.86 (m, 1H), 2.73-2.59 (m, 1H), 2.55-2.28 (m, 4H), 1.89-1.70 (m, 3H), 1.65-1.22 (m, 10H), 1.18-0.96 (m, 10H), MS m/z (APCI−): 746.1 (M−1).

Example 3-86

Compound AR00338066

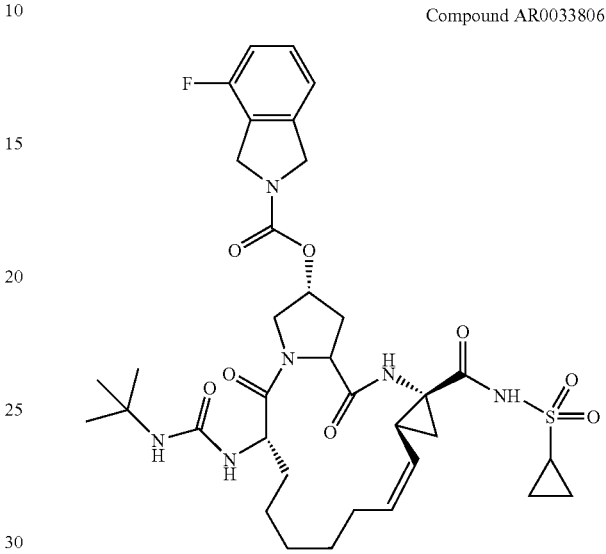

(1S,4R,6S,14S,18R)-4-Fluoro-1,3-dihydro-isoindole-2-carboxylic acid 14-(3-tert-butyl-ureido)-4-cyclopropanesulfonylaminocarbonyl-2,15-dioxo-3,16-diaza-tricyclo[14.3.0.0$^{4,6}$]nonadec-7-en-18-yl ester (Compound AR00338066) was synthesized according to the procedures described in Example 3-36, except that 4-fluoro-2,3-dihydro-1H-isoindole was used to replace 2,3-dihydro-1H-isoindole. $^1$H NMR (500 MHz, CD$_3$OD) δ 7.38-7.28 (m, 1H), 7.13 (d, 1H), 7.01 (p, 1H), 5.69 (q, 1H), 5.45 (br s, 1H), 5.07 (t, 1H), 4.83-4.66 (m, 4H), 4.59 (q, 1H), 4.49 (d, 1H), 4.37-4.17 (m, 2H), 3.94-3.84 (m, 1H), 3.72 (t, 1H), 2.95-2.87 (m, 1H), 2.68-2.29 (m, 5H), 2.09-1.22 (m, 11H), 1.12-0.95 (m, 12H); MS (APCI−): m/z 729.3 (M−1).

Example 3-87

Compound AR00338070

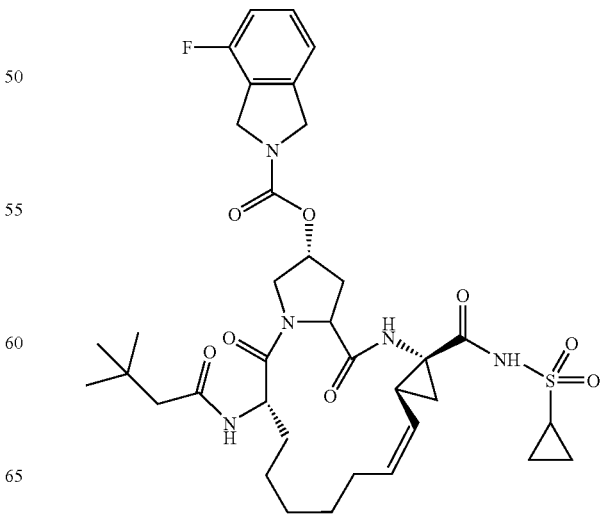

(1S,4R,6S,14S,18R)-4-Fluoro-1,3-dihydro-isoindole-2-carboxylic acid 4-cyclopropanesulfonylaminocarbonyl-14-(3,3-dimethyl-butyrylamino)-2,15-dioxo-3,16-diaza-tricyclo[14.3.0.0$^{4,6}$]nonadec-7-en-18-yl ester (Compound AR00338070) was synthesized according to the procedures described in Example 3-81, except that 3,3-dimethyl-butyryl chloride was used to replace (4-methoxy-phenyl)-acetyl chloride. MS (APCI−) m/z 728.3 (M−1).

Example 3-88

Compound AR00338071

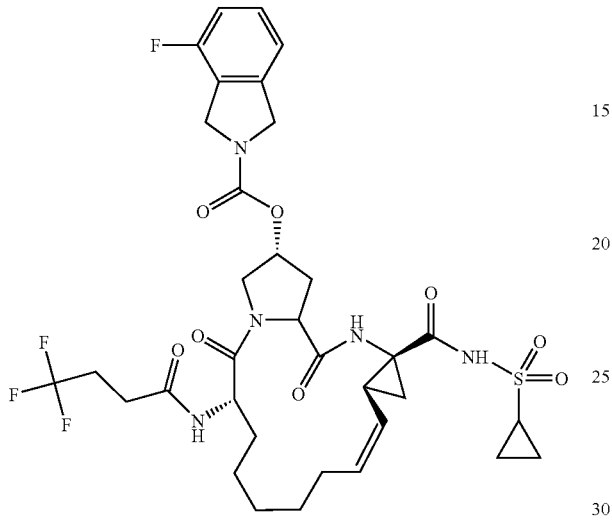

(1S,4R,6S,14S,18R)-4-Fluoro-1,3-dihydro-isoindole-2-carboxylic acid 4-cyclopropanesulfonylaminocarbonyl-2,15-dioxo-14-(4,4,4-trifluoro-butyrylamino)-3,16-diaza-tricyclo[14.3.0.0$^{4,6}$]nonadec-7-en-18-yl ester (Compound AR00338071) was synthesized according to the procedures described in Example 3-81, except that 4,4,4-trifluoro-butyryl chloride was used to replace (4-methoxy-phenyl)-acetyl chloride. MS (APCI−) m/z 754.3 (M−1).

Example 3-89

Compound AR00341649

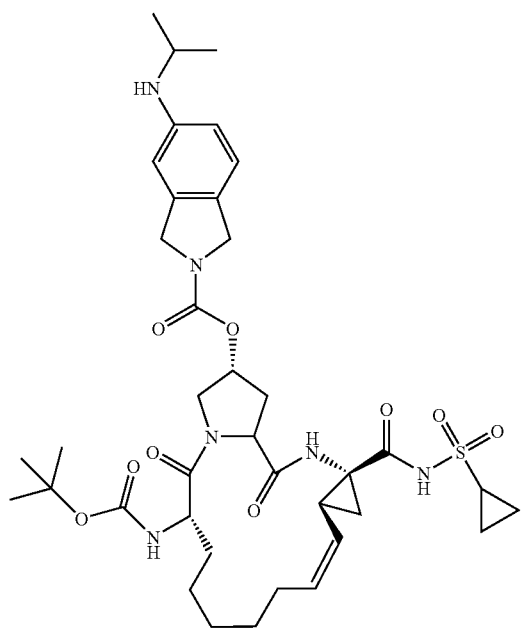

(1S,4R,6S,14S,18R)-5-Isopropylamino-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00341649) was synthesized according to the procedures described in Example 3-6, except that (2,3-Dihydro-1H-isoindol-5-yl)-isopropyl-amine (prepared by a similar fashion as described in: Org. Letters, 2003, Vol. 5, No. 6, 793-796.) was used to replace 2,3-dihydro-1H-isoindole. $^1$H NMR (500 MHz, CD$_3$OD) δ 8.94 (br d, 1H), 7.52 (s, 1H), 7.48 (d, 1H), 7.41-7.32 (m, 2H), 7.32-7.24 (m, 2H), 5.69 (q, 1H), 5.41 (br s, 1H), 5.07 (t, 1H), 4.82-4.66 (m, 3H), 4.60 (t, 1H), 4.52 (t, 1H), 4.08 (d, 1H), 3.85 (d, 1H), 3.80-3.68 (m, 1H), 2.94-2.87 (m, 1H), 2.71-2.59 (m, 1H), 2.55-2.45 (m, 1H), 2.45-2.30 (m, 3H), 1.88-1.69 (m, 3H), 1.61 (t, 1H), 1.58-0.94 (m, 25H); MS (APCI−): m/z 770.1 (M−1).

Example 3-90

Compound AR00364936

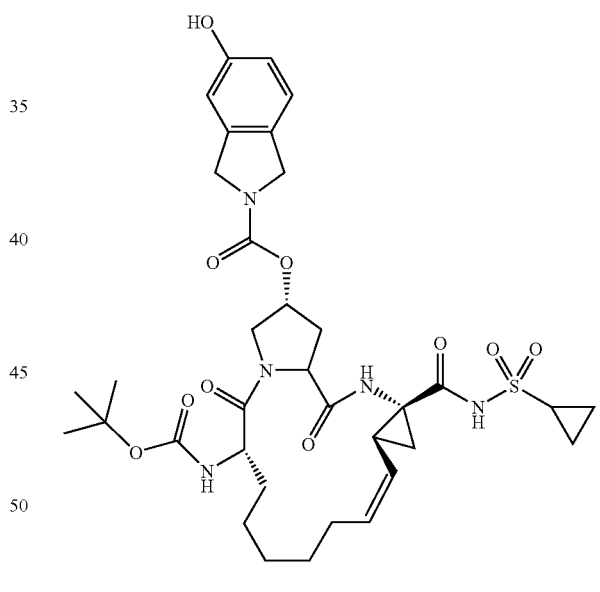

(1S,4R,6S,14S,18R)-5-Hydroxy-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00364936) was synthesized according to the procedures described in Example 3-6, except that 2,3-Dihydro-1H-isoindol-5-ol (prepared by a similar fashion as described in: JOC, Vol. 53, No. 22, 1988, pp. 5381-5383) was used to replace 2,3-dihydro-1H-isoindole. MS m/z (APCI−): 728.2 (M−1).

Example 3-91

Compound AR00365083

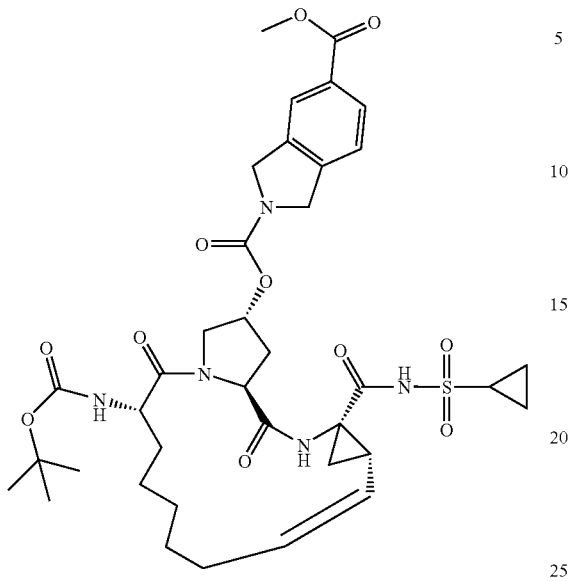

(1S,4R,6S,14S,18R)-1,3-Dihydro-isoindole-2,5-dicarboxylic acid 2-(14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl) ester 5-methyl ester (Compound AR00365083) was synthesized according to the procedures described in Example 3-57, except that 2,3-dihydro-1H-isoindole-5-carboxylic acid methyl ester (prepared as shown in Example 3-91a) was used to replace 2,3-dihydro-1H-isoindol-5-ylamine in Step 5 instead. MS m/z (APCI+): 672.2 (MH$^+$–Boc).

Example 3-91a

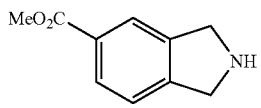

2,3-Dihydro-1H-isoindole-5-carboxylic acid methyl ester was synthesized according to the following scheme:

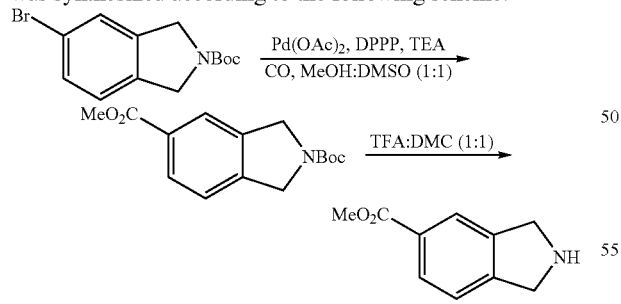

A mixture of 5-bromo-1,3-dihydro-isoindole-2-carboxylic acid tert-butyl ester (200 mg, 0.67 mmol), Pd(OAc)$_2$ (30 mg, 0.2 equiv), DPPP (55 mg, 0.2 equiv), TEA (0.93 mL, 10 equiv) and MeOH:DMSO (1:1, 4 mL) was stirred for 16 h under CO (balloon) at 80° C. LC-MS and TLC (20% EtOAc-Hexane) showed completion of the reaction. The Reaction mixture was concentrated to remove MeOH and diluted with EtOAc (10 mL), and washed with water (2×25 mL). The organic layer was dried (Na$_2$SO$_4$), concentrated and purified by silica gel column chromatography (eluent=20% EtOAc-Hexane), giving pure 1,3-dihydro-isoindole-2,5-dicarboxylic acid 2-tert-butyl ester 5-methyl ester (150 mg, 81%). MS (APCI+): m/z 178.1 (MH$^+$–Boc).

The product above was removed of the protective group by treating with 50% TFA-DCM for 1 h at 0° C.-RT. The reaction mixture was concentrated to dryness, re-dissolved in DCM, and neutralized with sat. NaHCO$_3$ solution. The organic layer was separated, dried and concentrated to give the target compound as a free base, which was directly used in the next coupling step without further purification.

Example 3-92

Compound AR00333831

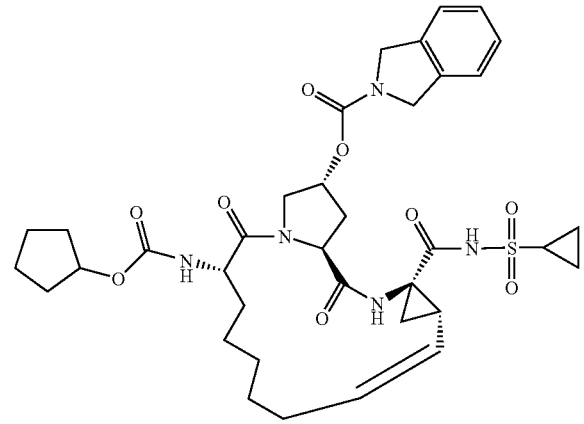

(1S,4R,6S,14S,18R)-1,3-Dihydro-isoindole-2-carboxylic acid 14-cyclopentyloxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00333831) was synthesized according to the procedures described in Example 3-5, except that 2,3-dihydro-1H-isoindole was used to replace 1,2,3,4-tetrahydro-isoquinoline instead. $^1$HNMR (400 MHz, CD$_3$OD): δ 7.36-7.22 (m, 3H), 7.21-7.16 (m, 1H), 5.74-5.60 (m, 1H), 5.40 (s, 1H), 5.20-5.03 (m, 1H), 4.80-4.54 (m, 6H), 4.38-4.28 (m, 1H), 4.18 (m, 1H), 3.90-3.80 (m, 1H), 2.96-2.85 (m, 1H), 2.70-2.31 (m, 4H), 1.92-0.98 (m, 24H). MS m/z (APCI–): 724.4 (M–1).

Example 3-93

Compound AR00340494

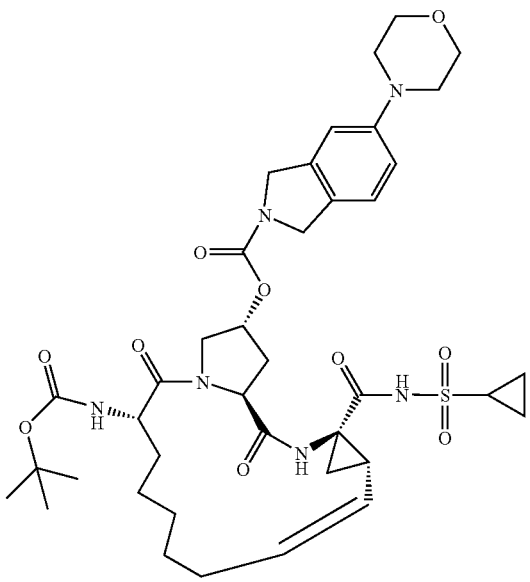

259

(1S,4R,6S,14S,18R)-5-Morpholin-4-yl-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00340494) was synthesized according to the procedures described in Example 3-6, except that 5-morpholin-4-yl-2,3-dihydro-1H-isoindole (prepared by a similar fashion as described in: J. Org. Chem. 2000, 65, 1144-1157) was used to replace 2,3-dihydro-1H-isoindole. $^1$HNMR (400 MHz, DMSO-d$^6$): δ 7.80-7.22 (m, 1H), 7.22-7.15 (m, 1H), 7.00-6.81 (m, 2H), 5.45 (m, 1H), 5.26 (m, 1H), 4.62-4.50 (m, 4H), 4.42 (m, 1H), 4.28-4.10 (m, 2H), 3.98 (m, 1H), 3.76 (m, 4H), 3.12 (m, 4H), 2.71-2.60 (m, 1H), 2.40-1.45 (m, 3H), 1.40-1.21 (m, 10H), 0.98-0.61 (m, 4H). MS m/z (APCI+): 699.2 (MH$^+$−Boc).

Example 3-94

Compound AR00365082

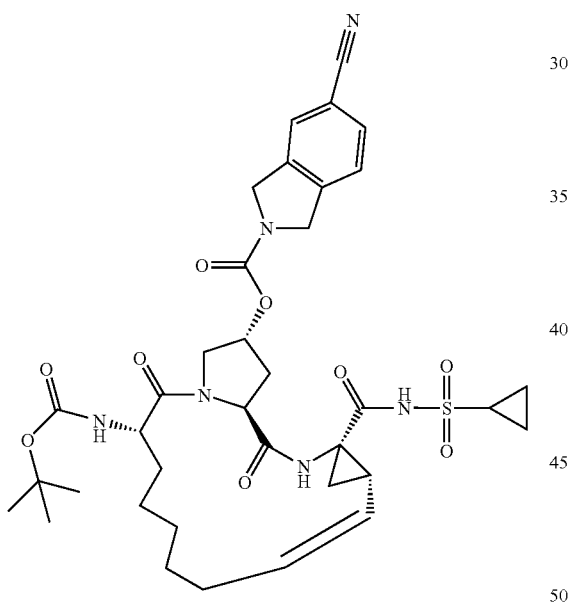

(1S,4R,6S,14S,18R)-5-Cyano-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00365082) was synthesized according to the procedures described in Example 3-6, except that 2,3-dihydro-1H-isoindole-5-carbonitrile (prepared by a similar fashion as described in: J. Org. Chem. 1998, 63, 8224-8228) was used to replace 2,3-dihydro-1H-isoindole. MS m/z (APCI+): 639.1 (MH$^+$−Boc).

260

Example 3-95

Compound AR00365252

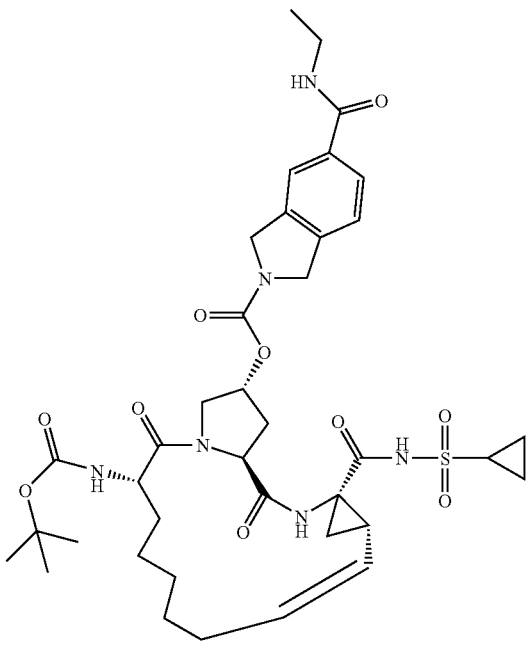

(1S,4R,6S,14S,18R)-5-Ethylcarbamoyl-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00365252) was synthesized according to the procedures described in the following scheme:

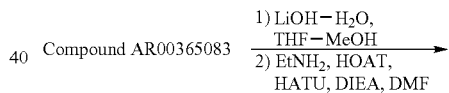

Compound AR00365083  
1) LiOH—H$_2$O, THF—MeOH  
2) EtNH$_2$, HOAT, HATU, DIEA, DMF

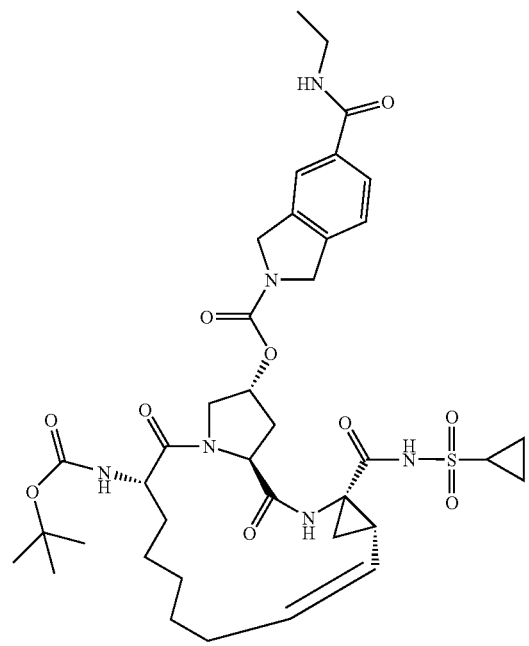

synthesis was described earlier in this document, was dissolved in a THF:MeOH (2:1, 3 mL) mixture, followed by addition of 1 mL aq. solution of LiOH—H$_2$O. The reaction was stirred for 1 h at rt. LC-MS indicated complete hydrolysis, the reaction was let continue for another 30 min before it was concentrated, neutralized with 0.1N HCl and extracted with 5 mL of EtOAc. The organic layer was dried (Na$_2$SO$_4$), concentrated and purified with silica gel column chromatography (eluent=5-7% MeOH-DCM) to give the hydrolysis product as a white solid. MS (APCI+): m/z 658.1 (MH$^+$–Boc).

The product from the above step (23 mg, 30 µmol) was first dissolved in anhydrous DMF (2 mL), followed by addition of ethylamine (3 equiv), HOAT (3 equiv), and HATU (3 equiv), and finally DIEA (6 equiv) was added dropwise. The reaction mixture was stirred at RT for overnight. LC-MS showed completion of the reaction. The reaction mixture was diluted with EtOAc (5 mL) and washed with water (2×10 mL). The organic layer was dried, concentrated and the crude product was purified by preparative TLC. MS (APCI+): 685.2 (MH$^+$–Boc).

Compound AR00334218

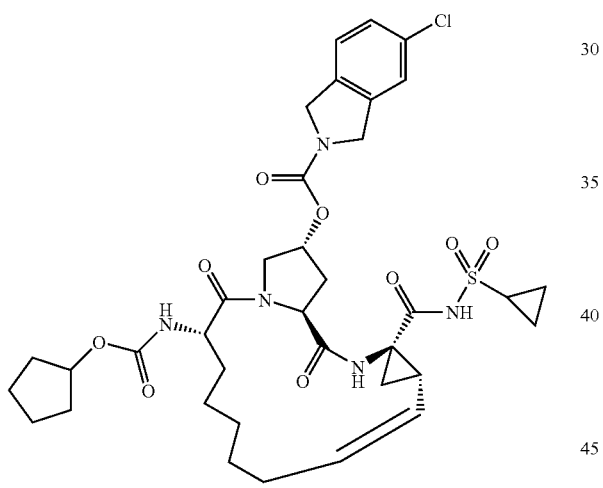

Example 3-96

(1S,4R,6S,14S,18R)-5-Chloro-1,3-dihydro-isoindole-2-carboxylic acid 14-cyclopentyloxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00334218) was synthesized according to the procedures described in Example 3-5, except that 5-chloro-2,3-dihydro-1H-isoindole was used to replace 1,2,3,4-tetrahydro-isoquinoline instead. $^1$H NMR (400 MHz, CD$_3$CN) δ 7.55 (bs, 1H), 7.19-7.33 (m, 3H), 5.63-5.73 (m, 2H), 5.27-5.34 (m, 1H), 4.98 (t, 1H), 4.52-4.72 (m, 5H), 4.48 (t, 1H), 4.34-4.44 (m, 1H), 4.06-4.15 (m, 1H), 2.77-2.90 (m, 2H), 2.54 (bs, 1H), 2.24-2.44 (m, 3H), 1.64-1.75 (m, 2H), 1.13-1.57 (m, 18H), 0.91-1.09 (m, 4H). MS m/z 759.9 (M+1).

Example 3-97

Compound AR00334220

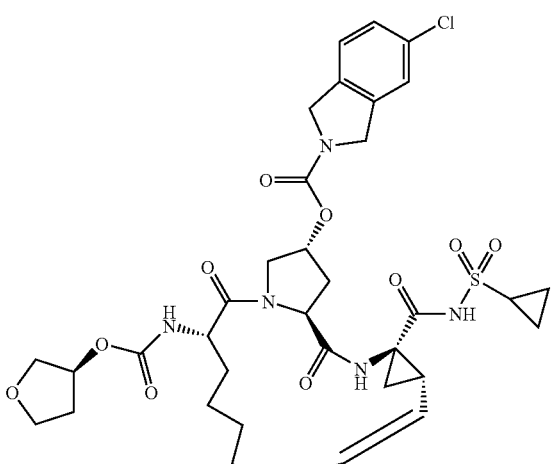

(1S,4R,6S,14S,18R)-5-Chloro-1,3-dihydro-isoindole-2-carboxylic acid 4-cyclopropanesulfonylaminocarbonyl-2,15-dioxo-14-(tetrahydro-furan-3-yloxycarbonylamino)-3,16-diaza-tricyclo[14.3.0.0$^{4,6}$]nonadec-7-en-18-yl ester (Compound AR00334220) was synthesized according to the procedures described in Example 3-16, except that 5-chloro-2,3-dihydro-1H-isoindole was used to replace 1,2,3,4-tetrahydro-isoquinoline instead. $^1$H NMR (400 MHz, CD$_3$CN) δ 7.57 (bs, 1H), 7.20-7.34 (m, 3H), 5.87-5.93 (m, 1H), 5.65 (q, 1H), 5.31 (bs, 1H), 5.23-5.29 (m, 1H), 4.98 (t, 1H), 4.44-4.71 (m, 5H), 4.29-4.39 (m, 1H), 4.07-4.18 (m, 1H), 3.70-3.87 (m, 4H), 3.61-3.70 (m, 1H), 3.44-3.55 (m, 2H), 3.30-3.42 (m, 1H), 2.76-2.89 (m, 2H), 2.54 (bs, 1H), 2.36-2.46 (m, 1H), 2.24-2.36 (m, 2H), 1.69-1.76 (m, 1H), 1.59-1.69 (m, 1H), 1.13-1.56 (m, 8H), 0.90-1.10 (m, 4H). MS m/z 762.0 (M+1)

Example 3-98

Compound AR00334222

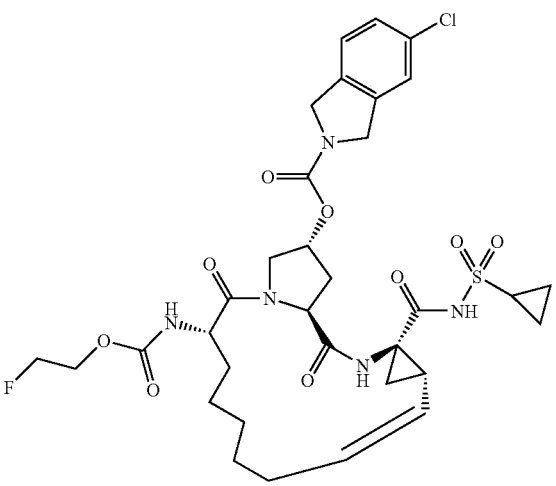

(1S,4R,6S,14S,18R)-5-Chloro-1,3-dihydro-isoindole-2-carboxylic acid 4-cyclopropanesulfonylaminocarbonyl-14-(2-fluoro-ethoxycarbonylamino)-2,15-dioxo-3,16-diaza-tricyclo[14.3.0.0$^{4,6}$]nonadec-7-en-18-yl ester (Compound AR00334222) was synthesized according to the procedures described in Example 3-28, except that 5-chloro-2,3-dihydro-1H-isoindole was used to replace 2,3-dihydro-1H-isoindole instead. $^1$H NMR (400 MHz, CD$_3$CN) δ 7.53 (bs, 1H), 7.20-7.33 (m, 3H), 5.93 (d, 1H), 5.67 (q, 1H), 5.32 (bs, 1H), 4.93-5.05 (m, 1H), 4.52-4.72 (m, 5H), 4.47 (t, 1H), 4.39 (t, 1H), 4.25-4.36 (m, 2H), 4.12-4.25 (m, 2H), 3.65-3.96 (m, 2H), 2.76-2.89 (m, 2H), 2.54 (bs, 1H), 2.22-2.44 (m, 3H), 1.67-1.76 (m, 1H), 1.13-1.60 (m, 10H), 0.91-1.13 (m, 4H). MS m/z 737.9 (M+1)

Example 3-99

Compound AR00334225

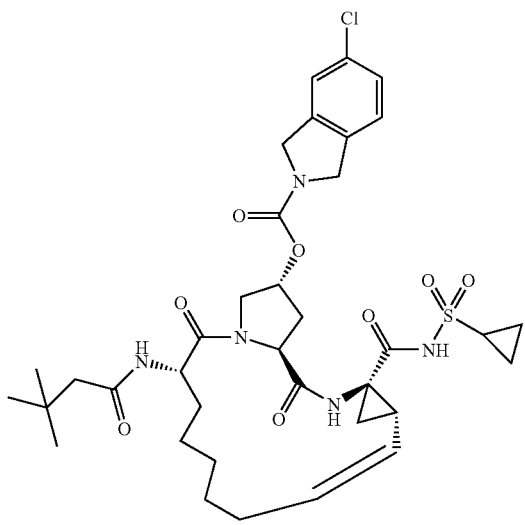

(1S,4R,6S,14S,18R)-5-Chloro-1,3-dihydro-isoindole-2-carboxylic acid 4-cyclopropanesulfonylaminocarbonyl-14-(3,3-dimethyl-butyrylamino)-2,15-dioxo-3,16-diaza-tricyclo[14.3.0.0$^{4,6}$]nonadec-7-en-18-yl ester (Compound AR00334225) was synthesized according to the procedures described in Example 3-81, except that 3,3-dimethyl-butyryl chloride was used to replace (4-Methoxy-phenyl)-acetyl chloride, and that 5-chloro-2,3-dihydro-1H-isoindole was used to replace 4-fluoro-2,3-dihydro-1H-isoindole instead. $^1$H NMR (400 MHz, CD$_3$CN) δ 7.60 (bs, 1H), 7.15-7.33 (m, 3H), 6.54-6.65 (m, 1H), 5.63-5.73 (m, 1H), 5.33 (bs, 1H), 4.93-5.02 (m, 1H), 4.53-4.65 (m, 3H), 4.39-4.48 (m, 2H), 4.28-4.38 (m, 1H), 3.74-3.83 (m, 2H), 2.77-2.89 (m, 1H), 2.54 (bs, 1H), 2.23-2.44 (m, 3H), 1.68-1.91 (m, 4H), 1.12-1.54 (m, 11H), 0.91-1.11 (m, 4H), 0.76-0.90 (m, 9H). MS m/z 746.2 (M+1)

Example 3-100

Compound AR00334226

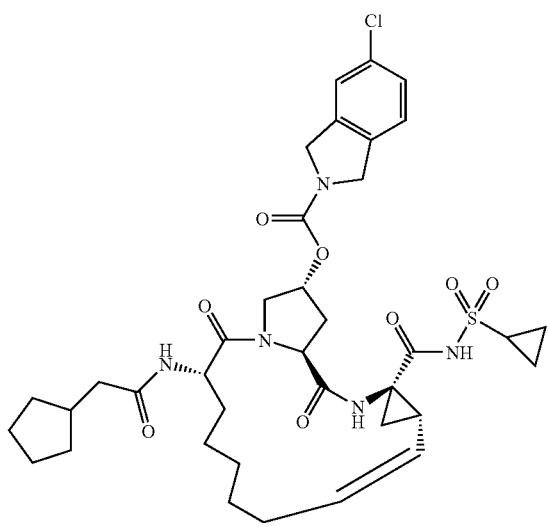

(1S,4R,6S,14S,18R)-5-Chloro-1,3-dihydro-isoindole-2-carboxylic acid 14-(2-cyclopentyl-acetylamino)-4-cyclopropanesulfonylaminocarbonyl-2,15-dioxo-3,16-diaza-tricyclo[14.3.0.0$^{4,6}$]nonadec-7-en-18-yl ester (Compound AR00334226) was synthesized according to the procedures described in Example 3-81, except that cyclopentyl-acetyl chloride was used to replace (4-Methoxy-phenyl)-acetyl chloride, and that 5-chloro-2,3-dihydro-1H-isoindole was used to replace 4-fluoro-2,3-dihydro-1H-isoindole instead. $^1$H NMR (400 MHz, CDCl$_3$) δ 10.85 (bs, 1H), 6.95-7.30 (m, 3H), 5.87-6.02 (m, 1H), 5.63-5.79 (m, 1H), 5.43-5.52 (m, 1H), 4.93-5.08 (m, 1H), 4.52-4.85 (m, 5H), 4.31-4.52 (m, 1H), 3.79-3.95 (m, 1H), 3.60-3.75 (m, 2H), 3.14 (q, 1H), 2.90 (bs, 1H), 2.37-2.63 (m, 3H), 2.14-2.29 (m, 1H), 1.73-2.12 (m, 6H), 1.16-1.74 (m, 13H), 0.96-1.16 (m, 4H), 0.68-0.96 (m, 9H). MS m/z 758.2 (M+1).

Example 3-101

Compound AR00340173

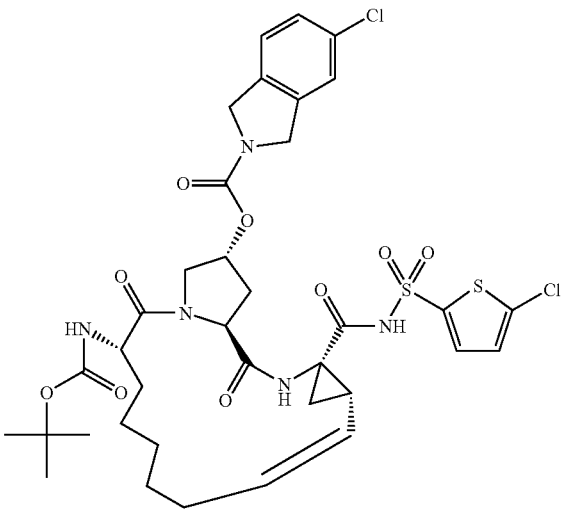

(1S,4R,6S,14S,18R)-5-Chloro-1,3-dihydro-isoindole-2-carboxylic acid 14-tert-butoxycarbonylamino-4-(5-chloro-thiophene-2-sulfonylaminocarbonyl)-2,15-dioxo-3,16-diaza-tricyclo[14.3.0.0$^{4,6}$]nonadec-7-en-18-yl ester (Compound AR00340173) was synthesized according to the procedures described in Example 3-6, except that 5-chloro-thiophene-2-sulfonic acid amide was used to replace cyclopropanesulfonamide, and that 5-chloro-2,3-dihydro-1H-isoindole was used to replace 2,3-dihydro-1H-isoindole instead. $^1$H NMR (400 MHz, CD$_3$CN) δ 8.07 (d, 1H), 7.50 (d, 1H), 7.16-7.32 (m, 3H), 6.98 (d, 1H), 5.86 (bs, 1H), 5.27-5.39 (m, 2H), 4.81-4.92 (m, 1H), 4.58-4.64 (m, 2H), 4.51-4.58 (m, 2H), 4.44 (t, 1H), 4.33 (d, 1H), 4.10-4.20 (m, 1H), 3.73-3.81 (m, 1H), 2.47 (bs, 1H), 2.16-2.41 (m, 3H), 1.63-1.77 (m, 2H), 1.47-1.57 (m, 2H), 1.07-1.47 (m, 17H). MS m/z 724.1 (M+1−Boc)

Example 3-102

Compound AR00340526

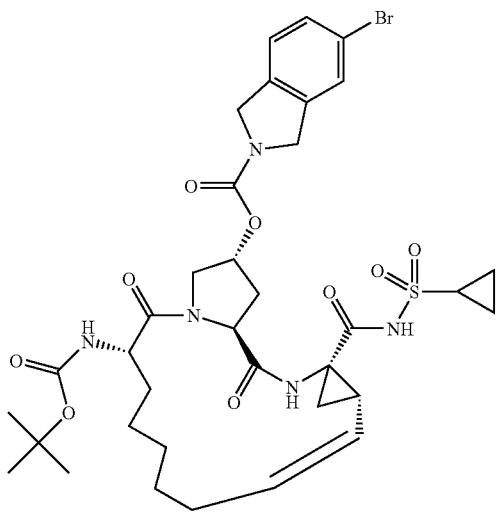

(1S,4R,6S,14S,18R)-5-Bromo-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00340526) was synthesized according to the procedures described in Example 3-6, except that 5-bromo-2,3-dihydro-1H-isoindole was used to replace 2,3-dihydro-1H-isoindole instead. $^1$H NMR (400 MHz, CDCl$_3$) δ 10.31 (bs, 1H), 7.36-7.44 (m, 1H), 6.99-7.32 (m, 3H), 5.70 (q, 1H), 5.42-5.49 (m, 1H), 5.06-5.13 (m, 1H), 4.99 (t, 1H), 4.52-4.78 (m, 5H), 4.32-4.44 (m, 1H), 4.16-4.27 (m, 1H), 3.78-3.89 (m, 1H), 3.33-3.42 (m, 1H), 2.85-2.94 (m, 1H), 2.40-2.64 (m, 3H), 2.20-2.32 (m, 1H), 1.68-1.97 (m, 4H), 1.17-1.67 (m, 16H), 1.01-1.17 (m, 3H), 0.80-0.98 (m, 2H). MS m/z 694.0 (M+1−Boc).

Example 3-103

Compound AR00333462

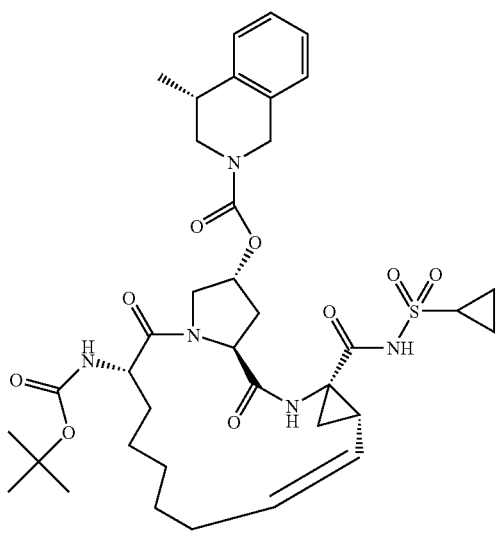

(1S,4R,6S,14S,18R)-4R-Methyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00333462) was synthesized according to the procedures described in Example 3-1, except that 4R-methyl-1,2,3,4-tetrahydro-isoquinoline (prepared according to similar procedures as in Example 1-17a, except that enantiomerically pure starting material was used instead of racemic one) was used to replace 1,2,3,4-tetrahydro-isoquinoline instead. MS m/z 642.2 (M+1−Boc).

Example 3-104

Compound AR00333463

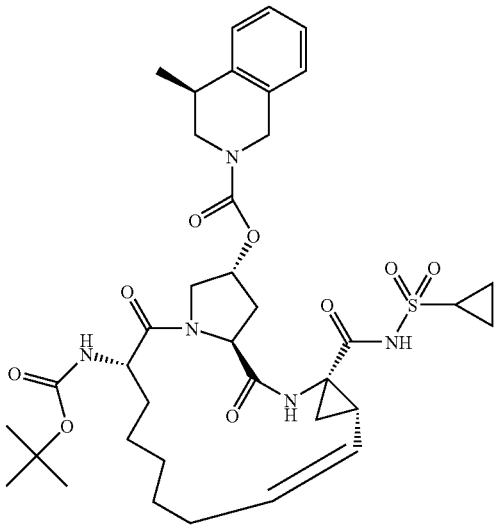

(1S,4R,6S,14S,18R)-4S-Methyl-3,4-dihydro-1H-isoquinoline-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00333463) was synthesized according to the procedures described in Example 3-1, except that 4S-methyl-1,2,3,4-tetrahydro-isoquinoline (prepared according to similar procedures as in Example 1-17a, except that enantiomerically pure starting material was used instead of racemic one) was used to replace 1,2,3,4-tetrahydro-isoquinoline instead. MS m/z 642.2 (M+1−Boc).

Example 3-105

Compound AR00345032

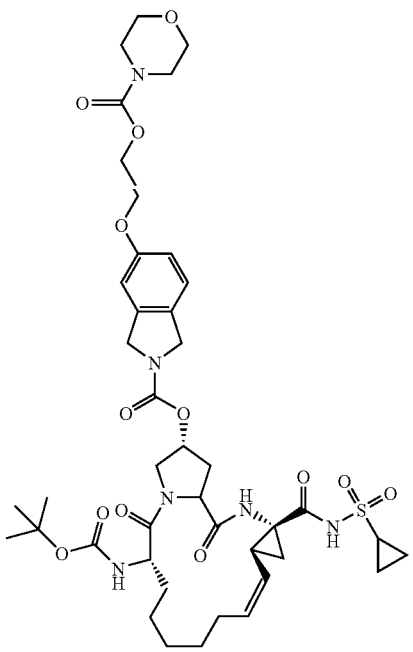

(1S,4R,6S,14S,18R)-5-[2-(Morpholine-4-carbonyloxy)-ethoxy]-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00345032) was synthesized according to the procedures described in Example 3-6, except that morpholine-4-carboxylic acid 2-(2,3-dihydro-1H-isoindol-5-yloxy)-ethyl ester (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI−): m/z 885.4 (M−1).

Example 3-106

Compound AR00345075

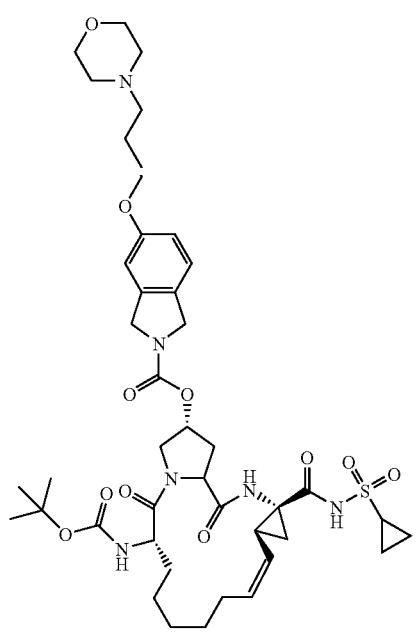

(1S,4R,6S,14S,18R)-5-(3-Morpholin-4-yl-propoxy)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00345075) was synthesized according to the procedures described in Example 3-6, except that 5-(3-Morpholin-4-yl-propoxy)-2,3-dihydro-1H-isoindole (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI−): m/z 855.6 (M−1).

Example 3-107

Compound AR00345090

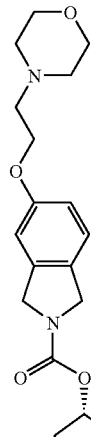
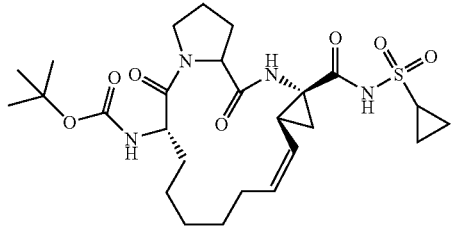

(1S,4R,6S,14S,18R)-5-(2-Morpholin-4-yl-ethoxy)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00345090) was synthesized according to the procedures described in Example 3-6, except that 5-(2-Morpholin-4-yl-ethoxy)-2,3-dihydro-1H-isoindole (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI−): m/z 841.5 (M−1).

Example 3-108

Compound AR00345094

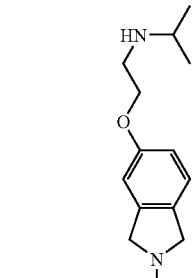
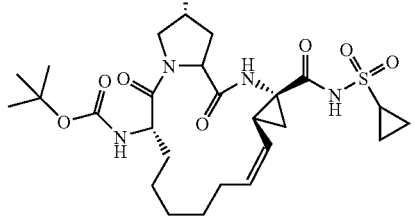

(1S,4R,6S,14S,18R)-5-(2-Isopropylamino-ethoxy)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00345094) was synthesized according to the procedures described in Example 3-6, except that [2-(2,3-Dihydro-1H-isoindol-5-yloxy)-ethyl]-isopropyl-amine (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI–): m/z 813.5 (M–1).

Example 3-109

Compound AR00345095

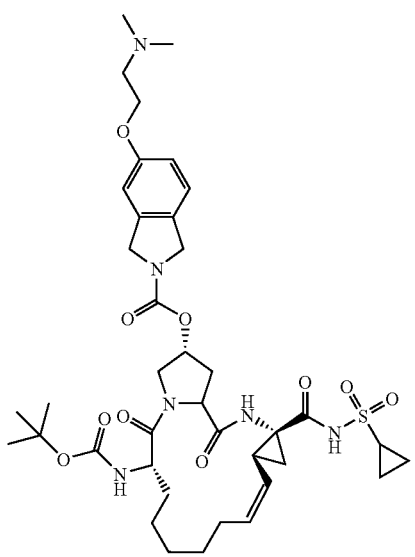

(1S,4R,6S,14S,18R)-5-(2-Dimethylamino-ethoxy)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00345095) was synthesized according to the procedures described in Example 3-6, except that [2-(2,3-Dihydro-1H-isoindol-5-yloxy)-ethyl]-dimethyl-amine (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI–): m/z 799.5 (M–1).

Example 3-110

Compound AR00345096

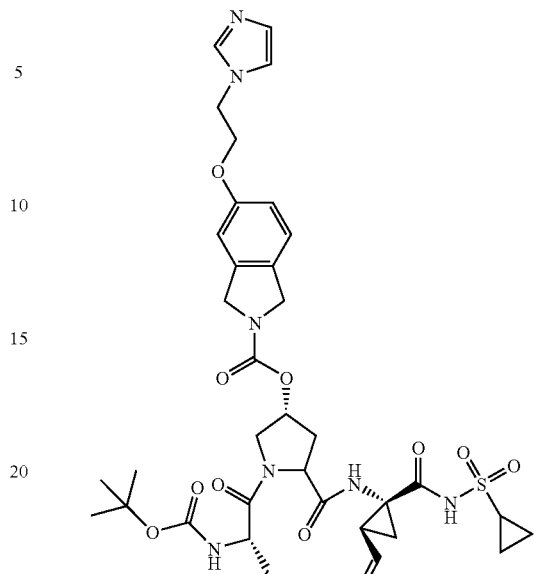

(1S,4R,6S,14S,18R)-5-(2-Imidazol-1-yl-ethoxy)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00345096) was synthesized according to the procedures described in Example 3-6, except that 5-(2-Imidazol-1-yl-ethoxy)-2,3-dihydro-1H-isoindole (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI–): m/z 822.5 (M–1).

Example 3-111

Compound AR00364924

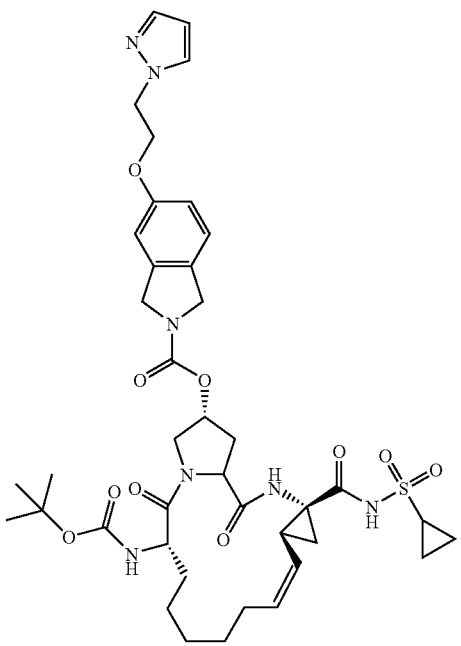

271

(1S,4R,6S,14S,18R)-5-(2-Pyrazol-1-yl-ethoxy)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00364924) was synthesized according to the procedures described in Example 3-6, except that 5-(2-Pyrazol-1-yl-ethoxy)-2,3-dihydro-1H-isoindole (prepared according to the procedures described in J. Med. Chem. 2002, Vol. 45, No. 26, 5771, preparation method D, and in Bioorg. Med. Chem. Lett. 11 (2001) 685-688) was used to replace 2,3-dihydro-1H-isoindole instead. MS (APCI−): m/z 742.1 [(M−100)+18].

Example 3-112

Compound AR00340495

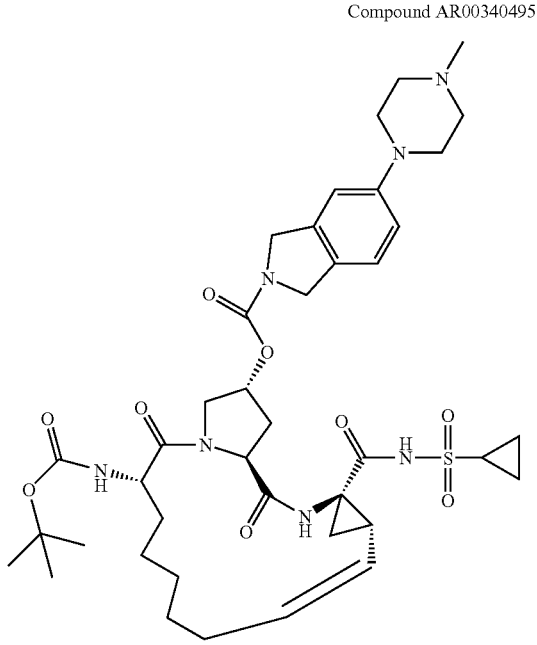

(1S,4R,6S,14S,18R)-5-(4-Methyl-piperazin-1-yl)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00340495) was synthesized by a similar fashion as that described in Example 3-57, substituting 2,3-Dihydro-1H-isoindol-5-ylamine in Step 5 with 5-(4-Methyl-piperazin-1-yl)-2,3-dihydro-1H-isoindole (prepared by a similar fashion as described in: J. Org. Chem. 2000, 65, 1144-1157) instead. $^1$H-NMR (400 MHz, DMSO-d$^6$): 7.72-7.40 (m, 1H), 7.22-7.05 (m, 1H), 6.95-6.70 (m, 2H), 5.55-5.45 (m, 1H), 5.35-5.22 (m, 2H), 4.62-4.50 (m, 4H), 4.40 (m, 1H), 4.30-4.08 (m, 2H), 4.0-3.89 (m, 1H), 3.10 (m, 3H), 2.65 (m, 1H), 2.42 (m, 3H), 2.33-2.20 (m, 6H), 1.85-1.50 (m, 5H), 1.42-1.0 (m, 14H), 0.82-0.55 (m, 4H). MS (APCI+): 712.3 (MH$^+$−Boc)

Example 3-113

Compound AR00365084

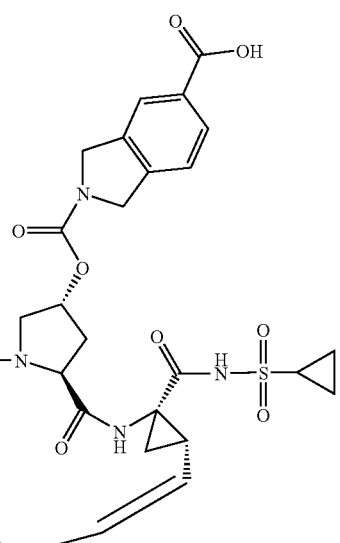

(1S,4R,6S,14S,18R)-1,3-Dihydro-isoindole-2,5-dicarboxylic acid 2-(14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl) ester (Compound AR00365084) was synthesized according to similar procedures described in Example 3-91, except that the product AR00365083 from that example was further hydrolyzed with LiOH in a mixture of THF-MeOH—H$_2$O to give AR00365084. MS: 658 (M−Boc).

Example 3-114

Compound AR00364989

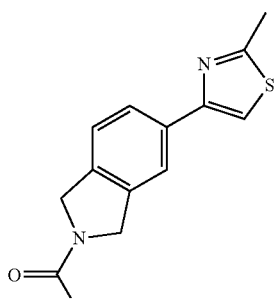

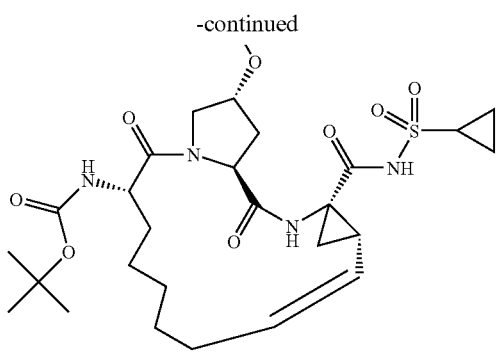

(1S,4R,6S,14S,18R)-5-(2-Methyl-thiazol-4-yl)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00364989) was synthesized by a similar fashion as that described in Example 3-57, substituting 2,3-Dihydro-1H-isoindol-5-ylamine in Step 5 with 5-(2-Methyl-thiazol-4-yl)-2,3-dihydro-1H-isoindole instead. $^1$H NMR (400 MHz, CD$_3$COCD$_3$) δ 10.69 (bs, 1H) 8.32 (bs, 1H), 7.94 (d, 1H) 7.88 (d, 1H) 7.70 (d, 1H) 7.34 (dd, 1H) 6.08-6.16 (m, 1H), 5.69 (q, 1H) 5.45 (bs, 1H) 5.00 (t, 1H) 4.58-4.81 (m, 5H), 4.44-4.53 (m, 1H), 4.12-4.21 (m, 1H), 3.83-3.91 (m, 1H), 2.86-2.97 (m, 1H), 2.57-2.71 (m, 1H), 2.33-2.54 (m, 3H), 1.81-1.96 (m, 2H), 1.75 (dd, 1H) 1.17-1.63 (m, 20H), 1.06-1.17 (m, 1H), 0.94-1.06 (m, 2H). MS m/z 711.2 (M+1−100).

Example 3-114a

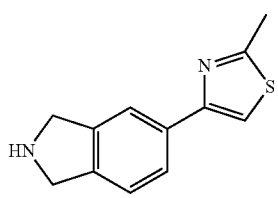

The synthesis of 5-(2-Methyl-thiazol-4-yl)-2,3-dihydro-1H-isoindole was prepared following the experimental of steps A through F in Example 3-115a, utilizing thioacetamide in step E instead.

Example 3-115

Compound AR00365019

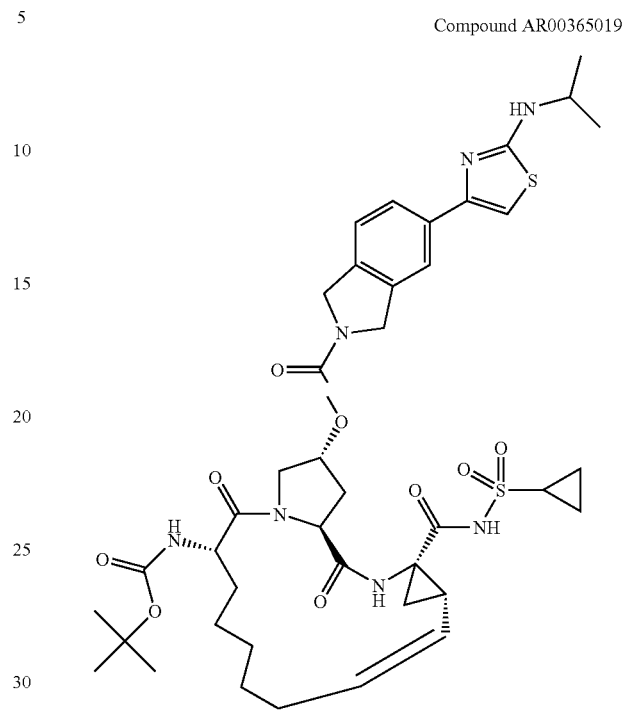

(1S,4R,6S,14S,18R)-5-(2-Isopropylamino-thiazol-4-yl)-1,3-dihydro-isoindole-2-carboxylic acid 14-tert-butoxycarbonylamino-4-cyclopropanesulfonylaminocarbonyl-2,15-dioxo-3,16-diaza-tricyclo[14.3.0.0$^{4,6}$]nonadec-7-en-18-yl ester (Compound AR00365019) was synthesized by a similar fashion as that described in Example 3-57, substituting 2,3-Dihydro-1H-isoindol-5-ylamine in Step 5 with [4-(2,3-Dihydro-1H-isoindol-5-yl)-thiazol-2-yl]-isopropyl-amine instead. $^1$H NMR (400 MHz, CD$_3$COCD$_3$) δ 10.69 (bs, 1H), 8.27-8.36 (m, 1H), 7.28-7.50 (m, 2H) 7.01-7.20 (m, 1H), 6.08-6.15 (m, 1H), 5.70 (q, 1H) 4.45 (bs, 1H) 4.94-5.05 (m, 1H), 4.68-4.76 (m, 4H), 4.59-4.64 (m, 1H) 4.45-4.53 (m, 1H), 4.10-4.20 (m, 1H), 3.81-3.90 (m, 1H) 3.65-3.76 (m, 1H), 2.86-2.98 (m, 1H), 2.63 (bs, 1H), 2.32-2.54 (m, 3H), 1.80-1.94 (m, 2H), 1.70-1.79 (m, 1H) 1.05-1.65 (m, 19H) 0.95-1.05 (m, 2H). MS m/z 754.2 (M+1−100).

Example 3-115a

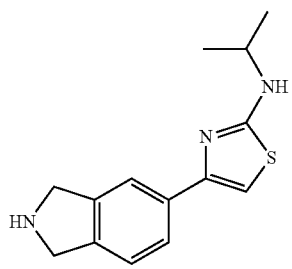

The synthesis of [4-(2,3-Dihydro-1H-isoindol-5-yl)-thiazol-2-yl]-isopropyl-amine is depicted in the following scheme:

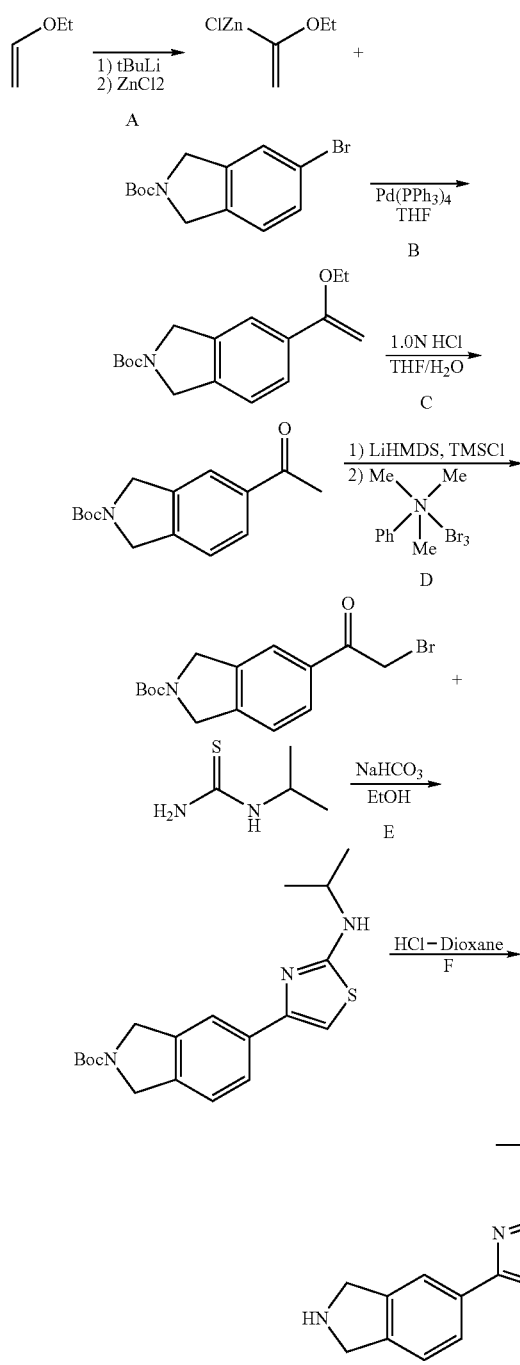

A. To a solution of 4 ml THF and 1 ml ethyl vinyl ether at −78 C, was added t-BuLi (0.79 ml, 1.34 mmol) dropwise. The solution was warmed to r.t. and stirred for 30 minutes. A 0.5 M solution of ZnCl₂ in THF (3.02 ml, 1.51 mmol) was added dropwise and the reaction was stirred at r.t. for 30 minutes. This mixture was used without further purification.

B. To solution of the aryl bromide (0.200 g, 0.67 mmol) and Pd(PPh₃)₄ (39 mg, 0.33 mmol) dissolved in THF under N₂ was cannulated the crude vinyl zinc species from step A. The reaction was heated at 50° C. for 36 hours, and the then filtered through a plug of Al₂O₃ with aid of EtOAc and concentrated to give an oil which was used without further purification.

C. The crude oil from step B was dissolved in THF (2 ml) and 1.0N HCl (2 ml) and stirred for one hour. The reaction was taken up in EtOAc and separated, and the organic layer was washed with saturated NaHCO₃ and brine, and dried over Na₂SO₄ and concentrated to an orange oil. This oil was chromatographed with 5:1 hex:EtOAc to give a white solid (95 mg, 54%)

D. To a solution of 1.0 M LiHMDS (4.0 ml, 4.0 mmol) under N₂ at −78° C., was added TMSCl (3.38 ml, 26.6 mmol) dropwise. To this solution was added the ketone from step C in 3 ml THF. The reaction was stirred at −78° C. for 30 minutes and warmed to 0° C. The PTTB (1.10 g, 2.93 mmol) was added and the reaction was stirred for 30 minutes at 0° C., concentrated to a solid, and taken up in EtOAc and water. The organic was washed with water and brine, and dried over Na₂SO₄ and concentrated, and the oil was purified with 5:1 Hex:EtOAc to give a yellow solid (0.64 g, 71%).

E. A slurry of the bromoketone (75 mg, 0.22 mmol), Na₂CO₃ (37 mg, 0.44 mmol) and 1-isopropyl thiourea (26 mg, 22 mmol) in EtOH was heat at reflux for 30 minutes. The reaction was taken up in EtOAc and separated, and the organic layer was washed with saturated NaHCO₃ and brine, and dried over Na₂SO₄ and concentrated a yellow oil. The oil was purified with 3:1 Hex:MTBE to give a clear oil (77 mg, 97%).

F. The Boc-amine from step E stirred in 4N HCl/dioxane (2.0 ml) for one hour and concentrated to a white solid. This solid was taken up in 0.1NHCl and washed with DCM. The aqueous layer was basified with 1.0N NaOH and extracted with DCM, dried, and concentrated and used without further purification.

Preparation of Macrocyclic Aminoproline Intermediate:

Example 4-1

Synthesis of (1S,4R,6S,14S,18R)-18-amino-14-tert-butoxycarbonylamino-2,15-dioxo-3,16-diaza-tricyclo[14.3.0.0⁴,⁶]nonadec-7-ene-4-carboxylic acid ethyl ester.

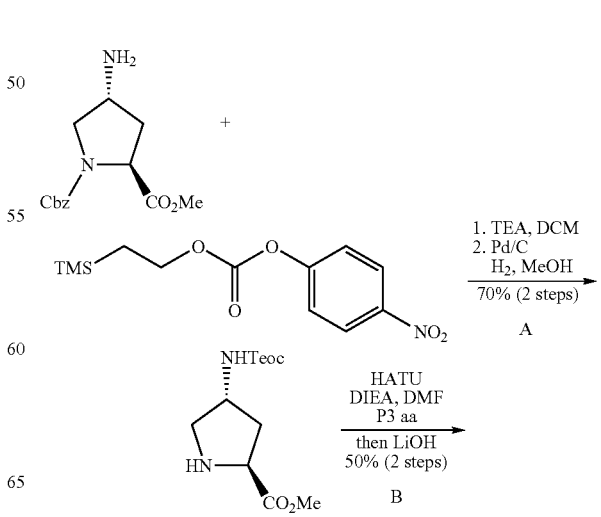

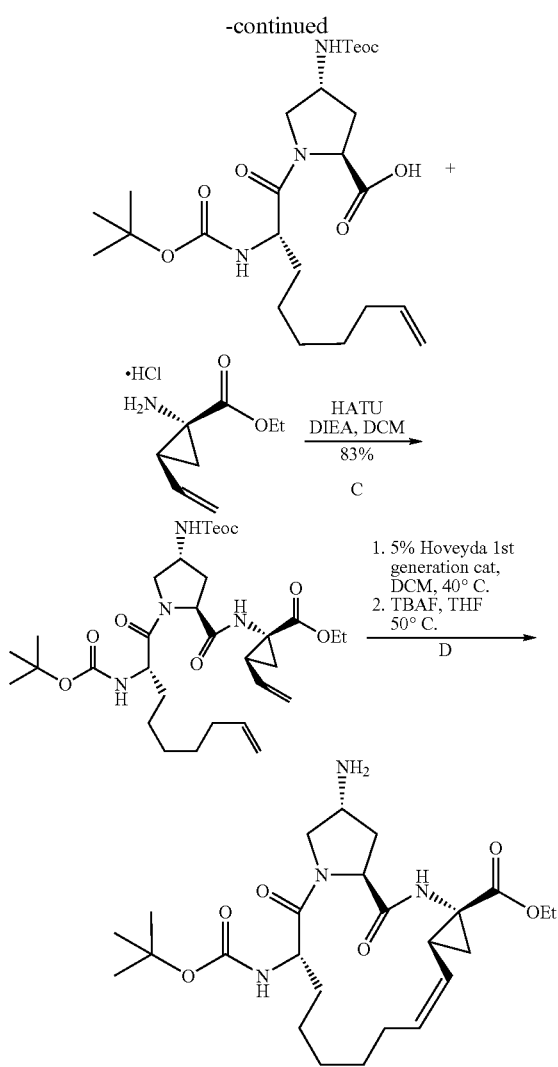

diluted with ethyl acetate (150 ml), washed with 1N aqueous HCl (2×100 ml), dried over magnesium sulfate and concentrated. Silica gel chromatography gave an oil which was stirred with lithium hydroxide (0.28 g, 6.76 mmol) in methanol (5 ml) for 2 h. The reaction was diluted with methylene chloride and washed with 1N aqueous HCl, dried over magnesium sulfate and concentrated to give 1.2 g (49%) of the product.

C To 1(R)-tert-butoxycarbonylamino-2(S)-vinyl-cyclopropanecarboxylic acid ethyl ester (0.70 g, 2.75 mmol) was added 4N HCl/dioane solution (2.87 ml, 11.46 mmol). After stirring for 2 h, the reaction was concentrated to give a solid. To this solid was added 1-(2(S)-tert-butoxycarbonylamino-non-8-enoyl)-4(R)-(2-trimethylsilylethyl carbonylamino)-pyrrolidine-2(S)-carboxylic acid (1.21 g, 2.29 mmol), HATU (1.05 g, 2.75 mmol) and diisopropylethylamine (1.60 ml, 9.17 mmol) and methylene chloride (10 ml) and the reaction was stirred for 18 h at room temperature. The reaction was placed onto silica gel and eluted with a solution of 50% ethyl acetate/hexanes to give the product as a colorless oil (1.27 g, 83%). 665(H+)

D A solution of 1-{[1-(2(S)-tert-butoxycarbonylamino-non-8-enoyl)-4(R)-(2-trimethylsilylethyl carbonylamino)-pyrrolidine-2(S)-carbonyl]-amino}-2(S)-vinyl-cyclopropane-1-(R)-carboxylic acid ethyl ester (1.27 g, 1.91 mmol) in methylene chloride (195 ml) was degassed for 1 h by bubbling $N_2$ throughout the solution. Dichloro(o-isopropoxyphenylmethyene)(tricyclohexylphosphine)ruthenium (II) (0.057 g, 0.096 mmol) was added and the reaction stirred at 40° C. for 16 h. The reaction was concentrated, placed onto silica gel and eluted with 50% ethyl acetate/hexanes. The resulting oil was treated with TBAF (1.0 M in THF, 2.87 ml) and heated to 50° C. for 4 h. The reaction was placed onto silica gel and eluted with 20% methanol/methyene chloride to give a tan solid (0.65 g, 69%). $^1$H NMR (CDCl$_3$, 400 MHz): δ 1.06-1.66 (m, 17H), 1.85-1.95 (m, 2H), 2.0-2.1 (m, 1H), 2.1-2.2 (m, 1H), 2.2-2.3 (m, 1H), 2.65-2.75 (M, 1H), 3.40 (m, 1H), 3.73-3.83 (m, 2H), 4.08-4.19 (m, 2H), 4.56 (m, 1H), 4.78 (d, J=5.5 Hz, 1H), 5.20 (t, J=8.1 Hz, 1H), 5.34 (d, J=8.1 Hz, 1H), 5.47 (dt, J=4.5, 10.8 Hz, 1H), 7.08 (s, 1H). 493(H+).

Preparation of Compounds with General Structure V

A. To a solution of (2S,4R)-4-amino-1-[benzyloxycarbonyl]pyrrolidine-2-methylcarboxlate hydrochloride (2.00 g, 2.34 mmol) in methylene chloride (25 ml) was added 2-(trimethyl silyl)ethyl p-nitrophenyl carbonate (1.98 g, 6.99 mmol) and triethylamine (1.81 ml, 13.34 mmol). The reaction was stirred for 3 days, placed onto silica gel and the product eluted with 40% EtOAc/hexanes to give a colorless oil. The oil was dissolved in methanol (20 ml) and stirred with 10% palladium on carbon under a balloon of hydrogen gas. After stirring for 4 h, the reaction was filtered and concentrated. The resulting solid was dissolved in 1N aqueous HCl (75 ml) and extracted with methylene chloride (75 ml). The aqueous layer was made basic by the addition of sodium hydroxide and again extracted with methylene chloride (100 ml). Both organic extractions were combined, concentrated, and the resulting residue purified by silica gel chromatography eluting with 10% methanol/methylene chloride to give a brownish solid (1.29 g, 70%). LCMS=289(H+).

B A solution of 4(R)-(2-trimethylsilylethyl carbonylamino)-pyrrolidine-2(S)-carboxylic acid methyl ester (1.29 g, 4.50 mmol), 2(S)-tert-butoxycarbonylamino-non-8-enoic acid (1.22 g, 4.51 mmol), HATU (2.06 g, 5.41 mmol) and diisopropylethylamine (1.18 ml, 6.76 mmol) in dimethylformamide (10 ml) was stirred overnight. The reaction was

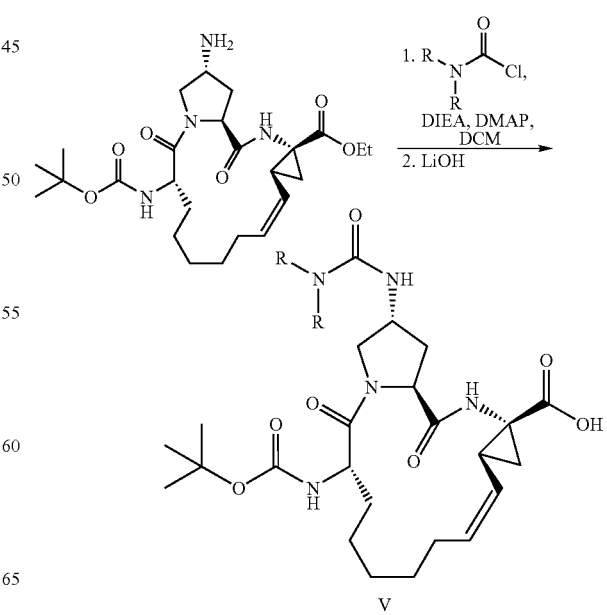

Example 5-1

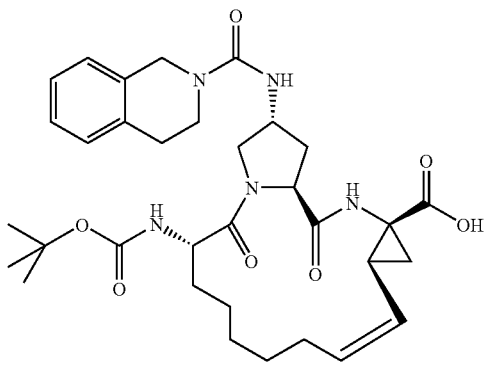

Compound AR00287262

Synthesis of (1S,4R,6S,14S,18R)-14-tert-butoxycarbonylamino-18-[(3,4-dihydro-1H-isoquinoline-2-carbonyl)-amino]-2,15-dioxo-3,16-diaza-tricyclo[14.3.0.0$^{4,6}$]nonadec-7-ene-4-carboxylic acid (Compound AR00287262)

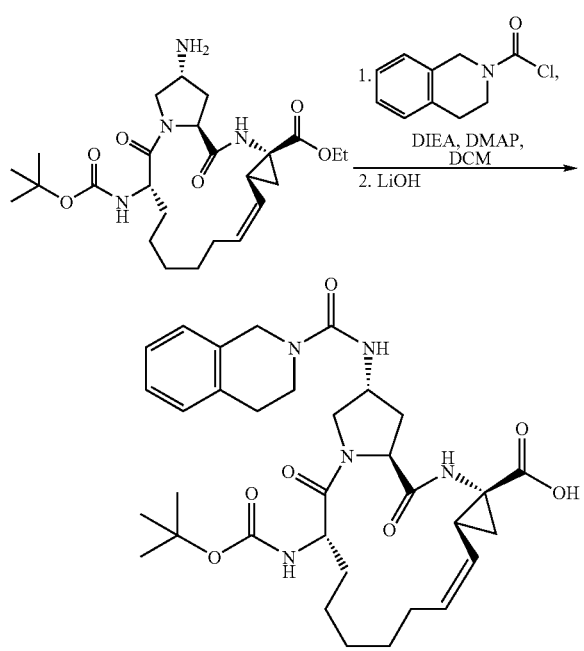

A solution of 3,4-dihydro-1H-isoquinoline-2-carbonyl chloride (0.030 g, 0.152 mmol), (1S,4R,6S,14S,18R)-18-amino-14-tert-butoxycarbonylamino-2,15-dioxo-3,16-diaza-tricyclo[14.3.0.0$^{4,6}$]nonadec-7-ene-4-carboxylic acid ethyl ester (0.025 g, 0.050 mmol), DIEA (0.027 ml, 0.153 mmol) and a catalytic amount of DMAP were stirred together in methylene chloride (0.3 ml) for 18 h. The reaction was placed onto silica gel and the product eluted with 40% acetone/hexanes and isolated as a white solid. The solid was dissolved in methanol and treated with lithium hydroxide (0.011 g, 0.254 mmol) and 1 drop of water. After stirring for 5 h, the reaction was diluted with methylene chloride (30 ml), washed with 1N aqueous HCl (30 ml), brine (30 ml), dried over magnesium sulfate and concentrated to give the title compound as a white solid. LCMS=624 (MH+).

The following compound was also prepared using the procedure described in Example 5-1, substituting 1,3-dihydro-isoindole-2-carbonyl chloride for 3,4-dihydro-1H-isoquinoline-2-carbonyl chloride. LCMS=610(H+)

Example 5-2

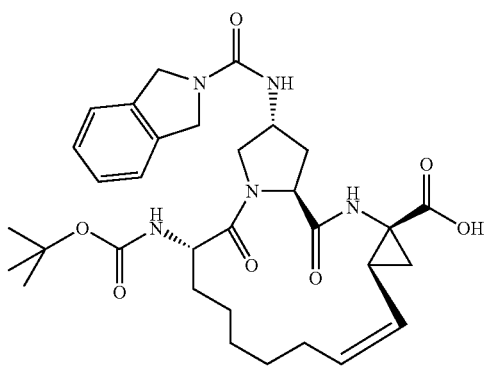

Compound AR00298980

(1S,4R,6S,14S,18R)-14-tert-Butoxycarbonylamino-18-[(1,3-dihydro-isoindole-2-carbonyl)-amino]-2,15-dioxo-3,16-diaza-tricyclo[14.3.0.0$^{4,6}$]nonadec-7-ene-4-carboxylic acid (Compound AR00298980) was prepared according to the procedures described in Example 5-1, substituting 3,4-Dihydro-1H-isoquinoline-2-carbonyl chloride with 1,3-Dihydro-isoindole-2-carbonyl chloride. MS m/e 608.2 (M−1).

Example 5-3

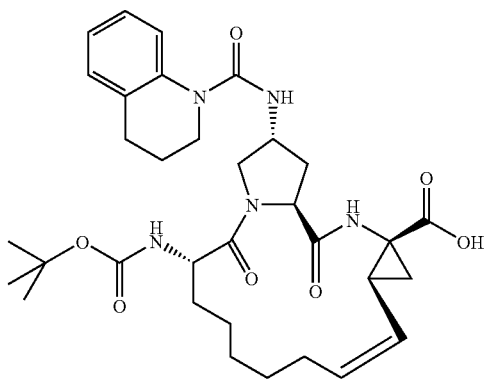

Compound AR00304160

(1S,4R,6S,14S,18R)-14-tert-Butoxycarbonylamino-18-[(3,4-dihydro-2H-quinoline-1-carbonyl)-amino]-2,15-dioxo-3,16-diaza-tricyclo[14.3.0.0$^{4,6}$]nonadec-7-ene-4-carboxylic acid (Compound AR00304160) was prepared according to the procedures described in Example 5-1, substituting 3,4-Dihydro-1H-isoquinoline-2-carbonyl chloride with 3,4-Dihydro-2H-quinoline-1-carbonyl chloride. MS m/e 524.3 (M$^+$+1−100).

Preparation of Compounds with General Structure VI

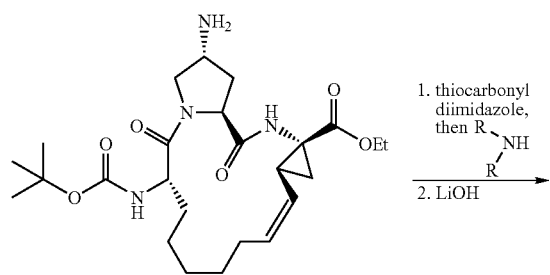

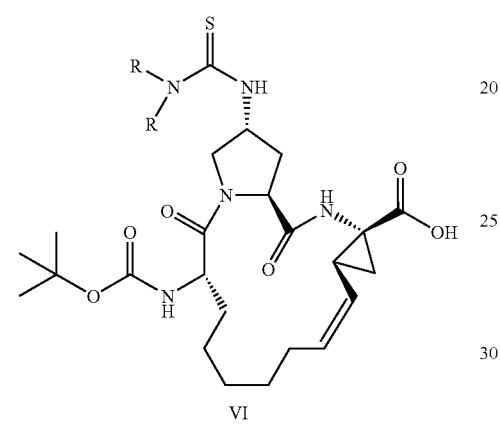

VI

Example 6-1

Compound AR00304010

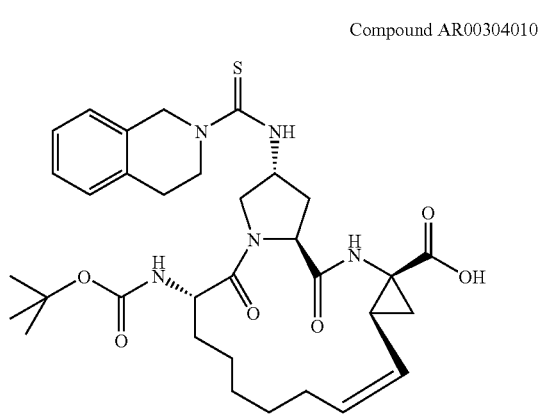

(1S,4R,6S,14S,18R)-14-tert-Butoxycarbonylamino-18-[(3,4-dihydro-1H-isoquinoline-2-carbothioyl)-amino]-2,15-dioxo-3,16-diaza-tricyclo[14.3.0.0$^{4,6}$]nonadec-7-ene-4-carboxylic acid (Compound AR00304010) was prepared using the same procedure described in Step 4 of example 1-2, except that carbonyl diimidazole was substituted by thiocarbonyl diimidazole. LCMS=640(H+). MS m/e 640.1 (M$^+$+1).

Preparation of Compounds with General Structure VII

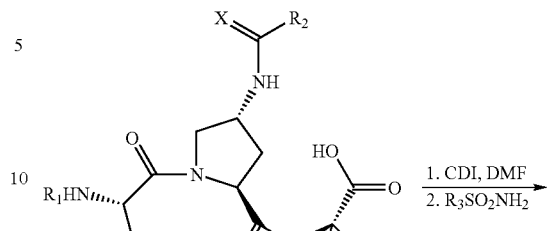

(X = O, S)

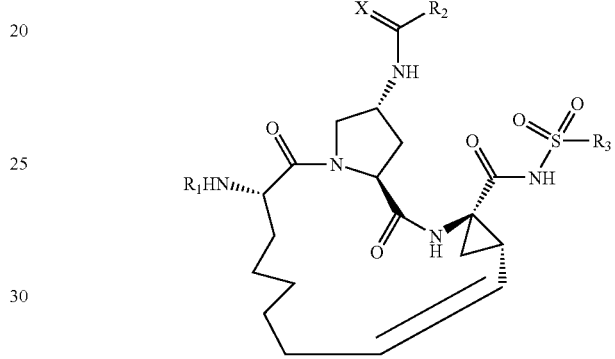

VII

Example 7-1

Compound AR00287266

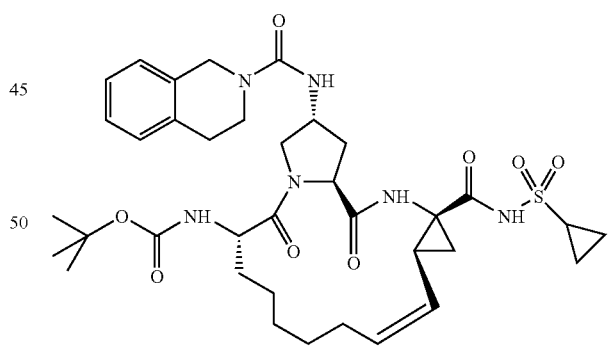

Synthesis of (is, 4R, 6S, 14S, 18R)-{4-Cyclopropanesulfonylaminocarbonyl-18-[(3,4-dihydro-1H-isoquinoline-2-carbonyl)-amino]-2,15-dioxo-3,16-diaza-tricyclo[14.3.0.0$^{4,6}$] nonadec-7-en-14-yl}-carbamic acid tert-butyl ester (Compound AR00287266) was prepared according to the same procedures as described in Example 3-1, starting from the acid prepared from the procedures described in Example 5-1. MS m/e 727.0 (M$^+$+1).

Example 7-2

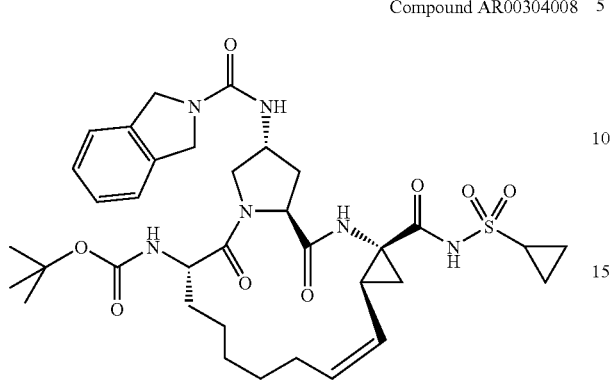

Compound AR00304008

(1S,4R,6S,14S,18R)-{4-Cyclopropanesulfonylaminocarbonyl-18-[(1,3-dihydro-isoindole-2-carbonyl)-amino]-2,15-dioxo-3,16-diaza-tricyclo[14.3.0.0$^{4,6}$]nonadec-7-en-14-yl}-carbamic acid tert-butyl ester (Compound AR00304008) was prepared according to the same procedures as described in Example 3-1, starting from the acid prepared from the procedures described in Example 5-2. MS m/e 613.2 (M$^+$+1−100).

Example 7-3

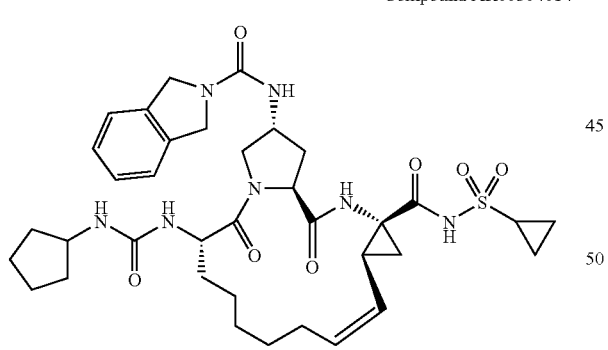

Compound AR00304014

(1S,4R,6S,14S,18R)-1,3-Dihydro-isoindole-2-carboxylic acid [14-(3-cyclopentyl-ureido)-4-cyclopropanesulfonylaminocarbonyl-2,15-dioxo-3,16-diaza-tricyclo[14.3.0.0$^{4,6}$]nonadec-7-en-18-yl]-amide (Compound AR00304014) was prepared according to the same procedures as described in Example 2-24, starting from the acylsulfonamide prepared from the procedures described in Example 7-4. MS m/e 724.2 (M$^+$+1).

Example 7-4

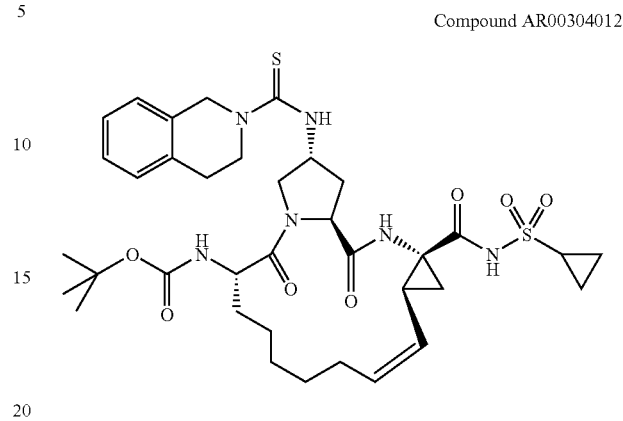

Compound AR00304012

(1S,4R,6S,14S,18R)-{4-Cyclopropanesulfonylaminocarbonyl-18-[(3,4-dihydro-1H-isoquinoline-2-carbothioyl)-amino]-2,15-dioxo-3,16-diaza-tricyclo[14.3.0.0$^{4,6}$]nonadec-7-en-14-yl}-carbamic acid tert-butyl ester (Compound AR00304012) was prepared according to the same procedures as described in Example 3-1, starting from the acid prepared from the procedures described in Example 6-1. MS m/e 743.0 (M$^+$+1).

Example 7-5

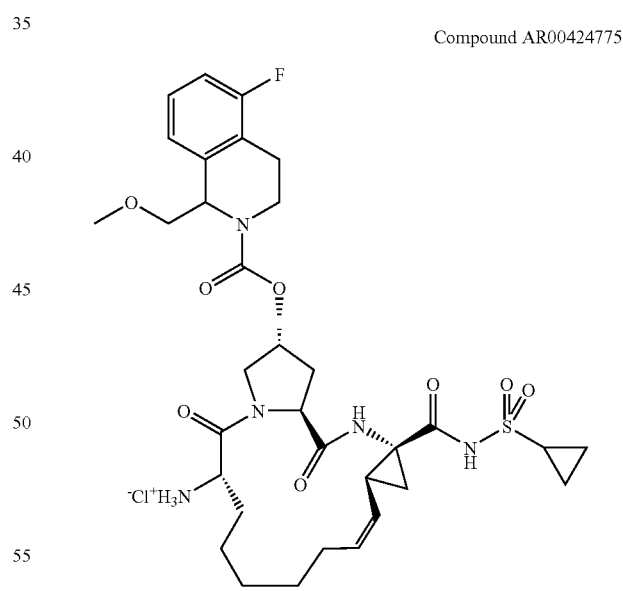

Compound AR00424775

(1S,4R,6S,14S,18R)-5-Fluoro-1-methoxymethyl-3,4-dihydro-1H-isoquinoline-2-carboxylic acid 14-amino-4-cyclopropanesulfonylaminocarbonyl-2,15-dioxo-3,16-diaza-tricyclo[14.3.0.0$^{4,6}$]nonadec-7-en-18-yl ester, HCl salt (Compound AR00424775) was synthesized by taking up AR00335293 (84 mg) in 0.5 mL of 4 M HCl/Dioxane and stirred at rt for 16 h. Reaction was then concentrated and taken up in acetonitrile for concentration again. The hydrochloride salt was then dried overnight on a high vacuum pump to give product as a white solid ester 80 mg. +APCI MS m/z 690.1 (M+1).

Example 7-6

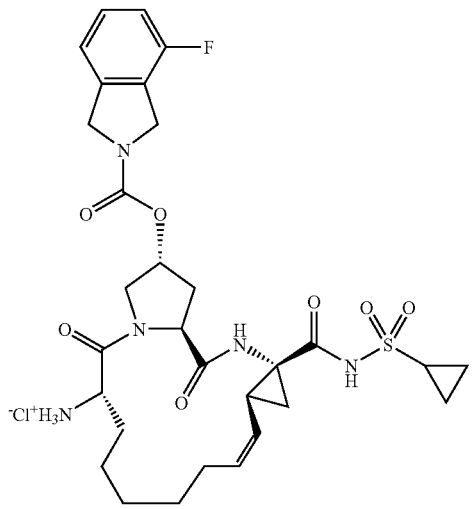

Compound AR00424874

(1S,4R,6S,14S,18R)-4-Fluoro-1,3-dihydro-isoindole-2-carboxylic acid 14-amino-4-cyclopropanesulfonylaminocarbonyl-2,15-dioxo-3,16-diaza-tricyclo[14.3.0.0$^{4,6}$]nonadec-7-en-18-yl ester, HCl salt (Compound AR00424874) was synthesized by taking up AR00334191 (98 mg) was taken up in 0.5 mL of 4 M HCl/Dioxane and stirred at rt for 16 h. Reaction was then concentrated and taken up in acetonitrile for concentration again. The hydrochloride salt was then dried overnight on a high vacuum pump to give product as a white solid (89 mg). +APCI MS m/z 632.1 (M+1).

Example 8

NS3-NS4A protease assay

NS3 complex formation with NS4A-2

Recombinant *E. coli* or Baculovirus full-length NS3 was diluted to 3.33 µM with assay buffer and the material transferred to an eppendorf tube and place in water bath in 4° C. refrigerator. The appropriate amount of NS4A-2 to 8.3 mM in assay buffer was added to equal the volume of NS3 in step 2.1.1 (conversion factor –3.8 mg/272 µL assay buffer). The material was transferred to an eppendorf tube and placed in a water bath in a 4° C. refrigerator.

After equilibration to 4° C., equal volumes of NS3 and NS4A-2 solutions were combined in an eppendorf tube, mixed gently with a manual pipettor, and the mixture incubated for 15 minutes in the 4° C. water bath. Final concentrations in the mixture were 1.67 µM NS3, 4.15 mM NS4A-2 (2485-fold molar excess NS4A-2).

After 15 minutes at 4° C., the NS3/NS4A-2 eppendorf tube was removed and placed in a room temperature water bath for 10 minutes. NS3/NS4A-2 was aliquoted at appropriate volumes and store at –80° C. (*E. coli* NS3 run at 2 nM in assay, aliquot at 25 µL. BV NS3 run at 3 nM in assay, aliquot at 30 µL.

NS3 inhibition assay

Step 2.2.5. Sample compounds were dissolved to 10 mM in DMSO then diluted to 2.5 mM (1:4) in DMSO. Typically, compounds were added to an assay plate at 2.5 mM concentration, yielding upon dilution a starting concentration of 50 microM in the assay inhibition curve. Compounds were serial diluted in assay buffer to provide test solutions at lower concentrations.

Step 2.2.6. The *E. coli* NS3/NS4A-2 was diluted to 4 nM NS3 (1:417.5 of 1.67 µM stock–18 µL 1.67 µM stock+7497 µL assay buffer).

The BV NS3/NS4A-2 was diluted to 6 nM NS3 (1:278.3 of 1.67 µM stock–24 µL 1.67 µM stock+6655 µL assay buffer).

Step 2.2.7. Using the manual multichannel pipettor, and being careful not to introduce bubbles into the plate, 50 µL assay buffer was added to wells A01-H01 of a black Costar 96-well polypropylene storage plate.

Step 2.2.8. Using the manual multichannel pipettor, and being careful not to introduce bubbles into the plate, 50 µL of diluted NS3/NS4A-2 from step 2.2.6 was added to wells A02-H12 of plate in step 2.2.7.

Step 2.2.9. Using the manual multichannel pipettor, and being careful not to introduce bubbles into the plate, 25 µL of the wells in drug dilution plate in step 2.2.5 were transferred to corresponding wells in assay plate in step 2.2.8. The tips on multichannel pipettor were changed for each row of compounds transferred.

Step 2.2.10. Using the manual multichannel pipettor, and being careful not to introduce bubbles into the plate, the wells from the assay plate in step 2.2.9 were mixed by aspirating and dispensing 35 µL of the 75 µL in each well five times. The tips on multichannel pipettor were changed for each row of wells mixed.

Step 2.2.11. The plate was covered with a polystyrene plate lid, and the plate from step 2.2.10 containing NS3 protease and sample compounds was pre-incubated 10 minutes at room temperature.

While the plate from step 2.2.11 was pre-incubating, the RETS1 substrate was diluted in a 15 mL polypropylene centrifuge tube. The RETS1 substrate was diluted to 8 µM (1:80.75 of 646 µM stock–65 µL 646 µM stock+5184 µL assay buffer).

After the plate in step 2.2.11 was done pre-incubating, and using the manual multichannel, 25 µL of substrate was added to all wells on the plate. The contents of the wells were quickly mixed, as in step 2.2.10, but mixing 65 µL of the 100 µL in the wells.

The plate was read in kinetic mode on the Molecular Devices SpectraMax Gemini XS plate reader. Reader settings: Read time: 30 minutes, Interval: 36 seconds, Reads: 51, Excitation λ: 335 nm, Emission λ: 495 nm, cutoff: 475 nm, Automix: off, Calibrate: once, PMT: high, Reads/well: 6, Vmax pts: 21 or 28/51 depending on length of linearity of reaction.

$IC_{50}$s were determined using a four parameter curve fit equation, and converted to Ki's using the following Km's:
Full-length *E. coli* NS3-2.03 µM
Full-length BV NS3-1.74 µM
where $Ki=IC_{50}/(1+[S]/Km))$ Quantitation by ELISA of the Selectable Marker Protein, Neomycin Phosphotransferase II (NPTII) in the HCV Sub-Genomic Replicon, GS4.3

The HCV sub-genomic replicon (1377/NS3-3', accession No. AJ242652), stably maintained in HuH-7 hepatoma cells, was created by Lohmann et al. Science 285: 110-113 (1999).

The replicon-containing cell culture, designated GS4.3, was obtained from Dr. Christoph Seeger of the Institute for Cancer Research, Fox Chase Cancer Center, Philadelphia, Pa.

GS4.3 cells were maintained at 37° C., 5% $CO_2$, in DMEM (Gibco 11965-092) supplemented with L-glutamine 200 mM (100×) (Gibco25030-081), non-essential amino acids (NEAA)(Biowhittaker 13-114E), heat-inactivated (HI) Fetal Bovine Serum(FBS)(Hyclone SH3007.03) and 750 μg/ml geneticin (G418)(Gibco 10131-035). Cells were sub-divided 1:3 or 4 every 2-3 days.

24 hours prior to the assay, GS4.3 cells were collected, counted, and plated in 96-well plates (Costar 3585) at 7500 cells/well in 100 μl standard maintenance medium (above) and incubated in the conditions above. To initiate the assay, culture medium was removed, cells were washed once with PBS (Gibco 10010-023) and 90 μl Assay Medium (DMEM, L-glutamine, NEAA, 10% HI FBS, no G418) was added. Inhibitors were made as a 10× stock in Assay Medium, (3-fold dilutions from 10 μM to 56 μM final concentration, final DMSO concentration 1%), 10 μl were added to duplicate wells, plates were rocked to mix, and incubated as above for 72 h.

An NPTII ELISA kit was obtained from AGDIA, Inc. (Compound direct ELISA test system for Neomycin Phosphotransferase II, PSP 73000/4800). Manufacturer's instructions were followed, with some modifications. 10×PEB-1 lysis buffer was made up to include 500 μM PMSF (Sigma P7626, 50 mM stock in isopropanol). After 72 h incubation, cells were washed once with PBS and 150 μl PEB-1 with PMSF was added per well. Plates were agitated vigorously for 15 minutes, room temperature, then frozen at −70° C. Plates were thawed, lysates were mixed thoroughly, and 100 μl were applied to an NPTII Elisa plate. A standard curve was made. Lysate from DMSO-treated control cells was pooled, serially diluted with PEB-1 with PMSF, and applied to duplicate wells of the ELISA plate, in a range of initial lysate amount of 150u1-2.5 ul. In addition, 100 μl buffer alone was applied in duplicate as a blank. Plates were sealed and gently agitated at room temperature for 2 h. Following capture incubation, the plates were washed 5×300 μl with PBS-T (0.5% Tween-20, PBS-T was supplied in the ELISA kit). For detection, a 1× dilution of enzyme conjugate diluent MRS-2 (5×) was made in PBS-T, into which 1:100 dilutions of enzyme conjugates A and B were added, as per instructions. Plates were resealed, and incubated with agitation, covered, room temperature, for 2 h. The washing was then repeated and 100 μl of room temperature TMB substrate was added. After approximately 30 minutes incubation (room temperature, agitation, covered), the reaction was stopped with 50 μl 3M sulfuric acid. Plates were read at 450 nm on a Molecular Devices Versamax plate reader.

Inhibitor effect was expressed as a percentage of DMSO-treated control signal, and inhibition curves were calculated using a 4-parameter equation: $y=A+((B-A)/(1+((C/x)^D)))$, where C is half-maximal activity or $EC_{50}$.

Examples of Activity:

Wherein:

A indicates an IC50 or EC50, as indicated, of less than 50 μM

B indicates an IC50 or EC50, as indicated, of less than 10 μM

C indicates an IC50 or EC50, as indicated, of less than 1 μM and D indicates an IC50 or EC50, as indicated, of less the 0.1 μM

TABLE 2

| Compound | NS3-NS4A $IC_{50}$ | Replicon $EC_{50}$ | Compound | NS3-NS4A $IC_{50}$ | Replicon $EC_{50}$ |
|---|---|---|---|---|---|
| AR00220042 | C | B | AR00301383 | B | N/A |
| AR00220122 | A | N/A | AR00301745 | C | B |
| AR00226824 | B | N/A | AR00301746 | D | D |
| AR00226825 | B | N/A | AR00301747 | D | D |
| AR00247310 | C | N/A | AR00301749 | C | B |
| AR00248687 | C | N/A | AR00301751 | D | D |
| AR00248688 | B | N/A | AR00304000 | C | B |
| AR00248689 | C | N/A | AR00304008 | D | D |
| AR00254906 | D | C | AR00304010 | C | B |
| AR00261407 | D | C | AR00304012 | D | C |
| AR00261408 | D | D | AR00304014 | D | D |
| AR00261409 | D | B | AR00304062 | B | N/A |
| AR00282131 | D | D | AR00304063 | C | B |
| AR00287262 | B | N/A | AR00304065 | C | B |
| AR00287266 | D | C | AR00304066 | C | B |
| AR00291871 | D | C | AR00304067 | C | B |
| AR00291875 | C | B | AR00304072 | C | B |
| AR00294376 |  |  | AR00304073 | C | B |
| AR00294377 | C | B | AR00304074 | C | B |
| AR00294378 | C | B | AR00304075 | C | B |
| AR00294381 | D | D | AR00304076 | D | C |
| AR00294382 | C | N/A | AR00304077 | D | B |
| AR00294383 | B | N/A | AR00304078 | D | C |
| AR00294384 | C | B | AR00304079 | D | C |
| AR00294980 | B | N/A | AR00304080 | D | D |
| AR00298989 | B | N/A | AR00304081 | D | C |
| AR00298990 | B | N/A | AR00304082 | D | D |
| AR00298996 | D | D | AR00304103 | B | B |
| AR00298997 | D | D | AR00304125 | C | B |
| AR00301338 | D | B | AR00304126 | C | B |
| AR00304183 | A | N/A | AR00304127 | C | B |
| AR00311814 | D | B | AR00304154 | B | N/A |
| AR00311815 | D | C | AR00304158 | A | N/A |
| AR00312023 | C | N/A | AR00304160 | A | N/A |
| AR00312024 | D | D | AR00304161 | D | D |
| AR00312025 | D | D | AR00304162 | D | D |
| AR00312026 | D | D | AR00304163 | D | D |
| AR00314578 | C | N/A | AR00320123 | C | B |
| AR00314635 | D | D | AR00320220 | D | D |
| AR00314654 | D | D | AR00320221 | C | N/A |
| AR00314656 | D | D | AR00320222 | D | B |
| AR00314685 | A | N/A | AR00320403 | D | C |
| AR00314719 | D | D | AR00320445 | B | N/A |
| AR00315997 | C | B | AR00320446 | D | D |
| AR00315998 | C | B | AR00320447 | D | C |
| AR00315999 | C | B | AR00320448 | C | B |
| AR00320001 | D | D | AR00320449 | D | B |
| AR00320002 | C | B | AR00320450 | C | B |
| AR00320073 | D | D | AR00320506 | D | D |
| AR00320074 | D | B | AR00320547 | D | D |
| AR00320075 | C | B | AR00320548 | D | D |
| AR00320076 | C | B | AR00320549 | D | D |
| AR00320077 | C | B | AR00320556 | D | D |
| AR00320078 | D | B | AR00320557 | D | D |
| AR00320079 | D | D | AR00320574 | D | D |
| AR00320080 | D | C | AR00320575 | D | C |
| AR00320081 | D | D | AR00320576 | B | N/A |
| AR00320082 | D | D | AR00320577 | C | B |
| AR00320119 | D | D | AR00320578 | D | D |
| AR00320120 | D | D | AR00320579 | D | D |
| AR00320121 | D | D | AR00320580 | D | D |
| AR00320122 | C | B | AR00320581 | D | D |
| AR00324375 | C | C | AR00320582 | D | D |
| AR00334286 | D | D | AR00320774 | D | C |
| AR00334385 | D | D | AR00333833 | D | D |
| AR00365387 | D | D | AR00334191 | D | D |
| AR00365425 | D | N/A | AR00340479 | D | D |
| AR00365572 | D | D | AR00365388 | D | N/A |
| AR00333802 | D | D | AR00365426 | D | B |
| AR00334188 | D | C | AR00333801 | D | D |
| AR00334248 | D | C | AR00333803 | D | C |
| AR00334250 | D | D | AR00334247 | D | C |
| AR00364266 | D | C | AR00334249 | D | C |
| AR00334339 | D | D | AR00334341 | D | D |
| AR00365438 | D | D | AR00365427 | D | D |

TABLE 2-continued

| Compound | NS3-NS4A IC$_{50}$ | Replicon EC$_{50}$ | Compound | NS3-NS4A IC$_{50}$ | Replicon EC$_{50}$ |
|---|---|---|---|---|---|
| AR00365349 | C | C | AR00365193 | D | D |
| AR00340303 | D | C | AR00333842 | C | B |
| AR00340156 | D | C | AR00365381 | C | C |
| AR00340188 | D | C | AR00340122 | D | C |
| AR00334399 | D | D | AR00340178 | D | D |
| AR00338070 | D | D | AR00334314 | D | D |
| AR00341649 | D | D | AR00338066 | D | D |
| AR00333224 | B | N/A | AR00338071 | D | D |
| AR00333248 | B | N/A | AR00364936 | D | C |
| AR00333277 | B | N/A | AR00333225 | B | N/A |
| AR00365083 | D | D | AR00333276 | B | N/A |
| AR00340494 | D | D | AR00365369 | D | C |
| AR00365252 | D | C | AR00333831 | D | D |
| AR00334220 | D | C | AR00365082 | D | C |
| AR00334225 | D | C | AR00334218 | D | D |
| AR00340173 | D | B | AR00334222 | D | D |
| AR00333462 | D | D | AR00334226 | D | D |
| AR00333463 | D | D | AR00340526 | D | D |
| AR00345032 | D | D | AR00345075 | D | C |
| AR00345090 | D | D | AR00345094 | D | D |
| AR00345095 | D | D | AR00345096 | D | D |
| AR00364924 | D | D | AR00371946 | D | N/A |
| AR00371947 | C | N/A | AR00371948 | D | N/A |
| AR00340495 | D | D | AR00365084 | D | B |
| AR00364989 | D | D | AR00365019 | D | D |
| AR00424775 | D | N/A | AR00424874 | D | N/A |

Specificity Assays

When the compounds were evaluated in specificity assays, the compounds of Formula I were found to be selective in that they do not show significant inhibition in Cathepsin B, Chymotrypsin, Thrombin, or Leukocyte Elastase.

Example 9

Pharmacokinetic Analysis of Compounds Methods

Compounds were initially synthesized and tested for potency (IC$_{50}$) in a fluorogenic NS3/4 protease assay and cell-based HCV replicon system as described in Example 8 above. Plasma pharmacokinetic analysis in *Rattus* sp. following IV administration was then used in conjunction with in vitro human liver microsome (HLM) and hepatocyte stability studies to direct the design of metabolically stable compounds from compounds with <20 nM potency. These leads were then further optimized for drug-like physical properties and administered in oral doses in *Rattus* sp. to assess liver, heart and plasma concentrations.

Compounds were tested for liver clearance over time following a single 3 mg/kg oral dose in rats. For any compound found to exhibit a concentration in liver at 8 hours post-administration that is at least 100-fold more than the concentration of the compound effective to inhibit 50% of maximum inhibition in the replicon assay (replicon EC$_{50}$), additional toxicological assessments were performed in rats using dosages of up to 30 mg/kg orally BID for seven days.

Results

Compounds AR294381, AR261408, AR333833 and AR334191 yielded replicon EC$_{50}$ values of approximately 2 nM and exhibited stability in vitro in rat, dog and human hepatocyte incubation assays, which data would predict low to moderate rates of clearance from liver. In addition, these compounds displayed a high degree of selectivity against a panel of other serine proteases, and no significant inhibition of Cytochrome P450 isoforms or hERG channel activity at even the highest concentrations tested (10 µM).

For compounds AR294381, AR261408, AR333833 and AR334191, a single 30 mg/kg oral dose in *Rattus* sp. yielded concentrations in liver at 24 hours post dose that were at least 200-fold more than their respective replicon EC$_{50}$ values.

Compound AR334191 yielded heart and plasma levels up to two orders of magnitude lower than, and correlated kinetically with, liver concentrations in the same animals. At a clinically more reasonable oral dose (3 mg/kg), compound AR334191 yielded a concentration in liver at 8 hours post dose that was over 100-fold more than the replicon EC$_{50}$ value of the compound. After exposure to compound AR334191 at a dosage of 30 mg/kg orally BID for 7 days, no mortality, change in weight, or abnormalities in clinical chemistries were observed in treated animals.

Conclusion

Potent, metabolically stable, orally available small molecule inhibitors of the HCV NS3 protease have been developed. At modest oral dosing concentrations (3 mg/kg) these compounds display high liver levels (100-fold greater than their respective replicon EC50 values) at 8 hours post dose. Exposure to plasma and heart is up to two orders of magnitude below that observed in liver, and such low concentrations minimizes any potential systemic toxicological issues.

Compound AR334191 did not display toxicity in *Rattus* sp. when dosed for seven days at 30 mg/kg BID, providing at least a 10-fold safety margin above the presumptive efficacious dose (3 mg/kg) that yields liver concentrations 100-fold in excess of the replicon EC$_{50}$ value of the compound.

Preparation of Section C Viral Inhibitors

The meanings of the terms and structural names used within this section are the same as those in Section C above. Any references within this section to a particular number or label should be understood in the context of the corresponding numbering or labeling scheme used within this section or Section C above, rather than in the context of a possibly similar or identical numbering or labeling scheme used elsewhere herein, unless otherwise indicated.

The compounds of formula XI-XVII may be synthesized according to the methods described below.

Methodology

NS3 inhibitors as shown in Examples 1-35 were prepared according to the chemistry illustrated in Scheme 1. Intermediates 1(R)-tert-butoxycarbonylamino-2(S)-vinyl-cyclopropanecarboxylic acid ethyl ester, 2(S)-tert-butoxycarbonylamino-non-8-enoic acid and the hydroxy macrocyclic intermediate (Step C) were prepared in similar fashion as described in International Application PCT/CA00/00353

(Publication No. WO 00/59929). 2(S)-tert-butoxycarbony-lamino-non-8-enoic acid was also purchased from RSP Amino Acids.

Example 1

Synthesis of Compound 101

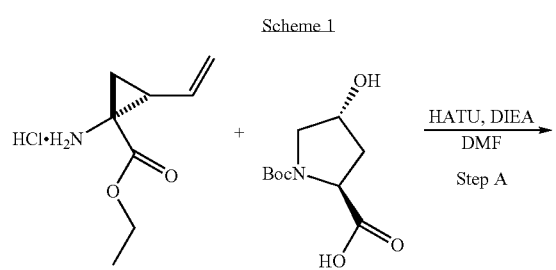

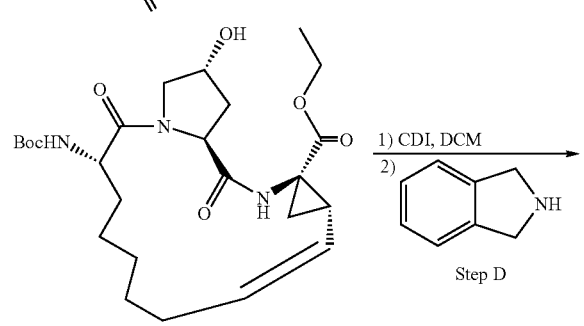

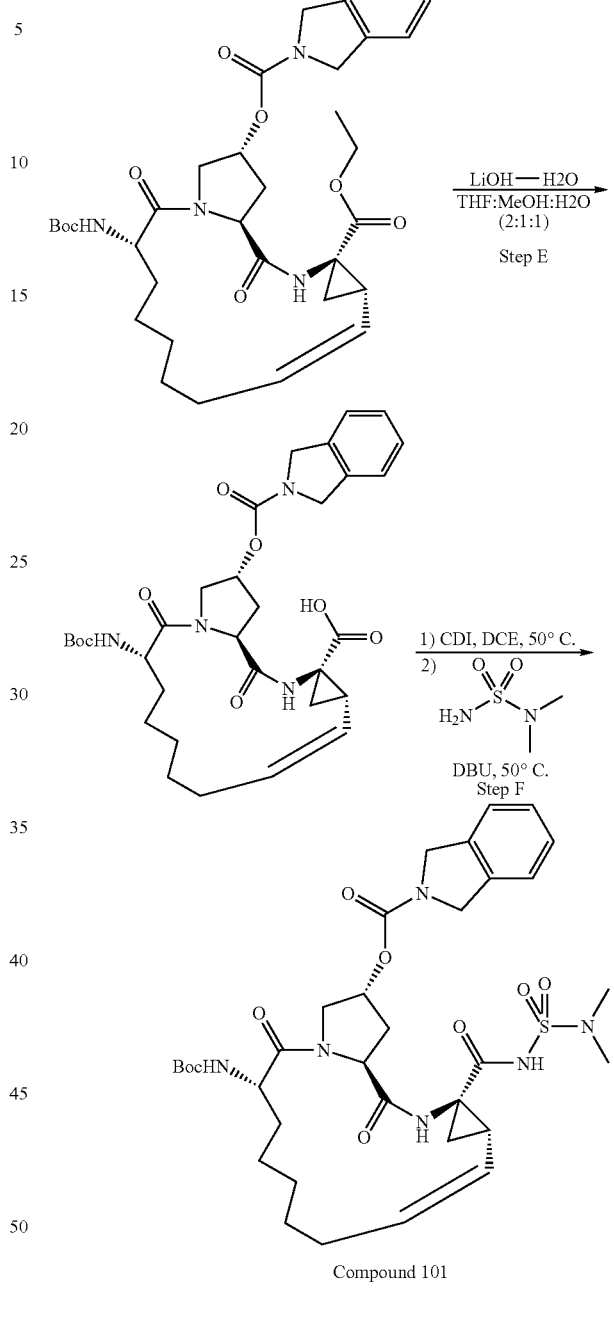

Step A: Synthesis of 2S-(1-Ethoxycarbonyl-2-vinyl-cyclopropylcarbamoyl)-4R-hydroxy-pyrrolidine-1-carboxylic acid tert-butyl ester To a flask charged with ethyl-(1R,2S)/(1S,2R)-1-amino-2-vinylcyclopropyl carboxylate (1.0 g, 5.2 mmol), trans-N-(tert-Butoxycarbonyl)-4-hydroxy-L-proline (1.3 g, 1.1 equiv), and HATU (2.7 g, 1.1 equiv) were added 30 mL DMF to make a solution. It was cooled to 0° C. in an ice-water bath, followed by slow addition of a solution of DIEA (4.4 mL, 4 equiv) in DMF (15 mL) while stirring. The reaction was allowed to warm up to rt and stirred overnight.

After 16 h, the reaction was complete as monitored by HPLC. It was diluted with EtOAc (100 mL), washed with water (3×40 mL), sat. NaHCO$_3$ (2×40 mL), and brine (2×40 mL), then dried over Na$_2$SO$_4$ and concentrated down to give a dark copper colored oil. The crude was purified on silica gel (eluent: acetone/hexanes 3:7), giving pure desired product as tan foamy powder (770 mg, 32%).

Step B: Synthesis of 1R-{[1-(2S-tert-Butoxycarbonylamino-non-8-enoyl)-4R-hydroxy-pyrrolidine-2S-carbonyl]-amino}-2S-vinyl-cyclopropanecarboxylic acid ethyl ester The dipeptide product from Step A (2.85 g, 7.7 mmol) was dissolved in 10 mL 4N HCl (dioxane) and left at rt for 90 min to remove the Boc protective group. It was then concentrated down, taken up in acetonitrile and concentrated down again twice. To this light brownish residue was added 2(S)-tert-butoxycarbonylamino-non-8-enoic acid (2.2 g, 8.1 mmol) and HATU (3.2 g, 8.5 mmol), followed by 80 mL DMF under nitrogen. The reaction was cooled on ice-water bath for 15 min, after which a 5 mL DMF solution of DIEA (5.4 mL, 30.9 mmol) was added to the reaction drop-wise while stirring. The ice bath was left to slowly rise to rt and the reaction stirred for overnight.

After 18 h, TLC showed reaction complete. The reaction was diluted with EtOAc (300 mL) and washed with water (3×150 mL), sat. NaHCO$_3$ (2×150 mL), brine (150 mL), dried (Na$_2$SO$_4$), and solvent removed. The crude was purified by silica gel flash chromatography on Biotage 40M (eluent=3% to 5% MeOH in DCM) to give desired product as a brownish foamy solid (3.5 g, 87%).

Step C: Synthesis of (1S,4R,6S,14S,18R)-14-tert-Butoxycarbonylamino-18-hydroxy-2,15-dioxo-3,16-diaza-tricyclo[14.3.0.0$^{4,6}$]nonadec-7-ene-4-carboxylic acid ethyl ester The product from Step B (2.6 g, 5.0 mmol) was dissolved in 500 mL DriSolve DCE in a 1 L round-bottomed flask to make a solution. It was degassed by bubbling nitrogen through for 1 h. Then the Hoveyda catalyst (0.25 equiv) was added at rt under nitrogen. The reaction was put on a preheated oil bath (50° C.) and stirred for overnight. After 16 h, the reaction had turned dark brownish. TLC (DCM/EtOAc 1:1) showed clean conversion to a new spot with slightly lower R$_f$. The reaction was concentrated down and purified on silica gel (Biotage 40 M, eluent=DCM/EtOAc gradient from 1:1 to 1:2), giving the desired product as a tan foamy powder (0.64 g, 52%). $^1$H NMR (CDCl$_3$, 400 MHz) δ 1.21 (t, J=7.0 Hz, 3H), 1.43 (s, 9H), 1.20-1.50 (m, 6H), 1.53-1.68 (m, 2H), 1.83-1.96 (m, 2H), 1.98-2.28 (m, 4H), 2.60 (m, 1H), 3.13 (brs, 1H), 3.68 (m, 1H), 3.94 (m, 1H), 4.01-4.19 (m, 2H), 4.48 (m, 1H), 4.56 (brs, 1H), 4.79 (m, 1H), 5.26 (t, J=9.4 Hz, 1H), 5.36 (d, J=7.8 Hz, 1H), 5.53 (m, 1H), 7.19 (brs, 1H). MS m/z 494.0 (M$^+$+1).

Step D: Synthesis of (1S,4R,6S,14S,18R)-14-tert-Butoxycarbonylamino-18-(1,3-dihydro-isoindole-2-carbonyloxy)-2,15-dioxo-3,16-diaza-tricyclo[14.3.0.0$^{4,6}$]nonadec-7-ene-4-carboxylic acid ethyl ester The macrocyclic product from Step C (110 mg, 0.22 mmol) was dissolved in DCM (2.2 mL), followed by addition of CDI (45 mg, 0.27 mmol) in one portion. The reaction was stirred at rt overnight. After 15 h, the reaction was complete as monitored by TLC (DCM/MeOH 9:1). Isoindoline (0.12 mL, 1.1 mmol) was added to the reaction drop-wise, and the reaction was stirred at 40° C. for overnight. After 22 h, TLC showed reaction complete. The reaction was cooled to rt, diluted with DCM (6 mL) and washed with 1N aq. HCl (2×2 mL), sat. sodium bicarbonate (2 mL), brine (2 mL), dried (Na$_2$SO$_4$), and concentrated down. The crude was purified on silica gel (Biotage 40S, eluent: 2 to 4% MeOH in DCM), giving the desired product as a white powder (131 mg, 90%).

Step E: Synthesis of (1S,4R,6S,14S,18R)-14-tert-Butoxycarbonylamino-18-(1,3-dihydro-isoindole-2-carbonyloxy)-2,15-dioxo-3,16-diaza-tricyclo[14.3.0.0$^{4,6}$]nonadec-7-ene-4-carboxylic acid The macrocyclic ester product from Step D (60 mg, 0.092 mmol) was dissolved in 0.9 mL of a mixed solvent (THF/MeOH/H$_2$O 2:1:1), followed by addition of LiOH—H$_2$O (23 mg, 6 equiv). The mixture was stirred at rt for overnight. After 18 h, TLC (DCM/MeOH 9:1) showed a clean new spot with a lower Rf. The reaction was concentrated down to almost dryness and partitioned between 1N aq. HCl (15 mL) and DCM (20 mL). The aqueous layer was extracted with DCM (2×10 mL). The organic layers were combined, dried over Na$_2$SO$_4$ and concentrated down, giving the desired product as a white foamy powder (50 mg, 87%). $^1$H NMR (CDCl$_3$, 500 MHz) δ 1.21-1.44 (m, 8H), 1.32 (s, 9H), 1.54-1.62 (m, 2H), 1.78-1.88 (m, 2H), 2.04-2.13 (m, 1H), 2.16-2.23 (m, 1H), 2.24-2.36 (m, 2H), 2.66-2.74 (m, 1H), 3.87-3.90 (m, 1H), 4.15 (d, J=11.0 Hz, 1H), 4.37-4.43 (m, 1H), 4.61-4.77 (m, 5H), 5.18 (t, J=10.3 Hz, 1H), 5.24-5.31 (m, 1H), 5.40-5.45 (m, 1H), 5.58-5.66 (m, 1H), 7.11-7.30 (m, 4H). MS m/z 611.0 (M$^+$+1).

Step F: Synthesis of (1S,4R,6S,14S,18R)-1,3-Dihydro-isoindole-2-carboxylic acid 14-tert-butoxycarbonylamino-4-(N,N-dimethylsulfonyl-aminocarbonyl)-2,15-dioxo-3,16-diaza-tricyclo[14.3.0.0$^{4,6}$]nonadec-7-en-18-yl ester (Compound 101)

The macrocyclic acid product from Step E (40 mg, 0.066 mmol) was dissolved in 0.7 mL DCE, followed by addition of CDI (13 mg, 0.079 mmol) in one portion. The mixture was stirred in a 50° C. oil bath for 2 h. TLC (10% methanol in dichloromethane) showed acid starting material gone and a new spot with much higher Rf appeared. Then N,N-dimethylsulfamide (12 mg, 0.098 mmol; purchased from TCI) was added to the reaction, followed by DBU (15 mg, 0.098 mmol). Heating was resumed at 50° C. for 2 h, both TLC and LCMS showed reaction complete and product formed. The reaction was concentrated down and directly loaded onto a Biotage 40 S silica gel column. It was purified by flash chromatography (eluent=40% ethyl acetate in hexanes with 1% formic acid), giving the desired product as a white solid (30 mg, 64%). MS m/z 715.5 (APCI−, M−1).

The following compounds in Examples 2-35 were prepared according to procedures similar to that described in Example 1 above, substituting N,N-dimethylsulfamide with other appropriate sulfamides in Step F, and/or substituting isoindoline with other amines instead. The sulfamides used were either purchased from commercial sources or prepared through routes A or B described in Scheme 2 below. Similar methods to that of Route A have been described in literature (e.g. Heteroatom Chemistry, 2001, 12 (1), 1-5). The sulfamoylating reagent a in Route B was prepared according to a literature procedure (Winum, J-Y et al, Organic Letters, 2001, 3, 2241-2243).

Scheme 2

Route A:

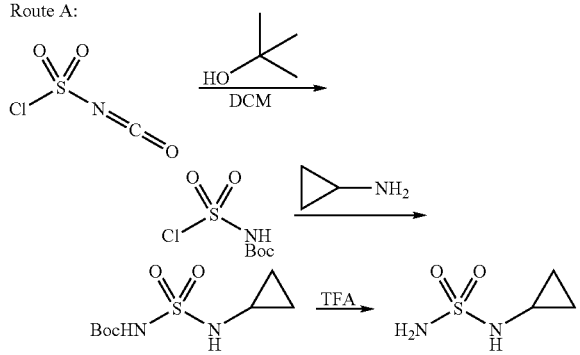

Route B:

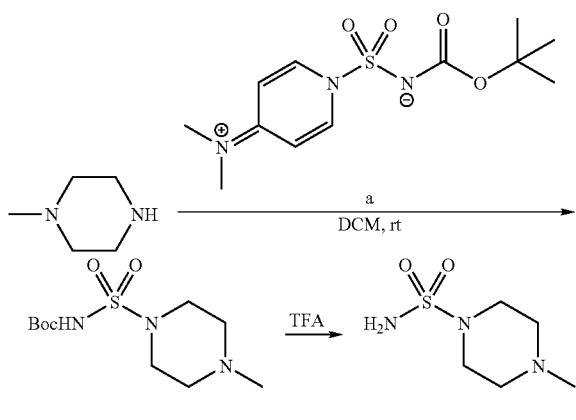

Synthesis of N-Cyclopropylsulfamide

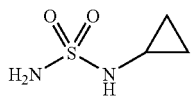

To a stirred solution of chlorosulfonyl isocyanate (1 mL, 11.5 mmol) in 20 mL DriSolve DCM was added anhydrous t-butanol (1.1 mL, 1 equiv) at 0° C. After stirring for 90 min, the resulting carbamatesulfamoyl chloride solution and 5 mL TEA in 20 mL DCM were added dropwise to a solution of cyclopropyl amine (0.66 g, 1 equiv) in 25 mL DCM and 3 mL TEA. The reaction temperature was kept under 5° C. during addition. The ice bath was removed after addition and the resulting mixture was stirred at rt for 3 h.

TLC (Hex/EA 1:1) showed one major spot with higher $R_f$. LCMS showed that product had formed. The reaction mixture was then diluted with 100 mL DCM and washed with 0.1 N HCl (2×200 mL) and brine (150 mL). The organic layer was dried over $Na_2SO_4$ and concentrated, giving the Boc-protected sulfamide as a light yellowish solid, 1.2 g. $^1$H-NMR showed it to be the desired product plus small amount of impurities. The crude product was recrystallized from EA/Hex (rt to 0° C.), giving 0.64 g offwhite crystalline pure product. $^1$H NMR (CDCl$_3$, 400 MHz) δ 0.71-0.77 (m, 4H), 1.51 (s, 9H), 2.44 (m, 1H), 5.58 (br s, 1H), 7.42 (br s, 1H). MS m/z 234.7 (APCI−, M−1).

To remove the Boc protective group, the product from above was dissolved in 10 mL 1:1 (v/v) mix of DCM:TFA and let stay at rt for 1 h. It was then concentrated down on rotovap and then on high vacuum. The thick oil solidified on high vac, giving the titled product as an offwhite solid. $^1$H NMR (CDCl$_3$, 400 MHz) δ 0.66-0.74 (m, 4H), 2.57-2.58 (m, 1H), 5.29 (br s, 2H), 5.42 (br s, 1H).

Synthesis of Pyrrolidinolsulfamide

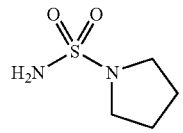

The titled compound was prepared according to the same procedures described for the synthesis of N-cyclopropylsulfamide above, substituting cyclopropyl amine with pyrrolidine. For the Boc-protected titled product: $^1$H NMR (CDCl$_3$, 400 MHz) δ 1.49 (s, 9H), 1.92-1.95 (m, 4H), 3.48-3.52 (m, 4H), 7.02 (br s, 1H). MS m/z 249(APCI−, M−1).

Synthesis of Morpholinolsulfamide

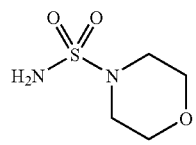

The titled compound was prepared according to the same procedures described for the synthesis of N-cyclopropylsulfamide above, substituting cyclopropyl amine with morpholine. For the Boc-protected titled product: $^1$H NMR (CDCl$_3$, 400 MHz) δ 1.50 (s, 9H), 3.39 (t, 4H), 3.76 (t, 4H), 7.18 (br s, 1H). MS m/z 265 (APCI−, M−1)

Synthesis of Thiazol-2-ylaminosulfamide

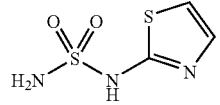

The titled compound was prepared according to the same procedures described for the synthesis of N-cyclopropylsulfamide above, substituting cyclopropyl amine with 2-amino thiozol. However, the Boc-protected intermediate was never isolated due to loss of the protection group during reaction work-up and the following recrystallization steps. The titled product was isolated after silica gel column chromatography (Biotage 40 M, eluent=5-10% MeOH in DCM). $^1$H NMR (d$^6$-DMSO, 400 MHz) δ 6.52 (br s, 2H), 6.75 (d, 1H), 7.19 (d, 1H), 12.1 (br s, 1H). MS m/z 180 (ESI+, MH$^+$).

297

Synthesis of 4-Methyl-Piperizinosulfamide

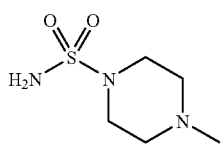

The titled compound was prepared according to Route B in Scheme 2. 4-Methyl-piperizine (0.15 g, 1.50 mmol) was dissolved in 3 mL DriSolve DCM in a 10 mL RBF, followed by addition of the sulfamoylating reagent a (0.45 g, 1.50 mmol). After ca. 5 min stirring the latter reagent gradually dissolved to give a clear and almost colorless solution. It was stirred at rt for overnight. After 17 h, TLC showed reaction complete (DCM:MeOH 9:1 with 1% TEA). The reaction was concentrated down and the resulting pinkish crude solid was flashed on Biotage 40 S silica gel column (eluent=DCM:MeOH 10:1 with 1% TEA), giving the Boc-protected titled product as a white powder in basically quantitative yield. $^1$H NMR (CDCl$_3$, 400 MHz) δ 1.48 (s, 9H), 2.33 (s, 3H), 2.52 (t, 4H), 3.43 (t, 4H). MS m/z 278 (APCI−, M−1).

The Boc protective group was then removed by the same fashion as described in the synthesis of N-cyclopropylsulfamide, and the resulting titled product was used directly for the next coupling steps without further purification.

Example 2

Compound 102

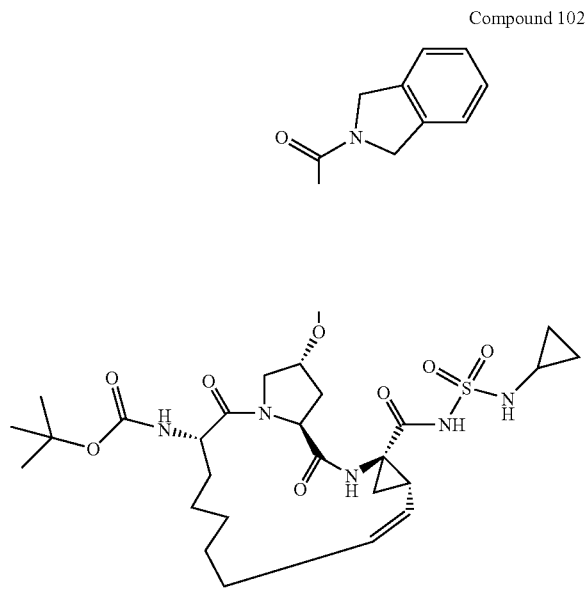

(1S,4R,6S,14S,18R)-1,3-Dihydro-isoindole-2-carboxylic acid 14-tert-butoxycarbonylamino-4-(N-cyclopropylsulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with N-cyclopropylsulfamide in Step F. MS m/z 728 (APCI−, M−1).

Example 3

Compound 103

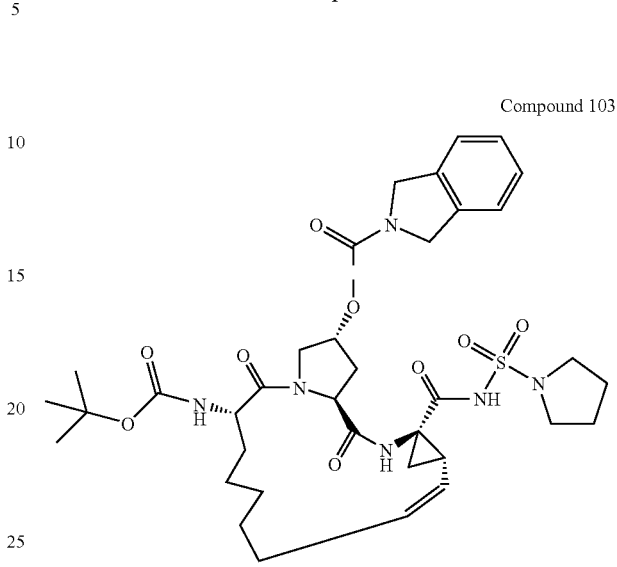

(1S,4R,6S,14S,18R)-1,3-Dihydro-isoindole-2-carboxylic acid 14-tert-butoxycarbonylamino-4-(pyrrolidinosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with pyrrolidinolsulfamide in Step F. MS m/z 742 (APCI−, M−1).

Example 4

Compound 104

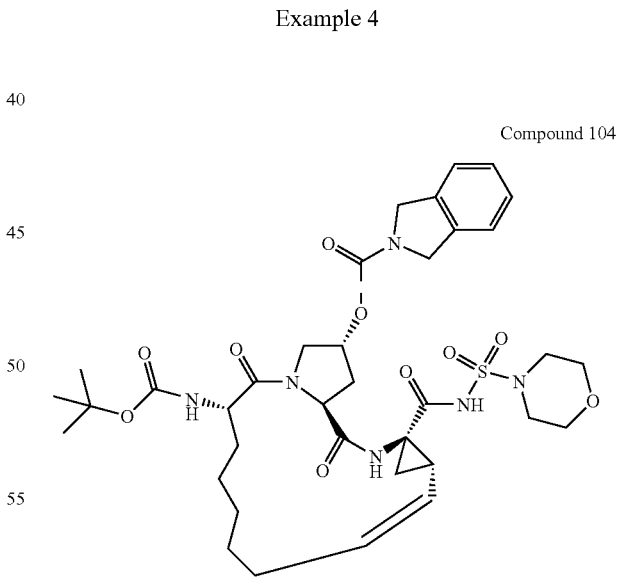

(1S,4R,6S,14S,18R)-1,3-Dihydro-isoindole-2-carboxylic acid 14-tert-butoxycarbonylamino-4-(morpholinosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with morpholinolsulfamide in Step F. MS m/z 758 (APCI−, M−1).

Example 5

Compound 105

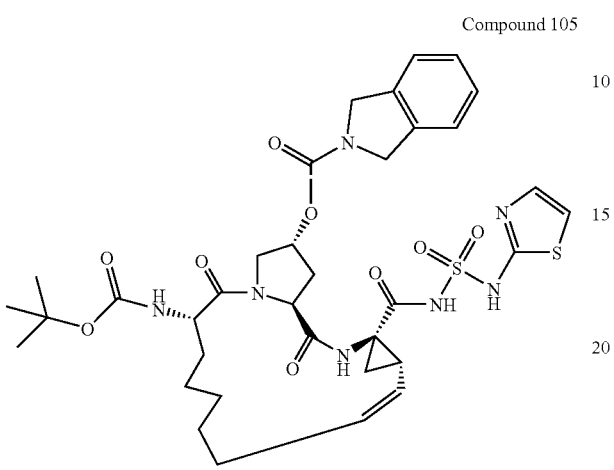

(1S,4R,6S,14S,18R)-1,3-Dihydro-isoindole-2-carboxylic acid 14-tert-butoxycarbonylamino-4-(thiazol-2-ylaminosulfonylaminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with thiozoyl-2-ylaminosulfamide in Step F. $^1$H NMR (400 MHz, d$^6$-acetone) δ 1.15 (s, 9H), 1.22-1.54 (m, 11H), 1.60 (m, 1H), 1.68-1.88 (m, 2H), 2.35-2.45 (m, 3H), 2.57 (m, 1H), 3.85 (m, 1H), 4.15 (br d, 1H), 4.48 (m, 1H), 4.65 (m, 4H), 4.74 (t, 1H), 4.92 (t, 1H), 5.43-5.52 (m, 2H), 6.92 (d, 1H), 7.20-7.33 (m, 5H), 8.18 (s, 1H). MS m/z 770 (ESI−, M−1).

Example 6

Compound 106

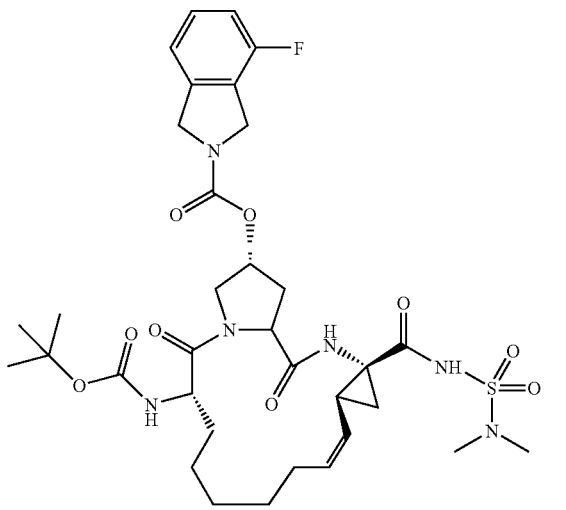

(1S,4R,6S,14S,18R)-5-Fluoro-1,3-Dihydro-isoindole-2-carboxylic acid 14-tert-butoxycarbonylamino-4-(N,N-dim-ethylsulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting isoindoline with 5-fluoroisoindoline in Step D instead. $^1$H NMR (400 MHz, CD$_3$OD) δ 7.31 (q, 1H), 7.13 (d, 1H), 7.03-6.97 (m, 2H), 6.63 (br s, 1H), 5.70 (q, 1H), 5.40 (br s, 1H), 5.07 (t, 1H), 4.78-4.51 (m, 7H), 4.10-4.02 (m, 1H), 3.83 (d, 1H), 2.84 (s, 6H), 2.73-2.64 (m, 1H), 2.55-2.47 (m, 1H), 2.43-2.29 (m, 3H), 1.84-1.67 (m, 4H), 1.64-1.57 (m, 2H), 1.13 (d, 9H), 0.94-0.82 (m, 4H). MS m/z 733.4 (APCI−, M−1).

Example 7

Compound 107

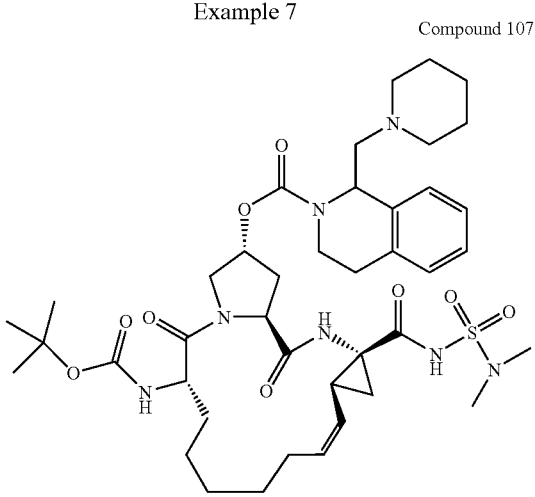

(1S,4R,6S,14S,18R)-1-Piperidin-1-ylmethyl-3,4-dihydro-1H-isoquinoline-2-carboxylic acid 14-tert-butoxycarbonylamino-2,15-dioxo-4-(N,N-dimethyl-sulfonylaminocarbonyl)-3,16-diaza-tricyclo[14.3.0.0$^{4,6}$]nonadec-7-en-18-yl ester was synthesized according to the same procedures as described in Example 1, substituting isoindoline with 1-piperidin-1-ylmethyl-3,4-dihydro-1H-isoquinoline in Step D instead. $^1$H NMR (400 MHz, CD$_3$OD) δ 7.32-7.16 (m, 4H), 5.75-5.64 (m, 2H), 5.47 (br s, 1H), 5.05 (t, 1H), 4.52-4.45 (m, 2H), 4.39-4.17 (m, 3H), 4.12-4.02 (m, 1H), 3.99-3.88 (m, 1H), 3.70-3.38 (m, 6H), 3.14-3.00 (m, 4H), 2.83 (d, 6H), 2.59-2.24 (m, 4H), 2.08-2.01 (m, 2H), 1.98-1.65 (m, 10H), 1.63-1.51 (m, 4H), 1.23 (d, 9H), 0.92-0.84 (m, 1H). MS m/z 826.6 (APCI−, M−1).

Example 8

Compound 108

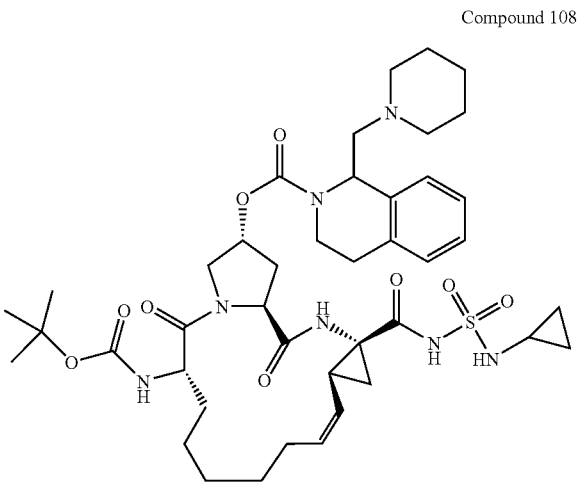

(1S,4R,6S,14S,18R)-1-Piperidin-1-ylmethyl-3,4-dihydro-1H-isoquinoline-2-carboxylic acid 14-tert-butoxycarbonylamino-2,15-dioxo-4-(N-cyclopropyl-sulfonylaminocarbonyl)-3,16-diaza-tricyclo[14.3.0.0$^{4,6}$]nonadec-7-en-18-yl ester was synthesized according to the same procedures as described in Example 1, substituting isoindoline with 1-piperidin-1-ylmethyl-3,4-dihydro-1H-isoquinoline in Step D, and substituting N,N-dimethylsulfamide with N-cyclopropylsulfamide in Step F instead. $^1$H NMR (400 MHz, CD$_3$OD) δ 7.31-7.15 (m, 4H), 5.75-5.58 (m, 2H), 5.47 (br s, 1H), 5.11 (t, 1H), 4.62-4.57 (m, 1H), 4.52-4.45 (m, 1H), 4.41-4.17 (m, 3H), 4.15-3.84 (m, 3H), 3.73-3.34 (m, 5H), 3.16-2.71 (m, 5H), 2.70-2.27 (m, 6H), 2.13-2.67 (m, 10H), 1.65-1.24 (m, 15H), 0.73-0.47 (m, 4H); MS m/z 838.4 (APCI−, M−1).

Example 9

Compound 109

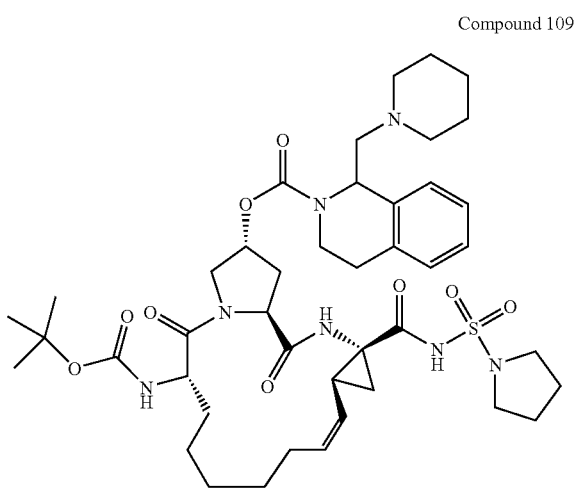

(1S,4R,6S,14S,18R)-1-Piperidin-1-ylmethyl-3,4-dihydro-1H-isoquinoline-2-carboxylic acid 14-tert-butoxycarbonylamino-2,15-dioxo-4-(pyrrolidino-sulfonylaminocarbonyl)-3,16-diaza-tricyclo[14.3.0.0$^{4,6}$]nonadec-7-en-18-yl ester was synthesized according to the same procedures as described in Example 1, substituting isoindoline with 1-piperidin-1-ylmethyl-3,4-dihydro-1H-isoquinoline in Step D, and substituting N,N-dimethylsulfamide with pyrrolidinosulfamide in Step F instead. $^1$H NMR (400 MHz, CD$_3$OD) δ 8.94 (d, 1H), 7.31-7.16 (m, 4H), 5.75-5.62 (m, 2H), 5.48 (br s, 1H), 5.08-4.99 (m, 1H), 4.66-3.84 (m, 7H), 3.72-3.39 (m, 7H), 3.28-3.20 (m, 2H), 3.17-2.25 (m, 10H), 2.12-1.99 (m, 2H), 1.98-1.66 (m, 11H), 1.64-1.22 (m, 15H); MS m/z 852.5 (APCI−, M−1).

Example 10

Compound 110

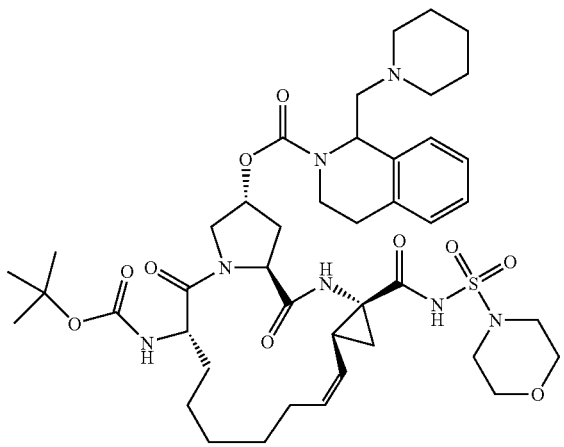

(1S,4R,6S,14S,18R)-1-Piperidin-1-ylmethyl-3,4-dihydro-1H-isoquinoline-2-carboxylic acid 14-tert-butoxycarbonylamino-2,15-dioxo-4-(morpholino-sulfonylaminocarbonyl)-3,16-diaza-tricyclo[14.3.0.0$^{4,6}$]nonadec-7-en-18-yl ester was synthesized according to the same procedures as described in Example 1, substituting isoindoline with 1-piperidin-1-ylmethyl-3,4-dihydro-1H-isoquinoline in Step D, and substituting N,N-dimethylsulfamide with morpholino-sulfamide in Step F instead. $^1$H NMR (400 MHz, CD$_3$OD) δ 7.33-7.14 (m, 4H), 5.78-5.63 (m, 2H), 5.47 (br s, 1H), 5.11 (t, 1H), 4.63-3.84 (m, 7H), 3.74-3.36 (m, 9H), 3.29-3.19 (m, 3H), 3.16-2.14 (m, 11H), 2.13-1.23 (m, 24H), 0.94-0.81 (m, 1H); MS m/z 868.6 (APCI−, M−1).

Example 11

Compound 111

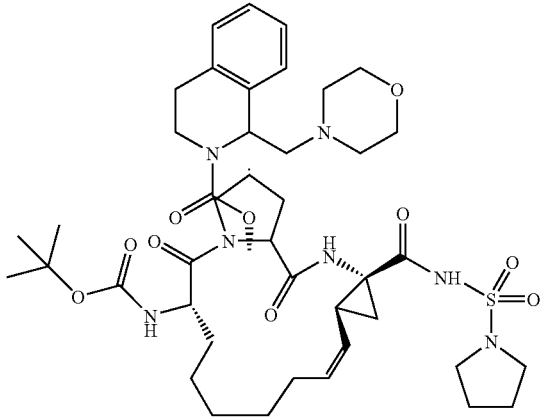

(1S,4R,6S,14S,18R)-1-Morpholine-4-ylmethyl-3,4-dihydro-1H-isoquinoline-2-carboxylic acid 14-tert-butoxycarbonylamino-2,15-dioxo-4-(pyrrolidine-1-sulfonylaminocarbonyl)-3,16-diaza-tricyclo[14.3.0.0^{4,6}]nonadec-7-en-18-yl ester was synthesized according to the same procedures as described in Example 1, substituting isoindoline with 1-morpholine-4-ylmethyl-3,4-dihydro-1H-isoquinoline in Step D, and substituting N,N-dimethylsulfamide with pyrrolidinosulfamide in Step F instead. MS m/z 874.3 (APCI−, M+18)

Example 12

Compound 112

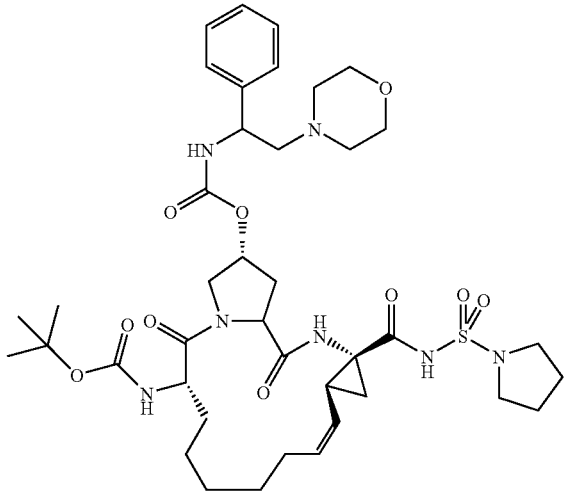

(1S,4R,6S,14S,18R)-(2-Morpholin-4-yl-1-phenyl-ethyl)-carbamic acid 14-tert-butoxycarbonylamino-2,15-dioxo-4-(pyrrolidine-1-sulfonylaminocarbonyl)-3,16-diaza-tricyclo[14.3.0.0^{4,6}]nonadec-7-en-18-yl ester was synthesized according to the same procedures as described in Example 1, substituting isoindoline with 2-morpholin-4-yl-1-phenyl-ethylamine in Step D, and substituting N,N-dimethylsulfamide with pyrrolidinosulfamide in Step F instead. MS m/z 828.3 (APCI−, M−1)

Example 13

Compound 113

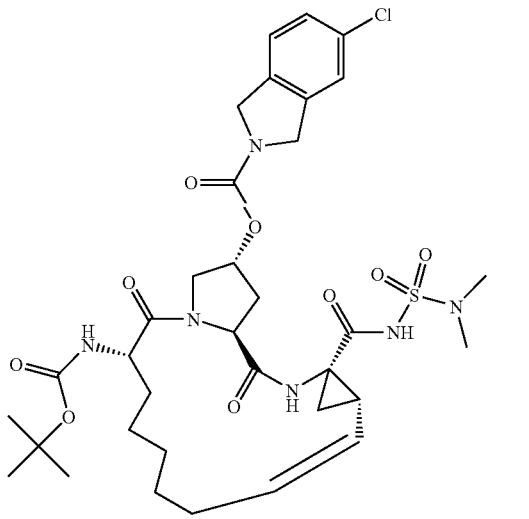

(1S,4R,6S,14S,18R)-5-Chloro-1,3-Dihydro-isoindole-2-carboxylic acid 14-tert-butoxycarbonylamino-4-(N,N-dimethylsulfonyl-aminocarbonyl)-2,15-dioxo-3,16-diaza-tricyclo[14.3.0.0^{4,6}]nonadec-7-en-18-yl ester was synthesized according to the same procedures as described in Example 1, substituting isoindoline with 5-chloroisoindoline in Step D instead. MS m/z 651 (APCI+, M−Boc).

Example 14

Compound 114

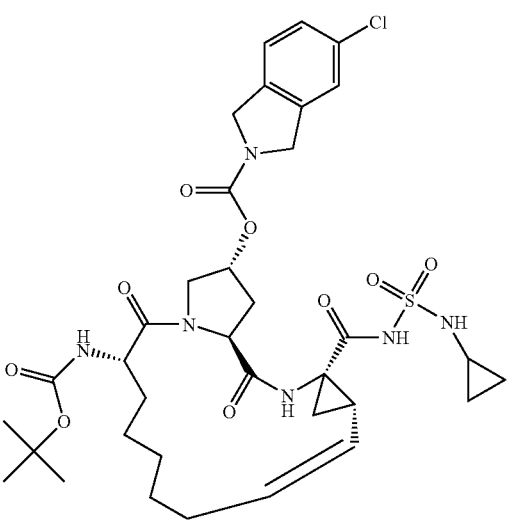

(1S,4R,6S,14S,18R)-5-Chloro-1,3-Dihydro-isoindole-2-carboxylic acid 14-tert-butoxycarbonylamino-4-(N-cyclopropyl-sulfonyl-aminocarbonyl)-2,15-dioxo-3,16-diaza-tricyclo[14.3.0.0^{4,6}]nonadec-7-en-18-yl ester was synthesized according to the same procedures as described in Example 1, substituting isoindoline with 5-chloroisoindoline in Step D, (1S,4R,6S,14S,18R)-5-Chloro-1,3-Dihydro-isoindole-2-carboxylic acid 14-tert-butoxycarbonylamino-4-(pyrrolidino-sulfonyl-aminocarbonyl)-2,15-dioxo-3,16-diaza-tricyclo[14.3.0.0^{4,6}]nonadec-7-en-18-yl ester was synthesized according to the same procedures as described in Example 1, substituting isoindoline with 5-chloroisoindoline in Step D, and substituting N,N-dimethylsulfamide with N-cyclopropylsulfamide in Step F instead. MS m/z 663 (APCI+, M−Boc).

Example 15

Compound 115

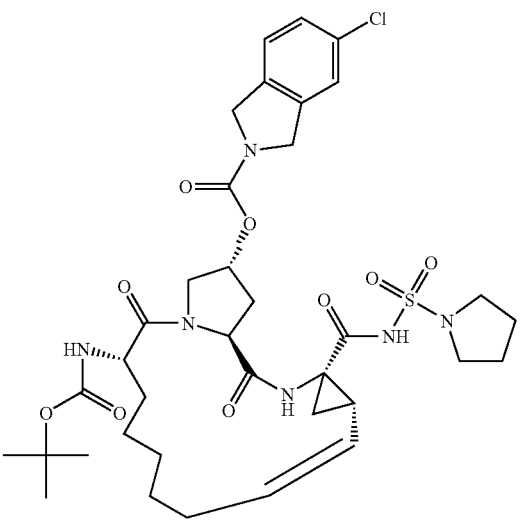

and substituting N,N-dimethylsulfamide with pyrrolidinosulfamide in Step F instead. MS m/z 677 (APCI+, M−Boc).

Example 16

Compound 116

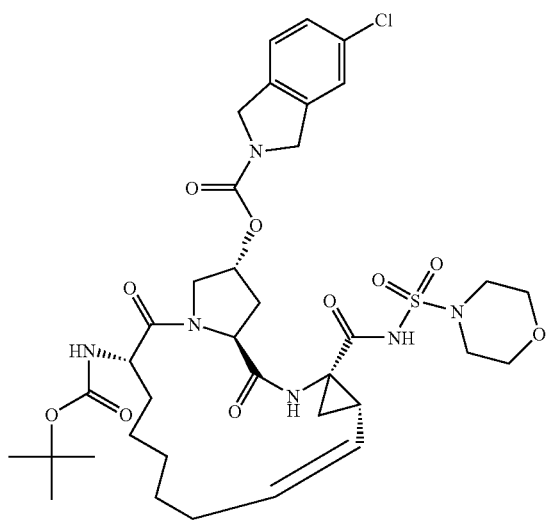

(1S,4R,6S,14S,18R)-5-Chloro-1,3-Dihydro-isoindole-2-carboxylic acid 14-tert-butoxycarbonylamino-4-(morpholino-sulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting isoindoline with 5-chloroisoindoline in Step D, and substituting N,N-dimethylsulfamide with morpholinosulfamide in Step F instead. MS m/z 693 (APCI+, M−Boc).

Example 17

Compound 117

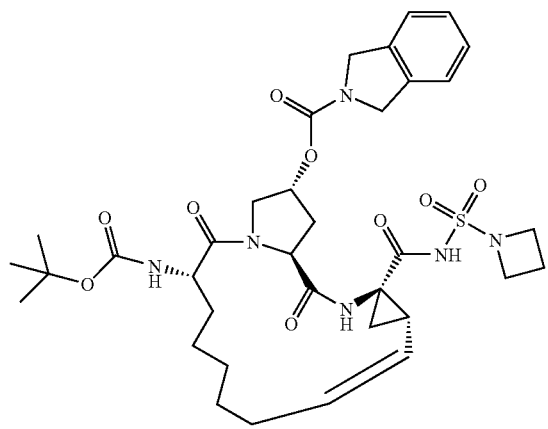

(1S,4R,6S,14S,18R)-1,3-Dihydro-isoindole-2-carboxylic acid 14-tert-butoxycarbonylamino-4-(azetidino-sulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with azetidine-1-sulfonamide in Step F instead. $^1$H NMR (400 MHz, d$^6$-acetone) δ 1.21 (s, 9H), 1.28-1.54 (m, 8H), 1.59-1.63 (m, 1H), 1.77-1.89 (m, 3H), 2.38-2.42 (m, 1H), 2.46-2.52 (m, 2H), 3.77 (t, 2H), 3.84-3.94 (m, 3H), 4.14-4.22 (m, 3H), 4.50 (br d, 1H), 4.61-4.72 (m, 5H), 5.12 (t, 1H), 5.44 (br s, 1H), 5.78 (q, 1H), 6.17 (br d, 1H), 7.23-7.36 (m, 4H), 8.38 (s, 1H). MS m/z 727.4 (APCI−, M−1).

Example 17a

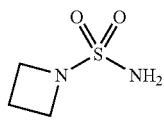

The title compound, azetidine-1-sulfonamide, was prepared according to Route B in Scheme 2. Azetidine (0.16 g, 2.8 mmol) was dissolved in 5.6 mL DriSolve DCM in a 10 mL RBF, followed by addition of the sulfamoylating reagent a (0.85 g, 2.8 mmol). After ca. 5 min stirring the latter reagent gradually dissolved to give a clear and almost colorless solution. It was stirred at rt for overnight. After 17 h, TLC showed reaction complete (DCM:MeOH 9:1). The reaction was concentrated down and the resulting white solid crude was flashed on Biotage 40 S silica gel column (eluent=5 to 10% MeOH/DCM), giving the Boc-protected titled product in basically quantitative yield. The product was initially a thick oil, which gradually solidified on high vacuum overnight. $^1$H NMR (CDCl$_3$, 400 MHz) δ 1.52 (s, 9H), 2.27 (m, 2H), 4.15 (t, 4H), 7.18 (br s, 1H).

The product from the above step (0.4 g, 2 mmol) was dissolved in 10 mL TFA/DCM (1:1 v/v) mixture, and left at rt for 2 h. The volatile was then removed. The resulting oily residue was treated with diethyl ether and filtered. The white powder product from filtration was used for the coupling step without further purification. $^1$H NMR (d$^6$-Acetone, 400 MHz) δ 2.12-2.19 (m, 2H), 3.77 (t, 4H), 6.05 (br s, 2H).

Example 18

Compound 118

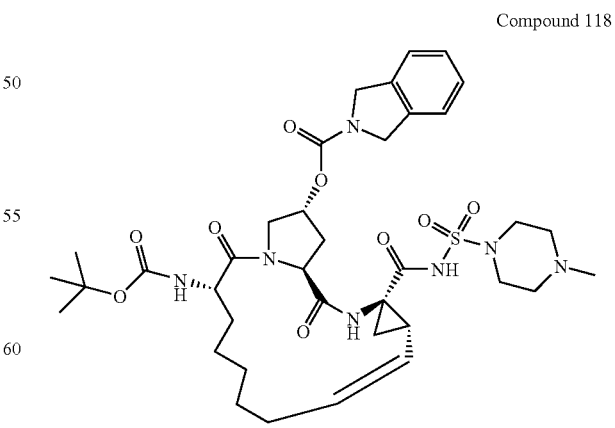

(1S,4R,6S,14S,18R)-1,3-Dihydro-isoindole-2-carboxylic acid 14-tert-butoxycarbonylamino-4-(4-methylpiperazine-1-sulfonyl-aminocarbonyl)-2,15-dioxo-3,16-diaza-tricyclo

[14.3.0.0$^{4,6}$]nonadec-7-en-18-yl ester was synthesized according to the same procedures as described in Example 1, substituting N,N-dimethylsulfamide with 4-methylpiperazine-1-sulfonamide in Step F instead. $^1$H NMR (400 MHz, d$^6$-acetone) δ 1.21 (s, 9H), 1.19-1.58 (m, 9H), 1.70-1.73 (m, 1H), 1.85-1.88 (m, 2H), 2.24 (s, 3H), 2.36-2.48 (m, 7H), 2.53 (m, 1H), 3.24-3.29 (m, 4H), 3.84-3.88 (m, 1H), 4.14-4.18 (m, 1H), 4.49 (br d, 1H), 4.60-4.72 (m, 5H), 5.04 (t, 1H), 5.44 (br s, 1H), 5.71 (q, 1H), 6.16 (br d, 1H), 7.23-7.36 (m, 4H), 8.31 (s, 1H). MS m/z 770.5 (APCI−, M−1).

Example 19

Compound 119

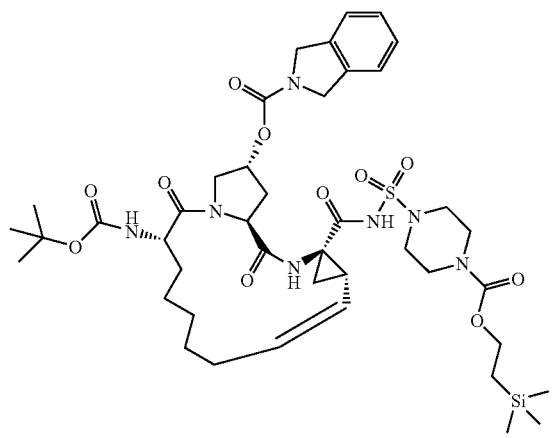

(1S,4R,6S,14S,18R)-1,3-Dihydro-isoindole-2-carboxylic acid 14-tert-butoxycarbonylamino-4-(4-(2-trimethylsilylethoxycarbonyl)piperazine-1-sulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with 4-(2-trimethylsilylethoxycarbonyl)piperazine-1-sulfonamide in Step F instead. $^1$H NMR (400 MHz, d$^6$-acetone) δ 0.06 (s, 9H), 0.94-0.98 (m, 2H), 1.15 (s, 9H), 1.17-1.50 (m, 8H), 1.50-1.54 (m, 1H), 1.65-1.68 (m, 1H), 1.75-1.82 (m, 2H), 2.30-2.44 (m, 3H), 2.56-2.68 (m, 1H), 3.17-3.26 (m, 4H), 3.44-3.47 (m, 4H), 3.78-3.81 (m, 1H), 4.08-4.14 (m, 3H), 4.44 (br d, 1H), 4.54-4.66 (m, 5H), 4.98 (t, 1H), 5.38 (br s, 1H), 5.56-5.63 (m, 1H), 6.12 (br d, 1H), 7.16-7.30 (m, 4H), 8.26 (s, 1H). MS m/z 901.3 (APCI−, M−1)

Example 19a

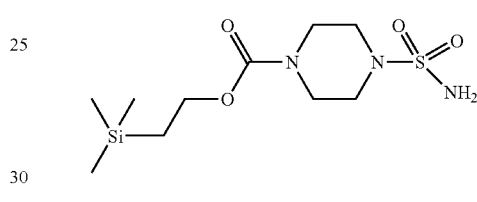

The title compound, 4-(2-trimethylsilylethoxycarbonyl)piperazine-1-sulfonamide, was prepared according to Scheme 3 shown below:

Scheme 3

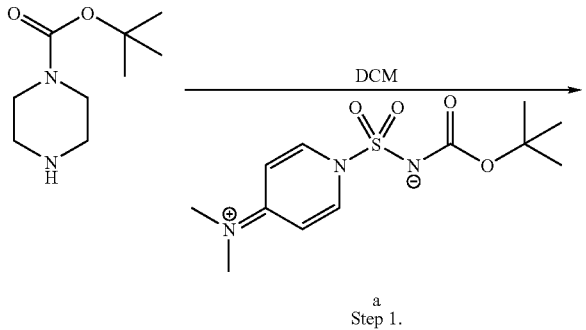

a
Step 1.

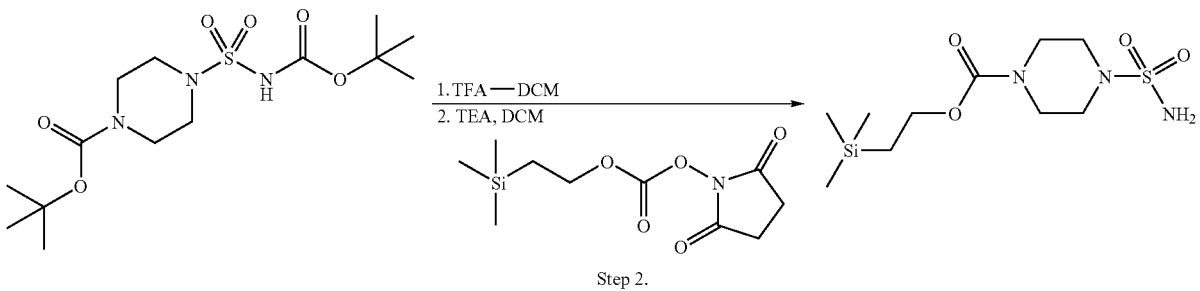

Step 2.

Step 1: Tert-butyl piperazine-1-carboxylate (1.0 g, 5.4 mmol) was dissolved in 10 mL DriSolve DCM in a 50 mL RBF, followed by addition of the sulfamoylating reagent a (1.6 g, 5.4 mmol). After ca. 5 min stirring the latter reagent gradually dissolved to give a clear and almost colorless solution. It was stirred at rt for overnight. After 17 h, TLC showed reaction complete (DCM:MeOH 20:1). The reaction was concentrated down and the resulting white solid crude was flashed on Biotage 40 M silica gel column (eluent=2% MeOH/DCM), giving the Boc-protected product as a white foamy solid. $^1$H NMR (d$^6$-acetone, 400 MHz) δ 1.45 (s, 9H), 1.46 (s, 9H), 3.30-3.32 (m, 4H), 3.48-3.50 (m, 4H). LCMS m/z 364.1 (APCI−, M−1).

Step 2: The product from Step 1 above (0.90 g, 2.5 mmol) was dissolved in ca. 20 mL 1:1 (v/v) TFA-DCM mixture and left at rt for 2 h. It was then concentrated down. The solid residue was taken up in MeCN and re-concentrated down, giving the de-protected product as a fine white powder.

To this de-protected product was added 20 mL DriSolve DCM, followed by 1 mL TEA. To the resulting white suspension was added the Teoc-succimate (0.70 g, 2.7 mmol) in one portion while stirring. The white suspension quickly disappeared and the colorless clear solution was stirred at rt for overnight. The reaction was then concentrated down and purified by silica chromatography (Biotage 40 S, eluent=Hex:EA 2:1), giving the pure product as a white solid, 0.65 g (85%). $^1$H NMR (d$^6$-acetone, 400 MHz) δ 0.06 (s, 9H), 0.94-0.98 (m, 2H), 3.01 (t, 4H), 3.48 (t, 4H), 4.10-4.14 (m, 2H), 6.03 (br s, 2H). LCMS m/z 308.2 (APCI−, M−1).

Example 20

Compound 120

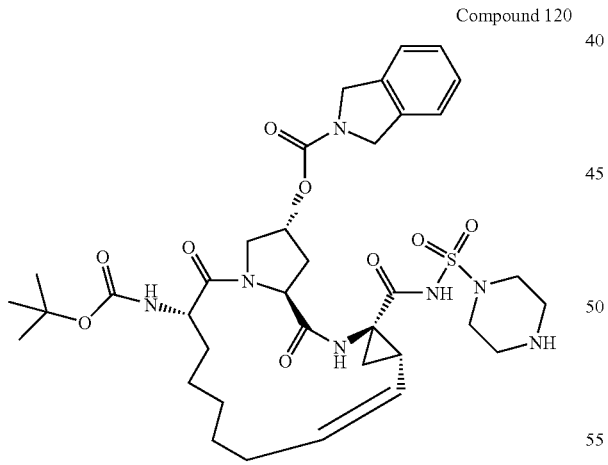

(1S,4R,6S,14S,18R)-1,3-Dihydro-isoindole-2-carboxylic acid 14-tert-butoxycarbonylamino-4-(piperazine-1-sulfonyl-aminocarbonyl)-2,15-dioxo-3,16-diaza-tricyclo[14.3.0.0$^{4,6}$]nonadec-7-en-18-yl ester was synthesized through removal of protective group of Compound 119. Compound 119 (54.8 mg, 60.7 μmol) was first dissolved in 0.5 mL DriSolve THF, followed by addition of 1.0 M TBAF THF solution (0.2 mL, 200 μmol). The reaction was heated in a 60° C. oil bath for 2 h, and TLC showed reaction complete. The reaction was purified through silica chromatography (Biotage 12 M; eluent =0 to 20% MeOH in DCM), giving Compound 120 as a white solid, 42.4 mg (92%). MS m/z 756.4 (APCI−, M−1).

Example 21

Compound 121

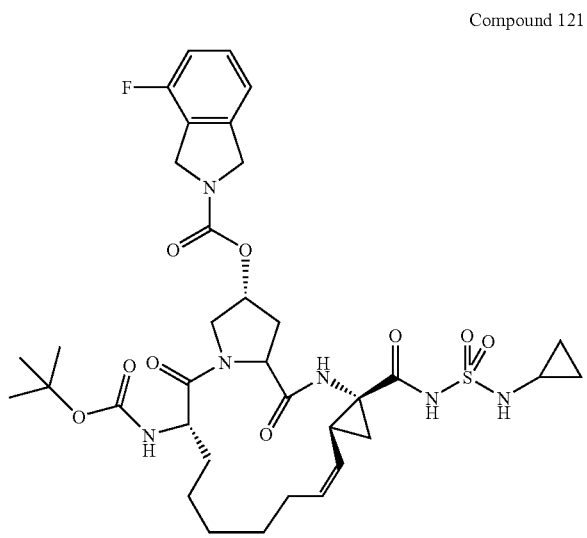

(1S,4R,6S,14S,18R)-4-Fluoro-1,3-Dihydro-isoindole-2-carboxylic acid 14-tert-butoxycarbonylamino-4-(N-cyclopropylsulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with N-cyclopropylsulfamide in Step F instead. $^1$H NMR (500 MHz, CD$_3$OD) δ 8.91 (d, 1H), 7.32 (q, 1H), 7.14 (d, 1H), 7.01 (t, 1H), 5.63 (q, 1H), 5.40 (br s, 1H), 5.13 (t, 1H), 4.80-4.68 (m, 4H), 4.61 (q, 1H), 4.56-4.49 (m, 1H), 4.06 (t, 1H), 3.83 (br s, 1H), 3.72 (p, 1H), 3.22 (p, 1H), 2.72-2.60 (m, 1H), 2.57-2.48 (m, 1H), 2.46-2.31 (m, 4H), 1.83-1.69 (m, 4H), 1.66-1.58 (m, 1H), 1.56-1.19 (m, 5H), 1.13 (d, 9H), 0.71-0.51 (m, 4H). MS m/z 745.3 (APCI−, M−1).

Example 22

Compound 122

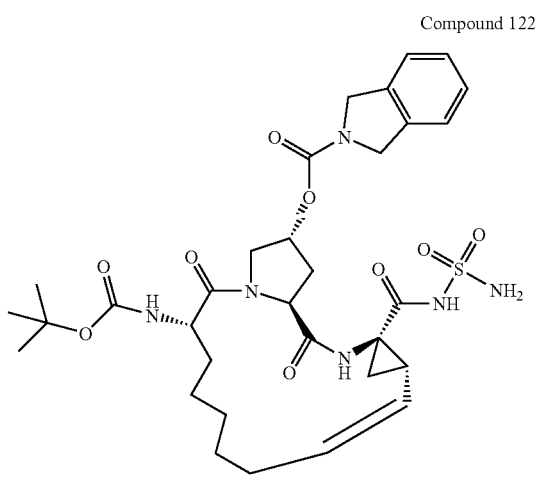

(1S,4R,6S,14S,18R)-1,3-Dihydro-isoindole-2-carboxylic acid 14-tert-butoxycarbonylamino-4-(aminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with sulfamide in Step F instead. MS m/z 688.2 (APCI–, M–1).

Example 23

Compound 123

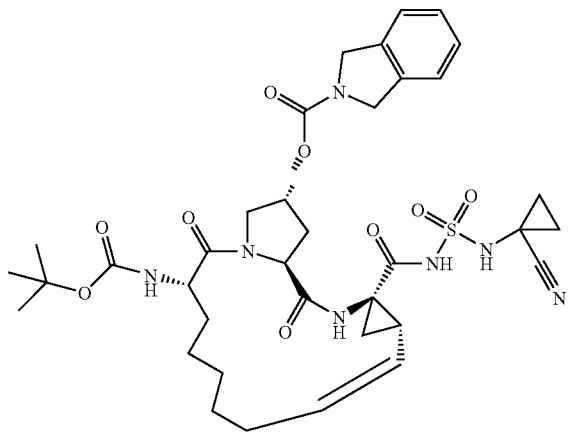

(1S,4R,6S,14S,18R)-1,3-Dihydro-isoindole-2-carboxylic acid 14-tert-butoxycarbonylamino-4-(N-(1-cyanocyclopropyl)aminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with 1-cyanocyclopropylsulfamide in Step F instead. $^1$H NMR (400 MHz, d$^6$-acetone) δ 1.22 (s, 9H), 1.20-1.55 (m, 11H), 1.58-1.61 (m, 1H), 1.66-1.69 (m, 1H), 1.71-1.75 (m, 1H), 1.81-1.90 (m, 2H), 2.42-2.48 (m, 3H), 2.60-2.70 (m, 1H), 3.84-3.88 (m, 1H), 4.16-4.20 (m, 1H), 4.48 (br d, 1H), 4.58-4.71 (m, 5H), 5.07 (t, 1H), 5.44 (br s, 1H), 5.62 (q, 1H), 6.14 (br d, 1H), 7.22-7.36 (m, 4H), 7.88 (br s, 1H), 8.20 (s, 1H). MS m/z 752.3 (APCI–, M–1)

Example 23a

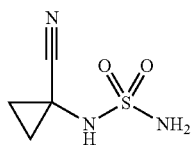

The title compound, 1-cyanocyclopropylsulfamide, was prepared according to the same procedures as described for the synthesis of N-cyclopropylsulfamide (Route A, Scheme 2), substituting cyclopropyl amine with 1-aminocyclopropanecarbonitrile hydrochloride. $^1$H NMR (CDCl$_3$, 400 MHz) δ 1.41-1.44 (m, 2H), 1.52-1.55 (m, 2H), 5.86 (br s, 2H), 7.19 (br s, 1H).

Example 24

Compound 124

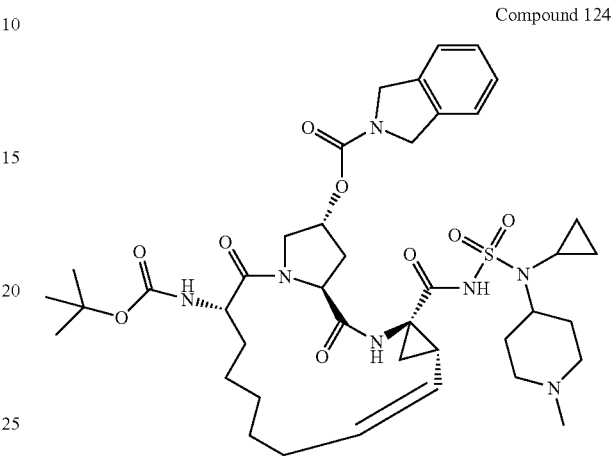

(1S,4R,6S,14S,18R)-1,3-Dihydro-isoindole-2-carboxylic acid 14-tert-butoxycarbonylamino-4-(cyclopropyl(1-methylpiperidin-4-yl)aminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with cyclopropyl(1-methylpiperidin-4-yl)sulfamide in Step F instead. $^1$H NMR (400 MHz, d$^6$-acetone) δ 0.75-0.77 (m, 2H), 0.96-1.01 (m, 2H), 1.21 (s, 9H), 1.20-1.57 (m, 7H), 1.60-1.66 (m, 1H), 1.71-1.74 (m, 1H), 1.80-1.92 (m, 3H), 1.97-2.06 (m, 1H), 2.38-2.60 (m, 5H), 2.68 (s, 3H), 2.88-3.02 (m, 2H), 3.32-3.41 (m, 2H), 3.90-3.96 (m, 2H), 4.17-4.23 (m, 2H), 4.41-4.47 (m, 2H), 4.59-4.72 (m, 5H), 5.10 (t, 1H), 5.45 (br s, 1H), 5.63-5.70 (m, 1H), 6.11 (br d, 1H), 6.95 (s, 1H), 7.19-7.35 (m, 4H), 8.42 (s, 1H). MS m/z 824.4 (APCI–, M–1).

Example 24a

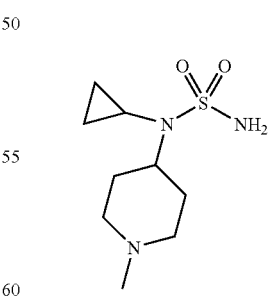

The title compound, cyclopropyl(1-methylpiperidin-4-yl)sulfamide, was prepared by the same fashion as described in Example 17a, substituting azetidine with N-cyclopropyl-1-methylpiperidin-4-amine. $^1$H NMR (d$^6$-DMSO, 400 MHz) δ 0.67-0.76 (m, 4H), 1.93-1.97 (m, 2H), 2.07-2.18 (m, 2H), 2.22-2.26 (m, 1H), 2.75 (s, 3H), 2.96-3.05 (m, 2H), 3.45-3.48 (m, 2H), 3.77-3.83 (m, 1H), 6.93 (br s, 2H), 9.78 (br s, 1H).

Example 25

Compound 125

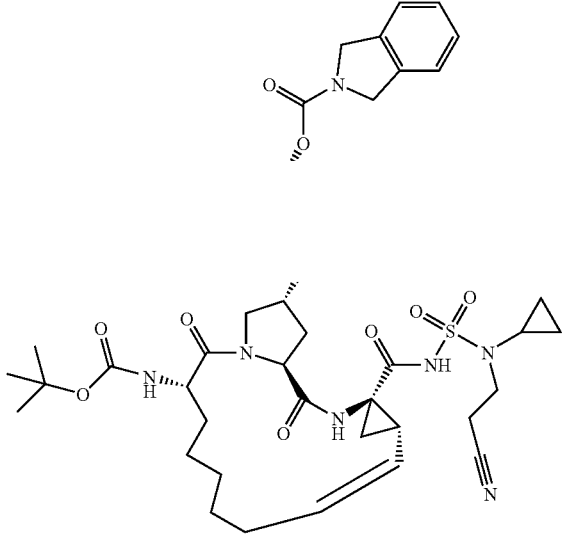

(1S,4R,6S,14S,18R)-1,3-Dihydro-isoindole-2-carboxylic acid 14-tert-butoxycarbonylamino-4-(2-cyanoethyl(cyclopropyl)aminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with 2-cyanoethyl(cyclopropyl)sulfamide in Step F instead. $^1$H NMR (400 MHz, d$^6$-acetone) δ 0.74-0.78 (m, 2H), 0.98-1.01 (m, 2H), 1.21 (s, 9H), 1.20-1.54 (m, 7H), 1.59-1.63 (m, 1H), 1.74-1.77 (m, 1H), 1.82-1.87 (m, 2H), 2.41-2.65 (m, 6H), 2.79-2.83 (m, 2H), 3.49-3.56 (m, 1H), 3.84-3.88 (m, 1H), 3.97-4.04 (m, 1H), 4.14-4.18 (m, 1H), 4.50 (br d, 1H), 4.60-4.72 (m, 5H), 5.05 (t, 1H), 5.45 (br s, 1H), 5.68 (q, 1H), 6.15 (br d, 1H), 7.22-7.36 (m, 4H), 8.33 (s, 1H). MS m/z 781.3 (APCI–, M).

Example 25a

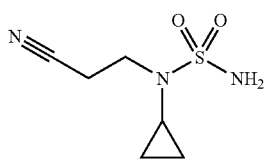

The title compound, 2-cyanoethyl(cyclopropyl)sulfamide, was prepared by the same fashion as described in Example 17a, substituting azetidine with 3-(cyclopropylamino)propanenitrile. $^1$H NMR (d$^6$-DMSO, 400 MHz) δ 0.68-0.76 (m, 4H), 2.36-2.37 (m, 1H), 2.78 (t, 2H), 3.35 (t, 2H), 7.05 (br s, 2H).

Example 26

Compound 126

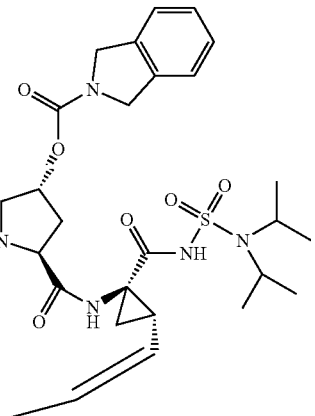

(1S,4R,6S,14S,18R)-1,3-Dihydro-isoindole-2-carboxylic acid 14-tert-butoxycarbonylamino-4-(N,N-diisopropylaminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with N,N-diisopropylsulfamide in Step F instead. $^1$H NMR (400 MHz, d$^6$-acetone) δ 1.21 (s, 9H), 1.25-1.53 (m, 20H), 1.68-1.71 (m, 1H), 1.81-1.87 (m, 2H), 2.38-2.45 (m, 3H), 2.56-2.68 (m, 1H), 3.84-3.87 (m, 1H), 3.94-4.01 (m, 2H), 4.14-4.18 (m, 1H), 4.47 (br d, 1H), 4.58-4.68 (m, 5H), 5.03 (t, 1H), 5.44 (br s, 1H), 5.62 (q, 1H), 6.11 (br d, 1H), 7.23-7.36 (m, 4H), 8.24 (s, 1H), 10.29 (br s, 1H). MS m/z 772.3 (APCI–, M).

Example 26a

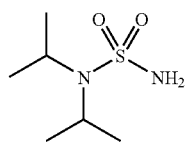

The title compound, N,N-diisopropylsulfamide, was prepared by the same fashion as described in Example 17a, substituting azetidine with diisopropylamine. $^1$H NMR (d$_6$-acetone, 400 MHz) δ 1.23 (d, 12H), 3.70-3.77 (m, 2H), 5.67 (br s, 2H).

Example 27

Compound 127

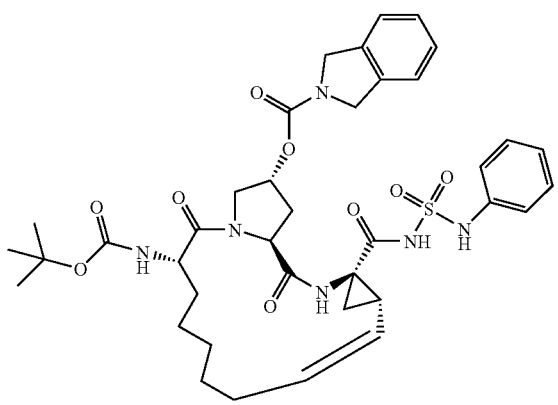

(1S,4R,6S,14S,18R)-1,3-Dihydro-isoindole-2-carboxylic acid 14-tert-butoxycarbonylamino-4-(phenylaminosulfonyl-aminocarbonyl)-2,15-dioxo-3,16-diaza-tricyclo[14.3.0.0^{4,6}]nonadec-7-en-18-yl ester was synthesized according to the same procedures as described in Example 1, substituting N,N-dimethylsulfamide with phenylsulfamide in Step F instead. $^1$H NMR (400 MHz, d$^6$-acetone) δ 1.20 (s, 9H), 1.20-1.50 (m, 8H), 1.60-1.70 (m, 2H), 1.78-1.86 (m, 1H), 2.30-2.44 (m, 4H), 3.81-3.85 (m, 1H), 4.12-4.17 (m, 1H), 4.45 (br d, 1H), 4.54-4.75 (m, 6H), 5.28 (q, 1H), 5.43 (br s, 1H), 6.11 (br d, 1H), 7.14-7.35 (m, 9H), 8.22 (s, 1H), 8.97 (br s, 1H), 10.80 (br s, 1H). MS m/z 764.3 (APCI−, M).

Example 27a

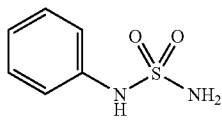

The title compound, phenylsulfamide, was prepared according to the same procedures as described for the synthesis of N-cyclopropylsulfamide (Route A, Scheme 2), substituting cyclopropyl amine with aniline. $^1$H NMR (d$^6$-DMSO, 400 MHz) δ 6.95-6.98 (m, 1H), 7.06 (br s, 2H), 7.14-7.16 (m, 2H), 7.24-7.28 (m, 2H), 9.46 (br s, 1H).

Example 28

Compound 128

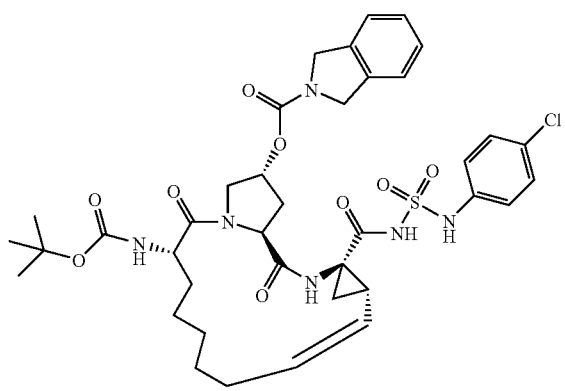

(1S,4R,6S,14S,18R)-1,3-Dihydro-isoindole-2-carboxylic acid 14-tert-butoxycarbonylamino-4-(4-chlorophenylamino-sulfonyl-aminocarbonyl)-2,15-dioxo-3,16-diaza-tricyclo [14.3.0.0^{4,6}]nonadec-7-en-18-yl ester was synthesized according to the same procedures as described in Example 1, substituting N,N-dimethylsulfamide with 4-chlorophenylsulfamide in Step F instead. $^1$H NMR (400 MHz, d$^6$-acetone) δ 1.19 (s, 9H), 1.18-1.51 (m, 8H), 1.61-1.72 (m, 2H), 1.76-1.87 (m, 1H), 2.32-2.44 (m, 4H), 3.82-3.86 (m, 1H), 4.12-4.16 (m, 1H), 4.45 (br d, 1H), 4.54-4.72 (m, 6H), 5.28 (q, 1H), 5.43 (br s, 1H), 6.10 (br d, 1H), 7.22-7.38 (m, 8H), 8.24 (s, 1H). MS m/z 798.2 (APCI−, M).

Example 28a

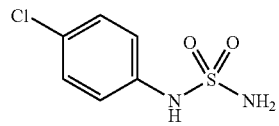

The title compound, 4-chlorophenylsulfamide, was prepared according to the same procedures as described for the synthesis of N-cyclopropylsulfamide (Route A, Scheme 2), substituting cyclopropyl amine with 4-chlorobenzenamine. $^1$H NMR (d$^6$-DMSO, 400 MHz) δ 7.09-7.12 (m, 4H), 7.27 (d, 2H), 9.59 (br s, 1H).

Example 29

Compound 129

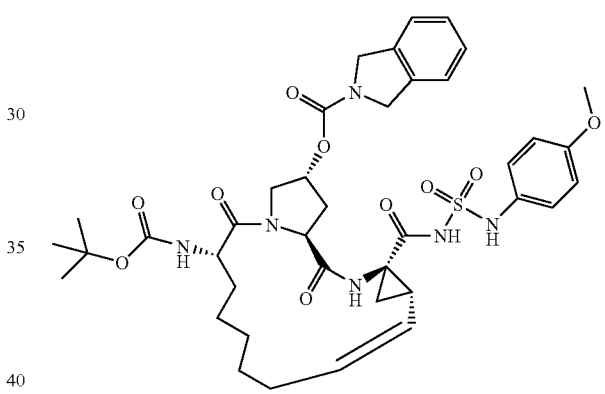

(1S,4R,6S,14S,18R)-1,3-Dihydro-isoindole-2-carboxylic acid 14-tert-butoxycarbonylamino-4-(4-methoxyphenylami-nosulfonyl-aminocarbonyl)-2,15-dioxo-3,16-diaza-tricyclo [14.3.0.0^{4,6}]nonadec-7-en-18-yl ester was synthesized according to the same procedures as described in Example 1, substituting N,N-dimethylsulfamide with 4-methoxyphenyl-sulfamide in Step F instead. $^1$H NMR (400 MHz, d$^6$-acetone) δ 1.20 (s, 9H), 1.18-1.54 (m, 8H), 1.64-1.87 (m, 3H), 2.22-2.46 (m, 4H), 3.80 (s, 3H), 3.77-3.82 (m, 1H), 4.14 (m, 1H), 4.43 (br d, 1H), 4.52-4.70 (m, 5H), 4.88 (t, 1H), 5.40-5.50 (m, 2H), 6.10 (br d, 1H), 6.88-6.90 (d, 2H), 7.18-7.35 (m, 6H), 8.18 (s, 1H). MS m/z 794.3 (APCI−, M).

Example 29a

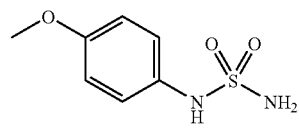

The title compound, 4-methoxyphenylsulfamide, was prepared according to the same procedures as described for the synthesis of N-cyclopropylsulfamide (Route A, Scheme 2), substituting cyclopropyl amine with 4-methoxybenzenamine. $^1$H NMR (d$^6$-DMSO, 400 MHz) δ 3.71 (s, 3H), 6.85-6.87 (m, 4H), 7.11 (d, 2H), 9.01 (br s, 1H).

Example 30

Compound 130

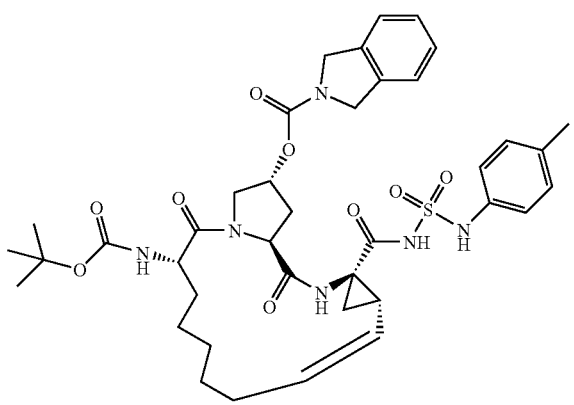

(1S,4R,6S,14S,18R)-1,3-Dihydro-isoindole-2-carboxylic acid 14-tert-butoxycarbonylamino-4-(4-methylphenylaminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with 4-methylphenylsulfamide in Step F instead. $^1$H NMR (400 MHz, d$^6$-acetone) δ 1.20 (s, 9H), 1.20-1.52 (m, 8H), 1.60-1.74 (m, 2H), 1.76-1.87 (m, 1H), 2.26-2.42 (m, 4H), 2.31 (s, 3H), 3.81-3.84 (m, 1H), 4.14-4.17 (m, 1H), 4.44 (br d, 1H), 4.52-4.79 (m, 6H), 5.32 (q, 1H), 5.42 (br s, 1H), 6.11 (br d, 1H), 7.14-7.35 (m, 8H), 8.20 (s, 1H), 8.79 (br s, 1H), 10.69 (br s, 1H). MS m/z 778.2 (APCI–, M).

Example 30a

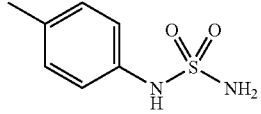

The title compound, 4-methylphenylsulfamide, was prepared according to the same procedures as described for the synthesis of N-cyclopropylsulfamide (Route A, Scheme 2), substituting cyclopropyl amine with 4-methylbenzenamine. $^1$H NMR (d$^6$-DMSO, 400 MHz) δ 2.18 (s, 3H), 6.91 (s, 2H), 7.01 (s, 4H), 9.20 (s, 1H).

Example 31

Compound 131

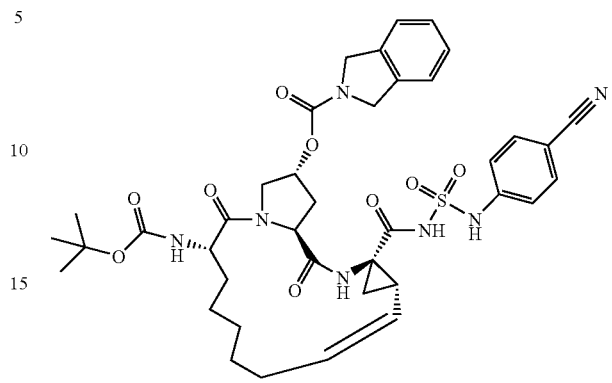

(1S,4R,6S,14S,18R)-1,3-Dihydro-isoindole-2-carboxylic acid 14-tert-butoxycarbonylamino-4-(4-cyanophenylaminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with 4-cyanophenylsulfamide in Step F instead. $^1$H NMR (400 MHz, d$^6$-acetone) δ 1.20 (s, 9H), 1.18-1.53 (m, 8H), 1.60-1.70 (m, 2H), 1.76-1.87 (m, 1H), 2.32-2.48 (m, 4H), 3.85-3.88 (m, 1H), 4.15-4.17 (m, 1H), 4.46 (br d, 1H), 4.57-4.71 (m, 6H), 5.16 (q, 1H), 5.46 (br s, 1H), 6.10 (br d, 1H), 7.24-7.35 (m, 4H), 7.42 (d, 2H), 7.76 (d, 2H), 8.28 (s, 1H). MS m/z 788.3 (APCI–, M–1).

Example 31a

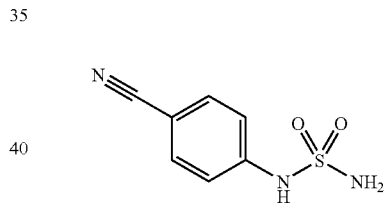

The title compound, 4-cyanophenylsulfamide, was prepared according to the same procedures as described for the synthesis of N-cyclopropylsulfamide (Route A, Scheme 2), substituting cyclopropyl amine with 4-aminobenzonitrile. $^1$H NMR (d$^6$-DMSO, 400 MHz) δ 7.22 (d, 2H), 7.40 (br s, 2H), 7.70 (d, 2H), 10.24 (br s, 1H).

Example 32

Compound 132

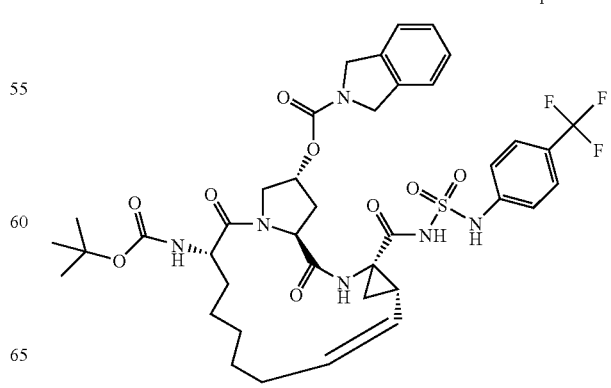

(1S,4R,6S,14S,18R)-1,3-Dihydro-isoindole-2-carboxylic acid 14-tert-butoxycarbonylamino-4-(4-trifluoromethylphenylaminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with 4-trifluoromethylphenylsulfamide in Step F instead. $^1$H NMR (400 MHz, d$^6$-acetone) δ 1.19 (s, 9H), 1.18-1.64 (m, 10H), 1.82 (q, 1H), 2.30-2.46 (m, 4H), 3.84-3.87 (m, 1H), 4.12-4.16 (m, 1H), 4.47 (br d, 1H), 4.57-4.71 (m, 6H), 5.11 (q, 1H), 5.45 (s, 1H), 6.12 (br d, 1H), 7.23-7.35 (m, 4H), 7.45 (d, 2H), 7.69 (d, 2H), 8.30 (s, 1H), 9.53 (br s, 1H), 11.06 (br s, 1H). MS m/z 832.2 (APCI−, M).

Example 32a

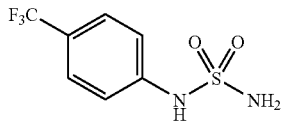

The title compound, 4-trifluoromethylphenylsulfamide, was prepared according to the same procedures as described for the synthesis of N-cyclopropylsulfamide (Route A, Scheme 2), substituting cyclopropyl amine with 4-(trifluoromethyl)benzenamine. $^1$H NMR (d$^6$-DMSO, 400 MHz) δ 7.26-7.30 (m, 4H), 7.59 (d, 2H), 10.05 (br s, 1H).

Example 33

Compound 133

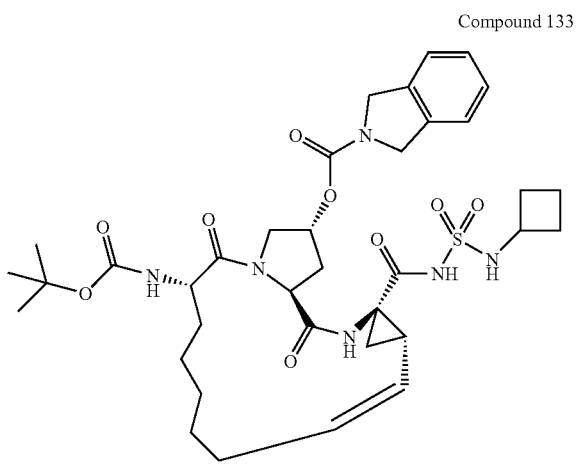

(1S,4R,6S,14S,18R)-1,3-Dihydro-isoindole-2-carboxylic acid 14-tert-butoxycarbonylamino-4-(cyclobutylaminosulfonyl-aminocarbonyl)-2,15-dioxo-3,16-diaza-tricyclo[14.3.0.0$^{4,6}$]nonadec-7-en-18-yl ester was synthesized according to the same procedures as described in Example 1, substituting N,N-dimethylsulfamide with cyclobutylsulfamide in Step F instead. $^1$H NMR (400 MHz, d$^6$-acetone) δ 1.21 (s, 9H), 1.20-1.70 (m, 11H), 1.80-1.90 (m, 2H), 2.02-2.09 (m, 2H), 2.21-2.30 (m, 2H), 2.41-2.47 (m, 3H), 2.58-2.68 (m, 1H), 3.75-3.87 (m, 2H), 4.15-4.18 (m, 1H), 4.47 (br d, 1H), 4.57-4.72 (m, 5H), 5.11 (t, 1H), 5.44 (s, 1H), 5.63 (q, 1H), 6.14 (br d, 1H), 6.34 (br d, 1H), 7.23-7.36 (m, 4H), 8.18 (s, 1H). MS m/z 741.4 (APCI−, M−1).

Example 33a

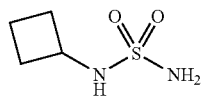

The title compound, cyclobutylsulfamide, was prepared by the same fashion as described in Example 17a, substituting azetidine with cyclobutanamine. $^1$H NMR (d$^6$-DMSO, 400 MHz) δ 1.20-1.60 (m, 2H), 1.89-1.94 (m, 2H), 2.14-2.21 (m, 2H), 3.67 (m, 1H), 6.42 (br s, 2H), 6.82 (br s, 1H).

Example 34

Compound 134

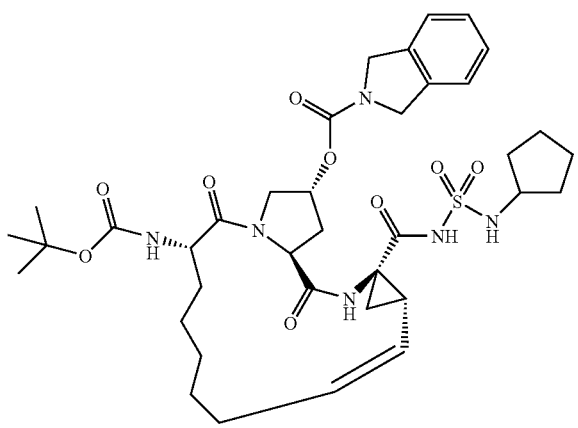

(1S,4R,6S,14S,18R)-1,3-Dihydro-isoindole-2-carboxylic acid 14-tert-butoxycarbonylamino-4-(cyclopentylaminosulfonyl-aminocarbonyl)-2,15-dioxo-3,16-diaza-tricyclo [14.3.0.0$^{4,6}$]nonadec-7-en-18-yl ester was synthesized according to the same procedures as described in Example 1, substituting N,N-dimethylsulfamide with cyclopentylsulfamide in Step F instead. $^1$H NMR (400 MHz, d$^6$-acetone) δ 1.21 (s, 9H), 1.20-1.73 (m, 15H), 1.87-1.96 (m, 4H), 2.41-2.49 (m, 3H), 2.56-2.68 (m, 1H), 3.55-3.60 (m, 1H), 3.84-3.87 (m, 1H), 4.15-4.18 (m, 1H), 4.48 (br d, 1H), 4.57-4.72 (m, 5H), 5.08 (t, 1H), 5.44 (s, 1H), 5.63 (q, 1H), 6.15 (br d, 1H), 6.24 (br d, 1H), 7.23-7.35 (m, 4H), 8.25 (s, 1H), 10.25 (br s, 1H). MS m/z 755.4 (APCI−, M−1).

Example 34a

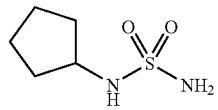

The title compound, cyclopentylsulfamide, was prepared by the same fashion as described in Example 17a, substituting azetidine with cyclopentanamine. ¹H NMR (d⁶-DMSO, 400 MHz) δ 1.43-1.61 (m, 6H), 1.80-1.83 (m, 2H), 3.54 (m, 1H), 6.42 (br s, 3H).

Example 35

Compound 135

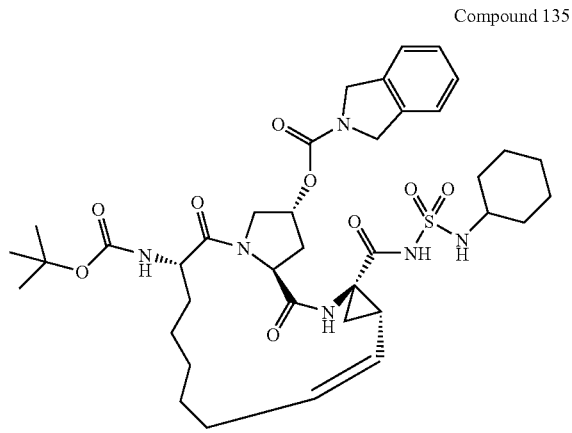

(1S,4R,6S,14S,18R)-1,3-Dihydro-isoindole-2-carboxylic acid 14-tert-butoxycarbonylamino-4-(cyclohexylaminosulfonyl-aminocarbonyl)-2,15-dioxo-3,16-diaza-tricyclo[14.3.0.0⁴,⁶]nonadec-7-en-18-yl ester was synthesized according to the same procedures as described in Example 1, substituting N,N-dimethylsulfamide with cyclohexylsulfamide in Step F instead. ¹H NMR (400 MHz, d⁶-acetone) δ 1.21 (s, 9H), 1.14-2.0 (m, 21H), 2.41-2.48 (m, 3H), 2.57-2.67 (m, 1H), 3.07-3.16 (m, 1H), 3.84-3.87 (m, 1H), 4.15-4.19 (m, 1H), 4.47 (br d, 1H), 4.57-4.72 (m, 5H), 5.08 (t, 1H), 5.44 (s, 1H), 5.64 (q, 1H), 6.13-6.17 (m, 2H), 7.23-7.36 (m, 4H), 8.23 (s, 1H), 10.30 (br s, 1H). MS m/z 769.4 (APCI−, M−1).

Example 35a

Compound 136

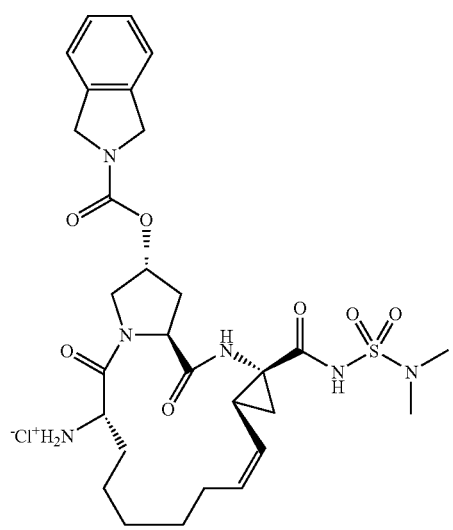

Synthesis of (1S,4R,6S,14S,18R)-1,3-Dihydro-isoindole-2-carboxylic acid 14-amino-4-(N,N-dimethylsulfonyl-aminocarbonyl)-2,15-dioxo-3,16-diaza-tricyclo[14.3.0.0⁴,⁶]nonadec-7-en-18-yl ester, HCl salt (Compound 136)

was synthesized by taking up Compound 101 (79 mg) was taken up in 0.5 mL of 4 M HCl/Dioxane and stirred at rt for 16 h. Reaction was then concentrated and taken up in acetonitrile for concentration again. The hydrochloride salt was then dried overnight on a high vacuum pump to give product as a white solid (76 mg). +APCI MS m/z 617.1 (M+1).

Example 35b

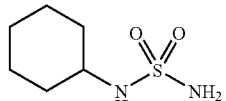

The title compound, cyclohexylsulfamide, was prepared by the same fashion as described in Example 17a, substituting azetidine with cyclohexanamine. ¹H NMR (d⁶-DMSO, 400 MHz) δ 1.08-1.23 (m, 5H), 1.50-1.54 (m, 1H), 1.65-1.68 (m, 2H), 1.86-1.89 (m, 2H), 3.02 (m, 1H), 6.40 (br s, 3H).

Example 36

NS3-NS4 Protease Assay

NS3 complex formation with NS4A-2.

Recombinant *E. coli* or Baculovirus full-length NS3 was diluted to 3.33 µM with assay buffer and transfered material to an eppendorf tube and place in water bath in 4° C. refrigerator. The appropriate amount of NS4A-2 to 8.3 mM in assay buffer was added to equal the volume of NS3 in step 2.1.1 (conversion factor −3.8 mg/272 µL assay buffer). The material was transferred to an eppendorf tube and place in water bath in 4° C. refrigerator.

After equilibration to 4° C., equal volumes of NS3 and NS4A-2 solutions were combined in an eppendorf tube, mix gently with a manual pipettor, and incubate mixture for 15 minutes in the 4° C. water bath. Final concentrations in the mixture are 1.67CM NS3, 4.15 mM NS4A-2 (2485-fold molar excess NS4A-2).

After 15 minutes at 4° C., the NS3/NS4A-2 eppendorf tube was removed and place it in a room temperature water bath for 10 minutes. NS3/NS4A-2 was alliquoted at appropriate volumes and store at −80° C. (*E. coli* NS3 run at 2 nM in assay, aliquot at 25 µL. BV NS3 run at 3 nM in assay, aliquot at 30 µL).

Example 37

NS3 Inhibition Assay

Step 2.2.5. Sample compounds were dissolved to 10 mM in DMSO then diluted to 2.5 mM (1:4) in DMSO. Typically, compounds were added to an assay plate at 2.5 mM concentration, yielding upon dilution a starting concentration of 50 microM in the assay inhibition curve. Compounds were serial diluted in assay buffer to provide test solutions at lower concentrations.

Step 2.2.6. The *E. coli*. NS3/NS4A-2 was diluted to 4 nM NS3 (1:417.5 of 1.67CM stock–18 µL 1.67 µM stock+7497 µL assay buffer). The BV NS3/NS4A-2 was diluted to 6 nM NS3 (1:278.3 of 1.67 µM stock–24 µL 1.67 µM stock+6655 µL assay buffer).

Step 2.2.7. Using the manual multichannel pipettor, and being careful not to introduce bubbles into the plate, 50 µL assay buffer were added to wells A01-H01 of a black Costar 96-well polypropylene storage plate.

Step 2.2.8. Using the manual multichannel pipettor, and being careful not to introduce bubbles into the plate, 50 µL of diluted NS3/NS4A-2 from step 2.2.6 were added to wells A02-H12 of plate in step 2.2.7.

Step 2.2.9. Using the manual multichannel pipettor, and being careful not to introduce bubbles into the plate, 25 µL of the wells in drug dilution plate in step 2.2.5 were transferred to corresponding wells in assay plate in step 2.2.8. The tips on multichannel pipettor were changed for each row of compounds transferred.

Step 2.2.10. Using the manual multichannel pipettor, and being careful not to introduce bubbles into the plate, the contents of the wells from the assay plate in step 2.2.9 were mixed by aspirating and dispensing 35 µL of the 75 µL in each well five times. The tips on the multichannel pipettor were changed for each row of wells mixed.

Step 2.2.11. The plate was covered with a polystyrene plate lid, and the plate from step 2.2.10 containing NS3 protease and sample compounds was pre-incubated 10 minutes at room temperature.

While the plate from step 2.2.11 was pre-incubating, the RETS1 substrate was diluted in a 15 mL polypropylene centrifuge tube. The RETS1 substrate was diluted to 8 µM (1:80.75 of 646 µM stock–65 µL 646 µM stock+5184 µL assay buffer).

After the plate in step 2.2.11 was done pre-incubating, and using the manual multichannel, 25 µL of substrate were added to all wells on the plate. The contents of the wells of plate were quickly mixed, as in step 2.2.10, but mixing 65 µL of the 100 µL in the wells.

The plate was read in kinetic mode on the Molecular Devices SpectraMax Gemini XS plate reader. Reader settings: Read time: 30 minutes, Interval: 36 seconds, Reads: 51, Excitation λ: 335 nm, Emission λ: 495 nm, cutoff: 475 nm, Automix: off, Calibrate: once, PMT: high, Reads/well: 6, Vmax pts: 21 or 28/51 depending on length of linearity of reaction.

$IC_{50}$s were determined using a four parameter curve fit equation, and converted to Ki's using the following Km's:

Full-length *E. coli* NS3-2.03 µM

Full-length BV NS3-1.74 µM where $Ki=IC_{50}/(1+[S]/Km))$

Quantitation by ELISA of the selectable marker protein, Neomycin phosphotransferase II (NPTII) in the HCV Sub-Genomic Replicon, GS4.3

The HCV sub-genomic replicon (1377/NS3-3', accession No. AJ242652), stably maintained in HuH-7 hepatoma cells, was created by Lohmann et al. Science 285: 110-113 (1999). The replicon-containing cell culture, designated GS4.3, was obtained from Dr. Christoph Seeger of the Institute for Cancer Research, Fox Chase Cancer Center, Philadelphia, Pa.

GS4.3 cells were maintained at 37° C., 5% $CO_2$, in DMEM (Gibco 11965-092) supplemented with L-glutamine 200 mM (100×) (Gibco25030-081), non-essential amino acids (NEAA)(Biowhittaker 13-114E), heat-inactivated (HI) Fetal Bovine Serum(FBS)(Hyclone SH3007.03) and 750 µg/ml geneticin (G418)(Gibco 10131-035). Cells were sub-divided 1:3 or 4 every 2-3 days.

24 h prior to the assay, GS4.3 cells were collected, counted, and plated in 96-well plates (Costar 3585) at 7500 cells/well in 100 µl standard maintenance medium (above) and incubated in the conditions above. To initiate the assay, culture medium was removed, cells were washed once with PBS (Gibco 10010-023) and 90 µl Assay Medium (DMEM, L-glutamine, NEAA, 10% HI FBS, no G418) was added. Inhibitors were made as a 10× stock in Assay Medium, (3-fold dilutions from 10 µM to 56 µM final concentration, final DMSO concentration 1%), 10 µl were added to duplicate wells, plates were rocked to mix, and incubated as above for 72 h.

An NPTII Elisa kit was obtained from AGDIA, Inc. (Compound direct ELISA test system for Neomycin Phosphotransferase II, PSP 73000/4800). Manufacturer's instructions were followed, with some modifications. 10×PEB-1 lysis buffer was made up to include 500 µM PMSF (Sigma P7626, 50 mM stock in isopropanol). After 72 h incubation, cells were washed once with PBS and 150 µl PEB-1 with PMSF was added per well. Plates were agitated vigorously for 15 minutes, room temperature, then frozen at −70° C. Plates were thawed, lysates were mixed thoroughly, and 100 µl were applied to an NPTII Elisa plate. A standard curve was made. Lysate from DMSO-treated control cells was pooled, serially diluted with PEB-1 with PMSF, and applied to duplicate wells of the ELISA plate, in a range of initial lysate amount of 150u1-2.5 ul. In addition, 100 µl buffer alone was applied in duplicate as a blank. Plates were sealed and gently agitated at room temperature for 2 h. Following capture incubation, the plates were washed 5×300 µl with PBS-T (0.5% Tween-20, PBS-T was supplied in the ELISA kit). For detection, a 1× dilution of enzyme conjugate diluent MRS-2 (5×) was made in PBS-T, into which 1:100 dilutions of enzyme conjugates A and B were added, as per instructions. Plates were resealed, and incubated with agitation, covered, room temperature, for 2 h. The washing was then repeated and 100 µl of room temperature TMB substrate was added. After approximately 30 minutes incubation (room temperature, agitation, covered), the reaction was stopped with 50 µl 3M sulfuric acid. Plates were read at 450 nm on a Molecular Devices Versamax plate reader.

Inhibitor effect was expressed as a percentage of DMSO-treated control signal, and inhibition curves were calculated using a 4-parameter equation: $y=A+((B-A)/(1+((C/x)^{\wedge}D)))$, where C is half-maximal activity or $EC_{50}$.

Examples of Activity:

Wherein:

A indicates an $IC_{50}$ or $EC_{50}$ of less than 1 µM and B indicates an $IC_{50}$ or $EC_{50}$ of less than 0.1 µM

TABLE 3

| Compound | NS3-NS4 $IC_{50}$ | $EC_{50}$ |
| --- | --- | --- |
| 101 | B | B |
| 102 | B | B |
| 103 | B | B |
| 104 | B | B |
| 105 | B | N/A |
| 106 | B | B |
| 107 | B | B |
| 108 | A | B |
| 109 | B | A |
| 110 | A | N/A |
| 111 | B | N/A |

TABLE 3-continued

| Compound | NS3-NS4 IC$_{50}$ | EC$_{50}$ |
|---|---|---|
| 112 | B | N/A |
| 113 | B | B |
| 114 | B | B |
| 115 | B | B |
| 116 | B | A |
| 117 | B | B |
| 118 | B | B |
| 119 | B | B |
| 120 | B | N/A |
| 121 | B | B |
| 122 | B | B |
| 123 | B | N/A |
| 124 | A | B |
| 125 | B | B |
| 126 | B | B |
| 127 | B | B |
| 128 | B | B |
| 129 | B | B |
| 130 | B | B |
| 131 | B | B |
| 132 | B | B |
| 133 | B | B |
| 134 | B | B |
| 135 | B | B |

Example 38

Specificity Assays

When the compounds were evaluated in specificity assays, the compounds of Formula I were found to be selective in that they do not show significant inhibition in Cathepsin B, Chymotrypsin, Thrombin or Leukocyte Elastase.

Example 39

Pharmacokinetic Analysis of Compounds

Compounds were initially synthesized and tested for potency (IC$_{50}$) in a fluorogenic NS3/4 protease assay and cell-based HCV replicon system as described above. Plasma pharmacokinetic analysis in *Rattus* sp. following IV administration was then used in conjunction with in vitro human liver microsome (HLM) and hepatocyte stability studies to direct the design of metabolically stable compounds from compounds with <20 nM potency. These leads were then further optimized for drug-like physical properties and administered in oral doses in *Rattus* sp. to assess liver, heart and plasma concentrations.

Methods

Compounds were initially synthesized and tested for potency (IC$_{50}$) in a fluorogenic NS3/4 protease assay and cell-based HCV replicon system as described in Example 8 above. Plasma pharmacokinetic analysis in *Rattus* sp. following IV administration was then used in conjunction with in vitro human liver microsome (HLM) and hepatocyte stability studies to direct the design of metabolically stable compounds from compounds with <20 nM potency. These leads were then further optimized for drug-like physical properties and administered in oral doses in *Rattus* sp. to assess liver, heart and plasma concentrations.

Compounds were tested for liver clearance over time following a single 3 mg/kg oral dose in rats. For any compound found to exhibit a concentration in liver at 8 hours post-administration that is at least 100-fold more than the concentration of the compound effective to inhibit 50% of maximum inhibition in the replicon assay (replicon EC$_{50}$), additional toxicological assessments were performed in rats using dosages of up to 30 mg/kg orally BID for seven days.

Results

Compound AR334187 yielded a replicon EC$_{50}$ value of approximately 2 nM and exhibited stability in vitro in rat, dog and human hepatocyte incubation assays, which data would predict low to moderate rates of clearance from liver. In addition, this compound displayed a high degree of selectivity against a panel of other serine proteases, and no significant inhibition of Cytochrome P450 isoforms or hERG channel activity at even the highest concentrations tested (10 µM).

For compound AR334187, a single 30 mg/kg oral dose in *Rattus* sp. yielded a concentration in liver at 24 hours post dose that was at least 200-fold more than the compound's replicon EC$_{50}$ value.

Compound AR334187 yielded heart and plasma levels up to two orders of magnitude lower than, and correlated kinetically with, liver concentrations in the same animals. At a clinically more reasonable oral dose (3 mg/kg), compound AR334187 yielded a concentration in liver at 8 hours post dose that was over 100-fold more than the replicon EC50 value of the compound. After exposure to compound AR334187 at a dosage of 30 mg/kg orally BID for 7 days, no mortality, change in weight, or abnormalities in clinical chemistries were observed in treated animals.

Conclusion

Potent, metabolically stable, orally available small molecule inhibitors of the HCV NS3 protease have been developed. At modest oral dosing concentrations (3 mg/kg) these compounds display high liver levels (100-fold greater than their respective replicon EC50 values) at 8 hours post dose. Exposure to plasma and heart is up to two orders of magnitude below that observed in liver, and such low concentrations minimizes any potential systemic toxicological issues.

Compound AR334187 did not display toxicity in *Rattus* sp. when dosed for seven days at 30 mg/kg BID, providing at least a 10-fold safety margin above the presumptive efficacious dose (3 mg/kg) that yields liver concentrations 100-fold in excess of the replicon EC$_{50}$ value of the compound.

Preparation of Section D Viral Inhibitors

The meanings of the terms and structural names used within this section are the same as those in Section D above. Any references within this section to a particular number or label should be understood in the context of the corresponding numbering or labeling scheme used within this section or Section D above, rather than in the context of a possibly similar or identical numbering or labeling scheme used elsewhere herein, unless otherwise indicated.

The compounds of formula XVIII may be synthesized according to the methods described below.

(2S,4R)-4-Amino-1-[benzyloxycarbonyl]pyrrolidine-2-methylcarboxylate hydrochloride was available from Array Biopharma, 2(S)-tert-butoxycarbonylamino-non-8-enoic acid and 1(R)-tert-butoxycarbonylamino-2(S)-vinyl-cyclopropanecarboxylic acid ethyl ester were prepared according to the procedures disclosed in International Application PCT/CA00/00353 (Publication No. WO 00/59929). 2(S)-tert-butoxycarbonylamino-non-8-enoic acid was also purchased from RSP Amino Acids.

Two key aminoproline macrocyclic intermediates A and B were used in preparing the NS3 inhibitors shown in Examples 1-69.

1. Preparation of Aminoproline Macrocyclic Acylsulfonamide Intermediate A

Synthesis of (1S,4R,6S,14S,18R)-(18-amino-4-cyclopropanesulfonylaminocarbonyl-2,15-dioxo-3,16-diaza-tricyclo[14.3.0.0$^{4,6}$]nonadec-7-en-14-yl)-carbamic acid tert-butyl ester Scheme 1

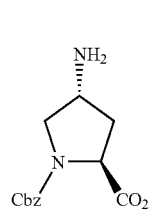

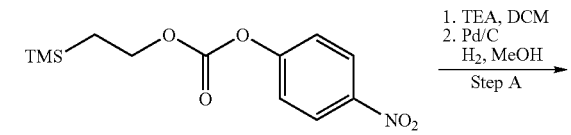

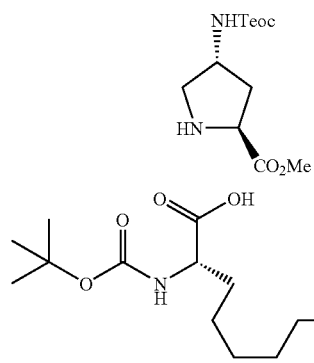

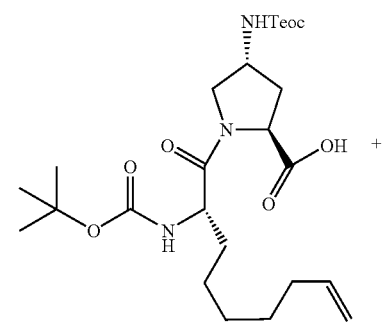

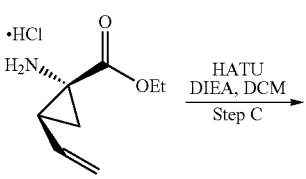

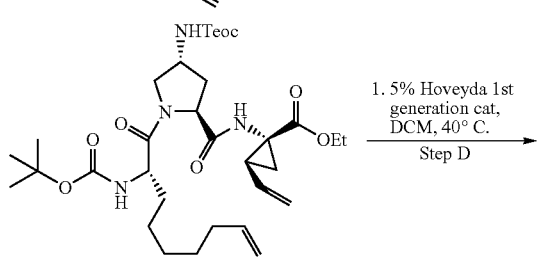

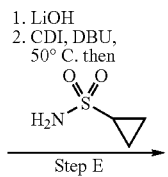

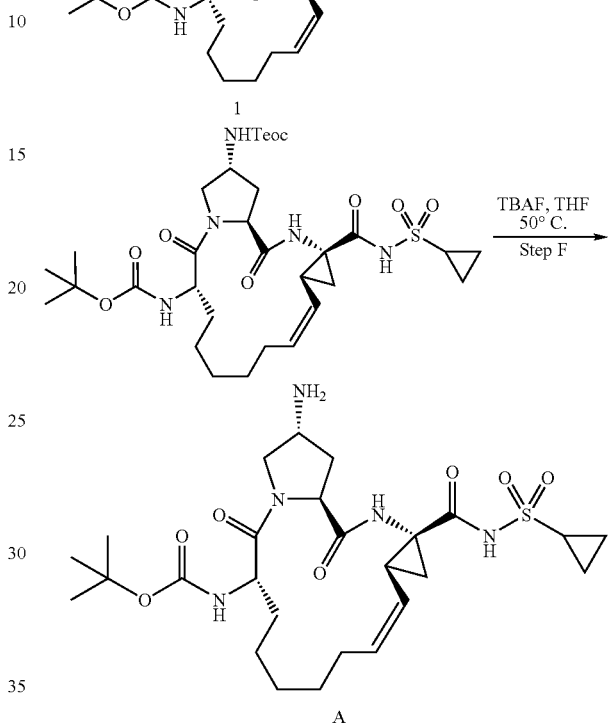

Step A. To a solution of (2S,4R)-4-amino-1-[benzyloxycarbonyl]pyrrolidine-2-methylcarboxlate hydrochloride (2.00 g, 2.34 mmol) in methylene chloride (25 ml) was added 2-(trimethyl silyl)ethyl p-nitrophenyl carbonate (1.98 g, 6.99 mmol) and triethylamine (1.81 ml, 13.34 mmol). The reaction was stirred for 3 days, placed onto silica gel and the product eluted with 40% EtOAc/hexanes to give a colorless oil. The oil was dissolved in methanol (20 ml) and stirred with 10% palladium on carbon under a balloon of hydrogen gas. After stirring for 4 h, the reaction was filtered and concentrated. The resulting solid was dissolved in 1N aqueous HCl (75 ml) and extracted with methylene chloride (75 ml). The aqueous layer was made basic by the addition of sodium hydroxide and again extracted with methylene chloride (100 ml). Both organic extractions were combined, concentrated, and the resulting residue purified by silica gel chromatography eluting with 10% methanol/methylene chloride to give a brownish solid (1.29 g, 70%). LCMS=289(H+).

Step B. A solution of 4(R)-(2-trimethylsilylethyl carbonylamino)-pyrrolidine-2(S)-carboxylic acid methyl ester (1.29 g, 4.50 mmol), 2(S)-tert-butoxycarbonylamino-non-8-enoic acid (1.22 g, 4.51 mmol), HATU (2.06 g, 5.41 mmol) and diisopropylethylamine (1.18 ml, 6.76 mmol) in dimethylformamide (10 ml) was stirred overnight. The reaction was diluted with ethyl acetate (150 ml), washed with 1N aqueous HCl (2×100 ml), dried over magnesium sulfate and concentrated. Silica gel chromatography gave an oil which was stirred with lithium hydroxide (0.28 g, 6.76 mmol) in methanol (5 ml) for 2 h. The reaction was diluted with methylene chloride and washed with 1N aqueous HCl, dried over magnesium sulfate and concentrated to give 1.2 g (49%) of the product.

Step C. To 1(R)-tert-butoxycarbonylamino-2(S)-vinyl-cyclopropanecarboxylic acid ethyl ester (0.70 g, 2.75 mmol) was added 4N HCl/dioane solution (2.87 ml, 11.46 mmol). After stirring for 2 h, the reaction was concentrated to give a solid. To this solid was added 1-(2(S)-tert-butoxycarbonylamino-non-8-enoyl)-4(R)-(2-trimethylsilylethyl carbonylamino)-pyrrolidine-2(S)-carboxylic acid (1.21 g, 2.29 mmol), HATU (1.05 g, 2.75 mmol) and diisopropylethylamine (1.60 ml, 9.17 mmol) and methylene chloride (10 ml) and the reaction was stirred for 18 h at room temperature. The reaction was placed onto silica gel and eluted with a solution of 50% ethyl acetate/hexanes to give the product as a colorless oil (1.27 g, 83%). 665(H+)

Step D. A solution of 1-{[1-(2(S)-tert-butoxycarbonylamino-non-8-enoyl)-4(R)-(2-trimethylsilylethyl carbonylamino)-pyrrolidine-2(S)-carbonyl]-amino}-2(S)-vinyl-cyclopropane-1-(R)-carboxylic acid ethyl ester (2.57 g, 3.87 mmol) in methylene chloride (500 ml) was degassed for 1 h by bubbling $N_2$ throught the solution. Dichloro(o-isopropoxyphenyl-methyene)(tricyclohexylphosphine)ruthenium (II) (0.116 g, 0.193 mmol) was added and the reaction stirred at 40° C. for 16 h. The reaction was concentrated, placed onto silica gel and eluted with 50% ethyl acetate/hexanes to give the product (2.01 g, 3.16 mmol, 82%). 637.0 (H+).

Step E. A solution of (1S,4R,6S,14S,18R)-(14-tert-butoxycarbonylamino-2,15-dioxo-18-(2-trimethylsilanyl-ethoxycarbonylamino)-3,16-diaza-tricyclo[14.3.0.0$^{4,6}$] nonadec-7-ene-4-carboxylic acid ethyl ester (1.94 g, 3.04 mmol) in 10:1 methanol/water (10 ml) was added lithium hydroxide (1.02 g, 24.37 mmol) and the reaction stirred at room temperature overnight. The reaction was quenched by the addition of 1N HCl (50 ml) and extrated into methylene chloride (2×50 ml). The combined organics were washed with brine (50 ml), dried over magnesium sulfate and concentrated to give a solid (1.78 g, 2.92 mmol). A solution of this acid and carbonyl diimidazole (0.711 g, 4.39 mmol) in dichloroethane was heated at 50° C. After 1 h, HPLC analysis indicated the presence of starting material, so additional carbonyl diimidazole (0.1 g) was added. After an additional 1 h stirring at 50° C., HPLC analysis indicated complete consumption of starting material. To the reaction was added a solution of cyclopropanesulfonyl chloride (0.46 g, 3.80 mmol) and DBU (0.57 g, 3.80 mmol) and the reaction was heated at 50° C. After 1 h, the reaction was not complete as judged by HPLC monitoring, so an additional 0.07 g of cyclopropyl sulfonamide and 0.1 g of DBU was added. After stirring for an additional 30 minutes, the reaction was judged complete. The reaction was cooled, placed onto silica gel and the product was eluted with a gradient of 3% methanol/DCM to 7.5% methanol/DCM as a white solid. LCMS 710.5 (H−)

Step F. A solution of 1 (0.80 g, 1.124 mmol) and tetrabutylammonium fluororide (1.0M solution in THF, 1.4 ml) was stirred together at 50° C. for 1 h. The reaction was cooled, placed onto silica gel and the product eluted with a gradient of 5% methanol/DCM to 25% methanol/DCM as a white solid (0.51 g). LCMS=568.0 (H+)

2. Preparation of Aminoproline Macrocyclic Ester Intermediate B

Synthesis of (1S,4R,6S,14S,18R)-18-amino-14-tert-butoxycarbonylamino-2,15-dioxo-3,16-diaza-tricyclo [14.3.0.0$^{4,6}$]nonadec-7-ene-4-carboxylic acid ethyl ester.

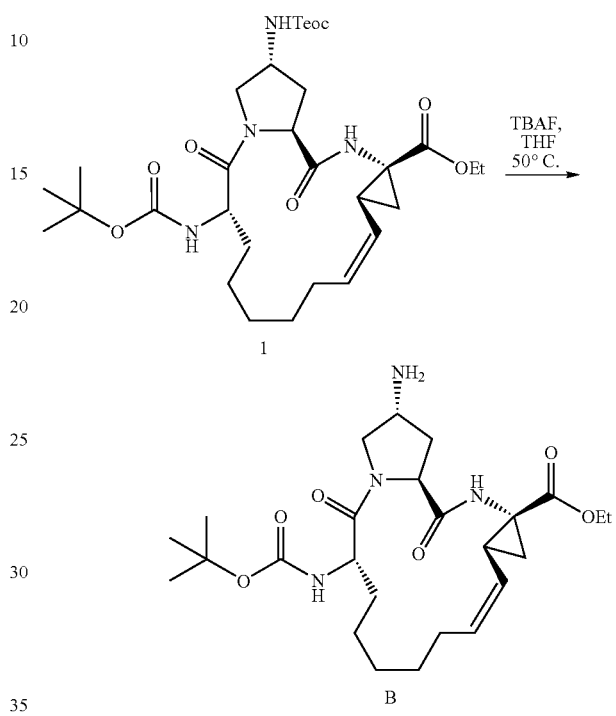

Compound 1 from Scheme 1 above was treated with TBAF (1.0 M in THF, 1.5 equiv) and heated to 50° C. for 4 h. The reaction was placed onto silica gel and eluted with 20% methanol/methyene chloride to give B as a tan solid (69% yield). $^1$H NMR (CDCl$_3$, 400 MHz): δ 1.06-1.66 (m, 17H), 1.85-1.95 (m, 2H), 2.0-2.1 (m, 1H), 2.1-2.2 (m, 1H), 2.2-2.3 (m, 1H), 2.65-2.75 (M, 1H), 3.40 (m, 1H), 3.73-3.83 (m, 2H), 4.08-4.19 (m, 2H), 4.56 (m, 1H), 4.78 (d, J=5.5 Hz, 1H), 5.20 (t, J=8.1 Hz, 1H), 5.34 (d, J=8.1 Hz, 1H), 5.47 (dt, J=4.5, 10.8 Hz, 1H), 7.08 (s, 1H). 493(H+).

The acylsulfonamide NS3 inhibitors shown in Examples 1-69 were then prepared via one of the following two routes utilizing the above two intermediates A and B. All the carboxylic acid NS3 inhibitors in the examples were prepared via route 2 in Scheme 3.

Scheme 3

Route 1:

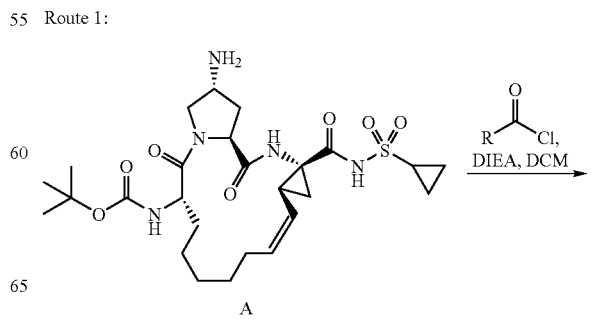

-continued
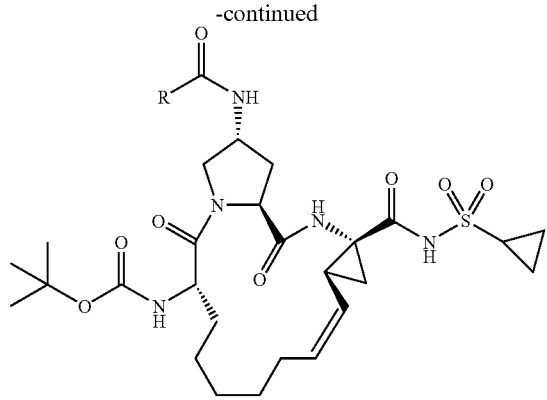
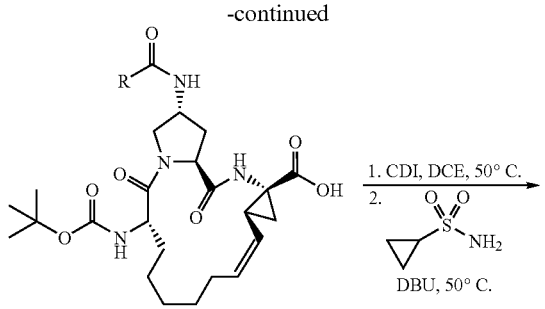
Route 2:
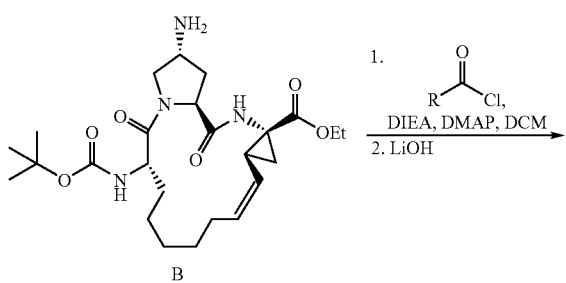
Example 1
Synthesis of (1S,4R,6S,14S,18R)-{[8-[(3-Chloro-benzo[b]thiophene-2-carbonyl)-amino]-4-cyclopropanesulfonylaminocarbonyl-2,15-dioxo-3,16-diaza-tricyclo[14.3.0.0^{4,6}]nonadec-7-en-14-yl}-carbamic acid tert-butyl ester
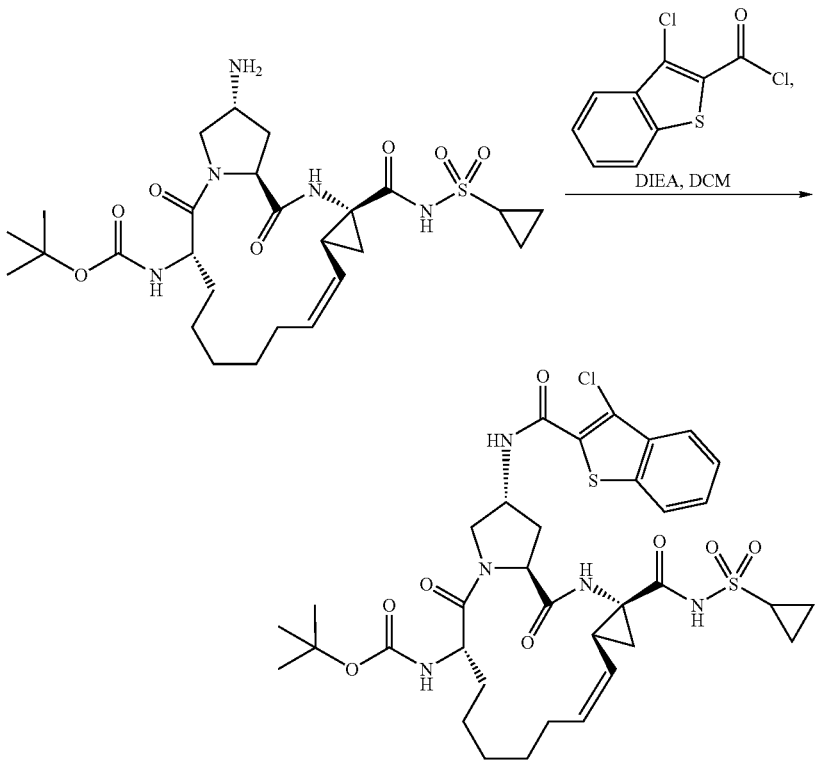

A solution of (1S,4R,6S,14S,18R)-(18-amino-4-cyclopropanesulfonylaminocarbonyl-2,15-dioxo-3,16-diaza-tricyclo[14.3.0.0$^{4,6}$]nonadec-7-en-14-yl)-carbamic acid tert-butyl ester (0.254 g, 0.44 mmol), 3-chloro-benzo[b]thiophene-2-carbonyl chloride (0.124 g, 0.54 mmol) and DIEA (0.087 g, 0.67 mmol) were stirred together in DCM at room temperature. After 1 h, the reaction was placed onto silica gel and the product eluted as a white solid using a gradient of 1% methanol/DCM to 5% methanol/DCM. $^1$H NMR(C$_6$D$_6$, 400 MHz) δ 7.66-7.70 (m, 1H), 7.22-7.24 (m, 1H), 7.04-7.07 (m, 2H), 6.97 (t, 1H), 6.83 (bs, 1H), 5.61 (d, 1H), 5.18 (t, 1H), 5.05 (d, 1H), 4.48-4.50 (b, 1H), 4.26 (t, 1H), 3.8-4.0 (m, 1H), 3.65-3.74 (m, 1H), 3.20-3.35 (M, 1H), 2.78-2.85 (M, 1H), 2.55-2.65 (m, 1H), 2.3-2.4 (m, 1H), 1.95-2.15 (m, 2H), 1.75-1.85 (m, 1H), 1.20-1.40 (m, 16H), 0.95-1.15 (m, 5H) 0.4-0.5 (M, 1H), 0.25-0.35 (M, 1H); LCMS=662 (H$^+$–Boc)

Examples 2-69

The following examples were made either following the general procedures described for the sythesis of Example 1 by substituting with the appropriate acid chloride or carboxylic acid/HATU for 3-chloro-benzo[b]thiophene-2-carbonyl chloride, or following similar amide and acylsulfonamide coupling procedures as described in Example 1 and in the synthesis of A, but adopting route 2 of Scheme 3 instead.

TABLE 4

| EXAMPLE | STRUCTURE | LCMS |
|---|---|---|
| 2 | 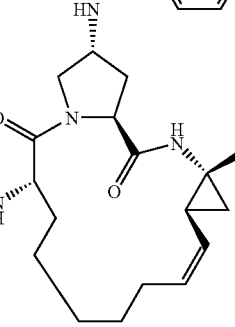 | 672.0 (H$^+$) |
| 3 | 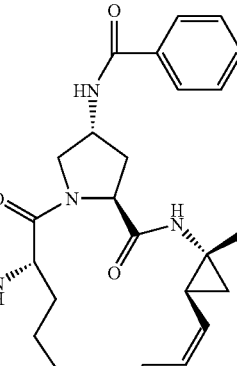 | 700.0 (H$^+$) |
| 4 | 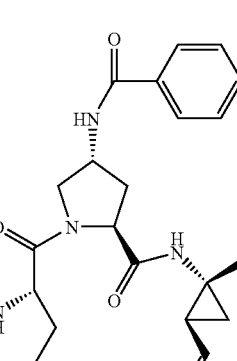 | 705.9 (H$^+$) |

TABLE 4-continued
| EXAMPLE | STRUCTURE | LCMS |
|---------|-----------|------|
| 5 | 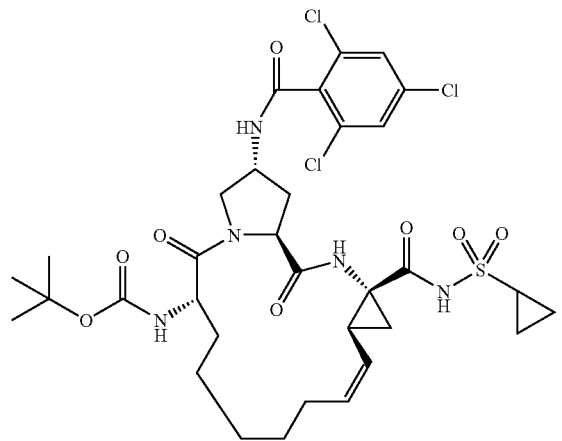 | 773.7 (H+) |
| 6 | 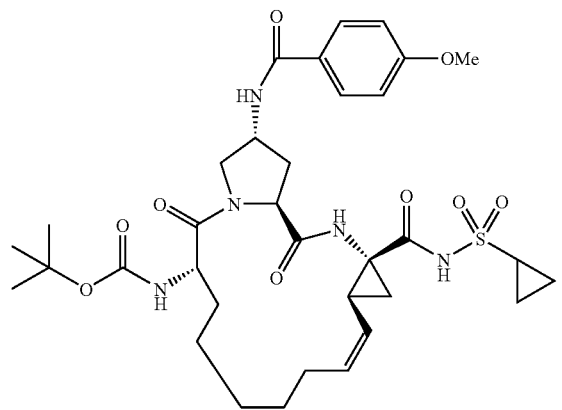 | 702.0 (H+) |
| 7 | 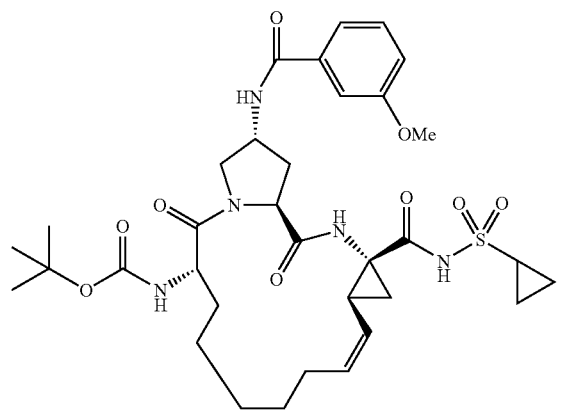 | 701.9 (H+) |

TABLE 4-continued

| EXAMPLE | STRUCTURE | LCMS |
|---------|-----------|------|
| 8 | 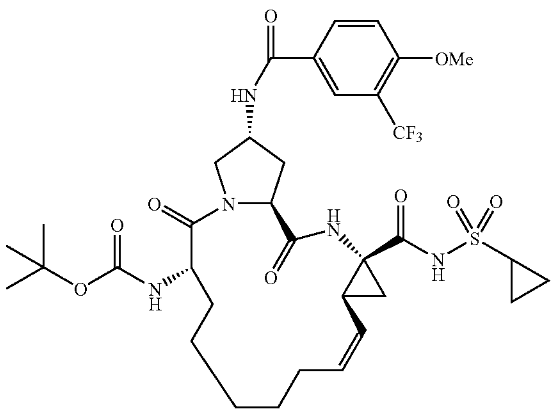 | 769.9 (H⁺) |
| 9 | 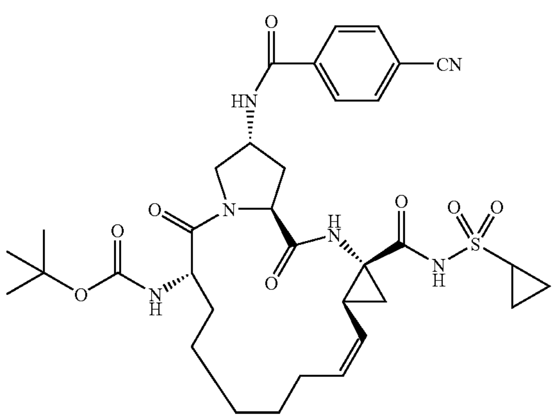 | 696.9 (H⁺) |
| 10 | 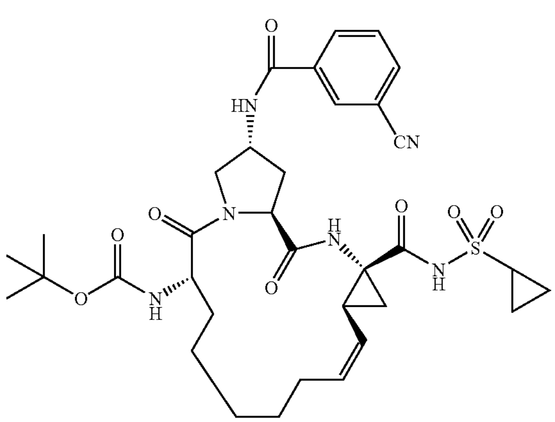 | 696.9 (H⁺) |

TABLE 4-continued

| EXAMPLE | STRUCTURE | LCMS |
|---------|-----------|------|
| 11 | 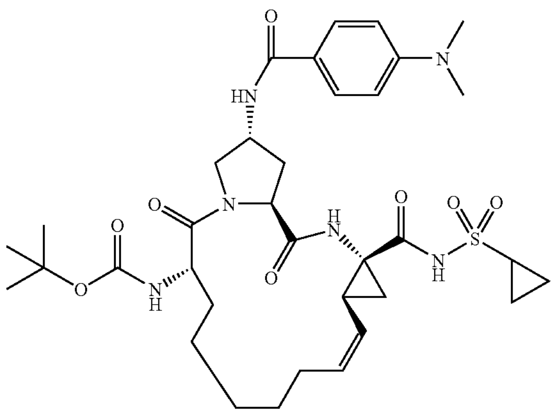 | 715.0 (H⁺) |
| 12 | 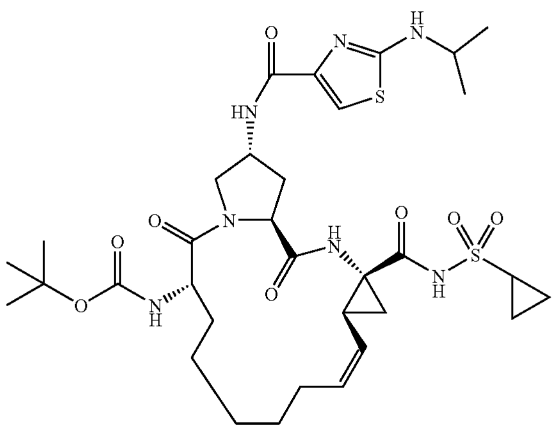 | 736.1 (H⁺) |
| 13 | 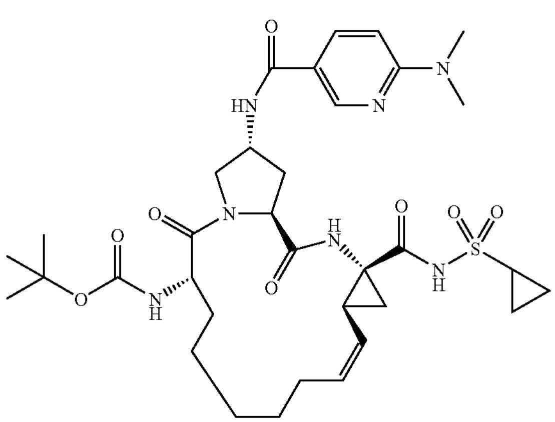 | 716.1 (H⁺) |

TABLE 4-continued

| EXAMPLE | STRUCTURE | LCMS |
|---------|-----------|------|
| 14 | 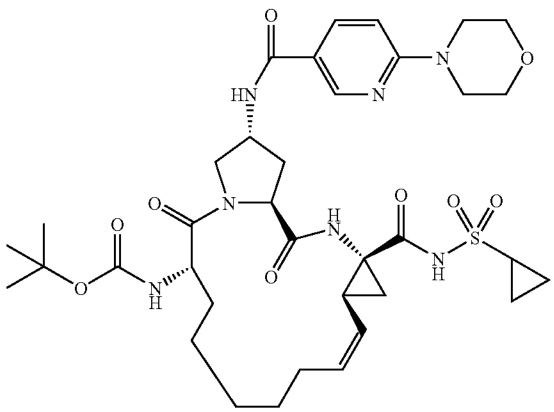 | 758.1 (H⁺) |
| 15 | 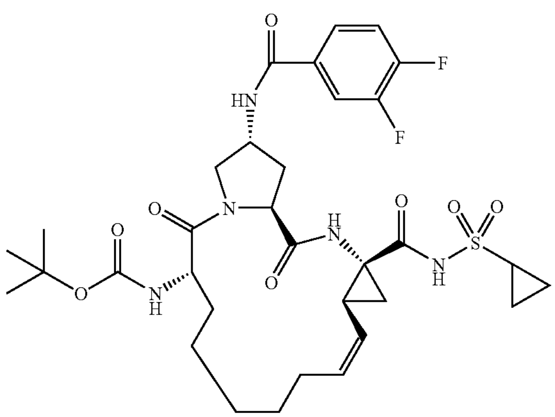 | 707.9 (H⁺) |
| 16 | 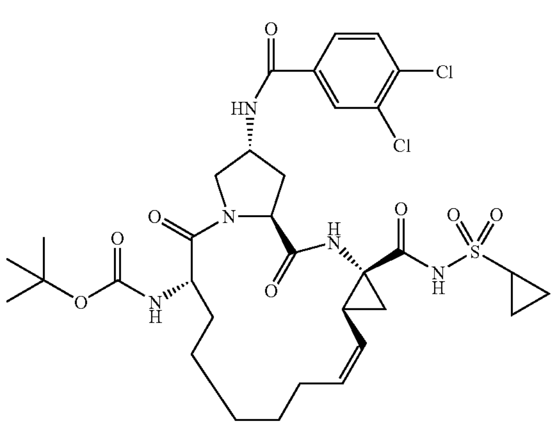 | 739.8 (H⁺) |

TABLE 4-continued

| EXAMPLE | STRUCTURE | LCMS |
|---------|-----------|------|
| 17 | 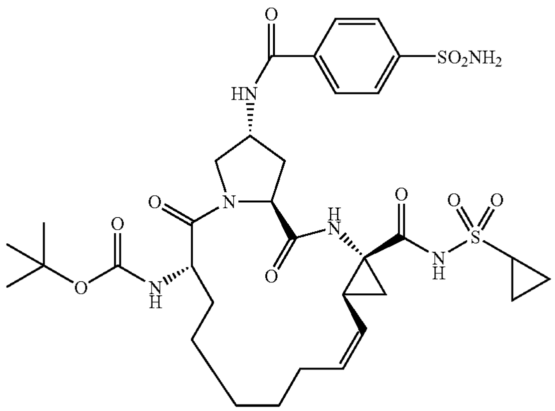 | 750.0 (H⁺) |
| 18 | 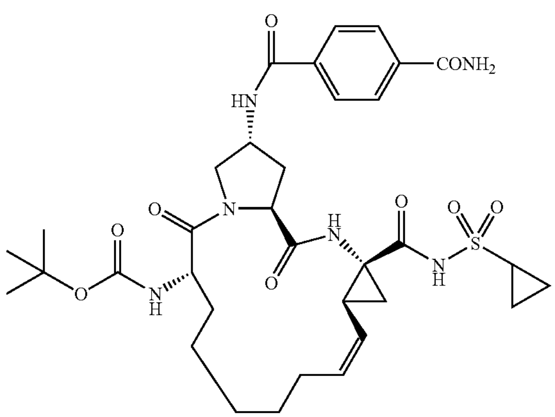 | 714.9 (H⁺) |
| 19 | 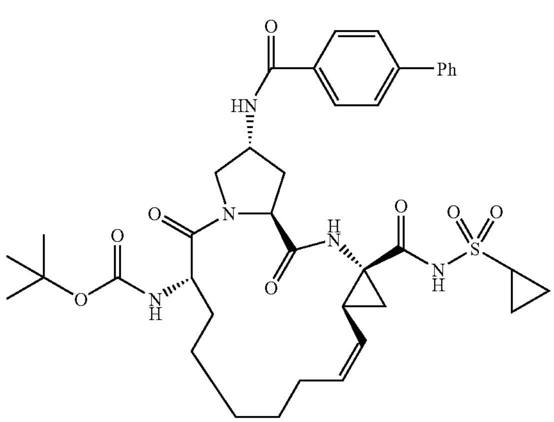 | 746.3 (−H) |

TABLE 4-continued
| EXAMPLE | STRUCTURE | LCMS |
|---|---|---|
| 20 | 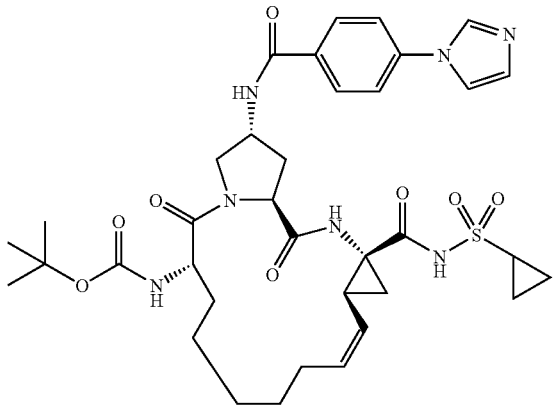 | 738.2 (H+) |
| 21 | 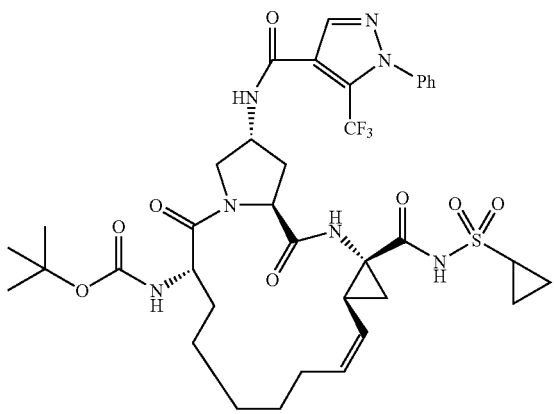 | 706.2 (H+ − Boc) |
| 22 | 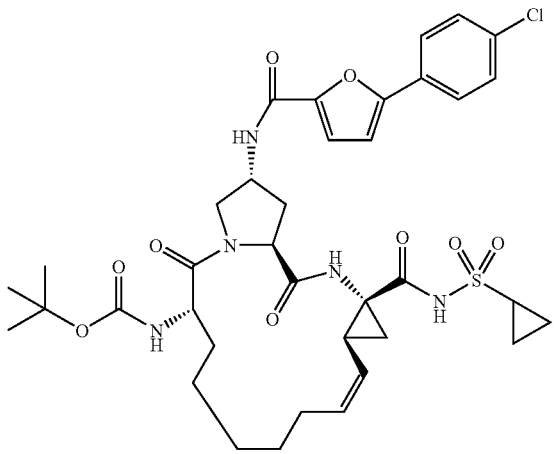 | 771.9 (H+) |

TABLE 4-continued

| EXAMPLE | STRUCTURE | LCMS |
| --- | --- | --- |
| 23 | 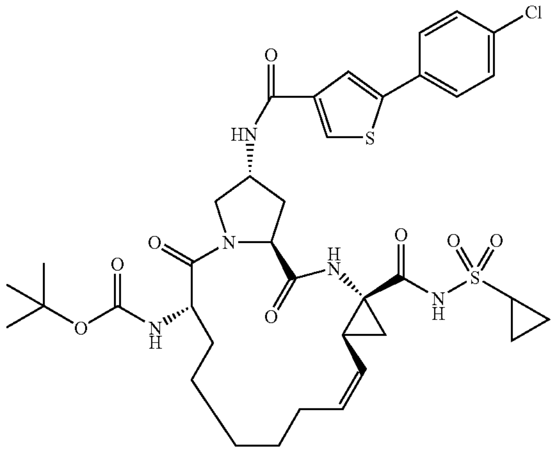 | 787.7 (H+) |
| 24 | 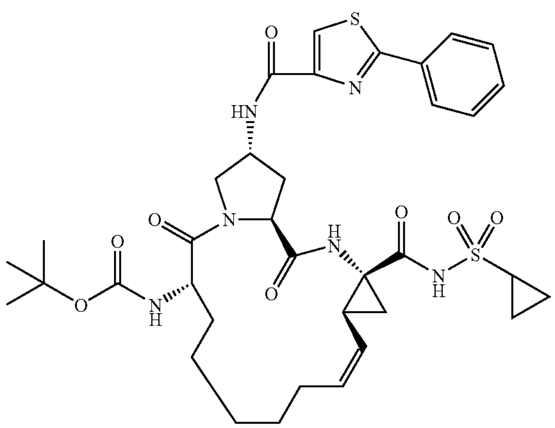 | 754.9 (H+) |
| 25 | 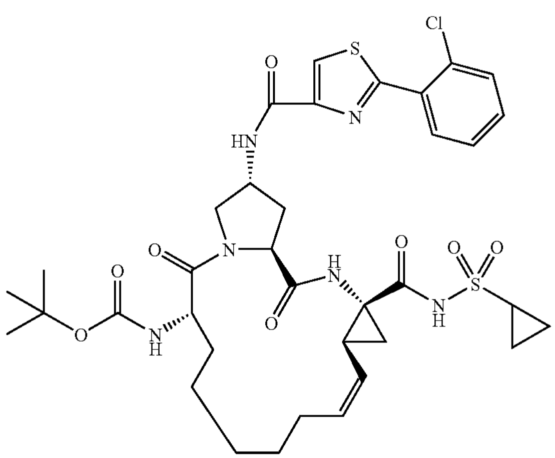 | 788.8 (H+) |

TABLE 4-continued

| EXAMPLE | STRUCTURE | LCMS |
|---------|-----------|------|
| 26 | 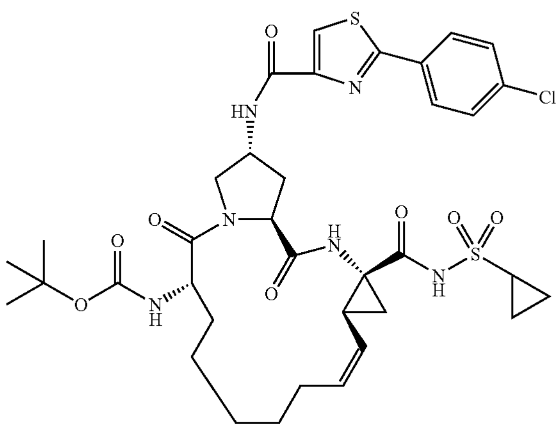 | 788.9 (H⁺) |
| 27 | 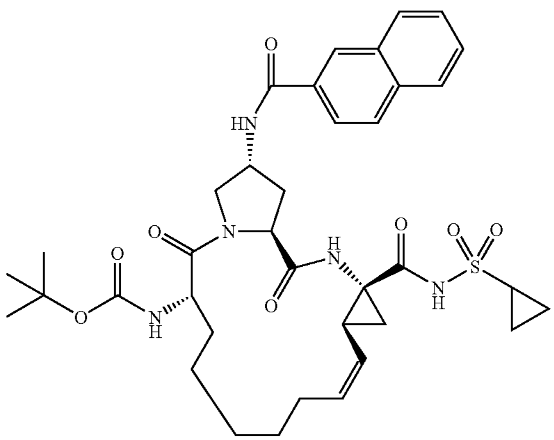 | 722.0 (H⁺) |
| 28 | 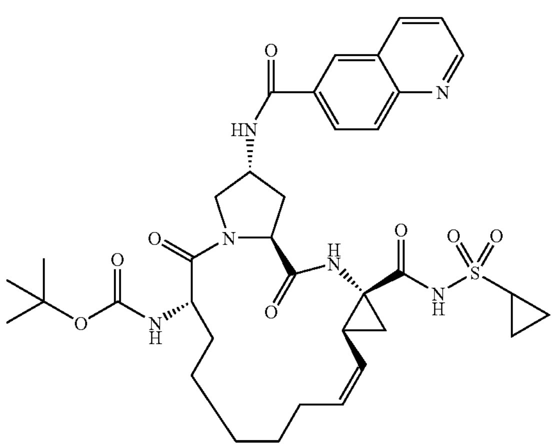 | 723.1 (H⁺) |

TABLE 4-continued

| EXAMPLE | STRUCTURE | LCMS |
|---------|-----------|------|
| 29 | 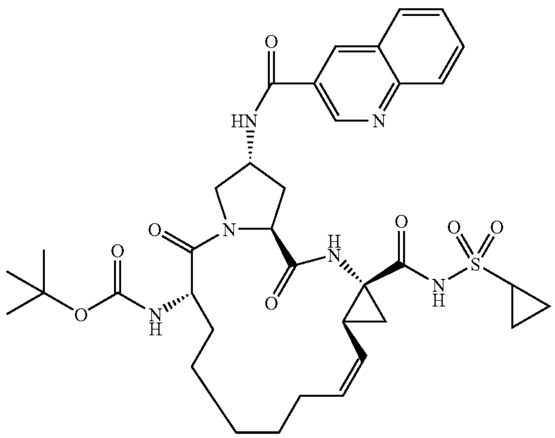 | 721.3 (H⁻) |
| 30 | 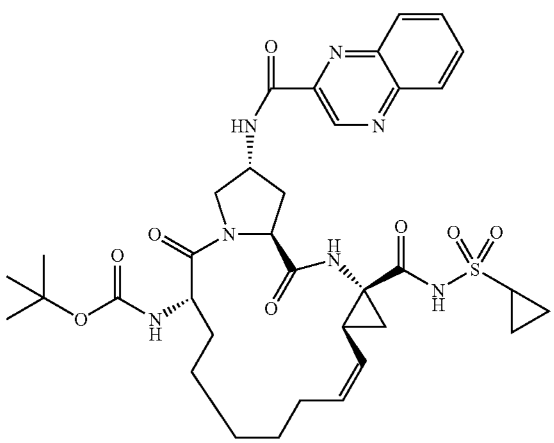 | 723.9 (H⁺) |
| 31 | 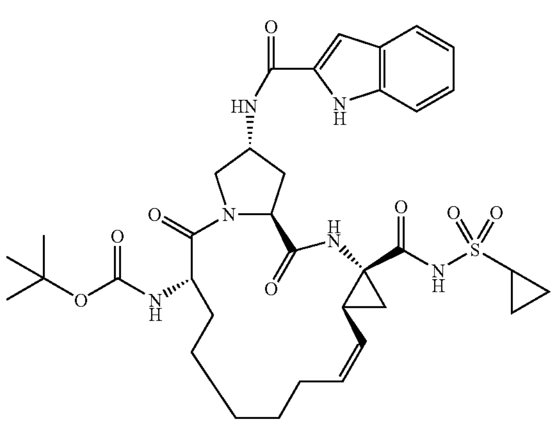 | 710.9 (H⁺) |

TABLE 4-continued

| EXAMPLE | STRUCTURE | LCMS |
|---------|-----------|------|
| 32 | 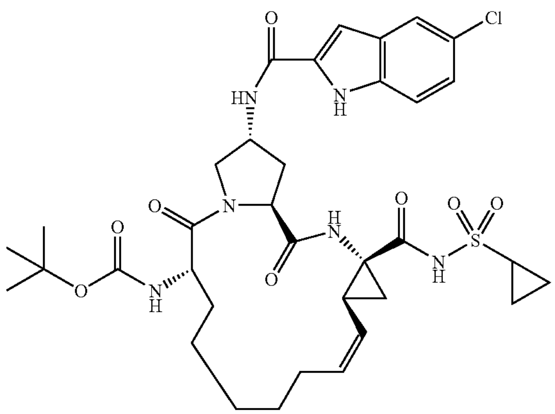 | 744.9 (H⁺) |
| 33 | 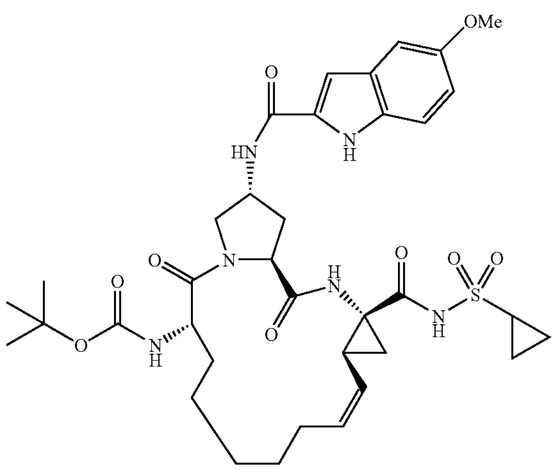 | 740.9 (H⁺) |
| 34 | 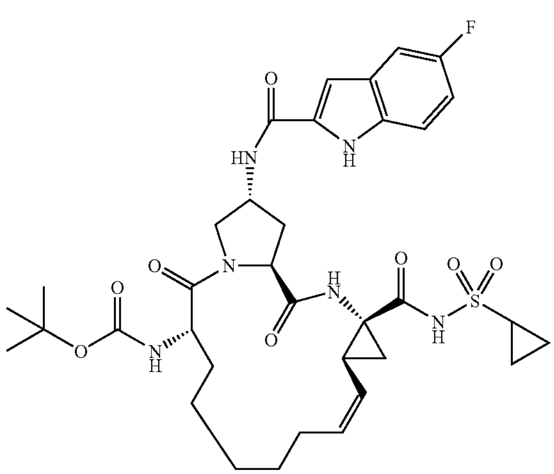 | 728.9 (H⁺) |

TABLE 4-continued

| EXAMPLE | STRUCTURE | LCMS |
|---------|-----------|------|
| 35 | 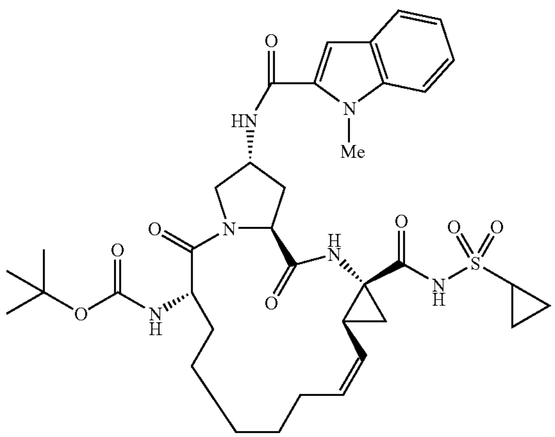 | 724.9 (H⁺) |
| 36 | 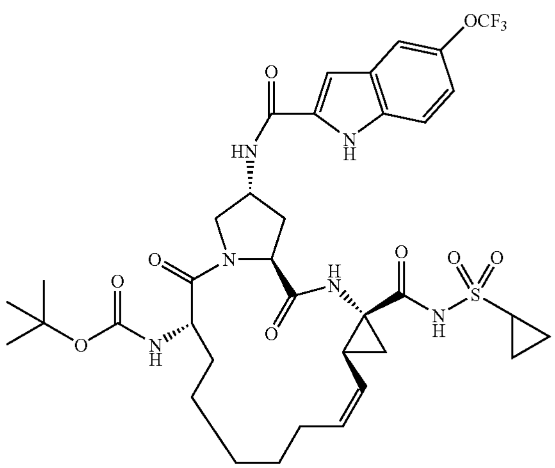 | 794.9 (H⁺) |
| 37 | 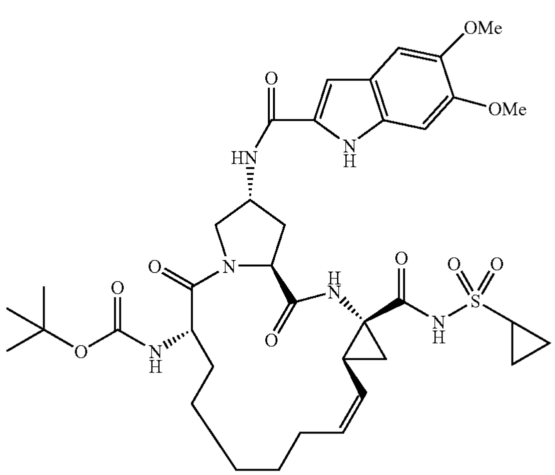 | 771.0 (H⁺) |

TABLE 4-continued
| EXAMPLE | STRUCTURE | LCMS |
|---|---|---|
| 38 | 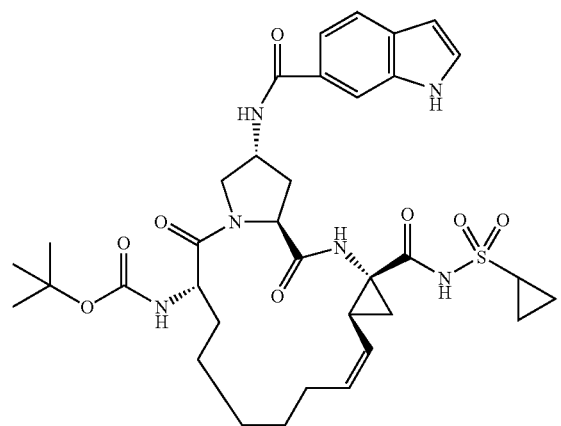 | 710.9 (H+) |
| 39 | 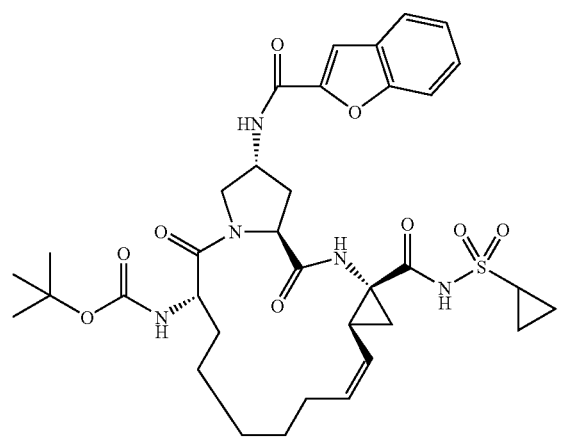 | 712.0 (H+) |
| 40 | 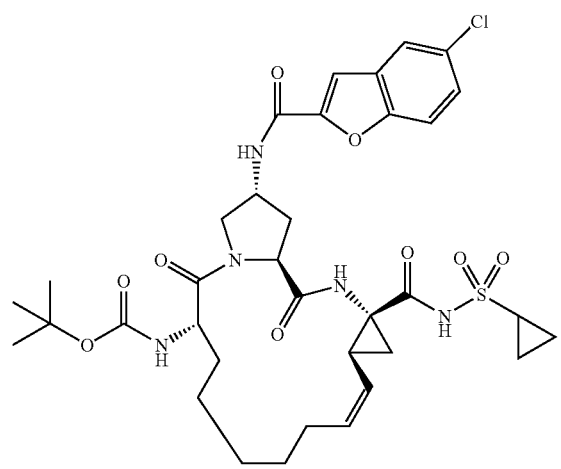 | 745.9 (H+) |

TABLE 4-continued

| EXAMPLE | STRUCTURE | LCMS |
|---------|-----------|------|
| 41 | 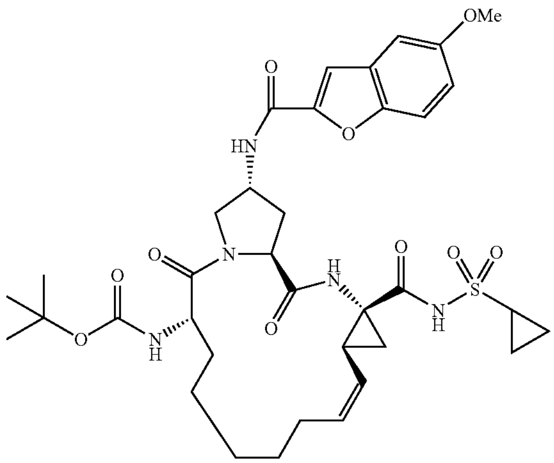 | 741.9 (H⁺) |
| 42 | 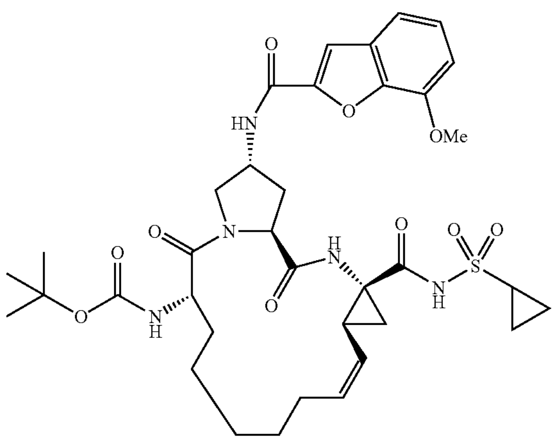 | 741.9 (H⁺) |
| 43 | 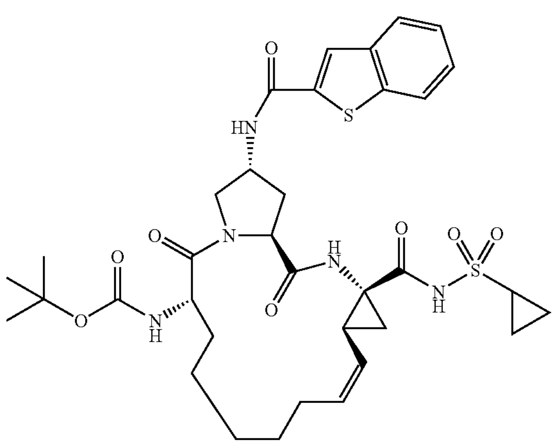 | 726.6 (H⁻) |

TABLE 4-continued

| EXAMPLE | STRUCTURE | LCMS |
|---|---|---|
| 44 | 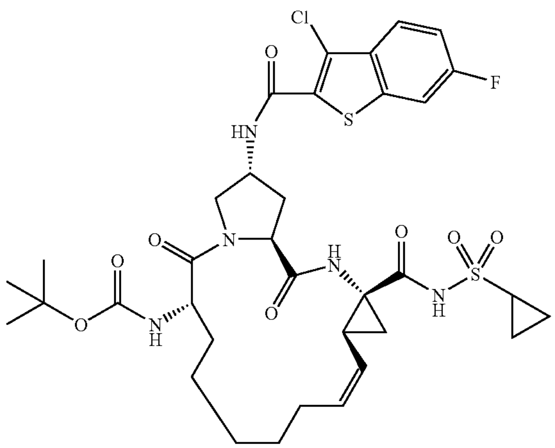 | 779.9 (H⁺) |
| 45 | 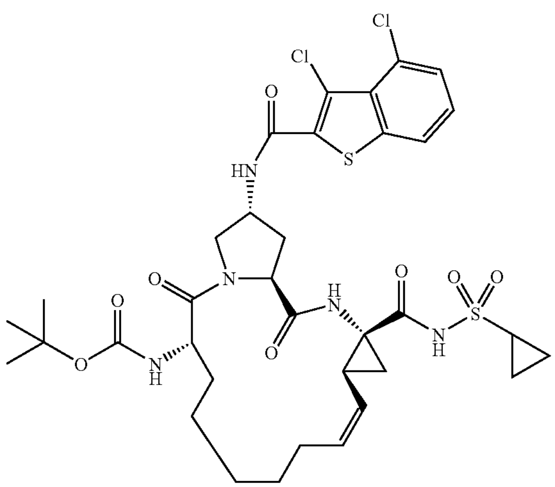 | 795.8 (H⁺) |
| 46 | 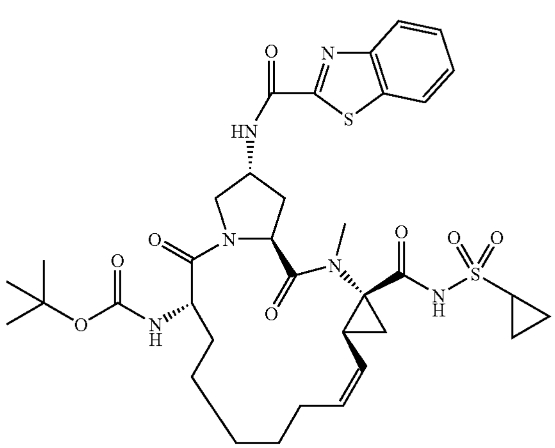 | 629.1 (H⁺ − Boc) |

TABLE 4-continued
| EXAMPLE | STRUCTURE | LCMS |
|---------|-----------|------|
| 47 | 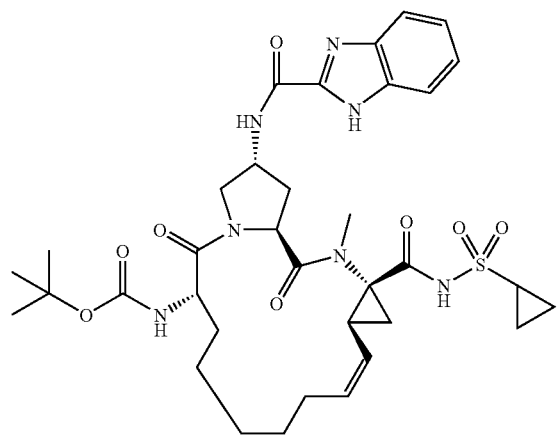 | 712.0 (H⁺) |
| 48 | 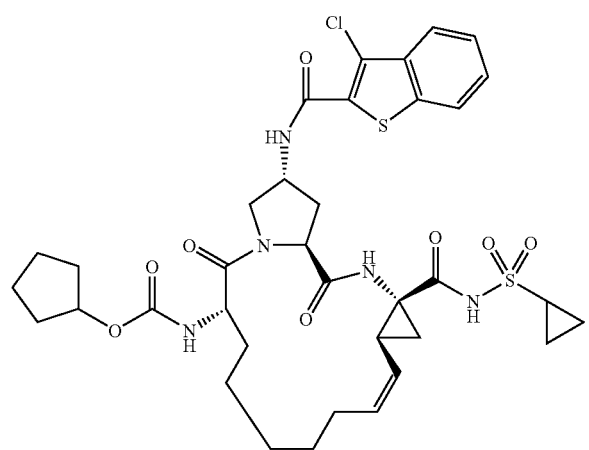 | 774.0 (H⁺) |
| 49 | 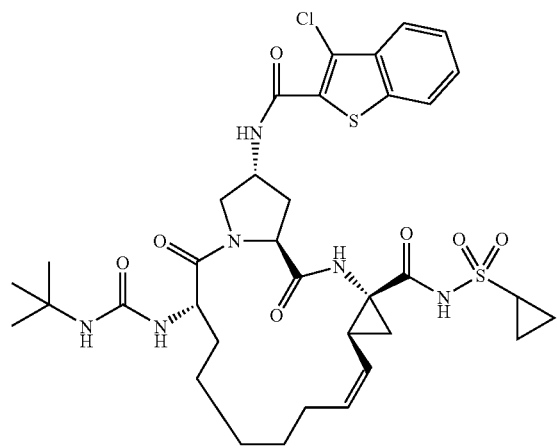 | 761.0 (H⁺) |

TABLE 4-continued
| EXAMPLE | STRUCTURE | LCMS |
|---|---|---|
| 50 | 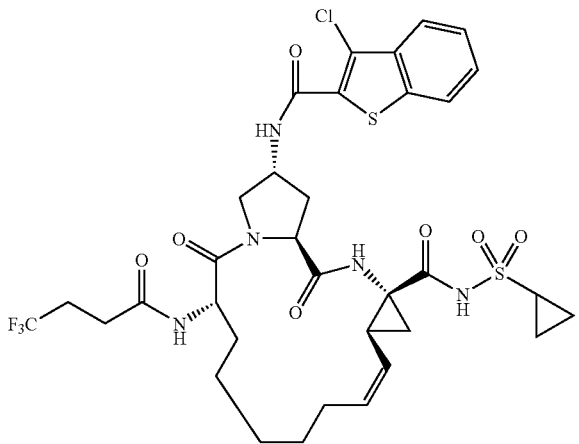 | 786.0 (H+) |
| 51 | 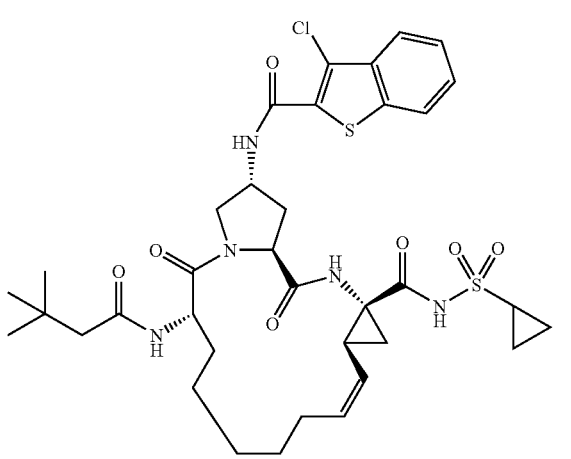 | 760.1 (H+) |
| 52 | 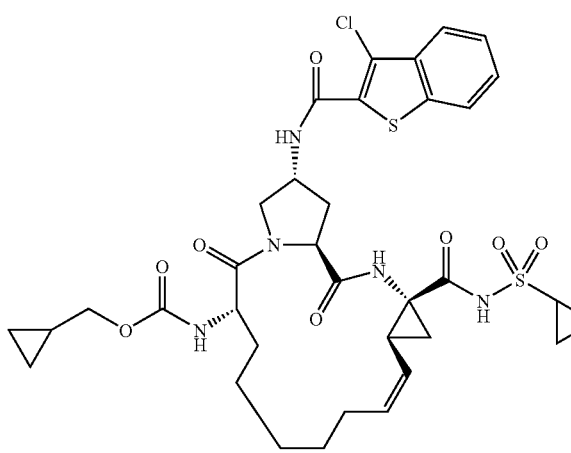 | 760.1 (H+) |

TABLE 4-continued
| EXAMPLE | STRUCTURE | LCMS |
|---|---|---|
| 53 | 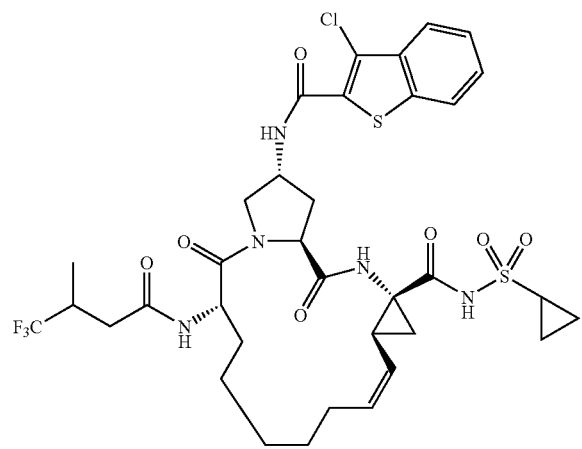 | 800.1 (H+) |
| 54 | 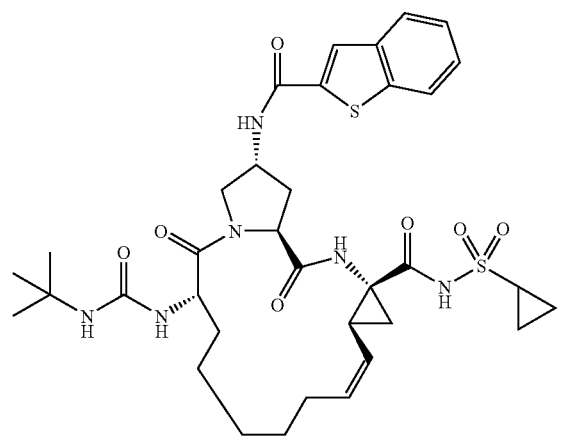 | 727.1 (H+) |
| 55 | 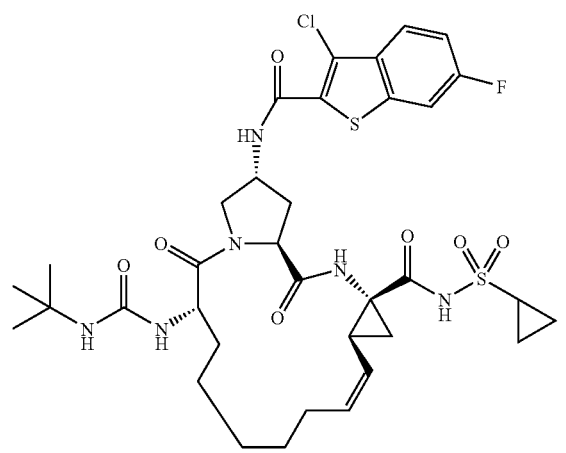 | 779.0 (H+) |

TABLE 4-continued

| EXAMPLE | STRUCTURE | LCMS |
|---------|-----------|------|
| 56 | 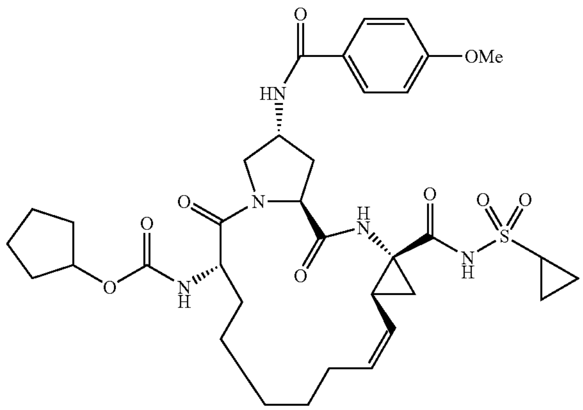 | 714.1 (H⁺) |
| 57 | 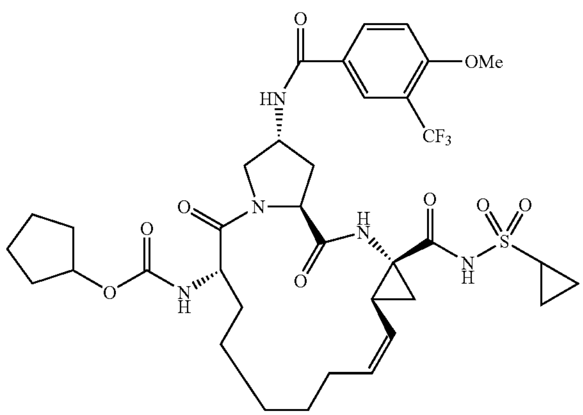 | 782.0 (H⁺) |
| 58 | 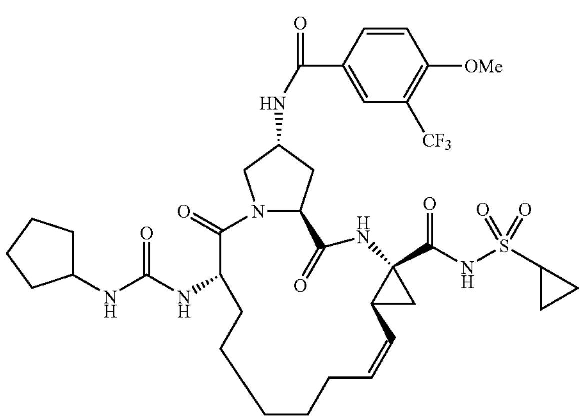 | 781.2 (H⁺) |

TABLE 4-continued
| EXAMPLE | STRUCTURE | LCMS |
|---------|-----------|------|
| 59 | 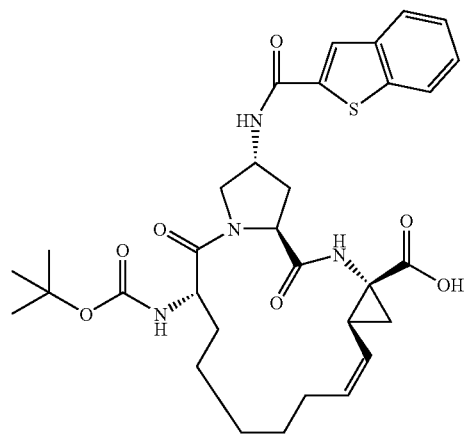 | 624.9 (H⁺) |
| 60 | 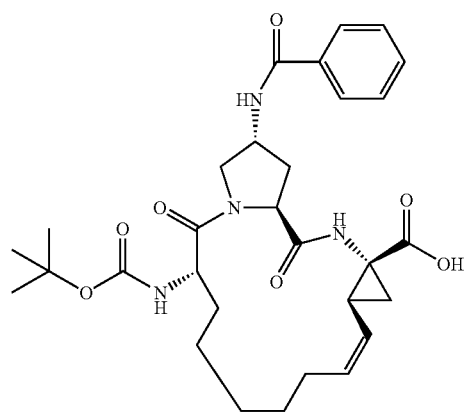 | 569.0 (H⁺) |
| 61 | 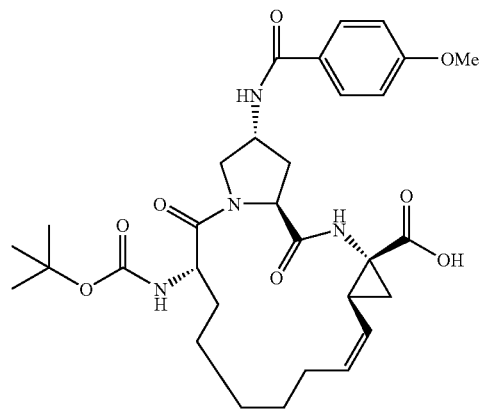 | 599.0 (H⁺) |

TABLE 4-continued

| EXAMPLE | STRUCTURE | LCMS |
|---|---|---|
| 62 | 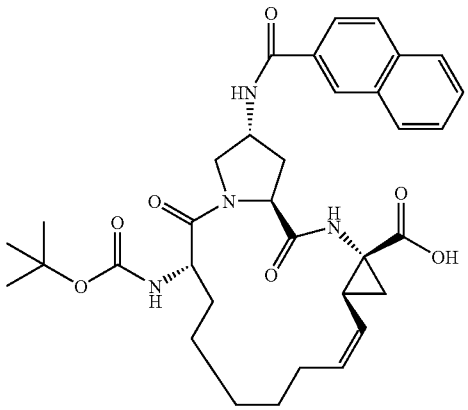 | 619.0 (H+) |
| 63 | 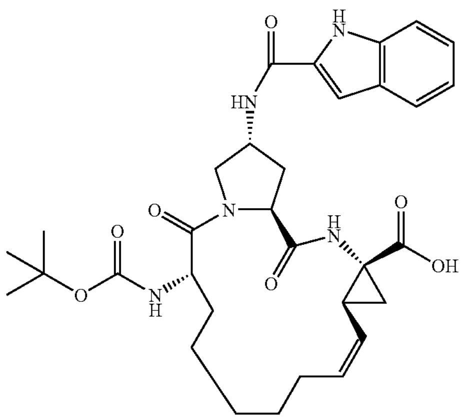 | 608.0 (H+) |
| 64 | 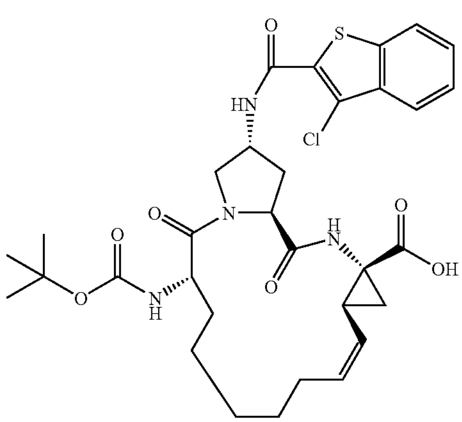 | 658.9 (H+) |

TABLE 4-continued
| EXAMPLE | STRUCTURE | LCMS |
|---|---|---|
| 65 | 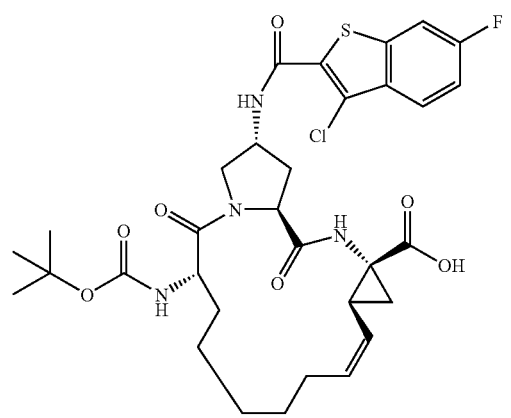 | 676.9 (H+) |
| 66 | 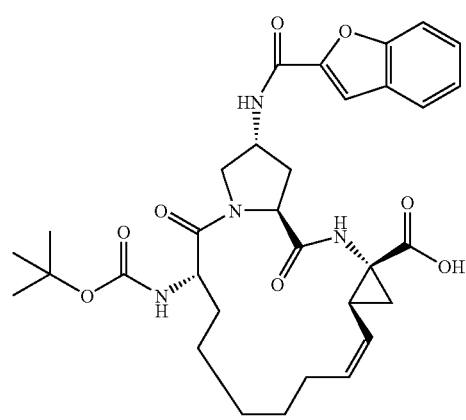 | 609.0 (H+) |
| 67 | 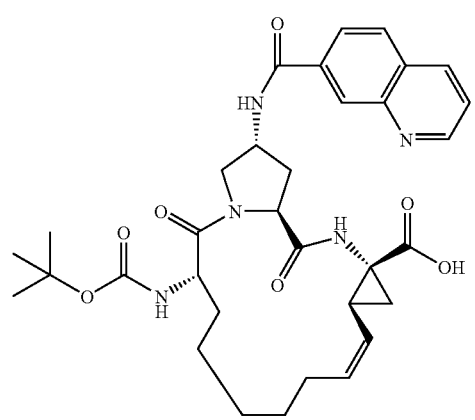 | 620.0 (H+) |

TABLE 4-continued

| EXAMPLE | STRUCTURE | LCMS |
|---|---|---|
| 68 | 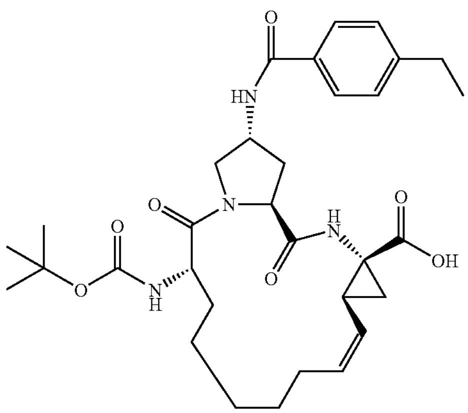 | 597.0 (H+) |
| 69 | 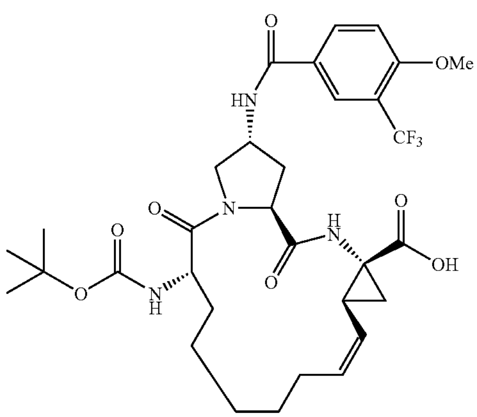 | 666.9 (H+) |

NS3-NS4 Protease Assay

NS3 complex formation with NS4A-2.

Recombinant *E. coli* or Baculovirus full-length NS3 was diluted to 3.33 μM with assay buffer and transferred material to an eppendorf tube and place in water bath in 4° C. refrigerator. The appropriate amount of NS4A-2 to 8.3 mM in assay buffer was added to equal the volume of NS3 in step 2.1.1 (conversion factor −3.8 mg/272 μL assay buffer). The material was transferred to an eppendorf tube and place in water bath in 4° C. refrigerator.

After equilibration to 4° C., equal volumes of NS3 and NS4A-2 solutions were combined in an eppendorf tube, mix gently with a manual pipettor, and incubate mixture for 15 minutes in the 4° C. water bath. Final concentrations in the mixture are 1.67 μM NS3, 4.15 mM NS4A-2 (2485-fold molar excess NS4A-2).

After 15 minutes at 4° C., the NS3/NS4A-2 eppendorf tube was removed and placed in a room temperature water bath for 10 minutes. NS3/NS4A-2 was alliquoted at appropriate volumes and store at −80° C. (*E. coli* NS3 run at 2 nM in assay, aliquot at 25 μL. BV NS3 run at 3 nM in assay, aliquot at 30 μL).

NS3 Inhibition Assay.

Sample compounds were dissolved to 10 mM in DMSO then diluted to 2.5 mM (1:4) in DMSO. Typically, compounds were added to an assay plate at 2.5 mM concentration, yielding upon dilution a starting concentration of 50 microM in the assay inhibition curve. Compounds were serial diluted in assay buffer to provide test solutions at lower concentrations.

The *E. coli*. NS3/NS4A-2 was diluted to 4 nM NS3 (1:417.5 of 1.67 μM stock−18 μL 1.67 μM stock+7497 μL assay buffer).

The BV NS3/NS4A-2 was diluted to 6 nM NS3 (1:278.3 of 1.67 μM stock−24 μL 1.67 μM stock+6655 μL assay buffer).

Using the manual multichannel pipettor, careful not to introduce bubbles into the plate, add 50 μL assay buffer to wells A01-H01 of a black Costar 96-well polypropylene storage plate.

Using the manual multichannel pipettor, careful not to introduce bubbles into the plate, add 50 μL of diluted NS3/NS4A-2 from step 2.2.6 to wells A02-H12 of plate in step 2.2.7.

Using the manual multichannel pipettor, careful not to introduce bubbles into the plate, transfer 25 μL of the wells in drug dilution plate in step 2.2.5 to corresponding wells in assay plate in step 2.2.8. Change tips on multichannel pipettor for each row of compounds transferred.

Using the manual multichannel pipettor, careful not to introduce bubbles into the plate, mix the wells from the assay plate in step 2.2.9 by aspirating and dispensing 35 μL of the 75 μL in each well five times. Change tips on multichannel pipettor for each row of wells mixed.

Cover plate with a polystyrene plate lid and pre-incubate the plate from step 2.2.10 containing NS3 protease and sample compounds 10 minutes at room temperature.

While plate from step 2.2.11 is pre-incubating, dilute RETS1 substrate in a 15 mL polypropylene centrifuge tube.

Dilute RETS1 substrate to 8 µM (1:80.75 of 646 µM stock– 65 µL 646 µM stock+5184 µL assay buffer).

After the plate in step is done pre-incubating, and using the manual multichannel, add 25 µL of substrate to all wells on the plate. Quickly mix the plate as in step 2.2.10, mixing 65 µL of the 100 µL in the wells.

Read the plate in kinetic mode on the Molecular Devices SpectraMax Gemini XS plate reader. Reader settings: Read time: 30 minutes, Interval: 36 seconds, Reads: 51, Excitation k: 335 nm, Emission k: 495 nm, cutoff: 475 nm, Automix: off, Calibrate: once, PMT: high, Reads/well: 6, Vmax pts: 21 or 28/51 depending on length of linearity of reaction.

$IC_{50}$s are determined using a four parameter curve fit equation, and converted to Ki's using the following Km's:

Full-length *E. coli* NS3-2.03 µM
Full-length BV NS3-1.74 µM
where $Ki=IC_{50}/(1+[S]/Km))$
Examples of Activity:
Wherein:
A indicates an $IC_{50}$ of less than 10 µM
B indicates an $IC_{50}$ of less than 1 µM
and C indicates an $IC_{50}$ of less the 0.1 µM

TABLE 5

| Example # | NS3-NS4 IC50 |
| --- | --- |
| 1 | C |
| 2 | C |
| 3 | C |
| 4 | C |
| 5 | C |
| 6 | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | C |
| 19 | C |
| 20 | C |
| 21 | C |
| 22 | C |
| 23 | C |
| 24 | C |
| 25 | C |
| 26 | C |
| 27 | C |
| 28 | C |
| 29 | C |
| 30 | C |
| 31 | C |
| 32 | C |
| 33 | C |
| 34 | C |
| 35 | C |
| 36 | C |
| 37 | C |
| 38 | C |
| 39 | C |
| 40 | C |
| 41 | C |
| 42 | C |
| 43 | C |
| 44 | C |
| 45 | C |
| 46 | C |

TABLE 5-continued

| Example # | NS3-NS4 IC50 |
| --- | --- |
| 47 | C |
| 48 | |
| 49 | C |
| 50 | C |
| 51 | C |
| 52 | C |
| 53 | C |
| 54 | C |
| 55 | C |
| 56 | C |
| 57 | C |
| 58 | C |
| 59 | A |
| 60 | A |
| 61 | A |
| 62 | B |
| 63 | B |
| 64 | B |
| 65 | B |
| 66 | B |
| 67 | A |
| 68 | A |
| 69 | A |

Synthetic Intermediates

Certain intermediates from the synthetic schemes are encompassed within embodiments. Examples of useful intermediates are shown below.

A compound having the formula:

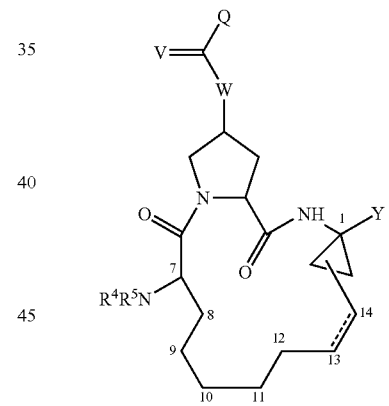

wherein:

Q is a core ring selected from:

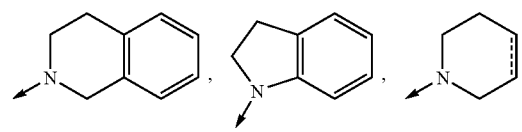

wherein the core ring can be unsubstituted or substituted with H, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl, substituted $C_{1-6}$ alkyl, $C_{1-6}$ alkoxy, substituted $C_{1-6}$ alkoxy, $C_{6\ OR\ 10}$ aryl, pyridyl, pyrimidyl, thienyl, furanyl, thiazolyl, oxazolyl, phenoxy, thiophenoxy, sulphonamido, urea, thiourea, amido, keto, carboxyl, carbamyl, sulphide, sulphoxide, sulphone, amino, alkoxyamino, alkyoxyheterocyclyl, alkylamino, alkylcarboxy, carbonyl, spirocyclic cyclopropyl, spirocyclic cyclobutyl, spirocyclic cyclopentyl, or spirocyclic cyclohexyl, or Q is $R^1$-$R^2$, wherein $R^1$ is $C_{1-6}$ alkyl, $C_{3-7}$ cycloalkyl, $C_{4-10}$ alkylcycloalkyl, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; and $R^2$ is H, phenyl, pyridine, pyrazine, pyrimidine, pyridazine, pyrrole, furan, thiophene, thiazole, oxazole, imidazole, isoxazole, pyrazole, isothiazole, naphthyl, quinoline, isoquinoline, quinoxaline, benzothiazole, benzothiophene, benzofuran, indole, benzimidazole, each optionally substituted with up to three $NR^6R^7$, halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is $C_{1-6}$ alkyl, $C(O)NR^6R^7$, $C(S)NR^6R^7$, $C(O)R^8$, $C(O)OR^8$, $S(O)_2R^8$, or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, or $C_{4-10}$ alkylcycloalkyl, which are all optionally substituted from one to three times with halo, cyano, nitro, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is $COOR^9$, wherein $R^9$ is $C_{1-6}$ alkyl;

V is selected from O, S, or NH;

when V is O or S, W is selected from O, $NR^{15}$, or $CR^{15}$; when V is NH, W is selected from $NR^{15}$ or $CR^{15}$, where $R^{15}$ is H, $C_{1-6}$ alkyl, $C_{3-7}$ cycloalkyl, $C_{4-10}$ alkylcycloalkyl or $C_{1-6}$ alkyl optionally substituted with up to 5 fluoro;

the dashed line represents an optional double bond;

$R^{21}$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, or $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

A compound having the formula:

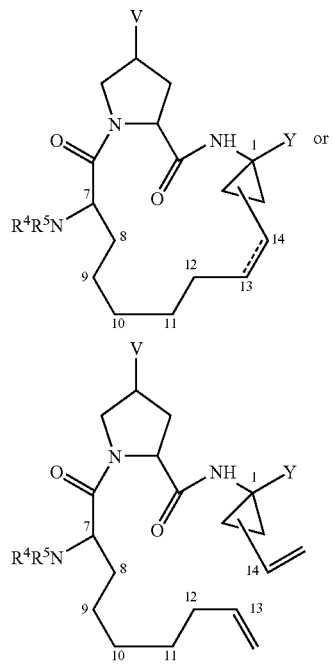

wherein:

$R^4$ is H, $C_{1-6}$ alkyl, $C_{3-7}$ cycloalkyl, $C_{4-10}$ alkylcycloalkyl, phenyl, or benzyl, said phenyl or benzyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro;

$R^5$ is H, $C_{1-6}$ alkyl, $C(O)NR^6R^7$, $C(S)NR^6R^7$, $C(O)R^8$, $C(O)OR^8$, $S(O)_2R^8$ or $(CO)CHR^{21}NH(CO)R^{22}$;

$R^6$ and $R^7$ are each independently H, $C_{1-6}$ alkyl, $C_{3-7}$ cycloalkyl, $C_{4-10}$ alkylcycloalkyl, or phenyl, said phenyl optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^6$ and $R^7$ are taken together with the nitrogen to which they are attached to form indolinyl, pyrrolidinyl, piperidinyl, piperazinyl, or morpholinyl;

$R^8$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, or phenyl; or $R^8$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, or $C_{1-6}$ alkoxy optionally substituted with up to 5 fluoro; or $R^8$ is $C_{1-6}$ alkyl optionally substituted with up to 5 fluoro groups; or $R^8$ is a tetrahydrofuran ring linked through the $C_3$ or $C_4$ position of the tetrahydrofuran ring; or $R^8$ is a tetrahydropyranyl ring linked through the $C_4$ position of the tetrahydropyranyl ring;

Y is $COOR^9$, wherein $R^9$ is $C_{1-6}$ alkyl;

V is selected from OH, SH, or $NH_2$;

the dashed line represents an optional double bond;

$R^{21}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkoxy, $C_{1-6}$ alkyl optionally substituted with up to 5 fluoro, or phenyl; or $R^{21}$ is $C_{6\ OR\ 10}$ aryl which is optionally substituted by up to three halo, cyano, nitro, hydroxy, $C_{1-6}$ alkyl, $C_{3-7}$ cycloalkyl, $C_{4-10}$ alkylcycloalkyl, $C_{2-6}$ alkenyl, $C_{1-6}$ alkoxy, hydroxy-$C_{1-6}$ alkyl, $C_{1-6}$ alkyl optionally substituted with up to 5 fluoro, $C_{1-6}$ alkoxy optionally substituted with up to 5 fluoro; or $R^{21}$ is pyridyl, pyrimidyl, pyrazinyl, thienyl, furanyl, thiazolyl, oxazolyl, phenoxy, or thiophenoxy; and $R^{22}$ is $C_{1-6}$ alkyl, $C_{3-7}$ cycloalkyl, $C_{4-10}$ alkylcycloalkyl, which are all optionally substituted from one to three times with halo, cyano, nitro, hydroxy, $C_{1-6}$ alkyl optionally substituted with up to 5 fluoro, or phenyl.

Metabolites

Certain embodiments are metabolites of compounds of the formulas I-XIX. In some cases, the metabolites are themselves compounds of the formulas I-XIX. Examples of useful metabolites are shown below.

Metabolites of the compounds of the formulas I-XIX may be identified by the following procedure:

1. Suspend Hepatocytes in supplemented KHB (Krebs-Henseleit Buffer @ pH 7.3) at a density of approximately $2 \times 10^6$ viable hepatocytes per ml.

2. Prepare stock solutions (20 μM) of ITMN-187 and ITMN-191 in KHB.

3. Add 50 μL of ITMN-187 or ITMN-191 to 50 μL of hepatocyte suspension in a 96-well polypropylene plate. Final concentration of substrate is 10 μM (~7 μg/mL).

4. Incubate plate at 37° C., 5% $CO_2$ in a saturating humidity for 0 or 2 hours.

5. Terminate reaction with 100 μl acetonitrile and shake plate at 700 rpm for 30 seconds.

6. Spin plates immediately in a centrifuge (1,500×g) for 10 min to pellet the denatured hepatocytes.

7. Transfer 180 μl of supernatant to another plate.

8. Pool wells, evaporate solvent with N2 at 37° C., reconstitute residue in 75/25 water/acetonitrile, v/v and analyze by LC-MS/MS.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the formula:

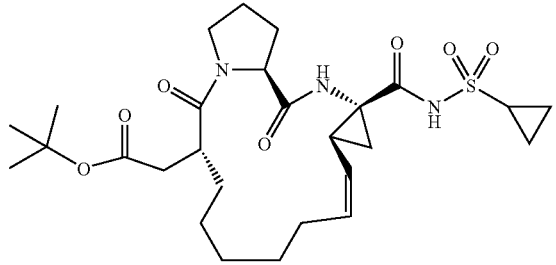

or a pharmaceutically acceptable salt thereof.

* * * * *

UNITED STATES PATENT AND TRADEMARK OFFICE
CERTIFICATE OF CORRECTION

PATENT NO. : 7,491,794 B2
APPLICATION NO. : 11/093884
DATED : February 17, 2009
INVENTOR(S) : Lawrence M. Blatt et al.

It is certified that error appears in the above-identified patent and that said Letters Patent is hereby corrected as shown below:

On the Title Page Item (56), in References Cited section, please delete "2/2000" and insert --2/2005--, therefor.

On the Title Page Item (56), on Page 2, in Other Publications section, please delete "fo" and insert --of--, therefor.

On the Title Page Item (56), on Page 2, in Other Publications section, please delete "PCT/US/2005/010494" and insert --PCT/US2005/010494--, therefor.

On the Title Page Item (56), on Page 3, in Other Publications section, please delete "hepatitus" and insert --hepatitis--, therefor.

At Column 384, Lines 20-40 (approximately), please delete

"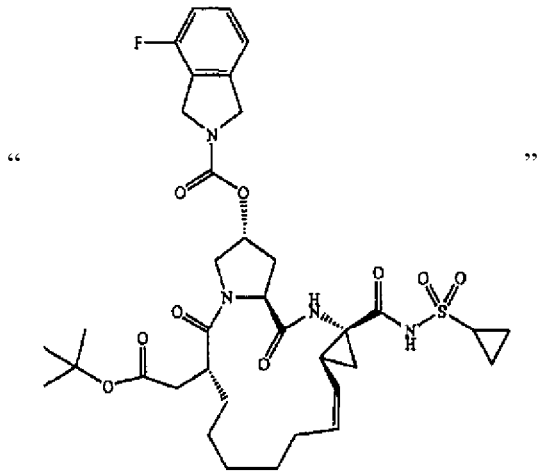"

and insert

UNITED STATES PATENT AND TRADEMARK OFFICE
CERTIFICATE OF CORRECTION

PATENT NO. : 7,491,794 B2  Page 2 of 2
APPLICATION NO. : 11/093884
DATED : February 17, 2009
INVENTOR(S) : Lawrence M. Blatt et al.

It is certified that error appears in the above-identified patent and that said Letters Patent is hereby corrected as shown below:

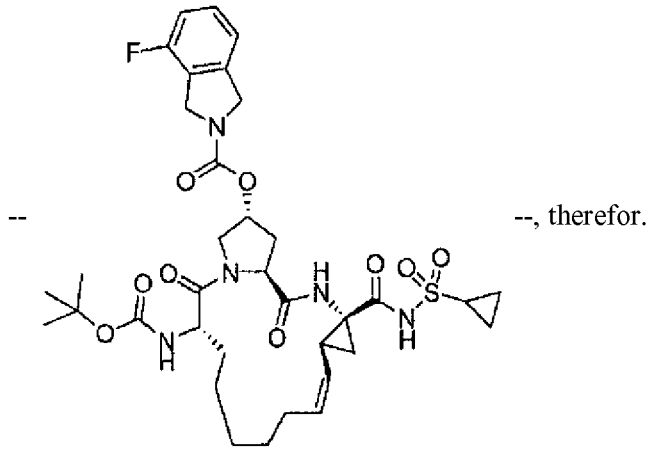 --, therefor.

Signed and Sealed this

Second Day of June, 2009

JOHN DOLL
*Acting Director of the United States Patent and Trademark Office*

UNITED STATES PATENT AND TRADEMARK OFFICE
Certificate

Patent No. 7,491,794 B2                          Patented: February 17, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Lawrence M. Blatt, San Francisco, CA (US); Steven W. Andrews, Longmont, CO (US); Kevin R. Condroski, Broomfield, CO (US); Yutong Jiang, Longmont, CO. (US); April L. Kennedy, Denver, CO (US); Peter J. Stengel, Longmont, CO (US); Steven M. Wenglowsky, Boulder, CO (US); and Scott D. Seiwert, Pacifica, CA (US).

Signed and Sealed this Fifteenth Day of December 2009.

*Cecilia Tsang*
*Supervisory Patent Examiner*
Art Unit 1654

UNITED STATES PATENT AND TRADEMARK OFFICE
CERTIFICATE OF CORRECTION

| | | |
|---|---|---|
| PATENT NO. | : 7,491,794 B2 | Page 1 of 1 |
| APPLICATION NO. | : 11/093884 | |
| DATED | : February 17, 2009 | |
| INVENTOR(S) | : Lawrence M. Blatt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 724 days.

Signed and Sealed this

Seventh Day of December, 2010

David J. Kappos
*Director of the United States Patent and Trademark Office*